US012595305B2

(12) United States Patent
Brand et al.

(10) Patent No.: US 12,595,305 B2
(45) Date of Patent: Apr. 7, 2026

(54) TREM2 STABILIZING ANTIBODIES

(71) Applicant: Novartis AG, Basel (CH)

(72) Inventors: Verena Brand, Munich (DE); Dominik Feuerbach, Müllheim (DE); Fabrizio Gasparini, Lausen (CH); Nathalie George, Village-Neuf (FR); Eveline Schaadt, Oberhaching (DE); Derya Shimshek, Loerrach (DE); Honnappa Srinivas, Brugg (CH); Markus Waldhuber, Munich (DE); Rainer Wilcken, Basel (CH)

(73) Assignee: Novartis AG, Basel (CH)

( * ) Notice: Subject to any disclaimer, the term of this patent is extended or adjusted under 35 U.S.C. 154(b) by 749 days.

(21) Appl. No.: 17/934,795

(22) Filed: Sep. 23, 2022

(65) Prior Publication Data

US 2023/0167174 A1 Jun. 1, 2023

Related U.S. Application Data

(62) Division of application No. 16/601,070, filed on Oct. 14, 2019, now Pat. No. 11,492,402.

(60) Provisional application No. 62/892,517, filed on Aug. 27, 2019, provisional application No. 62/890,665, filed on Aug. 23, 2019, provisional application No. 62/835,289, filed on Apr. 17, 2019, provisional application No. 62/745,798, filed on Oct. 15, 2018.

(51) Int. Cl.

| | |
|---|---|
| ***C07K 16/28*** | (2006.01) |
| ***A61K 39/395*** | (2006.01) |
| ***A61P 25/28*** | (2006.01) |
| ***C12N 7/00*** | (2006.01) |
| ***C12N 15/70*** | (2006.01) |
| *A61K 39/00* | (2006.01) |

(52) U.S. Cl.

CPC ...... *C07K 16/2803* (2013.01); *A61K 39/3955* (2013.01); *A61P 25/28* (2018.01); *C12N 7/00* (2013.01); *C12N 15/70* (2013.01); *A61K 2039/505* (2013.01); *C07K 2317/55* (2013.01); *C07K 2317/565* (2013.01); *C07K 2317/75* (2013.01); *C07K 2317/77* (2013.01); *C07K 2317/92* (2013.01); *C07K 2317/94* (2013.01); *C07K 2319/21* (2013.01); *C12N 2750/14143* (2013.01)

(58) Field of Classification Search

CPC .......... C07K 16/2803; C07K 2317/565; C12N 15/70

See application file for complete search history.

(56) References Cited

U.S. PATENT DOCUMENTS

| | | | |
|---|---|---|---|
| 6,878,687 | B1 | 4/2005 | Ruben et al. |
| 7,556,926 | B2 | 7/2009 | Tojo et al. |
| 7,612,181 | B2 | 11/2009 | Wu et al. |
| 8,101,345 | B1 | 1/2012 | Senn et al. |
| 8,231,878 | B2 | 7/2012 | Colonna et al. |
| 8,513,185 | B2 | 8/2013 | Sigalov |
| 9,144,593 | B2 | 9/2015 | Youn et al. |
| 11,084,875 | B2 | 8/2021 | Monroe et al. |
| 11,492,402 | B2 | 11/2022 | Brand et al. |
| 2002/0165875 | A1 | 11/2002 | Verta et al. |
| 2003/0077282 | A1 | 4/2003 | Bigler et al. |
| 2003/0165875 | A1 | 9/2003 | Colonna et al. |
| 2004/0175744 | A1 | 9/2004 | Hu et al. |
| 2005/0208500 | A1 | 9/2005 | Erlander et al. |
| 2009/0081199 | A1 | 3/2009 | Colonna et al. |
| 2011/0110852 | A1 | 5/2011 | Miller et al. |
| 2011/0256213 | A1 | 10/2011 | Onyuksel et al. |
| 2017/0218091 | A1 | 8/2017 | Ambrosi |
| 2017/0240631 | A1 | 8/2017 | Monroe et al. |
| 2017/0291946 | A1 | 10/2017 | Krummel et al. |
| 2018/0194861 | A1 | 7/2018 | Dong et al. |
| 2019/0330335 | A1 | 10/2019 | Schwabe et al. |
| 2020/0277373 | A1 | 9/2020 | Chen et al. |
| 2024/0166742 | A1 | 5/2024 | Welzenbach et al. |
| 2025/0136685 | A1 | 5/2025 | Brand et al. |
| 2025/0215080 | A1 | 7/2025 | Brand et al. |

FOREIGN PATENT DOCUMENTS

| | | | |
|---|---|---|---|
| CN | 105218669 | A | 1/2016 |
| EP | 2500352 | A1 | 9/2012 |
| JP | 7326135 | | 2/2016 |
| JP | 6669749 | | 5/2022 |
| JP | 2024-022882 | | 2/2024 |
| WO | WO 1998039446 | A2 | 9/1998 |
| WO | 2009033743 | A1 | 3/2009 |
| WO | WO 2011034605 | A2 | 3/2011 |
| WO | WO 2011069104 | A2 | 6/2011 |
| WO | WO 2011133886 | A2 | 10/2011 |
| WO | WO 2012064733 | A2 | 5/2012 |
| WO | WO 2012080359 | A2 | 6/2012 |
| WO | WO 2012088290 | A2 | 6/2012 |

(Continued)

OTHER PUBLICATIONS

Talaev, "The Mechanisms Controlling Migration of Myeloid Dendritic Cells and Langerhans Cells, " Immunology (2012) No. 2, pp. 104-112. Russian with English abstract.

Cheng et al., "TREM2-activating antibodies abrogate the negative pleiotropic effects of the Alzheimer's disease variant Trem2R47H on murine myeloid cell function," Journal of Biological Chemistry, 2018, vol. 293, No. 32, 12620-12633.

Schlepckow et al., "Alzheimer-associated TREM2 variant occurs at the ADAM cleavage site and affects shedding and phagocytic function," Embo Molecular Medicine, 2017, vol. 9, No. 10, 1356-1365.

Bouchon et al., "Cutting edge: inflammatory responses can be triggered by TREM-1, a novel receptor expressed on neutrophils and monocytes," Journal of Immunology, 2000, vol. 164, No. 10, pp. 4991-4995.

(Continued)

*Primary Examiner* — Mary Maille Lyons
(74) *Attorney, Agent, or Firm* — Han Gao

(57) ABSTRACT

The present invention provides antibodies that bind to and stabilize human Triggering Receptor Expressed on Myeloid cells 2 (TREM2) protein and methods of using these antibodies.

10 Claims, 30 Drawing Sheets

Specification includes a Sequence Listing.

(56) References Cited

FOREIGN PATENT DOCUMENTS

| | | | | |
|---|---|---|---|---|
| WO | WO 2012088302 A2 | 6/2012 | | |
| WO | WO 2012106587 A1 | 8/2012 | | |
| WO | WO 2013096291 A2 | 6/2013 | | |
| WO | WO 2013119964 A2 | 8/2013 | | |
| WO | WO 2013055958 A1 | 4/2014 | | |
| WO | WO 2014074942 A1 | 5/2014 | | |
| WO | WO-2016023019 A2 * | 2/2016 | ............. | A61P 25/28 |
| WO | WO 2016049641 A1 | 3/2016 | | |
| WO | WO 2016201388 A2 | 12/2016 | | |
| WO | 2017058866 A1 | 4/2017 | | |
| WO | 2017062672 A2 | 4/2017 | | |
| WO | 2018015573 A2 | 1/2018 | | |
| WO | 2018140831 A2 | 8/2018 | | |
| WO | 2018195506 A1 | 10/2018 | | |
| WO | WO 2019028292 A1 | 2/2019 | | |
| WO | WO 2019118513 A1 | 6/2019 | | |

OTHER PUBLICATIONS

Zhong et al., "DAP12 Stabilizes the C-terminal Fragment of the Triggering Receptor Expressed on Myeloid Cells-2 (TREM2) and Protects against LPS-induced Pro-inflammatory Response," Journal of Biological Chemistry, 2015, vol. 290, No. 25, pp. 15866-15877.

Wunderlich et al., "Sequential Proteolytic Processing of the Triggering Receptor Expressed on Myeloid Cells-2 (TREM2) Protein by Ectodomain Shedding and γ-Secretase-dependent Intramembranous Cleavage," Journal of Biological Chemistry, 2013, vol. 288, pp. 33027-22036.

Kleinberger et al., "TREM2 mutations impliated in neurodegeneration impair cell surface transport and phagocytosis," Science Translational Medicine, 2014, vol. 6,No. 243, pp. 243ra86.

Lue et al., "TREM2 Protein Expression Changes with Alzheimer's Disease Neurodegenerative Pathologies in Post-Mortem Temporal Cortices," Brain Pathology, 2015, vol. 25, No. 4, pp. 469-480.

Janeway et al., Immunobiology; the immune system in health and disease, Third Ed., New York: Garland Pub, 1997, pp. 2:19-2:20.

Gratuze et al., "New insights into the role of TREM2 in Alzheimer's disease," Molecular Neurodegeneration (2018) vol. 13, Article 66, 16 pages.

Jay et al., "TREM2 in Neurodegenerative Diseases," Molecular Neurodegeneration (2017) vol. 12, Article 56, 33 pages.

International Search Report for WO2020049580 dated Jan. 23, 2020.

Chen et al., (2013) "Triggering Receptor Expressed on Myeloid Cells-2 Protects against Polymicrobial Sepsis by Enhancing Bacterial Clearance" *American Journal of Respiratory and Critical Care Medicine*, 188(2):201-212.

Colonna et al., (2003) "TREMS in the Immune System and Beyond" *Nature Reviews Immunology*, 3:1-9.

Frank et al., (2008) "TREM2 is upregulated in amyloid plaque-associated microglia in aged APP23 transgenic mice" *GLIA*, 56:1438-1447.

De Haas et al., (2008) "Region-specific expression of immunoregulatory proteins on microglia in the healthy CNS" *GLIA*, 56:888-894.

Hickman et al., (2014) "TREM2 and the neuroimmunology of Alzheimer's disease" *Biochem Pharmacol*, 88(4):495-498.

Humphrey et al., (2006) "TREM2, a DAP12-associated receptor, regulates osteoclast differentiation and function" *American Society for Bone and Mineral Research*, 21(2):237-245.

Ito et al., (2012) "TREM2, triggering receptor expressed on myeloid cell 2 negatively regulates TLR responses in dendritic cells" *Eur. J. Immunol*, 42:176-185.

Jiang et al., (2014) "Upregulation of TREM2 ameliorates neuropathology and rescues spatial cognitive impairment in a transgenic mouse model of Alzheimer's disease" *Neuropsychopharmacology*, 39:2949-2962.

Paloneva et al., (2002) "Mutations in two genes encoding different subunits of a receptor signaling complex result in an identical disease phenotype" *Am J Hum Genet*, 71:656-662.

Peng et al., (2010) "TREM2- and DAP12-dependent activation of PI3K requires DAP10 and is inhibited by SHIP1" *Sci Signal*, 3(122):1-30.

Rayaprolu et al., (2013) "TREM2 in neurodegeneration: evidence for association of the p. R47H variant with frontotemporal dementia and Parkinson's disease" *Molecular Neurodegeneration*, 8(19):1-5.

R&D Systems "MAB17291 Product Datasheet" Retrieved from URL:https://www.rndsystems.com/products/human-mouse-trem2-antibody-237920_mab17291.

Satoh et al., (2011) "Immunohistochemical characterization of microglia in Nasu-Hakola disease brains" *Neuropathology*, 31:363-375.

Satoh et al., (2013) "A survey of TREM2 antibodies reveals neuronal but not microglial staining in formalin-fixed paraffin-embedded postmortem Alzheimer's brain tissues" *Alzheimer's Research and Therapy*, 5(30):1-3.

Sun et al., (2013) "TREM-2 promotes host resistance against Pseudomonas aeruginosa infection by suppressing corneal inflammation via a PI3K/Akt signaling pathway" *The Association for Research in Vision and Ophthalmology*, 54(5):3451-3462.

Takahashi et al., (2007) "TREM2-transduced myeloid precursors mediate nervous tissue debris clearance and facilitate recovery in an animal model of multiple sclerosis, " *PLoS Med*, 4(4):0675-0689.

* cited by examiner

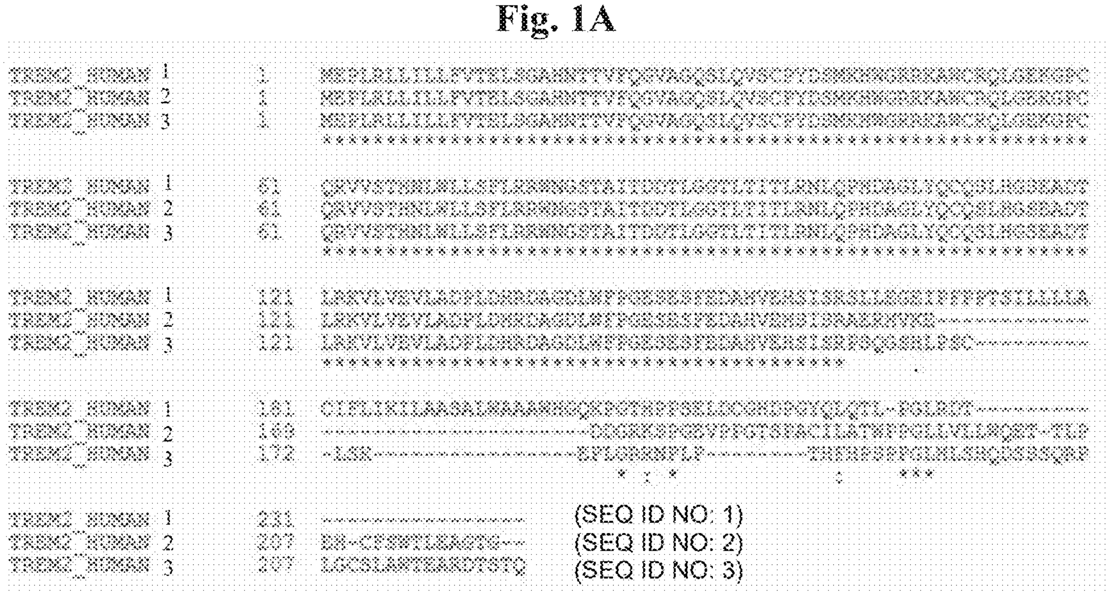

Fig. 1A

```
TREM2_HUMAN 1     1    MEPLRLLILLFVTELSGAHNTTVFQGVAGQSLQVSCPYDSMKHWGRRKAWCRQLGEKGPC
TREM2_HUMAN 2     1    MEPLRLLILLFVTELSGAHNTTVFQGVAGQSLQVSCPYDSMKHWGRRKAWCRQLGEKGPC
TREM2_HUMAN 3     1    MEPLRLLILLFVTELSGAHNTTVFQGVAGQSLQVSCPYDSMKHWGRRKAWCRQLGEKGPC
                       ************************************************************

TREM2_HUMAN 1     61   QRVVSTHNLWLLSFLRRWNGSTAITDDTLGGTLTITLRNLQPHDAGLYQCQSLHGSEADT
TREM2_HUMAN 2     61   QRVVSTHNLWLLSFLRRWNGSTAITDDTLGGTLTITLRNLQPHDAGLYQCQSLHGSEADT
TREM2_HUMAN 3     61   QRVVSTHNLWLLSFLRRWNGSTAITDDTLGGTLTITLRNLQPHDAGLYQCQSLHGSEADT
                       ************************************************************

TREM2_HUMAN 1     121  LRKVLVEVLADPLDHRDAGDLWFPGESESFEDAHVEHSISRSLLEGEIPFPPTSILLLLA
TREM2_HUMAN 2     121  LRKVLVEVLADPLDHRDAGDLWFPGESESFEDAHVEHSISRSLLEGEIPFPPTSILLLLA
TREM2_HUMAN 3     121  LRKVLVEVLADPLDHRDAGDLWFPGESESFEDAHVEHSISRPQQSRLPSC----------
                       *****************************************

TREM2_HUMAN 1     181  CIFLIKILAASALWAAAWHGQKPGTHPPSELDCGHDPGYQLQTL-PGLRDT---------
TREM2_HUMAN 2     169  ---------------------DDGKSPGSVPPGTSACLIATMFPGLLVLLRQET-TLP
TREM2_HUMAN 3     172  -LSR-------------------EPLQRNFLP---------THRPSPPGLRLSRQSSSQRP
                                                 *   *                  *  ***

TREM2_HUMAN 1     231  -------------------  (SEQ ID NO: 1)
TREM2_HUMAN 2     207  DR-CPSPTLEAGTG--     (SEQ ID NO: 2)
TREM2_HUMAN 3     207  LGCSLASTERDTSTQ      (SEQ ID NO: 3)
```

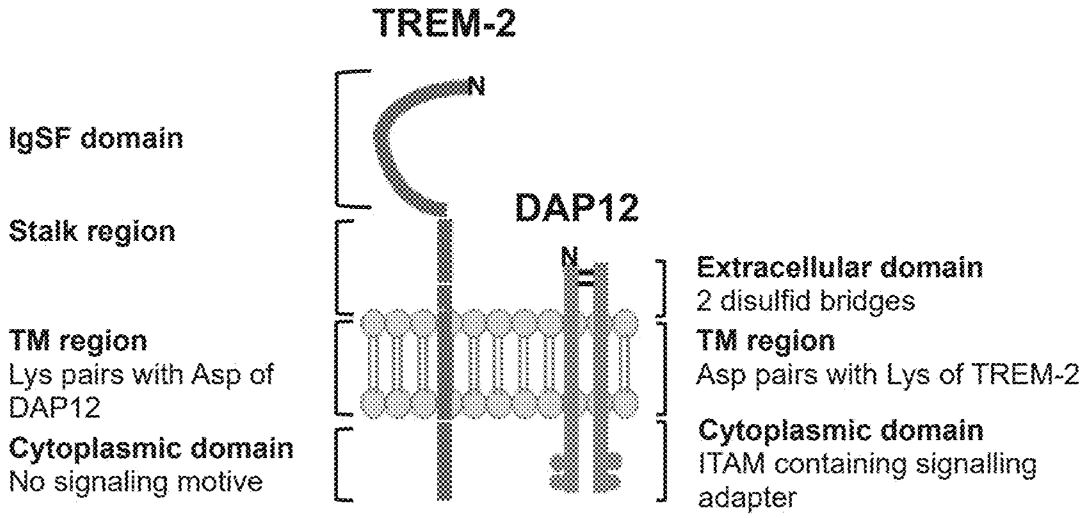

Fig. 1B

TREM-2

DAP12

IgSF domain

Stalk region

TM region
Lys pairs with Asp of DAP12

Cytoplasmic domain
No signaling motive

Extracellular domain
2 disulfid bridges

TM region
Asp pairs with Lys of TREM-2

Cytoplasmic domain
ITAM containing signalling adapter

Data are presented as mean +/- s.d. (N = 3).Statistical analysis done using Student t-test: *P < 0.05; P < 0.01; *P . 0.001.

Data are presented as mean +/- s.d. (N = 3).Statistical analysis done using Student t-test: *P < 0.05; P < 0.01; *P . 0.001.

Data are presented as mean +/- s.d. (N = 3). Statistical analysis done using Student t-test: *P < 0.05; P < 0.01; *P . 0.001.

Data are presented as mean +/- s.d. (N = 3).Statistical analysis done using Student t-test: *P < 0.05; P < 0.01; *P < 0.001,****P < 0.0001 .

Data are presented as mean +/- s.d. (N = 3).Statistical analysis done using Student t-test: *P < 0.05; P < 0.01; *P . 0.001.

TREM2 STABILIZING ANTIBODIES

CROSS REFERENCE TO RELATED APPLICATIONS

This application is a divisional of U.S. patent application Ser. No. 16/601,070, filed Oct. 14, 2019, now U.S. Pat. No. 11,492,402, which claims the benefit of U.S. Provisional Application No. 62/745,798, filed on Oct. 15, 2018, U.S. Provisional Application No. 62/835,289, filed Apr. 17, 2019, U.S. Provisional Application No. 62/890,665, filed Aug. 23, 2019, and U.S. Provisional Application No. 62/892,517, filed Aug. 27, 2019, each of which is hereby incorporated by reference in its entirety.

SEQUENCE LISTING

The instant application contains a Sequence Listing which has been submitted electronically in XML format and is hereby incorporated by reference in its entirety. Said XML copy, created on Sep. 21, 2022, is named N2067-720920_SL.xml and is 211,309 bytes in size.

TECHNICAL FIELD

The present invention provides antibodies that bind to and stabilize human Triggering Receptor Expressed on Myeloid cells 2 (TREM2) protein and methods of using these antibodies.

BACKGROUND

Triggering receptors expressed on myeloid cells or "TREMs" are a group of transmembrane glycoproteins that are expressed on different types of myeloid cells, such as macrophage, dendritic cell, osteoclast, microglia, mast cells, monocytes, lung epithelial cells, Langerhans cells of skin, Kupffer cells, and neutrophils (Takaki, R. et al., Immunol. Rev., 2006, 214: 118-29). TREMs have an immunoglobulin (Ig)-type fold in their extracellular domain and thus belong to the immunoglobulin superfamily (IgSF). TREM receptors contain a short intracellular domain, but lack docking motifs for signaling mediators and require adapter proteins, such as DAP12 (DNAX-activating protein of 12 kDa) for cell activation. Two members of TREMs have been reported: TREM1 and TREM2, both of which play an important role in immune and inflammatory responses. The genes encoding human TREMs map to chromosome 6p21.1, bearing a cluster of genes encoding TREM1, TREM2, TREM3, TREM4 and TREM5, as well as TREM-like genes.

TREM2 is a glycoprotein of about 40 kDa, which is reduced to 26 kDa after N-deglycosylation. The entire TREM2 protein consists of a leading signal peptide (amino acids 1-18), a single V-type IgSF extracellular region, (amino acids 19-132), a stalk region (amino acids 133-172), a positively-charged transmembrane domain (amino acids 173-197), and a cytosolic tail (amino acids 198-230), (Kober et al., Elife 5 (2016); Kober et al., J Mol. Biol. 429 (2017) 1607-1629.). The extracellular region, encoded by exon 2, is composed of a single type V IgSF domain, containing three potential N-glycosylation sites. The putative transmembrane region contains a charged lysine residue. The cytoplasmic tail of TREM2 lacks signaling motifs and is thought to signal through the signaling adaptor molecule DAP12/TRYROBP.

TREM2 physically associates with DAP12, which acts as a signaling adaptor protein for TREM2 and a number of other cell surface receptors. The cytoplasmic domain of DAP12 contains an immunoreceptor tyrosine activation motif (ITAM) (Wunderlich, *J. Biol. Chem.* 288, 33027-33036, 2013). After activation of the interacting receptor, DAP12 undergoes phosphorylation at conserved ITAM tyrosine residues by Src kinases. Subsequent recruitment and activation of the Syk protein kinase triggers downstream signaling pathways, including the activation of mitogen-activated protein kinase (MAPK), PI3K, NFκB and phospholipase Cγ (PLCγ).

TREM2 can be activated by lipopolysaccharides (LPS), heat shock protein 60, neuritic debris, bacteria, apolipoprotein E and a broad array of anionic and zwitterionic lipids, e.g. phosphatidic acid (PA), phosphatidylglycerol (PG), phosphatidylserine (PS), phosphatidylinositol (PI), phosphatidylcholine (PC), cardiolipin and sphingomyelin. TREM2 activation increases phagocytic capacity of microglia and macrophages, reduces the release of proinflammatory cytokines and limits TLR signaling. TREM2 sustains microglial survival by synergizing with CSF-1 receptor signaling. Furthermore, TREM2 interacts with Plexin-A1 regulating cellular adhesion and motility. TREM2 is also enriched at those microglia cell surface regions which contact AR plaques or neuronal debris (Yuan et al., Neuron 90 (2016) 724-739). Some of the ligands that are sensed by TREM2 in this environment have recently been identified, for example phospholipids and myelin lipids (Poliani et al., *J. Clin. Invest.* 125 (2015): 2161-2170) as well as ApoE (Atagi et al., *J. Biol. Chem.* 290 (2015): 26043-26050; Bailey et al., *J Biol. Chem.* 290 (2015): 26033-26042). Other ligands could be AR and plaque associated neuronal debris since TREM2 contributes to the uptake of Aβ into microglia (Xiang et al., *EMBO Mol. Med.* 8 (2016): 992-1004). TREM2 has also been shown to play a role in the clearance of apoptotic cells (Takahashi et al., *J. Exp. Med.* 201 (2005), 647-657), myelin debris (Poliani et al., *J. Clin. Invest.* 125 (2015): 2161-2170) and bacterial beads (Cen et al., *Am. J Respir.* 188 (2013) 201-212). TREM2 signaling facilitates degradation of ingested prey and is crucial for lipid metabolism, myelin uptake and intracellular breakdown.

TREM2 undergoes sequential proteolytic processing by ectodomain shedding and intramembrane proteolysis (Wunderlich, J Biol. Chem. 288, 33027-33036, 2013). During ectodomain shedding, the ectodomain of TREM2 is released by proteases such as members of the ADAM (a disintegrin and metalloproteinase domain containing protein) or BACE (beta-site APP cleaving enzyme) family (Kleinberger, *Sci. Transl. Med.* 2014; 6(243):243ra86).

After removal of the ectodomain, the remaining membrane-retained fragment is further processed by γ-secretase mediated intramembranous proteolysis. Soluble fragments of TREM2 (sTREM2) produced by ectodomain shedding have been observed in supernatants of dendritic cell cultures as well as in plasma and CSF (Cerebrospinal fluid) samples from patients with noninflammatory neurological diseases and multiple sclerosis (Kleinberger, 2014). The shed ectodomain of TREM2, i.e., sTREM2, in human CSF has been assessed as a potential Alzheimer's disease (AD) biomarker and has been shown to be increased during ageing in general (Suarez-Calvet, *EMBO Mol. Med.* 8, 466-476, 2016). Detailed analysis during the course of AD revealed that sTREM2 increases early in AD before clinical symptoms appear, peaks in MCI-AD, and stays elevated but at lower levels compared to the MCI-AD stage in AD dementia (Suarez-Calvet, 2016).

Increase of TREM2 expression at peak of disease drives resolution (e.g. peritonitis, wound healing) (Tumbull, 2006; Gawish, 2015). Under chronic inflammatory conditions like in neuroinflammation, TREM2 is constantly shed and cannot exert its signalling function in microglia and macrophages. Hence, stabilizing and/or preventing of shedding of TREM2 at the cell surface will restore functional, signaling-capable TREM2 expression in microglia and macrophages.

Human genetic studies indicate that loss of surface TREM2 rather than lack of sTREM2 drives disease risk. For example, an amino acid mutation at position 47 from R to H in the TREM2 protein, e.g., in SEQ ID NO: 1, causes slightly reduced cell surface expression (Kleinberger 2014), and reduced ligand binding capacity of TREM2 (Wang 2015, Atagi 2015, Bailey 2015). The amino acid mutation T66M in TREM2 results in lack of expression of TREM2 at the cell surface (Kleinberger 2014) and hence no soluble TREM2 is generated. A mutation at the cleavage site of TREM2: H157Y enhances the expression of sTREM2 and reduces full length membrane bound TREM2, and is associated with an increased AD risk (Thornton 2017, Schlepckow 2017). Therefore these genetic studies suggest that stabilizing TREM2 at the cell surface is desirable to both reduce sTREM2 and increase plasma membrane-bound TREM2.

Haass et al. (WO18015573) generated antibodies binding to a 10-amino acid peptide (AHVEHSISRS SEQ ID NO: 132) spanning amino acids 152-161 located in the stalk region of TREM2 and inhibiting TREM2 cleavage. Such antibodies prevent cleavage of TREM2 by directly binding and thereby blocking the cleavage site. Schwabe et al. (WO17062672) disclose antibodies binding to TREM2. However, no stabilizing effect is indicated for any of the disclosed antibodies. In contrast, for some of the antibodies described in WO17062672, a destabilizing effect is reported (Example 15).

Therefore there is a need for identifying and developing hTREM2 antibodies which would stabilize TREM2 and activate and/or facilitate or TREM2 related functions, which have good developability characteristics and which are suitable for the treatment of patients suffering from a neurodegenerative disease for which TREM2 stabilization is beneficial.

SUMMARY OF THE INVENTION

The published literature has targeted the stalk region of TREM2 for generating antibodies which stabilize TREM2 as the cleavage site for ADAM17 resides within the stalk region. Indeed, it is expected that a large molecule such as an antibody (or a binding fragment thereof) would sterically hinder the access of a sheddase to the relatively small region of the stalk (aminoacids 133-172). Therefore, it is unsurprising that previous efforts to generate stabilizing antibodies to TREM2 have targeted the stalk region of TREM2. The IgSF region of TREM2 (amino acids 19-132 of any one of SEQ ID NO: 1, 2 or 3, is located further away from the cleavage site (H157) and is part of the ectodomain. Thus far, the IgSF region has not been considered as a potential target for antibodies which would stabilize TREM2 since antibodies against the IgSF region of TREM2 would not be expected to sterically hinder a sheddase from accessing the TREM2 cleavage site.

Surprisingly, we found that antibodies as disclosed herein, bind to the IgSF region and are able to effectively stabilize TREM2 on the cell surface. We have also shown that such antibodies are able to show functional downstream effects such as facilitating TREM2-dependent phagocytosis in human M2A macrophages. Furthermore, such antibodies may also enhance TREM2-dependent functions in vivo, e.g., by increasing phagocytic capacity of microglia or macrophages in the brain.

Accordingly, provided herein are antibodies or antigen-binding fragments thereof, e.g., monoclonal antibodies or antigen-binding fragments thereof, that specifically bind to the IgSF domain of human TREM2 (hTREM2) and stabilize the hTREM2 protein. Such an antibody is referred to herein as an "hTREM2 antibody or an antigen-binding fragment thereof". These hTREM2 antibodies or antigen-binding fragments thereof can (i) reduce or inhibit the shedding of the TREM2 ectodomain; (ii) stabilize the TREM2 protein on the cell surface; and/or (iii) maintain or increase TREM2 functions, such as binding to its cognate ligands, intracellular signaling, increasing phagocytosis, facilitating degradation of phagocytic material, and promote TREM2-dependent downstream regulatory functions. Since dysfunctional TREM2 or absent surface TREM2 is associated with human neuroinflammatory and neurodegenerative pathologies, the hTREM2 antibody or an antigen-binding fragment thereof described herein can be used to treat, prevent, or diagnose a neuroinflammatory or neurodegenerative disease such as Alzheimer's disease, frontotemporal dementia, Parkinson's disease, amyotrophic lateral sclerosis, Nasu-Hakola disease, multiple sclerosis, amyotrophic lateral sclerosis (ALS), anti-NMDA receptor encephalitis, autism, brain lupus (NP-SLE), chemo-induced peripheral neuropathy (CIPN), postherpetic neuralgia, chronic inflammatory demyelinating polyneuropathy (CIDP), epilepsy, Guillain-Barre Syndrome (GBS), inclusion body myositis, lysosomal storage diseases, e.g., sphingomyelinlipidose (Niemann-Pick C) and mucopolysaccharidose II/IIIB, metachromatic leukodystrophy, multifocal motor neuropathy, Myasthenia Gravis, Neuro-Behcet's Disease, neuromyelitis optica (NMO), optic neuritis, polymyositis, dermatomyositis, Rasmussen's encephalitis, Rett's Syndrome, stroke, transverse myelitis, traumatic brain injury, spinal cord injury, viral encephalitis, or bacterial meningitis. The hTREM2 antibodies or an antigen-binding fragment thereof described herein are also suitable for treating, preventing or diagnosing autoimmune, inflammatory, or malignant disorders mediated by or associated with extensive proteolytic cleavage of TREM2 or cells expressing aberrant or mutated variants of the TREM2 receptor. In some preferred embodiments, the hTREM2 antibody or an antigen-binding fragment thereof described herein can be used to treat, prevent, or diagnose a disease selected from Alzheimer's disease, frontotemporal dementia, Parkinson's disease, amyotrophic lateral sclerosis, or Nasu-Hakola disease. Also provided herein are methods of diagnosing and/or treating TREM2-associated diseases using the TREM2-binding antibodies or antigen-binding fragments disclosed herein.

In one aspect, provided herein are antibodies or antigen-binding fragments thereof that specifically bind to the IgSF domain of TREM2 protein and stabilize the TREM2 protein. In some preferred embodiments, these antibodies or antigen-binding fragments thereof stabilize the TREM2 protein on the cell surface of a TREM2-expressing cell such as macrophage, dendritic cell, osteoclast, microglia, mast cells, monocytes, lung epithelial cells, Langerhans cells of skin, Kupffer cells, neutrophils or hepatocarcinoma cells. In some embodiments, these antibodies or antigen-binding fragments thereof reduce proteolytic shedding of the ectodomain of the TREM2 protein.

In some embodiments, provided herein are antibodies or antigen-binding fragments thereof that specifically bind to the IgSF domain of human TREM2. For example, such antibodies or antigen-binding fragments thereof bind to the IgSF domain of human TREM2 that comprises the amino acid residues 19 to 132 of SEQ ID NO: 1, the amino acid residues 19 to 132 of SEQ ID NO: 2, or the amino acid residues 19 to 132 of SEQ ID NO: 3. In some embodiments, the TREM2 antibodies are human or humanized antibodies. In some embodiments, the antigen binding fragment is a Fab, $F(ab')_2$, Fv fragments, scFv, minibody, or a diabody.

In some embodiments, the TREM2 antibody is a bispecific antibody. In some embodiments, the bispecific antibody specifically binds to human TREM2 and DAP12.

In some embodiments, the TREM2 antibody comprises an Fc region. In some embodiments, the Fc region is a modified IgG1 Fc region that has one or more mutations and has reduced antibody-dependent cellular cytotoxicity (ADCC) or complement-dependent cytotoxicity (CDC) activity when compared to the parental antibody. In some embodiments, the Fc region is selected from an IgG2 Fc region, an IgG4 Fc region, or an IgG2/IgG4 hybrid Fc region.

In some embodiments, the hTREM2 antibodies or antigen binding fragments thereof are monoclonal. Provided herein are nucleic acids encoding such monoclonal antibodies or antigen binding fragments thereof, and vectors and host cells comprising nucleic acid encoding such monoclonal antibodies or antigen binding fragments thereof.

In another aspect, provided herein are pharmaceutical compositions comprising one or more of the TREM2 antibodies or antigen-binding fragments thereof described herein, or nucleic acid encoding such antibodies or antigen-binding fragments, or cells comprising such nucleic acids, and a pharmaceutically acceptable carrier.

In another aspect, provided herein are methods of treating a disease associated with TREM2 loss of function in a subject in need thereof by administering to the subject a therapeutically effective amount of any of the TREM2 antibodies or antigen-binding fragments thereof described herein. Such methods can include one or more of the following steps: (1) assaying the cell surface TREM2 level in a sample obtained from a subject; (2) selecting a subject whose cell surface TREM2 level is lower than a reference level, wherein the reference level is the cell surface TREM2 level in a sample obtained from a healthy subject; and (3) administering to the subject a therapeutically effective amount of an antibody or antigen-binding fragment thereof that specifically binds to the IgSF domain of TREM2 protein and stabilizes the TREM2 protein. In some embodiments, such methods further include administering a second agent to the subject. The cell surface TREM2 level in a sample can be determined by an assay selected from flow cytometry, immunohistochemistry, Western blotting, immunofluorescent assay, radioimmunoassay (RIA), enzyme-linked immunosorbent assay (ELISA), homogeneous time resolved fluorescence (HTRF), or positron emission tomography (PET). In some embodiments, the sample comprises cerebrospinal fluid and its cellular components. In some embodiments, the disease associated with TREM2 loss of function is a neuroinflammatory or neurodegenerative disease such as Alzheimer's disease, frontotemporal dementia, Parkinson's disease, amyotrophic lateral sclerosis, Nasu-Hakola disease, multiple sclerosis, amyotrophic lateral sclerosis (ALS), anti-NMDA receptor encephalitis, autism, brain lupus (NP-SLE), chemo-induced peripheral neuropathy (CIPN), postherpetic neuralgia, chronic inflammatory demyelinating polyneuropathy (CIDP), epilepsy, Guillain-Barre Syndrome (GBS), inclusion body myositis, lysosomal storage diseases, e.g., sphingomyelinlipidose (Niemann-Pick C) and mucopolysaccharidose II/IIIB, metachromatic leukodystrophy, multifocal motor neuropathy, Myasthenia Gravis, Neuro-Behcet's Disease, neuromyelitis optica (NMO), optic neuritis, polymyositis, dermatomyositis, Rasmussen's encephalitis, Rett's Syndrome, stroke, transverse myelitis, traumatic brain injury, spinal cord injury, viral encephalitis, or bacterial meningitis. In some preferred embodiments, the disease associated with TREM2 loss of function is a neurodegenerative disease selected from Alzheimer's disease, frontotemporal dementia, Parkinson's disease, amyotrophic lateral sclerosis, or Nasu-Hakola disease. In a further preferred embodiment, the disease is Alzheimer's disease. In some embodiments, the TREM2 antibodies or antigen-binding fragments thereof stabilize the TREM2 protein on the cell surface of a TREM2-expressing cell selected from a macrophage, dendritic cell, osteoclast, microglia, mast cells, monocytes, lung epithelial cells, Langerhans cells of skin, Kupffer cells, neutrophils or hepatocarcinoma cells. In some embodiments, the TREM2 antibody or antigen-binding fragment thereof is administered to the subject through an oral, intravenous, intracranial, intrathecal, subcutaneous, or intranasal route.

In another aspect, provided herein are TREM2 antibodies or antigen-binding fragments thereof for use in the treatment of a disease associated with TREM2 loss of function. In some preferred embodiments, these antibodies or antigen-binding fragments thereof specifically bind to the IgSF domain of TREM2 protein (i.e. the amino acid residues 19 to 132 of SEQ ID NO: 1, the amino acid residues 19 to 132 of SEQ ID NO: 2, or the amino acid residues 19 to 132 of SEQ ID NO: 3) and stabilize the TREM2 protein. In some preferred embodiments, the antibodies or antigen-binding fragments thereof stabilize the TREM2 protein on the cell surface of a TREM2 expressing cell selected from a macrophage, dendritic cell, osteoclast, microglia, mast cells, monocytes, lung epithelial cells, Langerhans cells of skin, Kupffer cells, neutrophils or hepatocarcinoma cells. In some embodiments, the disease associated with TREM2 loss of function is a neuroinflammatory or neurodegenerative disease such as Alzheimer's disease, frontotemporal dementia, Parkinson's disease, amyotrophic lateral sclerosis, Nasu-Hakola disease, multiple sclerosis, amyotrophic lateral sclerosis (ALS), anti-NMDA receptor encephalitis, autism, brain lupus (NP-SLE), chemo-induced peripheral neuropathy (CIPN), postherpetic neuralgia, chronic inflammatory demyelinating polyneuropathy (CIDP), epilepsy, Guillain-Barre Syndrome (GBS), inclusion body myositis, lysosomal storage diseases, e.g., sphingomyelinlipidose (Niemann-Pick C) and mucopolysaccharidose II/IIIB, metachromatic leukodystrophy, multifocal motor neuropathy, Myasthenia Gravis, Neuro-Behcet's Disease, neuromyelitis optica (NMO), optic neuritis, polymyositis, dermatomyositis, Rasmussen's encephalitis, Rett's Syndrome, stroke, transverse myelitis, traumatic brain injury, spinal cord injury, viral encephalitis, or bacterial meningitis. In some preferred embodiments, the disease associated with TREM2 loss of function is a neurodegenerative disease selected from Alzheimer's disease, frontotemporal dementia, Parkinson's disease, amyotrophic lateral sclerosis, or Nasu-Hakola disease. In a further preferred embodiment, the disease is Alzheimer's disease. In some embodiments, the TREM2 antibodies or antigen-binding fragments thereof stabilize the TREM2 protein on the cell surface of a TREM2-expressing cell selected from a macrophage, dendritic cell, osteoclast, microglia, mast cells, monocytes, lung epithelial cells, Langerhans cells of skin, Kupffer cells, neutrophils or hepatocarcinoma cells.

BRIEF DESCRIPTION OF THE DRAWINGS

FIG. 1A shows exemplary alignment of the amino acid sequences of human TREM2 isoform 1 (SEQ ID NO: 1), isoform 2 (SEQ ID NO: 2), and isoform 3 (SEQ ID NO: 3).

FIG. 1B illustrates the structure of TREM2 and its interaction with the signaling adaptor protein DAP12. Mature TREM2 includes a single immunoglobulin (IgSF) domain, a stalk region, a transmembrane (TM) domain, and a cytoplasmic domain.

(FIG. 9B) indicates quantification of pSyk under different conditions in correlation to total Syk of the western blot shown in (FIG. 9A).

FIG. 19), comparing MOR042596 (crystal structure) and MOR044698 (homology model). TREM2 residues within 5 Å of the Fabs are shown as sticks, and residues proximal to LCDR3 (D39-K42) are marked. The heavy chain (dark grey, top right) as well as LCDR1 and LCDR2 of the light chain (light grey, top left) are identical for both Fabs. LCDR3 has several shared key residues (positions 90, 93, 95) keeping the backbone loop conformation of LCDR3 the same for both Fabs. There are changes in positions 89, 91, 92, 94, 96 and there is one additional insertion in MOR044698 (S95a). The overall epitope is conserved between MOR042596 and MOR044698.

DETAILED DESCRIPTION

Figure 2:
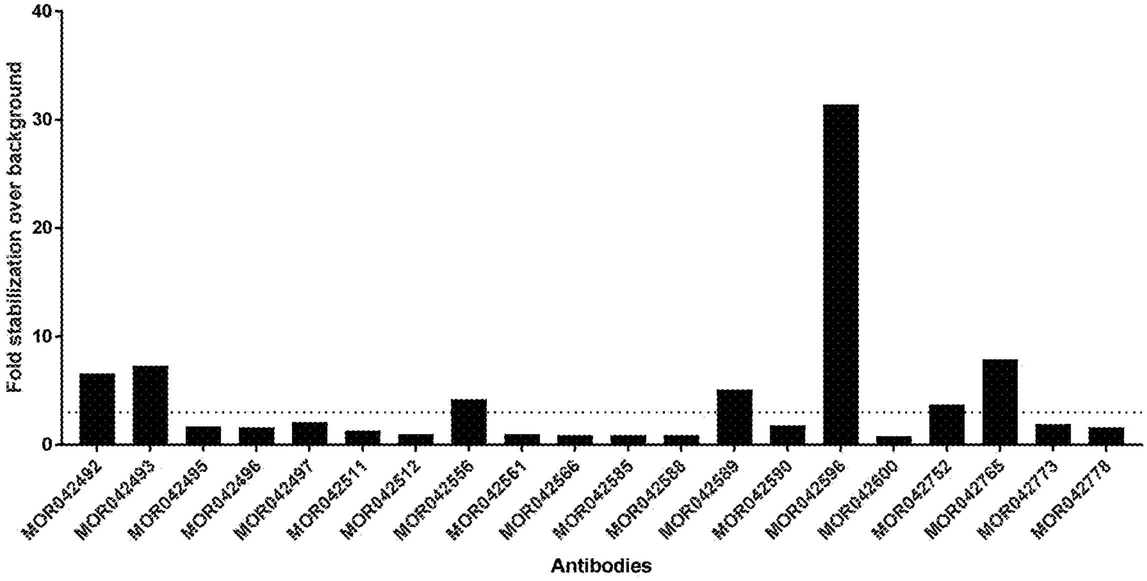
FIG. 2 shows stabilization of TREM2 in CHO-hDAP12-hTREM2 cells by antibody treatment.

Provided herein are antibodies and antigen-binding fragments thereof that specifically bind to the extracellular domain of human TREM2 and stabilize the TREM2 protein. Those TREM2-antibodies and antigen-binding fragments thereof can reduce or inhibit the shedding of the TREM2 ectodomain; can stabilize the TREM2 protein on the cell surface; and can optionally maintain or increase TREM2 functions, such as binding to its cognate ligands, intracellular signaling, increasing phagocytosis, and facilitating degradation of phagocytic material. Since dysfunctional TREM2 or absent surface TREM2 is associated with human neuroinflammatory and neurodegenerative pathologies, the TREM2-stabilizing antibodies and antigen-binding fragments thereof described herein can be used to treat, prevent, or diagnose neuroinflammatory or neurodegenerative disease such as Alzheimer's disease, frontotemporal dementia, Parkinson's disease, amyotrophic lateral sclerosis, Nasu-Hakola disease, multiple sclerosis, amyotrophic lateral sclerosis (ALS), anti-NMDA receptor encephalitis, autism, brain lupus (NP-SLE), chemo-induced peripheral neuropathy (CIPN), postherpetic neuralgia, chronic inflammatory demyelinating polyneuropathy (CIDP), epilepsy, Guillain-Barre Syndrome (GBS), inclusion body myositis, lysosomal storage diseases, e.g., sphingomyelinlipidose (Niemann-Pick C) and mucopolysaccharidose II/IIIB, metachromatic leukodystrophy, multifocal motor neuropathy, Myasthenia Gravis, Neuro-Behcet's Disease, neuromyelitis optica (NMO), optic neuritis, polymyositis, dermatomyositis, Rasmussen's encephalitis, Rett's Syndrome, stroke, transverse myelitis, traumatic brain injury, spinal cord injury, viral encephalitis, or bacterial meningitis. The TREM2-binding antibodies and antigen-binding fragments thereof described herein are also suitable for treating, preventing or diagnosing autoimmune, inflammatory, or malignant disorders mediated by or associated with extensive proteolytic cleavage of TREM2 or cells expressing aberrant or mutated variants of the TREM2 receptor. In some preferred embodiments, the hTREM2 antibody or an antigen-binding fragment thereof described herein can be used to treat, prevent, or diagnose a disease selected from Alzheimer's disease, frontotemporal dementia, Parkinson's disease, amyotrophic lateral sclerosis, or Nasu-Hakola disease. Also provided herein are methods of diagnosing and/or treating TREM2 associated diseases using the TREM2-binding antibodies and antigen-binding fragments thereof disclosed herein.

TREM2 mediates nonphlogistic phagocytosis of bacteria and dying cells and dampens inflammatory responses. Homozygous loss of function of TREM2 causes Nasu-Hakola disease (polycystic lipomembranous osteodysplasia with sclerosing leukoencephalopathy, "PLOSL"), or frontotemporal dementia (FTD)-like syndrome, diseases characterized by bone cysts, neuroinflammation, progressive neurodegeneration and presenile dementia. A heterozygous loss of function mutation R47H of TREM2 is also an important risk factor for late-onset Alzheimer's disease (AD), with an effect size that is similar to that of the apolipoprotein E ε4 allele. TREM2 is expressed in the microglia found in the white matter, hippocampus and neocortex, which is partly consistent with the pathological features reported in AD brains, supporting the possible involvement of TREM2 in AD pathogenesis. Genetic screenings have now also identified heterozygous missense mutations in TREM2 as risk factors for Parkinson's disease (PD), amyotrophic lateral sclerosis (ALS), and fronto-temporal dementia (FTD), in addition to AD (Kleinberger, Sci Transl Med. 2014 Jul. 2; 6(243):243ra86). Thus, functional TREM2 is required to protect against ageing-related neuroinflammatory and neurodegenerative diseases that cause severe cognitive impairment and dementia.

Due to alternative splicing, three TREM2 isoforms are present in the human, with the isoform 1 being the longest isoform. Alignment of the amino acid sequences of human TREM2 isoform 1 (SEQ ID NO: 1), human TREM2 isoform 2 (SEQ ID NO: 2), and human TREM2 isoform 3 (SEQ ID NO: 3) is presented in FIG. 1A. FIG. 1B illustrates the structure of TREM2 and its interaction with the signaling adaptor protein DAP12.

Definitions

As used in the specification and claims, the singular form "a", "an" and "the" include plural references unless the context clearly dictates otherwise. For example, the term "a cell" includes a plurality of cells, including mixtures thereof.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about." The term "about" in relation to a numerical value X means, for example, X±15%, including all the values within this range. It also is to be understood, although not always explicitly stated, that the reagents described herein are merely examples and that equivalents of such are known in the art.

Throughout this specification and the claims which follow, unless the context requires otherwise, the word "comprise", and variations such as "comprises" and "comprising", are used herein in their open-ended and non-limiting sense unless otherwise noted.

When used herein "consisting of" excludes any element, step, or ingredient not specified in the aspect, embodiment and/or claim element. When used herein, "consisting essentially of" does not exclude materials or steps that do not materially affect the basic and novel characteristics of the aspect, embodiment and/or claim.

As used herein, "TREM2" (also known as "triggering receptor expressed on myeloid cells 2", TREM2, TREM2a, TREM2b, or TREM2c) refers to a transmembrane glycoprotein that belongs to the immunoglobulin superfamily (IgSF). The entire TREM2 protein (SEQ ID NO: 1) consists of a leading signal peptide (amino acids 1-18), a single V-type IgSF extracellular region (amino acids 19-132), a stalk region (amino acids 133-172), a positively-charged transmembrane domain (amino acids 173-197), and a cytosolic tail (amino acids 198-230) (Feuerbach et al., Neurosci. Lett. 660 (2017): 109-114). The human TREM2 gene is mapped to chromosomal location 6p21.1, and the genomic sequence of TREM2 gene can be found in GenBank (Gene ID: 54209). Due to alternative splicing, three TREM2 isoforms are present in the human (protein sequences available in ENSEMBL under IDs ENSP00000362205, ENSP00000342651, and ENSP00000362214). The term "TREM2" is used to refer collectively to all isoforms of TREM2. The protein and mRNA sequences for the longest human TREM2 isoform are: Triggering receptor expressed on myeloid cells 2 precursor isoform 1 precursor [*Homo sapiens*](NP_061838.1)

```
                                          (SEQ ID NO: 1)
MEPLRLLILLFVTELSGAHNTTVFQGVAGQSLQVSCPYDSMKHWGRRKAW

CRQLGEKGPCQRVVSTHNLWLLSFLRRWNGSTAITDDTLGGTLTITLRNL

QPHDAGLYQCQSLHGSEADTLRKVLVEVLADPLDHRDAGDLWFPGESESF

EDAHVEHSISRSLLEGEIPFPPTSILLLLACIFLIKILAASALWAAAWHG

QKPGTHPPSELDCGHDPGYQLQTLPGLRDT
```

*Homo sapiens* triggering receptor expressed on myeloid cells 2 (TREM2), transcript variant 1, mRNA (NCBI Reference Sequence: NM 018965.3)

```
                                        (SEQ ID NO: 133)
   gggcagcgcc tgacatgcct gatcctctct tttctgcagt

   tcaagggaaa gacgagatct tgcacaaggc actctgcttc

   tgcccttggc tggggaaggg tggcatggag cctctccggc

   tgctcatctt actctttgtc acagagctgt ccggagccca

   caacaccaca gtgttccagg gcgtggcggg ccagtccctg

   caggtgtctt gcccctatga ctccatgaag cactggggga

   ggcgcaaggc ctggtgccgc cagctgggag agaagggccc

   atgccagcgt gtggtcagca cgcacaactt gtggctgctg

   tccttcctga ggaggtggaa tgggagcaca gccatcacag

   acgataccct gggtggcact ctcaccatta cgctgcggaa

   tctacaaccc catgatgcgg gtctctacca gtgccagagc

   ctccatggca gtgaggctga caccctcagg aaggtcctgg

   tggaggtgct ggcagacccc ctggatcacc gggatgctgg

   agatctctgg ttccccgggg agtctgagag cttcgaggat
```

-continued

```
gcccatgtgg agcacagcat ctccaggagc ctcttggaag

gagaaatccc cttcccaccc acttccatcc ttctcctcct

ggcctgcatc tttctcatca agattctagc agccagcgcc

ctctgggctg cagcctggca tggacagaag ccagggacac

atccacccag tgaactggac tgtggccatg acccagggta

tcagctccaa actctgccag ggctgagaga cacgtgaagg

aagatgatgg gaggaaaagc ccaggagaag tcccaccagg

gaccagccca gcctgcatac ttgccacttg gccaccagga

ctccttgttc tgctctggca agagactact ctgcctgaac

actgcttctc ctggaccctg gaagcaggga ctggttgagg

gagtggggag gtggtaagaa cacctgacaa cttctgaata

ttggacattt taaacactta caaataaatc caagactgtc

atatttagct ggataaaaaa aaaaaaaaaa aaaaaa
```

The amino acid sequences of human TREM2 isoform 2 (SEQ ID NO: 2) and isoform 3 (SEQ ID NO: 3) are shown in FIG. 1A. As used herein, human TREM2 protein also encompasses proteins that have over its full length at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity with any of SEQ ID No: 1, 2, or 3, wherein such proteins still have the ligand binding, intracellular signaling, facilitating phagocytosis and degradation of phagocytic material, and other regulatory function of TREM2. The sequences of murine, cynomolgus (cyno), and other animal TREM2 proteins are known in the art (for example, NP_112544.1 and NP_001259007.1 for murine TREM2 protein).

The term "extracellular domain" refers to the portion of a transmembrane protein that is exposed on the extracellular side of a lipid bilayer of a cell. Methods for determining the ectodomain of a protein are known in the art (Singer (1990); High et al. (1993), and McVector software, Oxford Molecular). For example, the extracellular domain of human TREM2 protein can include the amino acid residues 19 to 172 of SEQ ID NO: 1.

The term "ectodomain" of TREM2 refers to a portion of the extracellular domain of TREM2 that is released after sheddase cleavage. Cleavage site is reported to be between amino acid H157 and S158 (Feuerbach et al., Neurosci. Lett. 660 (2017): 109-114). Therefore, the ectodomain of hTREM2 will consist of the amino acids 19-157 of any one of SEQ ID NOs: 1, 2, or 3.

The term "IgSF domain" refers to a part of the extracellular domain of TREM2 containing an immunoglobulin (Ig)-type fold and thus belonging to the immunoglobulin superfamily. In human, for example, the IgSF domain consists of the amino acid residues 19 to 132 of any one of SEQ ID NOs: 1, 2 and 3.

The term "stalk region" of TREM2 refers to a portion of the extracellular domain of TREM2 that connects the V-type immunoglobulin (IgSF) domain and the transmembrane domain. For example, the stalk region of human TREM2 isoform 1 protein can include an amino acids 133-172 of SEQ ID NO: 1.

The term "transmembrane domain" refers to the portion of a transmembrane protein that spans the lipid bilayer of a cell. Methods for determining the transmembrane domain of a protein are known in the art (Elofsson et al., Annu. Rev. Biochem. 76 (2007):125-140; Bernsel et al., Protein Science 14 (2005):1723-1728).

The terms "cytoplasmic domain" and "cytoplasmic tail" are used interchangeably and refer to the portion of a transmembrane protein that is on the cytoplasmic side of the lipid bilayer of a cell. Methods for determining the cytoplasmic tail of a protein are known in the art (Elofsson et al. (2007) and Bernsel et al. (2005)).

The term "stabilize" as used herein refers to the maintenance, restoration or increase of TREM2 cell surface level in a TREM2-expressing cell, e.g., to the TREM2 level in a corresponding TREM2-expressing cell in a healthy subject without inflammatory or neurodegenerative disease. This may be accomplished, for example, by reducing or inhibiting the shedding of TREM2 ectodomain, or by increasing cell surface expression of TREM2. TREM2 cell surface level can be assessed by flow cytometry/FACS or by TREM2 cell surface immunoprecipitation or by the reduction of soluble TREM2 over time. TREM2 cell surface expression can also be detected by enzyme-linked immunosorbent assay (ELISA), radioimmunoassay (RIA), bioassays (e.g., increase in phagocytosis), Western Blot assay, flow cytometry, immunohistochemistry, immunofluorescent assay, homogeneous time resolved fluorescence (HTRF), or positron emission tomography (PET).

The term "activate" herein refers to the initiation or preservation of downstream signaling of TREM2 expressed at the cell surface, e.g., in TREM2-expressing cells in healthy subjects or individuals with inflammatory or neurodegenerative diseases where proper TREM2 dependent activities are impaired. This may be accomplished but is not limited to phosphorylation of TREM2 associated DAP12 or DAP10, leading via different intracellular signaling cascades to enhancement of Syk phosphorylation, phagocytosis, increased target-directed cellular motility (chemotaxis), increased cellular survival, modulating cytokine or chemokine release of cells expressing TREM2, increasing degradation of intracellular phagocytosed material, or changes in gene expression. Increased TREM2 dependent DAP12 or Syk phosphorylation can be assessed by Western blot, ELISA or flow cytometry/FACS. Directed motility of cells, e.g., chemotaxis can be assessed by bioassays. Modulation of cytokine release can be assessed by enzyme-linked immunosorbent assay (ELISA), radioimmunoassay (RIA) or flow cytometry/FACS. Changes in gene expression can be assessed by quantitative RT-PCR on the mRNA level or by Western blot or flow cytometry at the protein level.

The term "facilitate" herein refers to the enhancement or restoration of disease impaired TREM2 dependent activities. These activities may comprise phagocytosis, increased target-directed cellular motility (chemotaxis), increased cellular survival, modulating cytokine or chemokine release of cells expressing TREM2, increasing degradation of intracellular phagocytosed material, modulating cellular responses of neighbouring cells (astrocytes/neurons) or changes in gene expression.

The term "antibody," as used herein, refers to a protein, or polypeptide sequence derived from an immunoglobulin molecule that specifically binds to an antigen. Antibodies can be polyclonal or monoclonal, multiple or single chain, or intact immunoglobulins, and may be derived from natural sources or from recombinant sources. A naturally occurring "antibody" is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxyl-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. An antibody can be a monoclonal antibody, human antibody, humanized antibody, camelised antibody, or chimeric antibody. The antibodies can be of any isotype (e.g., IgG, IgE, IgM, IgD, IgA and IgY), class (e.g., IgG1, IgG2, IgG3, IgG4, IgAQ1 and IgA2) or subclass. Throughout this document, the term "antibody" or "antibody molecule" also includes any fragments thereof and any derivatives thereof, unless the context indicates otherwise.

The term "antibody fragment" or "antigen-binding fragment" refers to at least one portion of an antibody, that retains the ability to specifically interact with (e.g., by binding, steric hindrance, stabilizing/destabilizing, spatial distribution) an epitope of an antigen. Examples of antibody fragments include, but are not limited to, Fab, Fab', F(ab')2, Fv fragments, scFv antibody fragments, disulfide-linked Fvs (sdFv), a Fd fragment consisting of the VH and CH1 domains, linear antibodies, single domain antibodies such as sdAb (either VL or VH), camelid VHH domains, multi-specific antibodies formed from antibody fragments such as a bivalent fragment comprising two Fab fragments linked by a disulfide bridge at the hinge region, and an isolated CDR or other epitope binding fragments of an antibody. An antigen binding fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can also be grafted into scaffolds based on polypeptides such as a fibronectin type III (Fn3) (see U.S. Pat. No. 6,703,199, which describes fibronectin polypeptide minibodies). The term "scFv" refers to a fusion protein comprising at least one antibody fragment comprising a variable region of a light chain and at least one antibody fragment comprising a variable region of a heavy chain, wherein the light and heavy chain variable regions are contiguously linked, e.g., via a synthetic linker, e.g., a short flexible polypeptide linker, and capable of being expressed as a single-chain polypeptide, and wherein the scFv retains the specificity of the intact antibody from which it is derived. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

The terms "complementarity determining region" or "CDR," as used herein, refer to the sequences of amino acids within antibody variable regions which confer antigen specificity and binding affinity. For example, in general, there are three CDRs in each heavy chain variable region (e.g., HCDR1, HCDR2, and HCDR3) and three CDRs in each light chain variable region (LCDR1, LCDR2, and LCDR3). The precise amino acid sequence boundaries of a given CDR can be determined using any of a number of well-known schemes, including those described by Kabat et al. (1991), "Sequences of Proteins of Immunological Interest," 5$^{th}$ Ed. Public Health Service, National Institutes of Health, Bethesda, MD ("Kabat" numbering scheme), Al-Lazikani et al., (1997) JMB 273,927-948 ("Chothia" numbering scheme), or a combination thereof, and ImMunoGenTics (IMGT) numbering (Lefranc, M.-P., The Immunologist, 7, 132-136 (1999); Lefranc, M.-P. et al., Dev. Comp. Immunol., 27, 55-77 (2003); Lefranc et al., (2015) Nucleic Acids Res. 43, D413-422) ("IMGT" numbering scheme). In a combined Kabat and Chothia numbering scheme for a given CDR region (for example, HCDR1, HCDR2, HCDR3, LCDR1, LCDR2 or LCDR3), in some embodiments, the CDRs correspond to the amino acid residues that are defined as part of the Kabat CDR, together with the amino acid residues that are defined as part of the Chothia CDR. As used herein, the CDRs defined according to the "Chothia" number scheme are also sometimes referred to as "hypervariable loops." Under IMGT, the CDR regions of an antibody can be determined using the program IMGT/DomainGap Align. Generally, unless specifically indicated, the antibody molecules can include any combination of one or more Kabat CDRs and/or Chothia CDRs.

The term "epitope" includes any protein determinant capable of specific binding to an immunoglobulin or otherwise interacting with a molecule. Epitopic determinants generally consist of chemically active surface groupings of molecules such as amino acids or carbohydrate or sugar side chains and can have specific three-dimensional structural characteristics, as well as specific charge characteristics. An epitope may be "linear" or "conformational." Conformational and linear epitopes are distinguished for example in that the binding to the former but not the latter is lost in the presence of denaturing solvents.

"Binds the same epitope as" means the ability of an antibody, antibody fragment or other antigen-binding moiety to bind to a specific antigen and binding to the same epitope as the exemplified antibody when using the same epitope mapping technique for comparing the antibodies. The epitopes of the exemplified antibody and other antibodies can be determined using epitope mapping techniques. Epitope mapping techniques are well known in the art. For example, conformational epitopes are readily identified by determining spatial conformation of amino acids such as by, e.g., hydrogen/deuterium exchange, x-ray crystallography and two dimensional nuclear magnetic resonance.

In another embodiment, the present disclosure refers to an antibody or antibody fragment that cross-competes with an antibody described in Table 1.

In one embodiment the present disclosure refers to an antibody or antibody fragment, wherein said antibody or antibody fragment cross-competes with an antibody or antibody fragment comprising 6 CDRs defined by any of the Kabat, Chothia, IMGT, or combined Kabat/Chothia method of one or more of the antibodies in Table 1.

In another embodiment, the present disclosure refers to an antibody or antibody fragment that binds to (e.g., by binding and/or stabilizing) the same epitope as one of the antibodies in Table 1.

In a further embodiment said antibody or antigen-binding fragment thereof binds to (e.g., by binding and/or stabilizing) an epitope overlapping the epitope of an antibody or antibody fragment comprising 6 CDRs defined by any one of the Kabat, Chothia, IMGT, or combined Kabat/Chothia methods of any one of the antibodies in Table 1.

The term “monovalent antibody” as used herein, refers to an antibody that binds to a single epitope on a target molecule.

The term “bivalent antibody” as used herein, refers to an antibody that binds to two epitopes on at least two identical target molecules. The bivalent antibody may also crosslink the target molecules to one another. A “bivalent antibody” also refers to an antibody that binds to two different epitopes on at least two identical target molecules.

The term “multivalent antibody” refers to a single binding molecule with more than one valency, where “valency” is described as the number of antigen-binding moieties present per molecule of an antibody construct. As such, the single binding molecule can bind to more than one binding site on a target molecule. Examples of multivalent antibodies include, but are not limited to bivalent antibodies, trivalent antibodies, tetravalent antibodies, pentavalent antibodies, and the like, as well as bispecific antibodies and biparatopic antibodies. For example, for TREM2, the multivalent antibody (e.g., a TREM2 biparatopic antibody) has a binding moiety for two domains of TREM2, respectively.

The term “multivalent antibody” also refers to a single binding molecule that has more than one antigen-binding moiety for two separate target molecules. For example, an antibody that binds to TREM2 and a second target molecule that is not TREM2. In one embodiment, a multivalent antibody is a tetravalent antibody that has four epitope binding domains. A tetravalent molecule may be bispecific and bivalent for each binding site on that target molecule.

The term “bispecific antibody” as used herein, refers to an antibody that binds to two or more different epitopes. In some embodiments, a bispecific antibody binds to two different targets. In some embodiments, a bispecific antibody binds to two different epitopes on a single target molecule. An antibody that binds to two different epitopes on a single target molecule is also known as a “biparatopic antibody.”

The phrases “monoclonal antibody” or “monoclonal antibody composition” as used herein refers to polypeptides, including antibodies, bispecific antibodies, etc., that have substantially identical amino acid sequence or are derived from the same genetic source. This term also includes preparations of antibody molecules of single molecular composition. A monoclonal antibody composition displays a single binding specificity and affinity for a particular epitope.

The phrase “human antibody,” as used herein, includes antibodies having variable regions in which both the framework and CDR regions are derived from sequences of human origin. The constant region is also derived from human sequences, e.g., human germline sequences, or mutated versions of human germline sequences or antibody containing consensus framework sequences derived from human framework sequences analysis, for example, as described in Knappik, et al. (2000. J Mol Biol 296, 57-86). The structures and locations of immunoglobulin variable domains, e.g., CDRs, may be defined using well-known numbering schemes, e.g., the Kabat numbering scheme, the Chothia numbering scheme, or a combination of Kabat and Chothia, and ImMunoGenTics (IMGT) numbering (see, e.g., Sequences of Proteins of Immunological Interest, U.S. Department of Health and Human Services (1991), eds. Kabat et al.; Al Lazikani et al., (1997) J. Mol. Bio. 273:927 948); Kabat et al., (1991) Sequences of Proteins of Immunological Interest, 5th edit., NIH Publication no. 91-3242 U.S. Department of Health and Human Services; Chothia et al., (1987) J. Mol. Biol. 196:901-917; Chothia et al., (1989) Nature 342:877-883; and Al-Lazikani et al., (1997) J. Mal. Biol. 273:927-948; Lefranc, M.-P., The Immunologist, 7, 132-136 (1999); Lefranc, M.-P. et al., Dev. Comp. Immunol., 27, 55-77 (2003); Lefranc et al., (2015) Nucleic Acids Res. 43, D413-422.

The human antibodies of the invention may include amino acid residues not encoded by human sequences (e.g., mutations introduced by random or site-specific mutagenesis in vitro or by somatic mutation in vivo, or a conservative substitution to promote stability or manufacturing). However, the term “human antibody” as used herein, is not intended to include antibodies in which CDR sequences derived from the germline of another mammalian species, such as a mouse, have been grafted onto human framework sequences.

The phrase “recombinant human antibody” as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g. from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term “Fc region” as used herein refers to a polypeptide comprising the CH3, CH2 and at least a portion of the hinge region of a constant domain of an antibody. Optionally, an Fc region may include a CH4 domain, present in some antibody classes. An Fc region may comprise the entire hinge region of a constant domain of an antibody. In one embodiment, the invention comprises an Fc region and a CH1 region of an antibody. In one embodiment, the invention comprises an Fc region CH3 region of an antibody. In another embodiment, the invention comprises an Fc region, a CH1 region and a Ckappa/lambda region from the constant domain of an antibody. In one embodiment, a binding molecule of the invention comprises a constant region, e.g., a heavy chain constant region. In one embodiment, such a constant region is modified compared to a wild-type constant region. That is, the polypeptides of the invention disclosed herein may comprise alterations or modifications to one or more of the three heavy chain constant domains (CH1, CH2 or CH3) and/or to the light chain constant region domain (CL). Example modifications include additions, deletions or substitutions of one or more amino acids in one or more domains. Such changes may be included to optimize effector function, half-life, etc.

As used herein, the term “affinity” refers to the strength of interaction between antibody and antigen at single antigenic sites. Within each antigenic site, the variable regions of the antibody interact through weak non-covalent forces with the antigen at numerous sites; the more interactions, the stronger the affinity. As used herein, the term "high affinity" for an IgG antibody or fragment thereof (e.g., a Fab fragment) refers to an antibody having an affinity of $10^{-8}$ M or less, $10^{-9}$ M or less, or $10^{-10}$ M, or $10^{-11}$ M or less, or $10^{-12}$ M or less, or $10^{-13}$ M or less for a target antigen. However, high affinity binding can vary for other antibody isotypes. For example, high affinity binding for an IgM isotype refers to an antibody having an affinity of $10^{-7}$ M or less, or $10^{-8}$ M or less.

As used herein, the terms "Kassoc", "Ka" or "Kon", are intended to refer to the association rate of a particular antibody-antigen interaction, whereas the term "Kdis," "Kd," or "$K_{off}$", are intended to refer to the dissociation rate of a particular antibody-antigen interaction. In one embodiment, the term "KD" (or "$K_D$"), as used herein, is intended to refer to the dissociation constant, which is obtained from the ratio of Kd to Ka (i.e. Kd/Ka) and is expressed as a molar concentration (M). KD values for antibodies can be determined using methods well established in the art. A method for determining the KD of an antibody is by using surface plasmon resonance, or using a biosensor system such as a Biacore® system.

As used herein, the term "avidity" refers to an informative measure of the overall stability or strength of the antibody-antigen complex. It is controlled by three major factors: antibody epitope affinity; the valency of both the antigen and antibody; and the structural arrangement of the interacting parts. Ultimately these factors define the specificity of the antibody, that is, the likelihood that the particular antibody is binding to a precise antigen epitope.

The term "binding specificity" or "specifically binds" as used herein refers to the ability of an individual antibody combining site to react with one antigenic determinant and not with a different antigenic determinant. The combining site of the antibody is located in the Fab portion of the molecule and is constructed from the hypervariable regions of the heavy and light chains. Binding affinity of an antibody is the strength of the reaction between a single antigenic determinant and a single combining site on the antibody. It is the sum of the attractive and repulsive forces operating between the antigenic determinant and the combining site of the antibody.

The terms "treat" and "treatment" refer to therapeutic treatment, wherein the object is to slow down an undesired physiological change or disorder. For purpose of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

The terms "prevention", "prevent" and "preventing" of any particular disease or disorder refers to prophylactic or preventive measures such as the administration of a compound of the present invention to a subject before any symptoms of that disease or disorder are apparent.

The term "subject" refers to an animal, human or non-human, to whom treatment according to the methods of the present invention is provided. Veterinary and non-veterinary applications are contemplated. The term includes, but is not limited to, mammals, e.g., humans, other primates, pigs, rodents such as mice and rats, rabbits, guinea pigs, hamsters, cows, horses, cats, dogs, sheep and goats. Typical subjects include humans, farm animals, and domestic pets such as cats and dogs. In some preferred embodiments, the subject is a human.

An "effective amount" refers to an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A "therapeutically effective amount" of a therapeutic compound (i.e., an effective dosage) depends on the therapeutic compounds selected. The compositions can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, or a combination thereof.

The term "conservative sequence modifications" refers to amino acid modifications that do not significantly affect or alter the binding characteristics of the antibody or antibody fragment containing the amino acid sequence. Such conservative modifications include amino acid substitutions, additions and deletions. Modifications can be introduced into an antibody or antibody fragment of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within an antibody or an antigen-binding fragment thereof of the invention can be replaced with other amino acid residues from the same side chain family and the altered antibody or antigen-binding fragment can be tested using the functional assays described herein.

The term "homologous" or "identical" refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous or identical at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous. Percentage of "sequence identity" can be determined by comparing two optimally aligned sequences over a comparison window, where the fragment of the amino acid sequence in the comparison window may comprise additions or deletions (e.g., gaps or overhangs) as compared to the reference sequence (which does not comprise additions or deletions) for optimal alignment of the two sequences. The percentage can be calculated by determining the number of positions at which the identical amino acid residue occurs in both sequences to yield the number of matched positions, dividing the number of matched positions by the total number of positions in the window of comparison, and multiplying the result by 100 to yield the percentage of sequence identity. The output is the percent identity of the subject sequence with respect to the query sequence.

The term "isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell. An isolated antibody is substantially free of other antibodies having different antigenic specificities (e.g., an isolated antibody that specifically binds TREM2 is substantially free of antibodies that specifically bind antigens other than TREM2). An isolated antibody that specifically binds a target molecule may, however, have cross-reactivity to the same antigens from other species, e.g., an isolated antibody that specifically binds TREM2 may bind TREM2 molecules from other species. An isolated antibody may be a monoclonal antibody. An isolated antibody may be a recombinant monoclonal antibody. Moreover, an isolated antibody may be substantially free of other cellular material and/or chemicals.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, prevail. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

Antibodies that Stabilize Functional TREM2

Provided herein are antibodies and antigen-binding fragments thereof that stabilize TREM2 on the cell surface. Those antibodies or antigen-binding fragments thereof can achieve stabilization of TREM2 by interfering with the proteolytic cleavage of TREM2 and/or reducing shedding of the ectodomain of the TREM2 protein. In some preferred embodiments, those antibodies or antigen-binding fragments thereof specifically bind to the IgSF domain of human TREM2, e.g., the amino acid residues 19 to 132 of any one of SEQ ID NOs: 1, 2 or 3.

Since reduction or absence of cell surface TREM2 is associated with human neuroinflammatory and neurodegenerative pathologies, the TREM2-stabilizing antibodies or antigen-binding fragments thereof described herein can be used to treat, prevent, or diagnose neuroinflammatory and neurodegenerative diseases such as Alzheimer's disease, frontotemporal dementia, Parkinson's disease, amyotrophic lateral sclerosis, Nasu-Hakola disease, multiple sclerosis, amyotrophic lateral sclerosis (ALS), anti-NMDA receptor encephalitis, autism, brain lupus (NP-SLE), chemo-induced peripheral neuropathy (CIPN), postherpetic neuralgia, chronic inflammatory demyelinating polyneuropathy (CIDP), epilepsy, Guillain-Barre Syndrome (GBS), inclusion body myositis, lysosomal storage diseases, e.g., sphingomyelinlipidose (Niemann-Pick C) and mucopolysaccharidose II/IIIB, metachromatic leukodystrophy, multifocal motor neuropathy, Myasthenia Gravis, Neuro-Behcet's Disease, neuromyelitis optica (NMO), optic neuritis, polymyositis, dermatomyositis, Rasmussen's encephalitis, Rett's Syndrome, stroke, transverse myelitis, traumatic brain injury, spinal cord injury, viral encephalitis, or bacterial meningitis. In some preferred embodiments, the hTREM2 antibody or an antigen-binding fragment thereof described herein can be used to treat, prevent, or diagnose a disease selected from Alzheimer's disease, frontotemporal dementia, Parkinson's disease, amyotrophic lateral sclerosis, or Nasu-Hakola disease.

Due to their pharmacological profiles, the hTREM2 antibodies or antigen-binding fragments thereof described herein will be useful for the treatment of diseases or conditions as diverse as CNS related diseases, PNS related diseases, systemic inflammation and other diseases related to inflammation, pain and withdrawal symptoms caused by an abuse of chemical substances. Diseases or disorders related to the CNS include general anxiety disorders, cognitive disorders, learning and memory deficits and dysfunctions, Alzheimer's disease (mild, moderate and severe), attention deficit and hyperactivity disorder, Parkinson's disease, dementia in Parkinson's disease, Huntington's disease, ALS, prionic neurodegenerative disorders such as Creutzfeld-Jacob disease and kuru disease, Gilles de la Tourette's syndrome, psychosis, depression and depressive disorders, mania, manic depression, schizophrenia, the cognitive deficits in schizophrenia, obsessive compulsive disorders, panic disorders, eating disorders, narcolepsy, nociception, AIDS-dementia, senile dementia, mild cognitive impairment related to age (MCI), age associated memory impairment, autism, dyslexia, tardive dyskinesia, epilepsy, and convulsive disorders, post-traumatic stress disorders, transient anoxia, pseudodementia, pre-menstrual syndrome, late luteal phase syndrome, chronic fatigue syndrome and jet lag.

The hTREM2 antibodies or antigen-binding fragments thereof described herein are particularly suitable for treating, preventing or diagnosing autoimmune, inflammatory, or malignant disorders mediated by or associated with extensive proteolytic cleavage of TREM2 or cells expressing aberrant or mutated variants of the TREM2 receptor. Examples of autoimmune diseases include, without limitation, arthritis (for example rheumatoid arthritis, arthritis chronica progrediente and arthritis deformans) and rheumatic diseases, including inflammatory conditions and rheumatic diseases involving bone loss, inflammatory pain, spondyloarhropathies including ankylosing spondylitis, Reiter syndrome, reactive arthritis, psoriatic arthritis, and enterophathic arthritis, hypersensitivity (including both airways hypersensitivity and dermal hypersensitivity) and allergies. Autoimmune diseases include autoimmune haematological disorders (including e.g. hemolytic anaemia, aplastic anaemia, pure red cell anaemia and idiopathic thrombocytopenia), systemic lupus erythematosus, inflammatory muscle disorders, polychondritis, sclerodoma, Wegener granulomatosis, dermatomyositis, chronic active hepatitis, myasthenia gravis, psoriasis, Steven-Johnson syndrome, idiopathic sprue, endocrine ophthalmopathy, Graves disease, sarcoidosis, multiple sclerosis, primary biliary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including gout, langerhans cell histiocytosis, idiopathic nephrotic syndrome or minimal change nephropathy), tumors, inflammatory disease of skin and comea, myositis, loosening of bone implants, metabolic disorders, such as atherosclerosis, diabetes, and dislipidemia.

The hTREM2 antibodies or antigen-binding fragments thereof described herein are also useful for the treatment, prevention, or amelioration of asthma, bronchitis, pneumoconiosis, pulmonary emphysema, and other obstructive or inflammatory diseases of the airways including idiopathic pulmonary fibrosis or COPD.

The hTREM2 antibodies or antigen-binding fragments thereof described herein can be used to treat hematopoietic or hepatopoetic malignant disorder such as acute myeloid leukemia, chronic myeloid leukemia, myeloproliferative disorders, myelodysplastic syndromes, multiple myeloma, paroxysmal nocturnal hemoglobinuria, fanconi anemi, thalassemia major, Wiskott-Aldrich syndrome, hemophagocytic lymphohistiocytosis.

The hTREM2 antibodies or antigen-binding fragments thereof described herein can be used to treat any disease or disorder directly or indirectly associated with aberrant TREM2 activity and/or expression. The TREM2-related disorders include: immunological disorders, especially involving inflammatory disorders (e.g., bacterial infection, fungal infection, viral infection, protozoa or other parasitic infection, psoriasis, septicemia, cerebral malaria, inflammatory bowel disease, arthritis, such as rheumatoid arthritis, folliculitis, impetigo, granulomas, lipoid pneumonias, vasculitis, and osteoarthritis), autoimmune disorders (e.g., rheumatoid arthritis, thyroiditis, such as Hashimoto's thyroiditis and Graves' disease, insulin-resistant diabetes, pernicious anemia, Addison's disease, pemphigus, vitiligo, ulcerative colitis, systemic lupus erythematosus (SLE), Sjogren's syndrome, multiple sclerosis, dermatomyositis, mixed connective tissue disease, scleroderma, polymyositis, graft rejection, such as allograft rejection), T cell disorders (e.g., AIDS), allergic inflammatory disorders (e.g., skin and/or mucosal allergies, such as allergic rhinitis, asthma, psoriasis), neurological disorders, eye disorders, embryonic disorders, or any other disorders (e.g., tumors, cancers, leukemia, myeloid diseases, and traumas) which are directly or indirectly associated with aberrant TREM2 activity and/or expression.

In some embodiments, the TREM2-related disorder is selected from asthma, encephalitis, inflammatory bowel disease, chronic obstructive pulmonary disease (COPD), allergic disorders, septic shock, pulmonary fibrosis, undifferentiated spondyloarthropathy, undifferentiated arthropathy, arthritis, inflammatory osteolysis, or chronic inflammation resulting from chronic viral or bacterial infections.

In some embodiments, the TREM2-related disorder is selected from dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, Taupathy disease, Nasu-Hakola disease, stroke, acute trauma, chronic trauma, lupus, acute and chronic colitis, wound healing, Crohn's disease, inflammatory bowel disease, ulcerative colitis, obesity, Malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, Sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer. In some preferred embodiments, the TREM2-related disorder is selected from a list consisting of Alzheimer's disease, frontotemporal dementia, Parkinson's disease, amyotrophic lateral sclerosis, or Nasu-Hakola disease.

In some preferred embodiments, the TREM2-related disorder is selected from dementia, frontotemporal dementia, Alzheimer's disease, Nasu-Hakola disease, and multiple sclerosis. In some preferred embodiments, TREM2-related disorder is a dementia such as frontotemporal dementia, Alzheimer's disease, vascular dementia, semantic dementia, or dementia with Lewy bodies. In a more preferred embodiment, the TREM2-related disorder is Alzheimer's disease. In another preferred embodiment, the disorder is Parkinson's disease.

Antibodies and Antigen-Binding Fragments Thereof that Specifically Bind to Human TREM2

In one aspect, provided herein are antibodies or antigen-binding fragments thereof, e.g. monoclonal antibodies or antigen-binding fragments thereof, that specifically bind to the IgSF domain of human TREM2 protein ("hTREM2 antibodies or antigen-binding fragments thereof"). Those antibodies or antigen-binding fragments can stabilize the TREM2 protein on the cell surface, and/or reduce shedding of the ectodomain of the TREM2 protein.

In some embodiments, the hTREM2 antibodies or antigen-binding fragments thereof provided herein include a heavy chain CDR1 (HCDR1), a heavy chain CDR2 (HCDR2), a heavy chain CDR3 (HCDR3), and a light chain CDR1 (LCDR1), a light chain CDR2 (LCDR2), and a light chain CDR3 (LCDR3). In some embodiments, the hTREM2 antibodies or antigen-binding fragments provided herein include a heavy chain variable region (VH) comprising CDR1, CDR2, and CDR3 and a light chain variable region (VL) comprising CDR1, CDR2, and CDR3. In some embodiments, the hTREM2 antibodies or antigen-binding fragments provided herein include a full length heavy chain sequence (HC) and a full length light chain sequence (LC).

Table 1 lists the sequences of exemplary the TREM2 antibodies or antigen binding fragments that specifically bind to human TREM2 protein. Throughout the text of this application, should there be a discrepancy between the text of the specification (e.g., Table 1) and the sequence listing, the text of the specification shall prevail. Table 1. Sequences of Exemplary Monoclonal Antibodies That Bind Human TREM2.

TABLE 1

Sequences of Exemplary Monoclonal Antibodies That Bind Human TREM2.

MOR44698A

| | | |
|---|---|---|
| SEQ ID NO: 4 | HCDR1 (Combined) | GYTFTGYHMS |
| SEQ ID NO: 5 | HCDR2 (Combined) | VINPVSGNTVYAQKFQG |
| SEQ ID NO: 6 | HCDR3 (Combined) | IPSYTYAFDY |
| SEQ ID NO: 7 | HCDR1 (Kabat) | GYHMS |
| SEQ ID NO: 5 | HCDR2 (Kabat) | VINPVSGNTVYAQKFQG |
| SEQ ID NO: 6 | HCDR3 (Kabat) | IPSYTYAFDY |
| SEQ ID NO: 8 | HCDR1 (Chothia) | GYTFTGY |
| SEQ ID NO: 9 | HCDR2 (Chothia) | NPVSGN |
| SEQ ID NO: 6 | HCDR3 (Chothia) | IPSYTYAFDY |
| SEQ ID NO: 10 | HCDR1 (IMGT) | GYTFTGYH |
| SEQ ID NO: 11 | HCDR2 (IMGT) | INPVSGNT |
| SEQ ID NO: 12 | HCDR3 (IMGT) | ARIPSYTYAFDY |
| SEQ ID NO: 13 | VH | QVQLVQSGAEVKKPGASVKVSCKASGYTFTGYHMSWVRQAPGQGL<br>EWMGVINPVSGNTVYAQKFQGRVTMTRDTSISTAYMELSRLRSED<br>TAVYYCARIPSYTYAFDYWGQGTLVTVSS |
| SEQ ID NO: 14 | DNA VH | CAGGTGCAATTGGTGCAGAGCGGTGCGGAAGTGAAAAAACCGGGT<br>GCCAGCGTGAAAGTTAGCTGCAAAGCGTCCGGATATACCTTCACT<br>GGTTACCATATGTCTTGGGTGCGCCAGGCCCCGGGCCAGGGCCTC<br>GAGTGGATGGGCGTTATCAACCCGGTTTCTGGCAACACGGTTTAC<br>GCGCAGAAATTTCAGGGCCGGGTGACCATGACCCGTGATACCAGC<br>ATTAGCACCGCGTATATGGAACTGAGCCGTCTGCGTAGCGAAGAT<br>ACGGCCGTGTATTATTGCGCGCGTATCCCGTCTTACACTTACGCT<br>TTCGATTACTGGGGCCAAGGCACCCTGGTGACTGTTAGCTCA |
| SEQ ID NO: 15 | Heavy Chain | QVQLVQSGAEVKKPGASVKVSCKASGYTFTGYHMSWVRQAPGQGL<br>EWMGVINPVSGNTVYAQKFQGRVTMTRDTSISTAYMELSRLRSED<br>TAVYYCARIPSYTYAFDYWGQGTLVTVSSASTKGPSVFPLAPSSK<br>STSGGTAALGCLVKDYFPEPVTVSWNSGALTSGVHTFPAVLQSSG<br>LYSLSSVVTVPSSSLGTQTYICNVNHKPSNTKVDKRVEPKSCDKT<br>HTCPPCPAPEAAGGPSVFLFPPKPKDTLMISRTPEVTCVVVDVSH<br>EDPEVKFNWYVDGVEVHNAKTKPREEQYNSTYRVVSVLTVLHQDW<br>LNGKEYKCKVSNKALPAPIEKTISKAKGQPREPQVYTLPPSREEM<br>TKNQVSLTCLVKGFYPSDIAVEWESNGQPENNYKTTPPVLDSDGS<br>FFLYSKLTVDKSRWQQGNVFSCSVMHEALHNHYTQKSLSLSPGK |
| SEQ ID NO: 16 | DNA Heavy Chain | CAGGTGCAATTGGTGCAGAGCGGTGCGGAAGTGAAAAAACCGGGT<br>GCCAGCGTGAAAGTTAGCTGCAAAGCGTCCGGATATACCTTCACT<br>GGTTACCATATGTCTTGGGTGCGCCAGGCCCCGGGCCAGGGCCTC<br>GAGTGGATGGGCGTTATCAACCCGGTTTCTGGCAACACGGTTTAC<br>GCGCAGAAATTTCAGGGCCGGGTGACCATGACCCGTGATACCAGC<br>ATTAGCACCGCGTATATGGAACTGAGCCGTCTGCGTAGCGAAGAT<br>ACGGCCGTGTATTATTGCGCGCGTATCCCGTCTTACACTTACGCT<br>TTCGATTACTGGGGCCAAGGCACCCTGGTGACTGTTAGCTCAGCC<br>TCCACCAAGGGTCCATCGGTCTTCCCCCTGGCACCCTCCTCCAAG<br>AGCACCTCTGGGGGCACAGCGGCCCTGGGCTGCCTGGTCAAGGAC<br>TACTTCCCCGAACCGGTGACGGTGTCGTGGAACTCAGGCGCCCTG<br>ACCAGCGGCGTGCACACCTTCCCGGCTGTCCTACAGTCCTCAGGA<br>CTCTACTCCCTCAGCAGCGTGGTGACCGTGCCCTCCAGCAGCTTG<br>GGCACCCAGACCTACATCTGCAACGTGAATCACAAGCCCAGCAAC<br>ACCAAGGTGGACAAGAGAGTTGAGCCCAAATCTTGTGACAAAACT<br>CACACATGCCCACCGTGCCCAGCACCTGAAGCAGCGGGGGGACCG<br>TCAGTCTTCCTCTTCCCCCCAAAACCCAAGGACACCCTCATGATC<br>TCCCGGACCCCTGAGGTCACATGCGTGGTGGTGGACGTGAGCCAC<br>GAAGACCCTGAGGTCAAGTTCAACTGGTACGTGGACGGCGTGGAG |

TABLE 1-continued

| Sequences of Exemplary Monoclonal Antibodies That Bind Human TREM2. | | |
|---|---|---|
| | | GTGCATAATGCCAAGACAAAGCCGCGGGAGGAGCAGTACAACAGC<br>ACGTACCGGGTGGTCAGCGTCCTCACCGTCCTGCACCAGGACTGG<br>CTGAATGGCAAGGAGTACAAGTGCAAGGTCTCCAACAAAGCCCTC<br>CCAGCCCCCATCGAGAAAACCATCTCCAAAGCCAAAGGGCAGCCC<br>CGAGAACCACAGGTGTACACCCTGCCCCCATCCCGGGAGGAGATG<br>ACCAAGAACCAGGTCAGCCTGACCTGCCTGGTCAAAGGCTTCTAT<br>CCCAGCGACATCGCCGTGGAGTGGGAGAGCAATGGGCAGCCGGAG<br>AACAACTACAAGACCACGCCTCCCGTGCTGGACTCCGACGGCTCC<br>TTCTTCCTCTACAGCAAGCTCACCGTGGACAAGAGCAGGTGGCAG<br>CAGGGGAACGTCTTCTCATGCTCCGTGATGCATGAGGCTCTGCAC<br>AACCACTACACGCAGAAGAGCCTCTCCCTGTCTCCGGGTAAA |
| SEQ ID NO: 17 | LCDR1 (Combined) | RASQDISNYLA |
| SEQ ID NO: 18 | LCDR2 (Combined) | RASSLQS |
| SEQ ID NO: 19 | LCDR3 (Combined) | FQYRHMPSQT |
| SEQ ID NO: 17 | LCDR1 (Kabat) | PASQDISNYLA |
| SEQ ID NO: 18 | LCDR2 (Kabat) | PASSLQS |
| SEQ ID NO: 19 | LCDR3 (Kabat) | FQYRHMPSQT |
| SEQ ID NO: 20 | LCDR1 (Chothia) | SQDISNY |
| SEQ ID NO: 21 | LCDR2 (Chothia) | PAS |
| SEQ ID NO: 22 | LCDR3 (Chothia) | YRHMPSQ |
| SEQ ID NO: 23 | LCDR1 (IMGT) | QDISNY |
| SEQ ID NO: 21 | LCDR2 (IMGT) | RAS |
| SEQ ID NO: 19 | LCDR3 (IMGT) | FQYRHMPSQT |
| SEQ ID NO: 24 | VL | DIQMTQSPSSLSASVGDRVTITCRASQDISNYLAWYQQKPGKAPK<br>LLIYRASSLQSGVPSRFSGSGSGTDFTLTISSLQPEDFATYYCFQ<br>YRHMPSQTFGQGTKVEIK |
| SEQ ID NO: 25 | DNA VL | GATATCCAGATGACCCAGAGCCCGAGCAGCCTGAGCGCCAGCGTG<br>GGCGATCGCGTGACCATTACCTGCAGAGCCAGCCAGGACATTTCT<br>AACTACCTGGCTTGGTACCAGCAGAAACCGGGCAAAGCGCCGAAA<br>CTATTAATCTACCGTGCTTCTTCTCTGCAAAGCGGCGTGCCGAGC<br>CGCTTTAGCGGCAGCGGATCCGGCACCGATTTCACCCTGACCATT<br>AGCTCTCTGCAACCGGAAGACTTTGCGACCTATTATTGCTTCCAG<br>TACCGTCATATGCCGTCTCAGACCTTTGGCCAGGGCACGAAAGTT<br>GAAATTAAA |
| SEQ ID NO: 26 | Light Chain | DIQMTQSPSSLSASVGDRVTITCRASQDISNYLAWYQQKPGKAPK<br>LLIYRASSLQSGVPSRFSGSGSGTDFTLTISSLQPEDFATYYCFQ<br>YRHMPSQTFGQGTKVEIKRTVAAPSVFIFPPSDEQLKSGTASVVC<br>LLNNFYPREAKVQWKVDNALQSGNSQESVTEQDSKDSTYSLSSTI<br>TLSKADYEKHKVYACEVTHQGLSSPVTKSFNRGEC |
| SEQ ID NO: 27 | DNA Light Chain | GATATCCAGATGACCCAGAGCCCGAGCAGCCTGAGCGCCAGCGTG<br>GGCGATCGCGTGACCATTACCTGCAGAGCCAGCCAGGACATTTCT<br>AACTACCTGGCTTGGTACCAGCAGAAACCGGGCAAAGCGCCGAAA<br>CTATTAATCTACCGTGCTTCTTCTCTGCAAAGCGGCGTGCCGAGC<br>CGCTTTAGCGGCAGCGGATCCGGCACCGATTTCACCCTGACCATT<br>AGCTCTCTGCAACCGGAAGACTTTGCGACCTATTATTGCTTCCAG<br>TACCGTCATATGCCGTCTCAGACCTTTGGCCAGGGCACGAAAGTT<br>GAAATTAAACGTACGGTGGCCGCTCCCAGCGTGTTCATCTTCCCC<br>CCCAGCGACGAGCAGCTGAAGAGCGGCACCGCCAGCGTGGTGTGC<br>CTGCTGAACAACTTCTACCCCCGGGAGGCCAAGGTGCAGTGGAAG<br>GTGGACAACGCCCTGCAGAGCGGCAACAGCCAGGAAAGCGTCACC<br>GAGCAGGACAGCAAGGACTCCACCTACAGCCTGAGCAGCACCCTG<br>ACCCTGAGCAAGGCCGACTACGAGAAGCACAAGGTGTACGCCTGC<br>GAGGTGACCCACCAGGGCCTGTCCAGCCCCGTGACCAAGAGCTTC<br>AACCGGGGCGAGTGT |
| | | MOR44698B |
| SEQ ID NO: 4 | HCDR1 (Combined) | GYTFTGYHMS |
| SEQ ID NO: 5 | HCDR2 (Combined) | VINPVSGNTVYAQKFQG |
| SEQ ID NO: 6 | HCDR3 (Combined) | IPSYTYAFDY |
| SEQ ID NO: 7 | HCDR1 (Kabat) | GYHMS |
| SEQ ID NO: 5 | HCDR2 (Kabat) | VINPVSGNTVYAQKFQG |
| SEQ ID NO: 6 | HCDR3 (Kabat) | IPSYTYAFDY |
| SEQ ID NO: 8 | HCDR1 (Chothia) | GYTFTGY |
| SEQ ID NO: 9 | HCDR2 (Chothia) | NPVSGN |
| SEQ ID NO: 6 | HCDR3 (Chothia) | IPSYTYAFDY |
| SEQ ID NO: 10 | HCDR1 (IMGT) | GYTFTGYH |
| SEQ ID NO: 11 | HCDR2 (IMGT) | INPVSGNT |
| SEQ ID NO: 12 | HCDR3 (IMGT) | ARIPSYTYAFDY |
| SEQ ID NO: 13 | VH | QVQLVQSGAEVKKPGASVKVSCKASGYTFTGYHMSWVRQAPGQGL<br>EWMGVINPVSGNTVYAQKFQGRVTMTRDTSISTAYMELSRLRSED<br>TAVYYCARIPSYTYAFDYWGQGTLVTVSS |

TABLE 1-continued

| Sequences of Exemplary Monoclonal Antibodies That Bind Human TREM2. | | |
|---|---|---|
| SEQ ID NO: 28 | DNA VH | CAAGTGCAACTCGTGCAGTCAGGAGCCGAAGTCAAGAAGCCTGGA GCCTCGGTCAAGGTGTCCTGCAAGGCCAGCGGATACACTTTCACT GGATACCACATGTCGTGGGTCAGACAGGCTCCTGGCCAAGGGCTG GAGTGGATGGGCGTCATCAACCCGGTGTCGGGTAATACCGTGTAC GCCCAGAAGTTCCAGGGTCGCGTGACCATGACCCGGGATACCTCC ATTAGCACCGCGTACATGGAGCTCAGCCGGTTGAGATCCGAGGAT ACCGCCGTGTACTACTGTGCGCGGATCCCGTCCTACACTTACGCC TTCGACTATTGGGGCCAGGGGACTCTTGTCACCGTGTCCTCG |
| SEQ ID NO: 29 | Heavy Chain | QVQLVQSGAEVKKPGASVKVSCKASGYTFTGYHMSWVRQAPGQGL EWMGVINPVSGNTVYAQKFQGRVTMTRDTSISTAYMELSRLRSED TAVYYCARIPSYTYAFDYWGQGTLVTVSSASTKGPSVFPLAPSSK STSGGTAALGCLVKDYFPEPVTVSWNSGALTSGVHTFPAVLQSSG LYSLSSVVTVPSSSLGTQTYICNVNHKPSNTKVDKRVEPKSCDKT HTCPPCPAPELLGGPSVFLFPPKPKDTLMISRTPEVTCVVVDVSH EDPEVKFNWYVDGVEVHNAKTKPREEQYNSTYRVVSVLTVLHQDW LNGKEYKCKVSNKALPAPIEKTISKAKGQPREPQVYTLPPSREEM TKNQVSLTCLVKGFYPSDIAVEWESNGQPENNYKTTPPVLDSDGS FFLYSKLTVDKSRWQQGNVFSCSVMHEALHNHYTQKSLSLSPGK |
| SEQ ID NO: 30 | DNA Heavy Chain | CAAGTGCAACTCGTGCAGTCAGGAGCCGAAGTCAAGAAGCCTGGA GCCTCGGTCAAGGTGTCCTGCAAGGCCAGCGGATACACTTTCACT GGATACCACATGTCGTGGGTCAGACAGGCTCCTGGCCAAGGGCTG GAGTGGATGGGCGTCATCAACCCGGTGTCGGGTAATACCGTGTAC GCCCAGAAGTTCCAGGGTCGCGTGACCATGACCCGGGATACCTCC ATTAGCACCGCGTACATGGAGCTCAGCCGGTTGAGATCCGAGGAT ACCGCCGTGTACTACTGTGCGCGGATCCCGTCCTACACTTACGCC TTCGACTATTGGGGCCAGGGGACTCTTGTCACCGTGTCCTCGGCC TCCACTAAGGGCCCAAGTGTGTTTCCCCTGGCCCCCAGCAGCAAG TCTACTTCCGGCGGAACTGCTGCCCTGGGTTGCCTGGTGAAGGAC TACTTCCCCGAGCCCGTGACAGTGTCCTGGAACTCTGGGGCTCTG ACTTCCGGCGTGCACACCTTCCCCGCCGTGCTGCAGAGCAGCGGC CTGTACAGCCTGAGCAGCGTGGTGACAGTGCCCTCCAGCTCTCTG GGAACCCAGACCTATATCTGCAACGTGAACCACAAGCCCAGCAAC ACCAAGGTGGACAAGAGAGTGGAGCCCAAGAGCTGCGACAAGACC CACACCTGCCCCCCCTGCCCAGCTCCAGAACTGCTGGGAGGGCCT TCCGTGTTCCTGTTCCCCCCCAAGCCCAAGGACACCCTGATGATC AGCAGGACCCCCGAGGTGACCTGCGTGGTGGTGGACGTGTCCCAC GAGGACCCAGAGGTGAAGTTCAACTGGTACGTGGACGGCGTGGAG GTGCACAACGCCAAGACCAAGCCCAGAGAGGAGCAGTACAACAGC ACCTACAGGGTGGTGTCCGTGCTGACCGTGCTGCACCAGGACTGG CTGAACGGCAAAGAATACAAGTGCAAAGTCTCCAACAAGGCCCTG CCAGCCCCAATCGAAAAGACAATCAGCAAGGCCAAGGGCCAGCCA CGGGAGCCCCAGGTGTACACCCTGCCCCCCAGCCGGGAGGAGATG ACCAAGAACCAGGTGTCCCTGACCTGTCTGGTGAAGGGCTTCTAC CCCAGCGATATCGCCGTGGAGTGGGAGAGCAACGGCCAGCCCGAG AACAACTACAAGACCACCCCCCCAGTGCTGGACAGCGACGGCAGC TTCTTCCTGTACAGCAAGCTGACCGTGGACAAGTCCAGGTGGCAG CAGGGCAACGTGTTCAGCTGCAGCGTGATGCACGAGGCCCTGCAC AACCACTACACCCAGAAGTCCCTGAGCCTGAGCCCCGGCAAG |
| SEQ ID NO: 17 | LCDR1 (Combined) | RASQDISNYLA |
| SEQ ID NO: 18 | LCDR2 (Combined) | RASSLQS |
| SEQ ID NO: 19 | LCDR3 (Combined) | FQYRHMPSQT |
| SEQ ID NO: 17 | LCDR1 (Kabat) | RASQDISNYLA |
| SEQ ID NO: 18 | LCDR2 (Kabat) | RASSLQS |
| SEQ ID NO: 19 | LCDR3 (Kabat) | FQYRHMPSQT |
| SEQ ID NO: 20 | LCDR1 (Chothia) | SQDISNY |
| SEQ ID NO: 21 | LCDR2 (Chothia) | RAS |
| SEQ ID NO: 22 | LCDR3 (Chothia) | YRHMPSQ |
| SEQ ID NO: 23 | LCDR1 (IMGT) | QDISNY |
| SEQ ID NO: 21 | LCDR2 (IMGT) | RAS |
| SEQ ID NO: 19 | LCDR3 (IMGT) | FQYRHMPSQT |
| SEQ ID NO: 24 | VL | DIQMTQSPSSLSASVGDRVTITCRASQDISNYLAWYQQKPGKAPK LLIYRASSLQSGVPSRFSGSGSGTDFTLTISSLQPEDFATYYCFQ YRHMPSQTFGQGTKVEIK |
| SEQ ID NO: 31 | DNA VL | GACATTCAGATGACCCAGTCCCCGTCGTCCCTGTCCGCATCCGTG GGCGACAGAGTCACCATCACTTGCCGGGCCTCACAGGATATTTCC AACTACCTGGCCTGGTATCAGCAGAAGCCTGGAAAGGCCCCGAAG CTGCTGATCTACCGGGCGTCCTCCTTGCAATCGGGAGTGCCAAGC CGCTTTTCTGGTTCCGGGAGCGGGACTGACTTCACCCTGACTATT AGCAGCCTGCAGCCCGAAGATTTCGCTACCTACTACTGCTTCCAG TACCGGCACATGCCCTCACAAACCTTCGGACAGGGCACCAAAGTC GAGATCAAG |
| SEQ ID NO: 26 | Light Chain | DIQMTQSPSSLSASVGDRVTITCRASQDISNYLAWYQQKPGKAPK LLIYRASSLQSGVPSRFSGSGSGTDFTLTISSLQPEDFATYYCFQ YRHMPSQTFGQGTKVEIKRTVAAPSVFIFPPSDEQLKSGTASVVC LLNNFYPREAKVQWKVDNALQSGNSQESVTEQDSKDSTYSLSSTI |

TABLE 1-continued

| Sequences of Exemplary Monoclonal Antibodies That Bind Human TREM2. | | |
|---|---|---|
| | | TLSKADYEKHKVYACEVTHQGLSSPVTKSFNRGEC |
| SEQ ID NO: 32 | DNA Light Chain | GACATTCAGATGACCCAGTCCCCGTCGTCCCTGTCCGCATCCGTG<br>GGCGACAGAGTCACCATCACTTGCCGGGCCTCACAGGATATTTCC<br>AACTACCTGGCCTGGTATCAGCAGAAGCCTGGAAAGGCCCCGAAG<br>CTGCTGATCTACCGGGCGTCCTCCTTGCAATCGGGAGTGCCAAGC<br>CGCTTTTCTGGTTCCGGGAGCGGGACTGACTTCACCCTGACTATT<br>AGCAGCCTGCAGCCCGAAGATTTCGCTACCTACTACTGCTTCCAG<br>TACCGGCACATGCCCTCACAAACCTTCGGACAGGGCACCAAAGTC<br>GAGATCAAGCGTACGGTGGCCGCTCCCAGCGTGTTCATCTTCCCC<br>CCCAGCGACGAGCAGCTGAAGAGCGGCACCGCCAGCGTGGTGTGC<br>CTGCTGAACAACTTCTACCCCCGGGAGGCCAAGGTGCAGTGGAAG<br>GTGGACAACGCCCTGCAGAGCGGCAACAGCCAGGAGAGCGTCACC<br>GAGCAGGACAGCAAGGACTCCACCTACAGCCTGAGCAGCACCCTG<br>ACCCTGAGCAAGGCCGACTACGAGAAGCATAAGGTGTACGCCTGC<br>GAGGTGACCCACCAGGGCCTGTCCAGCCCCGTGACCAAGAGCTTC<br>AACAGGGGCGAGTGC |
| MOR44698C | | |
| SEQ ID NO: 4 | HCDR1 (Combined) | GYTFTGYHMS |
| SEQ ID NO: 5 | HCDR2 (Combined) | VINPVSGNTVYAQKFQG |
| SEQ ID NO: 6 | HCDR3 (Combined) | IPSYTYAFDY |
| SEQ ID NO: 7 | HCDR1 (Kabat) | GYHMS |
| SEQ ID NO: 5 | HCDR2 (Kabat) | VINPVSGNTVYAQKFQG |
| SEQ ID NO: 6 | HCDR3 (Kabat) | IPSYTYAFDY |
| SEQ ID NO: 8 | HCDR1 (Chothia) | GYTFTGY |
| SEQ ID NO: 9 | HCDR2 (Chothia) | NPVSGN |
| SEQ ID NO: 6 | HCDR3 (Chothia) | IPSYTYAFDY |
| SEQ ID NO: 10 | HCDR1 (IMGT) | GYTFTGYH |
| SEQ ID NO: 11 | HCDR2 (IMGT) | INPVSGNT |
| SEQ ID NO: 12 | HCDR3 (IMGT) | ARIPSYTYAFDY |
| SEQ ID NO: 13 | VH | QVQLVQSGAEVKKPGASVKVSCKASGYTFTGYHMSWVRQAPGQGL<br>EWMGVINPVSGNTVYAQKFQGRVTMTRDTSISTAYMELSRLRSED<br>TAVYYCARIPSYTYAFDYWGQGTLVTVSS |
| SEQ ID NO: 28 | DNA VH | CAAGTGCAACTCGTGCAGTCAGGAGCCGAAGTCAAGAAGCCTGGA<br>GCCTCGGTCAAGGTGTCCTGCAAGGCCAGCGGATACACTTTCACT<br>GGATACCACATGTCGTGGGTCAGACAGGCTCCTGGCCAAGGGCTG<br>GAGTGGATGGGCGTCATCAACCCGGTGTCGGGTAATACCGTGTAC<br>GCCCAGAAGTTCCAGGGTCGCGTGACCATGACCCGGGATACCTCC<br>ATTAGCACCGCGTACATGGAGCTCAGCCGGTTGAGATCCGAGGAT<br>ACCGCCGTGTACTACTGTGCGCGGATCCCGTCCTACACTTACGCC<br>TTCGACTATTGGGGCCAGGGGACTCTTGTCACCGTGTCCTCG |
| SEQ ID NO: 33 | Heavy Chain | QVQLVQSGAEVKKPGASVKVSCKASGYTFTGYHMSWVRQAPGQGL<br>EWMGVINPVSGNTVYAQKFQGRVTMTRDTSISTAYMELSRLRSED<br>TAVYYCARIPSYTYAFDYWGQGTLVTVSSASTKGPSVFPLAPSSK<br>STSGGTAALGCLVKDYFPEPVTVSWNSGALTSGVHTFPAVLQSSG<br>LYSLSSVVTVPSSSLGTQTYICNVNHKPSNTKVDKRVEPKSCDKT<br>HTCPPCPAPELLGGPSVFLFPPKPKDTLMISRTPEVTCVVVAVSH<br>EDPEVKFNWYVDGVEVHNAKTKPREEQYNSTYRVVSVLTVLHQDW<br>LNGKEYKCKVSNKALAAPIEKTISKAKGQPREPQVYTLPPSREEM<br>TKNQVSLTCLVKGFYPSDIAVEWESNGQPENNYKTTPPVLDSDGS<br>FFLYSKLTVDKSRWQQGNVFSCSVMHEALHNHYTQKSLSLSPGK |
| SEQ ID NO: 34 | DNA Heavy Chain | CAAGTGCAACTCGTGCAGTCAGGAGCCGAAGTCAAGAAGCCTGGA<br>GCCTCGGTCAAGGTGTCCTGCAAGGCCAGCGGATACACTTTCACT<br>GGATACCACATGTCGTGGGTCAGACAGGCTCCTGGCCAAGGGCTG<br>GAGTGGATGGGCGTCATCAACCCGGTGTCGGGTAATACCGTGTAC<br>GCCCAGAAGTTCCAGGGTCGCGTGACCATGACCCGGGATACCTCC<br>ATTAGCACCGCGTACATGGAGCTCAGCCGGTTGAGATCCGAGGAT<br>ACCGCCGTGTACTACTGTGCGCGGATCCCGTCCTACACTTACGCC<br>TTCGACTATTGGGGCCAGGGGACTCTTGTCACCGTGTCCTCGGCC<br>TCCACTAAGGGCCCGTCAGTGTTCCCCCTTGCGCCATCCTCGAAG<br>TCAACCTCCGGAGGAACTGCCGCACTGGGTTGCCTCGTGAAAGAC<br>TATTTCCCGGAACCCGTCACTGTCTCCTGGAACTCAGGAGCGCTC<br>ACCAGCGGAGTGCATACCTTTCCTGCGGTGCTGCAGTCCAGCGGC<br>CTGTACTCCCTGAGCTCCGTCGTGACCGTCCCCTCGTCGTCCCTG<br>GGAACCCAAACCTACATTTGCAACGTCAATCACAAGCCAAGCAAC<br>ACTAAGGTGGACAAGAGAGTGGAGCCCAAGTCCTGCGATAAGACC<br>CACACCTGTCCTCCCTGTCCGGCACCTGAACTGCTTGGTGGACCT<br>TCCGTGTTCCTGTTCCCGCCCAAGCCAAAAGACACCCTGATGATC<br>TCCCGCACTCCGGAAGTCACTTGCGTGGTCGTGGCCGTGTCCCAC<br>GAGGACCCCGAGGTCAAGTTTAATTGGTACGTGGACGGAGTGGAA<br>GTGCACAACGCCAAGACCAAGCCGCGGGAAGAACAGTACAACTCC<br>ACCTACCGCGTGGTGTCCGTCCTGACTGTGCTCCACCAGGACTGG<br>CTGAACGGAAAGGAGTACAAGTGCAAAGTGTCCAACAAGGCACTG<br>GCTGCCCCTATCGAAAAGACTATCTCCAAGGCCAAGGGCCAACCT |

TABLE 1-continued

Sequences of Exemplary Monoclonal Antibodies That Bind Human TREM2.

| | | |
|---|---|---|
| | | AGGGAGCCCCAGGTGTACACGTTGCCTCCTTCCCGCGAAGAAATG ACTAAGAACCAGGTGTCGCTGACCTGTCTCGTGAAAGGGTTCTAC CCCTCTGACATCGCCGTGGAATGGGAGTCAAACGGACAGCCTGAG AACAACTATAAGACCACACCACCTGTCCTGGACTCCGACGGCTCC TTCTTCCTGTACTCAAAGTTGACCGTGGACAAGTCGCGGTGGCAA CAGGGCAACGTGTTCTCTTGCTCCGTGATGCACGAAGCCCTGCAC AACCACTACACCCAAAAGTCGCTCAGCCTCTCCCCCGGAAAG |
| SEQ ID NO: 17 | LCDR1 (Combined) | RASQDISNYLA |
| SEQ ID NO: 18 | LCDR2 (Combined) | RASSLQS |
| SEQ ID NO: 19 | LCDR3 (Combined) | FQYRHMPSQT |
| SEQ ID NO: 17 | LCDR1 (Kabat) | RASQDISNYLA |
| SEQ ID NO: 18 | LCDR2 (Kabat) | RASSLQS |
| SEQ ID NO: 19 | LCDR3 (Kabat) | FQYRHMPSQT |
| SEQ ID NO: 20 | LCDR1 (Chothia) | SQDISNY |
| SEQ ID NO: 21 | LCDR2 (Chothia) | RAS |
| SEQ ID NO: 22 | LCDR3 (Chothia) | YRHMPSQ |
| SEQ ID NO: 23 | LCDR1 (IMGT) | QDISNY |
| SEQ ID NO: 21 | LCDR2 (IMGT) | RAS |
| SEQ ID NO: 19 | LCDR3 (IMGT) | FQYRHMPSQT |
| SEQ ID NO: 24 | VL | DIQMTQSPSSLSASVGDRVTITCRASQDISNYLAWYQQKPGKAPK LLIYRASSLQSGVPSRFSGSGSGTDFTLTISSLQPEDFATYYCFQ YRHMPSQTFGQGTKVEIK |
| SEQ ID NO: 31 | DNA VL | GACATTCAGATGACCCAGTCCCCGTCGTCCCTGTCCGCATCCGTG GGCGACAGAGTCACCATCACTTGCCGGGCCTCACAGGATATTTCC AACTACCTGGCCTGGTATCAGCAGAAGCCTGGAAAGGCCCCGAAG CTGCTGATCTACCGGGCGTCCTCCTTGCAATCGGGAGTGCCAAGC CGCTTTTCTGGTTCCGGGAGCGGGACTGACTTCACCCTGACTATT AGCAGCCTGCAGCCCGAAGATTTCGCTACCTACTACTGCTTCCAG TACCGGCACATGCCCTCACAAACCTTCGGACAGGGCACCAAAGTC GAGATCAAG |
| SEQ ID NO: 26 | Light Chain | DIQMTQSPSSLSASVGDRVTITCRASQDISNYLAWYQQKPGKAPK LLIYRASSLQSGVPSRFSGSGSGTDFTLTISSLQPEDFATYYCFQ YRHMPSQTFGQGTKVEIKRTVAAPSVFIFPPSDEQLKSGTASVVC LLNNFYPREAKVQWKVDNALQSGNSQESVTEQDSKDSTYSLSSTI TLSKADYEKHKVYACEVTHQGLSSPVTKSFNRGEC |
| SEQ ID NO: 32 | DNA Light Chain | GACATTCAGATGACCCAGTCCCCGTCGTCCCTGTCCGCATCCGTG GGCGACAGAGTCACCATCACTTGCCGGGCCTCACAGGATATTTCC AACTACCTGGCCTGGTATCAGCAGAAGCCTGGAAAGGCCCCGAAG CTGCTGATCTACCGGGCGTCCTCCTTGCAATCGGGAGTGCCAAGC CGCTTTTCTGGTTCCGGGAGCGGGACTGACTTCACCCTGACTATT AGCAGCCTGCAGCCCGAAGATTTCGCTACCTACTACTGCTTCCAG TACCGGCACATGCCCTCACAAACCTTCGGACAGGGCACCAAAGTC GAGATCAAGCGTACGGTGGCCGCTCCCAGCGTGTTCATCTTCCCC CCCAGCGACGAGCAGCTGAAGAGCGGCACCGCCAGCGTGGTGTGC CTGCTGAACAACTTCTACCCCCGGGAGGCCAAGGTGCAGTGGAAG GTGGACAACGCCCTGCAGAGCGGCAACAGCCAGGAGAGCGTCACC GAGCAGGACAGCAAGGACTCCACCTACAGCCTGAGCAGCACCCTG ACCCTGAGCAAGGCCGACTACGAGAAGCATAAGGTGTACGCCTGC GAGGTGACCCACCAGGGCCTGTCCAGCCCCGTGACCAAGAGCTTC AACAGGGGCGAGTGC |

MOR44698D

| | | |
|---|---|---|
| SEQ ID NO: 4 | HCDR1 (Combined) | GYTFTGYHMS |
| SEQ ID NO: 5 | HCDR2 (Combined) | VINPVSGNTVYAQKFQG |
| SEQ ID NO: 6 | HCDR3 (Combined) | IPSYTYAFDY |
| SEQ ID NO: 7 | HCDR1 (Kabat) | GYHMS |
| SEQ ID NO: 5 | HCDR2 (Kabat) | VINPVSGNTVYAQKFQG |
| SEQ ID NO: 6 | HCDR3 (Kabat) | IPSYTYAFDY |
| SEQ ID NO: 8 | HCDR1 (Chothia) | GYTFTGY |
| SEQ ID NO: 9 | HCDR2 (Chothia) | NPVSGN |
| SEQ ID NO: 6 | HCDR3 (Chothia) | IPSYTYAFDY |
| SEQ ID NO: 10 | HCDR1 (IMGT) | GYTFTGYH |
| SEQ ID NO: 11 | HCDR2 (IMGT) | INPVSGNT |
| SEQ ID NO: 12 | HCDR3 (IMGT) | ARIPSYTYAFDY |
| SEQ ID NO: 13 | VH | QVQLVQSGAEVKKPGASVKVSCKASGYTFTGYHMSWVRQAPGQGL EWMGVINPVSGNTVYAQKFQGRVTMTRDTSISTAYMELSRLRSED TAVYYCARIPSYTYAFDYWGQGTLVTVSS |
| SEQ ID NO: 28 | DNA VH | CAAGTGCAACTCGTGCAGTCAGGAGCCGAAGTCAAGAAGCCTGGA GCCTCGGTCAAGGTGTCCTGCAAGGCCAGCGGATACACTTTCACT GGATACCACATGTCGTGGGTCAGACAGGCTCCTGGCCAAGGGCTG GAGTGGATGGGCGTCATCAACCCGGTGTCGGGTAATACCGTGTAC |

TABLE 1-continued

Sequences of Exemplary Monoclonal Antibodies That Bind Human TREM2.

| | | |
|---|---|---|
| | | GCCCAGAAGTTCCAGGGTCGCGTGACCATGACCCGGGATACCTCC ATTAGCACCGCGTACATGGAGCTCAGCCGGTTGAGATCCGAGGAT ACCGCCGTGTACTACTGTGCGCGGATCCCGTCCTACACTTACGCC TTCGACTATTGGGGCCAGGGGACTCTTGTCACCGTGTCCTCG |
| SEQ ID NO: 35 | Heavy Chain | QVQLVQSGAEVKKPGASVKVSCKASGYTFTGYHMSWVRQAPGQGL EWMGVINPVSGNTVYAQKFQGRVTMTRDTSISTAYMELSRLRSED TAVYYCARIPSYTYAFDYWGQGTLVTVSSASTKGPSVFPLAPSSK STSGGTAALGCLVKDYFPEPVTVSWNSGALTSGVHTFPAVLQSSG LYSLSSVVTVPSSSLGTQTYICNVNHKPSNTKVDKRVEPKSCDKT HTCPPCPAPELLGGPSVFLFPPKPKDTLMISRTPEVTCVVVDVSH EDPEVKFNWYVDGVEVHNAKTKPREEQYNSTYRVVSVLTVLHQDW LNGKEYKCKVSNKALPAPIEKTISKAKGQPREPQVYTLPPSREEM TKNQVSLTCLVKGFYPSDIAVEWESNGQPENNYKTTPPVLDSDGS FFLYSKLTVDKSRWQQGNVFSCSVLHEALHSHYTQKSLSLSPGK |
| SEQ ID NO: 36 | DNA Heavy Chain | CAAGTGCAACTCGTGCAGTCAGGAGCCGAAGTCAAGAAGCCTGGA GCCTCGGTCAAGGTGTCCTGCAAGGCCAGCGGATACACTTTCACT GGATACCACATGTCGTGGGTCAGACAGGCTCCTGGCCAAGGGCTG GAGTGGATGGGCGTCATCAACCCGGTGTCGGGTAATACCGTGTAC GCCCAGAAGTTCCAGGGTCGCGTGACCATGACCCGGGATACCTCC ATTAGCACCGCGTACATGGAGCTCAGCCGGTTGAGATCCGAGGAT ACCGCCGTGTACTACTGTGCGCGGATCCCGTCCTACACTTACGCC TTCGACTATTGGGGCCAGGGGACTCTTGTCACCGTGTCCTCGGCC TCCACTAAGGGCCCGTCAGTGTTCCCCCTTGCGCCATCCTCGAAG TCAACCTCCGGAGGAACTGCCGCACTGGGTTGCCTCGTGAAAGAC TATTTCCCGGAACCCGTCACTGTCTCCTGGAACTCAGGAGCGCTC ACCAGCGGAGTGCATACCTTTCCTGCGGTGCTGCAGTCCAGCGGC CTGTACTCCCTGAGCTCCGTCGTGACCGTCCCCTCGTCGTCCCTG GGAACCCAAACCTACATTTGCAACGTCAATCACAAGCCAAGCAAC ACTAAGGTGGACAAGAGAGTGGAGCCCAAGTCCTGCGATAAGACC CACACCTGTCCTCCCTGTCCGGCACCTGAACTGCTTGGTGGACCT TCCGTGTTCCTGTTCCCGCCCAAGCCAAAAGACACCCTGATGATC TCCCGCACTCCGGAAGTCACTTGCGTGGTCGTGGACGTGTCCCAC GAGGACCCCGAGGTCAAGTTTAATTGGTACGTGGACGGAGTGGAA GTGCACAACGCCAAGACCAAGCCGCGGGAAGAACAGTACAACTCC ACCTACCGCGTGGTGTCCGTCCTGACTGTGCTCCACCAGGACTGG CTGAACGGAAAGGAGTACAAGTGCAAAGTGTCCAACAAGGCACTG CCAGCCCCTATCGAAAAGACTATCTCCAAGGCCAAGGGCCAACCT AGGGAGCCCCAGGTGTACACGTTGCCTCCTTCCCGCGAAGAAATG ACTAAGAACCAGGTGTCGCTGACCTGTCTCGTGAAAGGGTTCTAC CCCTCTGACATCGCCGTGGAATGGGAGTCAAACGGACAGCCTGAG AACAACTATAAGACCACACCACCTGTCCTGGACTCCGACGGCTCC TTCTTCCTGTACTCAAAGTTGACCGTGGACAAGTCGCGGTGGCAA CAGGGCAACGTGTTCTCTTGCTCCGTGCTGCACGAAGCCCTGCAC AGCCACTACACCCAAAAGTCGCTCAGCCTCTCCCCCGGAAAG |
| SEQ ID NO: 17 | LCDR1 (Combined) | RASQDISNYLA |
| SEQ ID NO: 18 | LCDR2 (Combined) | RASSLQS |
| SEQ ID NO: 19 | LCDR3 (Combined) | FQYRHMPSQT |
| SEQ ID NO: 17 | LCDR1 (Kabat) | RASQDISNYLA |
| SEQ ID NO: 18 | LCDR2 (Kabat) | RASSLQS |
| SEQ ID NO: 19 | LCDR3 (Kabat) | FQYRHMPSQT |
| SEQ ID NO: 20 | LCDR1 (Chothia) | SQDISNY |
| SEQ ID NO: 21 | LCDR2 (Chothia) | RAS |
| SEQ ID NO: 22 | LCDR3 (Chothia) | YRHMPSQ |
| SEQ ID NO: 23 | LCDR1 (IMGT) | QDISNY |
| SEQ ID NO: 21 | LCDR2 (IMGT) | RAS |
| SEQ ID NO: 19 | LCDR3 (IMGT) | FQYRHMPSQT |
| SEQ ID NO: 24 | VL | DIQMTQSPSSLSASVGDRVTITCRASQDISNYLAWYQQKPGKAPK LLIYRASSLQSGVPSRFSGSGSGTDFTLTISSLQPEDFATYYCFQ YRHMPSQTFGQGTKVEIK |
| SEQ ID NO: 31 | DNA VL | GACATTCAGATGACCCAGTCCCCGTCGTCCCTGTCCGCATCCGTG GGCGACAGAGTCACCATCACTTGCCGGGCCTCACAGGATATTTCC AACTACCTGGCCTGGTATCAGCAGAAGCCTGGAAAGGCCCCGAAG CTGCTGATCTACCGGGCGTCCTCCTTGCAATCGGGAGTGCCAAGC CGCTTTTCTGGTTCCGGGAGCGGGACTGACTTCACCCTGACTATT AGCAGCCTGCAGCCCGAAGATTTCGCTACCTACTACTGCTTCCAG TACCGGCACATGCCCTCACAAACCTTCGGACAGGGCACCAAAGTC GAGATCAAG |
| SEQ ID NO: 26 | Light Chain | DIQMTQSPSSLSASVGDRVTITCRASQDISNYLAWYQQKPGKAPK LLIYRASSLQSGVPSRFSGSGSGTDFTLTISSLQPEDFATYYCFQ YRHMPSQTFGQGTKVEIKRTVAAPSVFIFPPSDEQLKSGTASVVC LLNNFYPREAKVQWKVDNALQSGNSQESVTEQDSKDSTYSLSSTI TLSKADYEKHKVYACEVTHQGLSSPVTKSFNRGEC |
| SEQ ID NO: 32 | DNA Light Chain | GACATTCAGATGACCCAGTCCCCGTCGTCCCTGTCCGCATCCGTG GGCGACAGAGTCACCATCACTTGCCGGGCCTCACAGGATATTTCC AACTACCTGGCCTGGTATCAGCAGAAGCCTGGAAAGGCCCCGAAG |

TABLE 1-continued

| Sequences of Exemplary Monoclonal Antibodies That Bind Human TREM2. | | |
|---|---|---|
| | | CTGCTGATCTACCGGGCGTCCTCCTTGCAATCGGGAGTGCCAAGC CGCTTTTCTGGTTCCGGGAGCGGGACTGACTTCACCCTGACTATT AGCAGCCTGCAGCCCGAAGATTTCGCTACCTACTACTGCTTCCAG TACCGGCACATGCCCTCACAAACCTTCGGACAGGGCACCAAAGTC GAGATCAAGCGTACGGTGGCCGCTCCCAGCGTGTTCATCTTCCCC CCCAGCGACGAGCAGCTGAAGAGCGGCACCGCCAGCGTGGTGTGC CTGCTGAACAACTTCTACCCCCGGGAGGCCAAGGTGCAGTGGAAG GTGGACAACGCCCTGCAGAGCGGCAACAGCCAGGAGAGCGTCACC GAGCAGGACAGCAAGGACTCCACCTACAGCCTGAGCAGCACCCTG ACCCTGAGCAAGGCCGACTACGAGAAGCATAAGGTGTACGCCTGC GAGGTGACCCACCAGGGCCTGTCCAGCCCCGTGACCAAGAGCTTC AACAGGGGCGAGTGC |
| | | MOR44698E |
| SEQ ID NO: 4 | HCDR1 (Combined) | GYTFTGYHMS |
| SEQ ID NO: 5 | HCDR2 (Combined) | VINPVSGNTVYAQKFQG |
| SEQ ID NO: 6 | HCDR3 (Combined) | IPSYTYAFDY |
| SEQ ID NO: 7 | HCDR1 (Kabat) | GYHMS |
| SEQ ID NO: 5 | HCDR2 (Kabat) | VINPVSGNTVYAQKFQG |
| SEQ ID NO: 6 | HCDR3 (Kabat) | IPSYTYAFDY |
| SEQ ID NO: 8 | HCDR1 (Chothia) | GYTFTGY |
| SEQ ID NO: 9 | HCDR2 (Chothia) | NPVSGN |
| SEQ ID NO: 6 | HCDR3 (Chothia) | IPSYTYAFDY |
| SEQ ID NO: 10 | HCDR1 (IMGT) | GYTFTGYH |
| SEQ ID NO: 11 | HCDR2 (IMGT) | INPVSGNT |
| SEQ ID NO: 12 | HCDR3 (IMGT) | ARIPSYTYAFDY |
| SEQ ID NO: 13 | VH | QVQLVQSGAEVKKPGASVKVSCKASGYTFTGYHMSWVRQAPGQGL EWMGVINPVSGNTVYAQKFQGRVTMTRDTSISTAYMELSRLRSED TAVYYCARIPSYTYAFDYWGQGTLVTVSS |
| SEQ ID NO: 28 | DNA VH | CAAGTGCAACTCGTGCAGTCAGGAGCCGAAGTCAAGAAGCCTGGA GCCTCGGTCAAGGTGTCCTGCAAGGCCAGCGGATACACTTTCACT GGATACCACATGTCGTGGGTCAGACAGGCTCCTGGCCAAGGGCTG GAGTGGATGGGCGTCATCAACCCGGTGTCGGGTAATACCGTGTAC GCCCAGAAGTTCCAGGGTCGCGTGACCATGACCCGGGATACCTCC ATTAGCACCGCGTACATGGAGCTCAGCCGGTTGAGATCCGAGGAT ACCGCCGTGTACTACTGTGCGCGGATCCCGTCCTACACTTACGCC TTCGACTATTGGGGCCAGGGGACTCTTGTCACCGTGTCCTCG |
| SEQ ID NO: 37 | Heavy Chain | QVQLVQSGAEVKKPGASVKVSCKASGYTFTGYHMSWVRQAPGQGL EWMGVINPVSGNTVYAQKFQGRVTMTRDTSISTAYMELSRLRSED TAVYYCARIPSYTYAFDYWGQGTLVTVSSASTKGPSVFPLAPSSK STSGGTAALGCLVKDYFPEPVTVSWNSGALTSGVHTFPAVLQSSG LYSLSSVVTVPSSSLGTQTYICNVNHKPSNTKVDKRVEPKSCDKT HTCPPCPAPELLGGPSVFLFPPKPKDTLMISRTPEVTCVVVAVSH EDPEVKFNWYVDGVEVHNAKTKPREEQYNSTYRVVSVLTVLHQDW LNGKEYKCKVSNKALAAPIEKTISKAKGQPREPQVYTLPPSREEM TKNQVSLTCLVKGFYPSDIAVEWESNGQPENNYKTTPPVLDSDGS FFLYSKLTVDKSRWQQGNVFSCSVLHEALHSHYTQKSLSLSPGK |
| SEQ ID NO: 38 | DNA Heavy Chain | CAAGTGCAACTCGTGCAGTCAGGAGCCGAAGTCAAGAAGCCTGGA GCCTCGGTCAAGGTGTCCTGCAAGGCCAGCGGATACACTTTCACT GGATACCACATGTCGTGGGTCAGACAGGCTCCTGGCCAAGGGCTG GAGTGGATGGGCGTCATCAACCCGGTGTCGGGTAATACCGTGTAC GCCCAGAAGTTCCAGGGTCGCGTGACCATGACCCGGGATACCTCC ATTAGCACCGCGTACATGGAGCTCAGCCGGTTGAGATCCGAGGAT ACCGCCGTGTACTACTGTGCGCGGATCCCGTCCTACACTTACGCC TTCGACTATTGGGGCCAGGGGACTCTTGTCACCGTGTCCTCGGCC TCCACTAAGGGCCCGTCAGTGTTCCCCCTTGCGCCATCCTCGAAG TCAACCTCCGGAGGAACTGCCGCACTGGGTTGCCTCGTGAAAGAC TATTTCCCGGAACCCGTCACTGTCTCCTGGAACTCAGGAGCGCTC ACCAGCGGAGTGCATACCTTTCCTGCGGTGCTGCAGTCCAGCGGC CTGTACTCCCTGAGCTCCGTCGTGACCGTCCCCTCGTCGTCCCTG GGAACCCAAACCTACATTTGCAACGTCAATCACAAGCCAAGCAAC ACTAAGGTGGACAAGAGAGTGGAGCCCAAGTCCTGCGATAAGACC CACACCTGTCCTCCCTGTCCGGCACCTGAACTGCTTGGTGGACCT TCCGTGTTCCTGTTCCCGCCCAAGCCAAAAGACACCCTGATGATC TCCCGCACTCCGGAAGTCACTTGCGTGGTCGTGGCCGTGTCCCAC GAGGACCCCGAGGTCAAGTTTAATTGGTACGTGGACGGAGTGGAA GTGCACAACGCCAAGACCAAGCCGCGGGAAGAACAGTACAACTCC ACCTACCGCGTGGTGTCCGTCCTGACTGTGCTCCACCAGGACTGG CTGAACGGAAAGGAGTACAAGTGCAAAGTGTCCAACAAGGCACTG GCTGCCCCTATCGAAAAGACTATCTCCAAGGCCAAGGGCCAACCT AGGGAGCCCCAGGTGTACACGTTGCCTCCTTCCCGCGAAGAAATG ACTAAGAACCAGGTGTCGCTGACCTGTCTCGTGAAAGGGTTCTAC CCCTCTGACATCGCCGTGGAATGGGAGTCAAACGGACAGCCTGAG AACAACTATAAGACCACACCACCTGTCCTGGACTCCGACGGCTCC |

TABLE 1-continued

| Sequences of Exemplary Monoclonal Antibodies That Bind Human TREM2. | | |
|---|---|---|
| | | TTCTTCCTGTACTCAAAGTTGACCGTGGACAAGTCGCGGTGGCAA CAGGGCAACGTGTTCTCTTGCTCCGTGCTGCACGAAGCCCTGCAC AGCCACTACACCCAAAAGTCGCTCAGCCTCTCCCCCGGAAAG |
| SEQ ID NO: 17 | LCDR1 (Combined) | RASQDISNYLA |
| SEQ ID NO: 18 | LCDR2 (Combined) | RASSLQS |
| SEQ ID NO: 19 | LCDR3 (Combined) | FQYRHMPSQT |
| SEQ ID NO: 17 | LCDR1 (Kabat) | RASQDISNYLA |
| SEQ ID NO: 18 | LCDR2 (Kabat) | RASSLQS |
| SEQ ID NO: 19 | LCDR3 (Kabat) | FQYRHMPSQT |
| SEQ ID NO: 20 | LCDR1 (Chothia) | SQDISNY |
| SEQ ID NO: 21 | LCDR2 (Chothia) | RAS |
| SEQ ID NO: 22 | LCDR3 (Chothia) | YRHMPSQ |
| SEQ ID NO: 23 | LCDR1 (IMGT) | QDISNY |
| SEQ ID NO: 21 | LCDR2 (IMGT) | RAS |
| SEQ ID NO: 19 | LCDR3 (IMGT) | FQYRHMPSQT |
| SEQ ID NO: 24 | VL | DIQMTQSPSSLSASVGDRVTITCRASQDISNYLAWYQQKPGKAPK LLIYRASSLQSGVPSRFSGSGSGTDFTLTISSLQPEDFATYYCFQ YRHMPSQTFGQGTKVEIK |
| SEQ ID NO: 31 | DNA VL | GACATTCAGATGACCCAGTCCCCGTCGTCCCTGTCCGCATCCGTG GGCGACAGAGTCACCATCACTTGCCGGGCCTCACAGGATATTTCC AACTACCTGGCCTGGTATCAGCAGAAGCCTGGAAAGGCCCCGAAG CTGCTGATCTACCGGGCGTCCTCCTTGCAATCGGGAGTGCCAAGC CGCTTTTCTGGTTCCGGGAGCGGGACTGACTTCACCCTGACTATT AGCAGCCTGCAGCCCGAAGATTTCGCTACCTACTACTGCTTCCAG TACCGGCACATGCCCTCACAAACCTTCGGACAGGGCACCAAAGTC GAGATCAAG |
| SEQ ID NO: 26 | Light Chain | DIQMTQSPSSLSASVGDRVTITCRASQDISNYLAWYQQKPGKAPK LLIYRASSLQSGVPSRFSGSGSGTDFTLTISSLQPEDFATYYCFQ YRHMPSQTFGQGTKVEIKRTVAAPSVFIFPPSDEQLKSGTASVVC LLNNFYPREAKVQWKVDNALQSGNSQESVTEQDSKDSTYSLSSTI TLSKADYEKHKVYACEVTHQGLSSPVTKSFNRGEC |
| SEQ ID NO: 32 | DNA Light Chain | GACATTCAGATGACCCAGTCCCCGTCGTCCCTGTCCGCATCCGTG GGCGACAGAGTCACCATCACTTGCCGGGCCTCACAGGATATTTCC AACTACCTGGCCTGGTATCAGCAGAAGCCTGGAAAGGCCCCGAAG CTGCTGATCTACCGGGCGTCCTCCTTGCAATCGGGAGTGCCAAGC CGCTTTTCTGGTTCCGGGAGCGGGACTGACTTCACCCTGACTATT AGCAGCCTGCAGCCCGAAGATTTCGCTACCTACTACTGCTTCCAG TACCGGCACATGCCCTCACAAACCTTCGGACAGGGCACCAAAGTC GAGATCAAGCGTACGGTGGCCGCTCCCAGCGTGTTCATCTTCCCC CCCAGCGACGAGCAGCTGAAGAGCGGCACCGCCAGCGTGGTGTGC CTGCTGAACAACTTCTACCCCCGGGAGGCCAAGGTGCAGTGGAAG GTGGACAACGCCCTGCAGAGCGGCAACAGCCAGGAGAGCGTCACC GAGCAGGACAGCAAGGACTCCACCTACAGCCTGAGCAGCACCCTG ACCCTGAGCAAGGCCGACTACGAGAAGCATAAGGTGTACGCCTGC GAGGTGACCCACCAGGGCCTGTCCAGCCCCGTGACCAAGAGCTTC AACAGGGGCGAGTGC |
| | MOR44698F | |
| SEQ ID NO: 4 | HCDR1 (Combined) | GYTFTGYHMS |
| SEQ ID NO: 5 | HCDR2 (Combined) | VINPVSGNTVYAQKFQG |
| SEQ ID NO: 6 | HCDR3 (Combined) | IPSYTYAFDY |
| SEQ ID NO: 7 | HCDR1 (Kabat) | GYHMS |
| SEQ ID NO: 5 | HCDR2 (Kabat) | VINPVSGNTVYAQKFQG |
| SEQ ID NO: 6 | HCDR3 (Kabat) | IPSYTYAFDY |
| SEQ ID NO: 8 | HCDR1 (Chothia) | GYTFTGY |
| SEQ ID NO: 9 | HCDR2 (Chothia) | NPVSGN |
| SEQ ID NO: 6 | HCDR3 (Chothia) | IPSYTYAFDY |
| SEQ ID NO: 10 | HCDR1 (IMGT) | GYTFTGYH |
| SEQ ID NO: 11 | HCDR2 (IMGT) | INPVSGNT |
| SEQ ID NO: 12 | HCDR3 (IMGT) | ARIPSYTYAFDY |
| SEQ ID NO: 13 | VH | QVQLVQSGAEVKKPGASVKVSCKASGYTFTGYHMSWVRQAPGQGL EWMGVINPVSGNTVYAQKFQGRVTMTRDTSISTAYMELSRLRSED TAVYYCARIPSYTYAFDYWGQGTLVTVSS |
| SEQ ID NO: 28 | DNA VH | CAAGTGCAACTCGTGCAGTCAGGAGCCGAAGTCAAGAAGCCTGGA GCCTCGGTCAAGGTGTCCTGCAAGGCCAGCGGATACACTTTCACT GGATACCACATGTCGTGGGTCAGACAGGCTCCTGGCCAAGGGCTG GAGTGGATGGGCGTCATCAACCCGGTGTCGGGTAATACCGTGTAC GCCCAGAAGTTCCAGGGTCGCGTGACCATGACCCGGGATACCTCC ATTAGCACCGCGTACATGGAGCTCAGCCGGTTGAGATCCGAGGAT ACCGCCGTGTACTACTGTGCGCGGATCCCGTCCTACACTTACGCC TTCGACTATTGGGGCCAGGGGACTCTTGTCACCGTGTCCTCG |

TABLE 1-continued

Sequences of Exemplary Monoclonal Antibodies That Bind Human TREM2.

| | | |
|---|---|---|
| SEQ ID NO: 39 | Heavy Chain | QVQLVQSGAEVKKPGASVKVSCKASGYTFTGYHMSWVRQAPGQGL<br>EWMGVINPVSGNTVYAQKFQGRVTMTRDTSISTAYMELSRLRSED<br>TAVYYCARIPSYTYAFDYWGQGTLVTVSSASTKGPSVFPLAPSSK<br>STSGGTAALGCLVKDYFPEPVTVSWNSGALTSGVHTFPAVLQSSG<br>LYSLSSVVTVPSSSLGTQTYICNVNHKPSNTKVDKRVEPKSCDKT<br>HTCPPCPAPELLGGPSVFLFPPKPKDTLYITREPEVTCVVVDVSH<br>EDPEVKFNWYVDGVEVHNAKTKPREEQYNSTYRVVSVLTVLHQDW<br>LNGKEYKCKVSNKALPAPIEKTISKAKGQPREPQVYTLPPSREEM<br>TKNQVSLTCLVKGFYPSDIAVEWESNGQPENNYKTTPPVLDSDGS<br>FFLYSKLTVDKSRWQQGNVFSCSVMHEALHNHYTQKSLSLSPGK |
| SEQ ID NO: 40 | DNA Heavy Chain | CAAGTGCAACTCGTGCAGTCAGGAGCCGAAGTCAAGAAGCCTGGA<br>GCCTCGGTCAAGGTGTCCTGCAAGGCCAGCGGATACACTTTCACT<br>GGATACCACATGTCGTGGGTCAGACAGGCTCCTGGCCAAGGGCTG<br>GAGTGGATGGGCGTCATCAACCCGGTGTCGGGTAATACCGTGTAC<br>GCCCAGAAGTTCCAGGGTCGCGTGACCATGACCCGGGATACCTCC<br>ATTAGCACCGCGTACATGGAGCTCAGCCGGTTGAGATCCGAGGAT<br>ACCGCCGTGTACTACTGTGCGCGGATCCCGTCCTACACTTACGCC<br>TTCGACTATTGGGGCCAGGGGACTCTTGTCACCGTGTCCTCGGCC<br>TCCACTAAGGGCCCGTCAGTGTTCCCCCTTGCGCCATCCTCGAAG<br>TCAACCTCCGGAGGAACTGCCGCACTGGGTTGCCTCGTGAAAGAC<br>TATTTCCCGGAACCCGTCACTGTCTCCTGGAACTCAGGAGCGCTC<br>ACCAGCGGAGTGCATACCTTTCCTGCGGTGCTGCAGTCCAGCGGC<br>CTGTACTCCCTGAGCTCCGTCGTGACCGTCCCCTCGTCGTCCCTG<br>GGAACCCAAACCTACATTTGCAACGTCAATCACAAGCCAAGCAAC<br>ACTAAGGTGGACAAGAGAGTGGAGCCCAAGTCCTGCGATAAGACC<br>CACACCTGTCCTCCCTGTCCGGCACCTGAACTGCTTGGTGGACCT<br>TCCGTGTTCCTGTTCCCGCCCAAGCCAAAAGACACCCTGTATATC<br>ACTCGCGAACCGGAAGTCACTTGCGTGGTCGTGGACGTGTCCCAC<br>GAGGACCCCGAGGTCAAGTTTAATTGGTACGTGGACGGAGTGGAA<br>GTGCACAACGCCAAGACCAAGCCGCGGGAAGAACAGTACAACTCC<br>ACCTACCGCGTGGTGTCCGTCCTGACTGTGCTCCACCAGGACTGG<br>CTGAACGGAAAGGAGTACAAGTGCAAAGTGTCCAACAAGGCACTG<br>CCAGCCCCTATCGAAAAGACTATCTCCAAGGCCAAGGGCCAACCT<br>AGGGAGCCCCAGGTGTACACGTTGCCTCCTTCCCGCGAAGAAATG<br>ACTAAGAACCAGGTGTCGCTGACCTGTCTCGTGAAAGGGTTCTAC<br>CCCTCTGACATCGCCGTGGAATGGGAGTCAAACGGACAGCCTGAG<br>AACAACTATAAGACCACACCACCTGTCCTGGACTCCGACGGCTCC<br>TTCTTCCTGTACTCAAAGTTGACCGTGGACAAGTCGCGGTGGCAA<br>CAGGGCAACGTGTTCTCTTGCTCCGTGATGCACGAAGCCCTGCAC<br>AACCACTACACCCAAAAGTCGCTCAGCCTCTCCCCCGGAAAG |
| SEQ ID NO: 17 (Combined) | LCDR1 | RASQDISNYLA |
| SEQ ID NO: 18 (Combined) | LCDR2 | RASSLQS |
| SEQ ID NO: 19 (Combined) | LCDR3 | FQYRHMPSQT |
| SEQ ID NO: 17 | LCDR1 (Kabat) | RASQDISNYLA |
| SEQ ID NO: 18 | LCDR2 (Kabat) | RASSLQS |
| SEQ ID NO: 19 | LCDR3 (Kabat) | FQYRHMPSQT |
| SEQ ID NO: 20 | LCDR1 (Chothia) | SQDISNY |
| SEQ ID NO: 21 | LCDR2 (Chothia) | RAS |
| SEQ ID NO: 22 | LCDR3 (Chothia) | YRHMPSQ |
| SEQ ID NO: 23 | LCDR1 (IMGT) | QDISNY |
| SEQ ID NO: 21 | LCDR2 (IMGT) | RAS |
| SEQ ID NO: 19 | LCDR3 (IMGT) | FQYRHMPSQT |
| SEQ ID NO: 24 | VL | DIQMTQSPSSLSASVGDRVTITCRASQDISNYLAWYQQKPGKAPK<br>LLIYRASSLQSGVPSRFSGSGSGTDFTLTISSLQPEDFATYYCFQ<br>YRHMPSQTFGQGTKVEIK |
| SEQ ID NO: 31 | DNA VL | GACATTCAGATGACCCAGTCCCCGTCGTCCCTGTCCGCATCCGTG<br>GGCGACAGAGTCACCATCACTTGCCGGGCCTCACAGGATATTTCC<br>AACTACCTGGCCTGGTATCAGCAGAAGCCTGGAAAGGCCCCGAAG<br>CTGCTGATCTACCGGGCGTCCTCCTTGCAATCGGGAGTGCCAAGC<br>CGCTTTTCTGGTTCCGGGAGCGGGACTGACTTCACCCTGACTATT<br>AGCAGCCTGCAGCCCGAAGATTTCGCTACCTACTACTGCTTCCAG<br>TACCGGCACATGCCCTCACAAACCTTCGGACAGGGCACCAAAGTC<br>GAGATCAAG |
| SEQ ID NO: 26 | Light Chain | DIQMTQSPSSLSASVGDRVTITCRASQDISNYLAWYQQKPGKAPK<br>LLIYRASSLQSGVPSRFSGSGSGTDFTLTISSLQPEDFATYYCFQ<br>YRHMPSQTFGQGTKVEIKRTVAAPSVFIFPPSDEQLKSGTASVVC<br>LLNNFYPREAKVQWKVDNALQSGNSQESVTEQDSKDSTYSLSSTI<br>TLSKADYEKHKVYACEVTHQGLSSPVTKSFNRGEC |
| SEQ ID NO: 32 | DNA Light Chain | GACATTCAGATGACCCAGTCCCCGTCGTCCCTGTCCGCATCCGTG<br>GGCGACAGAGTCACCATCACTTGCCGGGCCTCACAGGATATTTCC<br>AACTACCTGGCCTGGTATCAGCAGAAGCCTGGAAAGGCCCCGAAG<br>CTGCTGATCTACCGGGCGTCCTCCTTGCAATCGGGAGTGCCAAGC<br>CGCTTTTCTGGTTCCGGGAGCGGGACTGACTTCACCCTGACTATT<br>AGCAGCCTGCAGCCCGAAGATTTCGCTACCTACTACTGCTTCCAG<br>TACCGGCACATGCCCTCACAAACCTTCGGACAGGGCACCAAAGTC |

TABLE 1-continued

| Sequences of Exemplary Monoclonal Antibodies That Bind Human TREM2. | | |
|---|---|---|
| | | GAGATCAAGCGTACGGTGGCCGCTCCCAGCGTGTTCATCTTCCCC CCCAGCGACGAGCAGCTGAAGAGCGGCACCGCCAGCGTGGTGTGC CTGCTGAACAACTTCTACCCCCGGGAGGCCAAGGTGCAGTGGAAG GTGGACAACGCCCTGCAGAGCGGCAACAGCCAGGAGAGCGTCACC GAGCAGGACAGCAAGGACTCCACCTACAGCCTGAGCAGCACCCTG ACCCTGAGCAAGGCCGACTACGAGAAGCATAAGGTGTACGCCTGC GAGGTGACCCACCAGGGCCTGTCCAGCCCCGTGACCAAGAGCTTC AACAGGGGCGAGTGC |
| | | MOR44746A |
| SEQ ID NO: 41 | HCDR1 (Combined) | GDSVSSSSAAWN |
| SEQ ID NO: 42 | HCDR2 (Combined) | HIGYRSKWYNEYAVSVKS |
| SEQ ID NO: 43 | HCDR3 (Combined) | GMYGSVPYKEGYYFDI |
| SEQ ID NO: 44 | HCDR1 (Kabat) | SSSAAWN |
| SEQ ID NO: 42 | HCDR2 (Kabat) | HIGYRSKWYNEYAVSVKS |
| SEQ ID NO: 43 | HCDR3 (Kabat) | GMYGSVPYKEGYYFDI |
| SEQ ID NO: 45 | HCDR1 (Chothia) | GDSVSSSSA |
| SEQ ID NO: 46 | HCDR2 (Chothia) | GYRSKWY |
| SEQ ID NO: 43 | HCDR3 (Chothia) | GMYGSVPYKEGYYFDI |
| SEQ ID NO: 47 | HCDR1 (IMGT) | GDSVSSSSAA |
| SEQ ID NO: 48 | HCDR2 (IMGT) | IGYRSKWYN |
| SEQ ID NO: 49 | HCDR3 (IMGT) | ARGMYGSVPYKEGYYFDI |
| SEQ ID NO: 50 | VH | QVQLQQSGPGLVKPSQTLSLTCAISGDSVSSSSAAWNWIRQSPSR GLEWLGHIGYRSKWYNEYAVSVKSRITINPDTSKNQFSLQLNSVT PEDTAVYYCARGMYGSVPYKEGYYFDIWGQGTLVTVSS |
| SEQ ID NO: 51 | DNA VH | CAGGTGCAATTGCAGCAGAGCGGTCCGGGCCTGGTGAAACCGAGC CAGACCCTGAGCCTGACCTGCGCGATTTCCGGAGATAGCGTGAGC TCTTCTTCTGCTGCTTGGAACTGGATTCGTCAGAGCCCGAGCCGT GGCCTCGAGTGGCTGGGCCATATCGGTTACCGTAGCAAATGGTAC AACGAATATGCCGTGAGCGTGAAAAGCCGCATTACCATTAACCCG GATACTTCGAAAAACCAGTTTAGCCTGCAACTGAACAGCGTGACC CCGGAAGATACGGCCGTGTATTATTGCGCGCGTGGTATGTACGGT TCTGTTCCCTACAAAGAAGGTTACTACTTCGATATTTGGGGCCAA GGCACCCTGGTGACTGTTAGCTCA |
| SEQ ID NO: 52 | Heavy Chain | QVQLQQSGPGLVKPSQTLSLTCAISGDSVSSSSAAWNWIRQSPSR GLEWLGHIGYRSKWYNEYAVSVKSRITINPDTSKNQFSLQLNSVT PEDTAVYYCARGMYGSVPYKEGYYFDIWGQGTLVTVSSASTKGPS VFPLAPSSKSTSGGTAALGCLVKDYFPEPVTVSWNSGALTSGVHT FPAVLQSSGLYSLSSVVTVPSSSLGTQTYICNVNHKPSNTKVDKR VEPKSCDKTHTCPPCPAPEAAGGPSVFLFPPKPKDTLMISRTPEV TCVVVDVSHEDPEVKFNWYVDGVEVHNAKTKPREEQYNSTYRVVS VLTVLHQDWLNGKEYKCKVSNKALPAPIEKTISKAKGQPREPQVY TLPPSREEMTKNQVSLTCLVKGFYPSDIAVEWESNGQPENNYKTT PPVLDSDGSFFLYSKLTVDKSRWQQGNVFSCSVMHEALHNHYTQK SLSLSPGK |
| SEQ ID NO: 53 | DNA Heavy Chain | CAGGTGCAATTGCAGCAGAGCGGTCCGGGCCTGGTGAAACCGAGC CAGACCCTGAGCCTGACCTGCGCGATTTCCGGAGATAGCGTGAGC TCTTCTTCTGCTGCTTGGAACTGGATTCGTCAGAGCCCGAGCCGT GGCCTCGAGTGGCTGGGCCATATCGGTTACCGTAGCAAATGGTAC AACGAATATGCCGTGAGCGTGAAAAGCCGCATTACCATTAACCCG GATACTTCGAAAAACCAGTTTAGCCTGCAACTGAACAGCGTGACC CCGGAAGATACGGCCGTGTATTATTGCGCGCGTGGTATGTACGGT TCTGTTCCCTACAAAGAAGGTTACTACTTCGATATTTGGGGCCAA GGCACCCTGGTGACTGTTAGCTCAGCCTCCACCAAGGGTCCATCG GTCTTCCCCCTGGCACCCTCCTCCAAGAGCACCTCTGGGGGCACA GCGGCCCTGGGCTGCCTGGTCAAGGACTACTTCCCCGAACCGGTG ACGGTGTCGTGGAACTCAGGCGCCCTGACCAGCGGCGTGCACACC TTCCCGGCTGTCCTACAGTCCTCAGGACTCTACTCCCTCAGCAGC GTGGTGACCGTGCCCTCCAGCAGCTTGGGCACCCAGACCTACATC TGCAACGTGAATCACAAGCCCAGCAACACCAAGGTGGACAAGAGA GTTGAGCCCAAATCTTGTGACAAAACTCACACATGCCCACCGTGC CCAGCACCTGAAGCAGCGGGGGGACCGTCAGTCTTCCTCTTCCCC CCAAAACCCAAGGACACCCTCATGATCTCCCGGACCCCTGAGGTC ACATGCGTGGTGGTGGACGTGAGCCACGAAGACCCTGAGGTCAAG TTCAACTGGTACGTGGACGGCGTGGAGGTGCATAATGCCAAGACA AAGCCGCGGGAGGAGCAGTACAACAGCACGTACCGGGTGGTCAGC GTCCTCACCGTCCTGCACCAGGACTGGCTGAATGGCAAGGAGTAC AAGTGCAAGGTCTCCAACAAAGCCCTCCCAGCCCCCATCGAGAAA ACCATCTCCAAAGCCAAAGGGCAGCCCCGAGAACCACAGGTGTAC ACCCTGCCCCCATCCCGGGAGGAGATGACCAAGAACCAGGTCAGC CTGACCTGCCTGGTCAAAGGCTTCTATCCCAGCGACATCGCCGTG GAGTGGGAGAGCAATGGGCAGCCGGAGAACAACTACAAGACCACG CCTCCCGTGCTGGACTCCGACGGCTCCTTCTTCCTCTACAGCAAG CTCACCGTGGACAAGAGCAGGTGGCAGCAGGGGAACGTCTTCTCA |

TABLE 1-continued

Sequences of Exemplary Monoclonal Antibodies That Bind Human TREM2.

| | | |
|---|---|---|
| | | TGCTCCGTGATGCATGAGGCTCTGCACAACCACTACACGCAGAAG AGCCTCTCCCTGTCTCCGGGTAAA |
| SEQ ID NO: 54 | LCDR1 (Combined) | RASQGISSDLN |
| SEQ ID NO: 55 | LCDR2 (Combined) | AASNLQS |
| SEQ ID NO: 56 | LCDR3 (Combined) | QQYTDESMT |
| SEQ ID NO: 54 | LCDR1 (Kabat) | RASQGISSDLN |
| SEQ ID NO: 55 | LCDR2 (Kabat) | AASNLQS |
| SEQ ID NO: 56 | LCDR3 (Kabat) | QQYTDESMT |
| SEQ ID NO: 57 | LCDR1 (Chothia) | SQGISSD |
| SEQ ID NO: 58 | LCDR2 (Chothia) | AAS |
| SEQ ID NO: 59 | LCDR3 (Chothia) | YTDESM |
| SEQ ID NO: 60 | LCDR1 (IMGT) | QGISSD |
| SEQ ID NO: 58 | LCDR2 (IMGT) | AAS |
| SEQ ID NO: 56 | LCDR3 (IMGT) | QQYTDESMT |
| SEQ ID NO: 61 | VL | DIQMTQSPSSLSASVGDRVTITCRASQGISSDLNWYQQKPGKAPK LLIYAASNLQSGVPSRFSGSGSGTDFTLTISSLQPEDFATYYCQQ YTDESMTFGQGTKVEIK |
| SEQ ID NO: 62 | DNA VL | GATATCCAGATGACCCAGAGCCCGAGCAGCCTGAGCGCCAGCGTG GGCGATCGCGTGACCATTACCTGCAGAGCCAGCCAGGGTATTTCT TCTGACCTGAACTGGTACCAGCAGAAACCGGGCAAAGCGCCGAAA CTATTAATCTACGCTGCTTCTAACCTGCAAAGCGGCGTGCCGAGC CGCTTTAGCGGCAGCGGATCCGGCACCGATTTCACCCTGACCATT AGCTCTCTGCAACCGGAAGACTTTGCGACCTATTATTGCCAGCAG TACACTGACGAATCTATGACCTTTGGCCAGGGCACGAAAGTTGAA ATTAAA |
| SEQ ID NO: 63 | Light Chain | DIQMTQSPSSLSASVGDRVTITCRASQGISSDLNWYQQKPGKAPK LLIYAASNLQSGVPSRFSGSGSGTDFTLTISSLQPEDFATYYCQQ YTDESMTFGQGTKVEIKRTVAAPSVFIFPPSDEQLKSGTASVVCL LNNFYPREAKVQWKVDNALQSGNSQESVTEQDSKDSTYSLSSTLT LSKADYEKHKVYACEVTHQGLSSPVTKSFNRGEC |
| SEQ ID NO: 64 | DNA Light Chain | GATATCCAGATGACCCAGAGCCCGAGCAGCCTGAGCGCCAGCGTG GGCGATCGCGTGACCATTACCTGCAGAGCCAGCCAGGGTATTTCT TCTGACCTGAACTGGTACCAGCAGAAACCGGGCAAAGCGCCGAAA CTATTAATCTACGCTGCTTCTAACCTGCAAAGCGGCGTGCCGAGC CGCTTTAGCGGCAGCGGATCCGGCACCGATTTCACCCTGACCATT AGCTCTCTGCAACCGGAAGACTTTGCGACCTATTATTGCCAGCAG TACACTGACGAATCTATGACCTTTGGCCAGGGCACGAAAGTTGAA ATTAAACGTACGGTGGCCGCTCCCAGCGTGTTCATCTTCCCCCCC AGCGACGAGCAGCTGAAGAGCGGCACCGCCAGCGTGGTGTGCCTG CTGAACAACTTCTACCCCCGGGAGGCCAAGGTGCAGTGGAAGGTG GACAACGCCCTGCAGAGCGGCAACAGCCAGGAAAGCGTCACCGAG CAGGACAGCAAGGACTCCACCTACAGCCTGAGCAGCACCCTGACC CTGAGCAAGGCCGACTACGAGAAGCACAAGGTGTACGCCTGCGAG GTGACCCACCAGGGCCTGTCCAGCCCCGTGACCAAGAGCTTCAAC CGGGGCGAGTGT |
| | | MOR44746B |
| SEQ ID NO: 41 | HCDR1 (Combined) | GDSVSSSSAAWN |
| SEQ ID NO: 42 | HCDR2 (Combined) | HIGYRSKWYNEYAVSVKS |
| SEQ ID NO: 43 | HCDR3 (Combined) | GMYGSVPYKEGYYFDI |
| SEQ ID NO: 44 | HCDR1 (Kabat) | SSSAAWN |
| SEQ ID NO: 42 | HCDR2 (Kabat) | HIGYRSKWYNEYAVSVKS |
| SEQ ID NO: 43 | HCDR3 (Kabat) | GMYGSVPYKEGYYFDI |
| SEQ ID NO: 45 | HCDR1 (Chothia) | GDSVSSSSA |
| SEQ ID NO: 46 | HCDR2 (Chothia) | GYRSKWY |
| SEQ ID NO: 43 | HCDR3 (Chothia) | GMYGSVPYKEGYYFDI |
| SEQ ID NO: 47 | HCDR1 (IMGT) | GDSVSSSSAA |
| SEQ ID NO: 48 | HCDR2 (IMGT) | IGYRSKWYN |
| SEQ ID NO: 49 | HCDR3 (IMGT) | ARGMYGSVPYKEGYYFDI |
| SEQ ID NO: 50 | VH | QVQLQQSGPGLVKPSQTLSLTCAISGDSVSSSSAAWNWIRQSPSR GLEWLGHIGYRSKWYNEYAVSVKSRITINPDTSKNQFSLQLNSVT PEDTAVYYCARGMYGSVPYKEGYYFDIWGQGTLVTVSS |
| SEQ ID NO: 65 | DNA VH | CAAGTGCAACTCCAGCAGTCAGGACCGGGGTTGGTCAAGCCTTCG CAGACCCTGTCCCTCACTTGCGCCATTAGCGGAGATTCGGTGTCG TCGTCGTCAGCCGCCTGGAACTGGATTAGACAGTCCCCTTCCCGA GGGCTGGAGTGGCTGGGCCACATCGGATACCGCAGCAAGTGGTAC AACGAATACGCCGTCAGCGTGAAGTCACGCATCACCATCAACCCG GATACTAGCAAGAACCAGTTCAGCCTCCAGTTGAACTCCGTGACC CCGGAGGATACCGCCGTGTACTACTGTGCGCGGGGCATGTACGGA TCCGTGCCGTACAAGGAGGGATACTACTTCGACATTTGGGGCCAG GGGACTCTTGTCACCGTGTCCTCG |

TABLE 1-continued

| Sequences of Exemplary Monoclonal Antibodies That Bind Human TREM2. | | |
|---|---|---|
| SEQ ID NO: 66 | Heavy Chain | QVQLQQSGPGLVKPSQTLSLTCAISGDSVSSSSAAWNWIRQSPSR<br>GLEWLGHIGYRSKWYNEYAVSVKSRITINPDTSKNQFSLQLNSVT<br>PEDTAVYYCARGMYGSVPYKEGYYFDIWGQGTLVTVSSASTKGPS<br>VFPLAPSSKSTSGGTAALGCLVKDYFPEPVTVSWNSGALTSGVHT<br>FPAVLQSSGLYSLSSVVTVPSSSLGTQTYICNVNHKPSNTKVDKR<br>VEPKSCDKTHTCPPCPAPELLGGPSVFLFPPKPKDTLMISRTPEV<br>TCVVVDVSHEDPEVKFNWYVDGVEVHNAKTKPREEQYNSTYRVVS<br>VLTVLHQDWLNGKEYKCKVSNKALPAPIEKTISKAKGQPREPQVY<br>TLPPSREEMTKNQVSLTCLVKGFYPSDIAVEWESNGQPENNYKTT<br>PPVLDSDGSFFLYSKLTVDKSRWQQGNVFSCSVMHEALHNHYTQK<br>SLSLSPGK |
| SEQ ID NO: 67 | DNA Heavy Chain | CAAGTGCAACTCCAGCAGTCAGGACCGGGGTTGGTCAAGCCTTCG<br>CAGACCCTGTCCCTCACTTGCGCCATTAGCGGAGATTCGGTGTCG<br>TCGTCGTCAGCCGCCTGGAACTGGATTAGACAGTCCCCTTCCCGA<br>GGGCTGGAGTGGCTGGGCCACATCGGATACCGCAGCAAGTGGTAC<br>AACGAATACGCCGTCAGCGTGAAGTCACGCATCACCATCAACCCG<br>GATACTAGCAAGAACCAGTTCAGCCTCCAGTTGAACTCCGTGACC<br>CCGGAGGATACCGCCGTGTACTACTGTGCGCGGGGCATGTACGGA<br>TCCGTGCCGTACAAGGAGGGATACTACTTCGACATTTGGGGCCAG<br>GGGACTCTTGTCACCGTGTCCTCGGCCTCCACTAAGGGCCCAAGT<br>GTGTTTCCCCTGGCCCCCAGCAGCAAGTCTACTTCCGGCGGAACT<br>GCTGCCCTGGGTTGCCTGGTGAAGGACTACTTCCCCGAGCCCGTG<br>ACAGTGTCCTGGAACTCTGGGGCTCTGACTTCCGGCGTGCACACC<br>TTCCCCGCCGTGCTGCAGAGCAGCGGCCTGTACAGCCTGAGCAGC<br>GTGGTGACAGTGCCCTCCAGCTCTCTGGGAACCCAGACCTATATC<br>TGCAACGTGAACCACAAGCCCAGCAACACCAAGGTGGACAAGAGA<br>GTGGAGCCCAAGAGCTGCGACAAGACCCACACCTGCCCCCCCTGC<br>CCAGCTCCAGAACTGCTGGGAGGGCCTTCCGTGTTCCTGTTCCCC<br>CCCAAGCCCAAGGACACCCTGATGATCAGCAGGACCCCCGAGGTG<br>ACCTGCGTGGTGGTGGACGTGTCCCACGAGGACCCAGAGGTGAAG<br>TTCAACTGGTACGTGGACGGCGTGGAGGTGCACAACGCCAAGACC<br>AAGCCCAGAGAGGAGCAGTACAACAGCACCTACAGGGTGGTGTCC<br>GTGCTGACCGTGCTGCACCAGGACTGGCTGAACGGCAAAGAATAC<br>AAGTGCAAAGTCTCCAACAAGGCCCTGCCAGCCCCAATCGAAAAG<br>ACAATCAGCAAGGCCAAGGGCCAGCCACGGGAGCCCCAGGTGTAC<br>ACCCTGCCCCCCAGCCGGGAGGAGATGACCAAGAACCAGGTGTCC<br>CTGACCTGTCTGGTGAAGGGCTTCTACCCCAGCGATATCGCCGTG<br>GAGTGGGAGAGCAACGGCCAGCCCGAGAACAACTACAAGACCACC<br>CCCCCAGTGCTGGACAGCGACGGCAGCTTCTTCCTGTACAGCAAG<br>CTGACCGTGGACAAGTCCAGGTGGCAGCAGGGCAACGTGTTCAGC<br>TGCAGCGTGATGCACGAGGCCCTGCACAACCACTACACCCAGAAG<br>TCCCTGAGCCTGAGCCCCGGCAAG |
| SEQ ID NO: 54 | LCDR1 (Combined) | RASQGISSDLN |
| SEQ ID NO: 55 | LCDR2 (Combined) | AASNLQS |
| SEQ ID NO: 56 | LCDR3 (Combined) | QQYTDESMT |
| SEQ ID NO: 54 | LCDR1 (Kabat) | RASQGISSDLN |
| SEQ ID NO: 55 | LCDR2 (Kabat) | AASNLQS |
| SEQ ID NO: 56 | LCDR3 (Kabat) | QQYTDESMT |
| SEQ ID NO: 57 | LCDR1 (Chothia) | SQGISSD |
| SEQ ID NO: 58 | LCDR2 (Chothia) | AAS |
| SEQ ID NO: 59 | LCDR3 (Chothia) | YTDESM |
| SEQ ID NO: 60 | LCDR1 (IMGT) | QGISSD |
| SEQ ID NO: 58 | LCDR2 (IMGT) | AAS |
| SEQ ID NO: 56 | LCDR3 (IMGT) | QQYTDESMT |
| SEQ ID NO: 61 | VL | DIQMTQSPSSLSASVGDRVTITCRASQGISSDLNWYQQKPGKAPK<br>LLIYAASNLQSGVPSRFSGSGSGTDFTLTISSLQPEDFATYYCQQ<br>YTDESMTFGQGTKVEIK |
| SEQ ID NO: 68 | DNA VL | GACATTCAGATGACCCAGTCCCCGTCGTCCCTGTCCGCATCCGTG<br>GGCGACAGAGTCACCATCACTTGCCGGGCCTCACAGGGAATTTCC<br>TCCGACCTGAACTGGTATCAGCAGAAGCCTGGAAAGGCCCCGAAG<br>CTGCTGATCTACGCCGCGTCCAACTTGCAATCGGGAGTGCCAAGC<br>CGCTTTTCTGGTTCCGGGAGCGGGACTGACTTCACCCTGACTATT<br>AGCAGCCTGCAGCCCGAAGATTTCGCTACCTACTACTGCCAACAG<br>TACACAGATGAATCCATGACCTTCGGACAGGGCACCAAAGTCGAG<br>ATCAAG |
| SEQ ID NO: 63 | Light Chain | DIQMTQSPSSLSASVGDRVTITCRASQGISSDLNWYQQKPGKAPK<br>LLIYAASNLQSGVPSRFSGSGSGTDFTLTISSLQPEDFATYYCQQ<br>YTDESMTFGQGTKVEIKRTVAAPSVFIFPPSDEQLKSGTASVVCL<br>LNNFYPREAKVQWKVDNALQSGNSQESVTEQDSKDSTYSLSSTLT<br>LSKADYEKHKVYACEVTHQGLSSPVTKSFNRGEC |
| SEQ ID NO: 69 | DNA Light Chain | GACATTCAGATGACCCAGTCCCCGTCGTCCCTGTCCGCATCCGTG<br>GGCGACAGAGTCACCATCACTTGCCGGGCCTCACAGGGAATTTCC<br>TCCGACCTGAACTGGTATCAGCAGAAGCCTGGAAAGGCCCCGAAG<br>CTGCTGATCTACGCCGCGTCCAACTTGCAATCGGGAGTGCCAAGC<br>CGCTTTTCTGGTTCCGGGAGCGGGACTGACTTCACCCTGACTATT |

TABLE 1-continued

| Sequences of Exemplary Monoclonal Antibodies That Bind Human TREM2. | | |
|---|---|---|
| | | AGCAGCCTGCAGCCCGAAGATTTCGCTACCTACTACTGCCAACAG<br>TACACAGATGAATCCATGACCTTCGGACAGGGCACCAAAGTCGAG<br>ATCAAGCGTACGGTGGCCGCTCCCAGCGTGTTCATCTTCCCCCCC<br>AGCGACGAGCAGCTGAAGAGCGGCACCGCCAGCGTGGTGTGCCTG<br>CTGAACAACTTCTACCCCCGGGAGGCCAAGGTGCAGTGGAAGGTG<br>GACAACGCCCTGCAGAGCGGCAACAGCCAGGAGAGCGTCACCGAG<br>CAGGACAGCAAGGACTCCACCTACAGCCTGAGCAGCACCCTGACC<br>CTGAGCAAGGCCGACTACGAGAAGCATAAGGTGTACGCCTGCGAG<br>GTGACCCACCAGGGCCTGTCCAGCCCCGTGACCAAGAGCTTCAAC<br>AGGGGCGAGTGC |
| | | MOR44746C |
| SEQ ID NO: 41 | HCDR1 (Combined) | GDSVSSSSAAWN |
| SEQ ID NO: 42 | HCDR2 (Combined) | HIGYRSKWYNEYAVSVKS |
| SEQ ID NO: 43 | HCDR3 (Combined) | GMYGSVPYKEGYYFDI |
| SEQ ID NO: 44 | HCDR1 (Kabat) | SSSAAWN |
| SEQ ID NO: 42 | HCDR2 (Kabat) | HIGYRSKWYNEYAVSVKS |
| SEQ ID NO: 43 | HCDR3 (Kabat) | GMYGSVPYKEGYYFDI |
| SEQ ID NO: 45 | HCDR1 (Chothia) | GDSVSSSSA |
| SEQ ID NO: 46 | HCDR2 (Chothia) | GYRSKWY |
| SEQ ID NO: 43 | HCDR3 (Chothia) | GMYGSVPYKEGYYFDI |
| SEQ ID NO: 47 | HCDR1 (IMGT) | GDSVSSSSAA |
| SEQ ID NO: 48 | HCDR2 (IMGT) | IGYRSKWYN |
| SEQ ID NO: 49 | HCDR3 (IMGT) | ARGMYGSVPYKEGYYFDI |
| SEQ ID NO: 50 | VH | QVQLQQSGPGLVKPSQTLSLTCAISGDSVSSSSAAWNWIRQSPSR<br>GLEWLGHIGYRSKWYNEYAVSVKSRITINPDTSKNQFSLQLNSVT<br>PEDTAVYYCARGMYGSVPYKEGYYFDIWGQGTLVTVSS |
| SEQ ID NO: 65 | DNA VH | CAAGTGCAACTCCAGCAGTCAGGACCGGGGTTGGTCAAGCCTTCG<br>CAGACCCTGTCCCTCACTTGCGCCATTAGCGGAGATTCGGTGTCG<br>TCGTCGTCAGCCGCCTGGAACTGGATTAGACAGTCCCCTTCCCGA<br>GGGCTGGAGTGGCTGGGCCACATCGGATACCGCAGCAAGTGGTAC<br>AACGAATACGCCGTCAGCGTGAAGTCACGCATCACCATCAACCCG<br>GATACTAGCAAGAACCAGTTCAGCCTCCAGTTGAACTCCGTGACC<br>CCGGAGGATACCGCCGTGTACTACTGTGCGCGGGGCATGTACGGA<br>TCCGTGCCGTACAAGGAGGGATACTACTTCGACATTTGGGGCCAG<br>GGGACTCTTGTCACCGTGTCCTCG |
| SEQ ID NO: 70 | Heavy Chain | QVQLQQSGPGLVKPSQTLSLTCAISGDSVSSSSAAWNWIRQSPSR<br>GLEWLGHIGYRSKWYNEYAVSVKSRITINPDTSKNQFSLQLNSVT<br>PEDTAVYYCARGMYGSVPYKEGYYFDIWGQGTLVTVSSASTKGPS<br>VFPLAPSSKSTSGGTAALGCLVKDYFPEPVTVSWNSGALTSGVHT<br>FPAVLQSSGLYSLSSVVTVPSSSLGTQTYICNVNHKPSNTKVDKR<br>VEPKSCDKTHTCPPCPAPELLGGPSVFLFPPKPKDTLMISRTPEV<br>TCVVVAVSHEDPEVKFNWYVDGVEVHNAKTKPREEQYNSTYRVVS<br>VLTVLHQDWLNGKEYKCKVSNKALAAPIEKTISKAKGQPREPQVY<br>TLPPSREEMTKNQVSLTCLVKGFYPSDIAVEWESNGQPENNYKTT<br>PPVLDSDGSFFLYSKLTVDKSRWQQGNVFSCSVMHEALHNHYTQK<br>SLSLSPGK |
| SEQ ID NO: 71 | DNA Heavy Chain | CAAGTGCAACTCCAGCAGTCAGGACCGGGGTTGGTCAAGCCTTCG<br>CAGACCCTGTCCCTCACTTGCGCCATTAGCGGAGATTCGGTGTCG<br>TCGTCGTCAGCCGCCTGGAACTGGATTAGACAGTCCCCTTCCCGA<br>GGGCTGGAGTGGCTGGGCCACATCGGATACCGCAGCAAGTGGTAC<br>AACGAATACGCCGTCAGCGTGAAGTCACGCATCACCATCAACCCG<br>GATACTAGCAAGAACCAGTTCAGCCTCCAGTTGAACTCCGTGACC<br>CCGGAGGATACCGCCGTGTACTACTGTGCGCGGGGCATGTACGGA<br>TCCGTGCCGTACAAGGAGGGATACTACTTCGACATTTGGGGCCAG<br>GGGACTCTTGTCACCGTGTCCTCGGCCTCCACTAAGGGCCCGTCA<br>GTGTTCCCCCTTGCGCCATCCTCGAAGTCAACCTCCGGAGGAACT<br>GCCGCACTGGGTTGCCTCGTGAAAGACTATTTCCCGGAACCCGTC<br>ACTGTCTCCTGGAACTCAGGAGCGCTCACCAGCGGAGTGCATACC<br>TTTCCTGCGGTGCTGCAGTCCAGCGGCCTGTACTCCCTGAGCTCC<br>GTCGTGACCGTCCCCTCGTCGTCCCTGGGAACCCAAACCTACATT<br>TGCAACGTCAATCACAAGCCAAGCAACACTAAGGTGGACAAGAGA<br>GTGGAGCCCAAGTCCTGCGATAAGACCCACACCTGTCCTCCCTGT<br>CCGGCACCTGAACTGCTTGGTGGACCTTCCGTGTTCCTGTTCCCG<br>CCCAAGCCAAAAGACACCCTGATGATCTCCCGCACTCCGGAAGTC<br>ACTTGCGTGGTCGTGGCCGTGTCCCACGAGGACCCCGAGGTCAAG<br>TTTAATTGGTACGTGGACGGAGTGGAAGTGCACAACGCCAAGACC<br>AAGCCGCGGGAAGAACAGTACAACTCCACCTACCGCGTGGTGTCC<br>GTCCTGACTGTGCTCCACCAGGACTGGCTGAACGGAAAGGAGTAC<br>AAGTGCAAAGTGTCCAACAAGGCACTGGCTGCCCCTATCGAAAAG<br>ACTATCTCCAAGGCCAAGGGCCAACCTAGGGAGCCCCAGGTGTAC<br>ACGTTGCCTCCTTCCCGCGAAGAAATGACTAAGAACCAGGTGTCG<br>CTGACCTGTCTCGTGAAAGGGTTCTACCCCTCTGACATCGCCGTG<br>GAATGGGAGTCAAACGGACAGCCTGAGAACAACTATAAGACCACA |

TABLE 1-continued

| Sequences of Exemplary Monoclonal Antibodies That Bind Human TREM2. | | |
|---|---|---|
| | | CCACCTGTCCTGGACTCCGACGGCTCCTTCTTCCTGTACTCAAAG TTGACCGTGGACAAGTCGCGGTGGCAACAGGGCAACGTGTTCTCT TGCTCCGTGATGCACGAAGCCCTGCACAACCACTACACCCAAAAG TCGCTCAGCCTCTCCCCCGGAAAG |
| SEQ ID NO: 54 | LCDR1 (Combined) | RASQGISSDLN |
| SEQ ID NO: 55 | LCDR2 (Combined) | AASNLQS |
| SEQ ID NO: 56 | LCDR3 (Combined) | QQYTDESMT |
| SEQ ID NO: 54 | LCDR1 (Kabat) | RASQGISSDLN |
| SEQ ID NO: 55 | LCDR2 (Kabat) | AASNLQS |
| SEQ ID NO: 56 | LCDR3 (Kabat) | QQYTDESMT |
| SEQ ID NO: 57 | LCDR1 (Chothia) | SQGISSD |
| SEQ ID NO: 58 | LCDR2 (Chothia) | AAS |
| SEQ ID NO: 59 | LCDR3 (Chothia) | YTDESM |
| SEQ ID NO: 60 | LCDR1 (IMGT) | QGISSD |
| SEQ ID NO: 58 | LCDR2 (IMGT) | AAS |
| SEQ ID NO: 56 | LCDR3 (IMGT) | QQYTDESMT |
| SEQ ID NO: 61 | VL | DIQMTQSPSSLSASVGDRVTITCRASQGISSDLNWYQQKPGKAPK LLIYAASNLQSGVPSRFSGSGSGTDFTLTISSLQPEDFATYYCQQ YTDESMTFGQGTKVEIK |
| SEQ ID NO: 68 | DNA VL | GACATTCAGATGACCCAGTCCCCGTCGTCCCTGTCCGCATCCGTG GGCGACAGAGTCACCATCACTTGCCGGGCCTCACAGGGAATTTCC TCCGACCTGAACTGGTATCAGCAGAAGCCTGGAAAGGCCCCGAAG CTGCTGATCTACGCCGCGTCCAACTTGCAATCGGGAGTGCCAAGC CGCTTTTCTGGTTCCGGGAGCGGGACTGACTTCACCCTGACTATT AGCAGCCTGCAGCCCGAAGATTTCGCTACCTACTACTGCCAACAG TACACAGATGAATCCATGACCTTCGGACAGGGCACCAAAGTCGAG ATCAAG |
| SEQ ID NO: 63 | Light Chain | DIQMTQSPSSLSASVGDRVTITCRASQGISSDLNWYQQKPGKAPK LLIYAASNLQSGVPSRFSGSGSGTDFTLTISSLQPEDFATYYCQQ YTDESMTFGQGTKVEIKRTVAAPSVFIFPPSDEQLKSGTASVVCL LNNFYPREAKVQWKVDNALQSGNSQESVTEQDSKDSTYSLSSTLT LSKADYEKHKVYACEVTHQGLSSPVTKSFNRGEC |
| SEQ ID NO: 69 | DNA Light Chain | GACATTCAGATGACCCAGTCCCCGTCGTCCCTGTCCGCATCCGTG GGCGACAGAGTCACCATCACTTGCCGGGCCTCACAGGGAATTTCC TCCGACCTGAACTGGTATCAGCAGAAGCCTGGAAAGGCCCCGAAG CTGCTGATCTACGCCGCGTCCAACTTGCAATCGGGAGTGCCAAGC CGCTTTTCTGGTTCCGGGAGCGGGACTGACTTCACCCTGACTATT AGCAGCCTGCAGCCCGAAGATTTCGCTACCTACTACTGCCAACAG TACACAGATGAATCCATGACCTTCGGACAGGGCACCAAAGTCGAG ATCAAGCGTACGGTGGCCGCTCCCAGCGTGTTCATCTTCCCCCCC AGCGACGAGCAGCTGAAGAGCGGCACCGCCAGCGTGGTGTGCCTG CTGAACAACTTCTACCCCCGGGAGGCCAAGGTGCAGTGGAAGGTG GACAACGCCCTGCAGAGCGGCAACAGCCAGGAGAGCGTCACCGAG CAGGACAGCAAGGACTCCACCTACAGCCTGAGCAGCACCCTGACC CTGAGCAAGGCCGACTACGAGAAGCATAAGGTGTACGCCTGCGAG GTGACCCACCAGGGCCTGTCCAGCCCCGTGACCAAGAGCTTCAAC AGGGGCGAGTGC |
| | | MOR44746D |
| SEQ ID NO: 41 (Combined) | HCDR1 | GDSVSSSSAAWN |
| SEQ ID NO: 42 (Combined) | HCDR2 | HIGYRSKWYNEYAVSVKS |
| SEQ ID NO: 43 (Combined) | HCDR3 | GMYGSVPYKEGYYFDI |
| SEQ ID NO: 44 | HCDR1 (Kabat) | SSSAAWN |
| SEQ ID NO: 42 | HCDR2 (Kabat) | HIGYRSKWYNEYAVSVKS |
| SEQ ID NO: 43 | HCDR3 (Kabat) | GMYGSVPYKEGYYFDI |
| SEQ ID NO: 45 | HCDR1 (Chothia) | GDSVSSSSA |
| SEQ ID NO: 46 | HCDR2 (Chothia) | GYRSKWY |
| SEQ ID NO: 43 | HCDR3 (Chothia) | GMYGSVPYKEGYYFDI |
| SEQ ID NO: 47 | HCDR1 (IMGT) | GDSVSSSSAA |
| SEQ ID NO: 48 | HCDR2 (IMGT) | IGYRSKWYN |
| SEQ ID NO: 49 | HCDR3 (IMGT) | ARGMYGSVPYKEGYYFDI |
| SEQ ID NO: 50 | VH | QVQLQQSGPGLVKPSQTLSLTCAISGDSVSSSSAAWNWIRQSPSR GLEWLGHIGYRSKWYNEYAVSVKSRITINPDTSKNQFSLQLNSVT PEDTAVYYCARGMYGSVPYKEGYYFDIWGQGTLVTVSS |
| SEQ ID NO: 65 | DNA VH | CAAGTGCAACTCCAGCAGTCAGGACCGGGGTTGGTCAAGCCTTCG CAGACCCTGTCCCTCACTTGCGCCATTAGCGGAGATTCGGTGTCG TCGTCGTCAGCCGCCTGGAACTGGATTAGACAGTCCCCTTCCCGA GGGCTGGAGTGGCTGGGCCACATCGGATACCGCAGCAAGTGGTAC AACGAATACGCCGTCAGCGTGAAGTCACGCATCACCATCAACCCG GATACTAGCAAGAACCAGTTCAGCCTCCAGTTGAACTCCGTGACC CCGGAGGATACCGCCGTGTACTACTGTGCGCGGGGCATGTACGGA |

TABLE 1-continued

| Sequences of Exemplary Monoclonal Antibodies That Bind Human TREM2. | | |
|---|---|---|
| | | TCCGTGCCGTACAAGGAGGGATACTACTTCGACATTTGGGGCCAG GGGACTCTTGTCACCGTGTCCTCG |
| SEQ ID NO: 72 | Heavy Chain | QVQLQQSGPGLVKPSQTLSLTCAISGDSVSSSSAAWNWIRQSPSR GLEWLGHIGYRSKWYNEYAVSVKSRITINPDTSKNQFSLQLNSVT PEDTAVYYCARGMYGSVPYKEGYYFDIWGQGTLVTVSSASTKGPS VFPLAPSSKSTSGGTAALGCLVKDYFPEPVTVSWNSGALTSGVHT FPAVLQSSGLYSLSSVVTVPSSSLGTQTYICNVNHKPSNTKVDKR VEPKSCDKTHTCPPCPAPELLGGPSVFLFPPKPKDTLMISRTPEV TCVVVDVSHEDPEVKFNWYVDGVEVHNAKTKPREEQYNSTYRVVS VLTVLHQDWLNGKEYKCKVSNKALPAPIEKTISKAKGQPREPQVY TLPPSREEMTKNQVSLTCLVKGFYPSDIAVEWESNGQPENNYKTT PPVLDSDGSFFLYSKLTVDKSRWQQGNVFSCSVLHEALHSHYTQK SLSLSPGK |
| SEQ ID NO: 73 | DNA Heavy Chain | CAAGTGCAACTCCAGCAGTCAGGACCGGGGTTGGTCAAGCCTTCG CAGACCCTGTCCCTCACTTGCGCCATTAGCGGAGATTCGGTGTCG TCGTCGTCAGCCGCCTGGAACTGGATTAGACAGTCCCCTTCCCGA GGGCTGGAGTGGCTGGGCCACATCGGATACCGCAGCAAGTGGTAC AACGAATACGCCGTCAGCGTGAAGTCACGCATCACCATCAACCCG GATACTAGCAAGAACCAGTTCAGCCTCCAGTTGAACTCCGTGACC CCGGAGGATACCGCCGTGTACTACTGTGCGCGGGGCATGTACGGA TCCGTGCCGTACAAGGAGGGATACTACTTCGACATTTGGGGCCAG GGGACTCTTGTCACCGTGTCCTCGGCCTCCACTAAGGGCCCGTCA GTGTTCCCCCTTGCGCCATCCTCGAAGTCAACCTCCGGAGGAACT GCCGCACTGGGTTGCCTCGTGAAAGACTATTTCCCGGAACCCGTC ACTGTCTCCTGGAACTCAGGAGCGCTCACCAGCGGAGTGCATACC TTTCCTGCGGTGCTGCAGTCCAGCGGCCTGTACTCCCTGAGCTCC GTCGTGACCGTCCCCTCGTCGTCCCTGGGAACCCAAACCTACATT TGCAACGTCAATCACAAGCCAAGCAACACTAAGGTGGACAAGAGA GTGGAGCCCAAGTCCTGCGATAAGACCCACACCTGTCCTCCCTGT CCGGCACCTGAACTGCTTGGTGGACCTTCCGTGTTCCTGTTCCCG CCCAAGCCAAAAGACACCCTGATGATCTCCCGCACTCCGGAAGTC ACTTGCGTGGTCGTGGACGTGTCCCACGAGGACCCCGAGGTCAAG TTTAATTGGTACGTGGACGGAGTGGAAGTGCACAACGCCAAGACC AAGCCGCGGGAAGAACAGTACAACTCCACCTACCGCGTGGTGTCC GTCCTGACTGTGCTCCACCAGGACTGGCTGAACGGAAAGGAGTAC AAGTGCAAAGTGTCCAACAAGGCACTGCCAGCCCCTATCGAAAAG ACTATCTCCAAGGCCAAGGGCCAACCTAGGGAGCCCCAGGTGTAC ACGTTGCCTCCTTCCCGCGAAGAAATGACTAAGAACCAGGTGTCG CTGACCTGTCTCGTGAAAGGGTTCTACCCCTCTGACATCGCCGTG GAATGGGAGTCAAACGGACAGCCTGAGAACAACTATAAGACCACA CCACCTGTCCTGGACTCCGACGGCTCCTTCTTCCTGTACTCAAAG TTGACCGTGGACAAGTCGCGGTGGCAACAGGGCAACGTGTTCTCT TGCTCCGTGCTGCACGAAGCCCTGCACAGCCACTACACCCAAAAG TCGCTCAGCCTCTCCCCCGGAAAG |
| SEQ ID NO: 54 | LCDR1 (Combined) | RASQGISSDLN |
| SEQ ID NO: 55 | LCDR2 (Combined) | AASNLQS |
| SEQ ID NO: 56 | LCDR3 (Combined) | QQYTDESMT |
| SEQ ID NO: 54 | LCDR1 (Kabat) | RASQGISSDLN |
| SEQ ID NO: 55 | LCDR2 (Kabat) | AASNLQS |
| SEQ ID NO: 56 | LCDR3 (Kabat) | QQYTDESMT |
| SEQ ID NO: 57 | LCDR1 (Chothia) | SQGISSD |
| SEQ ID NO: 58 | LCDR2 (Chothia) | AAS |
| SEQ ID NO: 59 | LCDR3 (Chothia) | YTDESM |
| SEQ ID NO: 60 | LCDR1 (IMGT) | QGISSD |
| SEQ ID NO: 58 | LCDR2 (IMGT) | AAS |
| SEQ ID NO: 56 | LCDR3 (IMGT) | QQYTDESMT |
| SEQ ID NO: 61 | VL | DIQMTQSPSSLSASVGDRVTITCRASQGISSDLNWYQQKPGKAPK LLIYAASNLQSGVPSRFSGSGSGTDFTLTISSLQPEDFATYYCQQ YTDESMTFGQGTKVEIK |
| SEQ ID NO: 68 | DNA VL | GACATTCAGATGACCCAGTCCCCGTCGTCCCTGTCCGCATCCGTG GGCGACAGAGTCACCATCACTTGCCGGGCCTCACAGGGAATTTCC TCCGACCTGAACTGGTATCAGCAGAAGCCTGGAAAGGCCCCGAAG CTGCTGATCTACGCCGCGTCCAACTTGCAATCGGGAGTGCCAAGC CGCTTTTCTGGTTCCGGGAGCGGGACTGACTTCACCCTGACTATT AGCAGCCTGCAGCCCGAAGATTTCGCTACCTACTACTGCCAACAG TACACAGATGAATCCATGACCTTCGGACAGGGCACCAAAGTCGAG ATCAAG |
| SEQ ID NO: 63 | Light Chain | DIQMTQSPSSLSASVGDRVTITCRASQGISSDLNWYQQKPGKAPK LLIYAASNLQSGVPSRFSGSGSGTDFTLTISSLQPEDFATYYCQQ YTDESMTFGQGTKVEIKRTVAAPSVFIFPPSDEQLKSGTASVVCL LNNFYPREAKVQWKVDNALQSGNSQESVTEQDSKDSTYSLSSTLT LSKADYEKHKVYACEVTHQGLSSPVTKSFNRGEC |
| SEQ ID NO: 69 | DNA Light Chain | GACATTCAGATGACCCAGTCCCCGTCGTCCCTGTCCGCATCCGTG GGCGACAGAGTCACCATCACTTGCCGGGCCTCACAGGGAATTTCC TCCGACCTGAACTGGTATCAGCAGAAGCCTGGAAAGGCCCCGAAG |

TABLE 1-continued

| Sequences of Exemplary Monoclonal Antibodies That Bind Human TREM2. | | |
|---|---|---|
| | | CTGCTGATCTACGCCGCGTCCAACTTGCAATCGGGAGTGCCAAGC CGCTTTTCTGGTTCCGGGAGCGGGACTGACTTCACCCTGACTATT AGCAGCCTGCAGCCCGAAGATTTCGCTACCTACTACTGCCAACAG TACACAGATGAATCCATGACCTTCGGACAGGGCACCAAAGTCGAG ATCAAGCGTACGGTGGCCGCTCCCAGCGTGTTCATCTTCCCCCCC AGCGACGAGCAGCTGAAGAGCGGCACCGCCAGCGTGGTGTGCCTG CTGAACAACTTCTACCCCCGGGAGGCCAAGGTGCAGTGGAAGGTG GACAACGCCCTGCAGAGCGGCAACAGCCAGGAGAGCGTCACCGAG CAGGACAGCAAGGACTCCACCTACAGCCTGAGCAGCACCCTGACC CTGAGCAAGGCCGACTACGAGAAGCATAAGGTGTACGCCTGCGAG GTGACCCACCAGGGCCTGTCCAGCCCCGTGACCAAGAGCTTCAAC AGGGGCGAGTGC |
| | MOR44746E | |
| SEQ ID NO: 41 | HCDR1 (Combined) | GDSVSSSSAAWN |
| SEQ ID NO: 42 | HCDR2 (Combined) | HIGYRSKWYNEYAVSVKS |
| SEQ ID NO: 43 | HCDR3 (Combined) | GMYGSVPYKEGYYFDI |
| SEQ ID NO: 44 | HCDR1 (Kabat) | SSSAAWN |
| SEQ ID NO: 42 | HCDR2 (Kabat) | HIGYRSKWYNEYAVSVKS |
| SEQ ID NO: 43 | HCDR3 (Kabat) | GMYGSVPYKEGYYFDI |
| SEQ ID NO: 45 | HCDR1 (Chothia) | GDSVSSSSA |
| SEQ ID NO: 46 | HCDR2 (Chothia) | GYRSKWY |
| SEQ ID NO: 43 | HCDR3 (Chothia) | GMYGSVPYKEGYYFDI |
| SEQ ID NO: 47 | HCDR1 (IMGT) | GDSVSSSSAA |
| SEQ ID NO: 48 | HCDR2 (IMGT) | IGYRSKWYN |
| SEQ ID NO: 49 | HCDR3 (IMGT) | ARGMYGSVPYKEGYYFDI |
| SEQ ID NO: 50 | VH | QVQLQQSGPGLVKPSQTLSLTCAISGDSVSSSSAAWNWIRQSPSR GLEWLGHIGYRSKWYNEYAVSVKSRITINPDTSKNQFSLQLNSVT PEDTAVYYCARGMYGSVPYKEGYYFDIWGQGTLVTVSS |
| SEQ ID NO: 65 | DNA VH | CAAGTGCAACTCCAGCAGTCAGGACCGGGGTTGGTCAAGCCTTCG CAGACCCTGTCCCTCACTTGCGCCATTAGCGGAGATTCGGTGTCG TCGTCGTCAGCCGCCTGGAACTGGATTAGACAGTCCCCTTCCCGA GGGCTGGAGTGGCTGGGCCACATCGGATACCGCAGCAAGTGGTAC AACGAATACGCCGTCAGCGTGAAGTCACGCATCACCATCAACCCG GATACTAGCAAGAACCAGTTCAGCCTCCAGTTGAACTCCGTGACC CCGGAGGATACCGCCGTGTACTACTGTGCGCGGGGCATGTACGGA TCCGTGCCGTACAAGGAGGGATACTACTTCGACATTTGGGGCCAG GGGACTCTTGTCACCGTGTCCTCG |
| SEQ ID NO: 74 | Heavy Chain | QVQLQQSGPGLVKPSQTLSLTCAISGDSVSSSSAAWNWIRQSPSR GLEWLGHIGYRSKWYNEYAVSVKSRITINPDTSKNQFSLQLNSVT PEDTAVYYCARGMYGSVPYKEGYYFDIWGQGTLVTVSSASTKGPS VFPLAPSSKSTSGGTAALGCLVKDYFPEPVTVSWNSGALTSGVHT FPAVLQSSGLYSLSSVVTVPSSSLGTQTYICNVNHKPSNTKVDKR VEPKSCDKTHTCPPCPAPELLGGPSVFLFPPKPKDTLMISRTPEV TCVVVAVSHEDPEVKFNWYVDGVEVHNAKTKPREEQYNSTYRVVS VLTVLHQDWLNGKEYKCKVSNKALAAPIEKTISKAKGQPREPQVY TLPPSREEMTKNQVSLTCLVKGFYPSDIAVEWESNGQPENNYKTT PPVLDSDGSFFLYSKLTVDKSRWQQGNVFSCSVLHEALHSHYTQK SLSLSPGK |
| SEQ ID NO: 75 | DNA Heavy Chain | CAAGTGCAACTCCAGCAGTCAGGACCGGGGTTGGTCAAGCCTTCG CAGACCCTGTCCCTCACTTGCGCCATTAGCGGAGATTCGGTGTCG TCGTCGTCAGCCGCCTGGAACTGGATTAGACAGTCCCCTTCCCGA GGGCTGGAGTGGCTGGGCCACATCGGATACCGCAGCAAGTGGTAC AACGAATACGCCGTCAGCGTGAAGTCACGCATCACCATCAACCCG GATACTAGCAAGAACCAGTTCAGCCTCCAGTTGAACTCCGTGACC CCGGAGGATACCGCCGTGTACTACTGTGCGCGGGGCATGTACGGA TCCGTGCCGTACAAGGAGGGATACTACTTCGACATTTGGGGCCAG GGGACTCTTGTCACCGTGTCCTCGGCCTCCACTAAGGGCCCGTCA GTGTTCCCCCTTGCGCCATCCTCGAAGTCAACCTCCGGAGGAACT GCCGCACTGGGTTGCCTCGTGAAAGACTATTTCCCGGAACCCGTC ACTGTCTCCTGGAACTCAGGAGCGCTCACCAGCGGAGTGCATACC TTTCCTGCGGTGCTGCAGTCCAGCGGCCTGTACTCCCTGAGCTCC GTCGTGACCGTCCCCTCGTCGTCCCTGGGAACCCAAACCTACATT TGCAACGTCAATCACAAGCCAAGCAACACTAAGGTGGACAAGAGA GTGGAGCCCAAGTCCTGCGATAAGACCCACACCTGTCCTCCCTGT CCGGCACCTGAACTGCTTGGTGGACCTTCCGTGTTCCTGTTCCCG CCCAAGCCAAAAGACACCCTGATGATCTCCCGCACTCCGGAAGTC ACTTGCGTGGTCGTGGCCGTGTCCCACGAGGACCCCGAGGTCAAG TTTAATTGGTACGTGGACGGAGTGGAAGTGCACAACGCCAAGACC AAGCCGCGGGAAGAACAGTACAACTCCACCTACCGCGTGGTGTCC GTCCTGACTGTGCTCCACCAGGACTGGCTGAACGGAAAGGAGTAC AAGTGCAAAGTGTCCAACAAGGCACTGGCTGCCCCTATCGAAAAG ACTATCTCCAAGGCCAAGGGCCAACCTAGGGAGCCCCAGGTGTAC ACGTTGCCTCCTTCCCGCGAAGAAATGACTAAGAACCAGGTGTCG |

TABLE 1-continued

| Sequences of Exemplary Monoclonal Antibodies That Bind Human TREM2. | | |
|---|---|---|
| | | CTGACCTGTCTCGTGAAAGGGTTCTACCCCTCTGACATCGCCGTG GAATGGGAGTCAAACGGACAGCCTGAGAACAACTATAAGACCACA CCACCTGTCCTGGACTCCGACGGCTCCTTCTTCCTGTACTCAAAG TTGACCGTGGACAAGTCGCGGTGGCAACAGGGCAACGTGTTCTCT TGCTCCGTGCTGCACGAAGCCCTGCACAGCCACTACACCCAAAAG TCGCTCAGCCTCTCCCCCGGAAAG |
| SEQ ID NO: 54 | LCDR1 (Combined) | RASQGISSDLN |
| SEQ ID NO: 55 | LCDR2 (Combined) | AASNLQS |
| SEQ ID NO: 56 | LCDR3 (Combined) | QQYTDESMT |
| SEQ ID NO: 54 | LCDR1 (Kabat) | RASQGISSDLN |
| SEQ ID NO: 55 | LCDR2 (Kabat) | AASNLQS |
| SEQ ID NO: 56 | LCDR3 (Kabat) | QQYTDESMT |
| SEQ ID NO: 57 | LCDR1 (Chothia) | SQGISSD |
| SEQ ID NO: 58 | LCDR2 (Chothia) | AAS |
| SEQ ID NO: 59 | LCDR3 (Chothia) | YTDESM |
| SEQ ID NO: 60 | LCDR1 (IMGT) | QGISSD |
| SEQ ID NO: 58 | LCDR2 (IMGT) | AAS |
| SEQ ID NO: 56 | LCDR3 (IMGT) | QQYTDESMT |
| SEQ ID NO: 61 | VL | DIQMTQSPSSLSASVGDRVTITCRASQGISSDLNWYQQKPGKAPK LLIYAASNLQSGVPSRFSGSGSGTDFTLTISSLQPEDFATYYCQQ YTDESMTFGQGTKVEIK |
| SEQ ID NO: 68 | DNA VL | GACATTCAGATGACCCAGTCCCCGTCGTCCCTGTCCGCATCCGTG GGCGACAGAGTCACCATCACTTGCCGGGCCTCACAGGGAATTTCC TCCGACCTGAACTGGTATCAGCAGAAGCCTGGAAAGGCCCCGAAG CTGCTGATCTACGCCGCGTCCAACTTGCAATCGGGAGTGCCAAGC CGCTTTTCTGGTTCCGGGAGCGGGACTGACTTCACCCTGACTATT AGCAGCCTGCAGCCCGAAGATTTCGCTACCTACTACTGCCAACAG TACACAGATGAATCCATGACCTTCGGACAGGGCACCAAAGTCGAG ATCAAG |
| SEQ ID NO: 63 | Light Chain | DIQMTQSPSSLSASVGDRVTITCRASQGISSDLNWYQQKPGKAPK LLIYAASNLQSGVPSRFSGSGSGTDFTLTISSLQPEDFATYYCQQ YTDESMTFGQGTKVEIKRTVAAPSVFIFPPSDEQLKSGTASVVCL LNNFYPREAKVQWKVDNALQSGNSQESVTEQDSKDSTYSLSSTLT LSKADYEKHKVYACEVTHQGLSSPVTKSFNRGEC |
| SEQ ID NO: 69 | DNA Light Chain | GACATTCAGATGACCCAGTCCCCGTCGTCCCTGTCCGCATCCGTG GGCGACAGAGTCACCATCACTTGCCGGGCCTCACAGGGAATTTCC TCCGACCTGAACTGGTATCAGCAGAAGCCTGGAAAGGCCCCGAAG CTGCTGATCTACGCCGCGTCCAACTTGCAATCGGGAGTGCCAAGC CGCTTTTCTGGTTCCGGGAGCGGGACTGACTTCACCCTGACTATT AGCAGCCTGCAGCCCGAAGATTTCGCTACCTACTACTGCCAACAG TACACAGATGAATCCATGACCTTCGGACAGGGCACCAAAGTCGAG ATCAAGCGTACGGTGGCCGCTCCCAGCGTGTTCATCTTCCCCCCC AGCGACGAGCAGCTGAAGAGCGGCACCGCCAGCGTGGTGTGCCTG CTGAACAACTTCTACCCCCGGGAGGCCAAGGTGCAGTGGAAGGTG GACAACGCCCTGCAGAGCGGCAACAGCCAGGAGAGCGTCACCGAG CAGGACAGCAAGGACTCCACCTACAGCCTGAGCAGCACCCTGACC CTGAGCAAGGCCGACTACGAGAAGCATAAGGTGTACGCCTGCGAG GTGACCCACCAGGGCCTGTCCAGCCCCGTGACCAAGAGCTTCAAC AGGGGCGAGTGC |
| | MOR44746F | |
| SEQ ID NO: 41 | HCDR1 (Combined) | GDSVSSSSAAWN |
| SEQ ID NO: 42 | HCDR2 (Combined) | HIGYRSKWYNEYAVSVKS |
| SEQ ID NO: 43 | HCDR3 (Combined) | GMYGSVPYKEGYYFDI |
| SEQ ID NO: 44 | HCDR1 (Kabat) | SSSAAWN |
| SEQ ID NO: 42 | HCDR2 (Kabat) | HIGYRSKWYNEYAVSVKS |
| SEQ ID NO: 43 | HCDR3 (Kabat) | GMYGSVPYKEGYYFDI |
| SEQ ID NO: 45 | HCDR1 (Chothia) | GDSVSSSSA |
| SEQ ID NO: 46 | HCDR2 (Chothia) | GYRSKWY |
| SEQ ID NO: 43 | HCDR3 (Chothia) | GMYGSVPYKEGYYFDI |
| SEQ ID NO: 47 | HCDR1 (IMGT) | GDSVSSSSAA |
| SEQ ID NO: 48 | HCDR2 (IMGT) | IGYRSKWYN |
| SEQ ID NO: 49 | HCDR3 (IMGT) | ARGMYGSVPYKEGYYFDI |
| SEQ ID NO: 50 | VH | QVQLQQSGPGLVKPSQTLSLTCAISGDSVSSSSAAWNWIRQSPSR GLEWLGHIGYRSKWYNEYAVSVKSRITINPDTSKNQFSLQLNSVT PEDTAVYYCARGMYGSVPYKEGYYFDIWGQGTLVTVSS |
| SEQ ID NO: 65 | DNA VH | CAAGTGCAACTCCAGCAGTCAGGACCGGGGTTGGTCAAGCCTTCG CAGACCCTGTCCCTCACTTGCGCCATTAGCGGAGATTCGGTGTCG TCGTCGTCAGCCGCCTGGAACTGGATTAGACAGTCCCCTTCCCGA GGGCTGGAGTGGCTGGGCCACATCGGATACCGCAGCAAGTGGTAC AACGAATACGCCGTCAGCGTGAAGTCACGCATCACCATCAACCCG |

TABLE 1-continued

| Sequences of Exemplary Monoclonal Antibodies That Bind Human TREM2. | | |
|---|---|---|
| | | GATACTAGCAAGAACCAGTTCAGCCTCCAGTTGAACTCCGTGACCCCGGAGGATACCGCCGTGTACTACTGTGCGCGGGGCATGTACGGATCCGTGCCGTACAAGGAGGGATACTACTTCGACATTTGGGGCCAGGGGACTCTTGTCACCGTGTCCTCG |
| SEQ ID NO: 76 | Heavy Chain | QVQLQQSGPGLVKPSQTLSLTCAISGDSVSSSSAAWNWIRQSPSRGLEWLGHIGYRSKWYNEYAVSVKSRITINPDTSKNQFSLQLNSVTPEDTAVYYCARGMYGSVPYKEGYYFDIWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| SEQ ID NO: 77 | DNA Heavy Chain | CAAGTGCAACTCCAGCAGTCAGGACCGGGGTTGGTCAAGCCTTCGCAGACCCTGTCCCTCACTTGCGCCATTAGCGGAGATTCGGTGTCGTCGTCGTCAGCCGCCTGGAACTGGATTAGACAGTCCCCTTCCCGAGGGCTGGAGTGGCTGGGCCACATCGGATACCGCAGCAAGTGGTACAACGAATACGCCGTCAGCGTGAAGTCACGCATCACCATCAACCCGGATACTAGCAAGAACCAGTTCAGCCTCCAGTTGAACTCCGTGACCCCGGAGGATACCGCCGTGTACTACTGTGCGCGGGGCATGTACGGATCCGTGCCGTACAAGGAGGGATACTACTTCGACATTTGGGGCCAGGGGACTCTTGTCACCGTGTCCTCGGCCTCCACTAAGGGCCCGTCAGTGTTCCCCCTTGCGCCATCCTCGAAGTCAACCTCCGGAGGAACTGCCGCACTGGGTTGCCTCGTGAAAGACTATTTCCCGGAACCCGTCACTGTCTCCTGGAACTCAGGAGCGCTCACCAGCGGAGTGCATACCTTTCCTGCGGTGCTGCAGTCCAGCGGCCTGTACTCCCTGAGCTCCGTCGTGACCGTCCCCTCGTCGTCCCTGGGAACCCAAACCTACATTTGCAACGTCAATCACAAGCCAAGCAACACTAAGGTGGACAAGAGAGTGGAGCCCAAGTCCTGCGATAAGACCCACACCTGTCCTCCCTGTCCGGCACCTGAACTGCTTGGTGGACCTTCCGTGTTCCTGTTCCCGCCCAAGCCAAAAGACACCCTGTATATCACTCGCGAACCGGAAGTCACTTGCGTGGTCGTGGACGTGTCCCACGAGGACCCCGAGGTCAAGTTTAATTGGTACGTGGACGGAGTGGAAGTGCACAACGCCAAGACCAAGCCGCGGGAAGAACAGTACAACTCCACCTACCGCGTGGTGTCCGTCCTGACTGTGCTCCACCAGGACTGGCTGAACGGAAAGGAGTACAAGTGCAAAGTGTCCAACAAGGCACTGCCAGCCCCTATCGAAAAGACTATCTCCAAGGCCAAGGGCCAACCTAGGGAGCCCCAGGTGTACACGTTGCCTCCTTCCCGCGAAGAAATGACTAAGAACCAGGTGTCGCTGACCTGTCTCGTGAAAGGGTTCTACCCCTCTGACATCGCCGTGGAATGGGAGTCAAACGGACAGCCTGAGAACAACTATAAGACCACACCACCTGTCCTGGACTCCGACGGCTCCTTCTTCCTGTACTCAAAGTTGACCGTGGACAAGTCGCGGTGGCAACAGGGCAACGTGTTCTCTTGCTCCGTGATGCACGAAGCCCTGCACAACCACTACACCCAAAAGTCGCTCAGCCTCTCCCCCGGAAAG |
| SEQ ID NO: 54 | LCDR1 (Combined) | RASQGISSDLN |
| SEQ ID NO: 55 | LCDR2 (Combined) | AASNLQS |
| SEQ ID NO: 56 | LCDR3 (Combined) | QQYTDESMT |
| SEQ ID NO: 54 | LCDR1 (Kabat) | RASQGISSDLN |
| SEQ ID NO: 55 | LCDR2 (Kabat) | AASNLQS |
| SEQ ID NO: 56 | LCDR3 (Kabat) | QQYTDESMT |
| SEQ ID NO: 57 | LCDR1 (Chothia) | SQGISSD |
| SEQ ID NO: 58 | LCDR2 (Chothia) | AAS |
| SEQ ID NO: 59 | LCDR3 (Chothia) | YTDESM |
| SEQ ID NO: 60 | LCDR1 (IMGT) | QGISSD |
| SEQ ID NO: 58 | LCDR2 (IMGT) | AAS |
| SEQ ID NO: 56 | LCDR3 (IMGT) | QQYTDESMT |
| SEQ ID NO: 61 | VL | DIQMTQSPSSLSASVGDRVTITCRASQGISSDLNWYQQKPGKAPKLLIYAASNLQSGVPSRFSGSGSGTDFTLTISSLQPEDFATYYCQQYTDESMTFGQGTKVEIK |
| SEQ ID NO: 68 | DNA VL | GACATTCAGATGACCCAGTCCCCGTCGTCCCTGTCCGCATCCGTGGGCGACAGAGTCACCATCACTTGCCGGGCCTCACAGGGAATTTCCTCCGACCTGAACTGGTATCAGCAGAAGCCTGGAAAGGCCCCGAAGCTGCTGATCTACGCCGCGTCCAACTTGCAATCGGGAGTGCCAAGCCGCTTTTCTGGTTCCGGGAGCGGGACTGACTTCACCCTGACTATTAGCAGCCTGCAGCCCGAAGATTTCGCTACCTACTACTGCCAACAGTACACAGATGAATCCATGACCTTCGGACAGGGCACCAAAGTCGAGATCAAG |
| SEQ ID NO: 63 | Light Chain | DIQMTQSPSSLSASVGDRVTITCRASQGISSDLNWYQQKPGKAPKLLIYAASNLQSGVPSRFSGSGSGTDFTLTISSLQPEDFATYYCQQYTDESMTFGQGTKVEIKRTVAAPSVFIFPPSDEQLKSGTASVVCLLNNFYPREAKVQWKVDNALQSGNSQESVTEQDSKDSTYSLSSTLTISKADYEKHKVYACEVTHQGLSSPVTKSFNRGEC |

TABLE 1-continued

| Sequences of Exemplary Monoclonal Antibodies That Bind Human TREM2. | | |
|---|---|---|
| SEQ ID NO: 69 | DNA Light Chain | GACATTCAGATGACCCAGTCCCCGTCGTCCCTGTCCGCATCCGTG GGCGACAGAGTCACCATCACTTGCCGGGCCTCACAGGGAATTTCC TCCGACCTGAACTGGTATCAGCAGAAGCCTGGAAAGGCCCCGAAG CTGCTGATCTACGCCGCGTCCAACTTGCAATCGGGAGTGCCAAGC CGCTTTTCTGGTTCCGGGAGCGGGACTGACTTCACCCTGACTATT AGCAGCCTGCAGCCCGAAGATTTCGCTACCTACTACTGCCAACAG TACACAGATGAATCCATGACCTTCGGACAGGGCACCAAAGTCGAG ATCAAGCGTACGGTGGCCGCTCCCAGCGTGTTCATCTTCCCCCCC AGCGACGAGCAGCTGAAGAGCGGCACCGCCAGCGTGGTGTGCCTG CTGAACAACTTCTACCCCCGGGAGGCCAAGGTGCAGTGGAAGGTG GACAACGCCCTGCAGAGCGGCAACAGCCAGGAGAGCGTCACCGAG CAGGACAGCAAGGACTCCACCTACAGCCTGAGCAGCACCCTGACC CTGAGCAAGGCCGACTACGAGAAGCATAAGGTGTACGCCTGCGAG GTGACCCACCAGGGCCTGTCCAGCCCCGTGACCAAGAGCTTCAAC AGGGGCGAGTGC |
| | MOR042596 | |
| SEQ ID NO: 4 | HCDR1 (Combined) | GYTFTGYHMS |
| SEQ ID NO: 5 | HCDR2 (Combined) | VINPVSGNTVYAQKFQG |
| SEQ ID NO: 6 | HCDR3 (Combined) | IPSYTYAFDY |
| SEQ ID NO: 7 | HCDR1 (Kabat) | GYHMS |
| SEQ ID NO: 5 | HCDR2 (Kabat) | VINPVSGNTVYAQKFQG |
| SEQ ID NO: 6 | HCDR3 (Kabat) | IPSYTYAFDY |
| SEQ ID NO: 8 | HCDR1 (Chothia) | GYTFTGY |
| SEQ ID NO: 9 | HCDR2 (Chothia) | NPVSGN |
| SEQ ID NO: 6 | HCDR3 (Chothia) | IPSYTYAFDY |
| SEQ ID NO: 10 | HCDR1 (IMGT) | GYTFTGYH |
| SEQ ID NO: 11 | HCDR2 (IMGT) | INPVSGNT |
| SEQ ID NO: 12 | HCDR3 (IMGT) | ARIPSYTYAFDY |
| SEQ ID NO: 13 | VH | QVQLVQSGAEVKKPGASVKVSCKASGYTFTGYHMSWVRQAPGQGL EWMGVINPVSGNTVYAQKFQGRVTMTRDTSISTAYMELSRLRSED TAVYYCARIPSYTYAFDYWGQGTLVTVSS |
| SEQ ID NO: 14 | DNA VH | CAGGTGCAATTGGTGCAGAGCGGTGCGGAAGTGAAAAAACCGGGT GCCAGCGTGAAAGTTAGCTGCAAAGCGTCCGGATATACCTTCACT GGTTACCATATGTCTTGGGTGCGCCAGGCCCCGGGCCAGGGCCTC GAGTGGATGGGCGTTATCAACCCGGTTTCTGGCAACACGGTTTAC GCGCAGAAATTTCAGGGCCGGGTGACCATGACCCGTGATACCAGC ATTAGCACCGCGTATATGGAACTGAGCCGTCTGCGTAGCGAAGAT ACGGCCGTGTATTATTGCGCGCGTATCCCGTCTTACACTTACGCT TTCGATTACTGGGGCCAAGGCACCCTGGTGACTGTTAGCTCA |
| SEQ ID NO: 15 | Heavy Chain | QVQLVQSGAEVKKPGASVKVSCKASGYTFTGYHMSWVRQAPGQGL EWMGVINPVSGNTVYAQKFQGRVTMTRDTSISTAYMELSRLRSED TAVYYCARIPSYTYAFDYWGQGTLVTVSSASTKGPSVFPLAPSSK STSGGTAALGCLVKDYFPEPVTVSWNSGALTSGVHTFPAVLQSSG LYSLSSVVTVPSSSLGTQTYICNVNHKPSNTKVDKRVEPKSCDKT HTCPPCPAPEAAGGPSVFLFPPKPKDTLMISRTPEVTCVVVDVSH EDPEVKFNWYVDGVEVHNAKTKPREEQYNSTYRVVSVLTVLHQDW LNGKEYKCKVSNKALPAPIEKTISKAKGQPREPQVYTLPPSREEM TKNQVSLTCLVKGFYPSDIAVEWESNGQPENNYKTTPPVLDSDGS FFLYSKLTVDKSRWQQGNVFSCSVMHEALHNHYTQKSLSLSPGK |
| SEQ ID NO: 16 | DNA Heavy Chain | CAGGTGCAATTGGTGCAGAGCGGTGCGGAAGTGAAAAAACCGGGT GCCAGCGTGAAAGTTAGCTGCAAAGCGTCCGGATATACCTTCACT GGTTACCATATGTCTTGGGTGCGCCAGGCCCCGGGCCAGGGCCTC GAGTGGATGGGCGTTATCAACCCGGTTTCTGGCAACACGGTTTAC GCGCAGAAATTTCAGGGCCGGGTGACCATGACCCGTGATACCAGC ATTAGCACCGCGTATATGGAACTGAGCCGTCTGCGTAGCGAAGAT ACGGCCGTGTATTATTGCGCGCGTATCCCGTCTTACACTTACGCT TTCGATTACTGGGGCCAAGGCACCCTGGTGACTGTTAGCTCAGCC TCCACCAAGGGTCCATCGGTCTTCCCCCTGGCACCCTCCTCCAAG AGCACCTCTGGGGGCACAGCGGCCCTGGGCTGCCTGGTCAAGGAC TACTTCCCCGAACCGGTGACGGTGTCGTGGAACTCAGGCGCCCTG ACCAGCGGCGTGCACACCTTCCCGGCTGTCCTACAGTCCTCAGGA CTCTACTCCCTCAGCAGCGTGGTGACCGTGCCCTCCAGCAGCTTG GGCACCCAGACCTACATCTGCAACGTGAATCACAAGCCCAGCAAC ACCAAGGTGGACAAGAGAGTTGAGCCCAAATCTTGTGACAAAACT CACACATGCCCACCGTGCCCAGCACCTGAAGCAGCGGGGGGACCG TCAGTCTTCCTCTTCCCCCCAAAACCCAAGGACACCCTCATGATC TCCCGGACCCCTGAGGTCACATGCGTGGTGGTGGACGTGAGCCAC GAAGACCCTGAGGTCAAGTTCAACTGGTACGTGGACGGCGTGGAG GTGCATAATGCCAAGACAAAGCCGCGGGAGGAGCAGTACAACAGC ACGTACCGGGTGGTCAGCGTCCTCACCGTCCTGCACCAGGACTGG CTGAATGGCAAGGAGTACAAGTGCAAGGTCTCCAACAAAGCCCTC CCAGCCCCCATCGAGAAAACCATCTCCAAAGCCAAAGGGCAGCCC CGAGAACCACAGGTGTACACCCTGCCCCCATCCCGGGAGGAGATG |

TABLE 1-continued

| Sequences of Exemplary Monoclonal Antibodies That Bind Human TREM2. | | |
|---|---|---|
| | | ACCAAGAACCAGGTCAGCCTGACCTGCCTGGTCAAAGGCTTCTAT CCCAGCGACATCGCCGTGGAGTGGGAGAGCAATGGGCAGCCGGAG AACAACTACAAGACCACGCCTCCCGTGCTGGACTCCGACGGCTCC TTCTTCCTCTACAGCAAGCTCACCGTGGACAAGAGCAGGTGGCAG CAGGGGAACGTCTTCTCATGCTCCGTGATGCATGAGGCTCTGCAC AACCACTACACGCAGAAGAGCCTCTCCCTGTCTCCGGGTAAA |
| SEQ ID NO: 17 | LCDR1 (Combined) | RASQDISNYLA |
| SEQ ID NO: 18 | LCDR2 (Combined) | RASSLQS |
| SEQ ID NO: 78 | LCDR3 (Combined) | QQHGHSPTT |
| SEQ ID NO: 17 | LCDR1 (Kabat) | RASQDISNYLA |
| SEQ ID NO: 18 | LCDR2 (Kabat) | RASSLQS |
| SEQ ID NO: 78 | LCDR3 (Kabat) | QQHGHSPTT |
| SEQ ID NO: 20 | LCDR1 (Chothia) | SQDISNY |
| SEQ ID NO: 21 | LCDR2 (Chothia) | RAS |
| SEQ ID NO: 79 | LCDR3 (Chothia) | HGHSPT |
| SEQ ID NO: 23 | LCDR1 (IMGT) | QDISNY |
| SEQ ID NO: 21 | LCDR2 (IMGT) | RAS |
| SEQ ID NO: 78 | LCDR3 (IMGT) | QQHGHSPTT |
| SEQ ID NO: 80 | VL | DIQMTQSPSSLSASVGDRVTITCRASQDISNYLAWYQQKPGKAPK LLIYRASSLQSGVPSRFSGSGSGTDFTLTISSLQPEDFATYYCQQ HGHSPTTFGQGTKVEIK |
| SEQ ID NO: 81 | DNA VL | GATATCCAGATGACCCAGAGCCCGAGCAGCCTGAGCGCCAGCGTG GGCGATCGCGTGACCATTACCTGCAGAGCCAGCCAGGACATTTCT AACTACCTGGCTTGGTACCAGCAGAAACCGGGCAAAGCGCCGAAA CTATTAATCTACCGTGCTTCTTCTCTGCAAAGCGGCGTGCCGAGC CGCTTTAGCGGCAGCGGATCCGGCACCGATTTCACCCTGACCATT AGCTCTCTGCAACCGGAAGACTTTGCGACCTATTATTGCCAGCAG CATGGTCATTCTCCGACTACCTTTGGCCAGGGCACGAAAGTTGAA ATTAAA |
| SEQ ID NO: 82 | Light Chain | DIQMTQSPSSLSASVGDRVTITCRASQDISNYLAWYQQKPGKAPK LLIYRASSLQSGVPSRFSGSGSGTDFTLTISSLQPEDFATYYCQQ HGHSPTTFGQGTKVEIKRTVAAPSVFIFPPSDEQLKSGTASVVCL LNNFYPREAKVQWKVDNALQSGNSQESVTEQDSKDSTYSLSSTLT ISKADYEKHKVYACEVTHQGLSSPVTKSFNRGEC |
| SEQ ID NO: 83 | DNA Light Chain | GATATCCAGATGACCCAGAGCCCGAGCAGCCTGAGCGCCAGCGTG GGCGATCGCGTGACCATTACCTGCAGAGCCAGCCAGGACATTTCT AACTACCTGGCTTGGTACCAGCAGAAACCGGGCAAAGCGCCGAAA CTATTAATCTACCGTGCTTCTTCTCTGCAAAGCGGCGTGCCGAGC CGCTTTAGCGGCAGCGGATCCGGCACCGATTTCACCCTGACCATT AGCTCTCTGCAACCGGAAGACTTTGCGACCTATTATTGCCAGCAG CATGGTCATTCTCCGACTACCTTTGGCCAGGGCACGAAAGTTGAA ATTAAACGTACGGTGGCCGCTCCCAGCGTGTTCATCTTCCCCCCC AGCGACGAGCAGCTGAAGAGCGGCACCGCCAGCGTGGTGTGCCTG CTGAACAACTTCTACCCCCGGGAGGCCAAGGTGCAGTGGAAGGTG GACAACGCCCTGCAGAGCGGCAACAGCCAGGAAAGCGTCACCGAG CAGGACAGCAAGGACTCCACCTACAGCCTGAGCAGCACCCTGACC CTGAGCAAGGCCGACTACGAGAAGCACAAGGTGTACGCCTGCGAG GTGACCCACCAGGGCCTGTCCAGCCCCGTGACCAAGAGCTTCAAC CGGGGCGAGTGT |
| | MOR041877 | |
| SEQ ID NO: 84 | HCDR1 (Combined) | GFSLSTSGVGVS |
| SEQ ID NO: 85 | HCDR2 (Combined) | LIFSDHDKIYSTSLKT |
| SEQ ID NO: 86 | HCDR3 (Combined) | TLIDRSVYFDY |
| SEQ ID NO: 87 | HCDR1 (Kabat) | TSGVGVS |
| SEQ ID NO: 85 | HCDR2 (Kabat) | LIFSDHDKIYSTSLKT |
| SEQ ID NO: 86 | HCDR3 (Kabat) | TLIDRSVYFDY |
| SEQ ID NO: 88 | HCDR1 (Chothia) | GFSLSTSGV |
| SEQ ID NO: 89 | HCDR2 (Chothia) | FSDHD |
| SEQ ID NO: 86 | HCDR3 (Chothia) | TLIDRSVYFDY |
| SEQ ID NO: 90 | HCDR1 (IMGT) | GFSLSTSGVG |
| SEQ ID NO: 91 | HCDR2 (IMGT) | IFSDHDK |
| SEQ ID NO: 92 | HCDR3 (IMGT) | ARTLIDRSVYFDY |
| SEQ ID NO: 93 | VH | QVQLKESGPALVKPTQTLTLTCTFSGFSLSTSGVGVSWIRQPPGK ALEWLALIFSDHDKIYSTSLKTRLTISKDTSKNQVVLTMTNMDPV DTATYYCARTLIDRSVYFDYWGQGTLVTVSS |
| SEQ ID NO: 94 | DNA VH | CAGGTGCAATTGAAAGAAAGCGGTCCGGCGCTGGTGAAACCGACC CAGACCCTGACCCTGACGTGCACCTTTTCCGGATTCAGCCTGTCT ACTTCCGGTGTTGGTGTGAGCTGGATTCGCCAGCCGCCGGGCAAA GCGCTCGAGTGGCTGGCGCTGATCTTCTCTGACCATGACAAGATC TATAGCACCAGCCTGAAAACCCGTCTGACCATTAGCAAAGATACT |

TABLE 1-continued

| Sequences of Exemplary Monoclonal Antibodies That Bind Human TREM2. | | |
|---|---|---|
| | | TCGAAAAACCAGGTGGTGCTGACCATGACCAACATGGACCCGGTG GATACCGCGACCTATTATTGCGCGCGTACTCTGATCGACCGTTCT GTTTACTTCGATTACTGGGGCCAAGGCACCCTGGTGACTGTTAGC TCA |
| SEQ ID NO: 95 | Heavy Chain | QVQLKESGPALVKPTQTLTLTCTFSGFSLSTSGVGVSWIRQPPGK ALEWLALIFSDHDKIYSTSLKTRLTISKDTSKNQVVLTMTNMDPV DTATYYCARTLIDRSVYFDYWGQGTLVTVSSASTKGPSVFPLAPS SKSTSGGTAALGCLVKDYFPEPVTVSWNSGALTSGVHTFPAVLQS SGLYSLSSVVTVPSSSLGTQTYICNVNHKPSNTKVDKRVEPKSCD KTHTCPPCPAPEAAGGPSVFLFPPKPKDTLMISRTPEVTCVVVDV SHEDPEVKFNWYVDGVEVHNAKTKPREEQYNSTYRVVSVLTVLHQ DWLNGKEYKCKVSNKALPAPIEKTISKAKGQPREPQVYTLPPSRE EMTKNQVSLTCLVKGFYPSDIAVEWESNGQPENNYKTTPPVLDSD GSFFLYSKLTVDKSRWQQGNVFSCSVMHEALHNHYTQKSLSLSPG K |
| SEQ ID NO: 96 | DNA Heavy Chain | CAGGTGCAATTGAAAGAAAGCGGTCCGGCGCTGGTGAAACCGACC CAGACCCTGACCCTGACGTGCACCTTTTCCGGATTCAGCCTGTCT ACTTCCGGTGTTGGTGTGAGCTGGATTCGCCAGCCGCCGGGCAAA GCGCTCGAGTGGCTGGCGCTGATCTTCTCTGACCATGACAAGATC TATAGCACCAGCCTGAAAACCCGTCTGACCATTAGCAAAGATACT TCGAAAAACCAGGTGGTGCTGACCATGACCAACATGGACCCGGTG GATACCGCGACCTATTATTGCGCGCGTACTCTGATCGACCGTTCT GTTTACTTCGATTACTGGGGCCAAGGCACCCTGGTGACTGTTAGC TCAGCCTCCACCAAGGGTCCATCGGTCTTCCCCCTGGCACCCTCC TCCAAGAGCACCTCTGGGGGCACAGCGGCCCTGGGCTGCCTGGTC AAGGACTACTTCCCCGAACCGGTGACGGTGTCGTGGAACTCAGGC GCCCTGACCAGCGGCGTGCACACCTTCCCGGCTGTCCTACAGTCC TCAGGACTCTACTCCCTCAGCAGCGTGGTGACCGTGCCCTCCAGC AGCTTGGGCACCCAGACCTACATCTGCAACGTGAATCACAAGCCC AGCAACACCAAGGTGGACAAGAGAGTTGAGCCCAAATCTTGTGAC AAAACTCACACATGCCCACCGTGCCCAGCACCTGAAGCAGCGGGG GGACCGTCAGTCTTCCTCTTCCCCCCAAAACCCAAGGACACCCTC ATGATCTCCCGGACCCCTGAGGTCACATGCGTGGTGGTGGACGTG AGCCACGAAGACCCTGAGGTCAAGTTCAACTGGTACGTGGACGGC GTGGAGGTGCATAATGCCAAGACAAAGCCGCGGGAGGAGCAGTAC AACAGCACGTACCGGGTGGTCAGCGTCCTCACCGTCCTGCACCAG GACTGGCTGAATGGCAAGGAGTACAAGTGCAAGGTCTCCAACAAA GCCCTCCCAGCCCCCATCGAGAAAACCATCTCCAAAGCCAAAGGG CAGCCCCGAGAACCACAGGTGTACACCCTGCCCCCATCCCGGGAG GAGATGACCAAGAACCAGGTCAGCCTGACCTGCCTGGTCAAAGGC TTCTATCCCAGCGACATCGCCGTGGAGTGGGAGAGCAATGGGCAG CCGGAGAACAACTACAAGACCACGCCTCCCGTGCTGGACTCCGAC GGCTCCTTCTTCCTCTACAGCAAGCTCACCGTGGACAAGAGCAGG TGGCAGCAGGGGAACGTCTTCTCATGCTCCGTGATGCATGAGGCT CTGCACAACCACTACACGCAGAAGAGCCTCTCCCTGTCTCCGGGT AAA |
| SEQ ID NO: 97 | LCDR1 (Combined) | SGSSSNIGHHYVS |
| SEQ ID NO: 98 | LCDR2 (Combined) | DNTNRPS |
| SEQ ID NO: 99 | LCDR3 (Combined) | ATWDGLMNSIV |
| SEQ ID NO: 97 | LCDR1 (Kabat) | SGSSSNIGHHYVS |
| SEQ ID NO: 98 | LCDR2 (Kabat) | DNTNRPS |
| SEQ ID NO: 99 | LCDR3 (Kabat) | ATWDGLMNSIV |
| SEQ ID NO: 100 | LCDR1 (Chothia) | SSSNIGHHY |
| SEQ ID NO: 101 | LCDR2 (Chothia) | DNT |
| SEQ ID NO: 102 | LCDR3 (Chothia) | DGLMNSI |
| SEQ ID NO: 103 | LCDR1 (IMGT) | SSNIGHHY |
| SEQ ID NO: 101 | LCDR2 (IMGT) | DNT |
| SEQ ID NO: 99 | LCDR3 (IMGT) | ATWDGLMNSIV |
| SEQ ID NO: 104 | VL | DIVLTQPPSVSGAPGQRVTISCSGSSSNIGHHYVSWYQQLPGTAP KLLIYDNTNRPSGVPDRFSGSKSGTSASLAITGLQAEDEADYYCA TWDGLMNSIVFGGGTKLTVL |
| SEQ ID NO: 105 | DNA VL | GATATCGTGCTGACCCAGCCGCCGAGCGTGAGCGGTGCACCGGGC CAGCGCGTGACCATTAGCTGTAGCGGCAGCAGCAGCAACATTGGT CATCATTACGTGTCTTGGTACCAGCAGCTGCCGGGCACGGCGCCG AAACTGCTGATCTACGACAACACTAACCGCCCGAGCGGCGTGCCG GATCGCTTTAGCGGATCCAAAAGCGGCACCAGCGCCAGCCTGGCG ATTACCGGCCTGCAAGCAGAAGACGAAGCGGATTATTACTGCGCT ACTTGGGACGGTCTGATGAACTCTATCGTGTTTGGCGGCGGCACG AAGTTAACCGTCCTA |

TABLE 1-continued

| Sequences of Exemplary Monoclonal Antibodies That Bind Human TREM2. | | |
|---|---|---|
| SEQ ID NO: 106 | Light Chain | DIVLTQPPSVSGAPGQRVTISCSGSSSNIGHHYVSWYQQLPGTAP KLLIYDNTNRPSGVPDRFSGSKSGTSASLAITGLQAEDEADYYCA TWDGLMNSIVFGGGTKLTVLGQPKAAPSVTLFPPSSEELQANKAT LVCLISDFYPGAVTVAWKADSSPVKAGVETTTPSKQSNNKYAASS YLSLTPEQWKSHRSYSCQVTHEGSTVEKTVAPTECS |
| SEQ ID NO: 107 | DNA Light Chain | GATATCGTGCTGACCCAGCCGCCGAGCGTGAGCGGTGCACCGGGC CAGCGCGTGACCATTAGCTGTAGCGGCAGCAGCAGCAACATTGGT CATCATTACGTGTCTTGGTACCAGCAGCTGCCGGGCACGGCGCCG AAACTGCTGATCTACGACAACACTAACCGCCCGAGCGGCGTGCCG GATCGCTTTAGCGGATCCAAAAGCGGCACCAGCGCCAGCCTGGCG ATTACCGGCCTGCAAGCAGAAGACGAAGCGGATTATTACTGCGCT ACTTGGGACGGTCTGATGAACTCTATCGTGTTTGGCGGCGGCACG AAGTTAACCGTCCTAGGTCAGCCCAAGGCTGCCCCCTCGGTCACT CTGTTCCCGCCCTCCTCTGAGGAGCTTCAAGCCAACAAGGCCACA CTGGTGTGTCTCATAAGTGACTTCTACCCGGGAGCCGTGACAGTG GCCTGGAAGGCAGATAGCAGCCCCGTCAAGGCGGGAGTGGAGACC ACCACACCCTCCAAACAAAGCAACAACAAGTACGCGGCCAGCAGC TATCTGAGCCTGACGCCTGAGCAGTGGAAGTCCCACAGAAGCTAC AGCTGCCAGGTCACGCATGAAGGGAGCACCGTGGAGAAGACAGTG GCCCCTACAGAATGTTCA |

In some embodiments, the hTREM2 antibody or an antigen-binding fragment thereof comprises a VH domain having an amino acid sequence of any VH domain described in Table 1. Other suitable hTREM2 antibodies or antigen-binding fragments thereof can include amino acids that have been mutated, yet have at least 80, 85, 90, 95, 96, 97, 98, or 99 percent identity in the VH domain with the VH regions depicted in the sequences described in Table 1. The present disclosure in certain embodiments also provides antibodies or antigen-binding fragments thereof that specifically bind to human TREM2, wherein the antibodies or antibody fragments (e.g., antigen-binding fragments) comprise a VH CDR having an amino acid sequence of any one of the HCDRs listed in Table 1. In particular embodiments, the invention provides antibodies or antibody fragments (e.g., antigen-binding fragments) that specifically bind to human TREM2, comprising (or alternatively, consisting of) one, two, three, four, five or more VH CDRs having an amino acid sequence of any one of the HCDRs listed in Table 1.

In some embodiments, the hTREM2 antibody or antibody fragment (e.g., antigen binding fragment) comprises a VL domain having an amino acid sequence of any VL domain described in Table 1. Other suitable anti-human TREM2 antibodies or antibody fragments (e.g., antigen binding fragments) can include amino acids that have been mutated, yet have at least 80, 85, 90, 95, 96, 97, 98, or 99 percent identity in the VL domain with the VL regions depicted in the sequences described in Table 1. The present disclosure also provides antibodies or antibody fragments (e.g., antigen binding fragments) that specifically bind to human TREM2, the antibodies or antibody fragments (e.g., antigen binding fragments) comprise a VL CDR having an amino acid sequence of any one of the LCDRs listed in Table 1. In particular, the invention provides antibodies or antibody fragments (e.g., antigen binding fragments) that specifically bind to human TREM2, which comprise (or alternatively, consisting of) one, two, three or more VL CDRs having an amino acid sequence of any one of the LCDRs listed in Table 1.

Other anti-human TREM2 antibodies or antibody fragments (e.g., antigen binding fragment) disclosed herein include amino acids that have been mutated, yet have at least 80, 85, 90, 95, 96, 97, 98, or 99 percent identity in the CDR regions with the CDR regions depicted in the sequences described in Table 1. In some embodiments, it includes mutant amino acid sequences wherein no more than 1, 2, 3, 4 or 5 amino acids have been mutated in the CDR regions when compared with the CDR regions depicted in the sequence described in Table 1.

Also provided herein are nucleic acid sequences that encode VH, VL, full length heavy chain, and full length light chain of antibodies and antigen binding fragments thereof that specifically bind to human TREM2, e.g., the nucleic acid sequences in Table 1. Such nucleic acid sequences can be optimized for expression in the intended host cells, e.g. mammalian cells.

Other anti-human TREM2 antibodies disclosed herein include those where the amino acids or nucleic acids encoding the amino acids have been mutated, yet have at least 80, 85, 90 95, 96, 97, 98, or 99 percent identity to the sequences described in Table 1. In some embodiments, antibodies or antigen binding fragments thereof include mutant amino acid sequences wherein no more than 1, 2, 3, 4 or 5 amino acids have been mutated in the variable regions when compared with the variable regions depicted in the sequence described in Table 1, while retaining substantially the same therapeutic activity.

Since each provided antibody binds to human TREM2, the VH, VL, full length light chain, and full length heavy chain sequences (amino acid sequences and the nucleotide sequences encoding the amino acid sequences) can be "mixed and matched" to create other TREM2-binding antibodies disclosed herein. Such "mixed and matched" TREM2-binding antibodies can be tested using binding assays known in the art (e.g., ELISAs, assays described in the Exemplification). When chains are mixed and matched, a VH sequence from a particular VH/VL pairing should be replaced with a structurally similar VH sequence. A full length heavy chain sequence from a particular full length heavy chain/full length light chain pairing should be replaced with a structurally similar full length heavy chain sequence. A VL sequence from a particular VH/VL pairing should be replaced with a structurally similar VL sequence. A full length light chain sequence from a particular full length heavy chain/full length light chain pairing should be replaced with a structurally similar full length light chain sequence.

Accordingly, in one embodiment, the invention provides an isolated monoclonal antibody or antigen binding fragment thereof having: a heavy chain variable region (VH)

comprising an amino acid sequence selected from any one of SEQ ID NOs: 13 and 50; and a light chain variable region (VL) comprising an amino acid sequence selected from any one of SEQ ID NOs: 24 and 61; wherein the antibody specifically binds to human TREM2.

In another embodiment, the invention provides (i) an isolated monoclonal antibody having: a full length heavy chain (HC) comprising an amino acid sequence selected from any one of SEQ ID NOs: 15, 29, 33, 35, 37, 39, 52, 66, 70, 72, 74, 76; and a full length light chain (LC) comprising an amino acid sequence selected from any one of SEQ ID NOs: 26 and 63; or (ii) a functional protein comprising an antigen binding portion thereof.

In another embodiment, the present disclosure provides human TREM2-binding antibodies or antibody fragments thereof that comprise the heavy chain CDR1, CDR2 and CDR3 and light chain CDR1, CDR2 and CDR3 as described in Table 1, or combinations thereof. The amino acid sequences of the HCDR1s of the antibodies are shown in SEQ ID NOs: 4, 7, 8, 10, 41, 44, 45, 47. The amino acid sequences of the HCDR2s of the antibodies and are shown in SEQ ID NOs: 5, 9, 11, 42, 46, 48. The amino acid sequences of the HCDR3s of the antibodies are shown in SEQ ID NO: 6, 12, 43, 49. The amino acid sequences of the LCDR1s of the antibodies are shown in SEQ ID NOs: 17, 20, 23, 54, 57, 60. The amino acid sequences of the LCDR2s of the antibodies are shown in SEQ ID NOs: 18, 21, 55, 58. The amino acid sequences of the LCDR3s of the antibodies are shown in SEQ ID NOs: 19, 22, 56, 59, 56.

Given that each of the antibodies binds human TREM2 and that antigen-binding specificity is provided primarily by the CDR1, CDR2 and CDR3 regions, the VH CDR1, CDR2 and CDR3 sequences and VL CDR1, CDR2 and CDR3 sequences can be "mixed and matched" (i.e., CDRs from different antibodies can be mixed and matched), although each antibody must contain a VH CDR1, CDR2 and CDR3 and a VL CDR1, CDR2 and CDR3 to create other human TREM2-binding antibodies disclosed herein. Such "mixed and matched" TREM2-binding antibodies can be tested using the binding assays known in the art and those described in the Examples (e.g., ELISAs). When VH CDR sequences are mixed and matched, the CDR1, CDR2 and/or CDR3 sequence from a particular VH sequence should be replaced with a structurally similar CDR sequence(s). Likewise, when VL CDR sequences are mixed and matched, the CDR1, CDR2 and/or CDR3 sequence from a particular VL sequence should be replaced with a structurally similar CDR sequence(s). It will be readily apparent to the ordinarily skilled artisan that novel VH and VL sequences can be created by substituting one or more VH and/or VL CDR region sequences with structurally similar sequences from CDR sequences shown herein for monoclonal antibodies of the present invention.

Accordingly, the present disclosure provides an isolated monoclonal antibody or antigen binding region thereof comprising a heavy chain CDR1 comprising an amino acid sequence selected from the group consisting of SEQ ID NOs: 4, 7, 8, 10, 41, 44, 45, 47; a heavy chain CDR2 comprising an amino acid sequence selected from the group consisting of SEQ ID NOs: 5, 9, 11, 42, 46, 48; a heavy chain CDR3 comprising an amino acid sequence selected from the group consisting of SEQ ID NO: 6, 12, 43, 49; a light chain CDR1 comprising an amino acid sequence selected from the group consisting of SEQ ID NOs: 17, 20, 23, 54, 57, 60; a light chain CDR2 comprising an amino acid sequence selected from the group consisting of SEQ ID NOs: 18, 21, 55, 58; and a light chain CDR3 comprising an amino acid sequence selected from the group consisting of SEQ ID NOs: 19, 22, 56, 59, 56; wherein the antibody specifically binds human TREM2.

In certain embodiments, an antibody that specifically binds to human TREM2 is an antibody or antibody fragment (e.g., antigen binding fragment) that is described in Table 1. In some embodiments, the antibody or antigen binding region thereof that specifically binds to human TREM2 comprises a heavy chain complementary determining region 1 (HCDR1) comprising the amino acid sequence of SEQ ID NO: 4, 7, 8, or 10; a heavy chain complementary determining region 2 (HCDR2) comprising the amino acid sequence of SEQ ID NO: 5, 9, or 11; a heavy chain complementary determining region 3 (HCDR3) comprising the amino acid sequence of SEQ ID NO: 6 or 12; a light chain complementary determining region 1 (LCDR1) comprising the amino acid sequence of SEQ ID NO: 17, 20, or 23; a light chain complementary determining region 2 (LCDR2) comprising the amino acid sequence of SEQ ID NO: 18 or 21; and a light chain complementary determining region 3 (LCDR3) comprising the amino acid sequence of SEQ ID NO: 19 or 22.

In some embodiments, the antibody or antigen binding region thereof that specifically binds to human TREM2 comprises an HCDR1 comprising the amino acid sequence of SEQ ID NO: 41, 44, 45, or 47; an HCDR2 comprising the amino acid sequence of SEQ ID NO: 42, 46, or 48; an HCDR3 comprising the amino acid sequence of SEQ ID NO: 43 or 49; an LCDR1 comprising the amino acid sequence of SEQ ID NO: 54, 57, or 60; an LCDR2 comprising the amino acid sequence of SEQ ID NO: 55 or 58; and an LCDR3 comprising the amino acid sequence of SEQ ID NO: 56 or 59.

In some embodiments, the antibody or antigen binding region thereof that specifically binds to human TREM2 comprises a heavy chain variable region (VH) comprising the amino acid sequence of SEQ ID NO: 13 (or a sequence at least about 90%, 95%, 99% or more identical thereto, and/or having one, two, three or more substitutions, insertions, deletions, or modifications), and a light chain variable region (VL) comprising the amino acid sequence of SEQ ID NO: 24 (or a sequence at least about 90%, 95%, 99% or more identical thereto, and/or having one, two, three or more substitutions, insertions, deletions, or modifications).

In some embodiments, the antibody or antigen binding region thereof that specifically binds to human TREM2 comprises a heavy chain variable region (VH) comprising the amino acid sequence of SEQ ID NO: 50 (or a sequence at least about 90%, 95%, 99% or more identical thereto, and/or having one, two, three or more substitutions, insertions, deletions, or modifications), and a light chain variable region (VL) comprising the amino acid sequence of SEQ ID NO: 61 (or a sequence at least about 90%, 95%, 99% or more identical thereto, and/or having one, two, three or more substitutions, insertions, deletions, or modifications).

In some embodiments, the antibody that specifically binds to human TREM2 comprises a heavy chain comprising the amino acid sequence of SEQ ID NO: 15 (or a sequence at least about 90%, 95%, 99% or more identical thereto, and/or having one, two, three or more substitutions, insertions, deletions, or modifications), and a light chain comprising the amino acid sequence of SEQ ID NO: 26 (or a sequence at least about 90%, 95%, 99% or more identical thereto, and/or having one, two, three or more substitutions, insertions, deletions, or modifications).

In some embodiments, the antibody that specifically binds to human TREM2 comprises a heavy chain comprising the amino acid sequence of SEQ ID NO: 29 (or a sequence at least about 90%, 95%, 99% or more identical thereto, and/or having one, two, three or more substitutions, insertions, deletions, or modifications), and a light chain comprising the amino acid sequence of SEQ ID NO: 26 (or a sequence at least about 90%, 95%, 99% or more identical thereto, and/or having one, two, three or more substitutions, insertions, deletions, or modifications).

In some embodiments, the antibody that specifically binds to human TREM2 comprises a heavy chain comprising the amino acid sequence of SEQ ID NO: 33 (or a sequence at least about 90%, 95%, 99% or more identical thereto, and/or having one, two, three or more substitutions, insertions, deletions, or modifications), and a light chain comprising the amino acid sequence of SEQ ID NO: 26 (or a sequence at least about 90%, 95%, 99% or more identical thereto, and/or having one, two, three or more substitutions, insertions, deletions, or modifications).

In some embodiments, the antibody that specifically binds to human TREM2 comprises a heavy chain comprising the amino acid sequence of SEQ ID NO: 35 (or a sequence at least about 90%, 95%, 99% or more identical thereto, and/or having one, two, three or more substitutions, insertions, deletions, or modifications), and a light chain comprising the amino acid sequence of SEQ ID NO: 26 (or a sequence at least about 90%, 95%, 99% or more identical thereto, and/or having one, two, three or more substitutions, insertions, deletions, or modifications).

In some embodiments, the antibody that specifically binds to human TREM2 comprises a heavy chain comprising the amino acid sequence of SEQ ID NO: 37 (or a sequence at least about 90%, 95%, 99% or more identical thereto, and/or having one, two, three or more substitutions, insertions, deletions, or modifications), and a light chain comprising the amino acid sequence of SEQ ID NO: 26 (or a sequence at least about 90%, 95%, 99% or more identical thereto, and/or having one, two, three or more substitutions, insertions, deletions, or modifications).

In some embodiments, the antibody that specifically binds to human TREM2 comprises a heavy chain comprising the amino acid sequence of SEQ ID NO: 39 (or a sequence at least about 90%, 95%, 99% or more identical thereto, and/or having one, two, three or more substitutions, insertions, deletions, or modifications), and a light chain comprising the amino acid sequence of SEQ ID NO: 26 (or a sequence at least about 90%, 95%, 99% or more identical thereto, and/or having one, two, three or more substitutions, insertions, deletions, or modifications).

In some embodiments, the antibody that specifically binds to human TREM2 comprises a heavy chain comprising the amino acid sequence of SEQ ID NO: 52 (or a sequence at least about 90%, 95%, 99% or more identical thereto, and/or having one, two, three or more substitutions, insertions, deletions, or modifications), and a light chain comprising the amino acid sequence of SEQ ID NO: 63 (or a sequence at least about 90%, 95%, 99% or more identical thereto, and/or having one, two, three or more substitutions, insertions, deletions, or modifications).

In some embodiments, the antibody that specifically binds to human TREM2 comprises a heavy chain comprising the amino acid sequence of SEQ ID NO: 66 (or a sequence at least about 90%, 95%, 99% or more identical thereto, and/or having one, two, three or more substitutions, insertions, deletions, or modifications), and a light chain comprising the amino acid sequence of SEQ ID NO: 63 (or a sequence at least about 90%, 95%, 99% or more identical thereto, and/or having one, two, three or more substitutions, insertions, deletions, or modifications).

In some embodiments, the antibody that specifically binds to human TREM2 comprises a heavy chain comprising the amino acid sequence of SEQ ID NO: 70 (or a sequence at least about 90%, 95%, 99% or more identical thereto, and/or having one, two, three or more substitutions, insertions, deletions, or modifications), and a light chain comprising the amino acid sequence of SEQ ID NO: 63 (or a sequence at least about 90%, 95%, 99% or more identical thereto, and/or having one, two, three or more substitutions, insertions, deletions, or modifications).

In some embodiments, the antibody that specifically binds to human TREM2 comprises a heavy chain comprising the amino acid sequence of SEQ ID NO: 72 (or a sequence at least about 90%, 95%, 99% or more identical thereto, and/or having one, two, three or more substitutions, insertions, deletions, or modifications), and a light chain comprising the amino acid sequence of SEQ ID NO: 63 (or a sequence at least about 90%, 95%, 99% or more identical thereto, and/or having one, two, three or more substitutions, insertions, deletions, or modifications).

In some embodiments, the antibody that specifically binds to human TREM2 comprises a heavy chain comprising the amino acid sequence of SEQ ID NO: 74 (or a sequence at least about 90%, 95%, 99% or more identical thereto, and/or having one, two, three or more substitutions, insertions, deletions, or modifications), and a light chain comprising the amino acid sequence of SEQ ID NO: 63 (or a sequence at least about 90%, 95%, 99% or more identical thereto, and/or having one, two, three or more substitutions, insertions, deletions, or modifications).

In some embodiments, the antibody that specifically binds to human TREM2 comprises a heavy chain comprising the amino acid sequence of SEQ ID NO: 76 (or a sequence at least about 90%, 95%, 99% or more identical thereto, and/or having one, two, three or more substitutions, insertions, deletions, or modifications), and a light chain comprising the amino acid sequence of SEQ ID NO: 63 (or a sequence at least about 90%, 95%, 99% or more identical thereto, and/or having one, two, three or more substitutions, insertions, deletions, or modifications).

In some embodiments, the present invention provides an antibody or antigen-binding fragment thereof, which bind to the IgSF domain of TREM2 protein with a dissociation constant ($K_D$) of less than 200 pM, e.g. a $K_D$ of less than 150 pM, less than 120 pM, less than 100 pM, less than 90 pM, less than 70 pM, less than 50 pM, less than 40 pM, less than 30 pM, less than 20 pM, or less than 10 pM, e.g. as measured by Surface plasmon resonance (SPR). In some preferred embodiments, the antibodies or antigen-binding fragments provided herein bind to the IgSF domain of TREM2 protein with a dissociation constant ($K_D$) of less than 50 pM. In some preferred embodiments, the antibodies or antigen-binding fragments provided herein bind to the IgSF domain of TREM2 protein with a dissociation constant ($K_D$) of less than 5 pM.

Once a desired epitope on an antigen is determined, it is possible to generate antibodies to that epitope, e.g., using the techniques described in the present invention. Alternatively, during the discovery process, the generation and characterization of antibodies may elucidate information about desirable epitopes. From this information, it is then possible to competitively screen antibodies for binding to the same epitope. An approach to achieve this is to conduct cross-competition studies to find antibodies that competitively bind with one another, e.g., the antibodies compete for binding to the antigen. A high throughput process for "binning" antibodies based upon their cross-competition is described in International Patent Application No. WO 2003/48731. An epitope can comprises those residues to which the antibody binds.

Generally, antibodies specific for a particular target antigen will preferentially recognize an epitope on the target antigen in a complex mixture of proteins and/or macromolecules.

Regions of a given polypeptide that include an epitope can be identified using any number of epitope mapping techniques, well known in the art. See, e.g., Epitope Mapping Protocols in Methods in Molecular Biology, Vol. 66 (Glenn E. Morris, Ed., 1996, Humana Press, Totowa, N.J). For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., (1984) Proc. Natl. Acad. Sci. USA 8:3998-4002; Geysen et al., (1985) Proc. Natl. Acad. Sci. USA 82:78-182; Geysen et al., (1986) Mol. Immunol. 23:709-715. Similarly, conformational epitopes are readily identified by determining spatial conformation of amino acids such as by, e.g., x-ray crystallography and two-dimensional nuclear magnetic resonance. See, e.g., Epitope Mapping Protocols, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., (1981) Proc. Natl. Acad. Sci USA 78:3824-3828; for determining antigenicity profiles, and the Kyte-Doolittle technique, Kyte et al., (1982) J. Mol. Biol. 157:105-132; for hydropathy plots. In some embodiments, an anti-TREM2 antibody specifically binds to an epitope in the IgSF domain of human TREM2. For example, an anti-TREM2 antibody can specifically bind to an epitope within the amino acid residues 19 to 132 of any one of SEQ ID NOs: 1, 2, or 3.

The antibody molecule can be a polyclonal or a monoclonal antibody. A monoclonal antibody can be made by hybridoma technology or by other methods such as phage display or combinatorial methods.

Phage display and combinatorial methods for generating antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) Bio/Technology 9:1370-1372; Hay et al. (1992) Hum Antibod Hybridomas 3:81-85; Huse et al. (1989) Science 246:1275-1281; Griffths et al. (1993) EMBO J 12:725-734; Hawkins et al. (1992) J Mol Biol 226:889-896; Clackson et al. (1991) Nature 352:624-628; Gram et al. (1992) PNAS 89:3576-3580; Garrad et al. (1991) Bio/Technology 9:1373-1377; Hoogenboom et al. (1991) Nuc Acid Res 19:4133-4137; and Barbas et al. (1991) PNAS 88:7978-7982).

In one embodiment, the antibody is a human antibody (e.g., an antibody made in a transgenic mouse which has been genetically engineered to produce an antibody from a human immunoglobulin sequence), or a non-human antibody, e.g., a rodent (mouse or rat), goat, primate (e.g., monkey), camel antibody.

Chimeric and/or humanized antibodies can be engineered to minimize the immune response by a human patient to antibodies produced in non-human subjects or derived from the expression of non-human antibody genes. Chimeric antibodies comprise a non-human animal antibody variable region and a human antibody constant region. Such antibodies retain the epitope binding specificity of the original monoclonal antibody, but may be less immunogenic when administered to humans, and therefore more likely to be tolerated by the patient. For example, one or all (e.g., one, two, or three) of the variable regions of the light chain(s) and/or one or all (e.g., one, two, or three) of the variable regions the heavy chain(s) of a mouse antibody (e.g., a mouse monoclonal antibody) can each be joined to a human constant region, such as, without limitation an IgG1 human constant region. Chimeric monoclonal antibodies can be produced by recombinant DNA techniques known in the art. For example, a gene encoding the constant region of a non-human antibody molecule can be substituted with a gene encoding a human constant region (see Robinson et al., PCT Patent Application PCT/US86/02269; Akira, et al., European Patent Application 184,187; or Taniguchi, M., European Patent Application 171,496). In addition, other suitable techniques that can be used to generate chimeric antibodies are described, for example, in U.S. Pat. Nos. 4,816,567; 4,978,775; 4,975,369; and 4,816,397.

A chimeric antibody can be further "humanized" by replacing portions of the variable region not involved in antigen binding with equivalent portions from human variable regions. Humanized antibodies comprise one or more human framework regions in the variable region together with non-human (e.g., mouse, rat, or hamster) complementarity-determining regions (CDRs) of the heavy and/or light chain. In some embodiments, a humanized antibody comprises sequences that are entirely human except for the CDR regions. Humanized antibodies are typically less immunogenic to humans, relative to non-humanized antibodies, and thus offer therapeutic benefits in certain situations. Humanized TREM2 antibodies can be generated using methods known in the art. See for example, Hwang et al., Methods 36:35, 2005; Queen et al., Proc. Natl. Acad. Sci. U.S.A. 86:10029-10033, 1989; Jones et al., Nature 321:522-25, 1986; Riechmann et al., Nature 332:323-27, 1988; Verhoeyen et al., Science 239:1534-36, 1988; Orlandi et al., Proc. Natl. Acad. Sci. U.S.A. 86:3833-3837, 1989; U.S. Pat. Nos. 5,225,539; 5,530,101; 5,585,089; 5,693,761; 5,693,762; and 6,180,370; and WO 90/07861.

Human TREM2 antibodies may be generated using methods that are known in the art. For example, the humaneering technology used to converting non-human antibodies into engineered human antibodies. U.S. Patent Publication No. 20050008625 describes an in vivo method for replacing a nonhuman antibody variable region with a human variable region in an antibody while maintaining the same or providing better binding characteristics relative to that of the nonhuman antibody. The method relies on epitope guided replacement of variable regions of a non-human reference antibody with a fully human antibody. The resulting human antibody is generally structurally unrelated to the reference nonhuman antibody, but binds to the same epitope on the same antigen as the reference antibody. Briefly, the serial epitope-guided complementarity replacement approach is enabled by setting up a competition in cells between a "competitor" and a library of diverse hybrids of the reference antibody ("test antibodies") for binding to limiting amounts of antigen in the presence of a reporter system which responds to the binding of test antibody to antigen. The competitor can be the reference antibody or derivative thereof such as a single-chain Fv fragment. The competitor can also be a natural or artificial ligand of the antigen which binds to the same epitope as the reference antibody. The only requirements of the competitor are that it binds to the same epitope as the reference antibody, and that it competes with the reference antibody for antigen binding. The test antibodies have one antigen-binding V-region in common from the nonhuman reference antibody, and the other V-region selected at random from a diverse source such as a repertoire library of human antibodies. The common V-region from the reference antibody serves as a guide, positioning the test antibodies on the same epitope on the antigen, and in the same orientation, so that selection is biased toward the highest antigen-binding fidelity to the reference antibody.

Many types of reporter system can be used to detect desired interactions between test antibodies and antigen. For example, complementing reporter fragments may be linked to antigen and test antibody, respectively, so that reporter activation by fragment complementation only occurs when the test antibody binds to the antigen. When the test antibody- and antigen-reporter fragment fusions are co-expressed with a competitor, reporter activation becomes dependent on the ability of the test antibody to compete with the competitor, which is proportional to the affinity of the test antibody for the antigen. Other reporter systems that can be used include the reactivator of an auto-inhibited reporter reactivation system (RAIR) as disclosed in U.S. patent application Ser. No. 10/208,730 (Publication No. 20030198971), or competitive activation system disclosed in U.S. patent application Ser. No. 10/076,845 (Publication No. 20030157579).

With the serial epitope-guided complementarity replacement system, selection is made to identify cells expressing a single test antibody along with the competitor, antigen, and reporter components. In these cells, each test antibody competes one-on-one with the competitor for binding to a limiting amount of antigen. Activity of the reporter is proportional to the amount of antigen bound to the test antibody, which in turn is proportional to the affinity of the test antibody for the antigen and the stability of the test antibody. Test antibodies are initially selected on the basis of their activity relative to that of the reference antibody when expressed as the test antibody. The result of the first round of selection is a set of "hybrid" antibodies, each of which is comprised of the same non-human V-region from the reference antibody and a human V-region from the library, and each of which binds to the same epitope on the antigen as the reference antibody. One of more of the hybrid antibodies selected in the first round will have an affinity for the antigen comparable to or higher than that of the reference antibody.

In the second V-region replacement step, the human V-regions selected in the first step are used as guide for the selection of human replacements for the remaining non-human reference antibody V-region with a diverse library of cognate human V-regions. The hybrid antibodies selected in the first round may also be used as competitors for the second round of selection. The result of the second round of selection is a set of fully human antibodies which differ structurally from the reference antibody, but which compete with the reference antibody for binding to the same antigen. Some of the selected human antibodies bind to the same epitope on the same antigen as the reference antibody. Among these selected human antibodies, one or more binds to the same epitope with an affinity which is comparable to or higher than that of the reference antibody.

In some embodiments, the present invention provides an antibody or antigen-binding fragment thereof that bind to human TREM2 protein and facilitate TREM2-dependent physiological activities, e.g. enhance phagocytosis (e.g. in hM2A macrophages, or in human iPS-derived microglia-like cells, or in microglia/macrophages in the brain), enhance chemotaxis in human iPS-derived microglia-like cells, increase NFAT-driven reporter gene activity in a human monocytic cell line, or increase Syk phosphorylation in hM2A macrophages. This facilitation and/or enhancement can be e.g. at least 10%, at least 20%, at least 30%, at least 40%, at least 50%, at least 60%, at least 70%, at least 80%, or at least 90%.

Engineered and Modified Antibodies

An antibody of the invention can be prepared using an antibody having one or more of the VH and/or VL sequences described in Table 1 as a starting material to engineer a modified antibody, which modified antibody may have altered properties from the starting antibody. An antibody can be engineered by modifying one or more residues within one or both variable regions (i.e., VH and/or VL), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998 Nature 332:323-327; Jones, P. et al., 1986 Nature 321:522-525; Queen, C. et al., 1989 Proc. Natl. Acad., U.S.A. 86:10029-10033; U.S. Pat. No. 5,225,539 to Winter, and U.S. Pat. Nos. 5,530,101; 5,585,089; 5,693,762 and 6,180,370 to Queen et al.)

Such framework sequences can be obtained from public DNA databases or published references that include germline antibody gene sequences or rearranged antibody sequences. For example, germline DNA sequences for human heavy and light chain variable region genes can be found in the "VBase" human germline sequence database (available on the Internet at www.mrc-cpe.cam.ac.uk/vbase), as well as in Kabat, E. A., et al., 1991 Sequences of Proteins of Immunological Interest, Fifth Edition, U.S. Department of Health and Human Services, NIH Publication No. 91-3242; Tomlinson, I. M., et al., 1992 J. fol. Biol. 227:776-798; and Cox, J. P. L. et al., 1994 Eur. J Immunol. 24:827-836; the contents of each of which are expressly incorporated herein by reference. For example, germline DNA sequences for human heavy and light chain variable region genes and rearranged antibody sequences can be found in "IMGT" database (available on the Internet at www.imgt.org; see Lefranc, M. P. et al., 1999 Nucleic Acids Res. 27:209-212; the contents of each of which are expressly incorporated herein by reference.)

An example of framework sequences for use in the antibodies and antigen-binding fragments thereof of the invention are those that are structurally similar to the framework sequences used by selected antibodies and antigen-binding fragments thereof of the invention, e.g., consensus sequences and/or framework sequences used by monoclonal antibodies of the invention. The VH CDR1, 2 and 3 sequences, and the VL CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

Another type of variable region modification is to mutate amino acid residues within the VH and/or VL CDR1, CDR2 and/or CDR3 regions to thereby improve one or more binding properties (e.g., affinity) of the antibody of interest, known as "affinity maturation." Site-directed mutagenesis or PCR-mediated mutagenesis can be performed to introduce the mutation (s) and the effect on antibody binding, or other functional property of interest, can be evaluated in in vitro or in vivo assays as described herein and provided in the Examples. Conservative modifications (as discussed above) can be introduced. The mutations may be amino acid substitutions, additions or deletions. Moreover, typically no more than one, two, three, four or five residues within a CDR region are altered.

A wide variety of antibody/immunoglobulin frameworks or scaffolds can be employed so long as the resulting polypeptide includes at least one binding region which specifically binds to TREM2. Such frameworks or scaffolds include the 5 main idiotypes of human immunoglobulins, antigen-binding fragments thereof, and include immunoglobulins of other animal species, preferably having humanized features. Single heavy-chain antibodies such as those identified in camelids are of particular interest in this regard. Novel frameworks, scaffolds and fragments continue to be discovered and developed by those skilled in the art.

In one aspect, the invention pertains to a method of generating non-immunoglobulin based antibodies using non-immunoglobulin scaffolds onto which CDRs of the invention can be grafted. Known or future non-immunoglobulin frameworks and scaffolds may be employed, as long as they comprise a binding region specific for the target TREM2 protein. Known non-immunoglobulin frameworks or scaffolds include, but are not limited to, fibronectin (Compound Therapeutics, Inc., Waltham, Mass.), ankyrin (Molecular Partners AG, Zurich, Switzerland), domain antibodies (Domantis, Ltd., Cambridge, Mass., and Ablynx nv, Zwijnaarde, Belgium), lipocalin (Pieris Proteolab AG, Freising, Germany), small modular immuno-pharmaceuticals (Trubion Pharmaceuticals Inc., Seattle, Wash.), maxybodies (Avidia, Inc., Mountain View, Calif), Protein A (Affibody AG, Sweden), and affilin (gamma-crystallin or ubiquitin) (SciI Proteins GmbH, Halle, Germany).

The fibronectin scaffolds are based on fibronectin type III domain (e.g., the tenth module of the fibronectin type III (10 Fn3 domain)). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands (see U.S. Pat. No. 6,818,418). These fibronectin-based scaffolds are not an immunoglobulin, although the overall fold is closely related to that of the smallest functional antibody fragment, the variable region of the heavy chain, which comprises the entire antigen recognition unit in camel and llama IgG. Because of this structure, the non-immunoglobulin antibody mimics antigen binding properties that are similar in nature and affinity for those of antibodies. These scaffolds can be used in a loop randomization and shuffling strategy in vitro that is similar to the process of affinity maturation of antibodies in vivo. These fibronectin-based molecules can be used as scaffolds where the loop regions of the molecule can be replaced with CDRs of the invention using standard cloning techniques.

Camelid Antibodies

Antibody proteins obtained from members of the camel and dromedary (*Camelus bactrianus* and *Camelus dromaderius*) family including new world members such as llama species (*Lama paccos, Lama glama* and *Lama vicugna*) have been characterized with respect to size, structural complexity and antigenicity for human subjects. Certain IgG antibodies from this family of mammals as found in nature lack light chains, and are thus structurally distinct from the typical four-chain quaternary structure having two heavy and two light chains, for antibodies from other animals. See PCT/EP93/02214 (WO 94/04678 published 3 Mar. 1994).

A region of the camelid antibody which is the small single variable domain identified as VHH can be obtained by genetic engineering to yield a small protein having high affinity for a target, resulting in a low molecular weight antibody-derived protein known as a "camelid nanobody." See U.S. Pat. No. 5,759,808 issued Jun. 2, 1998; see also Stijlemans, B. et al., 2004 J Biol Chem 279: 1256-1261; Dumoulin, M. et al., 2003 Nature 424: 783-788; Pleschberger, M. et al. 2003 Bioconjugate Chem 14: 440-448; Cortez-Retamozo, V. et al. 2002 Int J Cancer 89: 456-62; and Lauwereys, M. et al. 1998 EMBO J 17: 3512-3520. Engineered libraries of camelid antibodies and antibody fragments are commercially available, for example, from Ablynx, Ghent, Belgium. As with other antibodies and antigen-binding fragments thereof of non-human origin, an amino acid sequence of a camelid antibody can be altered recombinantly to obtain a sequence that more closely resembles a human sequence, i.e., the nanobody can be "humanized." Thus the natural low antigenicity of camelid antibodies to humans can be further reduced.

The camelid nanobody has a molecular weight approximately one-tenth that of a human IgG molecule, and the protein has a physical diameter of only a few nanometers. One consequence of the small size is the ability of camelid nanobodies to bind to antigenic sites that are functionally invisible to larger antibody proteins, i.e., camelid nanobodies are useful as reagents detect antigens that are otherwise cryptic using classical immunological techniques, and as possible therapeutic agents. Thus, yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody.

The low molecular weight and compact size further result in camelid nanobodies being extremely thermostable, stable to extreme pH and to proteolytic digestion, and poorly antigenic. Another consequence is that camelid nanobodies readily move from the circulatory system into tissues, and even cross the blood-brain barrier and can treat disorders that affect nervous tissue. Nanobodies can further facilitated drug transport across the blood brain barrier. See U.S. patent application 20040161738 published Aug. 19, 2004. These features combined with the low antigenicity to humans indicate great therapeutic potential. Further, these molecules can be fully expressed in prokaryotic cells such as *E. coli* and are expressed as fusion proteins with bacteriophage and are functional.

Accordingly, a feature of the present invention is a camelid antibody or nanobody having high affinity for TREM2. In one embodiment herein, the camelid antibody or nanobody is naturally produced in the camelid animal, i.e., is produced by the camelid following immunization with TREM2 or a peptide fragment thereof, using techniques described herein for other antibodies. Alternatively, the TREM2-binding camelid nanobody is engineered, i.e., produced by selection for example from a library of phage displaying appropriately mutagenized camelid nanobody proteins using panning procedures with TREM2 as a target as described in the examples herein. Engineered nanobodies can further be customized by genetic engineering to have a half life in a recipient subject of from 45 minutes to two weeks. In a specific embodiment, the camelid antibody or nanobody is obtained by grafting the CDRs sequences of the heavy or light chain of the human antibodies of the invention into nanobody or single domain antibody framework sequences, as described for example in PCT/EP93/02214.

Bispecific Molecules and Multivalent Antibodies

In another aspect, the present invention features bispecific or multispecific molecules comprising an TREM2-binding antibody, or a fragment thereof, of the invention. An antibody of the invention, or antigen-binding regions thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multi-specific molecules that bind to more than two different binding sites and/or target molecules; such multi-specific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for TREM2 and a second binding specificity for a second target epitope. For example, the second target epitope is another epitope of TREM2 different from the first target epitope.

Additionally, for the invention in which the bispecific molecule is multi-specific, the molecule can further include a third binding specificity, in addition to the first and second target epitope.

In one embodiment, the bispecific molecules of the invention comprise as a binding specificity at least one antibody, or an antibody fragment thereof, including, e.g., a Fab, Fab', F (ab')2, Fv, or a single chain Fv. The antibody may also be a light chain or heavy chain dimer, or any minimal fragment thereof such as a Fv or a single chain construct as described in Ladner et al. U.S. Pat. No. 4,946,778.

Diabodies are bivalent, bispecific molecules in which VH and VL domains are expressed on a single polypeptide chain, connected by a linker that is too short to allow for pairing between the two domains on the same chain. The VH and VL domains pair with complementary domains of another chain, thereby creating two antigen binding sites (see e.g., Holliger et al., 1993 Proc. Natl. Acad. Sci. USA 90:6444-6448; Poijak et al., 1994 Structure 2:1121-1123). Diabodies can be produced by expressing two polypeptide chains with either the structure VHA-VLB and VHB-VLA (VH-VL configuration), or VLA-VHB and VLB-VHA (VL-VH configuration) within the same cell. Most of them can be expressed in soluble form in bacteria. Single chain diabodies (scDb) are produced by connecting the two diabody-forming polypeptide chains with linker of approximately 15 amino acid residues (see Holliger and Winter, 1997 Cancer Immunol. Immunother., 45 (3-4):128-30; Wu et al., 1996 Immunotechnology, 2 (1):21-36). scDb can be expressed in bacteria in soluble, active monomeric form (see Holliger and Winter, 1997 Cancer Immunol. Immunother., 45 (34): 128-30; Wu et al., 1996 Immunotechnology, 2 (1):21-36; Pluckthun and Pack, 1997 Immunotechnology, 3 (2): 83-105; Ridgway et al., 1996 Protein Eng., 9 (7):617-21). A diabody can be fused to Fc to generate a "di-diabody" (see Lu et al., 2004 J. Biol. Chem., 279 (4):2856-65).

Other antibodies which can be employed in the bispecific molecules of the invention are murine, chimeric and humanized monoclonal antibodies.

The bispecific molecules of the present invention can be prepared by conjugating the constituent binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), 5,5'-dithiobis (2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl)cyclohaxane-1-carboxylate (sulfo-SMCC) (see e.g., Karpovsky et al., 1984 J. Exp. Med. 160:1686; Liu, M A et al., 1985 Proc. Natl. Acad. Sci. USA 82:8648). Other methods include those described in Paulus, 1985 Behring Ins. Mitt. No. 78, 118-132; Brennan et al., 1985 Science 229:81-83), and Glennie et al., 1987 J. Immunol. 139: 2367-2375). Conjugating agents are SATA and sulfo-SMCC, both available from Pierce Chemical Co. (Rockford, Ill.).

When the binding specificities are antibodies, they can be conjugated by sulfhydryl bonding of the C-terminus hinge regions of the two heavy chains. In a particularly embodiment, the hinge region is modified to contain an odd number of sulfhydryl residues, for example one, prior to conjugation.

Alternatively, both binding specificities can be encoded in the same vector and expressed and assembled in the same host cell. This method is particularly useful where the bispecific molecule is a mAb X mAb, mAb X Fab, Fab X F (ab')2 or ligand X Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific molecules to their specific targets can be confirmed by, for example, enzyme-linked immunosorbent assay (ELISA), radioimmunoassay (REA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

In another aspect, the present invention provides multivalent compounds comprising at least two identical or different antigen-binding portions of the antibodies and antigen-binding fragments thereof of the invention binding to TREM2. The antigen-binding portions can be linked together via protein fusion or covalent or noncovalent linkage. Alternatively, methods of linkage has been described for the bispecific molecules. Tetravalent compounds can be obtained for example by cross-linking antibodies and antigen-binding fragments thereof of the invention with an antibody or antigen-binding fragment that binds to the constant regions of the antibodies and antigen-binding fragments thereof of the invention, for example the Fc or hinge region.

Trimerizing domain are described for example in patent EP 1 012 280B1. Pentamerizing modules are described for example in PCT/EP97/05897.

In some embodiments, the TREM2-binding molecule is a bispecific antibody that binds to both TREM2 and DAP12. In some embodiments, the TREM2-binding molecule is a bispecific antibody that recognizes a first antigen and a second antigen. In some embodiments, the first antigen is human TREM2 or a naturally occurring variant thereof. In some embodiments, the second antigen is human DAP12 or a naturally occurring variant thereof. In some embodiments, the second antigen is human DAP10 or a Siglec (Sialic acid-binding immunoglobulin-type lectin). In some embodiments, the second antigen is a disease-causing protein selected from amyloid beta or fragments thereof, Tau, IAPP, alpha-synuclein, TDP-43, FUS protein, prion protein, PrPSc, huntingtin, calcitonin, superoxide dismutase, ataxin, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, and proline-arginine (PR) repeat peptides. In some embodiments, the second antigen is a blood brain barrier targeting protein selected from transferrin receptor, insulin receptor, insulin like growth factor receptor, LRP-1, and LRP1; or ligands and/or proteins expressed on immune cells, wherein the ligands and/or proteins selected from the group consisting of: CD40, OX40, ICOS, CD28, CD137/4-1BB, CD27, GITR, PD-L1, CTLA4, PD-L2, PD-1, B7-H3, B7-H4, HVEM, BTLA, KIR, GAL9, TIM3, A2AR, LAG, and phosphatidylserine. Alternatively, the second antigen may be a protein expressed on one or more tumor cells.

Antibodies with Extended Half Life

The present invention provides for antibodies that specifically bind to TREM2 and have an extended half-life in vivo.

Many factors may affect the half life of a protein in vivo. For examples, kidney filtration, metabolism in the liver, degradation by proteolytic enzymes (proteases), and immunogenic responses (e.g., protein neutralization by antibodies and uptake by macrophages and dendritic cells). A variety of strategies can be used to extend the half life of the antibodies and antigen-binding fragments thereof of the present invention. For example, by chemical linkage to polyethylene glycol (PEG), reCODE PEG, antibody scaffold, polysialic acid (PSA), hydroxyethyl starch (HES), albumin-binding ligands, and carbohydrate shields; by genetic fusion to proteins binding to serum proteins, such as albumin, IgG, FcRn, and transferring; by coupling (genetically or chemically) to other binding moieties that bind to serum proteins, such as nanobodies, Fabs, DARPins, avimers, affibodies, and anticalins; by genetic fusion to rPEG, albumin, domain of albumin, albumin-binding proteins, and Fc; or by incorporation into nancarriers, slow release formulations, or medical devices.

To prolong the serum circulation of antibodies in vivo, inert polymer molecules such as high molecular weight PEG can be attached to the antibodies or a fragment thereof with or without a multifunctional linker either through site-specific conjugation of the PEG to the N- or C-terminus of the antibodies or via epsilon-amino groups present on lysine residues. To pegylate an antibody, the antibody, antigen-binding fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10)alkoxy- or aryloxy-polyethylene glycol or polyethylene glycol-maleimide. In one embodiment, the antibody to be pegylated is an aglycosylated antibody. Linear or branched polymer derivatization that results in minimal loss of biological activity will be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion-exchange chromatography. PEG-derivatized antibodies can be tested for binding activity as well as for in vivo efficacy using methods well-known to those of skill in the art, for example, by immunoassays described herein. Methods for pegylating proteins are known in the art and can be applied to the antibodies and antigen-binding fragments thereof of the invention. See for example, EP 0 154 316 by Nishimura et al. and EP 0 401 384 by Ishikawa et al.

Other modified pegylation technologies include reconstituting chemically orthogonal directed engineering technology (ReCODE PEG), which incorporates chemically specified side chains into biosynthetic proteins via a reconstituted system that includes tRNA synthetase and tRNA. This technology enables incorporation of more than 30 new amino acids into biosynthetic proteins in *E. coli*, yeast, and mammalian cells. The tRNA incorporates a normative amino acid any place an amber codon is positioned, converting the amber from a stop codon to one that signals incorporation of the chemically specified amino acid.

Recombinant pegylation technology (rPEG) can also be used for serum halflife extension. This technology involves genetically fusing a 300-600 amino acid unstructured protein tail to an existing pharmaceutical protein. Because the apparent molecular weight of such an unstructured protein chain is about 15-fold larger than its actual molecular weight, the serum halflife of the protein is greatly increased. In contrast to traditional PEGylation, which requires chemical conjugation and repurification, the manufacturing process is greatly simplified and the product is homogeneous.

Polysialytion is another technology, which uses the natural polymer polysialic acid (PSA) to prolong the active life and improve the stability of therapeutic peptides and proteins. PSA is a polymer of sialic acid (a sugar). When used for protein and therapeutic peptide drug delivery, polysialic acid provides a protective microenvironment on conjugation. This increases the active life of the therapeutic protein in the circulation and prevents it from being recognized by the immune system. The PSA polymer is naturally found in the human body. It was adopted by certain bacteria which evolved over millions of years to coat their walls with it. These naturally polysialylated bacteria were then able, by virtue of molecular mimicry, to foil the body's defense system. PSA, nature's ultimate stealth technology, can be easily produced from such bacteria in large quantities and with predetermined physical characteristics. Bacterial PSA is completely non-immunogenic, even when coupled to proteins, as it is chemically identical to PSA in the human body.

Another technology include the use of hydroxyethyl starch ("HES") derivatives linked to antibodies. HES is a modified natural polymer derived from waxy maize starch and can be metabolized by the body's enzymes. HES solutions are usually administered to substitute deficient blood volume and to improve the rheological properties of the blood. Hesylation of an antibody enables the prolongation of the circulation half-life by increasing the stability of the molecule, as well as by reducing renal clearance, resulting in an increased biological activity. By varying different parameters, such as the molecular weight of HES, a wide range of HES antibody conjugates can be customized.

Antibodies having an increased half-life in vivo can also be generated introducing one or more amino acid modifications (i.e., substitutions, insertions or deletions) into an IgG constant domain, or FcRn binding fragment thereof (preferably a Fc or hinge Fc domain fragment). See, e.g., International Publication No. WO 98/23289; International Publication No. WO 97/34631; and U.S. Pat. No. 6,277,375.

Further, antibodies can be conjugated to albumin in order to make the antibody or antibody fragment more stable in vivo or have a longer half life in vivo. The techniques are well-known in the art, see, e.g., International Publication Nos. WO 93/15199, WO 93/15200, and WO 01/77137; and European Patent No. EP 413,622.

The strategies for increasing half life is especially useful in nanobodies, fibronectin-based binders, and other antibodies or proteins for which increased in vivo half life is desired.

Antibody Conjugates

The present invention provides for antibodies or antigen-binding fragments thereof that specifically bind to the IgSF domain of human TREM2 recombinantly fused or chemically conjugated (including both covalent and non-covalent conjugations) to a heterologous protein or polypeptide (or antigen-binding fragment thereof, preferably to a polypeptide of at least 10, at least 20, at least 30, at least 40, at least 50, at least 60, at least 70, at least 80, at least 90 or at least 100 amino acids) to generate fusion proteins. In particular, the invention provides for fusion proteins comprising an antigen-binding fragment of an antibody described herein (e.g., a Fab fragment, Fd fragment, Fv fragment, F $(ab)_2$ fragment, a VH domain, a VH CDR, a VL domain or a VL CDR and a heterologous protein, polypeptide, or peptide. Methods for fusing or conjugating proteins, polypeptides, or peptides to an antibody or an antibody fragment are known in the art. See, e.g., U.S. Pat. Nos. 5,336,603, 5,622,929, 5,359,046, 5,349,053, 5,447,851, and 5,112,946; European Patent Nos. EP 307,434 and EP 367,166; International Publication Nos. WO 96/04388 and WO 91/06570; Ashkenazi et al., 1991, Proc. Natl. Acad. Sci. USA 88: 10535-10539; Zheng et al., 1995, J. Immunol. 154:5590-5600; and Vil et al., 1992, Proc. Natl. Acad. Sci. USA 89:11337-11341.

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies and antigen-binding fragments thereof of the invention (e.g., antibodies and antigen-binding fragments thereof with higher affinities and lower dissociation rates). See, generally, U.S. Pat. Nos. 5,605,793, 5,811,238, 5,830,721, 5,834,252, and 5,837,458; Patten et al., 1997, Curr. Opinion Biotechnol. 8:724-33; Harayama, 1998, Trends Biotechnol. 16 (2):76-82; Hansson, et al., 1999, J. Mol. Biol. 287:265-76; and Lorenzo and Blasco, 1998, Biotechniques 24 (2):308-313 (each of these patents and publications are hereby incorporated by reference in its entirety). Antibodies and antigen-binding fragments thereof, or the encoded antibodies and antigen-binding fragments thereof, may be altered by being subjected to random mutagenesis by error-prone PCR, random nucleotide insertion or other methods prior to recombination. A polynucleotide encoding an antibody antigen-binding fragment thereof that specifically binds to the IgSF region of TREM2 may be recombined with one or more components, motifs, sections, parts, domains, fragments, etc. of one or more heterologous molecules.

Moreover, the antibodies and antigen-binding fragments thereof can be fused to marker sequences, such as a peptide to facilitate purification. In one embodiment, the marker amino acid sequence is a hexa-histidine peptide, such as the tag provided in a pQE vector (QIAGEN, Inc., 9259 Eton Avenue, Chatsworth, Calif, 91311), among others, many of which are commercially available. As described in Gentz et al., 1989, Proc. Natl. Acad. Sci. USA 86:821-824, for instance, hexa-histidine provides for convenient purification of the fusion protein. Other peptide tags useful for purification include, but are not limited to, the hemagglutinin ("HA") tag, which corresponds to an epitope derived from the influenza hemagglutinin protein (Wilson et al., 1984, Cell 37:767), and the "FLAG" tag (Hopp et al., Bio/Technology 6 (1988): 1204-1210).

In one embodiment, antibodies and antigen-binding fragments thereof of the present invention are conjugated to a diagnostic or detectable agent. Such antibodies can be useful for monitoring or prognosing the onset, development, progression and/or severity of a disease or disorder as part of a clinical testing procedure, such as determining the efficacy of a particular therapy. Such diagnosis and detection can accomplished by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine (131I, 125I, 123I, and 121I), carbon (14C), sulfur (35S), tritium (3H), indium (115In, 113In, 112In, and 111In), technetium (99Tc), thallium (201Ti), gallium (68Ga, 67Ga), palladium (103Pd), molybdenum (99Mo), xenon (133Xe), fluorine (18F), 153Sm, 177Lu, 159Gd, 149 Pm, 140La, 175Yb, 166Ho, 90Y, 47Sc, 186Re, 188Re, 142Pr, 105Rh, 97Ru, 68Ge, 57Co, 65Zn, 85Sr, 32P, 153Gd, 169Yb, 51Cr, 54Mn, 75Se, 113Sn, and 117Tin; and positron emitting metals using various positron emission tomographies, and nonradioactive paramagnetic metal ions.

Further, an antibody or antigen-binding fragment thereof may be conjugated to a therapeutic moiety or drug moiety. Therapeutic moieties or drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, *pseudomonas* exotoxin, cholera toxin, or diphtheria toxin; a protein such as tumor necrosis factor, alpha-interferon, beta-interferon, nerve growth factor, platelet derived growth factor, tissue plasminogen activator, an apoptotic agent, an anti-angiogenic agent; or, a biological response modifier such as, for example, a lymphokine.

Moreover, an antibody can be conjugated to therapeutic moieties such as a radioactive metal ion, such as alpha-emitters such as 213Bi or macrocyclic chelators useful for conjugating radiometal ions, including but not limited to, 131In, 131LU, 131Y, 131Ho, 131Sm, to polypeptides. In one embodiment, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., 1998, Clin Cancer Res. 4 (10):2483-90; Peterson et al., 1999, Bioconjug. Chem. 10 (4):553-7; and Zimmerman et al., 1999, Nucl. Med. Biol. 26 (8):943-50, each incorporated by reference in their entireties.

Techniques for conjugating therapeutic moieties to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery ($2^{nd}$ Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., 1982, Immunol. Rev. 62:119-58.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Nucleic Acids Encoding the Antibodies

Also provided herein are nucleic acids encoding an antibody or antigen-binding fragment thereof described herein. Such nucleic acids can encode polypeptides comprising segments or domains of the hTREM2 antibodies or antigen-binding fragments thereof described herein. Such nucleic acids or polynucleotides can encode at least one CDR region and usually all three CDR regions from the heavy or light chain of the hTREM2 antibodies described herein. Such nucleic acids or polynucleotides can also encode all or substantially all of the variable region sequence of the heavy chain and/or the light chain of the hTREM2 antibodies described herein. Such nucleic acids or polynucleotides can also encode both a variable region and a constant region of the antibody. Because of the degeneracy of the genetic code, a variety of nucleic acid sequences will encode each of the immunoglobulin amino acid sequences. For example, the invention features a first and second nucleic acid encoding heavy and light chain variable regions, respectively, of a hTREM2 antibody or an antigen-binding fragment thereof chosen from one or more of the antibodies disclosed herein. The nucleic acid can comprise a nucleotide sequence as set forth in Table 1, or a sequence substantially identical thereto (e.g., a sequence having at least about 85%, 90%, 95%, or 99% sequence identity thereto, or which differs by no more than 3, 6, 15, 30, or 45 nucleotides from the sequences shown in Table 1). The nucleic acid can comprise more than one nucleotide sequence as set forth in Table 1 (for example a light chain variable domain sequence and a heavy chain variable domain sequence, or for example, a light chain sequence or a heavy chain sequence), or a sequence substantially identical thereto (e.g., a sequence having at least about 85%, 90%, 95%, or 99% sequence identity thereto, or which differs by no more than 3, 6, 15, 30, or 45 nucleotides from the sequences shown in Table 1).

In certain embodiments, the nucleic acid can comprise a nucleotide sequence encoding at least one, two, or three CDRs or hypervariable loops from a heavy chain variable region having an amino acid sequence as set forth in Table 1, or a sequence substantially homologous thereto (e.g., a sequence having at least about 85%, 90%, 95%, or 99% sequence identity thereto, and/or having one or more substitutions, e.g., conserved substitutions). In other embodiments, the nucleic acid can comprise a nucleotide sequence encoding at least one, two, or three CDRs or hypervariable loops from a light chain variable region having an amino acid sequence as set forth in Table 1, or a sequence substantially homologous thereto (e.g., a sequence having at least about 85%, 90%, 95%, or 99% sequence identity thereto, and/or having one or more substitutions, e.g., conserved substitutions). In yet another embodiment, the nucleic acid can comprise a nucleotide sequence encoding at least one, two, three, four, five, or six CDRs or hypervariable loops from heavy and light chain variable regions having an amino acid sequence as set forth in Table 1, or a sequence substantially homologous thereto (e.g., a sequence having at least about 85%, 90%, 95%, or 99% sequence identity thereto, and/or having one or more substitutions, e.g., conserved substitutions).

In certain embodiments, the nucleic acid can comprise a nucleotide sequence encoding at least one, two, or three CDRs or hypervariable loops from a heavy chain variable region having the nucleotide sequence as set forth in Table 1, a sequence substantially homologous thereto (e.g., a sequence having at least about 85%, 90%, 95%, or 99% sequence identity thereto). In another embodiment, the nucleic acid can comprise a nucleotide sequence encoding at least one, two, or three CDRs or hypervariable loops from a light chain variable region having the nucleotide sequence as set forth in Table 1, or a sequence substantially homologous thereto (e.g., a sequence having at least about 85%, 90%, 95%, or 99% sequence identity thereto). In yet another embodiment, the nucleic acid can comprise a nucleotide sequence encoding at least one, two, three, four, five, or six CDRs or hypervariable loops from heavy and light chain variable regions having the nucleotide sequence as set forth in Table 1, or a sequence substantially homologous thereto (e.g., a sequence having at least about 85%, 90%, 95%, or 99% sequence identity thereto).

The polynucleotide sequences can be produced by de novo synthesis (e.g. solid-phase DNA synthesis) or by PCR mutagenesis of an existing sequence encoding a hTREM2 antibody or an antigen-binding fragment thereof. Direct chemical synthesis of nucleic acids can be accomplished by methods known in the art, such as the phosphotriester method of Narang et al., 1979, Meth. Enzymol. 68:90; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, N.Y., 1992; PCR Protocols: A Guide to Methods and Applications, Innis et al. (Ed.), Academic Press, San Diego, Calif, 1990; Mattila et al., Nucleic Acids Res. 19:967, 1991; and Eckert et al., PCR Methods and Applications 1:17, 1991.

Also provided herein are vectors (e.g., expression vectors) comprising a polynucleotide encoding a polypeptide comprising a segment or domain of the hTREM2 antibodies or antigen-binding fragments thereof described herein. Such vectors may be used to express and/or produce, or affect the expression of, a hTREM2 antibody or antigen-binding fragments (e.g., as described herein), for example, in cells ex vivo or in cells in vivo, for example in a tissue or tissues of interest in an organism. Various expression vectors can be employed to express the polynucleotides encoding the hTREM2 antibodies or binding fragments thereof. Both viral-based and nonviral expression vectors can be used to produce the antibodies or fragments thereof in a cell, for example a mammalian cell. Nonviral vectors and systems include plasmids, episomal vectors, typically with an expression cassette for expressing a protein or RNA, and human artificial chromosomes (see, e.g., Harrington et al., Nat Genet. 15:345, 1997).). Such non-viral vectors may be delivered to a cell of interest using transfection or transduction methods known in the art, for example, using lipids (e.g., lipofectamine), electroporation, mechanical cell membrane distortion, and the like. The term "expression vector" refers to a carrier nucleic acid molecule into which a desired coding sequence can be inserted for introduction into a cell where it can be expressed. The vector can be a DNA vector, a RNA vector, a plasmid, a cosmid, or a viral vector, or artificial chromosomes (see, e.g., Harrington et al., Nat Genet 15:345, 1997). For example, non-viral vectors useful for expression of the hTREM2 antibodies or antigen-binding fragments thereof in mammalian (e.g., human) cells include pThioHis A, B & C, pcDNA3.1/His, pEBVHis A, B & C, (Invitrogen, San Diego, Calif), MPSV vectors, and numerous other vectors known in the art for expressing proteins. For example, one class of vectors utilizes DNA elements which are derived from animal viruses such as, for example, bovine papilloma virus, polyoma virus, adenovirus, vaccinia virus, baculovirus, retroviruses (Rous Sarcoma Virus, MMTV or MOMLV) or SV40 virus. Another class of vectors utilizes RNA elements derived from RNA viruses such as Semliki Forest virus, Eastern Equine Encephalitis virus and Flaviviruses. Useful viral vectors include vectors based on any one of the following viruses: retroviruses (e.g., lentivirus), lentiviruses adenoviruses, adeno-associated viruses, herpes viruses (e.g., Herpes Simplex Virus (HSV)), vectors based on SV40, papilloma virus, HBP Epstein Barr virus, vaccinia virus, Sinbis virus, influenza virus, reovirus, Newcastle disease virus (NDV), measles virus, vesicular stomatitis virus (VSV), parvovirus, poliovirus, poxvirus, Seneca Valley virus, coxsackievirus, enterovirus, myxoma virus, maraba virus, or Semliki Forest virus (SFV). See, Brent et al., supra; Smith, Annu. Rev. Microbiol. 49:807, 1995; and Rosenfeld et al., Cell 68:143, 1992.

In some embodiments the vector is a retroviral vector. In some embodiments, the vector is a lentiviral vector. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. A retroviral vector may also be, e.g., a gammaretroviral vector. A gammaretroviral vector may include, e.g., a promoter, a packaging signal (W), a primer binding site (PBS), one or more (e.g., two) long terminal repeats (LTR), and a transgene of interest, e.g., a gene encoding a CAR. A gammaretroviral vector may lack viral structural gens such as gag, pol, and env. Exemplary gammaretroviral vectors include Murine Leukemia Virus (MLV), Spleen-Focus Forming Virus (SFFV), and Myeloproliferative Sarcoma Virus (MPSV), and vectors derived therefrom. Other gammaretroviral vectors are described, e.g., in Tobias Maetzig et al., "Gammaretroviral Vectors: Biology, Technology and Application" Viruses. 2011 June; 3(6): 677-713.

In some embodiments, the vector is an adeno-associated virus (AAV) vector, e.g., a recombinant AAV (rAAV) vector. "AAV" is an abbreviation for adeno-associated virus, and may be used to refer to the virus itself or derivatives thereof. The term covers all subtypes and both naturally occurring and recombinant forms, except where required otherwise. The abbreviation "rAAV" refers to recombinant adeno-associated virus, also referred to as a recombinant AAV vector (or "rAAV vector"). The term "AAV" includes, for example, AAV type 1 (AAV1), AAV type 2 (AAV2), AAV type 3 (AAV3), AAV type 4 (AAV4), AAV type 5 (AAV5), AAV type 6 (AAV6), AAV type 7 (AAV7), AAV type 8 (AAV8), AAV type 9 (AAV9), AAV type 10 (AAV10, including AAVrh10), AAV type 12 (AAV12), avian AAV, bovine AAV, canine AAV, equine AAV, primate AAV, non-primate AAV, and ovine AAV. "Primate AAV" refers to AAV that infect primates, "non-primate AAV" refers to AAV that infect non-primate mammals, "bovine AAV" refers to AAV that infect bovine mammals, and so on.

The genomic sequences of various serotypes of AAV, as well as the sequences of the native inverted terminal repeats (ITRs), Rep proteins, and capsid subunits are known in the art. Such sequences may be found in the literature or in public databases such as GenBank. See, e.g., GenBank Accession NOs. NC-002077 (AAV1), AF063497 (AAV1), NC-001401 (AAV2), AF043303 (AAV2), NC-001729 (AAV3), NC-001829 (AAV4), U89790 (AAV4), NC-006152 (AAV5), AF513851 (AAV7), AF513852 (AAV8), and NC-006261 (AAV8); or in publications such as WO2005033321 (AAV1-9), the disclosures of which are incorporated by reference herein. See also, e.g., Srivistava et al. (1983) J. Virology 45:555; Chiorini et al. (1998) J. Virology 71:6823; Chiorini et al. (1999) J. Virology 73: 1309; Bantel-Schaal et al. (1999) J. Virology 73:939; Xiao et al. (1999) J. Virology 73:3994; Muramatsu et al. (1996) Virology 221:208; Shade et al., (1986) J. Virol. 58:921; Gao et al. (2002) Proc. Nat. Acad. Sci. USA 99: 11854; Moris et al. (2004) Virology 33:375-383; international patent publications WO 00/28061, WO 99/61601, WO 98/11244; and U.S. Pat. No. 6,156,303.

An "rAAV vector" as used herein refers to an AAV vector comprising a polynucleotide sequence not of AAV origin (i.e., a polynucleotide heterologous to AAV), typically a sequence of interest for the genetic transformation of a cell. In some embodiments, the heterologous polynucleotide may be flanked by at least one, and sometimes by two, AAV inverted terminal repeat (ITR) sequences. The term rAAV vector encompasses both rAAV vector particles and rAAV vector plasmids. An rAAV vector may either be single-stranded (ssAAV) or self-complementary (scAAV). An "AAV virus" or "AAV viral particle" or "rAAV vector particle" refers to a viral particle composed of at least one AAV capsid protein (typically by all of the capsid proteins of or derived from one or more wild-type AAV) and an encapsulated polynucleotide rAAV vector. If the particle comprises a heterologous polynucleotide (i.e., a polynucleotide other than a wild-type AAV genome such as a transgene to be delivered to a mammalian cell), it is typically referred to as an "rAAV vector particle" or simply an "rAAV vector." Thus, production of rAAV particle necessarily includes production of rAAV vector, as such a vector is contained within an rAAV particle.

In some embodiments, the vector can be a recombinant DNA molecule comprising a nucleic acid encoding a hTREM2 antibody or an antigen-binding fragment thereof, for example as described herein. "Recombinant" as used herein means that the vector, polynucleotide, polypeptide or cell is the product of various combinations of cloning, restriction or ligation steps (e.g. relating to a polynucleotide or polypeptide comprised therein), and/or other procedures that result in a construct that is distinct from a product found in nature. A recombinant virus or vector is a viral particle comprising a recombinant polynucleotide. The terms respectively include replicates of the original polynucleotide construct and progeny of the original virus construct.

The recombinant vector typically includes one or more regulatory sequences operatively linked to the nucleic acid sequence to be expressed. The term "regulatory sequence" includes promoters, enhancers, and other expression control elements (e.g., polyadenylation signals). Regulatory sequences include those which direct constitutive expression of a nucleotide sequence, as well as tissue-specific regulatory and/or inducible sequences. Expression vectors can also include elements designed to optimize messenger RNA stability and translatability in host cells, and/or drug selection markers for establishing permanent, stable cell clones expressing a hTREM2 antibody or an antigen-binding thereof, for example, as described herein. The design of the expression vector can depend on such factors as the choice of the host cell to be transformed, the level of expression of protein desired, and the like. General methods for generating such recombinant expression vectors can be found in Sambrook and Russell eds. (2001) Molecular Cloning: A Laboratory Manual, 3rd edition; the series Ausubel et al. eds. (2007 with updated through 2010) Current Protocols in Molecular Biology, among others known in the art.

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

Expression can employ any appropriate host cells known in the art, for example, mammalian host cells, bacterial host cells, yeast host cells, insect host cells, etc. Both prokaryotic and eukaryotic expression systems are widely available. In some embodiments, the expression system is a mammalian cell expression, such as a CHO cell expression system. In some embodiments, a nucleic acid may be codon-optimized to facilitate expression in a desired host cell. It will be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al. (2001).

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see Chandler et al., 1997, Proc. Natl. Acad. Sci. USA, 94(8):3596-601).

The vectors or constructs of the present disclosure will generally comprise at least one termination signal. A "termination signal" or "terminator" is comprised of the DNA sequences involved in specific termination of a RNA transcript by a RNA polymerase. Thus, in certain embodiments a termination signal that ends the production of a RNA transcript is contemplated. A terminator may be necessary in vivo to achieve desirable message levels. In eukaryotic systems, the terminator region may also comprise specific DNA sequences that permit site-specific cleavage of the new transcript so as to expose a polyadenylation site. This signals a specialized endogenous polymerase to add a stretch of about 200 A residues (poly A) to the 3' end of the transcript. RNA molecules modified with this polyA tail appear to more stable and are translated more efficiently. Thus, in other embodiments involving eukaryotes, it is preferred that the terminator comprises a signal for the cleavage of the RNA, and it is more preferred that the terminator signal promotes polyadenylation of the message. The terminator and/or polyadenylation site elements can serve to enhance message levels and/or to minimize read through from the cassette into other sequences. Terminators contemplated for use in the disclosure include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

In expression, particularly eukaryotic expression, one will typically include a polyadenylation signal to effect proper polyadenylation of the transcript. The nature of the polyadenylation signal is not believed to be crucial to the successful practice of the disclosure, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

To propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

In certain embodiments of the disclosure, cells containing a nucleic acid construct of the present disclosure may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (HSV-tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

The choice of expression vector depends on the intended cells in which one or more components of the vector is to be expressed. Typically, the vectors contain one or more regulatory sequences, such as a promoter and other regulatory sequence (e.g., enhancers) that are operably linked to the polynucleotides encoding a hTREM2 antibody or antigen-binding fragment thereof.

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned", "operatively linked", "under control", and "under transcriptional control" mean that a promoter is in a correct functional location and/or orientation in relation to a nucleic acid sequence to control transcriptional initiation and/or expression of that sequence. A promoter may or may not be used in conjunction with an "enhancer", which refers to a cis-acting regulatory sequence involved in the transcriptional activation of a nucleic acid sequence.

A promoter may be one naturally-associated with a gene or sequence, as may be obtained by isolating the 5' non-coding sequences located upstream of the coding segment and/or exon. Such a promoter can be referred to as "endogenous". Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally-occurring", i.e., containing different elements of different transcriptional regulatory regions and/or mutations that alter expression. In addition to producing nucleic acid sequences of promoters and enhancers synthetically, sequences may be produced using recombinant cloning and/or nucleic acid amplification technology, for example PCR, in connection with the compositions disclosed herein (see U.S. Pat. Nos. 4,683,202, 5,928,906). Furthermore, it is contemplated the control sequences that direct transcription and/or expression of sequences within non-nuclear organelles such as mitochondria, chloroplasts, and the like, can be employed as well.

The promoters employed can be constitutive, inducible, synthetic, tissue- or cell-specific, and/or useful under the appropriate conditions to direct high-level expression of the introduced DNA segment, such as is advantageous in the large-scale production of recombinant proteins and/or peptides. In addition, other regulatory elements may also be incorporated to improve expression of a nucleic acid encoding an antibody that binds to human TREM2 protein (i.e. hTREM2), e.g., enhancers, ribosomal binding site, transcription termination sequences, and the like.

In some embodiments, a constitutive promoter is employed to provide constant expression of a hTREM2 antibody or an antigen-binding fragment thereof. Examples of a constitutive promoter include, but not limited to, the immediate early cytomegalovirus (CMV) promoter, the simian virus 40 (SV40) early promoter, mouse mammary tumor virus (MMTV) promoter, human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the elongation factor-1$\alpha$ promoter, the hemoglobin promoter, and the creatine kinase promoter.

In one embodiment, an inducible promoter is employed to prevent expression of inserted sequences except under inducing conditions. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a.

Inducible promoters include, but are not limited to, e.g., an arabinose promoter, a lacZ promoter, a tetracycline promoter, a metallothionein promoter, a glucocorticoid promoter, a progesterone promoter, or a heat shock promoter.

In addition to promoters, other regulatory elements may also be required or desired for efficient expression of a hTREM2 antibody or of an antigen-binding fragment thereof. These elements include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

In some embodiments, a tissue- or cell-specific promoter is employed to provide expression of a hTREM2 antibody or of an antigen-binding fragment thereof only in specific tissues or cells. The identity of tissue- or cell-specific promoters or elements, as well as assays to characterize their activities, is well known to those of skill in the art. Examples include the human LIMK2 gene (Nomoto et al. 1999, Gene, 236(2):259-271), the somatostatin receptor 2 gene (Kraus et al., 1998, FEES Lett., 428(3): 165-170), murine epididymal retinoic acid-binding gene (Lareyre et al., 1999, J. Biol. Chem., 274(12):8282-8290), human CD4 (Zhao-Emonet et al., 1998, Biochirn. Biophys. Acta, 1442(2-3): 109-119), mouse alpha2 (XI) collagen (Tsumaki, et al., 1998, J. Biol. Chem., 273(36):22861-22864), D1A dopamine receptor gene (Lee, et al., 1997, J. Auton. Nerv. Syst., 74(2-3):86-90), insulin-like growth factor II (Wu et al., 1997, Biochem. Biophys. Res. Commun., 233(1):221-226), human platelet endothelial cell adhesion molecule-1 (Almendro et al., 1996, J. Immunol., 157(12):5411-5421), muscle creatine kinase (MCK) promoter (Wang et al., Gene Ther. 2008 November; 15(22):1489-99).

In some embodiments, a synthetic promoter is employed to provide expression of a hTREM2 antibody or an antigen-binding fragment thereof. Synthetic promoters can greatly exceed the transcriptional potencies of natural promoters. For example, the synthetic promoters that do not get shut off or reduced in activity by the endogenous cellular machinery or factors can be selected. Other elements, including trans-acting factor binding sites and enhancers may be inserted into the synthetic promoter to improve transcriptional efficiency. Synthetic promoters can be rationally designed and chemically synthesized to combine the best features of both synthetic and biological promoters. Synthetic oligos are annealed and ligated through several processes to generate the full-length chemically synthesized promoter. Synthetic promoters can be inducible or cell-type specific promoters.

In a preferred embodiment, the vector is an adenoassociated vector (AAV). In embodiments, the AAV vector comprises a polynucleotide encoding a hTREM2 antibody or antigen-binding fragment thereof, for example, as described herein. In typical embodiments, the AAV vector comprises a polynucleotide encoding a hTREM2 antibody or binding fragment thereof that is flanked on one or both sides by an inverted terminal repeat (ITR) sequence. The polynucleotide may additionally comprise one or more additional elements such as, for example, a promoter, an enhancer, one or more intron sequences, a poly(A) sequence and combinations thereof. In some embodiments the vector comprises a polynucleotide AAV vector plasmid comprising the polynucleotide encoding a hTREM2 antibody or an antigen-binding fragment thereof, for example, as described herein, encapsulated in an AAV capsid.

In some embodiments, the vector comprises the polynucleotide encoding a hTREM2 antibody or an antigen-binding fragment thereof, e.g., as described herein, operably linked to at least one target cell-compatible regulatory sequence, e.g., a promoter.

In some embodiments, the ITRs in the AAV vector are derived from the same AAV serotype. In some embodiments, the ITRs in the AAV vector are derived from different AAV serotypes. In some embodiments, the ITRs in the AAV particle are the same. In embodiments, the ITRs in the AAV particle are different.

In some embodiments the ITRs in the AAV vector are derived from the same AAV serotype as the AAV capsid. In embodiments, the ITRs in the AAV vector are derived from a serotype different from that of the AAV capsid. In one embodiment, the ITRs are derived from AAV2 and the AAV capsid is derived from a serotype other than AAV2, for example, AAV9.

The expression vectors may also provide a secretion signal sequence position to form a fusion protein with polypeptides encoded by inserted hTREM2 antibody or antigen-binding fragment thereof sequences. More often, the inserted sequences of a hTREM2 antibody or of an antigen-binding fragment thereof are linked to a signal sequence before inclusion in the vector. Vectors to be used to receive sequences encoding hTREM2 antibody light and heavy chain variable domains sometimes also encode constant regions or parts thereof. Such vectors allow expression of the variable regions as fusion proteins with the constant regions thereby leading to production of intact antibodies and antigen-binding fragments thereof. Typically, such constant regions are human.

Generation of an expression vector can utilize a vector that includes a multiple cloning site (MCS), which is a nucleic acid region that contains multiple restriction enzyme sites, any one of which can be used in conjunction with standard recombinant technology to digest the vector. See Carbonelli et al., 1999, Levenson et al., 1998, and Cocea, 1997. "Restriction enzyme digestion" refers to catalytic cleavage of a nucleic acid molecule with an enzyme that functions only at specific locations in a nucleic acid molecule. Many one of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts (see generally Sambrook et al., supra). Other methods include, e.g., electroporation, calcium phosphate treatment, liposome-mediated transformation, injection and microinjection, ballistic methods/gene gun, virosomes, immunoliposomes, polycation: nucleic acid conjugates, naked DNA, artificial virions, fusion to the herpes virus structural protein VP22, agent-enhanced uptake of DNA, ex vivo transduction, protoplast fusion, retroviral transduction, viral transfection, lipid based transfection or other conventional techniques. In the case of protoplast fusion, the cells are grown in media and screened for the appropriate activity. For long-term, high-yield production of recombinant proteins, stable expression will often be desired. For example, cell lines which stably express polypeptides can be prepared using expression vectors which contain viral origins of replication or endogenous expression elements and a selectable marker gene. Following the introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type. Methods and conditions for culturing the resulting transfected cells and for recovering the produced antibody are known to those skilled in the art, and may be varied or optimized depending upon the specific expression vector and mammalian host cell employed, based upon the present description.

Also provided herein are cells that include any one of the expression vectors described herein. In some embodiments, the disclosure features a host cell that includes a nucleic acid molecule described herein. Such cells can be a host cell or a therapeutic cell. The terms "host cell" and "recombinant host cell" are used interchangeably herein, which refer to not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

In one embodiment, the host cells are genetically engineered to comprise nucleic acids encoding the hTREM2 antibody or an antigen-binding fragment thereof. In one embodiment, the host cells are genetically engineered by using an expression cassette. The phrase "expression cassette" refers to nucleotide sequences, which are capable of affecting expression of a gene in hosts compatible with such sequences. Such cassettes may include a promoter, an open reading frame with or without introns, and a termination signal. Additional factors necessary or helpful in effecting expression may also be used, such as, for example, an inducible promoter.

The host cells for harboring and expressing the chains of the hTREM2 antibody or an antigen-binding fragment thereof can be, but are not limited to, a eukaryotic cell or a prokaryotic cell, such as a bacterial cell, an insect cell, or a human cell. *E. coli* is one prokaryotic host useful for cloning and expressing the polynucleotides of the present invention. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express the hTREM2antibodies or antigen-binding fragments thereof of the invention. Insect cells in combination with baculovirus vectors can also be used. Suitable insect cells include, but are not limited to, Sf9 cells.

In one embodiment, mammalian host cells are used to express and produce the hTREM2 antibodies or antigen-binding fragments thereof of the present invention. For example, they can be either a hybridoma cell line expressing endogenous immunoglobulin genes (e.g., the 1D6.C9 myeloma hybridoma cell) or a mammalian cell line harboring an exogenous expression vector (e.g., the SP2/0 myeloma cell). These include any normal mortal or normal or abnormal immortal animal or human cell. For example, a number of suitable host cell lines capable of secreting intact immunoglobulins have been developed including the CHO cell lines, various Cos cell lines, HeLa cells, myeloma cell lines, transformed B-cells and hybridomas. The use of mammalian tissue cell culture to express polypeptides is discussed generally in, e.g., Winnacker, From Genes to Clones, VCH Publishers, N.Y., N.Y., 1987. Expression vectors for mammalian host cells can include expression control sequences, such as an origin of replication, a promoter, and an enhancer (see, e.g., Queen, et al., Immunol. Rev. 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP pol III promoter, the constitutive MPSV promoter, the tetracycline-inducible CMV promoter (such as the human immediate-early CMV promoter), the constitutive CMV promoter, and promoter-enhancer combinations known in the art.

A host cell can be used to produce or express an antibody that binds to human TREM2 protein (i.e. hTREM2). Accordingly, the disclosure also features methods for producing a hTREM2 antibody or an antigen-binding fragment thereof using a host cell. In one embodiment, the method includes culturing the host cell (into which a recombinant expression vector encoding the antibody has been introduced) in a suitable medium, such that the hTREM2 antibody or an antigen-binding fragment thereof is produced. In another embodiment, the method further includes isolating the antibody from the medium or the host cell. Suitable eukaryotic cells include, but are not limited to, Vero cells, HeLa cells, COS cells, CHO cells, HEK293 cells, BHK cells and MDCKII cells. Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts. (See generally Sambrook, et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express the hTREM2 antibody chains or antigen-binding fragments can be prepared using expression vectors of the invention which contain viral origins of replication or endogenous expression elements and a selectable marker gene. Following the introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

Regulatory Sequence

A person skilled in the art may recognize that expression of one or more components of the vector in a target cell may require a regulatory sequence.

In one embodiment, the AAV vector plasmid comprises a regulatory sequence efficient for expression of a hTREM2 antibody or an antigen-binding fragment thereof, e.g., as described herein.

In one embodiment, the AAV vector plasmid comprises a regulatory sequence efficient for driving expression in the cell being targeted.

In one embodiment, the AAV vector plasmid comprises a regulatory sequence such as, but not limited to, promoters. As a non-limiting example, the promoter may be (1) CMV promoter, (2) CBA promoter, (3) FRDA or FXN promoter, (4) UBC promoter, (5) GUSB promoter, (6) NSE promoter, (7) Synapsin promoter, (8) MeCP2 promoter, (9) GFAP promoter, (10) HI promoter, (11) U6 promoter, (12) NFL promoter, (13) NFH promoter, (14) SCN8A promoter, or (15) PGK promoter.

Promoters

A person skilled in the art may recognize that expression of a hTREM2 antibody or an antigen-binding fragment thereof, e.g., as described herein, in a target cell may require a specific promoter including, but not limited to, a promoter that is species-specific, inducible, tissue-specific, or cell cycle-specific (Parr et al., Nat. Med. 3: 1145-9 (1997); the contents of which are herein incorporated by reference in its entirety).

In one embodiment, the AAV vector plasmid comprises a promoter efficient for expression of the hTREM2 antibody or an antigen-binding fragment thereof, e.g., as described herein.

In one embodiment, the AAV vector plasmid comprise a promoter efficient for driving expression in the cell being targeted.

In one embodiment, the promoter provides expression of a hTREM2 antibody or an antigen-binding fragment thereof, e.g., as described herein, for a period of time in targeted tissues such as, but not limited to, nervous system tissues. Expression of the hTREM2 antibody or an antigen-binding fragment thereof, e.g., as described herein, may be for a period of 1 hour, 2, hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 1 week, 8 days, 9 days, 10 days, 11 days, 12 days, 13 days, 2 weeks, 15 days, 16 days, 17 days, 18 days, 19 days, 20 days, 3 weeks, 22 days, 23 days, 24 days, 25 days, 26 days, 27 days, 28 days, 29 days, 30 days, 31 days, 1 month, 2 months, 3 months, 4 months, 5 months, 6 months, 7 months, 8 months, 9 months, 10 months, 11 months, 1 year, 13 months, 14 months, 15 months, 16 months, 17 months, 18 months, 19 months, 20 months, 21 months, 22 months, 23 months, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 21 years, 22 years, 23 years, 24 years, 25 years, 26 years, 27 years, 28 years, 29 years, 30 years, 31 years, 32 years, 33 years, 34 years, 35 years, 36 years, 37 years, 38 years, 39 years, 40 years, 41 years, 42 years, 43 years, 44 years, 45 years, 46 years, 47 years, 48 years, 49 years, 50 years, 55 years, 60 years, 65 years, or more than 65 years. Expression of the hTREM2 antibody or an antigen-binding fragment thereof, e.g., as described herein, may be for 1-5 hours, 1-12 hours, 1-2 days, 1-5 days, 1-2 weeks, 1-3 weeks, 1-4 weeks, 1-2 months, 1-4 months, 1-6 months, 2-6 months, 3-6 months, 3-9 months, 4-8 months, 6-12 months, 1-2 years, 1-5 years, 2-5 years, 3-6 years, 3-8 years, 4-8 years or 5-10 years or 10-15 years, or 15-20 years, or 20-25 years, or 25-30 years, or 30-35 years, or 35-40 years, or 40-45 years, or 45-50 years, or 50-55 years, or 55-60 years, or 60-65 years.

In one embodiment, the AAV vector plasmid comprises a region located about 5 kb upstream of the first exon of the encoded hTREM2 antibody or an antigen-binding fragment thereof, e.g., as described herein; more specifically, there is a 17-bp region located approximately 4.9 kb upstream of the first exon of the encoded Frataxin gene in order to allow for expression with the FRDA promoter (See e.g., Puspasari et al. Long Range Regulation of Human FXN Gene Expression, PLOS ONE, 2011; the contents of which is herein incorporated by reference in its entirety).

In one embodiment, the promoter is less than 1 kb. The promoter may have a length of 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800 or more than 800. The promoter may have a length between 200-300, 200-400, 200-500, 200-600, 200-700, 200-800, 300-400, 300-500, 300-600, 300-700, 300-800, 400-500, 400-600, 400-700, 400-800, 500-600, 500-700, 500-800, 600-700, 600-800 or 700-800.

In one embodiment, the promoter may be a combination of two or more components, regions or sequences of the same or different promoters such as, but not limited to, CMV and CBA. Each component may have a length of 200, 210, 220, 230, 240, 250, 260, 270, 280, 290, 300, 310, 320, 330, 340, 350, 360, 370, 380, 381, 382, 383, 384, 385, 386, 387, 388, 389, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800 or more than 800. Each component may have a length between 200-300, 200-400, 200-500, 200-600, 200-700, 200-800, 300-400, 300-500, 300-600, 300-700, 300-800, 400-500, 400-600, 400-700, 400-800, 500-600, 500-700, 500-800, 600-700, 600-800 or 700-800.

In one embodiment, the promoter is a combination of a CMV-enhancer sequence, for example an immediate/early CMV enhancer sequence (for example a 382-nucleotide CMV-enhancer sequence) and a chicken beta-actin (CBA)-promoter sequence (for example 260 nucleotide CBA promoter sequence).

In one embodiment, the promoter is a combination of a 280-nucleotide fragment of a CMV-enhancer sequence and a 266-nucleotide fragment of a chicken beta-actin (CBA)-promoter sequence. In some embodiments, the CMV enhancer sequence comprises, e.g., consists of:

(SEQ ID NO: 134)

```
cgttacat aacttacggt aaatggcccg cctggctgac
cgcccaacga cccccgccca ttgacgtcaa taatgacgta
tgttcccata gtaacgccaa tagggacttt ccattgacgt
caatgggtgg agtatttacg gtaaactgcc cacttggcag
```

-continued

```
tacatcaagt gtatcatatg ccaagtacgc cccctattga

cgtcaatgac ggtaaatggc ccgcctggca ttatgcccag

tacatgacct tatgggactt tcctacttgg cagtacatct ac
```

In some embodiments, the CBA promoter sequence comprises, e.g., consists of:

```
                                    (SEQ ID NO: 135)
cc acgttctgct tcactctccc catctccccc ccctccccac

ccccaatttt gtatttattt attttttaat tattttgtgc

agcgatgggg gcggggggg ggggggggcg cgcgccaggc

ggggcggggc ggggcgaggg gcggggcggg gcgaggcgga

gaggtgcggc ggcagccaat cagagcggcg cgctccgaaa

gtttcctttt atggcgaggc ggcggcggcg gcggccctat

aaaaagcgaa gcgcgcggcg ggcg
```

In one embodiment, the AAV vector comprises the hybrid CMV enhancer/chicken beta actin promoter comprising, e.g., consisting of, the sequence:

```
                                    (SEQ ID NO: 136)
cgttacat aacttacggt aaatggcccg cctggctgac

cgcccaacga cccccgccca ttgacgtcaa taatgacgta

tgttcccata gtaacgccaa tagggacttt ccattgacgt

caatgggtgg agtatttacg gtaaactgcc cacttggcag

tacatcaagt gtatcatatg ccaagtacgc cccctattga

cgtcaatgac ggtaaatggc ccgcctggca ttatgcccag

tacatgacct tatgggactt tcctacttgg cagtacatct

actcgaggcc acgttctgct tcactctccc catctccccc

ccctccccac ccccaatttt gtatttattt attttttaat

tattttgtgc agcgatgggg gcggggggg ggggggggcg

cgcgccaggc ggggcggggc ggggcgaggg gcggggcggg

gcgaggcgga gaggtgcggc ggcagccaat cagagcggcg

cgctccgaaa gtttcctttt atggcgaggc ggcggcggcg

gcggccctat aaaaagcgaa gcgcgcggcg ggcg
```

In one embodiment, the AAV vector plasmid comprises a ubiquitous promoter. Non-limiting examples of ubiquitous promoters include CMV, CBA (including derivatives CAG, CBh, etc.), EF-1a, PGK, UBC, GUSB (hGBp), and UCOE (promoter of HNRPA2B1-CBX3). In one embodiment, any of the promoters taught by Yu, Soderblom, Gill, Husain, Passini, Xu, Drews or Raymond may be used in the present inventions. Yu et al. (Molecular Pain 2011, 7:63; the contents of which are herein incorporated by reference in its entirety) evaluated the expression of eGFP under the CAG, EF-1a, PGK and UBC promoters in rat DRG cells and primary DRG cells using lentiviral vectors and found that UBC showed weaker expression than the other 3 promoters and there was only 10-12% glia expression seen for all promoters.

Soderblom et al. (E. Neuro 2015; the contents of which are herein incorporated by reference in its entirety) evaluated the expression of eGFP in AAV8 with CMV and UBC promoters and AAV2 with the CMV promoter after injection in the motor cortex. Intranasal administration of a plasmid containing a UBC or EF-1a promoter showed a sustained airway expression greater than the expression with the CMV promoter (See e.g., Gill et al., Gene Therapy 2001, Vol. 8, 1539-1546; the contents of which are herein incorporated by reference in its entirety). Husain et al. (Gene Therapy 2009; the contents of which are herein incorporated by reference in its entirety) evaluated a HOH construct with a hGUSB promoter, a HSV-1LAT promoter and a NSE promoter and found that the HOH construct showed weaker expression than NSE in mice brain. Passini and Wolfe (J. Virol. 2001, 12382-12392, the contents of which are herein incorporated by reference in its entirety) evaluated the long-term effects of the HβH vector following an intraventricular injection in neonatal mice and found that there was sustained expression for at least 1 year. Low expression in all brain regions was found by Xu et al. (Gene Therapy 2001, 8, 1323-1332; the contents of which are herein incorporated by reference in its entirety) when NF-L and NF-H promoters were used as compared to the CMV-lacZ, CMV-luc, EF, GFAP, hENK, nAChR, PPE, PPE+wpre, NSE (0.3 kb), NSE (1.8 kb) and NSE (1.8 kb+wpre). Xu et al. found that the promoter activity in descending order was NSE (1.8 kb), EF, NSE (0.3 kb), GFAP, CMV, hENK, PPE, NFL and NFH. NFL is a 650-nucleotide promoter and NFH is a 920 nucleotide promoter which are both absent in the liver but NFH is abundant in the sensory proprioceptive neurons, brain and spinal cord and NFH is present in the heart. SCN8A is a 470 nucleotide promoter which expresses throughout the DRG, spinal cord and brain with particularly high expression seen in the hippocampal neurons and cerebellar Purkinje cells, cortex, thalamus and hypothalamus (See e.g., Drews et al. Identification of evolutionary conserved, functional noncoding elements in the promoter region of the sodium channel gene SCN8A, Mamm Genome (2007) 18:723-731; and Raymond et al. Expression of Alternatively Spliced Sodium Channel a-subunit genes, Journal of Biological Chemistry (2004) 279(44) 46234-4624; the contents of each of which are herein incorporated by reference in their entireties).

In one embodiment, the AAV vector plasmid comprises a promoter which is not cell specific. In one embodiment, the promoter is a weak promoter (classified according to its affinity and other promoters affinity for RNA polymerase and/or sigma factor) for sustained expression of a hTREM2 antibody or an antigen-binding fragment thereof, e.g., as described herein, in nervous tissues. In one embodiment, the promoter is a weak promoter for sustained Frataxin expression in nervous system tissue such as, but not limited to, neuronal tissue and glial tissue.

In one embodiment, the AAV vector plasmid comprises a Friedreich's Ataxia (FRDA) promoter.

In one embodiment, the AAV vector plasmid comprises an ubiquitin c (UBC) promoter. The UBC promoter may have a size of 300-350 nucleotides. As a non-limiting example, the UBC promoter is 332 nucleotides.

In one embodiment, the AAV vector plasmid comprises a β-glucuronidase (GUSB) promoter. The GUSB promoter may have a size of 350-400 nucleotides. As a non-limiting example, the GUSB promoter is 378 nucleotides. As a non-limiting example, the AAV vector plasmid may be 5'-promoter-CMV/globin intron-hFXN-RBG-3', where the AAV vector plasmid may be self-complementary and the capsid may be the DJ serotype.

In one embodiment, the AAV vector plasmid comprises a neurofilament (NFL) promoter. The NFL promoter may have a size of 600-700 nucleotides. As a non-limiting example, the NFL promoter is 650 nucleotides. As a non-limiting example, the AAV vector plasmid may be 5'-promoter-CMV/globin intron-hFXN-RBG-3, where the AAV vector plasmid may be self-complementary and the capsid may be the DJ serotype.

In one embodiment, the AAV vector plasmid comprises a neurofilament heavy (NFH) promoter. The NFH promoter may have a size of 900-950 nucleotides. As a non-limiting example, the NFH promoter is 920 nucleotides. As a non-limiting example, the AAV vector plasmid may be 5'-promoter-CMV/globin intron-hFXN-RBG-3', where the AAV vector plasmid may be self-complementary and the capsid may be the DJ serotype.

In one embodiment, the AAV vector plasmid comprises a SCN8A promoter. The SCN8A promoter may have a size of 450-500 nucleotides. As a non-limiting example, the SCN8A promoter is 470 nucleotides. As a non-limiting example, the AAV vector plasmid may be d'-promoter-CMV/globin intron-hFXN-RBG-3, where the AAV vector plasmid may be self-complementary and the capsid may be the DJ serotype.

In one embodiment, the AAV vector plasmid comprises a frataxin (FXN) promoter.

In one embodiment, the AAV vector plasmid comprises a phosphoglycerate kinase 1 (PGK) promoter.

In one embodiment, the AAV vector plasmid comprises a chicken β-actin (CBA) promoter.

In one embodiment, the AAV vector plasmid comprises an immediate-early cytomegalovirus (CMV) promoter.

In one embodiment, the AAV vector plasmid comprises a H1 promoter.

In one embodiment, the AAV vector plasmid comprises a U6 promoter.

In one embodiment, the AAV vector plasmid comprises a liver or a skeletal muscle promoter. Non-limiting examples of liver promoters include hAAT and TBG. Non-limiting examples of skeletal muscle promoters include Desmin, MCK and C5-12.

In one embodiment, the AAV vector plasmid comprises an engineered promoter, for example a promoter derived from, but not identical to, a promoter described herein.

Enhancement Element

In one embodiment, the AAV vector plasmid may comprise at least one enhancer and/or expression element. The enhancer or expression element may be used in combination with a regulatory sequence (e.g., a promoter). In one embodiment, the AAV vector plasmid comprises a transgene enhancer, a promoter and/or a 5'UTR intron. The transgene enhancer, also referred to herein as an "enhancer," may be, but is not limited to, a CMV enhancer (or fragment thereof, e.g., as described herein). The promoter may be, but is not limited to, a CMV, CBA, UBC, GUSB, NSE, Synapsin, MeCP2, and GFAP promoter. The 5'UTR/intron may be, but is not limited to, SV40, and CBA-MVM.

In one embodiment, the AAV vector comprises an intron, optionally disposed between a promoter element and the polynucleotide encoding the hTREM2 antibody or the antigen-binding fragment thereof (e.g., as described herein). Without being bound by theory, inclusion of a 5' intron has been shown to enhance the level and steady state of mRNA encoding the hTREM2 antibody or the antigen-binding fragment thereof (e.g., as described herein). In embodiments, the enhancer is a 5' intron derived from SV40. In one embodiment, the SV40 intron comprises, e.g., consists of the sequence:

```
                                        (SEQ ID NO: 137)
gtaagtt tagtcttttt gtcttttatt tcaggtcccg

gatccggtgg tggtgcaaat caaagaactg ctcctcagtg

gatgttgcct ttacttctag
```

In one embodiment, the AAV vector plasmid (e.g., of the AAV vector) comprises an enhancer, a promoter and/or an intron combination such as, but not limited to, (1) CMV enhancer, CMV promoter, SV40 5'UTR intron (e.g., as described herein); (2) CMV enhancer, CBA promoter, SV40 5'UTR intron (e.g., as described herein); (3) CMV enhancer, CBA promoter, CBA-MVM 5'UTR intron (e.g., as described herein).

Transgene Enhancement

In one embodiment, the AAV vector plasmid comprises at least one transgene enhancer element which can enhance the transgene target specificity and expression (See e.g., Powell et al. Viral Expression Cassette Elements to Enhance Transgene Target Specificity and Expression in Gene Therapy, 2015; the contents of which are herein incorporated by reference in its entirety). Non-limiting examples of transgene enhancer elements to enhance the transgene target specificity and expression include promoters, endogenous miRNAs, post-transcriptional regulatory elements (PREs), polyadenylation (Poly A) signal sequences and upstream enhancers (USEs), CMV enhancers and introns.

In one embodiment, the AAV vector plasmid comprises at least one transgene enhancer element which is a CMV enhancer. In one embodiment, the AAV vector plasmid comprises at least one transgene enhancer element which is a promoter.

In one embodiment, the AAV vector plasmid comprises at least one transgene enhancer element which is an intron.

In one embodiment, the AAV vector plasmid comprises at least one transgene enhancer element which is endogenous miRNAs.

In one embodiment, the AAV vector plasmid comprises at least one transgene enhancer element which is post-transcriptional regulatory elements (PREs).

In one embodiment, the AAV vector plasmid comprises at least one transgene enhancer element which is polyadenylation (Poly A) signal sequences. In embodiments, the AAV vector plasmid of the AAV vector comprises a growth hormone poly A signal. In one embodiment the growth hormone poly A signal is derived from the bovine growth hormone (BGH) poly A signal. An example of a BGH poly A signal sequence is:

```
                                        (SEQ ID NO: 138)
ctagagct cgctgatcag cctcgactgt gccttctagt

tgccagccat ctgttgtttg cccctccccc gtgccttcct

tgaccctgga aggtgccact cccactgtcc tttcctaata

aaatgaggaa attgcatcgc attgtctgag taggtgtcat

tctattctgg ggggtggggt ggggcaggac agcaaggggg

aggattggga agacaatagc aggcatgctg ggga
```

In embodiments, the AAV vector plasmid comprises the poly A signal (e.g., the BGH poly A signal) downstream (e.g., 3' to) the polynucleotide encoding the hTREM2 antibody or an antigen-binding fragment thereof, e.g., as described herein.

In one embodiment, the AAV vector plasmid comprises at least one transgene enhancer element which is upstream enhancers (USEs).

Tissue-Specific Expression

In one embodiment, the vector genome may comprise a tissue-specific expression element to promote expression of the hTREM2 antibody or an antigen-binding fragment thereof, e.g., as described herein, in tissues and/or cells. As a non-limiting example, promoters can be tissue-specific expression elements include, but are not limited to, human elongation factor 1a-subunit (EF-1a), immediate-early cytomegalovirus (CMV), chicken (3-actin (CBA) and its derivative CAG, the R glucuronidase (GUSB), and ubiquitin C (UBC).

In one embodiment, the vector genome may comprise a tissue-specific expression elements which can be used to restrict expression to certain cell types such as, but not limited to, nervous system promoters which can be used to restrict expression to neurons, astrocytes, or oligodendrocytes.

In one embodiment, the vector genome may comprise a tissue-specific expression elements for neurons such as, but not limited to, neuron-specific enolase (NSE), platelet-derived growth factor (PDGF), platelet-derived growth factor B-chain (PDGF-0), the synapsin (Syn), the methyl-CpG binding protein 2 (MeCP2), Ca<2+>/calmodulin-dependent protein kinase II (CaMKII), metabotropic glutamate receptor 2 (mGluR2), NFL, NFH, -qP2, PPE, Enk and EAAT2 promoters.

In one embodiment, the vector genome may comprise a tissue-specific expression elements for astrocytes such as, but not limited to, the glial fibrillary acidic protein (GFAP) and EAAT2 promoters.

In one embodiment, the vector genome may comprise a tissue-specific expression elements for oligodendrocytes such as, but not limited to, the myelin basic protein (MBP) promoter.

Introns

In one embodiment, the AAV vector plasmid comprises at least one element to enhance the transgene expression such as one or more introns or portions thereof.

In one embodiment, the payload construct comprises at least one element to enhance the transgene expression such as one or more introns or portions thereof.

Non-limiting examples of introns include, MVM (67-97 bps), FIX truncated intron 1 (300 bps), β-globin SD/immunoglobulin heavy chain splice acceptor (250 bps), adenovirus splice donor/immunoglobin splice acceptor (500 bps), SV40 late splice donor/splice acceptor (19S/16S) (180 bps) and hybrid adenovirus splice donor/IgG splice acceptor (230 bps).

In one embodiment, the intron or intron portion may be 100-500 nucleotides in length. The intron may have a length of 80, 90, 100, 110, 120, 130, 140, 150, 160, 170, 171, 172, 173, 174, 175, 176, 177, 178, 179, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 or 500. The intron may have a length between 80-100, 80-120, 80-140, 80-160, 80-180, 80-200, 80-250, 80-300, 80-350, 80-400, 80-450, 80-500, 200-300, 200-400, 200-500, 300-400, 300-500, or 400-500.

In one embodiment, the AAV vector comprises an intron, optionally disposed between a promoter element and the polynucleotide encoding the hTREM2 antibody or an antigen-binding fragment thereof (e.g., as described herein). Without being bound by theory, inclusion of a 5' intron has been shown to enhance the level and steady state of mRNA encoding the hTREM2 antibody or the antigen-binding fragment thereof (e.g., as described herein). In embodiments, the enhancer is a 5' intron derived from SV40. In one embodiment, the SV40 intron comprises, e.g., consists of the sequence:

```
                                        (SEQ ID NO: 137)
gtaagtt tagtcttttt gtcttttatt tcaggtcccg

gatccggtgg tggtgcaaat caaagaactg ctcctcagtg

gatgttgcct ttacttctag
```

In one embodiment, the AAV vector plasmid of the AAV vector comprises (1) A CMV enhancer (e.g., SEQ ID NO: 134), (2) a CBA promoter (e.g., SEQ ID NO: 135), (3) an SV40 intron (e.g., SEQ ID NO: 137), (4) a polynucleotide encoding a hTREM2 antibody or an antigen-binding fragment thereof (e.g., as described herein), and (5) a BGH poly A signal (e.g., SEQ ID NO: 138). In one embodiment, elements (1) to (5) are disposed on the AAV vector plasmid from 5' to 3'. In embodiments, the elements (1) to (5) are disposed on a AAV vector plasmid which further comprises ITRs (e.g., a 5' ITR and a 3' ITR). In embodiments, the ITRs are derived from AAV2 ITRs.

In one embodiment, the AAV vector plasmid is a self-complementary AAV vector plasmid. "Self-complementary" or the abbreviation "sc" refers to self-complementary. "Self-complementary AAV" or "scAAV" refers a construct in which a coding region carried by a recombinant AAV nucleic acid sequence has been designed to form an intra-molecular double-stranded DNA template. Without being bound by theory, upon infection, rather than waiting for cell mediated synthesis of the second strand, the two complementary halves of scAAV will associate to form one double stranded DNA (dsDNA) unit that is ready for immediate replication and transcription. See, e.g., D M McCarty et al, "Self-complementary recombinant adeno-associated virus (scAAV) vectors promote efficient transduction independently of DNA synthesis", Gene Therapy, (August 2001), Vol 8, Number 16, Pages 1248-1254 (incorporated by reference in its entirety). Self-complementary AAVs are described in, e.g., U.S. Pat. Nos. 6,596,535; 7,125,717; and 7,456,683, each of which is incorporated herein by reference in its entirety. For example, the 5' ITR can be mutated, for example, by deleting the terminal resolution site to allow hairpin formation of the genome.

Capsids and Capsid Serotypes

In some embodiments, AAV particles of the present invention may be packaged in a capsid structure or may be capsid free. Such capsid free viral vector donor and/or acceptor sequences such as AAV, are described in, for example, US Publication 2014/0107186, the content of which is incorporated by reference in its entirety.

In some embodiments, AAV particles produced according to the present invention may comprise hybrid serotypes with enhanced transduction to specific cell types of interest in the central nervous system, prolonged transgene expression and/or a safety profile. The hybrid serotypes may be generated by transcapsidation, adsorption of bi-specific antibody to capsid surface, mosaic capsid, and chimeric capsid, and/or other capsid protein modifications.

In some embodiments, AAV particles of the present invention may be further modified toward a specific therapeutic application by rational mutagenesis of capsid proteins (see, e.g., Pulicherla et al, Mol Ther, 201 1, 19: 1070-1078), incorporation of peptide ligands to the capsid, for example a peptide derived from an NMDA receptor agonist for enhanced retrograde transport (Xu et al., Virology, 2005, 341: 203-214), and directed evolution to produce new AAV variants, for example, for increased CNS transduction.

In some embodiments, AAV particles produced according to the present invention may comprise different capsid proteins, either naturally occurring and/or recombinant, including, but not limited to, AAV1, AAV2, AAV3, AAV4, AAV5, AAV6, AAV7, AAV 8, AAV9, AAV 10, and AAV11, AAV 12, AAVrh8, AAVrh10, AAV-DJ, and AAV-DJ/8 capsid serotypes, or variants thereof (e.g., AAV3A and AAV3B). Nucleic acid sequences encoding one or more AAV capsid proteins useful in the present invention are disclosed in International Publication No. WO2015191508, the contents of which are herein incorporated by reference in their entirety.

In some embodiments, AAV particles of the present invention may comprise or be derived from any natural or recombinant AAV serotype. According to the present invention, the AAV particles may utilize or be based on a serotype selected from any of the following AAV1, AAV2, AAV2G9, AAV3, AAV3a, AAV3b, AAV3-3, AAV4, AAV4-4, AAV5, AAV6, AAV6.1, AAV6.2, AAV6.1.2, AAV7, AAV7.2, AAV8, AAV9, AAV9.11, AAV9.13, AAV9.16, AAV9.24, AAV9.45, AAV9.47, AAV9.61, AAV9.68, AAV9.84, AAV9.9, AAV10, AAV11, AAV 12, AAV16.3, AAV24.1, AAV27.3, AAV42.12, AAV42-1b, AAV42-2, AAV42-3a, AAV42-3b, AAV42-4, AAV42-5a, AAV42-5b, AAV42-6b, AAV42-8, AAV42-10, AAV42-11, AAV42-12, AAV42-13, AAV42-15, AAV42-aa, AAV43-1, AAV43-12, AAV43-20, AAV43-21, AAV43-23, AAV43-25, AAV43-5, AAV44.1, AAV44.2, AAV44.5, AAV223.1, AAV223.2, AAV223.4, AAV223.5, AAV223.6, AAV223.7, AAV1-7/rh.48, AAV1-8/rh.49, AAV2-15/rh.62, AAV2-3/rh.61, AAV2-4/rh.50, AAV2-5/rh.51, AAV3.1/hu.6, AAV3.1/hu.9, AAV3-9/rh.52, AAV3-1 1/rh.53, AAV4-8/r 11.64, AAV4-9/rh.54, AAV4-19/rh.55, AAV5-3/rh.57, AAV5-22/rh.58, AAV7.3/hu.7, AAV16.8/hu.10, AAV16.12/hu.11, AAV29.3/bb.1, AAV29.5/bb.2, AAV106.1/hu.37, AAV114.3/hu.40, AAV127.2/hu.41, AAV127.5/hu.42, AAV128.3/hu.44, AAV130.4/hu.48, AAV145.1/hu.53, AAV145.5/hu.54, AAV145.6/hu.55, AAV161.10/hu.60, AAV161.6/hu.61, AAV33.12/hu.17, AAV33.4/hu.15, AAV33.8/hu.16, AAV52/hu.19, AAV52.1/hu.20, AAV58.2/hu.25, AAV A3.3, AAV A3.4, AAV A3.5, AAV A3.7, AAVC1, AAVC2, AAVC5, AAV-DJ, AAV-DJ8, AAVF3, AAVF5, AAVH2, AAVrh.72, AAVhu.8, AAVrh.68, AAVrh.70, AAVpi.1, AAVpi.3, AAVpi.2, AAVrh.60, AAVrh.44, AAVrh.65, AAVrh.55, AAVrh.47, AAVrh.69, AAVrh.45, AAVrh.59, AAVhu.12, AAVH6, AAVLK03, AAVH-1/hu.1, AAVH-5/hu.3, AAVLG-10/rh.40, AAVLG-4/rh.38, AAVLG-9/hu.39, AAVN721-8/rh.43, AAVCh.5, AAVCh.5R1, AAVcy.2, AAVcy.3, AAVcy.4, AAVcy.5, AAVCy.5R1, AAVCy.5R2, AAVCy.5R3, AAVCy.5R4, AAVcy.6, AAVhu.1, AAVhu.2, AAVhu.3, AAVhu.4, AAVhu.5, AAVhu.6, AAVhu.7, AAVhu.9, AAVhu.10, AAVhu.11, AAVhu.13, AAVhu.15, AAVhu.16, AAVhu.17, AAVhu.18, AAVhu.20, AAVhu.21, AAVhu.22, AAVhu.23.2, AAVhu.24, AAVhu.25, AAVhu.27, AAVhu.28, AAVhu.29, AAVhu.29R, AAVhu.31, AAVhu.32, AAVhu.34, AAVhu.35, AAVhu.37, AAVhu.39, AAVhu.40, AAVhu.41, AAVhu.42, AAVhu.43, AAVhu.44, AAVhu.44R1, AAVhu.44R2, AAVhu.44R3, AAVhu.45, AAVhu.46, AAVhu.47, AAVhu.48, AAVhu.48R1, AAVhu.48R2, AAVhu.48R3, AAVhu.49, AAVhu.51, AAVhu.52, AAVhu.54, AAVhu.55, AAVhu.56, AAVhu.57, AAVhu.58, AAVhu.60, AAVhu.61, AAVhu.63, AAVhu.64, AAVhu.66, AAVhu.67, AAVhu.14/9, AAVhu.t 19, AAVrh.2, AAVrh.2R, AAVrh.8, AAVrh.8R, AAVrh.10, AAVrh.12, AAVrh.13, AAVrh.13R, AAVrh.14, AAVrh.17, AAVrh.18, AAVrh.19, AAVrh.20, AAVrh.21, AAVrh.22, AAVrh.23, AAVrh.24, AAVrh.25, AAVrh.31, AAVrh.32, AAVrh.33, AAVrh.34, AAVrh.35, AAVrh.36, AAVrh.37, AAVrh.37R2, AAVrh.38, AAVrh.39, AAVrh.40, AAVrh.46, AAVrh.48, AAVrh.48.1, AAVrh.48.1.2, AAVrh.48.2, AAVrh.49, AAVrh.51, AAVrh.52, AAVrh.53, AAVrh.54, AAVrh.56, AAVrh.57, AAVrh.58, AAVrh.61, AAVrh.64, AAVrh.64R1, AAVrh.64R2, AAVrh.67, AAVrh.73, AAVrh.74, AAVrh8R, AAVrh8R A586R mutant, AAVrh8R R533A mutant, AAAV, BAAV, caprine AAV, bovine AAV, AAVhE1.1, AAVhEr1.5, AAVhER1.14, AAVhEr1.8, AAVhEr1.16, AAVhEr1.18, AAVhEr1.35, AAVhEr1.7, AAVhEr1.36, AAVhEr2.29, AAVhEr2.4, AAVhEr2.16, AAVhEr2.30, AAVhEr2.31, AAVhEr2.36, AAVhER1.23, AAVhEr3.1, AAV2.5T, AAV-PAEC, AAV-LK01, AAV-LK02, AAV-LK03, AAV-LK04, AAV-LK05, AAV-LK06, AAV-LK07, AAV-LK08, AAV-LK09, AAV-LK10, AAV-LK11, AAV-LK12, AAV-LK13, AAV-LK14, AAV-LK15, AAV-LK16, AAV-LK17, AAV-LK18, AAV-LK19, AAV-PAEC2, AAV-PAEC4, AAV-PAEC6, AAV-PAEC7, AAV-PAEC8, AAV-PAEC11, AAV-PAEC 12, AAV-2-pre-miRNA-1O1, AAV-8h, AAV-8b, AAV-h, AAV-b, AAV SM 10-2, AAV Shuffle 100-1, AAV Shuffle 100-3, AAV Shuffle 100-7, AAV Shuffle 10-2, AAV Shuffle 10-6, AAV Shuffle 10-8, AAV Shuffle 100-2, AAV SM 10-1, AAV SM 10-8, AAV SM 100-3, AAV SM 100-10, BNP61 AAV, BNP62 AAV, BNP63 AAV, AAVrh.50, AAVrh.43, AAVrh.62, AAVrh.48, AAVhu.19, AAVhu. 1, AAVhu.53, AAV4-8/rh.64, AAVLG-9/hu.39, AAV54.5/hu.23, AAV54.2/hu.22, AAV54.7/hu.24, AAV54.1/hu.21, AAV54.4R/hu.27, AAV46.2/hu.28, AAV46.6/hu.29, AAV128.1/hu.43, true type AAV (ttAAV), UPEN AAV 10 and/or Japanese AAV 10 serotypes, and variants thereof.

As a non-limiting example, the capsid of the recombinant AAV virus is AAV2. As a non-limiting example, the capsid of the recombinant AAV virus is AAVrh10. As a non-limiting example, the capsid of the recombinant AAV virus is AAV9 (hul4). As a non-limiting example, the capsid of the recombinant AAV virus is AAV-DJ. As a non-limiting example, the capsid of the recombinant AAV virus is AAV9.47. As a non-limiting example, the capsid of the recombinant AAV virus is AAV-DJ8.

In some embodiments, the AAV particles of the present invention may comprise or be derived from an AAV serotype which may be, or have, a sequence as described in United States Publication No. US20030138772, the contents of which are herein incorporated by reference in their entirety, such as, but not limited to, AAV1 (SEQ ID NO: 6 and 64 of US20030138772), AAV2 (SEQ ID NO: 7 and 70 of US20030138772), AAV3 (SEQ ID NO: 8 and 71 of US20030138772), AAV4 (SEQ ID NO: 63 of US20030138772), AAV5 (SEQ ID NO: 114 of US20030138772), AAV6 (SEQ ID NO: 65 of US20030138772), AAV7 (SEQ ID NO: 1-3 of US20030138772), AAV 8 (SEQ ID NO: 4 and 95 of US20030138772), AAV9 (SEQ ID NO: 5 and 100 of US20030138772), AAV10 (SEQ ID NO: 117 of US20030138772), AAV11 (SEQ ID NO: 118 of US20030138772), AAV 12 (SEQ ID NO: 119 of US20030138772), AAVrh1O (amino acids 1 to 738 of SEQ ID NO: 81 of US20030138772), AAV16.3 (US20030138772 SEQ ID NO: 10), AAV29.3/bb. 1 (US20030138772 SEQ ID NO: 11), AAV29.4 (US20030138772 SEQ ID NO: 12), AAV29.5/bb.2 (US20030138772 SEQ ID NO: 13), AAV1.3 (US20030138772 SEQ ID NO: 14), AAV13.3

(US20030138772 SEQ ID NO: 15), AAV24.1 (US20030138772 SEQ ID NO: 16), AAV27.3 (US20030138772 SEQ ID NO: 17), AAV7.2 (US20030138772 SEQ ID NO: 18), AAVC1 (US20030138772 SEQ ID NO: 19), AAVC3 (US20030138772 SEQ ID NO: 20), AAVC5 (US20030138772 SEQ ID NO: 21), AAVF1 (US20030138772 SEQ ID NO: 22), AAVF3 (US20030138772 SEQ ID NO: 23), AAVF5 (US20030138772 SEQ ID NO: 24), AAVH6 (US20030138772 SEQ ID NO: 25), AAVH2 (US20030138772 SEQ ID NO: 26), AAV42-8 (US20030138772 SEQ ID NO: 27), AAV42-15 (US20030138772 SEQ ID NO: 28), AAV42-5b (US20030138772 SEQ ID NO: 29), AAV42-1b (US20030138772 SEQ ID NO: 30), AAV42-13 (US20030138772 SEQ ID NO: 31), AAV42-3a (US20030138772 SEQ ID NO: 32), AAV42-4 (US20030138772 SEQ ID NO: 33), AAV42-5a (US20030138772 SEQ ID NO: 34), AAV42-10 (US20030138772 SEQ ID NO: 35), AAV42-3b (US20030138772 SEQ ID NO: 36), AAV42-11 (US20030138772 SEQ ID NO: 37), AAV42-6b (US20030138772 SEQ ID NO: 38), AAV43-1 (US20030138772 SEQ ID NO: 39), AAV43-5 (US20030138772 SEQ ID NO: 40), AAV43-12 (US20030138772 SEQ ID NO: 41), AAV43-20 (US20030138772 SEQ ID NO: 42), AAV43-21 (US20030138772 SEQ ID NO: 43), AAV43-23 (US20030138772 SEQ ID NO: 44), AAV43-25 (US20030138772 SEQ ID NO: 45), AAV44.1 (US20030138772 SEQ ID NO: 46), AAV44.5 (US20030138772 SEQ ID NO: 47), AAV223.1 (US20030138772 SEQ ID NO: 48), AAV223.2 (US20030138772 SEQ ID NO: 49), AAV223.4 (US20030138772 SEQ ID NO: 50), AAV223.5 (US20030138772 SEQ ID NO: 51), AAV223.6 (US20030138772 SEQ ID NO: 52), AAV223.7 (US20030138772 SEQ ID NO: 53), AAV A3.4 (US20030138772 SEQ ID NO: 54), AAV A3.5 (US20030138772 SEQ ID NO: 55), AAV A3.7 (US20030138772 SEQ ID NO: 56), AAV A3.3 (US20030138772 SEQ ID NO: 57), AAV42.12 (US20030138772 SEQ ID NO: 58), AAV44.2 (US20030138772 SEQ ID NO: 59), AAV42-2 (US20030138772 SEQ ID NO: 9), or variants thereof.

In some embodiments, the AAV particles of the present invention may comprise or be derived from AAV serotype which may be, or have, a sequence as described in United States Publication No. US20150159173, the contents of which are herein incorporated by reference in their entirety, such as, but not limited to, AAV2 (SEQ ID NO: 7 and 23 of US20150159173), rh20 (SEQ ID NO: 1 of US20150159173), rh32/33 (SEQ ID NO: 2 of US20150159173), rh39 (SEQ ID NO: 3, 20 and 36 of US20150159173), rh46 (SEQ ID NO: 4 and 22 of US20150159173), rh73 (SEQ ID NO: 5 of US20150159173), rh74 (SEQ ID NO: 6 of US20150159173), AAV6.1 (SEQ ID NO: 29 of US20150159173), rh.8 (SEQ ID NO: 41 of US20150159173), rh.48.1 (SEQ ID NO: 44 of US20150159173), hu.44 (SEQ ID NO: 45 of US20150159173), hu.29 (SEQ ID NO: 42 of US20150159173), hu.48 (SEQ ID NO: 38 of US20150159173), rh54 (SEQ ID NO: 49 of US20150159173), AAV2 (SEQ ID NO: 7 of US20150159173), cy.5 (SEQ ID NO: 8 and 24 of US20150159173), rh.10 (SEQ ID NO: 9 and 25 of US20150159173), rh.13 (SEQ ID NO: 10 and 26 of US20150159173), AAV1 (SEQ ID NO: 11 and 27 of US20150159173), AAV3 (SEQ ID NO: 12 and 28 of US20150159173), AAV6 (SEQ ID NO: 13 and 29 of US20150159173), AAV7 (SEQ ID NO: 14 and 30 of US20150159173), AAV 8 (SEQ ID NO: 15 and 31 of US20150159173), hu.13 (SEQ ID NO: 16 and 32 of US20150159173), hu.26 (SEQ ID NO: 17 and 33 of US20150159173), hu.37 (SEQ ID NO: 18 and 34 of US20150159173), hu.53 (SEQ ID NO: 19 and 35 of US20150159173), rh.43 (SEQ ID NO: 21 and 37 of US20150159173), rh2 (SEQ ID NO: 39 of US20150159173), rh.37 (SEQ ID NO: 40 of US20150159173), rh.64 (SEQ ID NO: 43 of US20150159173), rh.48 (SEQ ID NO: 44 of US20150159173), ch.5 (SEQ ID NO 46 of US20150159173), rh.67 (SEQ ID NO: 47 of US20150159173), rh.58 (SEQ ID NO: 48 of US20150159173), or variants thereof including, but not limited to Cy5R1, Cy5R2, Cy5R3, Cy5R4, rh.13R, rh.37R2, rh.2R, rh.8R, rh.48.1, rh.48.2, rh.48.1.2, hu.44R1, hu.44R2, hu.44R3, hu.29R, ch.5R1, rh64R1, rh64R2, AAV6.2, AAV6.1, AAV6.12, hu.48R1, hu.48R2, and hu.48R3.

In some embodiments, the AAV particles of the present invention may comprise or be derived from AAV serotype which may be, or have, a sequence as described in U.S. Pat. No. 7,198,951, the contents of which are herein incorporated by reference in their entirety, such as, but not limited to, AAV9 (SEQ ID NO: 1-3 of U.S. Pat. No. 7,198,951), AAV2 (SEQ ID NO: 4 of U.S. Pat. No. 7,198,951), AAV1 (SEQ ID NO: 5 of U.S. Pat. No. 7,198,951), AAV3 (SEQ ID NO: 6 of U.S. Pat. No. 7,198,951), and AAV 8 (SEQ ID NO: 7 of U.S. Pat. No. 7,198,951).

In some embodiments, the AAV vectors comprise or are derived from AAV serotype which may be, or have, a mutation in the AAV9 sequence as described by N Pulicherla et al. (Molecular Therapy 19(6): 1070-1078 (2011), herein incorporated by reference in its entirety), such as but not limited to, AAV9.9, AAV9.11, AAV9.13, AAV9.16, AAV9.24, AAV9.45, AAV9.47, AAV9.61, AAV9.68, AAV9.84. In some embodiments, the AAV capsid comprises one or more sequences engineered to deliver the vector across the blood-brain barrier (See, e.g., B. E. Deverman et al, Nature Biotech, Vol. 34, No. 2, p 204-211 (published online 1 Feb. 2016) and Caltech press release, A. Wetherston, www.neurology-cenfrd.com/2016/02/10/successfd/brain-barrier; See, also, WO 2016/0492301 and U.S. Pat. No. 8,734,809 (the contents of each of these are incorporated by reference in their entirety).

In some embodiments, the AAV particles of the present invention may comprise or be derived from AAV serotype which may be, or have, a sequence as described in U.S. Pat. No. 6,156,303, the contents of which are herein incorporated by reference in their entirety, such as, but not limited to, AAV3B (SEQ ID NO: 1 and 10 of U.S. Pat. No. 6,156,303), AAV6 (SEQ ID NO: 2, 7 and 11 of U.S. Pat. No. 6,156,303), AAV2 (SEQ ID NO: 3 and 8 of U.S. Pat. No. 6,156,303), AAV3A (SEQ ID NO: 4 and 9, of U.S. Pat. No. 6,156,303), or derivatives thereof.

In some embodiments, the AAV particles of the present invention may comprise or be derived from AAV serotype which may be, or have, a sequence as described in United States Publication No. US20140359799, the contents of which are herein incorporated by reference in their entirety, such as, but not limited to, AAV 8 (SEQ ID NO: 1 of US20140359799), AAVDJ (SEQ ID NO: 2 and 3 of US20140359799), or variants thereof.

In some embodiments, the AAV particle may comprise a capsid from a serotype such as, but not limited to, AAVDJ or a variant thereof, such as AAVDJ8 (or AAV-DJ8), as described by Grimm et al. (Journal of Virology 82(12): 5887-5911 (2008), herein incorporated by reference in its entirety). The amino acid sequence of AAVDJ8 may comprise two or more mutations in order to remove the heparin binding domain (HBD). As a non-limiting example, the AAV-DJ sequence described as SEQ ID NO: 1 in U.S. Pat. No. 7,588,772, the contents of which are herein incorporated by reference in their entirety, may comprise two mutations: (1) R587Q where arginine (R; Arg) at amino acid 587 is changed to glutamine (Q; Gln) and (2) R590T where arginine (R; Arg) at amino acid 590 is changed to threonine (T; Thr). As another non-limiting example, may comprise three mutations: (1) K406R where lysine (K; Lys) at amino acid 406 is changed to arginine (R; Arg), (2) R587Q where arginine (R; Arg) at amino acid 587 is changed to glutamine (Q; Gln) and (3) R590T where arginine (R; Arg) at amino acid 590 is changed to threonine (T; Thr).

In some embodiments, the AAV particles of the present invention may comprise or be derived from AAV serotype which may be, or have, a sequence of AAV4 as described in International Publication No. WO 1998011244, the contents of which are herein incorporated by reference in their entirety, such as, but not limited to AAV4 (SEQ ID NO: 1-20 of WO 1998011244).

In some embodiments, the AAV particles of the present invention may comprise or be derived from AAV serotype which may be, or have, a mutation in the AAV2 sequence to generate AAV2G9 as described in International Publication No. WO2014144229 and herein incorporated by reference in its entirety.

In some embodiments, the AAV particles of the present invention may comprise or be derived from AAV serotype which may be, or have, a sequence as described in International Publication No. WO2005033321, the contents of which are herein incorporated by reference in their entirety, such as, but not limited to AAV3-3 (SEQ ID NO: 217 of WO2005033321), AAV1 (SEQ ID NO: 219 and 202 of WO2005033321), AAV106.1/hu.37 (SEQ ID No: 10 of WO2005033321), AAV114.3/hu.40 (SEQ ID No: 11 of WO2005033321), AAV127.2/hu.41 (SEQ ID NO:6 and 8 of WO2005033321), AAV128.3/hu.44 (SEQ ID No: 81 of WO2005033321), AAV130.4/hu.48 (SEQ ID NO: 78 of WO2005033321), AAV145.1/hu.53 (SEQ ID No: 176 and 177 of WO2005033321), AAV145.6/hu.56 (SEQ ID NO: 168 and 192 of WO2005033321), AAV16.12/hu.11 (SEQ ID NO: 153 and 57 of WO2005033321), AAV16.8/hu.10(SEQ ID NO: 156 and 56 of WO2005033321), AAV161.10/hu.60 (SEQ ID No: 170 of WO2005033321), AAV161.6/hu.61 (SEQ ID No: 174 of WO2005033321), AAV1-7/rh.48 (SEQ ID NO: 32 of WO2005033321), AAV1-8/rh.49 (SEQ ID NOs: 103 and 25 of WO2005033321), AAV2 (SEQ ID NO: 211 and 221 of WO2005033321), AAV2-15/rh.62 (SEQ ID No: 33 and 114 of WO2005033321), AAV2-3/rh.61 (SEQ ID NO: 21 of WO2005033321), AAV2-4/rh.50 (SEQ ID No: 23 and 108 of WO2005033321), AAV2-5/rh.51 (SEQ ID NO: 104 and 22 of WO2005033321), AAV3.1/hu.6 (SEQ ID NO: 5 and 84 of WO2005033321), AAV3.1/hu.9 (SEQ ID NO: 155 and 58 of WO2005033321), AAV3-1 1/rh.53 (SEQ ID NO: 186 and 176 of WO2005033321), AAV3-3 (SEQ ID NO: 200 of WO2005033321), AAV33.12/hu.17 (SEQ ID NO:4 of WO2005033321), AAV33.4/hu.15 (SEQ ID No: 50 of WO2005033321), AAV33.8/hu.16 (SEQ ID No: 51 of WO2005033321), AAV3-9/rh.52 (SEQ ID NO: 96 and 18 of WO2005033321), AAV4-19/rh.55 (SEQ ID NO: 117 of WO2005033321), AAV4-4 (SEQ ID NO: 201 and 218 of WO2005033321), AAV4-9/rh.54 (SEQ ID NO: 116 of WO2005033321), AAV5 (SEQ ID NO: 199 and 216 of WO2005033321), AAV52.1/hu.20 (SEQ ID NO: 63 of WO2005033321), AAV52/hu. 19 (SEQ ID NO: 133 of WO2005033321), AAV5-22/rh.58 (SEQ ID No: 27 of WO2005033321), AAV5-3/rh.57 (SEQ ID NO: 105 of WO2005033321), AAV5-3/rh.57 (SEQ ID No: 26 of WO2005033321), AAV58.2/hu.25 (SEQ ID No: 49 of WO2005033321), AAV6 (SEQ ID NO: 203 and 220 of WO2005033321), AAV7 (SEQ ID NO: 222 and 213 of WO2005033321), AAV7.3/hu.7 (SEQ ID No: 55 of WO2005033321), AAV 8 (SEQ ID NO: 223 and 214 of WO2005033321), AAVH-1/hu.1 (SEQ ID No: 46 of WO2005033321), AAVH-5/hu.3 (SEQ ID No: 44 of WO2005033321), AAVhu.1 (SEQ ID NO: 144 of WO2005033321), AAVhu.10 (SEQ ID NO: 156 of WO2005033321), AAVhu.11 (SEQ ID NO: 153 of WO2005033321), AAVhu.12 (WO2005033321 SEQ ID NO: 59), AAVhu.13 (SEQ ID NO: 129 of WO2005033321), AAVhu.14/AAV9 (SEQ ID NO: 123 and 3 of WO2005033321), AAVhu.15 (SEQ ID NO: 147 of WO2005033321), AAVhu.16 (SEQ ID NO: 148 of WO2005033321), AAVhu.17 (SEQ ID NO: 83 of WO2005033321), AAVhu.18 (SEQ ID NO: 149 of WO2005033321), AAVhu.19 (SEQ ID NO: 133 of WO2005033321), AAVhu.2 (SEQ ID NO: 143 of WO2005033321), AAVhu.20 (SEQ ID NO: 134 of WO2005033321), AAVhu.21 (SEQ ID NO: 135 of WO2005033321), AAVhu.22 (SEQ ID NO: 138 of WO2005033321), AAVhu.23.2 (SEQ ID NO: 137 of WO2005033321), AAVhu.24 (SEQ ID NO: 136 of WO2005033321), AAVhu.25 (SEQ ID NO: 146 of WO2005033321), AAVhu.27 (SEQ ID NO: 140 of WO2005033321), AAVhu.29 (SEQ ID NO: 132 of WO2005033321), AAVhu.3 (SEQ ID NO: 145 of WO2005033321), AAVhu.31 (SEQ ID NO: 121 of WO2005033321), AAVhu.32 (SEQ ID NO: 122 of WO2005033321), AAVhu.34 (SEQ ID NO: 125 of WO2005033321), AAVhu.35 (SEQ ID NO: 164 of WO2005033321), AAVhu.37 (SEQ ID NO: 88 of WO2005033321), AAVhu.39 (SEQ ID NO: 102 of WO2005033321), AAVhu.4 (SEQ ID NO: 141 of WO2005033321), AAVhu.40 (SEQ ID NO: 87 of WO2005033321), AAVhu.41 (SEQ ID NO: 91 of WO2005033321), AAVhu.42 (SEQ ID NO: 85 of WO2005033321), AAVhu.43 (SEQ ID NO: 160 of WO2005033321), AAVhu.44 (SEQ ID NO: 144 of WO2005033321), AAVhu.45 (SEQ ID NO: 127 of WO2005033321), AAVhu.46 (SEQ ID NO: 159 of WO2005033321), AAVhu.47 (SEQ ID NO: 128 of WO2005033321), AAVhu.48 (SEQ ID NO: 157 of WO2005033321), AAVhu.49 (SEQ ID NO: 189 of WO2005033321), AAVhu.51 (SEQ ID NO: 190 of WO2005033321), AAVhu.52 (SEQ ID NO: 191 of WO2005033321), AAVhu.53 (SEQ ID NO: 186 of WO2005033321), AAVhu.54 (SEQ ID NO: 188 of WO2005033321), AAVhu.55 (SEQ ID NO: 187 of WO2005033321), AAVhu.56 (SEQ ID NO: 192 of WO2005033321), AAVhu.57 (SEQ ID NO: 193 of WO2005033321), AAVhu.58 (SEQ ID NO: 194 of WO2005033321), AAVhu.6 (SEQ ID NO: 84 of WO2005033321), AAVhu.60 (SEQ ID NO: 184 of WO2005033321), AAVhu.61 (SEQ ID NO: 185 of WO2005033321), AAVhu.63 (SEQ ID NO: 195 of WO2005033321), AAVhu.64 (SEQ ID NO: 196 of WO2005033321), AAVhu.66 (SEQ ID NO: 197 of WO2005033321), AAVhu.67 (SEQ ID NO: 198 of WO2005033321), AAVhu.7 (SEQ ID NO: 150 of WO2005033321), AAVhu.8 (WO2005033321 SEQ ID NO: 12), AAVhu.9 (SEQ ID NO: 155 of WO2005033321), AAVLG-10/rh.40 (SEQ ID No: 14 of WO2005033321), AAVLG-4/rh.38 (SEQ ID NO: 86 of WO2005033321), AAVLG-4/rh.38 (SEQ ID No: 7 of WO2005033321), AAVN721-8/rh.43 (SEQ ID NO: 163 of WO2005033321), AAVN721-8/rh.43 (SEQ ID No: 43 of WO2005033321), AAVpi. 1 (WO2005033321 SEQ ID NO: 28), AAVpi.2 (WO2005033321 SEQ ID NO: 30), AAVpi.3 (WO2005033321 SEQ ID NO: 29), AAVrh.38 (SEQ ID NO: 86 of WO2005033321), AAVrh.40 (SEQ ID NO: 92 of WO2005033321), AAVrh.43 (SEQ ID NO: 163 of WO2005033321), AAVrh.44 (WO2005033321 SEQ ID NO: 34), AAVrh.45 (WO2005033321 SEQ ID NO: 41), AAVrh.47 (WO2005033321 SEQ ID NO: 38), AAVrh.48 (SEQ ID NO: 115 of WO2005033321), AAVrh.49 (SEQ ID NO: 103 of WO2005033321), AAVrh.50 (SEQ ID NO: 108 of WO2005033321), AAVrh.51 (SEQ ID NO: 104 of WO2005033321), AAVrh.52 (SEQ ID NO: 96 of WO2005033321), AAVrh.53 (SEQ ID NO: 97 of WO2005033321), AAVrh.55 (WO2005033321 SEQ ID NO: 37), AAVrh.56 (SEQ ID NO: 152 of WO2005033321), AAVrh.57 (SEQ ID NO: 105 of WO2005033321), AAVrh.58 (SEQ ID NO: 106 of WO2005033321), AAVrh.59 (WO2005033321 SEQ ID NO: 42), AAVrh.60 (WO2005033321 SEQ ID NO: 31), AAVrh.61 (SEQ ID NO: 107 of WO2005033321), AAVrh.62 (SEQ ID NO: 114 of WO2005033321), AAVrh.64 (SEQ ID NO: 99 of WO2005033321), AAVrh.65 (WO2005033321 SEQ ID NO: 35), AAVrh.68 (WO2005033321 SEQ ID NO: 16), AAVrh.69 (WO2005033321 SEQ ID NO: 39), AAVrh.70 (WO2005033321 SEQ ID NO: 20), AAVrh.72 (WO2005033321 SEQ ID NO: 9), or variants thereof including, but not limited to, AAVcy.2, AAVcy.3, AAVcy.4, AAVcy.5, AAVcy.6, AAVrh.12, AAVrh.17, AAVrh.18, AAVrh.19, AAVrh.21, AAVrh.22, AAVrh.23, AAVrh.24, AAVrh.25, AAVrh.25/42 15, AAVrh.31, AAVrh.32, AAVrh.33, AAVrh.34, AAVrh.35, AAVrh.36, AAVrh.37, AAVrh14. Non limiting examples of variants include SEQ ID NO: 13, 15, 17, 19, 24, 36, 40, 45, 47, 48, 51-54, 60-62, 64-77, 79, 80, 82, 89, 90, 93-95, 98, 100, 101, 109-113, 118-120, 124, 126, 131, 139, 142, 151,154, 158, 161, 162, 165-183, 202, 204-212, 215, 219, 224-236, of WO2005033321, the contents of which are herein incorporated by reference in their entirety.

In some embodiments, the AAV particles of the present invention may comprise or be derived from AAV serotype which may be, or have, a sequence as described in International Publication No. WO2015168666, the contents of which are herein incorporated by reference in their entirety, such as, but not limited to, AAVrh8R (SEQ ID NO: 9 of WO2015168666), AAVrh8R A586R mutant (SEQ ID NO: 10 of WO2015168666), AAVrh8R R533A mutant (SEQ ID NO: 11 of WO2015168666), or variants thereof.

In some embodiments, the AAV particles of the present invention may comprise or be derived from AAV serotype which may be, or have, a sequence as described in International Publication No. WO2018/160582, the contents of which are herein incorporated by reference in their entirety, such as, but not limited to, AAVhu68 (e.g., SEQ ID NO: 2 of WO2018160582), or variants thereof.

In some embodiments, the AAV particles of the present invention may comprise or be derived from AAV serotype which may be, or have, a sequence as described in U.S. Pat. No. 9,233,131, the contents of which are herein incorporated by reference in their entirety, such as, but not limited to, AAVhE1.1 (SEQ ID NO:44 of U.S. Pat. No. 9,233,131), AAVhEr1.5 (SEQ ID NO:45 of U.S. Pat. No. 9,233,131), AAVhER1.14 (SEQ ID NO:46 of U.S. Pat. No. 9,233,131), AAVhEr1.8 (SEQ ID NO:47 of U.S. Pat. No. 9,233,131), AAVhEr1.16 (SEQ ID NO:48 of U.S. Pat. No. 9,233,131), AAVhEr1.18 (SEQ ID NO:49 of U.S. Pat. No. 9,233,131), AAVhEr1.35 (SEQ ID NO:50 of U.S. Pat. No. 9,233,131), AAVhEr1.7 (SEQ ID NO:51 of U.S. Pat. No. 9,233,131), AAVhEr1.36 (SEQ ID NO:52 of U.S. Pat. No. 9,233,131), AAVhEr2.29 (SEQ ID NO:53 of U.S. Pat. No. 9,233,131), AAVhEr2.4 (SEQ ID NO:54 of U.S. Pat. No. 9,233,131), AAVhEr2.16 (SEQ ID NO:55 of U.S. Pat. No. 9,233,131), AAVhEr2.30 (SEQ ID NO:56 of U.S. Pat. No. 9,233,131), AAVhEr2.31 (SEQ ID NO:58 of U.S. Pat. No. 9,233,131), AAVhEr2.36 (SEQ ID NO:57 of U.S. Pat. No. 9,233,131), AAVhER1.23 (SEQ ID NO:53 of U.S. Pat. No. 9,233,131), AAVhEr3.1 (SEQ ID NO:59 of U.S. Pat. No. 9,233,131), AAV2.5T (SEQ ID NO:42 of U.S. Pat. No. 9,233,131), or variants thereof.

In some embodiments, the AAV particles of the present invention may comprise or be derived from AAV serotype which may be, or have, a sequence as described in United States Patent Publication No. US20150376607, the contents of which are herein incorporated by reference in their entirety, such as, but not limited to, AAV-PAEC (SEQ ID NO: 1 of US20150376607), AAV-LKO1 (SEQ ID NO:2 of US20150376607), AAV-LK02 (SEQ ID NO:3 of US20150376607), AAV-LK03 (SEQ ID NO:4 of US20150376607), AAV-LK04 (SEQ ID NO:5 of US20150376607), AAV-LK05 (SEQ ID NO:6 of US20150376607), AAV-LK06 (SEQ ID NO:7 of US20150376607), AAV-LK07 (SEQ ID NO:8 of US20150376607), AAV-LK08 (SEQ ID NO:9 of US20150376607), AAV-LK09 (SEQ ID NO: 10 of US20150376607), AAV-LK10 (SEQ ID NO: 1 of US20150376607), AAV-LK11 (SEQ ID NO: 12 of US20150376607), AAV-LK12 (SEQ ID NO: 13 of US20150376607), AAV-LK13 (SEQ ID NO: 14 of US20150376607), AAV-LK14 (SEQ ID NO: 15 of US20150376607), AAV-LK15 (SEQ ID NO: 16 of US20150376607), AAV-LK16 (SEQ ID NO: 17 of US20150376607), AAV-LK17 (SEQ ID NO: 18 of US20150376607), AAV-LK18 (SEQ ID NO: 19 of US20150376607), AAV-LK19 (SEQ ID NO:20 of US20150376607), AAV-PAEC2 (SEQ ID NO:21 of US20150376607), AAV-PAEC 4 (SEQ ID NO:22 of US20150376607), AAV-PAEC6 (SEQ ID NO:23 of US20150376607), AAV-PAEC7 (SEQ ID NO:24 of US20150376607), AAV-PAEC 8 (SEQ ID NO:25 of US20150376607), AAV-PAEC11 (SEQ ID NO:26 of US20150376607), AAV-PAEC 12 (SEQ ID NO:27, of US20150376607), or variants thereof.

In some embodiments, the AAV particles of the present invention may comprise or be derived from AAV serotype which may be, or have, a sequence as described in U.S. Pat. No. 9,163,261, the contents of which are herein incorporated by reference in their entirety, such as, but not limited to, AAV-2-pre-miRNA-101 (SEQ ID NO: 1 U.S. Pat. No. 9,163,261), or variants thereof.

In some embodiments, the AAV particles of the present invention may comprise or be derived from AAV serotype which may be, or have, a sequence as described in United States Patent Publication No. US20150376240, the contents of which are herein incorporated by reference in their entirety, such as, but not limited to, AAV-8h (SEQ ID NO: 6 of US20150376240), AAV-8b (SEQ ID NO: 5 of US20150376240), AAV-h (SEQ ID NO: 2 of US20150376240), AAV-b (SEQ ID NO: 1 of US20150376240), or variants thereof.

In some embodiments, the AAV particles of the present invention may comprise or be derived from AAV serotype which may be, or have, a sequence as described in United States Patent Publication No. US20160017295, the contents of which are herein incorporated by reference in their entirety, such as, but not limited to, AAV SM 10-2 (SEQ ID NO: 22 of US20160017295), AAV Shuffle 100-1 (SEQ ID NO: 23 of US20160017295), AAV Shuffle 100-3 (SEQ ID NO: 24 of US20160017295), AAV Shuffle 100-7 (SEQ ID NO: 25 of US20160017295), AAV Shuffle 10-2 (SEQ ID NO: 34 of US20160017295), AAV Shuffle 10-6 (SEQ ID NO: 35 of US20160017295), AAV Shuffle 10-8 (SEQ ID NO: 36 of US20160017295), AAV Shuffle 100-2 (SEQ ID NO: 37 of US20160017295), AAV SM 10-1 (SEQ ID NO: 38 of US20160017295), AAV SM 10-8 (SEQ ID NO: 39 of US20160017295), AAV SM 100-3 (SEQ ID NO: 40 of US20160017295), AAV SM 100-10 (SEQ ID NO: 41 of US20160017295), or variants thereof.

In some embodiments, the AAV particles of the present invention may comprise or be derived from AAV serotype which may be, or have, a sequence as described in United States Patent Publication No. US20150238550, the contents of which are herein incorporated by reference in their entirety, such as, but not limited to, BNP61 AAV (SEQ ID NO: 1 of US20150238550), BNP62 AAV (SEQ ID NO: 3 of US20150238550), BNP63 AAV (SEQ ID NO: 4 of US20150238550), or variants thereof.

In some embodiments, the AAV particles of the present invention may comprise or be derived from an AAV serotype which may be or may have a sequence as described in United States Patent Publication No. US20150315612, the contents of which are herein incorporated by reference in their entirety, such as, but not limited to, AAVrh.50 (SEQ ID NO: 108 of US20150315612), AAVrh.43 (SEQ ID NO: 163 of US20150315612), AAVrh.62 (SEQ ID NO: 114 of US20150315612), AAVrh.48 (SEQ ID NO: 115 of US20150315612), AAVhu.19 (SEQ ID NO: 133 of US20150315612), AAVhu. 11 (SEQ ID NO: 153 of US20150315612), AAVhu.53 (SEQ ID NO: 186 of US20150315612), AAV4-8/rh.64 (SEQ ID No: 15 of US20150315612), AAVLG-9/hu.39 (SEQ ID No: 24 of US20150315612), AAV54.5/hu.23 (SEQ ID No: 60 of US20150315612), AAV54.2/hu.22 (SEQ ID No: 67 of US20150315612), AAV54.7/hu.24 (SEQ ID No: 66 of US20150315612), AAV54.1/hu.21 (SEQ ID No: 65 of US20150315612), AAV54.4R/hu.27 (SEQ ID No: 64 of US20150315612), AAV46.2/hu.28 (SEQ ID No: 68 of US20150315612), AAV46.6/hu.29 (SEQ ID No: 69 of US20150315612), AAV128.1/hu.43 (SEQ ID No: 80 of US20150315612), or variants thereof.

In some embodiments, the AAV particles of the present invention may comprise or be derived from AAV serotype which may be, or have, a sequence as described in International Publication No. WO2015121501, the contents of which are herein incorporated by reference in their entirety, such as, but not limited to, true type AAV (ttAAV) (SEQ ID NO: 2 of WO2015121501), "UPenn AAV10" (SEQ ID NO: 8 of WO2015121501), "Japanese AAV10" (SEQ ID NO: 9 of WO2015121501), or variants thereof.

According to the present invention, the AAV particle may comprise an AAV capsid serotype which may be selected from or derived from a variety of species. In one embodiment, the AAV may be an avian AAV (AAAV). The AAAV serotype may be, or have, a sequence as described in U.S. Pat. No. 9,238,800, the contents of which are herein incorporated by reference in their entirety, such as, but not limited to, AAAV (SEQ ID NO: 1, 2, 4, 6, 8, 10, 12, and 14 of U.S. Pat. No. 9,238,800), or variants thereof.

In one embodiment, the AAV particle may comprise an AAV capsid serotype which may be or derived from a bovine AAV (BAAV). The BAAV serotype may be, or have, a sequence as described in U.S. Pat. No. 9,193,769, the contents of which are herein incorporated by reference in their entirety, such as, but not limited to, BAAV (SEQ ID NO: 1 and 6 of U.S. Pat. No. 9,193,769), or variants thereof. The BAAV serotype may be or have a sequence as described in U.S. Pat. No. 7,427,396, the contents of which are herein incorporated by reference in their entirety, such as, but not limited to, BAAV (SEQ ID NO: 5 and 6 of U.S. Pat. No. 7,427,396), or variants thereof.

In one embodiment, the AAV particle may comprise an AAV capsid serotype which may be or derived from a caprine AAV. The caprine AAV serotype may be, or have, a sequence as described in U.S. Pat. No. 7,427,396, the contents of which are herein incorporated by reference in their entirety, such as, but not limited to, caprine AAV (SEQ ID NO: 3 of U.S. Pat. No. 7,427,396), or variants thereof.

In other embodiments, the AAV particle may comprise an AAV capsid serotype which may be engineered as a hybrid AAV from two or more parental serotypes. In one embodiment, the AAV may be AAV2G9 which comprises sequences from AAV2 and AAV9. The AAV2G9 AAV serotype may be, or have, a sequence as described in United States Patent Publication No. US20160017005, the contents of which are herein incorporated by reference in its entirety.

In one embodiment, the AAV particle may comprise an AAV capsid serotype which may be generated by the AAV9 capsid library with mutations in amino acids 390-627 (VP1 numbering) as described by Pulicherla et al. (Molecular Therapy 19(6): 1070-1078 (2011), the contents of which are herein incorporated by reference in their entirety. The serotype and corresponding nucleotide and amino acid substitutions may be, but is not limited to, AAV9.1 (G1594C; D532H), AAV6.2 (T1418A and T1436X; V473D and I479K), AAV9.3 (T1238A; F413Y), AAV9.4 (T1250C and A1617T; F417S), AAV9.5 (A1235G, A1314T, A1642G, C1760T; Q412R, T548A, A587V), AAV9.6 (T1231A; F411I), AAV9.9 (G1203A, G1785T; W595C), AAV9.10 (A1500G, T1676C; M559T), AAV9.11 (A1425T, A1702C, A1769T; T568P, Q590L), AAV9.13 (A1369C, A1720T; N457H, T574S), AAV9.14 (T1340A, T1362C, T1560C, G1713A; L447H), AAV9.16 (A1775T; Q592L), AAV9.24 (T1507C, T1521G; W503R), AAV9.26 (A1337G, A1769C; Y446C, Q590P), AAV9.33 (A1667C; D556A), AAV9.34 (A1534G, C1794T; N512D), AAV9.35 (A1289T, T1450A, C1494T, A1515T, C1794A, G1816A; Q430L, Y484N, N98K, V6061), AAV9.40 (A1694T, E565V), AAV9.41 (A1348T, T1362C; T450S), AAV9.44 (A1684C, A1701T, A1737G; N562H, K567N), AAV9.45 (A1492T, C1804T; N498Y, L602F), AAV9.46 (G1441C, T1525C, T1549G; G481R, W509R, L517V), 9.47 (G1241A, G1358A, A1669G, C1745T; S414N, G453D, K557E, T582I), AAV9.48 (C1445T, A1736T; P482L, Q579L), AAV9.50 (A1638T, C1683T, T1805A; Q546H, L602H), AAV9.53 (G1301A, A1405C, C1664T, G1811T; R134Q, S469R, A555V, G604V), AAV9.54 (C1531A, T1609A; L511I, L537M), AAV9.55 (T1605A; F535L), AAV9.58 (C1475T, C1579A; T492I, H527N), AAV.59 (T1336C; Y446H), AAV9.61 (A1493T; N498I), AAV9.64 (C1531A, A1617T;

L511I), AAV9.65 (C1335T, T1530C, C1568A; A523D), AAV9.68 (C1510A; P504T), AAV9.80 (G1441A; G481R), AAV9.83 (C1402A, A1500T; P468T, E500D), AAV9.87 (T1464C, T1468C; S490P), AAV9.90 (A1196T; Y399F), AAV9.91 (T1316G, A1583T, C1782G, T1806C; L439R, K528I), AAV9.93 (A1273G, A1421G, A1638C, C1712T, G1732A, A1744T, A1832T; S425G, Q474R, Q546H, P571L, G578R, T582S, D611V), AAV9.94 (A1675T; M559L) and AAV9.95 (T1605A; F535L).

In one embodiment, AAV particles of the present invention may comprise capsid proteins having sequences of SEQ ID NOs: 1 and 3, which have increased tropism to the brain, of International Publication No. WO2014160092, the content of which is incorporated herein by reference in its entirety.

In one embodiment, AAV particles of the present invention may comprise capsid proteins which may target to oligodendrocytes in the central nervous system. The capsid proteins may comprise AAV capsid coding sequence of SEQ ID NO: 1 or AAV capsid proteins comprising amino acid sequences of SEQ ID NOs: 2 to 4 of International Publication No. WO2014052789, the content of which is herein incorporated by reference in its entirety.

In one embodiment, AAV particles of the present invention may comprise capsid proteins having increased capacity to cross the blood-brain barrier in CNS as disclosed in U.S. Pat. No. 8,927,514, the content of which is incorporated herein by reference in its entirety. The amino acid sequences and nucleic acid sequences of such capsid proteins may include, but are not limited to, SEQ ID NOs: 2-17 and SEQ ID NOs: 25-33, respectively, of U.S. Pat. No. 8,927,514.

In some embodiments, AAV particles of the present invention may comprise AAV2 capsid proteins or variants thereof. AAV particles with AAV2 capsid proteins have been shown to deliver genes to neurons effectively in the brain, retina and spinal cord. In one embodiment, AAV2 capsid proteins may be further modified such as addition of a targeting peptide to the capsid proteins that targets an AAV particle to brain vascular endothelium as disclosed in U.S. Pat. Nos. 6,691,948 and 8,299,215, the contents of each of which are herein incorporated by reference in their entirety. Such AAV particles may be used to deliver a functional hTREM2 antibody or an antigen-binding fragment thereof, e.g., as described herein.

In some embodiments, AAV particles of the present invention may comprise AAV5 capsid proteins or variants thereof. AAV particles with AAV5 capsid proteins can transduce neurons in various regions of the CNS, including the cortex, the hippocampus (HPC), cerebellum, substantia nigra (SN), striatum, globus pallidus, and spinal cord (Burger C et al, Mol Ther., 2004, 10(2): 302-317; Liu G et al, Mol Ther. 2007, 15(2): 242-247; and Colle M et al, Hum, Mol. Genet. 2010, 19(1): 147-158). In one embodiment, AAV particles having AAV 5 capsid proteins with increased transduction to cells in CNS may be those particles from U.S. Pat. No. 7,056,502, the content of which is incorporated herein by reference in its entirety.

In some embodiments, AAV particles of the present invention may comprise AAV6 capsid proteins or variants thereof. Recombinant AAV6 serotype can target motor neurons in the spinal cord by Intracerebroventricular (ICV) injection (Dirren E et al., Hum Gene Ther., 2014, 25(2): 109-120). In addition, a study from San Sebastian et al indicated that AAV6 serotype can be retrogradely transported from terminals to neuronal cell bodies in the rat brain (San Sebastian et al, Gen Ther., 2014, 20(12): 1178-1183).

In some embodiments, AAV particles of the present invention may comprise AAV8 capsid proteins or variants thereof. AAV particles with AAV8 capsid proteins can transduce neurons, for example in hippocampus (Klein R L et al, Mol Ther., 2006, 13(3): 517-527). In one embodiment, AAV8 capsid proteins may comprise the amino acid sequence of SEQ ID NO: 2 of U.S. Pat. No. 8,318,480, the content of which is herein incorporated by reference in its entirety.

In some embodiments, AAV particles of the present invention may comprise AAV9 capsid proteins or variants thereof. AAV9 capsid serotype mediated gene delivery has been observed in the brain with efficient and long-term expression of transgene after intraparenchymal injections to the CNS (Klein R L et al, Eur J Neurosci., 2008, 27: 1615-1625). AAV9 serotype can produce robust and wide-scale neuronal transduction throughout the CNS after a peripheral, systemic (e.g., intravenous) administration in neonatal subjects (Foust K D et al, Nat. Biotechnol, 2009, 27: 59-65; and Duque S et al, Mol Ther., 2009, 17: 1187-1196). Intrathecal (intra-cisterna *magna* routes) administration of AAV9 serotypes can also produce widespread spinal expression. In one embodiment, AAV9 serotype may comprise an AAV capsid protein having the amino acid sequence of SEQ ID NO: 2 of U.S. Pat. No. 7,198,951, the content of which is incorporated herein by reference in its entirety. In another aspect, AAV9 serotype may comprise VP1 capsid proteins of SEQ ID NOs: 2, 4 or 6 in which at least one of surface-exposed tyrosine residues in the amino acid sequence is substituted with another amino acid residue, as disclosed in US patent publication No. US20130224836, the content of which is incorporated herein by reference in its entirety. In embodiments the AAV vector comprising an AAV9 capsid is administered systemically, e.g., intravenously. In embodiments, the AAV vector comprising an AAV9 capsid is administered to the brain, spine or cerebrospinal fluid (CSF), e.g., intrathecally.

In some embodiments the AAV vector comprises a variant capsid protein engineered to attain a specific property. Such methods for obtaining engineered capsids are described in, for example, patent publication WO2011038187, the contents of which are incorporated herein by reference in their entirety. Such methods and vectors are also described in, for example, patent publication WO2012112832 and patent application publication WO2015054653, the contents of which are incorporated herein by reference in their entirety. Such variant capsids include, for example, SEQ ID NO: 23 of WO2015054653, or a variant thereof. Additional variant capsids include, for example, those capsid sequences described in patent publication WO2017/019994, the contents of which are incorporated by reference in their entirety. In embodiments, the AAV vector comprises a capsid of an Anc80 AAV capsid sequence (e.g., SEQ ID NO: 1 of WO2017019994), for example, Anc80L65 (e.g., SEQ ID NO: 23 of WO2017019994), or, for example, Anc10 (e.g., SEQ ID NO: 42 of WO2017019994).

In some embodiments, AAV particles of the present invention may comprise AAVrh10 capsid proteins or variants thereof. AAV particles comprising AAVrh10 capsid proteins can target neurons, other cells as well, in the spinal cord after intrathecal (IT) administration. In one embodiment, AAVrh10 capsid proteins may comprise the amino acid sequence of SEQ ID NO: 81 of EP patent NO: 2341068. [00188] In some embodiments, AAV of the present invention may comprise AAVDJ capsid proteins, AAVDJ/8 capsid proteins, or variants thereof. Holehonnur et al showed that AAVDJ/8 serotype can target neurons within the Basal and Lateral Amygdala (BLA) (Holehonnur R et al., BMC Neurosci, 2014, Feb. 18: 15:28). In one embodiment, AAVDJ capsid proteins and/or AAVDJ/8 capsid proteins may comprise an amino acid sequence comprising a first region that is derived from a first AAV serotype (e.g., AAV2), a second region that is derived from a second AAV serotype (e.g., AAV8), and a third region that is derived from a third AAV serotype (e.g., AAV 9), wherein the first, second and third region may include any amino acid sequences that are disclosed in this description.

In one embodiment, AAV particles of the present invention may comprise capsid proteins that have been shown to or are known to transduce dorsal root ganglions (DRGs).

In one embodiment, AAV particles of the present invention may comprise capsid proteins that have been shown or are known to transduce motor neurons.

In one embodiment, the AAV particles comprise a self-complementary (SC) vector genome.

In one embodiment, the AAV particles comprise a single stranded (SS) genome.

In one embodiment, an AAV particle comprising a self-complementary (sc) vector may be used to yield higher expression than an AAV particle comprising a corresponding single stranded vector genome.

In one embodiment, the serotype of the AAV particles described herein may depend on the desired distribution, transduction efficiency and cellular targeting required. As described by Sorrentino et al. (comprehensive map of CNS transduction by eight adeno-associated virus serotypes upon cerebrospinal fluid administration in pigs, Molecular Therapy accepted article preview online 7 Dec. 2015; doi: 10.1038/mt.2015.212; the contents of which are herein incorporated by reference in its entirety), AAV serotypes provided different distributions, transduction efficiencies and cellular targeting. In order to provide the desired efficacy, the AAV serotype needs to be selected that best matches not only the cells to be targeted but also the desired transduction efficiency and distribution.

In one embodiment, the AAV vector comprises an AAV9 capsid (as described herein) and a AAV vector plasmid comprising (1) ITRs derived from AAV2, (2) A CMV enhancer (e.g., SEQ ID NO: 134), (3) a CBA promoter (e.g., SEQ ID NO: 135), (4) an SV40 intron (e.g., SEQ ID NO: 137), (5) a polynucleotide encoding a hTREM2 antibody or an antigen-binding fragment thereof (e.g., as described herein), and (6) a BGH poly A signal (e.g., SEQ ID NO: 138). In one embodiment, elements (2) to (6) are disposed on the AAV vector plasmid from 5' to 3'. In embodiments, the elements (2) to (6) are disposed on the AAV vector plasmid between the 5' ITR and the 3' ITR. In an embodiment, the AAV vector is a scAAV vector.

Generation of Monoclonal Antibodies

Monoclonal antibodies (mAbs) can be produced by a variety of techniques, including conventional monoclonal antibody methodology, e.g., the standard somatic cell hybridization technique of Kohler and Milstein, 1975 Nature 256: 495. Many techniques for producing monoclonal antibody can be employed e.g., viral or oncogenic transformation of B lymphocytes.

An animal system for preparing hybridomas is the murine system. Hybridoma production in the mouse is a well established procedure. Immunization protocols and techniques for isolation of immunized splenocytes for fusion are known in the art. Fusion partners (e.g., murine myeloma cells) and fusion procedures are also known.

In some embodiments, the antibodies of the invention are humanized monoclonal antibodies. Chimeric or humanized antibodies and antigen-binding fragments thereof of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art. See e.g., U.S. Pat. No. 5,225,539 to Winter, and U.S. Pat. Nos. 5,530,101; 5,585,089; 5,693,762 and 6,180,370 to Queen et al.

In some embodiments, the antibodies of the invention are human monoclonal antibodies. Such human monoclonal antibodies directed against TREM2 can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb Mouse® (Medarex, Inc.) contains human immunoglobulin gene miniloci that encode un-rearranged human heavy (mu and gamma) and kappa light chain immunoglobulin sequences, together with targeted mutations that inactivate the endogenous mu and kappa chain loci (see e.g., Lonberg, et al., 1994 Nature 368 (6474): 856-859). Accordingly, the mice exhibit reduced expression of mouse IgM or K, and in response to immunization, the introduced human heavy and light chain transgenes undergo class switching and somatic mutation to generate high affinity human IgG-kappa monoclonal (Lonberg, N. et al., 1994 supra; reviewed in Lonberg, N., 1994 Handbook of Experimental Pharmacology 113:49-101; Lonberg, N. and Huszar, D., 1995 Intern. Rev. Immunol. 13: 65-93, and Harding, F. and Lonberg, N., 1995 Ann. N.Y. Acad. Sci. 764:536-546). The preparation and use of HuMAb mice, and the genomic modifications carried by such mice, is further described in Taylor, L. et al., 1992 Nucleic Acids Research 20:6287-6295; Chen, J. et al., 1993 International Immunology 5: 647-656; Tuaillon et al., 1993 Proc. Natl. Acad. Sci. USA 94:3720-3724; Choi et al., 1993 Nature Genetics 4:117-123; Chen, J. et al., 1993 EMBO J. 12: 821-830; Tuaillon et al., 1994 J. Immunol. 152:2912-2920; Taylor, L. et al., 1994 International Immunology 579-591; and Fishwild, D. et al., 1996 Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92103918, WO 93/12227, WO 94/25585, WO 97113852, WO 98/24884 and WO 99/45962, all to Lonberg and Kay; and PCT Publication No. WO 01/14424 to Korman et al.

In some embodiments, human antibodies can be raised using a mouse that carries human immunoglobulin sequences on transgenes and transchomosomes such as a mouse that carries a human heavy chain transgene and a human light chain trans chromosome. Such mice, referred to herein as "KM mice," are described in detail in PCT Publication WO 02/43478 to Ishida et al.

Still further, alternative transgenic animal systems expressing human immunoglobulin genes are available in the art and can be used to raise TREM2-binding antibodies and antigen-binding fragments thereof. For example, an alternative transgenic system referred to as the Xenomouse (Abgenix, Inc.) can be used. Such mice are described in, e.g., U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise TREM2-binding antibodies of the invention. For example, mice carrying both a human heavy chain transchromosome and a human light chain transchromosome, referred to as "TC mice" can be used; such mice are described in Tomizuka et al., 2000 Proc. Natl. Acad. Sci. USA 97:722-727. Furthermore, cows carrying human heavy and light chain transchromosomes have been described in the art (Kuroiwa et al., 2002 Nature Biotechnology 20:889-894) and can be used to raise TREM2-binding antibodies of the invention.

Human monoclonal antibodies can also be prepared using phage display methods for screening libraries of human immunoglobulin genes. Such phage display methods for isolating human antibodies are established in the art or described in the examples below. See for example: U.S. Pat. Nos. 5,223,409; 5,403,484; and U.S. Pat. No. 5,571,698 to Ladner et al; U.S. Pat. Nos. 5,427,908 and 5,580,717 to Dower et al; U.S. Pat. Nos. 5,969,108 and 6,172,197 to McCafferty et al; and U.S. Pat. Nos. 5,885,793; 6,521,404; 6,544,731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Framework or Fc Engineering

Engineered antibodies and antigen-binding fragments thereof of the invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis. Such "backmutated" antibodies are also intended to be encompassed by the invention.

Another type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In one embodiment, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another embodiment, one or more amino acid residues are altered to thereby alter the ability of the antibody to fix complement. This approach is described further in PCT Publication WO 94/29351 by Bodmer et al.

In some embodiments, the TREM2-binding molecule contains a human IgG1 constant region. In some embodiments, the human IgG1 constant region includes an Fc region.

In some embodiments, the Fc region of the TREM2-binding molecule includes one or more mutations mediating reduced or no antibody-dependent cellular cytotoxicity (ADCC) or complement-dependent cytotoxicity (CDC). In some embodiments, amino acid residues L234 and L235 of the IgG1 constant region are substituted to A234 and A235.

In some embodiments, amino acid residue N267 of the IgG1 constant region is substituted to A267. In some embodiments, amino acid residues D265 and P329 of the IgG1 constant region are substituted to A265 and A329. In certain embodiments, the Fc region optionally comprises a mutation or combination of mutations conferring reduced effector function selected from any of D265A, P329A, P329G, N297A, D265A/P329A, D265A/N297A, L234/L235A, P329A/L234A/L235A, and P329G/L234A/L235A. In some embodiments, the Fc region comprises a mutation or combination of mutations conferring reduced effector function selected from any of D265A, P329A, P329G, N297A, D265A/P329A, D265A/N297A, L234/L235A, P329A/L234A/L235A, and P329G/L234A/L235A (all positions by EU numbering).

In yet another embodiment, the Fc region is modified to increase the ability of the antibody to mediate antibody dependent cellular cytotoxicity (ADCC) and/or to increase the affinity of the antibody for an Fc-gamma receptor by modifying one or more amino acids. This approach is described further in PCT Publication WO 00/42072 by Presta. Moreover, the binding sites on human IgG1 for Fc-gamma RI, Fc-gamma RII, Fc-gamma RIII and FcRn have been mapped and variants with improved binding have been described (see Shields, R. L. et al., 2001 J. Biol. Chen. 276:6591-6604). For example, the Fc region can comprise a mutation or combination of mutations conferring increased effector function selected from any of S239D, 1332E, A330L, S298A, E333A, E333S, K334A, K236A, K236W, F243L, P2471, D280H, K290S, R292P, S298D, S298V, Y300L, V3051, A339D, A339Q, A339T, P396L (all positions by EU numbering).

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, LecI3 cells, with reduced ability to attach fucose to Asn (297)-linked carbohydrates, also resulting in hypofucosylation of antibodies expressed in that host cell (see also Shields, R. L. et al., 2002 J. Biol. Chem. 277:26733-26740). PCT Publication WO 99/54342 by Umana et al. describes cell lines engineered to express glycoprotein-modifying glycosyl transferases (e.g., beta (1,4)-N acetylglucosaminyltransferase III (GnTIII)) such that antibodies expressed in the engineered cell lines exhibit increased bisecting GlcNac structures which results in increased ADCC activity of the antibodies (see also Umana et al., 1999 Nat. Biotech. 17:176-180).

In some embodiments, the TREM2-binding molecule is an antibody. In some embodiments, the antibody has an IgG1 isotype with one or more mutations (e.g., relative to a wild-type Fc region of the same isotype). In some embodiments, the one or more mutations are selected from N297A, N297Q (BoltS et al. (1993) *Eur J Immunol* 23:403-411), D265A, L234A, L235A (McEarchem et al., (2007) *Blood,* 109:1185-1192), C226S, C229S (McEarchern et al., (2007) *Blood,* 109:1185-1192), P238S (Davis et al., (2007) *J Rheumatol,* 34:2204-2210), E233P, L234V (McEarchern et al., (2007) *Blood,* 109:1185-1192), P238A, A327Q, A327G, P329A (Shields R L. et al., (2001) *J Biol Chem.* 276(9): 6591-604), K322A, L234F, L235E (Hezareh, et al., (2001) J Viral 75, 12161-12168; Oganesyan et al., (2008). *Acta Crystallographica* 64, 700-704), P331S (Oganesyan et al., (2008) *Acta Crystallographica* 64, 700-704), T394D (Wilkinson et al. (2013) MAbs 5(3): 406-417), A330L, M252Y, S254T, and/or T256E, where the amino acid position is according to the EU or Kabat numbering convention. In certain embodiments, the Fc region further includes an amino acid deletion at a position corresponding to glycine 236 according to the EU or Kabat numbering convention.

In some embodiments, the antibody has an IgG1 isotype with a heavy chain constant region that contains a C220S mutation according to the EU or Kabat numbering convention.

In some embodiments, the Fc region further contains one or more additional mutations selected from A330L, L234F; L235E, and/or P331S according to EU or Kabat numbering convention.

In certain embodiments, the antibody has an IgG2 isotype. In some embodiments, the antibody contains a human IgG2 constant region. In some embodiments, the human IgG2 constant region includes an Fc region. In some embodiments, the Fc region contains one or more modifications. For example, in some embodiments, the Fc region contains one or more mutations (e.g., relative to a wild-type Fc region of the same isotype). In some embodiments, the one or more mutations are selected from V234A, G237A, H268E, V309L, N297A, N297Q, A330S, P331S, C232S, C233S, M252Y, S254T, and/or T256E, where the amino acid position is according to the EU or Kabat numbering convention.

In certain embodiments, the antibody has an IgG4 isotype. In some embodiments, the antibody contains a human IgG4 constant region. In some embodiments, the human IgG4 constant region includes an Fc region. In some embodiments, the Fc region contains one or more modifications. For example, in some embodiments, the Fc region contains one or more mutations (e.g., relative to a wild-type Fc region of the same isotype). In some embodiments, the one or more mutations are selected from E233P, F234V, L235A, G237A, E318A (Hutchins et al. (1995) *Proc Nat/A cad Sci* USA, 92:11980-11984), S228P, L236E, S241P, L248E (Reddy et al., (2000) J Immuno/, 164:1925-1933; Angal et al., (1993) Mol Immunol. 30(1):105-8; U.S. Pat. No. 8,614,299 B2), T394D, M252Y, S254T, T256E, N297A, and/or N297Q, where the amino acid position is according to the EU or Kabat numbering convention.

In some embodiments, the Fc region further contains one or more additional mutations selected from a M252Y, S254T, and/or T256E, where the amino acid position is according to the EU or Kabat numbering convention.

In some embodiments, one or more of the IgG1 variants described herein may be combined with an A330L mutation (Lazar et al., (2006) Proc Natl Acad Sci USA, 103:4005-4010), or one or more of L234F, L235E, and/or P331S mutations (Sazinsky et al., (2008) Proc Natl Acad Sci USA, 105:20167-20172), where the amino acid position is according to the EU or Kabat numbering convention, to eliminate complement activation. In some embodiments, the IgG variants described herein may be combined with one or more mutations to enhance the antibody half-life in human serum (e.g. M252Y, S254T,T256E mutations according to the EU or Kabat numbering convention) (Dall' Acqua et al., (2006) J Biol Chem, 281:23514-23524; and Strohl e al., (2009) Current Opinion in Biotechnology, 20:685-691).

In some embodiments, an IgG4 variant of the present disclosure may be combined with an S228P mutation according to the EU or Kabat numbering convention (Angal et al., (1993) Mol Immunol, 30:105-108) and/or with one or more mutations described in Peters et al., (2012) J Biol Chem. 13; 287(29):24525-33) to enhance antibody stabilization.

In some embodiments, the antibody has an Fc region selected from an IgG2 Fc region, an IgG4 Fc region, or an IgG2/IgG4 hybrid Fc region.

Methods of Engineering Altered Antibodies

As discussed above, the TREM2-binding antibodies having VH and VL sequences or full length heavy and light chain sequences shown herein can be used to create new TREM2-binding antibodies by modifying full length heavy chain and/or light chain sequences, VH and/or VL sequences, or the constant region (s) attached thereto. Thus, in another aspect of the invention, the structural features of TREM2-binding antibody of the invention are used to create structurally related TREM2-binding antibodies that retain at least one functional property of the antibodies and antigen-binding fragments thereof of the invention, such as binding to and stabilize human TREM2.

For example, one or more CDR regions of the antibodies and antigen-binding fragments thereof of the present invention, or mutations thereof, can be combined recombinantly with known framework regions and/or other CDRs to create additional, recombinantly-engineered, TREM2-binding antibodies and antigen-binding fragments thereof of the invention, as discussed above. Other types of modifications include those described in the previous section. The starting material for the engineering method is one or more of the VH and/or VL sequences provided herein, or one or more CDR regions thereof. To create the engineered antibody, it is not necessary to actually prepare (i.e., express as a protein) an antibody having one or more of the VH and/or VL sequences provided herein, or one or more CDR regions thereof. Rather, the information contained in the sequence (s) is used as the starting material to create a "second generation" sequence (s) derived from the original sequence (s) and then the "second generation" sequence (s) is prepared and expressed as a protein.

The altered antibody sequence can also be prepared by screening antibody libraries having fixed CDR3 sequences or minimal essential binding determinants as described in US20050255552 and diversity on CDR1 and CDR2 sequences. The screening can be performed according to any screening technology appropriate for screening antibodies from antibody libraries, such as phage display technology.

Standard molecular biology techniques can be used to prepare and express the altered antibody sequence. The antibody encoded by the altered antibody sequence (s) is one that retains one, some or all of the functional properties of the TREM2-binding antibodies described herein, which functional properties include, but are not limited to, specifically binding to and stabilize human TREM2 protein.

The functional properties of the altered antibodies can be assessed using standard assays available in the art and/or described herein, such as those set forth in the Examples (e.g., ELISAs).

In some embodiments, the methods of engineering antibodies and antigen-binding fragments thereof of the invention, mutations can be introduced randomly or selectively along all or part of an TREM2-binding antibody coding sequence and the resulting modified TREM2-binding antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Characterization of the Antibodies of the Invention

The antibodies and antigen-binding fragments thereof of the invention can be characterized by various functional assays. For example, they can be characterized by their ability to bind and stabilize TREM2.

The ability of an antibody to bind to TREM2 can be detected by labelling the antibody of interest directly, or the antibody may be unlabeled and binding detected indirectly using various sandwich assay formats known in the art.

In some embodiments, the TREM2-binding antibodies and antigen-binding fragments thereof of the invention block or compete with binding of a reference TREM2-binding antibody to TREM2 polypeptide. These can be fully human or humanized TREM2-binding antibodies described above. They can also be other human, mouse, chimeric or humanized TREM2-binding antibodies which bind to the same epitope as the reference antibody. The capacity to block or compete with the reference antibody binding indicates that TREM2-binding antibody under test binds to the same or similar epitope as that defined by the reference antibody, or to an epitope which is sufficiently proximal to the epitope bound by the reference TREM2-binding antibody. Such antibodies are especially likely to share the advantageous properties identified for the reference antibody. The capacity to block or compete with the reference antibody may be determined by, e.g., a competition binding assay. With a competition binding assay, the antibody under test is examined for ability to inhibit specific binding of the reference antibody to a common antigen, such as TREM2 polypeptide. A test antibody competes with the reference antibody for specific binding to the antigen if an excess of the test antibody substantially inhibits binding of the reference antibody. Substantial inhibition means that the test antibody reduces specific binding of the reference antibody usually by at least 10%, 25%, 50%, 75%, or 90%.

There are a number of known competition binding assays that can be used to assess competition of an antibody with a reference antibody for binding to a particular protein, in this case, TREM2. These include, e.g., solid phase direct or indirect radioimmunoassay (RIA), solid phase direct or indirect enzyme immunoassay (EIA), sandwich competition assay (see Stahli et al., Methods in Enzymology 9:242-253, 1983); solid phase direct biotin-avidin EIA (see Kirkland et al., J. Immunol. 137:3614-3619, 1986); solid phase direct labeled assay, solid phase direct labeled sandwich assay (see Harlow & Lane, supra); solid phase direct label RIA using I-125 label (see Morel et al., Mol. Immunol. 25:7-15, 1988); solid phase direct biotin-avidin EIA (Cheung et al., Virology 176:546-552, 1990); and direct labeled RIA (Moldenhauer et al., Scand. J. Immunol. 32:77-82, 1990). Typically, such an assay involves the use of purified antigen bound to a solid surface or cells bearing either of these, an unlabelled test TREM2-binding antibody and a labelled reference antibody. Competitive inhibition is measured by determining the amount of label bound to the solid surface or cells in the presence of the test antibody. Usually the test antibody is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

To determine if the selected TREM2-binding monoclonal antibodies bind to unique epitopes, each antibody can be biotinylated using commercially available reagents (e.g., reagents from Pierce, Rockford, Ill.). Competition studies using unlabeled monoclonal antibodies and biotinylated monoclonal antibodies can be performed using TREM2 polypeptide coated-ELISA plates. Biotinylated MAb binding can be detected with a strep-avidin-alkaline phosphatase probe. To determine the isotype of a purified TREM2-binding antibody, isotype ELISAs can be performed. For example, wells of microtiter plates can be coated with 1 μg/ml of anti-human IgG overnight at 4 degrees C. After blocking with 1% BSA, the plates are reacted with 1 μg/ml or less of the monoclonal TREM2-binding antibody or purified isotype controls, at ambient temperature for one to two hours. The wells can then be reacted with either human IgG1 or human IgM-specific alkaline phosphatase-conjugated probes. Plates are then developed and analyzed so that the isotype of the purified antibody can be determined.

To demonstrate binding of monoclonal TREM2-binding antibodies to live cells expressing TREM2 polypeptide, flow cytometry can be used. Briefly, cell lines expressing TREM2 (grown under standard growth conditions) can be mixed with various concentrations of TREM2-binding antibody in PBS containing 0.1% BSA and 10% fetal calf serum, and incubated at 37 degrees ° C. for 1 hour. After washing, the cells are reacted with Fluorescein-labeled anti-human IgG antibody under the same conditions as the primary antibody staining. The samples can be analyzed by FACScan instrument using light and side scatter properties to gate on single cells. An alternative assay using fluorescence microscopy may be used (in addition to or instead of) the flow cytometry assay. Cells can be stained exactly as described above and examined by fluorescence microscopy. This method allows visualization of individual cells, but may have diminished sensitivity depending on the density of the antigen.

TREM2-binding antibodies and antigen-binding fragments thereof of the invention can be further tested for reactivity with TREM2 polypeptide or antigenic fragment by Western blotting. Briefly, purified TREM2 polypeptides or fusion proteins, or cell extracts from cells expressing TREM2 can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

Examples of functional assays are also described in the Example section below.

Methods of Treatment

Provided herein are methods of treating a disease associated with TREM2 loss of function by using the TREM2-binding molecules disclosed herein. In some embodiments, the disease associated with TREM2 loss of function is a neuroinflammatory or neurodegenerative disease such as Alzheimer's disease, frontotemporal dementia, Parkinson's disease, amyotrophic lateral sclerosis, Nasu-Hakola disease, multiple sclerosis, amyotrophic lateral sclerosis (ALS), anti-NMDA receptor encephalitis, autism, brain lupus (NP-SLE), chemo-induced peripheral neuropathy (CIPN), postherpetic neuralgia, chronic inflammatory demyelinating polyneuropathy (CIDP), epilepsy, Guillain-Barre Syndrome (GBS), inclusion body myositis, lysosomal storage diseases, e.g., sphingomyelinlipidose (Niemann-Pick C) and mucopolysaccharidose II/IIIB, metachromatic leukodystrophy, multifocal motor neuropathy, Myasthenia Gravis, Neuro-Behcet's Disease, neuromyelitis optica (NMO), optic neuritis, polymyositis, dermatomyositis, Rasmussen's encephalitis, Rett's Syndrome, stroke, transverse myelitis, traumatic brain injury, spinal cord injury, viral encephalitis, or bacterial meningitis. In some preferred embodiments, the disease associated with TREM2 loss of function is selected from a list consisting of Alzheimer's disease, frontotemporal dementia, Parkinson's disease, amyotrophic lateral sclerosis, or Nasu-Hakola disease.

Provided herein are also methods of treating a TREM2 related disorder directly or indirectly associated with aberrant TREM2 activity and/or expression by using the TREM2-binding molecules disclosed herein. The Trem2-related disorders include CNS related diseases, PNS related diseases, systemic inflammation and other diseases related to inflammation, pain and withdrawal symptoms caused by an abuse of chemical substances, diseases or disorders related to the CNS include general anxiety disorders, cognitive disorders, learning and memory deficits and dysfunctions, Alzheimer's disease (mild, moderate and severe), attention deficit and hyperactivity disorder, Parkinson's disease, dementia in Parkinson's disease, Huntington's disease, ALS, prionic neurodegenerative disorders such as Creutzfeld-Jacob disease and kuru disease, Gilles de la Tourette's syndrome, psychosis, depression and depressive disorders, mania, manic depression, schizophrenia, the cognitive deficits in schizophrenia, obsessive compulsive disorders, panic disorders, eating disorders, narcolepsy, nociception, AIDS-dementia, senile dementia, mild cognitive impairment related to age (MCI), age associated memory impairment, autism, dyslexia, tardive dyskinesia, epilepsy, and convulsive disorders, post-traumatic stress disorders, transient anoxia, pseudodementia, pre-menstrual syndrome, late luteal phase syndrome, chronic fatigue syndrome and jet lag. In some preferred embodiments, the Trem2-related disorders is selected from a list consisting of Alzheimer's disease, frontotemporal dementia, Parkinson's disease, amyotrophic lateral sclerosis, or Nasu-Hakola disease.

Trem2-related disorders also include: immunological disorders, especially involving inflammatory disorders (e.g., bacterial infection, fungal infection, viral infection, protozoa or other parasitic infection, psoriasis, septicemia, cerebral malaria, inflammatory bowel disease, arthritis, such as rheumatoid arthritis, folliculitis, impetigo, granulomas, lipoid pneumonias, vasculitis, and osteoarthritis), autoimmune disorders (e.g., rheumatoid arthritis, thyroiditis, such as Hashimoto's thyroiditis and Graves' disease, insulin-resistant diabetes, pernicious anemia, Addison's disease, pemphigus, vitiligo, ulcerative colitis, systemic lupus erythematosus (SLE), Sjogren's syndrome, multiple sclerosis, dermatomyositis, mixed connective tissue disease, scleroderma, polymyositis, graft rejection, such as allograft rejection), T cell disorders (e.g., AIDS), allergic inflammatory disorders (e.g., skin and/or mucosal allergies, such as allergic rhinitis, asthma, psoriasis), neurological disorders, eye disorders, embryonic disorders, or any other disorders (e.g., tumors, cancers, leukemia, myeloid diseases, and traumas) which are directly or indirectly associated with aberrant TREM2 activity and/or expression.

In some embodiments, the TREM2-related disorder is an autoimmune, inflammatory, or malignant disorder mediated by or associated with extensive proteolytic cleavage of TREM2 or cells expressing aberrant or mutated variants of the TREM2 receptor. Examples of autoimmune diseases include, without limitation, arthritis (for example rheumatoid arthritis, arthritis chronica progrediente and arthritis deformans) and rheumatic diseases, including inflammatory conditions and rheumatic diseases involving bone loss, inflammatory pain, spondyloarhropathies including ankolsing spondylitis, Reiter syndrome, reactive arthritis, psoriatic arthritis, and enterophathic arthritis, hypersensitivity (including both airways hypersensitivity and dermal hypersensitivity) and allergies. Autoimmune diseases include autoimmune haematological disorders (including e.g. hemolytic anaemia, aplastic anaemia, pure red cell anaemia and idiopathic thrombocytopenia), systemic lupus erythematosus, inflammatory muscle disorders, polychondritis, sclerodoma, Wegener granulomatosis, dermatomyositis, chronic active hepatitis, myasthenia gravis, psoriasis, Steven-Johnson syndrome, idiopathic sprue, endocrine ophthalmopathy, Graves disease, sarcoidosis, multiple sclerosis, primary biliary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including gout, langerhans cell histiocytosis, idiopathic nephrotic syndrome or minimal change nephropathy), tumors, inflammatory disease of skin and comea, myositis, loosening of bone implants, metabolic disorders, such as atherosclerosis, diabetes, and dislipidemia.

In some embodiments, the TREM2-related disorder is selected from asthma, bronchitis, pneumoconiosis, pulmonary emphysema, other obstructive or inflammatory diseases of the airways including idiopathic pulmonary fibrosis or COPD.

In some embodiments, the TREM2-related disorder is a hematopoietic or hepatopoetic malignant disorder such as acute myeloid leukemia, chronic myeloid leukemia, myeloproliferative disorders, myelodysplastic syndromes, multiple myeloma, paroxysmal nocturnal hemoglobinuria, fanconi anemi, thalassemia major, Wiskott-Aldrich syndrome, hemophagocytic lymphohistiocytosis.

In some embodiments, the TREM2-related disorder is selected from asthma, encephalitis, inflammatory bowel disease, chronic obstructive pulmonary disease (COPD), allergic disorders, septic shock, pulmonary fibrosis, undifferentiated spondyloarthropathy, undifferentiated arthropathy, arthritis, inflammatory osteolysis, or chronic inflammation resulting from chronic viral or bacterial infections.

In some embodiments, the TREM2-related disorder is selected from dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, Taupathy disease, Nasu-Hakola disease, stroke, acute trauma, chronic trauma, lupus, acute and chronic colitis, wound healing, Crohn's disease, inflammatory bowel disease, ulcerative colitis, obesity, Malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, Sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer. In some preferred embodiments, the TREM2-related disorder is selected from a list consisting of Alzheimer's disease, frontotemporal dementia, Parkinson's disease, amyotrophic lateral sclerosis, or Nasu-Hakola disease.

In some embodiments, the TREM2-related disorder is selected from dementia, frontotemporal dementia, Alzheimer's disease, Nasu-Hakola disease, and multiple sclerosis. In some preferred embodiments, TREM2-related disorder is a dementia such as frontotemporal dementia, Alzheimer's disease, Parkinson's disease, vascular dementia, semantic dementia, or dementia with Lewy bodies.

In some embodiments, such methods include administering to a subject in need of treatment a therapeutically effective amount of an antibody or antigen-binding fragment thereof that specifically binds to the IgSF domain of TREM2 protein, e.g. the amino acid residues 19 to 132 of any one of SEQ ID NOs: 1, 2, and 3, and stabilizes the TREM2 protein.

In some embodiments, such methods of treating a disease associated with TREM2 loss of function include: (1) assaying the cell surface TREM2 level in a sample obtained from a subject, e.g., a cerebrospinal fluid sample obtained from a subject; (2) selecting a subject whose level of cell surface TREM2 is lower than a reference level, wherein the reference level is the level of cell surface TREM2 in a sample obtained from a healthy subject, e.g., a cerebrospinal fluid sample obtained from a healthy subject; and (3) administering to the subject a therapeutically effective amount of an antibody or antigen-binding fragment thereof that specifically binds to the IgSF domain of TREM2 protein and stabilizes the TREM2 protein. The antibody or antigen-binding fragment thereof that specifically bind to the IgSF domain of TREM2 protein can stabilize the TREM2 protein on the cell surface, and/or reduce shedding of the ectodomain of the TREM2 protein. These antibodies or antigen-binding fragments thereof can be administered to the subject through an oral, intravenous, intracranial, intrathecal, subcutaneous or intranasal route. The level of cell surface TREM2 in the sample can be determined by an assay known in the art, e.g., by flow cytometry, immunohistochemistry, Western blotting, immunofluorescent assay, radioimmunoassay (RIA), enzyme-linked immunosorbent assay (ELISA), homogeneous time resolved fluorescence (HTRF), positron emission tomography (PET), or any other immune detection with an antibody or antibody fragment against TREM2.

Combination Therapies

The various treatments described above can be combined with other treatment partners such as the current standard of care for a disease associated with TREM2 loss of function, e.g., the current standard of care for Alzheimer's disease, frontotemporal dementia, Parkinson's disease, amyotrophic lateral sclerosis, or Nasu-Hakola disease. For example, the hTREM2 antibodies or an antigen-binding fragment thereof described herein can be combined with one or more of BACE inhibitors, anti-Tau antibodies, anti-amvloid beta antibodies, fingolimod, BG12, interferon beta or tysabri. Accordingly, the methods of treating a disease associated with TREM2 loss of function described herein can further include administering a second agent to the subject in need of treatment.

The term "combination" refers to either a fixed combination in one dosage unit form, or a combined administration where a compound of the present invention and a combination partner (e.g. another drug as explained below, also referred to as "therapeutic agent" or "co-agent") may be administered independently at the same time or separately within time intervals, especially where these time intervals allow that the combination partners show a cooperative, e.g. synergistic effect. The single components may be packaged in a kit or separately. One or both of the components (e.g., powders or liquids) may be reconstituted or diluted to a desired dose prior to administration. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "pharmaceutical combination" as used herein means a product that results from the mixing or combining of more than one therapeutic agent and includes both fixed and non-fixed combinations of the therapeutic agents. The term "fixed combination" means that the therapeutic agents, e.g. a compound of the present invention and a combination partner, are both administered to a patient simultaneously in the form of a single entity or dosage. The term "non-fixed combination" means that the therapeutic agents, e.g., a compound of the present invention and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more therapeutic agent.

The term "pharmaceutical combination" as used herein refers to either a fixed combination in one dosage unit form, or non-fixed combination or a kit of parts for the combined administration where two or more therapeutic agents may be administered independently at the same time or separately within time intervals, especially where these time intervals allow that the combination partners show a cooperative, e.g. synergistic effect.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., tablets, capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

Sample Preparation

Samples used in the methods described herein can be obtained from a subject using any of the methods known in the art, e.g., by biopsy or surgery. For example, a sample comprising cerebrospinal fluid can be obtained by lumbar puncture, in which a fine needle attached to a syringe is inserted into the spinal canal in the lumbar area and a vacuum is created such that cerebrospinal fluid may be sucked through the needle and collected in the syringe. CT imaging, ultrasound, or an endoscope can be used to guide this type of procedure. The sample may be flash frozen and stored at −80° C. for later use. The sample may also be fixed with a fixative, such as formaldehyde, paraformaldehyde, or acetic acid/ethanol. RNA or protein may be extracted from a fresh, frozen or fixed sample for analysis.

Pharmaceutical Compositions, Dosage, and Methods of Administration

Also provided herein are compositions, e.g., pharmaceutical compositions, for use in treatment of a TREM2-associated disease. Such compositions include one or more hTREM2 antibodies or an antigen-binding fragment thereof as described herein. Such compositions can further include another agent, e.g., a current standard of care for the disease to be treated.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Pharmaceutical compositions are typically formulated to be compatible with its intended route of administration. Examples of routes of administration include parenteral (e.g., intravenous, intraarterial, intraperitoneal), oral, intracranial, intrathecal, or intranasal (e.g., inhalation), intradermal, subcutaneous, or transmucosal administration. In some embodiments, the pharmaceutical compositions are formulated to deliver hTREM2 antibodies or antigen-binding fragments thereof to cross the blood-brain barrier.

In some embodiments, the pharmaceutical compositions comprise one or more pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

Methods of formulating suitable pharmaceutical compositions are known in the art, see, e.g., Remington: The Science and Practice of Pharmacy. 21$^{st}$ ed., 2005; and the books in the series Drugs and the Pharmaceutical Sciences: a Series of Textbooks and Monographs (Dekker, NY). For example, solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders, for the extemporaneous preparation of sterile injectable solutions or dispersion. For intravenous administration, suitable carriers include physiological saline, bacteriostatic water, Cremophor EL™ (BASF, Parsippany, NJ) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization.

Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Parenteral formulations can be a single bolus dose, an infusion or a loading bolus dose followed with a maintenance dose. These compositions can be administered at specific fixed or variable intervals, e.g., once a day, or on an "as needed" basis.

A suitable pharmaceutical composition for injection can comprise a buffer (e.g., acetate, phosphate or citrate buffer), a surfactant (e.g., polysorbate), optionally a stabilizer agent (e.g., human albumin), etc. Preparations for peripheral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include, e.g., water, alcoholic/aqueous solutions, emulsions or suspensions, including saline and buffered media. In some embodiments, the pharmaceutical composition comprises 0.01-0.1 M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives can also be present such as, for example, antimicrobials, antioxidants, chelating agents, and inert gases and the like.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798. Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one embodiment, the therapeutic compounds are prepared with carriers that will protect the therapeutic compounds against rapid elimination from the body, such as a controlled release formulation, including implants and microencapsulated delivery systems.

The pharmaceutical compositions can be included in a container, pack, or dispenser together with instructions for administration.

In non-limiting examples, the pharmaceutical composition containing at least one pharmaceutical agent is formulated as a liquid (e.g., a thermosetting liquid), as a component of a solid (e.g., a powder or a biodegradable biocompatible polymer (e.g., a cationic biodegradable biocompatible polymer)), or as a component of a gel (e.g., a biodegradable biocompatible polymer). In some embodiments, the at least composition containing at least one pharmaceutical agent is formulated as a gel selected from the group of an alginate gel (e.g., sodium alginate), a cellulose-based gel (e.g., carboxymethyl cellulose or carboxyethyl cellulose), or a chitosan-based gel (e.g., chitosan glycerophosphate). Additional, non-limiting examples of drug-eluting polymers that can be used to formulate any of the pharmaceutical compositions described herein include, carrageenan, carboxymethylcellulose, hydroxypropylcellulose, dextran in combination with polyvinyl alcohol, dextran in combination with polyacrylic acid, polygalacturonic acid, galacturonic polysaccharide, polysalactic acid, polyglycolic acid, tamarind gum, xanthum gum, cellulose gum, guar gum (carboxymethyl guar), pectin, polyacrylic acid, polymethacrylic acid, N-isopropylpolyacrylomide, polyoxyethylene, polyoxypropylene, pluronic acid, polylactic acid, cyclodextrin, cycloamylose, resilin, polybutadiene, N-(2-Hydroxypropyl)methacrylamide (HP MA) copolymer, maleic anhydrate-alkyl vinyl ether, polydepsipeptide, polyhydroxybutyrate, polycaprolactone, polydioxanone, polyethylene glycol, polyorganophosphazene, polyortho ester, polyvinylpyrrolidone, polylactic-co-glycolic acid (PLGA), polyanhydrides, polysilamine, poly N-vinyl caprolactam, and gellan.

An “effective amount” is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Kits

Also provided herein are kits including one or more of the compositions provided herein and instructions for use. Instructions for use can include instructions for diagnosis or treatment of a TREM2-associated disease. Kits as provided herein can be used in accordance with any of the methods described herein. Those skilled in the art will be aware of other suitable uses for kits provided herein, and will be able to employ the kits for such uses. Kits as provided herein can also include a mailer (e.g., a postage paid envelope or mailing pack) that can be used to return the sample for analysis, e.g., to a laboratory. The kit can include one or more containers for the sample, or the sample can be in a standard blood collection vial. The kit can also include one or more of an informed consent form, a test requisition form, and instructions on how to use the kit in a method described herein. Methods for using such kits are also included herein. One or more of the forms (e.g., the test requisition form) and the container holding the sample can be coded, for example, with a bar code for identifying the subject who provided the sample.

One skilled in the art will recognize many methods and materials similar or equivalent to those described herein, which could be used in the practice of the present invention. Indeed, the present invention is in no way limited to the methods and materials described.

Embodiments

1. An antibody or an antigen-binding fragment thereof that binds to the immunoglobulin superfamily (IgSF) domain of human triggering expression on myeloid cells 2 (hTREM2) protein and stabilizes the hTREM2 protein (e.g. SEQ ID NO:1, 2 or 3).
2. The antibody or antigen-binding fragment thereof of embodiment 1, wherein the antibody or antigen-binding fragment thereof binds one or more residues selected from a group consisting of D39, 540, M41, K42, W44, G45, R46, R47, H67, N68, L69, W70, L71, L72, F74, L75, R77, D87, T88, L89 and G90 of hTREM2.
3. The antibody or antigen-binding fragment thereof of embodiment 1, wherein the antibody or antigen-binding fragment thereof binds one or more residues selected from a group consisting of D39, 540, M41, K42, W44, G45, R46 and R47, one or more residues selected from a group consisting of H67, N68, L69, W70, L71, L72, F74, L75 and R77, and one or more residues selected from a group consisting of D87, T88, L89 and G90 of hTREM2.
4. The antibody or antigen-binding fragment thereof of embodiment 1, wherein the antibody or antigen-binding fragment thereof binds five or more residues selected from a group consisting of D39, 540, M41, K42, W44, G45, R46 and R47, four or more residues selected from a group consisting of H67, N68, L69, W70, L71, L72, F74, L75 and R77, and three or more residues selected from a group consisting of D87, T88, L89 and G90 of hTREM2.
5. The antibody or antigen-binding fragment thereof of embodiment 1, wherein the antibody or antigen-binding fragment thereof binds seven or more residues selected from a group consisting of D39, 540, M41, K42, W44, G45, R46 and R47, four or more residues selected from a group consisting of H67, N68, L69, W70, L71, L72, F74, L75 and R77, and three or more residues selected from a group consisting of D87, T88, L89 and G90 of hTREM2.

6. The antibody or antigen-binding fragment thereof of embodiment 1, wherein the antibody or antigen-binding fragment thereof binds five or more residues selected from a group consisting of D39, S40, M41, K42, W44, G45, R46 and R47, all residues H67, N68, L69, W70, L71, L72, F74, L75 and R77, and three or more residues selected from a group consisting of D87, T88, L89 and G90 of hTREM2.
7. The antibody or antigen-binding fragment thereof of embodiment 1, wherein the antibody or antigen-binding fragment thereof binds one or more residues selected from a group consisting of S40, M41, W44, G45, W70, L71, L72, F74, T88 and L89 of hTREM2.
8. The antibody or antigen-binding fragment thereof of embodiment 1, wherein the antibody or antigen-binding fragment thereof binds two or more residues selected from a group consisting of S40, M41, W44, G45, W70, L71, L72, F74, T88 and L89 of hTREM2.
9. The antibody or antigen-binding fragment thereof of embodiment 1, wherein the antibody or antigen-binding fragment thereof binds three or more residues selected from a group consisting of S40, M41, W44, G45, W70, L71, L72, F74, T88 and L89 of hTREM2.
10. The antibody or antigen-binding fragment thereof of embodiment 1, wherein the antibody or antigen-binding fragment thereof binds four or more residues selected from a group consisting of S40, M41, W44, G45, W70, L71, L72, F74, T88 and L89 of hTREM2.
11. The antibody or antigen-binding fragment thereof of embodiment 1, wherein the antibody or antigen-binding fragment thereof binds five or more residues selected from a group consisting of S40, M41, W44, G45, W70, L71, L72, F74, T88 and L89 of hTREM2.
12. The antibody or antigen-binding fragment thereof of embodiment 1, wherein the antibody or antigen-binding fragment thereof binds six or more residues selected from a group consisting of S40, M41, W44, G45, W70, L71, L72, F74, T88 and L89 of hTREM2.
13. The antibody or antigen-binding fragment thereof of embodiment 1, wherein the antibody or antigen-binding fragment thereof binds seven or more residues selected from a group consisting of S40, M41, W44, G45, W70, L71, L72, F74, T88 and L89 of hTREM2.
14. The antibody or antigen-binding fragment thereof of embodiment 1, wherein the antibody or antigen-binding fragment thereof binds eight or more residues selected from a group consisting of S40, M41, W44, G45, W70, L71, L72, F74, T88 and L89 of hTREM2.
15. The antibody or antigen-binding fragment thereof of embodiment 1, wherein the antibody or antigen-binding fragment thereof binds nine or more residues selected from a group consisting of S40, M41, W44, G45, W70, L71, L72, F74, T88 and L89 of hTREM2.
16. The antibody or antigen-binding fragment thereof of embodiment 1, wherein the antibody or antigen-binding fragment thereof binds all the residues S40, M41, W44, G45, W70, L71, L72, F74, T88 and L89 of hTREM2.
17. The antibody or antigen-binding fragment thereof of any one of embodiments 7 to 16, wherein the antibody or antigen-binding fragment thereof binds one or more residues selected from a group consisting of D39, K42, R46 and G90 of hTREM2.
18. The antibody or antigen-binding fragment thereof of any one of embodiments 7 to 16, wherein the antibody or antigen-binding fragment thereof binds two or more residues selected from a group consisting of D39, K42, R46 and G90 of hTREM2.
19. The antibody or antigen-binding fragment thereof of any one of embodiments 7 to 16, wherein the antibody or antigen-binding fragment thereof binds three or more residues selected from a group consisting of D39, K42, R46 and G90 of hTREM2.
20. The antibody or antigen-binding fragment thereof of any one of embodiments 7 to 15, wherein the antibody or antigen-binding fragment thereof binds all the residues D39, K42, R46 and G90 of hTREM2.
21. The antibody or antigen-binding fragment thereof of embodiment 1, wherein the antibody or antigen-binding fragment thereof binds all the residues S40, M41, W44, G45, W70, L71, L72, F74, T88, L89, D39, K42, R46 and G90 of hTREM2.
22. The antibody or antigen-binding fragment thereof of any one of embodiments 7 to 16, wherein the antibody or antigen-binding fragment thereof binds one or more residues selected from a group consisting of R47, H67, N68, L69, L75, R77 and D87 of hTREM2.
23. The antibody or antigen-binding fragment thereof of any one of embodiments 7 to 16, wherein the antibody or antigen-binding fragment thereof binds two or more residues selected from a group consisting of R47, H67, N68, L69, L75, R77 and D87 of hTREM2.
24. The antibody or antigen-binding fragment thereof of any one of embodiments 7 to 16, wherein the antibody or antigen-binding fragment thereof binds three or more residues selected from a group consisting of R47, H67, N68, L69, L75, R77 and D87 of hTREM2.
25. The antibody or antigen-binding fragment thereof of any one of embodiments 7 to 16, wherein the antibody or antigen-binding fragment thereof binds four or more residues selected from a group consisting of R47, H67, N68, L69, L75, R77 and D87 of hTREM2.
26. The antibody or antigen-binding fragment thereof of any one of embodiments 7 to 16, wherein the antibody or antigen-binding fragment thereof binds five or more residues selected from a group consisting of R47, H67, N68, L69, L75, R77 and D87 of hTREM2.
27. The antibody or antigen-binding fragment thereof of any one of embodiments 7 to 15, wherein the antibody or antigen-binding fragment thereof binds six or more residues selected from a group consisting of R47, H67, N68, L69, L75, R77 and D87 of hTREM2.
28. The antibody or antigen-binding fragment thereof of embodiment 1, wherein the antibody or antigen-binding fragment thereof binds all the residues S40, M41, W44, G45, W70, L71, L72, F74, T88, L89, R47, H67, N68, L69, L75, R77 and D87 of hTREM2.
29. The antibody or antigen-binding fragment thereof of any one of embodiments 1 to 28, wherein the antibody or antigen-binding fragment thereof activates hTREM2.
30. The antibody or antigen-binding fragment thereof of any one of embodiments 1 to 29, wherein the antibody or antigen-binding fragment thereof facilitates one or more hTREM2-dependent physiological activities in a TREM2 expressing cell.
31. The antibody or antigen-binding fragment thereof of any one of embodiments 1 to 30, wherein the antibody or antigen-binding fragment thereof:

a) increases phagocytosis, e.g., in a hTREM2-expressing cell, e.g., wherein the TREM2 expressing cell is a hM2A macrophage or a human iPS-derived microglia-like cell.
b) increases chemotaxis, e.g., in a hTREM2-expressing cell, e.g., wherein the TREM2 expressing cell is a hM2a macrophage or a human iPS-derived microglia-like cell.
c) increases NFAT-driven reporter gene activity in a human monocytic cell line,
d) increases Syk phosphorylation, e.g., in a hTREM2-expressing cell, e.g., wherein the TREM2 expressing cell is a hM2A macrophage, or
e) increases any combination of two or more of a) to d).

32. The antibody or antigen-binding fragment thereof of any one of embodiments 1 to 31, wherein the antibody or antigen-binding fragment thereof binds hTREM2 e.g., on a cell surface, with a half maximal effective concentration ($EC_{50}$) of 1 nM or less, e.g., as measured by FACS analysis on hM2a macrophages.
33. The antibody or antigen-binding fragment thereof of any one of embodiments 1 to 32, wherein the antibody or antigen-binding fragment thereof binds hTREM2, e.g., on a cell surface, with a half maximal effective concentration ($EC_{50}$) of 0.59 nM or less, e.g., as measured by FACS analysis on hM2a macrophages.
34. The antibody or antigen-binding fragment thereof of any one of embodiments 1 to 33, wherein the antibody or antigen-binding fragment thereof binds hTREM2 with a dissociation constant ($K_D$) of 150 pM or less, e.g., as measured by surface plasmon resonance (SPR).
35. The antibody or antigen-binding fragment thereof of any one of embodiments 1 to 34, wherein the antibody or antigen-binding fragment thereof binds hTREM2 with a dissociation constant ($K_D$) of 50 pM or less, e.g., as measured by surface plasmon resonance (SPR).
36. The antibody or antigen-binding fragment thereof of any one of embodiments 1 to 35, wherein the antibody or antigen-binding fragment thereof stabilizes hTREM2 protein on a cell surface of a hTREM2-expressing cell.
37. The antibody or antigen-binding fragment thereof of embodiment 36, wherein the hTREM2-expressing cell is a macrophage, e.g., an M2a macrophage, a dendritic cell, an osteoclast, a microglia, a mast cell, a monocyte, a lung epithelial cell, a Langerhans cell of skin, a Kupffer cell, a neutrophil or a hepatocarcinoma cell.
38. The antibody or antigen-binding fragment thereof of any one of embodiments 1 to 37, wherein the antibody or antigen-binding fragment thereof reduces shedding of the ectodomain of hTREM2 protein at a concentration of 100 nM or lower in hM2A macrophages.
39. The antibody or antigen-binding fragment thereof of any one of embodiments 1 to 38, wherein TREM2 cell surface expression is increased 3 fold or higher.
40. The antibody or antigen-binding fragment thereof of any one of embodiments 1 to 39, wherein the IgSF domain of hTREM2 comprises amino acid residues 19 to 132 of any one of SEQ ID NOs 1, 2, and 3.
41. The antibody or antigen-binding fragment thereof of any one of embodiments 1 to 40, wherein said antibody or antigen-binding fragment thereof comprises:
  a) a heavy chain variable region CDR1 comprising, e.g., consisting of, SEQ ID NO: 41 or SEQ ID NO: 44 or SEQ ID NO: 45 or SEQ ID NO: 47; a heavy chain variable region CDR2 comprising, e.g., consisting of, SEQ ID NO: 42 or SEQ ID NO: 46, or SEQ ID NO: 48; a heavy chain variable region CDR3 comprising, e.g., consisting of, SEQ ID NO: 43 or SEQ ID NO: 49; a light chain variable region CDR1 comprising, e.g., consisting of, SEQ ID NO: 54 or SEQ ID NO: 57 or SEQ ID NO: 60; a light chain variable region CDR2 comprising, e.g., consisting of, SEQ ID NO: 55 or SEQ ID NO: 58; and a light chain variable region CDR3 comprising, e.g., consisting of, SEQ ID NO: 56 or SEQ ID NOs: 59;
  b) a heavy chain variable region CDR1 comprising, e.g., consisting of, SEQ ID NO: 4 or SEQ ID NO: 7 or SEQ ID NO: 8 or SEQ ID NO: 10; a heavy chain variable region CDR2 comprising, e.g., consisting of, SEQ ID NO: 5 or SEQ ID NO: 9 or SEQ ID NO: 11; a heavy chain variable region CDR3 comprising, e.g., consisting of, SEQ ID NO: 6 or SEQ ID NO: 12; a light chain variable region CDR1 comprising, e.g., consisting of, SEQ ID NO: 17 or SEQ ID NO: 20 or SEQ ID NO: 23; a light chain variable region CDR2 comprising, e.g., consisting of, SEQ ID NO: 18 or SEQ ID NO: 21; and a light chain variable region CDR3 comprising, e.g., consisting of, SEQ ID NO: 19 or SEQ ID NO: 22;
  c) a heavy chain variable region CDR1 comprising, e.g., consisting of, SEQ ID NO: 4 or SEQ ID NO: 7 or SEQ ID NO: 8 or SEQ ID NO: 10; a heavy chain variable region CDR2 comprising, e.g., consisting of, SEQ ID NO: 5 or SEQ ID NO: 9 or SEQ ID NO: 11; a heavy chain variable region CDR3 comprising, e.g., consisting of, SEQ ID NO: 6 or SEQ ID NO: 12; a light chain variable region CDR1 comprising, e.g., consisting of, SEQ ID NO: 17 or SEQ ID NO: 20 or SEQ ID NO: 23; a light chain variable region CDR2 comprising, e.g., consisting of, SEQ ID NO: 18 or SEQ ID NO: 21; and a light chain variable region CDR3 comprising, e.g., consisting of, SEQ ID NO: 78 or SEQ ID NO: 79; or
  d) a heavy chain variable region CDR1 comprising, e.g., consisting of, SEQ ID NO: 84 or SEQ ID NO: 87 or SEQ ID NO: 88 or SEQ ID NO: 90; a heavy chain variable region CDR2 comprising, e.g., consisting of, SEQ ID NO: 85 or SEQ ID NO: 89 or SEQ ID NO: 91; a heavy chain variable region CDR3 comprising, e.g., consisting of, SEQ ID NO: 86 or SEQ ID NO: 92; a light chain variable region CDR1 comprising, e.g., consisting of, SEQ ID NO: 97 or SEQ ID NO: 100 or SEQ ID NO: 103; a light chain variable region CDR2 comprising, e.g., consisting of, SEQ ID NO: 98 or SEQ ID NO: 101; and a light chain variable region CDR3 comprising, e.g., consisting of, SEQ ID NO: 99 or SEQ ID NO: 102.
42. An antibody or antigen-binding fragment thereof that binds to the IgSF domain of hTREM2 protein, wherein said antibody or antigen-binding fragment thereof comprises:
a) a heavy chain variable region CDR1 comprising, e.g., consisting of, SEQ ID NO: 41 or SEQ ID NO: 44 or SEQ ID NO: 45 or SEQ ID NO: 47; a heavy chain variable region CDR2 comprising, e.g., consisting of, SEQ ID NO: 42 or SEQ ID NO: 46, or SEQ ID NO: 48; a heavy chain variable region CDR3 comprising, e.g., consisting of, SEQ ID NO: 43 or SEQ ID NO: 49; a light chain variable region CDR1 comprising, e.g., consisting of, SEQ ID NO: 54 or SEQ ID NO: 57 or SEQ ID NO: 60; a light chain variable region CDR2 comprising, e.g., consisting of, SEQ ID NO: 55 or SEQ ID NO: 58; and a light chain variable region CDR3 comprising, e.g., consisting of, SEQ ID NO: 56 or SEQ ID NOs: 59;

b) a heavy chain variable region CDR1 comprising, e.g., consisting of, SEQ ID NO: 4 or SEQ ID NO: 7 or SEQ ID NO: 8 or SEQ ID NO: 10; a heavy chain variable region CDR2 comprising, e.g., consisting of, SEQ ID NO: 5 or SEQ ID NO: 9 or SEQ ID NO: 11; a heavy chain variable region CDR3 comprising, e.g., consisting of, SEQ ID NO: 6 or SEQ ID NO: 12; a light chain variable region CDR1 comprising, e.g., consisting of, SEQ ID NO: 17 or SEQ ID NO: 20 or SEQ ID NO: 23; a light chain variable region CDR2 comprising, e.g., consisting of, SEQ ID NO: 18 or SEQ ID NO: 21; and a light chain variable region CDR3 comprising, e.g., consisting of, SEQ ID NO: 19 or SEQ ID NO: 22;

c) a heavy chain variable region CDR1 comprising, e.g., consisting of, SEQ ID NO: 4 or SEQ ID NO: 7 or SEQ ID NO: 8 or SEQ ID NO: 10; a heavy chain variable region CDR2 comprising, e.g., consisting of, SEQ ID NO: 5 or SEQ ID NO: 9 or SEQ ID NO: 11; a heavy chain variable region CDR3 comprising, e.g., consisting of, SEQ ID NO: 6 or SEQ ID NO: 12; a light chain variable region CDR1 comprising, e.g., consisting of, SEQ ID NO: 17 or SEQ ID NO: 20 or SEQ ID NO: 23; a light chain variable region CDR2 comprising, e.g., consisting of, SEQ ID NO: 18 or SEQ ID NO: 21; and a light chain variable region CDR3 comprising, e.g., consisting of, SEQ ID NO: 78 or SEQ ID NO: 79; or d) a heavy chain variable region CDR1 comprising, e.g., consisting of, SEQ ID NO: 84 or SEQ ID NO: 87 or SEQ ID NO: 88 or SEQ ID NO: 90; a heavy chain variable region CDR2 comprising, e.g., consisting of, SEQ ID NO: 85 or SEQ ID NO: 89 or SEQ ID NO: 91; a heavy chain variable region CDR3 comprising, e.g., consisting of, SEQ ID NO: 86 or SEQ ID NO: 92; a light chain variable region CDR1 comprising, e.g., consisting of, SEQ ID NO: 97 or SEQ ID NO: 100 or SEQ ID NO: 103; a light chain variable region CDR2 comprising, e.g., consisting of, SEQ ID NO: 98 or SEQ ID NO: 101; and a light chain variable region CDR3 comprising, e.g., consisting of, SEQ ID NO: 99 or SEQ ID NO: 102.

43. The antibody or antigen-binding fragment thereof of any one of embodiments 1 to 42 wherein the antibody or antigen-binding fragment thereof comprises a) a VH polypeptide sequence having at least 95% sequence identity to SEQ ID NO: 13 or to SEQ ID NO: 50, and a VL polypeptide sequence having at least 95% sequence identity to SEQ ID NO: 24 or to SEQ ID NO: 61; or b) a VH polypeptide sequence having at least 95% sequence identity to SEQ ID NO: 13 or to SEQ ID NO: 93, and a VL polypeptide sequence having at least 95% sequence identity to SEQ ID NO: 80 or to SEQ ID NO: 104.

44. The antibody or antigen-binding fragment thereof of any one of embodiments 1 to 43 comprising:

a) a heavy chain variable region CDR1 comprising, e.g., consisting of, SEQ ID NO: 7; a heavy chain variable region CDR2 comprising, e.g., consisting of, SEQ ID NO: 5; a heavy chain variable region CDR3 comprising, e.g., consisting of, SEQ ID NO: 6; a light chain variable region CDR1 comprising, e.g., consisting of, SEQ ID NO: 17; a light chain variable region CDR2 comprising, e.g., consisting of, SEQ ID NO: 18; and a light chain variable region CDR3 comprising, e.g., consisting of, SEQ ID NO: 19;

b) a heavy chain variable region CDR1 comprising, e.g., consisting of, SEQ ID NO: 44; a heavy chain variable region CDR2 comprising, e.g., consisting of, SEQ ID NO: 42; a heavy chain variable region CDR3 comprising, e.g., consisting of, SEQ ID NO: 43; a light chain variable region CDR1 comprising, e.g., consisting of, SEQ ID NO: 54; a light chain variable region CDR2 comprising, e.g., consisting of SEQ ID NO: 55; and a light chain variable region CDR3 comprising, e.g., consisting of, SEQ ID NO: 56;

c) a heavy chain variable region CDR1 comprising, e.g., consisting of, SEQ ID NO: 7; a heavy chain variable region CDR2 comprising, e.g., consisting of, SEQ ID NO: 5; a heavy chain variable region CDR3 comprising, e.g., consisting of, SEQ ID NO: 6; a light chain variable region CDR1 comprising, e.g., consisting of, SEQ ID NO: 17; a light chain variable region CDR2 comprising, e.g., consisting of, SEQ ID NO: 18; and a light chain variable region CDR3 comprising, e.g., consisting of, SEQ ID NO: 78; or d) a heavy chain variable region CDR1 comprising, e.g., consisting of, SEQ ID NO: 87; a heavy chain variable region CDR2 comprising, e.g., consisting of, SEQ ID NO: 85; a heavy chain variable region CDR3 comprising, e.g., consisting of, SEQ ID NO: 86; a light chain variable region CDR1 comprising, e.g., consisting of, SEQ ID NO: 97; a light chain variable region CDR2 comprising, e.g., consisting of, SEQ ID NO: 98; and a light chain variable region CDR3 comprising, e.g., consisting of, SEQ ID NO: 99.

45. The antibody or antigen-binding fragment thereof of any one of embodiments 1 to 43 comprising:

a) a heavy chain variable region CDR1 of SEQ ID NO: 8; a heavy chain variable region CDR2 comprising, e.g., consisting of, SEQ ID NO: 9; a heavy chain variable region CDR3 comprising, e.g., consisting of, SEQ ID NO: 6; a light chain variable region CDR1 comprising, e.g., consisting of, SEQ ID NO: 20; a light chain variable region CDR2 comprising, e.g., consisting of, SEQ ID NO: 21; and alight chain variable region CDR3 comprising, e.g., consisting of, SEQ ID NO: 22;

b) a heavy chain variable region CDR1 comprising, e.g., consisting of, SEQ ID NO: 45; a heavy chain variable region CDR2 comprising, e.g., consisting of, SEQ ID NO: 46; a heavy chain variable region CDR3 comprising, e.g., consisting of, SEQ ID NO: 43; a light chain variable region CDR1 comprising, e.g., consisting of, SEQ ID NO: 57; a light chain variable region CDR2 comprising, e.g., consisting of, SEQ ID NO: 58; and a light chain variable region CDR3 comprising, e.g., consisting of, SEQ ID NO: 59;

c) a heavy chain variable region CDR1 comprising, e.g., consisting of, SEQ ID NO: 8; a heavy chain variable region CDR2 comprising, e.g., consisting of, SEQ ID NO: 9; a heavy chain variable region CDR3 comprising, e.g., consisting of, SEQ ID NO: 6; a light chain variable region CDR1 comprising, e.g., consisting of, SEQ ID NO: 20; a light chain variable region CDR2 comprising, e.g., consisting of, SEQ ID NO: 21; and a light chain variable region CDR3 comprising, e.g., consisting of, SEQ ID NO: 79; or d) a heavy chain variable region CDR1 comprising, e.g., consisting of, SEQ ID NO: 88; a heavy chain variable region CDR2 comprising, e.g., consisting of, SEQ ID NO: 89; a heavy chain variable region CDR3 comprising, e.g., consisting of, SEQ ID NO: 86; a light chain variable region CDR1 comprising, e.g., consisting of, SEQ ID NO: 100; a light chain variable region CDR2 comprising, e.g., consisting of, SEQ ID NO: 101; and a light chain variable region CDR3 comprising, e.g., consisting of, SEQ ID NO: 102.

46. The antibody or antigen-binding fragment thereof of any one of embodiments 1 to 43 comprising:

a) a heavy chain variable region CDR1 comprising, e.g., consisting of, SEQ ID NO: 10; a heavy chain variable region CDR2 comprising, e.g., consisting of, SEQ ID NO: 11; a heavy chain variable region CDR3 comprising, e.g., consisting of, SEQ ID NO: 12; a light chain variable region CDR1 comprising, e.g., consisting of, SEQ ID NO: 23; a light chain variable region CDR2 comprising, e.g., consisting of, SEQ ID NO: 21; and a light chain variable region CDR3 comprising, e.g., consisting of, SEQ ID NO: 19;

b) a heavy chain variable region CDR1 comprising, e.g., consisting of, SEQ ID NO: 47; a heavy chain variable region CDR2 comprising, e.g., consisting of, SEQ ID NO: 48; a heavy chain variable region CDR3 comprising, e.g., consisting of, SEQ ID NO: 49; a light chain variable region CDR1 comprising, e.g., consisting of, SEQ ID NO: 60; a light chain variable region CDR2 comprising, e.g., consisting of, SEQ ID NO: 58; and a light chain variable region CDR3 comprising, e.g., consisting of, SEQ ID NO: 56;

c) a heavy chain variable region CDR1 comprising, e.g., consisting of, SEQ ID NO: 10; a heavy chain variable region CDR2 comprising, e.g., consisting of, SEQ ID NO: 11; a heavy chain variable region CDR3 comprising, e.g., consisting of, SEQ ID NO: 12; a light chain variable region CDR1 comprising, e.g., consisting of, SEQ ID NO: 23; a light chain variable region CDR2 comprising, e.g., consisting of, SEQ ID NO: 21; and a light chain variable region CDR3 comprising, e.g., consisting of, SEQ ID NO: 78; or d) a heavy chain variable region CDR1 comprising, e.g., consisting of, SEQ ID NO: 90; a heavy chain variable region CDR2 comprising, e.g., consisting of, SEQ ID NO: 91; a heavy chain variable region CDR3 comprising, e.g., consisting of, SEQ ID NO: 92; a light chain variable region CDR1 comprising, e.g., consisting of, SEQ ID NO: 103; a light chain variable region CDR2 comprising, e.g., consisting of, SEQ ID NO: 101; and a light chain variable region CDR3 comprising, e.g., consisting of, SEQ ID NO: 99.

47. The antibody or antigen-binding fragment thereof of any one of embodiments 1 to 43 comprising:

a) a heavy chain variable region CDR1 comprising, e.g., consisting of, SEQ ID NO: 4; a heavy chain variable region CDR2 comprising, e.g., consisting of, SEQ ID NO: 5; a heavy chain variable region CDR3 comprising, e.g., consisting of, SEQ ID NO: 6; a light chain variable region CDR1 comprising, e.g., consisting of, SEQ ID NO: 17; a light chain variable region CDR2 comprising, e.g., consisting of, SEQ ID NO: 18; and a light chain variable region CDR3 comprising, e.g., consisting of, SEQ ID NO: 19;

b) a heavy chain variable region CDR1 comprising, e.g., consisting of, SEQ ID NO: 41; a heavy chain variable region CDR2 comprising, e.g., consisting of, SEQ ID NO: 42; a heavy chain variable region CDR3 comprising, e.g., consisting of, SEQ ID NO: 43; a light chain variable region CDR1 comprising, e.g., consisting of, SEQ ID NO: 54; a light chain variable region CDR2 comprising, e.g., consisting of, SEQ ID NO: 55; and a light chain variable region CDR3 comprising, e.g., consisting of, SEQ ID NO: 56;

c) a heavy chain variable region CDR1 comprising, e.g., consisting of, SEQ ID NO: 4; a heavy chain variable region CDR2 comprising, e.g., consisting of, SEQ ID NO: 5; a heavy chain variable region CDR3 comprising, e.g., consisting of, SEQ ID NO: 6; a light chain variable region CDR1 comprising, e.g., consisting of, SEQ ID NO: 17; a light chain variable region CDR2 comprising, e.g., consisting of, SEQ ID NO: 18; and a light chain variable region CDR3 comprising, e.g., consisting of, SEQ ID NO: 78; or d) a heavy chain variable region CDR1 comprising, e.g., consisting of, SEQ ID NO: 84; a heavy chain variable region CDR2 comprising, e.g., consisting of, SEQ ID NO: 85; a heavy chain variable region CDR3 comprising, e.g., consisting of, SEQ ID NO: 86; a light chain variable region CDR1 comprising, e.g., consisting of, SEQ ID NO: 97; a light chain variable region CDR2 comprising, e.g., consisting of, SEQ ID NO: 98; and a light chain variable region CDR3 comprising, e.g., consisting of, SEQ ID NO: 99.

48. The antibody or antigen-binding fragment thereof of any one of embodiments 1-47, wherein the antibody or antigen-binding fragment thereof comprises:

a) a VH comprising, e.g., consisting of, SEQ ID NO: 13 and a VL comprising, e.g., consisting of, SEQ ID NO: 24; or b) a VH comprising, e.g., consisting of, SEQ ID NO: 50 and a VL comprising, e.g., consisting of, SEQ ID NO: 61; or c) a VH comprising, e.g., consisting of, a sequence having at least 95% homology to SEQ ID NO: 13 and a VL comprising, e.g., consisting of, a sequence having at least 95% homology to SEQ ID NO: 24; or d) a VH comprising, e.g., consisting of, a sequence having at least 95% homology to SEQ ID NO: 50 and a VL comprising, e.g., consisting of, a sequence having at least 95% homology to SEQ ID NO: 61; or e) a VH comprising, e.g. consisting of, a sequence that differs by at least 1, 2, 3, 4, 5, or 6 amino acids from SEQ ID NO: 13 and a VL comprising, e.g. consisting of, a sequence that differs by at least 1, 2, 3, 4, 5, or 6 amino acids from SEQ ID NO: 24; or f) a VH comprising, e.g. consisting of, a sequence that differs by at least 1, 2, 3, 4, 5, or 6 amino acids from SEQ ID NO: 50 and a VL comprising, e.g. consisting of, a sequence that differs by at least 1, 2, 3, 4, 5, or 6 amino acids from SEQ ID NO: 61.

g) a VH comprising, e.g., consisting of, SEQ ID NO: 13 and a VL comprising, e.g., consisting of, SEQ ID NO: 80; or h) a VH comprising, e.g., consisting of, SEQ ID NO: 93 and a VL comprising, e.g., consisting of, SEQ ID NO: 104; or i) a VH comprising, e.g., consisting of, a sequence having at least 95% homology to SEQ ID NO: 13 and a VL comprising, e.g., consisting of, a sequence having at least 95% homology to SEQ ID NO: 80; or j) a VH comprising, e.g., consisting of, a sequence having at least 95% homology to SEQ ID NO: 93 and a VL comprising, e.g., consisting of, a sequence having at least 95% homology to SEQ ID NO: 104; or k) a VH comprising, e.g. consisting of, a sequence that differs by at least 1, 2, 3, 4, 5, or 6 amino acids from SEQ ID NO: 13 and a VL comprising, e.g. consisting of, a sequence that differs by at least 1, 2, 3, 4, 5, or 6 amino acids from SEQ ID NO: 80; or l) a VH comprising, e.g. consisting of, a sequence that differs by at least 1, 2, 3, 4, 5, or 6 amino acids from SEQ ID NO: 93 and a VL comprising, e.g. consisting of, a sequence that differs by at least 1, 2, 3, 4, 5, or 6 amino acids from SEQ ID NO: 104.

49. The antibody or antigen-binding fragment thereof of any one of embodiments 1-48, wherein the antibody or antigen-binding fragment thereof comprises:

a) a heavy chain amino acid sequence comprising, e.g., consisting of, SEQ ID NO: 15, SEQ ID NO: 29, SEQ ID NO: 33, SEQ ID NO: 35, SEQ ID NO: 37, or SEQ ID NO: 39, and a light chain amino acid sequence comprising, e.g., consisting of, SEQ ID NO: 26;

b) a heavy chain amino acid sequence comprising, e.g., consisting of, SEQ ID NO: 52, SEQ ID NO: 66, SEQ ID NO: 70, SEQ ID NO: 72, SEQ ID NO: 74, or SEQ ID NO: 76, and a light chain amino acid sequence comprising, e.g., consisting of, SEQ ID NO: 63;

c) a heavy chain amino acid sequence having at least 95% sequence identity to SEQ ID NO: 15, SEQ ID NO: 29, SEQ ID NO: 33, SEQ ID NO: 35, SEQ ID NO: 37, or SEQ ID NO: 39, and a light chain amino acid sequence having at least 95% sequence identity to SEQ ID NO: 26;

d) a heavy chain amino acid sequence having at least 95% sequence identity to SEQ ID NO: 52, SEQ ID NO: 66, SEQ ID NO: 70, SEQ ID NO: 72, SEQ ID NO: 74, or SEQ ID NO: 76, and a light chain amino acid sequence having at least 95% sequence identity to SEQ ID NO: 63;

e) a heavy chain amino acid sequence comprising, e.g., consisting of, SEQ ID NO: 15, and a light chain amino acid sequence comprising, e.g., consisting of, SEQ ID NO: 82;

f) a heavy chain amino acid sequence comprising, e.g., consisting of, SEQ ID NO: 95, and a light chain amino acid sequence comprising, e.g., consisting of, SEQ ID NO: 106;

g) a heavy chain amino acid sequence having at least 95% sequence identity to SEQ ID NO: 15, and a light chain amino acid sequence having at least 95% sequence identity to SEQ ID NO: 82; or h) a heavy chain amino acid sequence having at least 95% sequence identity to SEQ ID NO: 95, and a light chain amino acid sequence having at least 95% sequence identity to SEQ ID NO: 106.

50. An antibody or antigen-binding fragment thereof that binds to the immunoglobulin superfamily (IgSF) domain of human triggering expression on myeloid cells 2 (hTREM2) comprising:

a) a heavy chain sequence comprising, e.g., consisting of, SEQ ID NO: 15 and a light chain sequence comprising, e.g., consisting of, SEQ ID NO: 26;

b) a heavy chain sequence comprising, e.g., consisting of, SEQ ID NO: 29 and a light chain sequence comprising, e.g., consisting of, SEQ ID NO: 26;

c) a heavy chain sequence comprising, e.g., consisting of, SEQ ID NO: 33 and a light chain sequence comprising, e.g., consisting of, SEQ ID NO: 26;

d) a heavy chain sequence comprising, e.g., consisting of, SEQ ID NO: 35 and a light chain sequence comprising, e.g., consisting of, SEQ ID NO: 26;

e) a heavy chain sequence comprising, e.g., consisting of, SEQ ID NO: 37 and a light chain sequence comprising, e.g., consisting of, SEQ ID NO: 26;

f) a heavy chain sequence comprising, e.g., consisting of, SEQ ID NO: 39 and a light chain sequence comprising, e.g., consisting of, SEQ ID NO: 26;

g) a heavy chain sequence comprising, e.g., consisting of, SEQ ID NO: 52 and a light chain sequence comprising, e.g., consisting of, SEQ ID NO: 63;

h) a heavy chain sequence comprising, e.g., consisting of, SEQ ID NO: 66 and light chain sequence comprising, e.g., consisting of, SEQ ID NO: 63;

i) a heavy chain sequence comprising, e.g., consisting of, SEQ ID NO: 70 and light chain sequence comprising, e.g., consisting of, SEQ ID NO: 63;

j) a heavy chain sequence comprising, e.g., consisting of, SEQ ID NO: 72 and light chain sequence comprising, e.g., consisting of, SEQ ID NO: 63;

k) a heavy chain sequence comprising, e.g., consisting of, SEQ ID NO: 74 and light chain sequence comprising, e.g., consisting of, SEQ ID NO: 63;

l) a heavy chain sequence comprising, e.g., consisting of, SEQ ID NO: 76 and light chain sequence comprising, e.g., consisting of, SEQ ID NO: 63;

m) a heavy chain sequence comprising, e.g., consisting of, SEQ ID NO: 15 and light chain sequence comprising, e.g., consisting of, SEQ ID NO: 82; or n) a heavy chain sequence comprising, e.g., consisting of, SEQ ID NO: 95 and light chain sequence comprising, e.g., consisting of, SEQ ID NO: 106.

51. An antibody or an antigen-binding fragment thereof that competes with any antibody or antigen-binding fragment thereof of any one of embodiments 1-50 for binding to hTREM2 protein.

52. An antibody or an antigen-binding fragment thereof that binds to an epitope that overlaps with the epitope of any antibody or antigen-binding fragment thereof of any one of embodiments 1-51.

53. The antibody or antigen-binding fragment thereof of any one of embodiments 1-52, wherein the antibody has an IgG1, IgG2, IgG3 or IgG4 isotype.

54. The antibody or antigen-binding fragment thereof of any one of embodiments 1-52, wherein the antibody or antigen binding fragment thereof comprises an Fc region selected from an IgG1 Fc region, an IgG2 Fc region, an IgG4 Fc region, or an IgG2/IgG4 hybrid Fc region.

55. The antibody or antigen-binding fragment thereof of any one of embodiments 1-49, or 51-54, wherein the antibody or antigen-binding fragment thereof comprises a modified Fc region that has reduced antibody-dependent cellular cytotoxicity (ADCC) or complement-dependent cytotoxicity (CDC) activity compared to the parental antibody.

56. The antibody or antigen-binding fragment thereof of any one of embodiments 1-55, wherein the antibody or antigen-binding fragment thereof is a human or humanized antibody or fragment thereof.
57. The antibody or antigen-binding fragment thereof of any one of embodiments 1-56, wherein the antibody or antigen-binding fragment thereof is conjugated to a further moiety.
58. The antibody according to any one of embodiments 1-57, wherein said antibody is of the IgG1 isotype.
59. The antibody according to any one of embodiments 1-56, wherein said antibody is a human or humanized antibody.
60. The antigen-binding fragment of the antibody according to any one of embodiments 1-57, wherein the antigen-binding fragment is selected from a Fab, F(ab') 2, Fv fragments, scFv, minibody, or diabody.
61. The antibody or antigen-binding fragment thereof of any of embodiments 1-60, wherein said antibody or antigen-binding fragment thereof is monoclonal.
62. The antibody of any one of embodiments 1-61, wherein the antibody is a multispecific antibody, e.g., a bispecific antibody.
63. The antibody of embodiment 62, wherein the multispecific antibody, e.g., the bispecific antibody, specifically binds to hTREM2 and human DAP12 (DNAX-activating protein of 12 kDa).
64. The antibody according to any one of embodiments 1-63, wherein said antibody has altered effector function through mutation of the Fc region.
65. A nucleic acid molecule or set of nucleic acid molecules encoding any one of the antibodies or antigen-binding fragment thereof according to any one of embodiments 1 to 64.
66. The nucleic acid molecule according to embodiment 65, wherein the nucleic acid is DNA.
67. The nucleic acid molecule or set of nucleic acid molecules according to embodiment 65 or 66, comprising one or more of SEQ ID NOs: 14, 28, 51, 65, 16, 30, 34, 36, 38, 40, 53, 67, 71, 73, 75, 77, 25, 31, 62, 68, 27, 32, 64, 69, 13, 93, 15, 95, 80, 104, 82 or 106.
68. A vector comprising the nucleic acid molecules according to any one of embodiments 65-67.
69. The vector of embodiment 68, wherein the vector is a cloning vector or an expression vector.
70. A vector according to embodiment 68 or 69, wherein said vector comprises one or more of SEQ ID NOs: 14, 28, 51, 65, 16, 30, 34, 36, 38, 40, 53, 67, 71, 73, 75, 77, 25, 31, 62, 68, 27, 32, 64, 69, 13, 93, 15, 95, 80, 104, 82 or 106, or a fragment thereof encoding at least one CDR region.
71. A vector according to any one of embodiments 68-70, wherein the vector is able to replicate in a prokaryotic and/or a eukaryotic cell.
72. A vector according to any one of embodiments 68-71, wherein the vector is selected from a DNA vector, a RNA vector, a plasmid, a cosmid, or a viral vector.
73. A vector according to any one of embodiments 68-72 further comprising a detectable and/or selectable marker.
74. A set of two expression vectors according to any one of embodiments 68-73, one vector encoding a) at least one VH domain comprising SEQ ID NO: 13 or 50, and the other vector encoding at least one VL domain comprising SEQ ID NO: 24 or 61; or
    b) at least one VH domain comprising SEQ ID NO: 13 or 93, and the other vector encoding at least one VL domain comprising SEQ ID NO: 80 or 104.
75. A vector according to any one of embodiments 68-74, wherein the vector is a viral vector, optionally wherein the viral vectors is a lentivirus, an adenovirus, an adeno-associated virus (AAV), a Herpes Simplex Virus (HSV), a parvovirus, a retrovirus, a vaccinia virus, a Sinbis virus, an influenza virus, a reovirus, a Newcastle disease virus (NDV), a measles virus, a vesicular stomatitis virus (VSV), a poliovirus, a poxvirus, a Seneca Valley virus, a coxsackievirus, an enterovirus, a myxoma virus, or a maraba virus.
76. A vector according to embodiment 75, wherein the vector is an AAV vector.
77. A vector according to any one of embodiments 68-76, wherein the vector further comprises a promoter.
78. A vector according to any one of embodiments 68-77, wherein the vector comprises an AAV9 capsid and an AAV vector plasmid comprising (1) ITRs derived from AAV2, (2) A CMV enhancer (e.g., comprising SEQ ID NO: 134), (3) a CBA promoter (e.g., comprising SEQ ID NO: 135), (4) an SV40 intron (e.g., comprising SEQ ID NO: 137), (5) a polynucleotide encoding a hTREM2 antibody or antigen-binding fragment thereof (e.g., as described herein), and (6) a BGH poly A signal (e.g., comprising SEQ ID NO: 138).
79. The vector of embodiment 78, wherein elements (2) to (6) are disposed on the AAV vector plasmid from 5' to 3'.
80. The vector of embodiment 78 or 79, wherein any of the elements (2) to (6) are disposed on the AAV vector plasmid between the 5' ITR and the 3' ITR.
81. The vector of any one embodiments 78-80, wherein the AAV vector is a scAAV vector.
82. A vector according to any one of embodiments 68-75, wherein the vector is a lentiviral vector.
83. A cell comprising the nucleic acid molecule or set of nucleic acid molecules according to any one of embodiments 64-66 or the vector of any one of embodiments 68-82.
84. A method of producing a hTREM2 antibody or antigen-binding fragment thereof, the method comprising: (i) culturing the cell of embodiment 83 and (ii) isolating the hTREM2 antibody or antigen-binding fragment thereof from the culture.
85. A pharmaceutical composition comprising the antibody or antigen-binding fragment thereof of any one of embodiments 1-64, the nucleic acid molecule or set of nucleic acid molecules of any one of embodiments 65-67, the vector of any one of embodiments 68-82, or the cell of embodiment 83, and a pharmaceutically acceptable carrier.
86. The antibody or antigen-binding fragment thereof of any one of embodiments 1-64, the nucleic acid molecule or set of nucleic acid molecules of any one of embodiments 65-67, the vector of any one of embodiments 68-82, the cell of embodiment 83, or the pharmaceutical composition of embodiment 85, for use as a medicament.
87. The antibody or antigen-binding fragment thereof of any one of embodiments 1-64, the nucleic acid molecule or set of nucleic acid molecules of any one of embodiments 65-67, the vector of any one of embodiments 68-82, the cell of embodiment 83, or the pharmaceutical composition of embodiment 85, for use in the treatment of a disease associated with hTREM2 loss of function.

88. Use of the antibody or antigen-binding fragment thereof of any one of embodiments 1-64, the nucleic acid molecule or set of nucleic acid molecules of any one of embodiments 65-67, the vector of any one of embodiments 68-82, the cell of embodiment 83, or the pharmaceutical composition of embodiment 85, for the manufacture of a medicament for treatment of a disease associated with hTREM2 loss of function.

89. The antibody or antigen-binding fragment thereof, the nucleic acid molecule or set of nucleic acid molecules, the vector, the cell, or the pharmaceutical composition of embodiment 87, or the use according to embodiment 88, wherein the disease is a neuroinflammatory or neurodegenerative disease, optionally wherein the neuroinflammatory or neurodegenerative disease is Alzheimer's disease, frontotemporal dementia, Parkinson's disease, amyotrophic lateral sclerosis, Nasu-Hakola disease, multiple sclerosis, amyotrophic lateral sclerosis (ALS), anti-NMDA receptor encephalitis, autism, brain lupus (NP-SLE), chemo-induced peripheral neuropathy (CIPN), postherapeutic neuralgia, chronic inflammatory demyelinating polyneuropathy (CIDP), epilepsy, Guillain-Barre Syndrome (GBS), inclusion body myositis, lysosomal storage diseases, sphingomyelinlipidose (Niemann-Pick C), mucopolysaccharidose II/IIIB, metachromatic leukodystrophy, multifocal motor neuropathy, Myasthenia Gravis, Neuro-Behcet's Disease, neuromyelitis optica (NMO), optic neuritis, polymyositis, dermatomyositis, Rasmussen's encephalitis, Rett's Syndrome, stroke, transverse myelitis, traumatic brain injury, spinal cord injury, viral encephalitis, or bacterial meningitis.

90. The antibody or antigen-binding fragment thereof, the nucleic acid molecule or set of nucleic acid molecules, the vector, the cell, or the pharmaceutical composition of embodiment 87, or the use according to embodiment 88, wherein the disease is Alzheimer's disease.

91. The antibody or antigen-binding fragment thereof, the nucleic acid molecule or set of nucleic acid molecules, the vector, the cell, or the pharmaceutical composition of embodiment 87, or the use according to embodiment 88, wherein the disease is Parkinson's disease.

92. The antibody or antigen-binding fragment thereof, the nucleic acid molecule or set of nucleic acid molecules, the vector, the cell, or the pharmaceutical composition of embodiment 87, or the use according to embodiment 88, wherein the disease is multiple sclerosis.

93. The antibody or antigen-binding fragment thereof, the nucleic acid molecule or set of nucleic acid molecules, the vector, the cell, or the pharmaceutical composition of embodiment 87, or the use according to embodiment 88, wherein the disease is frontotemporal dementia.

94. The antibody or antigen-binding fragment thereof, the nucleic acid molecule or set of nucleic acid molecules, the vector, the cell, or the pharmaceutical composition of embodiment 87, or the use according to embodiment 88, wherein the antibody or antigen-binding fragment thereof, the nucleic acid molecule or set of nucleic acid molecules, the vector, the cell, or the pharmaceutical composition is administered to the subject through an oral, intravenous, intracranial, intrathecal, subcutaneous, or intranasal route.

95. The antibody or antigen-binding fragment thereof, the nucleic acid molecule or set of nucleic acid molecules, the vector, the cell, or the pharmaceutical composition of embodiment 87, or the use according to embodiment 88, wherein the antibody or antigen-binding fragment thereof, the nucleic acid molecule or set of nucleic acid molecules, the vector, the cell, or the pharmaceutical composition is administered to the subject in combination with at least one additional therapeutic agent or procedure.

96. The antibody or antigen-binding fragment thereof, the nucleic acid molecule or set of nucleic acid molecules, the vector, the cell, or the pharmaceutical composition of embodiment 87, or the use according to embodiment 88, wherein the antibody or antigen-binding fragment thereof, the nucleic acid molecule or set of nucleic acid molecules, the vector, the cell, or the pharmaceutical composition is administered to the subject in combination with at least one additional therapeutic agent, wherein said agent comprises one or more of BACE inhibitors, anti-Tau antibodies, Tau antisense oligonucleotides, anti-amyloid beta antibodies, fingolimod, BG12 or dimethyl fumarate, interferon beta or tysabri.

97. A method of treating a disease associated with hTREM2 loss of function in a subject in need thereof, the method comprising administering to the subject a therapeutically effective amount of the antibody or antigen-binding fragment thereof of any one of embodiments 1-64, the nucleic acid molecule or set of nucleic acid molecules of any one of embodiments 65-67, the vector of any one of embodiments 68-82, the cell of embodiment 83, or the pharmaceutical composition of embodiment 85.

98. The method of embodiment 97, wherein the method comprises:
   a) assaying the cell surface hTREM2 level in a sample obtained from a subject;
   b) selecting a subject whose cell surface hTREM2 level is lower than a reference level, wherein the reference level is the cell surface hTREM2 level in a sample obtained from a healthy subject; and
   c) administering to the selected subject a therapeutically effective amount of the antibody or antigen-binding fragment thereof of any one of embodiments 1 to 64, the nucleic acid molecule or set of nucleic acid molecules of any one of embodiments 65-67, the vector of any one of embodiments 68-82, the cell of embodiment 83, or the pharmaceutical composition of embodiment 85.

99. The method of embodiment 98, wherein the sample comprises cerebrospinal fluid.

100. The method of embodiment 98 or 99, wherein the cell surface TREM2 level in said sample is determined by an assay selected from flow cytometry, immunohistochemistry, Western blotting, immunofluorescent assay, radioimmunoassay (RIA), enzyme-linked immunosorbent assay (ELISA), homogeneous time resolved fluorescence (HTRF), or positron emission tomography (PET).

101. The method of any one of embodiments 97-100, wherein the disease associated with TREM2 loss of function is a neuroinflammatory or neurodegenerative disease, optionally wherein the neuroinflammatory or neurodegenerative disease is Alzheimer's disease, frontotemporal dementia, Parkinson's disease, amyotrophic lateral sclerosis, Nasu-Hakola disease, multiple sclerosis, amyotrophic lateral sclerosis (ALS), anti-NMDA receptor encephalitis, autism, brain lupus (NP-SLE), chemo-induced peripheral neuropathy (CIPN), postherapeutic neuralgia, chronic inflammatory demyelinating polyneuropathy (CIDP), epilepsy, Guillain-Barre Syndrome (GBS), inclusion body myositis, lysosomal storage diseases, sphingomyelinlipidose (Niemann-Pick C), mucopolysaccharidose II/IIIB, metachromatic leukodystrophy, multifocal motor neuropathy, Myasthenia Gravis, Neuro-Behcet's Disease, neuromyelitis optica (NMO), optic neuritis, polymyositis, dermatomyositis, Rasmussen's encephalitis, Rett's Syndrome, stroke, transverse myelitis, traumatic brain injury, spinal cord injury, viral encephalitis, or bacterial meningitis.

102. The method of any one of embodiments 97-101, wherein the disease is Alzheimer's disease.

103. The method of any one of embodiments 97-101, wherein the disease is Parkinson's disease.

104. The method of any one of embodiments 97-101, wherein the disease is multiple sclerosis.

105. The method of any one of embodiments 97-101, wherein the disease is frontotemporal dementia.

106. The method of any one of embodiments 97-105, wherein said antibody or antigen-binding fragment thereof, the nucleic acid molecule or set of nucleic acid molecules, the vector, the cell, or the pharmaceutical composition is administered to the subject through an oral, intravenous, intracranial, intrathecal, subcutaneous, or intranasal route.

107. A method of stabilizing hTREM2 protein in a subject, the method comprising administering to the subject the antibody or antigen-binding fragment thereof of any one of embodiments 1-64, the nucleic acid molecule or set of nucleic acid molecules of any one of embodiments 65-67, the vector of any one of embodiments 68-82, the cell of embodiment 83, or the pharmaceutical composition of embodiment 85, in an amount effective to stabilize hTREM2.

108. The method of any one of embodiments 97-107, the method further comprising administering at least one additional therapeutic agent to the subject or performing at least one additional therapeutic procedure.

109. The method of embodiment 108, wherein said additional therapeutic agent comprises one or more of BACE inhibitors, anti-Tau antibodies, Tau antisense oligonucleotides, anti-amyloid beta antibodies, fingolimod, BG12 or dimethyl fumarate, interferon beta or tysabri.

110. The method of embodiment 108 or 109, wherein the antibody or antigen-binding fragment thereof of any one of embodiments 1-64, the nucleic acid molecule or set of nucleic acid molecules of any one of embodiments 65-67, the vector of any one of embodiments 68-82, the cell of embodiment 83, or the pharmaceutical composition of embodiment 85 is administered concurrently with, prior to, or subsequent to, the additional therapeutic agent.

111. The method of any one of embodiments 97-110, wherein administering the antibody or antigen-binding fragment thereof, the nucleic acid molecule or set of nucleic acid molecules, the vector, the cell, or the pharmaceutical composition has one or more of the following effects a-d:

a) Increasing TREM2-dependent cellular activities like phagocytosis and chemotaxis, b) Triggering TREM2-dependent gene transcription, c) Increasing TREM2-dependent intracellular signaling pathways via Syk-phosphorylation, d) Increasing clearance of cellular debris.

EXAMPLES

The invention is further described in the following examples, which do not limit the scope of the invention described in the claims.

Example 1: Generation of Antibodies for Human TREM2

Materials and Methods

Reagents

For selection of antibodies recognizing human, mouse and cynomolgus TREM2 multiple panning strategies were employed. Antibodies against TREM2 proteins were generated by selection of clones having high binding affinities, using the phagemid libraries HuCAL PLATINUM® which is based on the HuCAL® (Prassler et al. 2011; Rothe et al. 2008; Knappik et al. 2000). MorphoSys phage display libraries employ the CysDisplay™ technology for displaying the Fab on the phage surface (WO 01/05950). For the isolation of anti-TREM2 antibodies, standard as well as RapMAT maturation panning strategies were performed using solid phase, solution, whole cell and differential whole cell panning approaches.

Initial Pannings

To receive initial candidates binding towards the antigen TREM2 solution, Fc capture panning and differential whole cell pannings were performed.

TABLE 2

Initial and Backup panning strategies and applied antigen concentrations.

| Panning strategy | Panning mode | Antigen $1^{st}$ round | Antigen $2^{nd}$ round | Antigen $3^{rd}$ round |
|---|---|---|---|---|
| 1 | Solution | hTREM2 ECD (19-174)-hFc-bio (100 nM) | hTREM2 ECD (19-174)-hFc-bio (20 nM) | hTREM2 ECD (19-174)-hFc-bio (4 nM) |
| 2 | Fc capture | hTREM2 ECD (19-174)-hFc (2 μg/ml) pre-clearing hTREM2 IgSF-hTREMI stalk-hFc (2 μg/ml) | hTREMI IgSF-hTREM2 stalk-hFc (2 μg/ml) pre-clearing hTREM2 IgSF-hTREM1 stalk-hFc (2 μg/ml) | hTREMI IgSF-hTREM2 stalk-hFc (0.4 μg/ml) pre-clearing hTREM2 IgSF-hTREMI stalk-hFc (2 μg/ml) |
| 3 | dWCP | CHO-hDAP12-hTREM2 (NVP-10-17 treated) post-adsorption CHO- | hTREM2 ECD (19-174)-hFc-bio (100 nM) blocking hTREM2- | CHO-hDAP12-cy TREM2 (NVP-10-17 treated) |

TABLE 2-continued

| Initial and Backup panning strategies and applied antigen concentrations. | | | | |
|---|---|---|---|---|
| Panning strategy | Panning mode | Antigen $1^{st}$ round | Antigen $2^{nd}$ round | Antigen $3^{rd}$ round |
| | | hDAP12 pre-clearing hTREM2-IgSF-hFc | IgSF-hFc (500 nM) | |

Fc Capture Panning

Prior to the antigen selection process, performance of a coating check ELISA is mandatory in order to determine the optimal antigen coating concentration. For capture panning, the antigen (hTREM1 IgSF-hTREM2 stalk-hFc, hTREM2 ECD (19-174)-hFc or hTREM2 ECD-His) was immobilized on a 96-well plate via an appropriate capture antibody, which depended on the tag fused to the respective antigen (goat and mouse anti-human Fc for Fc tagged antigen, for details see Table 2.

The number of wells depended on the number of sub-library pools used. In parallel to well preparation, phages were blocked with Chemiblocker containing 0.05% Tween-20; additional blocking reagents were added to the blocking buffer to avoid selection of antibodies against the tag or the capture antibody (human, goat and mouse γ globulin for Fc capture panning). For pre-clearing of the blocked phages an appropriate number of wells of a 96-well plate were coated with hTREM2-IgSF-hTREM1 stalk-hFc. Phages were added and incubated for 30 min at room temperature. The supernatant was transferred to another counter-target coated well and incubation was repeated three times. Following the blocking and pre-clearing procedure, the phage mix was added to respective antigen coated wells and the phage-antibodies were allowed to bind to the antigen for 1.5 hours at room temperature. Washing using PBS/Tween 20 and PBS ensured removal of non-specifically bound phage, followed by elution of specifically bound phage using DTT. The eluate was transferred to an *E. coli* TG1 culture for phage infection. Following incubation at 37° C. for 45 min, cultures were centrifuged, the bacterial pellets resuspended in fresh medium and plated on agar plates. After outgrowth, colonies were scraped off the plates and were used for phage rescue, polyclonal amplification of selected clones, and phage production as described below. With purified phage the next panning round was started.

The second and third round of capture panning was performed according to the protocol of the first panning round. Amounts of antigen were decreased and washing conditions with increased stringency were applied.

Parental binder MOR041874 was derived from this panning strategy.

Solution Panning with Streptavidin-Coupled Magnetic Beads

A prerequisite for solution panning was biotinylation of the antigen and confirmation of retained activity of biotinylated antigen. During solution panning, the Fab displaying phage and the biotinylated antigen were incubated in solution, which facilitated the accessibility of the antigen by the phage.

An appropriate amount of streptavidin beads was blocked with Chemiblocker. In parallel, an appropriate amount of phages was blocked with Chemiblocker containing 0.05% Tween-20 and human gamma globulin #1 (0.05 mg/ml) to avoid the selection of hFc-binding clones. For removal of streptavidin- or bead-binding phage, pre-adsorption of blocked phage particles was performed using blocked Streptavidin beads. Then, biotinylated TREM2 was added to the pre-adsorbed and blocked phage particles and the phage-antibodies were allowed to bind to the antigen in solution for 1 hour at room temperature. The phage-antigen complexes were captured using blocked Streptavidin beads and phage particles bound to the Streptavidin beads were collected with a magnetic separator. Unspecifically bound phage were washed off in several washing steps. Specifically bound phage were eluted from streptavidin beads by addition of DTT. The eluate was transferred to an *E. coli* TG1 culture for phage infection. Following incubation at 37° C. for 45 min, cultures were centrifuged, the bacterial pellets were resuspended in fresh medium and plated on agar plates. After outgrowth, colonies were scraped off the plates and were used for phage rescue, polyclonal amplification of selected clones, and phage production as described below. With purified phage the next panning round was started.

The second and third round of bead-based solution panning was performed according to the protocol of the first panning round. Washing conditions with increased stringency were applied. Parental binders MOR042492, MOR042493 and MOR042556 were derived from this panning strategy.

Differential Whole Cell Panning (dWCP)

The day before panning cells were pre-treated overnight with 5 μM DPC333 (Qian et al. 2007. Drug Metab and Disp 35:1916-1925) to increase surface expression of TREM2. For each panning, an appropriate amount of phages were blocked with wash buffer (DPBS+/5% FCS/0.02% $NaN_3$) and pre-cleared according to the methods described above for Fc capture panning. In parallel, an appropriate amount of target cells expressing antigen TREM2 ($1\times10^7$ cells/sub-code) and an appropriate amount of adsorption cells without expression of antigen TREM2 per phage pool were blocked with wash buffer. The blocked target cells were spun down, resuspended in the pre-blocked phage particles and the phage-antibodies were allowed to bind to the antigen presented on the cell at 4° C. for 2 hours to avoid receptor internalization. The phage-cell complexes were washed several times. Specifically bound phages were eluted from target cells by centrifuging the cells and resuspending the pellet in 50 mM citrate buffer pH 3.5/150 mM NaCl and incubated for 10 min at room temperature. After centrifugation, the supernatant (eluate) was neutralized using 2 M Tris-base and applied to adsorption cells for removal of phage binding to cell surface molecules other than the target antigen (post-adsorption). Specifically bound phages were eluted from target cells using DTT and the final supernatant transferred to *E. coli* TG1 culture for phage infection as described above.

The second panning round was performed according to solution panning described above. The third round of the whole cell panning was performed according to the protocol of the first panning round.

Parental binders MOR042596, MOR042752 and MOR042765 were derived from this panning strategy.

Production of Fab-Presenting Phage Particles

New phage particles presenting Fab fragments on their surface were produced for each selection round. For each phage preparation, 12 ml 2×YT/Cam/Glc medium were inoculated with bacteria from the corresponding library glycerol stock resulting in an OD600 of 0.1-0.2. Cultures were shaken for 30-90 min at 120 rpm and 37° C. until an OD600 of 0.45-0.55 was reached. Then, helper phage was added at a multiplicity of infection of 10 to the bacterial culture followed by an incubation for 30 min at 37° C. without shaking and then for 30 min at 37° C. shaking at 160 rpm. Bacteria were spun down and helper phage containing supernatant was discarded. Phage-infected bacteria were resuspended in 400 ml 2×YT/Cam/Kan/IPTG medium and incubated overnight at 22° C. with shaking at 120 rpm. The next day bacteria from the overnight culture were pelleted and the supernatant containing the Fab-presenting phage was collected. Phage precipitation was performed by adding 1/5 total volume of pre-cooled PEG/NaCl to the phage-containing supernatant. The sample was incubated for at least 30 min on ice until clouds of precipitating phage became visible. Precipitated phages were spun down and resuspended in PBS. Phage titers were determined by spot titration.

PTM Removal before Affinity Maturation

As the parental candidate MOR042492 included a critical post-translational modification (PTM) in its HCDR3, this candidate was repaired before entering the affinity determination. Therefore, three repaired variants were generated by oligonucleotide exchange, while successfully performed oligonucleotide exchange was confirmed by sequencing. The repaired variants were tested as Fab-containing crude bacterial lysates on hTREM2-ECD (19-174)-hFc. Variants exhibiting similar binding profiles were pooled for affinity maturation (MOR043962 and MOR043963).

Generation of HuCAL PLATINUM® Maturation Libraries and HuCAL PLATINUM® RapMAT Libraries To increase affinity and biological activity of selected antibodies CDR-L3 and CDR-H2 regions were optimized by cassette mutagenesis using trinucleotide directed mutagenesis, while the framework regions were kept constant (Virnekas et al. (1994) Nucleic Acids Res 22, 5600-5607).

Cloning of the maturation libraries was performed in CysDisplay™ vector encoding for the parental Fab fragments. If not already present in the CysDisplay™ vector, the DNA sequences encoding for the parental Fab fragments were transferred into the respective vector via restriction digest and ligation prior to library cloning.

The generation of HuCAL PLATINUM® maturation libraries was performed for each maturation candidate individually or a set of different parental antibodies was pooled prior to library generation. For CDR-L3 optimization, a ~400 bp DNA fragment encoding for the CDR-L3, framework 4 as well as the constant region of the light chain was removed from the sequence encoding the parental antibodies by restriction digest and replaced by a repertoire of DNA fragments encoding for diversified CDR-L3 regions together with framework 4 and the constant domain.

In a second library set the CDR-H2-encoding sequence was diversified, while the connecting framework regions were kept constant. In order to reduce the background of the parental undiversified sequence a 150 bp DNA fragment containing the parental CDR-H2 and the framework 3 sequences was replaced by a ~590 bp dummy sequence via restriction digest and ligation, before the diversified CDR-H2 cassette (incl. framework 3) was inserted also via restriction digest and ligation. This method was used for all maturation candidates except MOR042556.

The generation of HuCAL PLATINUM® RapMAT Libraries was performed for selected clones (parental candidate MOR042556). Therefore, a ~370 bp DNA fragment compromising the DNA sequence from the phoA signal to framework 3 (incl. the H-CDR1 and the CDR-H2) was removed by restriction digest and replaced by a repertoire of DNA fragments encoding for diversified CDR-H2 regions and a non-diversified framework-specific CDR-H1. Electroporation of ligation mixtures in MC1061F' cells yielded approximately $10^8$ to $10^9$ in $>5\times10^6$ independent colonies. Amplification of the library was performed as described previously (Rauchenberger et al. 2003). For quality control, approx. 10-20 single clones per library were randomly picked and sequenced.

Maturation Pannings

To increase affinity and biological activity of previously selected antibody fragments, CDR-L3 and CDR-H2 regions were exchanged in parallel by diversified cassettes/modules (Prassler et al. 2009) as described above. If required, parental Fab fragments were transferred from the corresponding expression vector into the CysDisplay™ vector prior to library cloning for affinity maturation.

For the selection of affinity improved candidates, phages derived from maturation libraries were subjected to three rounds of maturation panning. Solution pannings and dWCP were performed as described in above, and in accordance with the conditions described in Table 3.

TABLE 3

Maturation pannings strategies and applied antigen concentrations.

| Panning strategy | Panning mode | Contains parental | Maturation Libraries | Antigen $1^{st}$ round | Antigen $2^{nd}$ round | Antigen $3^{rd}$ round |
|---|---|---|---|---|---|---|
| 4 | Solution | MOR043962 MOR043963 | HCDR2 | hTREM2 ECD (19-174)-hFc-bio (2 nM) | cyTREM2 ECD (19-174)-hFc-bio (0.5 nM) | hTREM2 ECD (19-174)-hFc-bio (0.1 nM) |
| 5 | | MOR042493 | HCDR2 LCDR3 | hTREM2 ECD (19-174)-hFc-bio (2 nM) | cyTREM2 ECD (19-174)-hFc-bio (0.5 nM) | hTREM2 ECD (19-174)-hFc-bio (0.1 nM) |
| 6 | | MOR042493 | LCDR3 | hTREM2 ECD (19-174)-hFc- | cyTREM2 ECD (19-174)-hFc- | hTREM2 ECD (19-174)-hFc-bio |

TABLE 3-continued

Maturation pannings strategies and applied antigen concentrations.

| Panning strategy | Panning mode | Contains parental | Maturation Libraries | Antigen 1st round | Antigen 2nd round | Antigen 3rd round |
|---|---|---|---|---|---|---|
| | | | | bio (5 nM) | bio (2.5 nM) | (0.75 nM) |
| 7 | | MOR042596 | HCDR2 LCDR3 | hTREM2 ECD (19-174)-hFc-bio (2 nM) | cyTREM2 ECD (19-174)-hFc-bio (1 nM) | hTREM2 ECD (19-174)-hFc-bio (0.2 nM) |
| 8 | | MOR042752 | HCDR2 | hTREM2 ECD (19-174)-hFc-bio (2 nM) | cyTREM2 ECD (19-174)-hFc-bio (1 nM) | hTREM2 ECD (19-174)-hFc-bio (0.2 nM) |
| 9 | | MOR042765 | HCDR2 | hTREM2 ECD (19-174)-hFc-bio (5 nM) | cyTREM2 ECD (19-174)-hFc-bio (2.5 nM) | hTREM2 ECD (19-174)-hFc-bio (0.75 nM) |
| 10 | | MOR043962 | HCDR2/LCDR3 | hTREM2 ECD (19-174)-hFc-bio (2 nM) | CHO-hDAP12-cyTREM2 (w/o NVP-10-17) | hTREM2 ECD (19-174)-hFc-bio (0.1 nM) |
| 11 | | MOR042556 | HCDR1_2/LCDR3 | hTREM2 ECD (19-174)-hFc-bio (2 nM) | CHO-hDAP12-cyTREM2 (w/o NVP-10-17) | hTREM2 ECD (19-174)-hFc-bio (0.1 nM) |
| 12 | dWCP | MOR042596 | HCDR2/LCDR3 | hTREM2 ECD (19-174)-hFc-bio (2 nM) | CHO-hDAP12-cyTREM2 (w/o NVP-10-17) | hTREM2 ECD (19-174)-hFc-bio (0.2 nM) |
| 13 | | MOR041874 | HCDR2/LCDR3 | cyTREM2 ECD (19-174)-hFc-bio (5 nM) | CHO-hDAP12-cyTREM2 (w/o NVP-10-17) | hTREM2 ECD (19-174)-hFc-bio (0.5 nM) |
| 14 | | MOR042556 | HCDR1_2/LCDR3 | hTREM2 ECD (19-174)-hFc-bio (2 nM) | BV2 (NVP-10-17 treated) | cyTREM2 ECD (19-174)-hFc-bio (0.2 nM) |
| 15 | | MOR042765 | HCDR2/LCDR3 | hTREM2 ECD (19-174)-hFc-bio (5 nM) | BV2 (NVP-10-17 treated) | cyTREM2 ECD (19-174)-hFc-bio (0.5 nM) $K_{off}$ selection with unbiotinylated antigen (100 × molar excess) |

Panning stringency was increased by lowering the antigen concentration in each panning round (Low et al. 1996). In addition to antigen reduction, off-rate selection was performed in the third panning round (Hawkins et al. 1992): the antigen-phage complex was incubated with excess unbiotinylated TREM2 antigen to enrich only high-affine binders; weak binders were expected to preferentially bind the excess antigen in solution and could therefore be removed. This was combined with extensive washing steps. Elution of the high affinity phages from TREM2 coupled to magnetic beads was performed with DTT.

Subcloning from Display Vector into Fab-Expression Vector for *E. coli*

To facilitate rapid expression of soluble Fab in *E. coli*, the Fab encoding inserts of the selected HuCAL PLATINUM® phage were subcloned from pMORPH®30 display vector into the Fab-expression vector pMORPH®×11_Fab-FH. Subcloning was performed by triple digest via EcoRI|XbaI|BmtI.

Subcloning Into IgG & FabCys Expression Vector for HKB11 Cells

For full length IgG or monovalent FabCys expression in HKB11 cells, selected candidates or candidate pools were cloned into the respective expression vector, comprising the features/tags desired. A summary of the IgG & FabCys formats as well as respective vectors available are described in Table 4.

Subcloning was performed as a two-step method for a convenient and efficient conversion of a large amount of sequence-unique Fab clones into the IgG format.

TABLE 4

| HuCAL PLATINUM ® pMorph4 IgG & FabCys Expression vector Series | | | |
|---|---|---|---|
| Vector name | Format | Tags | |
| pM4_h_FabCys | Human FabCys | N/A | His6 |
| pM4_h_FabCys-AviH | Human FabCys | Avi-tag | |
| pM4_h_IgGlf_LALA | Human IgG | N/A | |
| pM4_h/m_IgG2a | Chimeric IgG | N/A | |

Subcloning from HuCAL PLATINUM® RapCLONE®

In a first cloning step, a eukaryotic expression cassette was introduced into the display vector or the vector for Fab expression in *E. coli* via BsiWI|MfeI (for κ pools) or HpaI|MfeI (for λ pools) digestion and subsequent ligation. This was followed by a second cloning step, in which the Fab pools containing the expression cassette were digested using EcoRV|BlpI (κ and λ pools) and subsequently cloned into the acceptor vector for expression in mammalian cells.

Production in *E. coli*

Generation of Fab Containing Crude Bacterial Lysates 96-well/384-well microtiter plates pre-filled with growth medium (2×YT containing chloramphenicol, IPTG and low glucose) were inoculated. Plates were incubated at 37° C. for bacterial outgrowth and shaken overnight at 22° C. for Fab expression. The next day expression cultures were lysed by addition of BEL buffer containing borate buffer, EDTA and lysozyme. EDTA was omitted if lysates were used for sensitive cell screenings.

Exploratory Scale Production of His-Tagged Fab Fragments

Expression of Fab fragments encoded by bacterial expression vector in *E. coli* TG1 F-cells was carried out in shake flask cultures using 500 mL of 2×YT medium supplemented with 0.1% glucose and 34 μg/mL chloramphenicol. Cultures were shaken until the OD600 reached a value of 0.5. Fab expression was induced by adding IPTG (isopropyl-ß-D-thiogalactopyranoside) and further cultivation for 20 h. Cells were harvested and disrupted using lysozyme. His6-tagged Fab fragments were isolated via IMAC (Bio-Rad) and eluted using imidazole. Buffer exchange to 1× Dulbecco's PBS (pH 7.2) was performed using 'PD10' columns (GE Healthcare). Samples were sterile filtered (0.2 μm). Protein concentrations were determined by UV-spectrophotometry and purities of IgG were analyzed under denaturing, reducing and non-reducing conditions using CE-SDS (LabChip GXII, Perkin Elmer). HP-SEC was performed to analyze IgG preparations in native state.

Production of IgG in HKB11 Cells

Advanced Micro Scale Production of IgG

Eukaryotic HKB11 cells were transfected with mammalian expression vector DNA encoding both heavy and light chains of IgG. Cell culture supernatants were harvested 7 days post transfection and subjected to Protein A affinity chromatography (MabSelect SURE™, GE Healthcare). Samples remained in neutralized elution buffer (NaPS: 137 mM NaPhosphate, 81 mM NaCl, pH 7). Samples were sterile filtered (0.2 μm). Protein concentrations were determined by UV-spectrophotometry and purities of IgG were analyzed under denaturing, reducing conditions using CE-SDS (LabChip GXII™, Perkin Elmer). HP-SEC was performed to analyze IgG preparations in native state.

Exploratory Scale Production of IgG

Eukaryotic HKB11 cells were transfected with mammalian expression vector DNA encoding both heavy and light chains of IgG. Cell culture supernatants were harvested on day 3 or 6 post transfection and subjected to standard Protein A affinity chromatography (MabSelect SURE, GE Healthcare). Buffer exchange was performed to 1× Dulbecco's PBS (pH 7.2, Invitrogen) and samples were sterile filtered (0.2 μm). Protein concentrations were determined by UV-spectrophotometry and purities of IgG were analyzed under denaturing, reducing and non-reducing conditions using CE-SDS (LabChip GXII, Perkin Elmer). HP-SEC was performed to analyze IgG preparations in native state.

Material Production for In Vivo Characterization

Eukaryotic HKB11 cells were transfected with mammalian expression vector DNA encoding both heavy and light chains of IgG. Cell culture supernatants were harvested on day 6 post transfection and subjected to Protein A affinity chromatography (MabSelect SURE, GE Healthcare). If needed, a second purification step (preparative SEC, Superdex 200, GE Healthcare) was performed to remove aggregates. Buffer exchange was performed to 1× Dulbecco's PBS (pH 7.2, Invitrogen) and samples were sterile filtered (0.2 μm). Protein concentrations were determined by UV-spectrophotometry and purities of IgG were analyzed under denaturing, reducing and non-reducing conditions using CE-SDS (LabChip GXII, Perkin Elmer). HP-SEC was performed to analyze IgG preparations in native state. Endotoxin levels were determined by KQCL assay (Lonza). Protein identities were confirmed using Mass Spectrometry analysis.

Production of FabCys in HKB11 Cells

Exploratory Scale Production of Tagless FabCys

Eukaryotic HKB11 cells were transfected with mammalian expression vector DNA encoding both heavy and light chains of disulfide-bridged FabCys. Cell culture supernatants were harvested on day 3 or 7 post transfection and subjected to CH1 affinity chromatography (Capture Select IgG-CHT, Thermo Scientific). Buffer exchange was performed to 1× Dulbecco's PBS (pH 7.2, Invitrogen) and samples were sterile filtered (0.2 μm pore size). Protein concentrations were determined by UV-spectrophotometry and purities of FabCys were analyzed under denaturing, reducing and non-reducing conditions using CE-SDS (LabChip GXII, Perkin Elmer). HP-SEC was performed to analyze FabCys preparations in native state.

Exploratory Scale Production of AviHis-Tagged FabCys

Eukaryotic HKB11 cells were transfected with mammalian expression vector DNA encoding both heavy and light chains of disulfide-bridged FabCysAviHis. Cell culture supernatants were harvested on day 3 or 7 post transfection and subjected to metal ion affinity chromatography (Protino Ni-NTA, Macherey Nagel). Buffer exchange was performed to 1× Dulbecco's PBS (pH 7.2, Invitrogen) and samples were sterile filtered (0.2 μm pore size).

Protein concentrations were determined by UV-spectrophotometry and purities of FabCysAviHis were analyzed under denaturing, reducing and non-reducing conditions using CE-SDS (LabChip GXII, Perkin Elmer). HP-SEC was performed to analyze FabCysAviHis preparations in native state.

Summary Panning Strategies

Initial and back-up panning strategies aimed for selection of antibodies against both extracellular domains of TREM2, IgSF domain and stalk region. Therefore, strategies on complete TREM2 ECD were included as well as more specific strategies for selection of stalk region and even sheddase cleavage site specific clones. For each targeted TREM2 domain specificity, 3 different antigen presentation modes were applied: solution panning using biotinylated antigen, Fc capture panning and differential whole cell panning with antigen expressing cells in 1$^{st}$ and 3$^{rd}$ panning rounds and recombinant antigen in $2^{nd}$ panning round. Stalk region specificity could be achieved by making use of switch constructs consisting of TREM1 IgSF domain in combination with TREM2 stalk region or vice versa as panning antigen (hTREM1 IgSF-hTREM2 stalk) or for blocking (hTREM2 IgSF-hTREM1 stalk). Based on mapping experiments, the sheddase cleavage site region comprises 20 aa in the juxtamembrane part of the TREM2 stalk region; the corresponding peptide 78 was used to enrich cleavage site specific clones.

Antibodies against all targeted TREM2 ECD regions could be identified. However, only a low number of clones with the most promising profile for stabilizing activity (i.e. stalk region specificity in combination with cyno cross-reactivity and cell binding) were selected.

Summary Screening Results

Primary Screening

All subcodes of initial pannings were screened on biotinylated hTREM2, mTREM2, hTREM1 IgSF-hTREM2 stalk, hTREM2 IgSF-hTREM1 stalk and hTREM1 in a multiplexing approach using Intellicyt device (368 clones per subcode). In total, 9200 clones from initial pannings were screened and resulted in selection of 736 primary hits. Most IgSF domain specific clones originate from solution panning on hTREM2, whereas most stalk region specific antibodies come from differential whole cell pannings.

Back-up pannings were screened in a similar way than initial pannings. In parallel, all subcodes involving cell panning round(s) were screened on parental CHO-DAP12 as well as CHO-DAP12-hTREM2 cells. Furthermore—dependent on cell type used in cell panning round—some subcodes were additionally screened on CHO-DAP12-cyTREM2, CHO-DAP12-mTREM2, CHO-DAP12-hTREM1 IgSF-hTREM2 stalk, HEK-DAP12-hTREM2 fusion and THP1-NFAT-luc cells. In total, 10304 clones were screened and led to the selection of 402 primary hits.

Secondary Screening and Diversity Determination

Based on secondary screening of 736 primary hits from initial pannings (binding to hu/cy/mu TREM2 using different recombinant proteins and cell lines, domain specificity using TREM2/TREM1 switch constructs and cleavage site peptide 78, TREM1 counter-screen), 284 clones were selected for VH sequencing. Among them, 104 clones had unique HCDR3 sequences. Similarly, 402 primary hits from back-up pannings underwent secondary screening and VH sequencing of selected clones, resulting in 186 new, HDR3 unique clones. Only 5 sequences were identified that were already known from initial campaign.

Confirmation and Further Characterization of Unique Clones

By further confirmatory screening assays, 81/104 unique clones from initial campaign and 165/186 unique clones from back-up campaign were defined as hTREM2 specific antibody clones and selected for subsequent functional characterization (in total 246 clones). According to their binding behaviour, these clones could be divided into different profile groups. The majority of clones were IgSF domain specific (173 clones, 70%). Most of these clones bind specifically to TREM2 over-expressing cells and are cross-reactive to cyno TREM2 (157 clones). In addition, 53 (22%) stalk region specific antibodies were identified. 19/53 clones did not bind the cleavage site peptide 78 and are thus called “stalk (outside cleavage site)” antibodies; 14 of these clones show TREM2 specific cell binding. 34/53 clones bind TREM2 within its cleavage site region (“stalk (cleavage site)” antibodies). The remaining 20 clones (8%) bind TREM2-ECD but neither one of the two switch constructs and are thus specified as “unclear domain within ECD” binding antibodies; 10/20 clones do specifically bind TREM2 over-expressing cells.

Selection of Maturation Candidates

Selection of maturation candidates was mainly based on functional characteristics of the identified antibodies. SinceTREM2 belongs to the family of innate immune receptors it is known to interact with LPS and other bacterial surface proteins. Therefore, it was essential to switch from bacterial to mammalian platforms for anti-TREM2 antibody production in order to generate material that is suited for relevant functional assays.

IgG Characterization

Besides binding characteristics (domain specificity, species cross-reactivity, specific cell binding, counter-target binding, affinity, epitope binning) different functional aspects were addressed (stabilization of TREM2 cell surface level in different cellular systems, signal activation in NFAT RGA, internalization, competition with ligand binding, phagocytosis).

Only few antibodies turned out to have TREM2 stabilizing effects, i.e. protect against TREM2 ectodomain shedding. Considering all other criteria, five promising TREM2 stabilizing antibodies were identified: MOR042492, MOR042493 and, MOR042589, MOR042596, MOR042556.

In addition to the stabilizing candidates, TREM2 signal activating antibodies could be identified. Again considering other relevant criteria, the most interesting candidates were MOR041874, MOR042785, MOR042752, MOR042765.

These nine candidates are depicted in Table 5.

TABLE 5

Maturation candidates.

| MOR# | | 42492 | 42493 | 42556 | 42589 | 42596 | 41874 | 42752 | 42765 | 42785 |
|---|---|---|---|---|---|---|---|---|---|---|
| Type | | Stabilizing antibodies | | | | | Activating antibodies | | | |
| Framework | | VH1A κ1 | VH6 κ1 | VH6 κ1 | VH3-23 κ1 | VH1B κ1 | VH1B λ1 | VH1A κ1 | VH5 λ2 | VH1B λ1 |
| Domain | | IgSF | IgSF | IgSF | IgSF | IgSF | Stalk | IgSF | IgSF | Stalk |
| Panning strategy | | Solution, hu ECD | Solution, hu ECD | Solution, hu ECD | dWCP, NGS, solution hu stalk | dWCP, NGS, hu/cy ECD, cell binding | Fc capture, hu stalk | dWCP, NGS, hu/cy ECD, cell binding | dWCP, NGS, hu/cy ECD, cell binding | dWCP, NGS, solution hu stalk |
| sDAS risk | | Medium | Low | Medium | Low | Low | Low | Medium | Low | Medium |
| Biacore | Human | 0.2 | 0.1 | 0.2 | 43 | 12 | 23 | 5.1 | 31 | 7.2 |
| $K_D$ [nM] | Cyno | 0.2 | 0.1 | <0.1 | 100 * | 6.6 | Slight nonspecific | 9.1 | 67 * | 117 * (Steady |

TABLE 5-continued

Maturation candidates.

| MOR# | | 42492 | 42493 | 42556 | 42589 | 42596 | 41874 | 42752 | 42765 | 42785 |
|---|---|---|---|---|---|---|---|---|---|---|
| Type | | Stabilizing antibodies | | | | | Activating antibodies | | | |
| | | | | | | | binding *** | | | state KD) |
| | Mouse | 1 | 17 * | 0.2 | 100 ** | 0.9 | Slight nonspecific binding *** | 72 * | 160 ** | 86 * (Steady state KD) |
| | Cyno | + | + | + | + | + | Weak | + | + | Weak |
| Cross-reactivity | Mouse | + | + | + | Weak | + | Weak | Weak | + | Weak |
| Epitope | | A | A | n.d. | A | A | B | n.d. | A | n.d. |
| Internalization (fold over control) | | 16 | 32 | 72 | 92 | 76 | n.d | 13 | 91 | 65 |
| Ligand competition | | No | No | No | No | No | n.d. | Yes | Yes | n.d. |
| TREM2 activation (fold in RGA) | | 1.2 | 1.4 | 1.5 | 1.8 | 1.6 | 3.3 | 2.1 | 2.4 | 3.1 |
| Stabilization Mph-FACS | | +++ | +++ | n.d. | + | ++++ | No | + | ++ | n.d. |
| Phagocytosis enhancing | | +++ | +++ | +++ | +++ | +++ | n.d. | n.d. | n.d. | n.d. |

* heterogenous binding;
** weak binding, fast dissociation;
*** no specific binding up to 300 nM PTM Removal As two of the nine maturation candidates (MOR042492, MOR042589) included post-translational modifications (PTMs) in their HCDR3, these clones were repaired before affinity maturation. Therefore, three repaired variants per maturation candidate were generated by oligonucleotide exchange, while successfully performed oligonucleotide exchange was confirmed by sequencing. The repaired variants were further tested for functionality via BEL screening. Variants exhibiting similar binding profiles were pooled for affinity maturation. The parental MOR042589 was additionally used for affinity maturation, as variants exhibited lower binding than their parental clone.

Generation of Affinity Maturation Libraries

Finally, nine maturation libraries (see Table 6) composed of six lead candidates entered maturation separately. The selection included also three pools of up to three clones. Those were either clones with identical frameworks targeting the same epitope or child clones derived from one parental clone by PTM removal.

TABLE 6

Selected maturation candidates and library composition.

| Library | | Parental antibody | Child antibodies after PTM removal | Profile |
|---|---|---|---|---|
| #1 | Pool1 | MOR042492 | MOR043962<br>MOR043963 | IgSF; stabilizing |
| #2 | Lead1 | MOR042493 | | IgSF; stabilizing |
| #3 | Lead2 | MOR042556 | | IgSF; stabilizing |
| #4 | Pool2 | MOR042389 | MOR043959<br>MOR043960<br>MOR043961 | IgSF; stabilizing |
| #5 | Lead3 | MOR042589 | | IgSF; stabilizing |
| #6 | Lead4 | MOR042596 | | IgSF; stabilizing |
| #7 | Lead5 | MOR042752 | | IgSF; activating |
| #8 | Lead6 | MOR042765 | | IgSF; activating |
| #9 | Pool3 | MOR041874<br>MOR042785 | | IgSF; activating |

Summary Maturation Pannings

As most of the maturation candidates were derived from solution or differential whole cell pannings during the initial pannings, mainly solution pannings under high stringency as well as cell pannings were performed to identify improved binders after library generation. Therefore, solution panning which was the most successful strategy from initial pannings was performed over three rounds with every VH and VL library of each clone separately. Additionally, panning outputs derived from the solution pannings of the $1^{st}$ round were pooled. In this way, VH and VL maturated subcodes of each panning library as well as VH and VL libraries of clones exhibiting similar binding profiles were pooled before they entered the $2^{nd}$ panning round. The pools entered cell pannings using CHO-DAP12-cyTREM2 cells without DPC333 treatment to lower TREM2 levels and thereby increase stringency of these cell pannings. These pannings should assure the generation of high affinity cell binders, while pannings using the murine BV2 cells, applied on pools of multiple candidates, were performed to receive hu/m/cy cross-reactive clones. An increase of stringency over the three panning rounds was achieved by reduction of antigen concentrations as well as $k_{off}$ selection during the $3^{rd}$ round by competition with non-biotinylated antigen in solution. Additionally, subsequent adjustment of antigen concentrations during pannings according to outputs of the previous panning rounds ensured suitable panning outputs and enrichment of high affinity binders. In summary, the clones listed in Table 7 were identified.

TABLE 7

| Overview Pre-final Candidates. | | | | |
|---|---|---|---|---|
| MOR# | Parental | Panning strategy (initial) | Panning strategy (maturation) | Engineering |
| MOR044743 | MOR041874 | 2 | 13 | |
| MOR044693 | MOR042493 | 1 | 5 | |
| MOR044694 | MOR042493 | 1 | 6 | |
| MOR044702 | MOR042493 | 1 | 5 | |
| MOR044746 | MOR042493 | 1 | 5 | |
| MOR044695 | MOR042556 | 1 | 14 | PTM removal |
| MOR044728 | MOR042556 | 1 | 14 | PTM removal |
| MOR044734 | MOR042556 | 1 | 14 | PTM removal |
| MOR044737 | MOR042556 | 1 | 14 | PTM removal |
| MOR044738 | MOR042556 | 1 | 14 | PTM removal |
| MOR044739 | MOR042556 | 1 | 11 | PTM removal |
| MOR044697 | MOR042596 | 3 | 12 | |
| MOR044698 | MOR042596 | 3 | 7 | |
| MOR044705 | MOR042596 | 3 | 7 | |
| MOR044708 | MOR042596 | 3 | 12 | |
| MOR044713 | MOR042752 | 3 | 8 | |
| MOR044716 | MOR042752 | 3 | 8 | |
| MOR044710 | MOR042765 | 3 | 15 | Germlining |
| MOR044717 | MOR042765 | 3 | 9 | Germlining |
| MOR044720 | MOR042765 | 3 | 9 | Germlining |
| MOR044721 | MOR043962 | 1 | 10 | |
| MOR044722 | MOR043962 | 1 | 4 | |
| MOR044724 | MOR043962 | 1 | 10 | |
| MOR044726 | MOR043963 | 1 | 4 | |

Screenings and Characterization

ELISA

ELISA techniques were used for both screening of single Fab clones identified from panning outputs on target antigens as well as for characterization of purified antibodies.

Direct Coating of Antigen

Antigens were immobilized on microtiter plates (see Table 8). Plates were blocked and incubated with antibodies such as Fab containing crude *E. coli* lysates or purified Fab or IgG samples. Bound antibodies were detected using respective alkaline-phosphatase (AP) coupled secondary antibodies in combination with 'AttoPhos' fluorescence substrate. Multiple washing steps were performed between individual assay steps.

TABLE 8

| Antigens and coating for direct ELISA. | | |
|---|---|---|
| Antigen | Coating (initial) µg/ml | Coating (maturation) µg/ml |
| hTREM2-ECD (19-174)-hFc | 1 | N/A |
| cyTREM2-ECD (19-174)-hFc | 5 | N/A |
| mTREM2-ECD (19-171)-mFc | 5 | N/A |
| hTREM1 IgSF-hTREM2 stalk-hFc | 1 | N/A |
| hTREM2 IgSF-hTREM1 stalk-hFc | 1 | N/A |
| mTREM2-ECD (19-168)-his | 3 | 1 |
| mTREM2-IgSF (19-134)-mFc | 5 | N/A |
| hTREM1-hFc-His | 1.5 | N/A |
| cyTREM2-ECD (19-174)-APP-Avi | 4 | N/A |

Antigen Capture ELISA

In other ELISA settings, antigen (cyTREM2-ECD (19-174)-hFc, 1.0 µg/ml) was captured on plates via a tag-specific antibody coated on microtiter plates (e.g. anti-Fc). Bound antibodies were detected using respective alkaline-phosphatase (AP) coupled secondary antibodies in combination with 'AttoPhos' fluorescence substrate. Multiple washing steps were performed between individual assay steps.

Fab-Expression Check

For verification of Fab expression in crude bacterial lysates, plates were coated with Fd-fragment specific antibodies. Bound Fabs were detected using respective alkaline-phosphatase (AP) coupled anti-Fab specific antibody in combination with 'AttoPhos' fluorescence substrate. Multiple washing steps were performed between individual assay steps.

Multiplexing by IntelliCyt

To evaluate species cross-reactivity and/or unwanted binding to countertargets simultaneously, screening in 384-well plate format was performed using the HTFC/iQue screening platform (IntelliCyt).

Screening on Recombinant Protein Covered Beads

Beads with various amounts of intrinsic fluorescence were coupled to antigens, physically combined into a single suspension and incubated with antibodies to be tested. Individual antigens were identified via the fluorescence of the respective bead that had been coated. SPHERO streptavidin fluorescent particles were used in combination with biotinylated antigens and optimal coating densities were tested in pre-experiments using tool antibodies. Crude bacterial cell lysates were combined with antigen-coated (see Table 9) and blocked beads and were incubated for 1 hour at room temperature in the dark, shaking gently. After subsequent incubation with fluorescently labeled secondary antibody, measurement was performed with the IntelliCyt HTFC/iQue device. Between incubation steps, no washing was required. Raw data were evaluated using 'ForeCyt' software.

TABLE 9

| Antigens and bead coupling for multiplex screenings. | | |
|---|---|---|
| Antigen | Coupling (initial) pmol/ 50 µl beads | Coupling (maturation) pmol/ 50 µl beads |
| hTREM2-ECD (19-174)-hFc-bio | 5 | 5 |
| cyTREM2-ECD (19-174)-hFc-bio | 5 | 5 |
| hTREM1 IgSF-hTREM2 stalk-hFc-bio | 5 | 5 |
| hTREM2 IgSF-hTREM1 stalk-hFc-bio | 5 | 5 |
| hTREM2 peptide 78-bio | 25 | |
| hTREM1-hFc-His-bio | | 5 |

$EC_{50}$ Determination on Recombinant Protein Covered Beads

Bead based assays were used for evaluating EC50 values of purified antibodies, including on multiple antigens in parallel. Thereby, beads with various amounts of intrinsic fluorescence were coupled to antigens, physically combined into a single suspension and incubated with different antibody concentrations to be tested. Individual antigens were identified via the fluorescence of the respective bead that had been coated. SPHERO streptavidin fluorescent particles were used in combination with biotinylated antigens (see Table 10) and optimal coating densities were tested in pre-experiments using tool antibodies. Washing steps after incubation with antibody and detection antibody were performed.

TABLE 10

| Antigens and bead coupling for IgG characterization and EC50 determination. | | |
|---|---|---|
| Antigen | Coupling (initial) pmol/ 50 μl beads | Coupling (maturation) pmol/ 50 μl beads |
| hTREM2-ECD (19-174)-hFc-bio | 5 | 0.5 |
| cyTREM2-ECD (19-174)-hFc-bio | 5 | 0.5 |
| hTREM1 IgSF-hTREM2 stalk-hFc-bio | 5 | 0.5/2 |
| hTREM2 IgSF-hTREM1 stalk-hFc-bio | 5 | 0.5 |
| hTREM2 peptide 78-bio | 25 | |
| hTREM1-hFc-His-bio | | 5 |

FACS

Using flow cytometry, binding events to cell surface expressed antigen were identified, using crude *E. coli* lysates from the panning output as well as purified antibodies in different concentrations for evaluation of EC50 values. Cell lines used for FACS analyses are listed in Table 11.

TABLE 11

| Cell lines used in FACS analysis. | | |
|---|---|---|
| Cell line | Origin | Surface TREM2 expression level |
| BV2 | mouse | Endogenous, low surface level |
| THP1-dr | human | Endogenous, low surface level |
| THP1-NFAT-luc | human | Endogenous, low surface level |
| THP1-CRISPR/ Cas-Trem2-knockout | human | Knockout |
| CHO-hDAP12 | human | No |
| CHO-hDAP12-hTREM2 | human | Transgenic overexpressed |
| CHO-hDAP12-cyTREM2 | human | Transgenic overexpressed |
| CHO-hDAP12-mTREM2 | human | Transgenic overexpressed |
| CHO-hDAP12- hTREM1IgSF-hTREM2stalk | human | Transgenic overexpressed |
| HEK293-hDAP12-hTREM2 | human | Transgenic overexpressed |
| HEK293 parental | human | No |

Depending on the setup cells were pre-treated with DPC333 for 24 hours before incubation with the antibodies. All steps were performed in FACS buffer including FCS and azide to prevent receptor internalization. Cell suspensions were transferred to microtiter plates and antibody samples were added followed by subsequent incubation of plates for 1 hour at 4° C., gently shaking. Following incubation, cells were spun down and washed with FACS buffer. Fluorophore-conjugated secondary reagents were used for detection of bound antibodies. Plates were measured using the Intellicyt HTFC/iQue System and data was analyzed using appropriate software.

Screening on Cells

The HTFC/iQue Screening System was also used for evaluation of binding to multiple target cell lines or evaluation of unwanted/unspecific binding in parallel. Different cell populations were distinguished by pre-labeling with distinct amounts of fluorescent dyes such as Calcein or Cell-Tracker Green, establishing a unique signature of fluorescence intensity for each cell population=fluorescence barcoding. The color-coded cell lines were then physically combined and mixed together with Fab containing crude bacterial lysates to be tested. Individual cell-lines were identified via the fluorescence of the respective cell-line that had been pre-labeled. Crude bacterial cell lysates were combined with cells (CHO-hDAP12-hTREM2 and CHO-DAP12) and incubated for 1 h at 4° C. in the dark, shaking gently. Fluorescence measurement was performed with the IntelliCyt HTFC/iQue device. In between incubation steps, no washing was required. Raw data were evaluated using 'ForeCyt' software. After data acquisition, the cell lines from each sample were identified according to their fluorescence signature and individually evaluated for antibody binding. Results are shown in Titrations of the IgGs on CHO-hDAP12-hTREM2 and CHO-hDAP12-mTREM2 cells were used to determine the EC50 values.

Epitope Binning

Time-Resolved Epitope Binning Via Octet

Time-resolved epitope binning on Octet (QK384 or HTX) instruments was performed to classify IgG samples into groups of identical, or significantly overlapping epitopes, i.e. antibodies that were able to inhibit each other's binding. The same sample prerequisites as for $K_D$ determination applied as described for KD determinations by label-free kinetics via SPR (Biacore). One representative candidate per parental family was selected.

Antibody samples were tested pairwise in a full factorial assay design, e.g. for two antibody samples A and B the following pairwise binding events were required: A-A, A-B, B-A, B-B. For epitope binning in "sandwich" assay setup, Octet sensor tips were modified with all different antibody samples present in sample set. A medium to high immobilization level was applied. Sensors bearing the different antibodies were loaded with monomeric antigen, and subsequently subjected to one of the antibody samples to check for binding to the captured antigen. Additional binding was only expected to occur, if the second antibody recognized a different epitope.

For evaluation, the signals at the end of antigen loading and secondary antibody binding were monitored, and curves inspected in terms of sufficient antigen loading and possible dissociation of antigen. For the controls, i.e. double binding steps of the identical antibodies (A-A, B-B); no additional binding was expected for the second antibody. Double binding events of all different antibody sample pairs were compared for consistency, e.g. if additional binding of B was observed in the sample order A-B (different epitopes), the sample order B-A was expected to result in additional binding of A, too. Possible causes for creating such inconsistencies were e.g. partially overlapping epitopes, or insufficient loading of antigen. Results are shown in Table 12.

TABLE 12

| Epitope Binning. | | | |
|---|---|---|---|
| MOR# | Representative | Parental | Bin |
| MOR044721 | MOR044727 | MOR043962 | A1 |
| MOR044722 | MOR044727 | MOR043962 | A1 |
| MOR044724 | MOR044727 | MOR043962 | A1 |
| MOR044726 | MOR044727 | MOR043963 | A1 |
| MOR044693 | MOR044747 | MOR042493 | A3 |
| MOR044694 | MOR044747 | MOR042493 | A3 |
| MOR044702 | MOR044747 | MOR042493 | A3 |
| MOR044746 | MOR044747 | MOR042493 | A3 |
| MOR044695 | MOR044730 | MOR042556 | A1 |
| MOR044728 | MOR044730 | MOR042556 | A1 |
| MOR044734 | MOR044730 | MOR042556 | A1 |
| MOR044737 | MOR044730 | MOR042556 | A1 |
| MOR044738 | MOR044730 | MOR042556 | A1 |
| MOR044739 | MOR044730 | MOR042556 | A1 |
| MOR044697 | MOR044707 | MOR042596 | AB |
| MOR044698 | MOR044707 | MOR042596 | AB |
| MOR044705 | MOR044707 | MOR042596 | AB |
| MOR044708 | MOR044707 | MOR042596 | AB |
| MOR044713 | MOR044715 | MOR042752 | A3 |
| MOR044716 | MOR044715 | MOR042752 | A3 |

TABLE 12-continued

| Epitope Binning. | | | |
|---|---|---|---|
| MOR# | Representative | Parental | Bin |
| MOR044710 | MOR044709 | MOR042765 | A3 |
| MOR044717 | MOR044709 | MOR042765 | A3 |
| MOR044720 | MOR044709 | MOR042765 | A3 |

Internalization Assay

To analyze the internalization of an antibody-receptor complex, a human Fc-specific pHrodo-labeled Fab ("MorpHin") was used. MorpHin binds to the analyzed antibody and after target recognition and internalization the antibody complex can be detected via red fluorescence signals (emission maxima: 566-590 nm) which rise in an acidic environment (lysosomal compartments).

CHO-hDAP12-hTREM2 cells were seeded in a 96-well plate (50 μl/well, 4.0E+05 cells/ml) and allowed to attach overnight at 37° C. and 5% $CO_2$. Next day, the plates were cooled down on ice for 30-60 min. The IgGs (40 nM in culture medium) were pre-incubated with 200 nM pHrodo labeled Fab MorpHin (70 μl each) for 30 min at 37° C. and subsequently cooled down on ice for 15 min, before 50 μl of each mixture were added to the cells and incubated at 37° C. and 5% $CO_2$ for 6 h. After washing the cells twice with DPBS (100 μl/well), the cells were detached using Accutase (50 μl/well, 20-30 min, 37° C., 5% CO2). After addition of 150 μl wash buffer (DPBS+/3% FBS/0.02% $NaN_3$) cells were centrifuged and resuspended in 100 μl wash buffer. Fluorescence was measured using the FACS Array device (96-well, 532 nm, yellow/PE-channel) and results were analyzed using FlowJo Software. MOR03207 was used as negative control. Results are shown in Table 13.

TABLE 13

| Internalization of TREM2 upon antibody binding after 6 h compared to control (MOR03207) or the respective parental IgG. | | | |
|---|---|---|---|
| MOR# | Parental | Internalization; fold over background after 6 h | Internalization compared to parental after 6 h |
| MOR044721 | MOR043962 | 19.6 | 0.3 |
| MOR044722 | MOR043962 | 18.1 | 0.3 |
| MOR044724 | MOR043962 | 5.5 | 0.1 |
| MOR044726 | MOR043963 | 26.1 | 0.5 |
| MOR044693 | MOR042493 | 33.5 | 0.7 |
| MOR044694 | MOR042493 | 37.2 | 0.8 |
| MOR044702 | MOR042493 | 40.1 | 0.8 |
| MOR044746 | MOR042493 | 33.3 | 0.7 |
| MOR044695 | MOR042556 | 39.4 | 0.9 |
| MOR044728 | MOR042556 | 32.2 | 0.7 |
| MOR044734 | MOR042556 | 34.9 | 0.8 |
| MOR044737 | MOR042556 | 29.3 | 0.6 |
| MOR044738 | MOR042556 | 33.7 | 0.7 |
| MOR044739 | MOR042556 | 30.2 | 0.7 |
| MOR044697 | MOR042596 | 30.0 | 0.8 |
| MOR044698 | MOR042596 | 57.1 | 1.5 |
| MOR044705 | MOR042596 | 62.4 | 1.6 |
| MOR044708 | MOR042596 | 36.6 | 0.9 |
| MOR044713 | MOR042752 | 34.5 | 1.0 |
| MOR044716 | MOR042752 | 33.4 | 0.9 |
| MOR044710 | MOR042765 | 37.6 | 1.2 |
| MOR044717 | MOR042765 | 35.4 | 1.1 |
| MOR044720 | MOR042765 | 37.2 | 1.1 |

Stabilization Assay—PMA-Induced Shedding on CHO-hDAP12-hTREM2

In order to investigate the ability of the developed IgGs to stabilize the TREM2 receptor on the cells' surfaces against PMA-induced shedding, CHO-hDAP12-hTREM2 cells were used for a FACS based stabilization assay. To avoid inactivation of PMA, antibodies and controls were diluted in azide-free assay buffer (final concentration 200 nM and 20 nM) and incubated with pre-cooled cells ($5.0\times10^4$ cells per well, diluted in azide-free assay buffer) for 45 min at 30° C., shaking at 300 rpm. The sheddase stimulator PMA was added at a final concentration of 50 ng/ml and incubated with the cell-antibody-mix for 30 min at 4° C., shaking at 300 rpm. After washing, the bound IgGs were detected by incubation with fluorescently labeled detection antibodies (goat anti-human IgG-Alexa 647; mouse anti-goat IgG-Alexa 647) for 1 h at 4° C. Fluorescence was measured using the ForeCyt software at the iQUE device (384-well, ~37 μL, sip time 1 sec).

Stabilization Assay—Constitutive Shedding on CHO-hDAP12-hTREM2

In order to investigate the ability of the developed IgGs to stabilize the TREM2 receptor on the cells' surfaces CHO-hDAP12-hTREM2 cells as well as the parental cell line CHO-hDAP12 were used for a FACS based stabilization assay. $3.0\times10^4$ cells per well were transferred into the wells of the 96-well cell culture plates and allowed to attach for ~5-6 h at 37° C. and 5% $CO_2$. IgGs and control antibodies (MOR03207, polyclonal goat anti-hTREM2 antibody (R&D Systems; AF1828)) were diluted in culture medium and added to the cells at final concentrations of 100 nM and 10 nM. The sheddase inhibitor DPC 333 was used as positive control (5 μM in culture medium). The cell culture plates were incubated o/n at 37° C. and 5% $CO_2$.

Next day, the supernatant was removed and the adherent cells were detached using 50 μL accutase per well for ~20-30 min at 37° C. and 5% CO2. After washing, the bound IgGs were detected by incubation with fluorescently labeled detection antibodies (goat anti-human IgG-Alexa 647; mouse anti-goat IgG-Alexa 647) for 1 h at 4° C. Fluorescence was measured using ForeCyt software on the iQUE device (384-well, ~37 μL, sip time 2 sec).

Lead Candidates

Upon in-depth characterization of 57 matured IgGs, 23 clones were selected as lead candidates. An overview of the 23 selected candidates is depicted in Table 14.

TABLE 14

| Lead candidates. | | | | | | | | | | | | | |
|---|---|---|---|---|---|---|---|---|---|---|---|---|---|
| MOR# | Parental | Type | Frame-work | Domain | sDAS risk | SET $K_D$ [pM] Human | Cyno | Mouse cross reactivity | TREM2 activation (fold in RGA) | Stabilization Mph-FACS | Phagocytosis enhancing | Engineering |
| 44693 | 42493 | Stabil-izing | VH6 κ1 | IgSF | medium | 2 | 4 | Weak | 1.5 | ++ | + | No |
| 44694 | | anti-bodies | VH6 κ1 | IgSF | low | 9 | 4 | + | 1.3 | ++ | ++ | No |
| 44702 | | | VH6 κ1 | IgSF | low | 5 | 4 | + | 1.6 | ++ | ++ | No |
| 44746 | | | VH6 κ1 | IgSF | low | 3 | 4 | + | 1.3 | ++ | ++ | No |
| 44695 | | | VH6 κ1 | IgSF | medium | 15 | 1 * | Weak | n.d. | ++ | + | PTM removal |
| 44728 | | | VH6 κ1 | IgSF | low | 2 | 1 | + | 1.1 | ++ | ++ | PTM removal |
| 44734 | 42556 | | VH6 κ1 | IgSF | medium | 5 | 1 | + | 1.1 | ++ | ++ | PTM removal |
| 44737 | | | VH6 κ1 | IgSF | medium | 3 | 1 | + | 1.1 | ++ | + | PTM removal |
| 44738 | | | VH6 κ1 | IgSF | medium | 3 | 1 | + | 1 | ++ | ++ | PTM removal |
| 44739 | | | VH6 κ1 | IgSF | medium | 4 | 2 | + | 1.1 | ++ | ++ | PTM removal |
| 44697 | | | VH1B κ1 | IgSF | low | 57 | 56 | Weak | n.d. | ++ | + | No |
| 44698 | 42596 | | VH1B κ1 | IgSF | low | 46 | 39 | Weak | 1 | ++ | ++ | No |
| 44705 | | | VH1B κ1 | IgSF | low | 12 | 6 * | + | 1 | ++ | ++ | No |
| 44708 | | | VH1B κ1 | IgSF | high | 15 | 7 | + | n.d. | ++ | ++ | No |
| 44721 | | | VH1A κ1 | IgSF | medium | 5 | 10 | + | 0.9 | + | ++ | No |
| 44722 | 43962/3 | | VH1A κ1 | IgSF | medium | 8 | 13 | + | 0.9 | + | ++ | No |
| 44724 | | | VH1A κ1 | IgSF | medium | 85 | 130 | + | 1.7 | + | ++ | No |
| 44726 | | | VH1A κ1 | IgSF | medium | 9 | 16 | + | 0.9 | + | + | No |
| 44713 | 42752 | Ac-tivating | VH1A κ1 | IgSF | low | 11 | 4 | Weak | n.d. | + | + | No |
| 44716 | | anti-bodies | VH1A κ1 | IgSF | low | 150 * | 100 | Weak | 2 | + | ++ | No |
| 44710 | | | VH5 λ2 | IgSF | medium | 27 | 26 | + | 2.3 | ++ | + | Germlining |
| 44717 | 42765 | | VH5 λ2 | IgSF | low | 18 | 33 | + | n.d. | + | no | Germlining |
| 44720 | | | VH5 λ2 | IgSF | medium | 8 | 10 | + | n.d. | + | ++ | Germlining |

* KD restriction due to outliers or to high concentration of applied IgG

For the columns "Stabilization Mph-FACS" and "Phagocytosis enhancing", moderate and strong fulfilment of the desired criteria are indicated by + and ++, respectively.

Example 2: Stabilization of Cell Surface TREM2 by an Anti-TREM2 Antibody

Material and Methods

Solution Equilibrium Titration (SET)

Affinity determination in solution was basically performed as described in the literature (Friguet, B et al. J Immunol Methods, 1985. 77(2):p. 305-319). In order to improve the sensitivity and accuracy of the SET method, it was transferred from classical ELISA to ECL-based technology (Haenel, C et al. Anal Biochem, 2005. 339(1):p. 182-184).

1 mg/mL goat-anti-human Fab fragment specific antibodies (Bethyl) were labeled with MSD Sulfo TAG™ NHS-Ester (Meso Scale Discovery|Gaithersburg MD|USA) according to the manufacturer's instructions.

The experiments were carried out in polypropylene microtiter plates and PBS (GIBCO 14190|pH 7.0-7.2) containing 0.5% BSA and 0.02% Tween20 as assay buffer. Serial dilutions of unlabeled antigen were prepared, starting with a concentration at least 10 times higher than the expected $K_D$. Wells without antigen were used to determine Bmax values; wells containing only assay buffer were used to determine background. After addition of appropriate amount of binder (antibody concentration similar to or below the expected $K_D$, 60 μL final volume), the mixture was incubated over night at RT.

MSD plates were blocked with 3% BSA in PBS and coated with biotinylated antigen (hTREM2 ECD (19-174)-hFc-bio) on streptavidin plates (30 μL per well). After washing the plate with PBS with 0.05% Tween 20, the equilibrated samples were transferred to the plates and incubated for 20 min. Following incubation, 30 μL per well of the MSD-Sulfo-tag labeled detection antibody (anti-human Fab|final dilution typically 1:2,000) was added to the washed MSD plate and incubated for 60 min at RT on an Eppendorf shaker (700 rpm).

After washing the MSD plate and adding 30 μL/well MSD Read Buffer T with surfactant, electrochemiluminescence signals were detected using a Sector Imager 6000 (Meso Scale Discovery, Gaithersburg, MD, USA).

The data was evaluated with XLfit (IDBS) software applying customized fitting models. For $K_D$ determination of Fab molecules the fit model according to Haenel, 2005 was used (Haenel, C et al. Anal Biochem, 2005. 339(1):p. 182-184). For $K_D$ determination of IgG molecules and monomeric antigens a fit model for IgG was used, modified according to (Piehler, J et al. J Immunol Methods, 1997. 201:p. 189-206)). For equations also refer to (Della Ducata, D et al. J Biomol Screening, 2015. 20(10):p. 1256-1267). SET screening (Della Ducata, D et al. J Biomol Screening, 2015. 20(10):p. 1256-1267) was in principle performed as described above. For ranking of the matured binders by Solution Equilibrium Titration a model was applied based on the principles described by Haenel and coworkers (Haenel, C et al. Anal Biochem, 2005. 339(1):p. 182-184). A constant amount of diluted BEL extract (containing borate buffer, EDTA and lysozyme) was equilibrated over night with different concentrations of antigen.

The mixture was then transferred to MSD plates, which were previously coated with antigen, and after incubation and washing, a suitable MSD-Sulfo-tag labeled detection antibody was added.

Subsequently, the concentration of unbound Fab was quantified via ECL detection using the Sector Imager 6000 (Meso Scale Discovery|Gaithersburg|MD|USA).

Results were processed using XLfit (IDBS) software, applying the corresponding fit model as described above to estimate affinities and thus identify clones most improved by maturation.

Determination of $K_D$ by Label-Free Kinetics Via SPR (Biacore)

For $K_D$ determinations, monomer fractions of antibody protein (IgG) were used (at least 90% monomer content, as analyzed by analytical SEC).

Affinity determination by determining kinetic rate constants was performed by SPR (Biacore T200) instruments as described below.

$K_D$ Determination Via Antibody Capture Setup

An appropriate high-capacity capture surface was prepared, e.g. by covalently immobilizing an appropriate capture ligand onto a CM5 chip (Biacore, GE Healthcare) using EDC/NHS chemistry. Examples for appropriate capture systems were anti-hu-Fc antibody (Biacore|GE Healthcare), or MabSelect SuRe Ligand (GE Healthcare).

For $K_D$ determination of Fab fragments, hTREM2 ECD (19-174)-hFc was captured as ligand, and Fab fragments used as analytes in solution. For $K_D$ determination of IgG samples, IgG was captured as ligand, and monomeric TREM2 proteins used as analytes in solution (e.g. hTREM2 ECD (19-174)-His, mTREM2 ECD (19-168)-His, or cyTREM2 ECD (19-174)-APP-Avi).

Six to eight different analyte concentrations (e.g. 2-fold serial dilution) were used for analysis during kinetic experiments. After each cycle, the sensor surface was regenerated to remove captured antibody/antigen complexes, while maintaining the integrity of the capture surface. A blank injection of running buffer was used for referencing.

Evaluation of Data

Sensorgrams were evaluated with the corresponding instrument's evaluation software, i.e. Biacore T200 Evaluation Software 2.x or 3.x, respectively (Biacore, GE Healthcare). All sensorgrams were fitted to a 1:1 binding model to determine kon and koff rate constants, which were used to calculate $K_D$.)

Protein Panel Profiling (3P)

For protein panel profiling (Frese, K. et al. mAbs, 2013. 5(2):p. 279-287), 32 different proteins and controls were coated on two 384-well MSD standard plates at a concentration of 1.0 μg/mL at 4° C., overnight.

The coating solution was discarded and plates were blocked with 50 μL 3% (w/v) BSA in PBS for one hour at RT on a microtiter plate shaker (~500 rpm) followed by three washing steps with 50 μL washing buffer (PBS with 0.05% (v/v) Tween 20).

Antibody samples (Fab fragment or IgG) were diluted to 100 nM and 10 nM in assay buffer (PBS with 0.5% (w/v) BSA, 0.05% (v/v) Tween 20). As controls, MOR reference mAb anti-lysozyme MOR03207 Fab or IgG (depending on the sample format) and assay buffer were used. Samples and controls were added at 30 μL/well and incubated for three hours at RT on a microtiter plate shaker.

The plates were washed three times and 30 μL detection antibody (ECL-labeled anti-human Fab) were added per well and incubated for one hour on a microtiter plate shaker (~500 rpm). After washing the MSD plate and adding 35 μL/well MSD Read Buffer T with surfactant, electrochemiluminescence signals were detected using a Sector Imager 6000 (Meso Scale Discovery, Gaithersburg, MD, USA).

For evaluation, signals of the antibody sample on a certain protein were divided by the respective signals of the reference mAb MOR03207 resulting in a binding ratio (BR). The cumulative binding ratio (CBR) of all proteins except the controls (25 in total) was then calculated.

Binding Profile Assessment Using a Human Plasma Membrane Protein Cell Array

Background Screen

Human HEK293 cells were grown on glass slides and fixed. Test antibodies were added at 2 μg/ml. Slides were subsequently incubated with an AlexaFluor647 labelled anti-human IgG Fc detection antibody, followed by fluorescence imaging. This detection antibody has been validated previously for use in Retrogenix's system for detecting human IgGs and human Fc fusion proteins.

Primary Screen 4955 biscistronic expression vectors, each encoding ZsGreen1 and a full-length human plasma membrane protein, were spotted in duplicates onto slides, and human HEK293 cells were reverse-transfected (14 slide sets per antibody). Of the 4955 human plasma membrane proteins screened, more than 3500 are unique genes.

Test antibodies were added to each slide after cell fixation and detection of binding was performed by using the same fluorescent secondary antibody as used in the Pre-screen. ZsGreen1 fluorescence signal was used to confirm proper transfection and localize spots of transfected cells. A protein 'hit' is defined as a duplicate spot showing a raised signal compared to background levels (Alexa 647 channel). This is achieved by visual inspection using the images gridded on the ImageQuant software. Hits were classified as 'strong, medium, weak or very weak', depending on the intensity of the duplicate spots.

Cell Lines

A hTREM2 and hDAP12 protein expressing CHO cell line was produced according to standard cell culture procedures. CHO cells were sequentially transfected with eukaryotic expression vectors containing cDNAs for human hDAP12 and hTREM2. Resulting CHO-hTREM2/hDAP12 double transfected cells (CHO-hTREM2) were grown in DMEM/F12 medium supplemented with 10% fetal bovine serum, 0.2 mg/ml G418 and 0.2 mg/mL hygromycin. Confluent CHO cells were harvested by cell dissociation buffer (Gibco 13151-014) and cell surface TREM2 was quantified by flow cytometry as described below. Similarly CHO clonal cell lines were generated that recombinantly express hDAP12 and mouseTREM2 or hDAP12 and cynomolgus TREM2.

Chimeric human TREM2-human TREM1 constructs were generated using standard cloning procedures. The TREM2-IGSF-TREM1 stalk construct contained the IGSF domain of TREM2, the stalk region of TREM1 followed by TM and intracellular domain of TREM2. The TREM1-IGSF-TREM2 stalk construct contained the IGSF domain of TREM1, the stalk region of TREM2 followed by TM and intracellular domain of TREM2. The domain-boundaries were determined using uniprot Q9NZC2 for TREM2 and Q9NP99 for TREM1. From each construct a stable clonal cell line was generated that stably expressed the chimeric construct and hDAP12. Confluent adherent CHO cell clones were harvested using cell dissociation buffer (Gibco 13151-014) and cell surface expressed chimeric hTREM2stalk-hTREM1-IGSF or TREM1-IGSF-TREM2 stalk was quantified by flow cytometry as described below.

A HEK cell line stably expressing a chimeric receptor consisting of TREM2-extracellular domain and DAP12 was first described by Kleinberger et al. 2014 (Kleinberger, G et al. Sci Transl Med, 2014. 6(243):p. 243ra86). In analogy a human TREM2/DAP12 chimeric receptor expressing cell line was produced by Novartis scientists according to standard cell culture procedures.

THP1 cells are human monocytic cells that express endogenously TREM2 and DAP12. These cells were transfected according to standard cell culture procedures with a luciferase gene driven by an NFAT promotor. After limited dilution clones were stimulated with PMA/ionomycine and one clone was selected (THP1-B5) that displayed more than 10 fold increase in reporter gene activity (RGA).

Macrophage Generation

Human monocytes were isolated from fully anonymized buffy-coats by negative selection using the easySep™ Human Monocyte Isolation Kit (Stemcell technologies) according to the manufacturers protocol. Monocytes were differentiated over 5-6 days into hM2A in RPMI (supplemented with 10% fetal bovine serum, glutamax (1×, Gibco, 61870-044), sodium pyruvate (Gibco, 11360-070), Non Essential Amino Acids, HEPES) with MCSF 40 ng/mL (R&D systems, 216-MC-025) and 50 ng/mL IL4 (R&D systems, 204-IL-050) differentiation-medium). M2A macrophages were harvested with cell dissociation buffer (Gibco 13151-014) and cell surface TREM2 was assessed by flow cytometry as described below. For most experiments antibodies were assessed in parallel on buffy-coats from two different donors.

FACS

To determine cellular $EC_{50}$ of antibodies on hM2A, CHO-hTREM2 or CHO-cynoTREM2, cells were treated o/n with 5 μM DPC333 (ADAM10 and 17 inhibitor; Qian, M et al. Drug Metab Dispos, 2007. 35:p. 1916-1925). Macrophages were detached with accutase (Biolegend, 423201) followed by resuspension in FACS buffer (PBS, 2% FBS, 0.5 mM EDTA, pH 8.0) supplemented with 50 μg/ml Fc block (BD, 564220) and incubated for at least 20 min on ice. Next cells were stained for 1 h at 4° C. in the same buffer with a broad concentration range of the different anti-TREM2 antibodies followed by a washing step with PBS (250 g, 4° C., 3 min). Next cells were incubated in FACS/Fc block buffer with AlexaFluor® 647 AffiniPure $F(ab')_2$ Fragment Goat Anti-Human IgG, $F(ab')_2$ fragment (Jackson Immuno Research, 109-606-097) and LIVE/DEAD® Fixable Aqua Dead Cell Stain Kit, for 405 nm excitation (Molecular Probes, L34966) for 30 min at 4° C. After a second washing step with PBS (250 g, 4° C., 3 min), cells were fixed with fixation buffer (Biolegend, 420801) for 15 min at RT, washed again and fluorescence was assessed using a BD FACS Canto II (BD, V96300323) or a FacsCalibur flow cytometer. Median fluorescence intensities corresponding to the degree of TREM2 antibody bound to cells were evaluated using FlowJo software (Millipore INC).

Stabilization Assay—Constitutive Shedding on CHO-hDAP12-hTREM2

In order to investigate the ability of the developed IgGs to stabilize TREM2 receptor on the cell surface of CHO-hDAP12-hTREM2 cells as well as the parental cell line CHO-hDAP12 were used for a FACS based stabilization assay. 3.0×10^4 cells per well were transferred into the wells of a 96-well cell culture plate and allowed to attach for ~5-6 h at 37° C. in a cell culture incubator. IgG isotype controls and control antibodies (MOR03207, polyclonal goat anti-hTREM2 antibody (R&D Systems; AF1828)) were diluted in culture medium and added to the cells at final concentrations as indicated in the figures. The sheddase inhibitor DPC333 was used as positive control (5 μM in culture medium). The cell culture plates were incubated o/n at 37° C. in a cell culture incubator.

On the following day, the supernatant was removed and adherent cells were detached using 50 μL accutase per well for ~20-30 min at 37° C. and 5% CO2. After washing, the bound IgGs were detected by incubation with fluorescently labeled detection antibodies (goat anti-human IgG-Alexa 647; mouse anti-goat IgG-Alexa 647) for 1 h at 4° C. Fluorescence was measured using the ForeCyt software at the iQUE device (384-well, ~37 μL, sip time 2 sec). Alternatively direct detection of TREM2 independent from the stabilizing antibody was achieved by using the non-cross-blocking MOR041895 Fab fragment.

Stabilization of TREM2 Expressed on hM2A by Anti-TREM2 Antibodies

M2A differentiated macrophages were detached with accutase (Biolegend, 423201) washed once with PBS followed by resuspension in FACS buffer (PBS, 2% FBS, 0.5 mM EDTA, pH 8.0) supplemented with 50 μg/ml Fc block (Fab fragment anti-Fc receptors, produced by Novartis) and incubated for at least 20 min at room temperature. Next anti-TREM2 antibodies were added to cells (concentrations indicated in the figures) followed by 24 h incubation in a cell culture incubator at 37° C. On the next day, cells were subjected to FACS analysis. FACS staining was done either with direct staining of the anti-TREM2 antibody used for stabilization or by staining with an anti-TREM2 Fab-His fragment (MOR041895) that recognized a different non-overlapping epitope at TREM2 with regard to the antibody used for stabilization. M2A macrophages were washed twice with PBS/1 mM EDTA to remove excess serum and once with FACS buffer followed by addition of 50 μg/ml Fc block (BD, 564220). To detect bound anti-TREM2 antibody that had been used for stabilization AlexaFluor® 647 AffiniPure $F(ab')_2$ fragment Goat Anti-Human IgG, $F(ab')_2$ (Jackson Immuno Research, 109-606-097) and LIVE/DEAD® Fixable Aqua Dead Cell Stain (Molecular Probes, L34966) was added for 30 min on ice. To directly stain TREM2 a different sample was treated with His labelled Fab fragment MOR041895 (100 nM) for 10 min on ice followed by addition of Anti-His PE (Miltenyi, 130-092-691) and LIVE/

DEAD® Fixable Aqua Dead Cell Stain (Molecular Probes, L34966). After 30 min on ice cells were washed once with FACS buffer then fixed with fixation buffer (Biolegend, 420801) for 15 min at RT, washed again and fluorescence was assessed using a BD FACS Canto II (BD, V96300323) or a FacsCalibur flow cytometer. Median fluorescence intensities corresponding to the degree of TREM2 antibody of Fab fragment bound to cells were evaluated using FlowJo software (Millipore INC).

Phagocytosis Assay (FACS)

M2A differentiated macrophages were detached with accutase (Biolegend, 423201) and seeded in differentiation-medium supplemented with Fc block (20 μl/ml) in tissues culture plates. After 2.5 hour in a humidified cell culture incubator at 37 deg C., antibodies were added to macrophages at concentrations indicated in the figures and incubated for another 18 h in a humidified cell culture incubator at 37 deg C. Cell culture medium was removed, macrophages were washed twice with PBS and resuspended in differentiation medium. Next the same volume of differentiation medium supplemented with pHrodo Red *S. aureus* Bioparticles (Conjugate for Phagocytosis, Molecular Probes, A10010) was added and the solution was subjected to centrifugation (1 min, 500 g) to synchronize phagocytosis followed by 2.5 h incubation in a humidified cell culture incubator at 37 deg C. Cells were washed twice with PBS, detached with accutase, washed again on ice with FACS buffer and resuspended on ice in FACS buffer followed by FACS analysis on a FACS Canto II (BD). Median fluorescence intensities corresponding to the degree of phagocytosis taken up by cells were evaluated using FlowJo software (Millipore INC). Experiments included always an isotype control (MOR03207) antibody with identical Fc silencing mutations. This antibody does not recognize epitopes on hM2A macrophages.

Phagocytosis Assay (Incucyte)

Human M2A differentiated macrophages or human iPS derived microglia were detached with accutase StemPro (Gibco #A11105-01, Lot #1648949) and suspended in M2a macrophages complete medium. Cell culture medium was removed and the cells were resuspended in RPMI+0.5% FCS. 50 μL of prepared cell suspension were plated into each insert of 96 well black clear plate, Poly-D-Lysine, BD plate (7500 (M2A)-10000 (iPS derived microglia) cells/well) and allowed to adhere for 3 h at 37° C. pHrodo labeled bioparticles (Either: pHrodoGreen *S. aureus* Bioparticles—Essen Bioscience #4620 or pHrodoGreen labeled apoptotic SH-SY5Y cells (1.2x10^5 cells/well)) were added and the plates were transferred into the IncuCyte ZOOM platform which was housed inside a cell incubator at 37° C./5% $CO_2$, until the end of the assay. Two images per well from three technical replicates were taken every 30 min for 20 h using a 10× objective lens and then analyzed using the IncuCyte™ Basic Software.

Chemotaxis Assay (Incucyte)

M2A differentiated macrophages, or human iPS derived microglia were plated in complete medium at 5000 (M2A macrophages) or 7500 (iPS derived microglia) cells/well in transwell plates (Essen Bioscience) precoated Matrigel (GFR-Corning #354230 Lot: 631008). For migration assays with antibody treatment, microglia each anti-TREM2 antibody was supplemented at 100 nM or the corresponding isotype control at 100 nM. Transwells were placed into a reservoir plate containing 200 μl of complete medium with 20 ng/ml recombinant C5a or 100 ng/ml recombinant C5a. Transwell migration was monitored and analyzed using Incucyte S3® software (Essen Bioscience).

Reporter Gene Assay

To stimulate RGA activity full length antibodies were coated at a concentration of 10 μg/ml to high-protein-binding cell culture plates (Greiner #781094) for 8-16 h. After washing of the plates, THP-B5 cells, that had been treated for 16 h with DPC333 in full culture medium were seeded on antibody coated 384-well-plates for 16 hours. Next, luciferase activity was determined using steadylite plus according to the manufacturers protocol (Steadylite plus Luciferase detection reagent, Perkin Elmer, #6066751). Results are expressed as fold stimulation over control Ab (IgG isotype).

Syk Phosphorylation Assay $2\times10^6$ human M2A macrophages per well were seeded in 6 well dishes in culture medium containing 2 μM DPC333. After 24 h cells were washed once with PBS and assay buffer (RPMI supplemented with 1% FCS, 10 mM HEPES, 2 μM DPC333 and 50 μg/ml anti-Fc Fab block) was added. Cells were incubated for 4 h at 37 deg C. Next cells were removed from the incubator, placed on ice and washed once with ice cold PBS. Then 1 ml assay buffer containing isotype control antibody or anti-TREM2 antibody (100 nM) was added. A commercially available anti-TREM2 antibody was also included (Rat monoclonal IgG2B, R&D, MAB17291). Incubation on ice was continued for 18 min. Thereafter medium was removed and cells were washed with ice cold PBS to remove surplus, unbound TREM2 antibody. Then 1 ml of pre-warmed assay buffer without anti-Fc block but supplemented with 100 nM of crosslinking antibody (for rat anti-TREM2 first antibody: Jackson Immuno Research #112005008, goat anti rat IgG Fc-gamma fragment; for human anti-TREM2 antibody: Jackson Immuno Research #109-005-008, goat anti human IgG Fc-gamma fragment) was added. Incubation was continued for 10 min at 37 deg C. Next plates were placed on ice, washed once with cold PBS and cold lysis buffer (800 μl/well; Thermo scientific, #78501, M-PER mammalian protein extraction reagent) supplemented with protease/phosphostop (Thermo scientific, #1861281, Halt protease and phosphatase inhibitor cocktail; 1:100). Cell lysis was carried out for 5 min followed by centrifugation for 20 min at 10'000 g at 4 deg. Supernatant was incubated with anti-syk antibody (Cell Signaling, clone D3Z1E-XP, #13198; 2.45 μg/ml) at RT for 1 h with gentle agitation. 50 μl protein A/G beads (Thermo Scientific, #88802) were added to each sample and incubation was continued for 1 h at RT with gentle agitation. Next samples were placed into a magnet (Thermo Scientific) and supernatant was removed. Beads were washed 3 times with PBS-T (PBS+0.1% Tween20), and bound proteins were eluted with 30 μl 1×WB loading dye (NuPAGE, LDS Sample Buffer Novex, NP0008).

Next samples were heated for 10 minutes at 70 deg C., separated by magnet and 25 μl of each sample was loaded on a 4-12% gel (NuPAGE 4-12% Bis-Tris Midi Protein Gels, 10-well, Novex, WG1403BOX) using MES (NuPAGE MES, Novex, NP0002) as running buffer. Proteins were transferred to PVDF membranes and membranes were blocked for 1 h with 3% TopBlock buffer (LuBio, in PBS-T 0.1%), followed by incubation with anti phospho-tyrosine AB 4G10 (mouse monoclonal, Millipore #05-1050) at 4 deg C. overnight. Membranes were washed and incubated at RT for 1 h with clean blot antibodies (Clean-Blot, IP Detection Reagent (HRP), 21230) followed by another washing step and detection with ECL (ECL Select reagent, GE Healthcare, RPN 2235) according to the manufacturers protocol.

For detection of total Syk, membranes were treated with Restore stripping buffer followed by detection of total Syk using a rabbit anti human Syk antibody (Cell Signaling #2712) and clean blot detection reagent.

CRISPR Knock-In (KI) of Human TREM2 (hTREM2 KI)

Humanized TREM2 mice are generated by introducing the human TREM2 cDNA (isoform 1, UniProt: Q9NZC2-1) including a bovine growth hormone polyA signal into the ATG of the mouse TREM2 gene in exon1 by CRISPR. Founder animals are screened by PCR for hTREM2 expression and bred to homozygosity. Bone marrow derived macrophages are generated from different founder animals and expression of hTREM2 as well as lack of mouse TREM2 is confirmed by FACS analysis. One founder line is selected and subjected to sequence analysis of the TREM2 locus to verify correct insertion of TREM2 cDNA into the genome.

Cuprizone Model in Humanized TREM2 Crispr-Knock-In Mice

Prophylactic/Concomitant Treatment of the Murinized MOR44698 TREM2 Antibody In the Cuprizone Model The cuprizone model is a toxin-induced demyelination model to study myelination processes in the CNS with only minor involvement of the peripheral immune system. Cuprizone, a copper chelator, induces mitochondrial damage and eventually oligondendrocyte dell death, whereas oligodendrocyte precursor cells are not affected and can still exert their proper function (proliferate, maturate and remyelinate). Intoxication induced by cuprizone in rodents induces neuroinflammation, neuronal damage and demyelination followed by recovery. The cuprizone model is well suited to test regenerative treatment paradigms for demyelinating disease such as e.g. MS that enhance remyelination independently of invading peripheral immune cells.

Humanized TREM2 Crispr-knock-in mice (hTREM-KI) were treated; (0.2% in food) with cuprizone (Bis(cyclohexanone) oxaldihydrazone, Sigma-Aldrich) for 7 weeks with 1 day before and twice weekly thereafter with 44698 and the isotype control MOR03207 (short: 3207) i.p., 30 mg/kg. During the study longitudinal, non-invasive magnetic resonance imaging (MRI) was performed measuring magnetization transfer ration (MTR) and intensity/contrast, which is considered to detect myelin and neuroinflammation, respectively. After 7 weeks of prophylactic/concomitant treatment with antibody and cuprizone, animals were killed and histology on coronal brain paraffin sections was performed. Iba1 antibody was used to evaluate microglia numbers and morphology, and Luxol fast blue staining was used to analyze myelin content.

Therapeutic Treatment of the Murinized MOR44698 TREM2 Antibody in the Cuprizone Model hTREM-KI mice were treated with cuprizone (0.2% in food) for 5 weeks then switched to normal food and were treated twice weekly with 44698 and the isotype control 3207 i.p., 30 mg/kg for 2 weeks. During the study longitudinal, non-invasive magnetic resonance imaging (MRI) was performed measuring magnetization transfer ration (MTR) and intensity/contrast. After 2 weeks of therapeutic treatment with antibody after a 5-week cuprizone intoxication animals were killed and histology on coronal brain paraffin sections was performed. Iba1 antibody was used to evaluate microglia numbers and morphology, Luxol fast blue staining was used to analyze myelin content.

MRI: Measurements are performed with a Biospec 70/30 spectrometer (Bruker Medical Systems, Ettlingen, Germany) operating at 7 T. The operational software of the scanner is Paravision 5.1 (Bruker). Images are acquired from anesthetized, spontaneously breathing animals using a mouse brain circularly polarized coil (Bruker, Model 1P T20063 V3; internal diameter 23 mm) for radiofrequency excitation and detection. Neither cardiac nor respiratory triggering is applied. Following a short period of introduction in a box, animals are maintained in anesthesia with 1.5% isoflurane (Abbott, Chain, Switzerland) in oxygen, administered via a nose cone. During MRI signal acquisitions, animals are placed in prone position in a cradle made of Plexiglas, the body temperature is kept at 37±1° C. using a heating pad, and the respiration is monitored. AT2-weighted, two-dimensional multi slice RARE (Rapid Acquisition with Relaxation Enhancement) sequence is used for determining the anatomical orientation and for evaluating signal intensities. This is followed by a two-dimensional multi slice gradient-recalled FLASH (Fast Low-Angle Shot) acquisition for assessment of MTR. As both sequences have the same anatomical parameters, the choice of the regions-of-interest for evaluations is performed on the RARE images and then transferred to the FLASH images. MRI images are analyzed using the ParaVision software. The parameters of the acquisitions are the following: (a) RARE sequence: effective echo time 80 milliseconds (ms), repetition time 3280 ms, RARE factor 16, 12 averages, field of view 20×18 mm2, matrix size 213×192, pixel size 0.094×0.094 mm2, slice thickness 0.5 mm, 15 adjacent slices. Hermite pulses of duration/bandwidth 1 ms/5400 Hz and 0.64 ms/5344 Hz are used for radiofrequency excitation and refocusing, respectively. Fat suppression is achieved by a gauss512 pulse of 2.61 ms/1051 Hz duration/bandwidth followed by a 2-ms-long gradient spoiler. The total acquisition time is of 7 min 52.3 s; (b) FLASH sequence: echo time 2.8 ms, repetition time 252.8 ms, 4 averages, field of view 20×18 mm2,matrix size 213×192, pixel size 0.094×0.094 mm2, slice thickness 0.5 mm, 15 adjacent slices. A hermite pulse of 0.9 ms/6000 Hz duration/bandwidth and flip angle 300 is used for radiofrequency excitation. MTR contrast is introduced by a gauss pulse of 15 ms/182.7 Hz duration/bandwidth applied with radiofrequency peak amplitude of 7.5 μT and an irradiation offset of 2500 Hz. The acquisition is then repeated with the same parameters but without the introduction of the MTR contrast. MTR is then computed using the formula MTR=(S0−SMTR)/S0 where S0 and SMTR represent respectively the signal intensities in the FLASH acquisitions without and with the introduction of the MTR contrast. The total acquisition time for both data sets is 6 min 31.6 s.

Before killing animals are perfused trans-cardiac by phosphate-buffered saline (PBS) and in some cases then with 4% paraformaldehyde (PFA). The brains or half-brains are subsequently isolated and fixed in 4% PFA for 48 h at 4° C. Some half-brains are deep frozen.

Histology: After fixation brains are processed for paraffin embedding by dehydration through increasing ethanol series. Automated immunohistochemistry of paraffin sections is performed on 3 μm paraffin sections mounted on SuperFrost+ slides (Thermo Fisher Scientific) and automatically immunostained using the Discovery XT technology (Ventana, Roche Diagnostics). Sections are deparaffinized, rehydrated, subjected to antigen retrieval by heating with CC1 cell conditioning buffer for 28-68 min according to the antibody, incubated for 1-3 h according to the antibody at room temperature with primary antibody diluted in antibody diluent (Ventana), incubated with the respective biotinylated secondary antibody diluted in antibody diluent, reacted with DAB-Mab kit and counterstained with Hematoxylin II and Bluing reagent (Ventana). Slides are washed with soap in hot tap water and rinsed under cold running tap water to remove the soap, then dehydrated and embedded with Pertex. For LFB staining, slides are deparaffinized and rehydrated to 95% ethanol. Slides are then incubated in LFB solution (Solvent Blue 38 (Sigma S3382) in 95% ethanol and 10% acetic acid (Sigma 695092)) overnight at 60° C., rinsed in 95% ethanol for 1 min, then in distilled water for 2 min and in 0.05% lithium carbonate for 5 s. Subsequently, slides are rinsed in 70% ethanol twice for 10 s, then in distilled water for 2 min. The rinsing is repeated in 0.05% lithium carbonate (Merck 105680) prepared freshly, 70% ethanol and distilled water until there is a sharp contrast between the blue of the white matter (myelin) and the colorless grey-matter. Finally, slides are dehydrated starting with 95% ethanol and mounted in Pertex.

Antibodies: Primary antibodies are: rabbit anti-mouse MBP (Dako A0623) 1:1000; rabbit anti-mouse GST-7r (MBL 312) 1:500; Rabbit anti-Iba1 (Wako 019-19741, 50 µg/100 µl) 1:500; rabbit anti-GFAP (Dako Z0334) 1:5000; rabbit anti-mouse MOG (abeam ab32760) 1:100; rabbit anti-dMBP (Millipore AB5864) 1:3000; mouse anti-Neuro-filament (Covance SMI312) 1:5000; rabbit anti-mouse ALDH1L1 (abeam ab87117) 1:1000; rabbit anti-mouse NeuN (Milli-pore ABN78) 1:2000; rat anti-mouse CD107a (Biorad MCA4707T) 1:200; rabbit anti-mouse NG2 (abeam ab129051) 1:200; goat anti-Iba1 (Thermo Fisher Scientific PA5-18039) 1:250. Secondary detection antibodies are: Goat anti-rabbit IgG biotinylated (Jackson ImmunoResearch 111-065-144) 1:1000; Goat anti-rabbit IgG biotinylated (Vector BA-1000) 1:200 or 1:1000; Goat anti-mouse IgG biotinylated (Vector BA-9200) 1:1000; Goat anti-rat biotinylated (Vector BA-9400) 1:200.

Analysis of histological images: For the quantitative evaluation of microglia/astrocyte numbers and morphology based on image analysis from histological stained brain sections, a proprietary image analysis platform (ASTORIA, Automated Stored Image Analysis, Novartis Pharma AG) is developed based on MS Visual Studio 2010 and many functions from Matrox MIL V9 libraries (Matrox Inc). For the detection and analysis of soma, proximal and distal processes, the following sequence of steps is performed: 1. Slides with brain sections for assessment of (brown) immunohistochemically stained microglia (Iba1) or astrocyte (GFAP) soma and their proximal and distal processes were scanned with Aperio's Scanscope (Leica Biosystems AG) at 20× magnification. 2. Each image is processed using the ImageScope software (V12.1.0.5029, Aperio, Leica Biosystems AG) according to the following steps: A: color deconvolution to obtain brown staining without blue; B: segmentation of brain tissue from white background through thresholding, morphological closing, filling of holes, opening and elimination of too small objects, resulting in a binary mask of the valid tissue and sample area; C: adaptive thresholding for the individual segmentation of soma, based on the average gray value of the blue channel of the color-deconvoluted brown image at sufficiently dark regions (indicative for soma). The computed threshold is used for binarization, and after size filtering yielded the soma mask image (within the valid sample region); D: segmentation of processes through morphological tophat transformation with a size to pick thin processes. Adaptive thresholding is applied again to segment the processes (using the previously determined gray average of brown objects), followed by binarization of the top hat image and size filtering of the resulting objects; E: subtraction of soma (that may also have been picked by top hat thresholding) to obtain an image mask of true processes; F: ultimate thinning of processes for length computation; G: proximal processes: A predefined number of dilations of soma is used to define a reference (marker) region for proximal soma, employing a circle around the soma center to define the cutoff boundary for proximal processes. Thinned proximal processes with marker in dilated soma and limited by circular influence zone (set of "proximal thinned processes") are then reconstructed around the soma center. "Final proximal processes" are collected through reconstruction of all processes having markers in the "proximal thinned processes" set; H: soma is added to proximal processes to obtain a set of "visible microglia"; I: Distal processes: Reconstruction of processes from proximal processes only (i.e. ignoring those in background or from soma in different focus plane), then subtract circular region defining proximal processes, to yield set of distal processes; J: in the optical density computation for soma as well as "visible microglia" (individual soma+proximal processes complex within circular reference region, local background (non-visible microglia) is used for reference; K: morphometric features (size, form factor, length) are computed for soma, proximal and distal processes.

Microglia Depletion and Repopulation with the CSF1R Kinase Inhibitor BLZ945

BLZ945 depletion model allows to assess the efficacy of the anti-TREM2 antibodies to support the trophic activities of TREM2.

The colony-stimulating factor 1 receptor (CSF1R) signaling pathway is essential for microglia survival. The CSF1R kinase inhibitor BLZ945 induces depletion of microglia and upon BLZ945 removal microglia repopulate the brain. The BLZ945 treatment and analysis is performed as previously described (Beckmann, N et al., Acta Neuropathol Commun, 2018. 6(1)).

Animals were treated with 169 mg/kg of BLZ945, once per day (qd), per os (p.o.) 10 ml/kg for at least 5 days. BLZ945 was prepared in 0.5% methylcellulose in water and 0.1% Tween-80. The animals were given access to food and water ad libitum.

Animals were treated with 30 mg/kg i.p. once per week antibody or isotpye control before (at least 1 day), during (for at least 5 days) or after BLZ945 treatment for at least 3 days. Before killing animals were perfused trans-cardiac by phosphate-buffered saline (PBS) and in some cases then with 4% paraformaldehyde (PFA). The brains or half-brains were subsequently isolated and fixed in 4% PFA for 48 h at 4° C. Some half-brains were deep frozen or were put fresh in cold PBS.

Histology: After fixation brains were processed for paraffin embedding by dehydration through increasing ethanol series. Automated immunohistochemistry of paraffin sections was performed on 3 µm paraffin sections mounted on SuperFrost+slides (Thermo Fisher Scientific) and automatically immunostained using the Discovery XT technology (Ventana, Roche Diagnostics). Sections were deparaffinized, rehydrated, subjected to antigen retrieval by heating with CCT cell conditioning buffer for 28-68 min according to the antibody, incubated for 1-3 h according to the antibody at room temperature with primary antibody diluted in antibody diluent (Ventana), incubated with the respective biotinylated secondary antibody diluted in antibody diluent, reacted with DAB-Mab kit and counterstained with Hematoxylin II and Bluing reagent (Ventana). Slides were washed with soap in hot tap water and rinsed under cold running tap water to remove the soap, then dehydrated and embedded with Pertex. For LFB staining, slides were deparaffinized and rehydrated to 95% ethanol. Slides were then incubated in LFB solution (Solvent Blue 38 (Sigma S3382) in 95% ethanol and 10% acetic acid (Sigma 695092)) overnight at 60° C., rinsed in 95% ethanol for 1 min, then in dis-tilled water for 2 min and in 0.05% lithium carbonate for 5 s. Subsequently, slides were rinsed in 70% ethanol twice for 10 s, then in distilled water for 2 min. The rinsing was repeated in 0.05% lithium carbonate (Merck 105680) prepared freshly, 70% ethanol and distilled water until there was a sharp contrast between the blue of the white matter (myelin) and the colorless grey-matter. Finally, slides were dehydrated starting with 95% ethanol and mounted in Pertex.

Antibodies: Primary antibodies are: Rabbit anti-Iba1 (Wako 019-19741, 50 μg/100 μl) 1:500; rabbit anti-GFAP (Dako Z0334) 1:5000; mouse anti-Neurofilament (Covance SM1312) 1:5000; rabbit anti-mouse ALDH1L1 (abcam ab87117) 1:1000; rabbit anti-mouse NeuN (Milli-pore ABN78) 1:2000; rat anti-mouse CD107a (Biorad MCA4707T) 1:200; goat anti-Iba1 (Thermo Fisher Scientific PA5-18039) 1:250. Secondary detection antibodies are: Goat anti-rabbit IgG biotinylated (Jackson ImmunoResearch 111-065-144) 1:1000; Goat anti-rabbit IgG biotinylated (Vector BA-1000) 1:200 or 1:1000; Goat anti-mouse IgG biotinylated (Vector BA-9200) 1:1000; Goat anti-rat biotinylated (Vector BA-9400) 1:200.

Analysis of histological images: For the quantitative evaluation of microglia/astrocyte numbers and morphology based on image analysis from histological stained brain sections, a proprietary image analysis platform (ASTORIA, Automated Stored Image Analysis, Novartis Pharma AG) was developed based on MS Visual Studio 2010 and many functions from Matrox MIL V9 libraries (Matrox Inc). For the detection and analysis of soma, proximal and distal processes, the following sequence of steps was performed: 1. Slides with brain sections for assessment of (brown) immunohistochemically stained microglia (Iba1) or astrocyte (GFAP) soma and their proximal and distal processes were scanned with Aperio's Scanscope (Leica Biosystems AG) at 20× magnification. 2. Each image was processed using the ImageScope soft-ware (V12.1.0.5029, Aperio, Leica Biosystems AG) according to the following steps: A: color deconvolution to obtain brown staining without blue; B: segmentation of brain tissue from white background through thresholding, morphological closing, filling of holes, opening and elimination of too small objects, resulting in a binary mask of the valid tissue and sample area; C: adaptive thresholding for the individual segmentation of soma, based on the average gray value of the blue channel of the color-deconvoluted brown image at sufficiently dark regions (indicative for soma). The computed threshold was used for binarization, and after size filtering yielded the soma mask image (within the valid sample region); D: segmentation of processes through morphological tophat transformation with a size to pick thin processes. Adaptive thresholding was applied again to segment the processes (using the previously determined gray average of brown objects), followed by binarization of the top hat image and size filtering of the resulting objects; E: subtraction of soma (that may also have been picked by top hat thresholding) to obtain an image mask of true processes; F: ultimate thinning of processes for length computation; G: proximal processes: A predefined number of dilations of soma was used to define a reference (marker) region for proximal soma, employing a circle around the soma center to define the cutoff boundary for proximal processes. Thinned proximal processes with marker in dilated soma and limited by circular influence zone (set of "proximal thinned processes") were then reconstructed around the soma center. "Final proximal processes" were collected through reconstruction of all processes having markers in the "proximal thinned processes" set; H: soma was added to proximal processes to obtain a set of "visible microglia"; I: Distal processes: Reconstruction of processes from proximal processes only (i.e. ignoring those in back-ground or from soma in different focus plane), then sub-tract circular region defining proximal processes, to yield set of distal processes; J: in the optical density computation for soma as well as "visible microglia" (individual soma+proximal processes complex within circular reference region, local background (non-visible microglia) was used for reference; K: morphometric features (size, form factor, length) were computed for soma, proximal and distal processes.

MPTP Model in Humanized TREM2 Crispr-Knock-In Mice

1-Methyl-4-phenyl-1,2,3,6-tetrahydropyridin (MPTP) is a toxin that can cause symptoms in humans that are similar to Parkinson's disease. MPTP is metabolized by astrocytic monoamine oxidase-B to generate the active metabolite 1-methyl-4-phenylpyridinium (MPP+) which is then being taken up by neurons via the dopamine (DA) transporters (DATs). Amongst others, MPP+ accumulates in the mitochondrial matrix and inhibits complex I of the respiratory chain which impairs mitochondrial ATP generation. This ATP depletion together with excessive reactive oxygen species (ROS) formation due to the complex I inhibition leads to cell death. Systemic MPTP administration induces specifically dopaminergic cell death in mice which is accompanied by an increased neuroinflammation. The MPTP model was described previously (Ren, M et al., Exp Neurol, 2018. 302:p. 205-213).

Humanized TREM2 Crispr-knock-in mice (hTREM-KI) were treated with MPTP 4 times for 1 day with 15 mg/kg i.p. injections of 2 hours apart. Injections with 44698 and the isotype control MOR03207 (short: 3207) i.p., 30 mg/kg were performed at the day before MPTP, two days and four days after MPTP treatment. Seven days after the MPTP treatment animals were killed and immunofluorescence on coronal brain free-floating sections was performed. Tyrosine hydroxylase (TH) was stained with an antibody, microscopic pictures taken (with a 10× objective) and the area stained in the striatum was quantified with the Fiji software.

Before killing animals were perfused trans-cardiac by phosphate-buffered saline (PBS) and in some cases then with 4% paraformaldehyde (PFA). The brains or half-brains were subsequently isolated and fixed in 4% PFA for 24-48 h at 4° C. Some half-brains were deep frozen or were put fresh in cold PBS.

Histology: After fixation brains were embedded in 2% agarose in PBS and free floating section (at least 20-30 μm thick) were generated. Slices was transferred in a 24-well plate, washed with PBS, and incubated for 1 h in 2% (v/v) normal goat or horse serum (Vector Laboratories) in PBS supplemented with 1% (w/v) bovine serum albumin (BSA) and 0.3% (v/v) Triton X-100 (referred to here as day 1 buffer). Slices were then placed overnight in day 1 buffer containing the respective primary antibodies (rabbit anti-tyrosine hydroxlyase (TH), Millipore AB152). The following day, slices were washed twice with PBS supplemented with 0.3% BSA and 0.1% Triton X-100 (referred to here as day 2 buffer), incubated for 1 hr with the respective secondary fluorescently-labeled antibodies in day 2 buffer, washed twice with day 2 buffer, three times in PBS, and then mounted on glass slides and coverslipped. Immunostained slices were analyzed by ImageJ.

PK Study in Cynomolgus Monkey

To evaluate PK of the antibodies in non-human primate and to enable PK modeling in humans a PK study in cynomolgus monkeys was performed. 4 groups, each with 3 animals was treated with vehicle, 10, 30 or 100 mg/kg of MOR044698 at day 1 and day 106. CSF was taken predose and 48 and 168 postdose. Blood was taken predose and 0.5, 4, 8, 24, 48, 72, 96, and 168 hours postdose and further days 15, 29, 43, 57, 71, 85, and 99 postdose.

Concentration of antibody in CSF and blood will be assessed via Elisa as well as binding of antibody to sTREM2 in both compartments.

Results

Properties of Antibodies Derived from Initial and Backup Pannings

Screening efforts that followed panning experiments identified antibodies that bound in vitro with nM affinities the human extracellular domain of TREM2 (table 15). To identify whether antibodies recognize the stalk region of TREM2 or the IgSF domain, the antibodies were assessed in an ELISA assays using two different TREM2-TREM1 chimeric proteins. One construct contained the TREM2 IgSF domain followed by the TREM1 stalk region, the other protein was assembled by a TREM1 IgSF domain followed by TREM2 stalk region. Most antibodies recognize the TREM2-IgSF-TREM1stalk construct. MOR041874 binds to the stalk region of TREM2 and does not recognize the hTREM2 IgSF-T1 stalk protein. MOR041895 only binds to full length TREM2.

Antibodies also bind to recombinantly expressed human TREM2 in CHO cells with nM affinities and activate TREM2 dependent signaling via the NFAT premotor in the THP1-B5 cells (table 15).

Antibodies also bind to TREM2 endogenously expressed in human M2A macrophages (table 15, last column).

TABLE 15

| Antibody | hTREM2 Fc direct Elisa $EC_{50}$ [nM] | Elisa hTREM1 IgSF-T2 stalk-hFc-bio | Elisa hTREM2 IgSF-T1 stalk-hFc-bio | FACS CHO-DAP12-hTREM2 $EC_{50}$ [nM] | Activation THP1 B5-NFAT reporter fold activation | Binding to hM2A (FACS) |
|---|---|---|---|---|---|---|
| MOR042492 | 1.0 | no | yes | 6.1 | 1.2 | yes |
| MOR042493 | 0.9 | no | yes | 6.8 | 1.4 | yes |
| MOR042495 | 1.3 | no | yes | N.D. | N.D. | — |
| MOR042496 | 2.5 | no | yes | 9.7 | N.D. | — |
| MOR042497 | 1.0 | no | yes | 3.8 | N.D. | weak |
| MOR042511 | 3.2 | no | yes | 7.9 | N.D. | |
| MOR042512 | 3.0 | no | yes | 8.3 | N.D. | |
| MOR042556 | 1.7 | no | yes | 8.1 | 1.5 | yes |
| MOR042561 | 2.9 | no | yes | 3.5 | N.D. | |
| MOR042566 | 1.8 | no | yes | 3.4 | N.D. | |
| MOR042585 | 1.3 | no | yes | 1.9 | N.D. | weak |
| MOR042588 | 1.7 | no | yes | 2.5 | N.D. | weak |
| MOR042589 | 10.9 | no | yes | 4.9 | 1.8 | yes |
| MOR042590 | 1.6 | no | yes | 4.2 | N.D. | weak |
| MOR042596 | 2.4 | no | yes | 3.4 | 1.6 | yes |
| MOR042600 | 0.8 | weak | yes | 4.8 | 1.7 | yes |
| MOR042733 | 0.6 | no | yes | N.D. | N.D. | yes |
| MOR042752 | 1.4 | no | yes | N.D. | 2.1 | yes |
| MOR042765 | 1.6 | no | yes | N.D. | 2.4 | yes |
| MOR042778 | 3.4 | no | yes | 0.4 | N.D. | weak |
| MOR041874 | 46.1 | yes | no | 0.3 | | yes |
| MOR041895 | 16.7 | no | no | 2.5 | | |

To assess stabilizing properties of anti-TREM2 antibodies CHO-hDAP12-hTREM2 cells were treated for about 16 h with 100 nM of the antibodies. Thereafter TREM2 cell surface expression was assessed with FACS analysis.

As shown in FIG. 2, some of the IgSF binder increase TREM2 cell surface expression indicating that shedding of TREM2 by ADAM17 is impaired (e.g. MOR042492, MOR042493, MOR042556, MOR042589, MOR042596, MOR042752, MOR042765).

In a next step PTMs were removed for antibodies MOR042492 and MOR042589 and affinity maturation was carried out on several stabilizing antibodies.

TABLE 16

Determination of $K_D$ by SET screening.

| Antibody | $K_D$ [pM] |
|---|---|
| MOR044743 | 10585 |
| MOR044741 | 6886 |
| MOR044742 | 5699 |
| MOR044744 | 6801 |
| MOR044746 | <600 |
| MOR044698 | <600 |
| MOR044724 | <600 |
| MOR044722 | <600 |
| MOR044700 | <600 |
| MOR044701 | <600 |
| MOR044703 | <600 |
| MOR044747 | <600 |
| MOR044695 | <600 |
| MOR044728 | <600 |
| MOR044734 | <600 |
| MOR044737 | <600 |
| MOR044738 | <600 |
| MOR044739 | <600 |
| MOR044729 | <600 |
| MOR044730 | <600 |
| MOR044731 | <600 |
| MOR044733 | <600 |
| MOR044735 | <600 |
| MOR044736 | <600 |
| MOR044740 | <600 |
| MOR044716 | <600 |

TABLE 16-continued

Determination of $K_D$ by SET screening.

| Antibody | $K_D$ [pM] |
|---|---|
| MOR044726 | <600 |
| MOR044705 | <600 |
| MOR044708 | <600 |

TABLE 16-continued

| Determination of $K_D$ by SET screening. | |
|---|---|
| Antibody | $K_D$ [pM] |
| MOR044704 | <600 |
| MOR044706 | <600 |
| MOR044707 | <600 |
| MOR044748 | <600 |
| MOR044721 | <600 |
| MOR044702 | <600 |
| MOR044714 | <600 |
| MOR044715 | <600 |
| MOR044710 | <600 |
| MOR044720 | <600 |
| MOR044713 | <600 |
| MOR044709 | <600 |
| MOR044711 | <600 |
| MOR044712 | <600 |
| MOR044718 | <600 |
| MOR044719 | <600 |
| MOR044745 | <600 |
| MOR044749 | <600 |
| MOR044694 | <600 |
| MOR044697 | 660 |
| MOR044693 | <600 |
| MOR044723 | <600 |
| MOR044717 | <600 |
| MOR044725 | <600 |
| MOR044727 | <600 |
| MOR044750 | <600 |

As a rough estimate for the binding affinities of affinity maturated antibodies at human TREM2, SET screening experiments were carried out using hTREM2 ECD (19-174). Several antibodies have subnanomolar binding affinities at recombinantly expressed human TREM2 in this in vitro assay (Table 16).

TABLE 17

| Potencies of antibodies in hM2A and selectivity at recombinantly expressed proteins and cell lines. | | | |
|---|---|---|---|
| Antibodies | $EC_{50}$ at hM2A using FACS [nM] | Unspecific binding to parental CHO or THP-1 deficient of TREM2 (FACS) | Binding to PMA treated hM2A (FACS) |
| MOR044743 | <2 | Yes | Yes |
| MOR044741 | <2 | Yes | Yes |
| MOR044742 | <2 | Yes | No |
| MOR044744 | <2 | Yes | No |
| MOR044746 | <2 | No | No |
| MOR044698 | <2 | No | No |
| MOR044724 | <2 | No | No |
| MOR044722 | <2 | No | No |
| MOR044700 | >2 | | No |
| MOR044701 | <2 | No | No |
| MOR044703 | >2 | No | No |
| MOR044747 | <2 | No | No |
| MOR044695 | >2 | No | No |
| MOR044728 | <2 | No | Yes |
| MOR044734 | <2 | No | No |
| MOR044737 | <2 | No | No |
| MOR044738 | <2 | No | No |
| MOR044739 | <2 | No | No |
| MOR044729 | >2 | No | No |
| MOR044730 | <2 | No | Yes |
| MOR044731 | <2 | No | No |
| MOR044733 | >2 | Yes | Yes |
| MOR044735 | >2 | No | No |
| MOR044736 | >2 | Yes | No |
| MOR044740 | >2 | Yes | No |
| MOR044716 | <2 | No | No |
| MOR044726 | >2 | Yes | No |
| MOR044705 | <2 | No | No |

TABLE 17-continued

| Potencies of antibodies in hM2A and selectivity at recombinantly expressed proteins and cell lines. | | | |
|---|---|---|---|
| Antibodies | $EC_{50}$ at hM2A using FACS [nM] | Unspecific binding to parental CHO or THP-1 deficient of TREM2 (FACS) | Binding to PMA treated hM2A (FACS) |
| MOR044708 | <2 | No | No |
| MOR044706 | >2 | Yes | No |
| MOR044707 | >2 | No | No |
| MOR044748 | >2 | No | No |
| MOR044721 | <2 | No | No |
| MOR044702 | <2 | No | No |
| MOR044714 | >2 | Yes | No |
| MOR044715 | <2 | Yes | No |
| MOR044710 | >2 | Yes | No |
| MOR044720 | <2 | No | No |
| MOR044713 | <2 | No | No |
| MOR044709 | >2 | Yes | No |
| MOR044711 | >2 | Yes | No |
| MOR044712 | >2 | No | No |
| MOR044718 | >2 | Yes | No |
| MOR044719 | >2 | Yes | No |
| MOR044745 | >2 | Yes | No |
| MOR044749 | >2 | No | No |
| MOR044694 | >2 | No | No |
| MOR044697 | <2 | No | No |
| MOR044693 | <2 | No | No |
| MOR044723 | <2 | Yes | No |
| MOR044717 | >2 | No | No |
| MOR044725 | <2 | Yes | No |
| MOR044727 | >2 | Yes | No |
| MOR044750 | >2 | Yes | No |

Next antibodies were screened for binding to endogenously expressed TREM2 in hM2A macrophages from different donors using FACS analysis. Several antibodies show binding $EC_{50}$ that are below 2 nM. In addition, most antibodies did not bind to parental (untransfected) CHO cells or to THP-1 cells that had been genetically engineered by CRISPR to be devoid of TREM2 expression (Table 17).

TABLE 18

| Determination of cellular EC50 at human TREM2 endogenously expressed in hM2A macrophages derived from different donors. | | | | | | |
|---|---|---|---|---|---|---|
| Antibodies | Median ± SD [nM] | n | Donor1 [nM] | Donor2 [nM] | Donor3 [nM] | Donor4 [nM] |
| MOR044746 | 0.59 ± 0.09 | 4 | 0.73 | 0.54 | 0.54 | 0.64 |
| MOR044698 | 0.56 ± 0.15 | 4 | 0.86 | 0.55 | 0.55 | 0.56 |
| MOR044713 | 0.85 ± 1.79 | 4 | 4.38 | 0.73 | 0.89 | 0.80 |
| MOR044716 | 0.45 ± 0.22 | 4 | 0.55 | 0.08 | 0.35 | 0.35 |
| MOR044724 | 0.28 ± 6.19 | 4 | 12.64 | 0.26 | 0.20 | 0.30 |
| MOR044743 | 0.46 ± 0.19 | 4 | 0.46 | 0.79 | 0.35 | 0.46 |
| MOR044741 | 0.74 ± 0.13 | 4 | 0.83 | 0.81 | 0.55 | 0.67 |
| MOR044735 | 7.63 ± 67.89 | 4 | 141.10 | 8.56 | 0.68 | 6.69 |

In contrast to recombinant expression systems, human M2A macrophages express endogenously TREM2 and DAP12. In this cellular system TREM2 protein is post-translationally processed and expressed very similar compared to the in vivo situation in humans.

$EC_{50}$ of antibodies was determined at endogenously expressed human TREM2 in hM2A macrophages (Table 18). n depicts the number of different experiments, and in every experiment macrophages that had been differentiated from $CD14^+$ monocytes were derived from different donors. Results indicate subnanomolar binding affinities of the antibodies of most of the antibodies to human M2A using FACS analysis. Individual values for each donor are given. Most surprisingly, some antibodies show high variability in binding affinities between different donors e.g. 44724, 44713, 44735 and 44716, while others show a consistent binding pattern among the different donors tested e.g. MOR044746 and MOR44698.

TABLE 19

Determining TREM2 domain recognized by antibodies and binding to cynomolgus TREM2.

| Antibody | hTREM2 ECD (19-174)-hFc \| S/BG | cyTREM2 ECD (19-174)-hFc \| S/BG | hTREM1 IgSF-hTREM2 stalk-hFc \| S/BG | hTREM2 IgSF-hTREM1 stalk-hFc\| S/BG |
|---|---|---|---|---|
| MOR044743 | >5 | >5 | >30 | <11 |
| MOR044741 | >5 | >5 | >30 | <11 |
| MOR044742 | >5 | >5 | >30 | <11 |
| MOR044744 | >5 | >5 | >30 | <11 |
| MOR044746 | >5 | >5 | <2 | >20 |
| MOR044698 | >5 | >5 | <2 | >20 |
| MOR044724 | >5 | >5 | <2 | >20 |
| MOR044722 | >5 | >5 | <2 | 19 |
| MOR044700 | >5 | >5 | <2 | >20 |
| MOR044701 | >5 | >5 | <2 | >20 |
| MOR044703 | >5 | >5 | <2 | >20 |
| MOR044747 | >5 | >5 | <2 | >20 |
| MOR044695 | >5 | >5 | <2 | >20 |
| MOR044728 | >5 | >5 | <2 | >20 |
| MOR044734 | >5 | >5 | <2 | >20 |
| MOR044737 | >5 | >5 | <2 | >20 |
| MOR044738 | >5 | >5 | <2 | >20 |
| MOR044739 | >5 | >5 | <2 | >20 |
| MOR044729 | >5 | >5 | <2 | >20 |
| MOR044730 | >5 | >5 | <2 | >20 |
| MOR044731 | >5 | >5 | <2 | >20 |
| MOR044733 | >5 | >5 | <2 | >20 |
| MOR044735 | >5 | >5 | <2 | >20 |
| MOR044736 | >5 | >5 | <2 | >20 |
| MOR044740 | >5 | >5 | <2 | >20 |
| MOR044716 | >5 | >5 | <2 | >20 |
| MOR044726 | >5 | >5 | <2 | 19 |
| MOR044705 | >5 | >5 | <2 | 11 |
| MOR044708 | >5 | >5 | <2 | 13 |
| MOR044706 | >5 | >5 | <2 | 11 |
| MOR044707 | >5 | >5 | <2 | 17 |
| MOR044748 | >5 | >5 | <2 | 10 |
| MOR044721 | >5 | >5 | <2 | >20 |
| MOR044702 | >5 | >5 | <2 | >20 |
| MOR044714 | >5 | >5 | <2 | >20 |
| MOR044715 | >5 | >5 | <2 | >20 |
| MOR044710 | >5 | >5 | <2 | >20 |
| MOR044720 | >5 | >5 | <2 | 20 |
| MOR044713 | >5 | >5 | <2 | >20 |
| MOR044709 | >5 | >5 | <2 | >20 |
| MOR044711 | >5 | >5 | <2 | >20 |
| MOR044712 | >5 | >5 | <2 | >20 |
| MOR044718 | >5 | >5 | <2 | 19 |
| MOR044719 | >5 | >5 | <2 | >20 |
| MOR044745 | >5 | >5 | <2 | >20 |
| MOR044749 | >5 | >5 | <2 | >20 |
| MOR044694 | >5 | >5 | <2 | >20 |
| MOR044697 | >5 | >5 | <2 | >20 |
| MOR044693 | >5 | >5 | <2 | >20 |
| MOR044723 | >5 | >5 | <2 | >20 |
| MOR044717 | >5 | >5 | <2 | 20 |
| MOR044725 | >5 | >5 | <2 | 19 |
| MOR044727 | >5 | >5 | <2 | >20 |
| MOR044750 | >5 | >5 | <2 | >20 |

Using recombinantly produced proteins, it was investigated which protein domain of TREM2 (IGSF of stalk region) is recognized by the anti-TREM2 antibodies (Table 19). All antibodies bind with a more than 5× signal:background ratio to the full length extracellular TREM2 construct. Antibodies MOR044743, MOR044741, MOR0044742 and MOR044744 interact strongly with the stalk region of TREM2, while most other antibodies are IGSF binder.

These experiments also show cross-reactivity of these antibodies with the ECD of cynomolgus TREM2 (Table 19).

TABLE 20

Exploratory determination of physico-chemical properties of antibodies.

| Antibodies | analytical SEC (% monomer) | pI (in-silco prediction) | Tm (° C., pH 5.5, IgG data) | Hydrophobicity ($M(NH_4)_2SO_4$, His pH 6.0) |
|---|---|---|---|---|
| MOR044743 | 97.9 | 9.4 | 74.0 | 1.01 |
| MOR044741 | 98.2 | 9.4 | 76.5 | 1.01 |
| MOR044742 | 95.1 | 9.3 | 73.0 | 0.84 |
| MOR044744 | 90.6 | 9.3 | 72.5 | 0.89 |
| MOR044746 | 95.8 | 8.6 | 76.0 | 0.87 |
| MOR044698 | 97.9 | 9.4 | 75.5 | 1.03 |
| MOR044724 | 94.4 | 7.2 | 82.5 | 0.53 |
| MOR044722 | 95.2 | 7.2 | 84.0 | 0.49 |
| MOR044700 | 96.4 | 8.9 | 77.0 | 0.87 |
| MOR044701 | 95.9 | 9 | 77.5 | 0.79 |
| MOR044703 | 95.6 | 9 | 79.5 | 0.89 |
| MOR044747 | 94.4 | 8.9 | 85.0 | 0.81 |
| MOR044695 | 95.3 | 9.1 | 71.0 | 0.55 |
| MOR044728 | 94.1 | 8.6 | 85.0 | 0.63 |
| MOR044734 | 94.1 | 8.9 | 80.0 | 0.76 |
| MOR044737 | 95.3 | 9.1 | 81.0 | 0.75 |
| MOR044738 | 92.2 | 8.6 | 83.0 | 0.80 |
| MOR044739 | 94.9 | 8.9 | 81.5 | 0.73 |
| MOR044729 | 93.2 | 8.9 | 81.0 | 0.76 |
| MOR044730 | 95.4 | 8.9 | 80.0 | 0.73 |
| MOR044731 | 97.1 | 8.6 | 79.5 | 0.80 |
| MOR044733 | 95.5 | 9.1 | 79.0 | 0.81 |
| MOR044735 | 91.1 | 8.6 | 82.0 | 0.80 |
| MOR044736 | 94.8 | 8.9 | 84.5 | 0.62 |
| MOR044740 | 95.1 | 8.2 | 79.0 | 0.49 |
| MOR044716 | 96.3 | 8.9 | 79.0 | 0.37 |
| MOR044726 | 92.5 | 7.5 | 84.5 | 0.70 |
| MOR044705 | 98.0 | 9.4 | 71.0 | 0.95 |
| MOR044708 | 84.3 | 9.4 | 65.0 | 0.44 |
| MOR044706 | 87.7 | 9.4 | 69.5 | 0.78 |
| MOR044707 | 98.2 | 9.4 | 72.5 | 0.97 |
| MOR044748 | 95.8 | 9.4 | 74.0 | 0.82 |
| MOR044721 | 94.0 | 7.2 | 83.5 | 0.59 |
| MOR044702 | 95.6 | 9 | 79.0 | 0.81 |
| MOR044714 | 99.2 | 9.1 | 83.5 | 0.21 |
| MOR044715 | 96.2 | 9.1 | 83.0 | 0.48 |
| MOR044710 | 98.1 | 9.2 | 65.5 | 0.48 |
| MOR044720 | 98.5 | 9 | 64.0 | 0.65 |
| MOR044713 | 97.6 | 8.7 | 80.0 | 0.83 |
| MOR044709 | 98.6 | 9.2 | 82.0 | 0.54 |
| MOR044711 | 98.6 | 9 | 69.5 | 0.08 |
| MOR044712 | 97.7 | 9.2 | 65.0 | 0.19 |
| MOR044718 | 98.4 | 9.2 | 68.5 | 0.26 |
| MOR044719 | 99.4 | 9.3 | 64.0 | 0.50 |
| MOR044745 | 97.3 | 9.3 | 77.5 | 0.56 |
| MOR044749 | 98.8 | 9 | 76.0 | 0.42 |
| MOR044694 | 95.9 | 8.6 | 76.0 | 0.84 |
| MOR044697 | 97.4 | 9.4 | 75.0 | 0.90 |
| MOR044693 | 95.6 | 8.6 | 74.5 | 0.86 |
| MOR044723 | 93.6 | 7.5 | 82.5 | 0.44 |
| MOR044717 | 99.3 | 9.2 | 63.0 | 0.92 |
| MOR044725 | 94.1 | 7.8 | 83.0 | 0.33 |
| MOR044727 | 95.2 | 7.5 | 83.0 | 0.44 |
| MOR044750 | 93.6 | 7.8 | 83.0 | 0.40 |

To further characterize the biochemical and biophysical properties of the antibodies, monomer content, iso-electrical point, melting temperature and hydrophobicity of the antibodies was evaluated (Table 20).

Several antibodies displayed excellent biochemical and biophysical properties (i.e. monomer content >94%, pI>7.1, TM>75 and hydrophobicity >0.4), e.g. MOR044746, MOR044698, MOR044724, MOR044722, MOR044716, MOR044705, MOR044713.

TABLE 21

Determination of $K_D$ by label free kinetics via SPR.

| Antibodies | hTREM2 ECD (19-174)-hFc [pM] | cyTREM2 ECD (19-174)-APP-Avi) [pM] |
|---|---|---|
| MOR044746 | 3 | 4 |
| MOR044698 | 46 | 39 |
| MOR044713 | 11 | 4 |
| MOR044716 | 150 | 100 |
| MOR044724 | 85 | 130 |

For a precise assessment of the binding affinities of the antibodies affinity-determination by measuring kinetic rate constants was performed by SPR. In addition a comparison to cynomolgus TREM2 was performed (Table 21). Before running these experiments, the amount of monomer fractions of antibody protein (IgG) were analyzed (at least 90% monomer content by analytical SEC).

The determination of $K_D$ of the antibodies at recombinantly expressed cynomolgus or human TREM2 ECD domain reveals pM affinities. These affinities are similar comparing human and cynomolgus TREM2.

Figure 3:
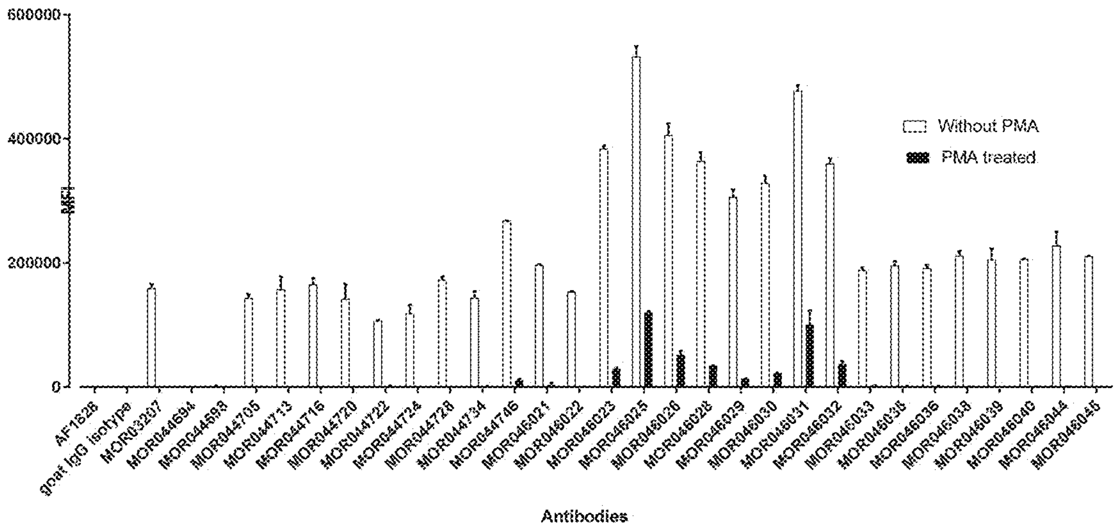
FIG. 3 shows binding of TREM2 antibodies to human M2A macrophages before and after treatment with PMA.

To further assess specificity of TREM2 antibodies, human M2A macrophages were treated with PMA and binding of antibodies to these macrophages was evaluated using FACS analysis (FIG. 3). PMA has been shown to activate proteases like ADAM17 resulting in shedding of TREM2 ECD from hM2A (Feuerbach, D et al. Neurosci Lett, 2017. 92:p. 202-209). After PMA treatment, AF1828 Ab does not bind anymore to M2A macrophages (compare first and second bar).

However, several antibodies still bind to structures at the cell surface of human M2A macrophages (e.g. MOR44728, MOR46021, MOR46022, MOR46023, MOR46025, MOR46026, MOR46028, MOR46029 and MOR46030), indicating unspecific binding. Several antibodies lack binding to human M2A macrophages after PMA treatment (e.g. MOR44694, MOR44698, MOR44705, MOR44746).

To further investigate non-target related binding properties of the antibodies, a selected set of antibodies was subjected to protein panel profiling. Results show that cumulative binding ratios of antibodies are below 150, representing IgGs without detectable unspecific binding (Table 22).

TABLE 22

Determination of unspecific binding in protein panel profiling (3P).

| Antibodies | Cumulative binding ratio |
|---|---|
| MOR044746 | <150 |
| MOR044698 | <150 |
| MOR044713 | <150 |
| MOR044716 | <150 |
| MOR044724 | <150 |
| MOR044743 | <150 |

Figure 4A:
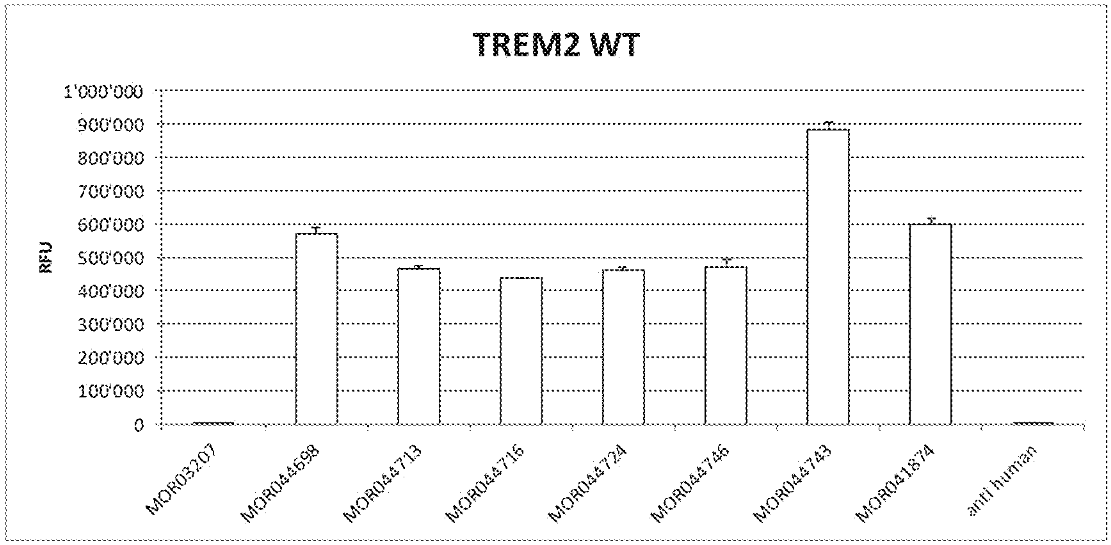
FIG. 4A shows binding of antibodies to WT-TREM2.
Figure 4B:
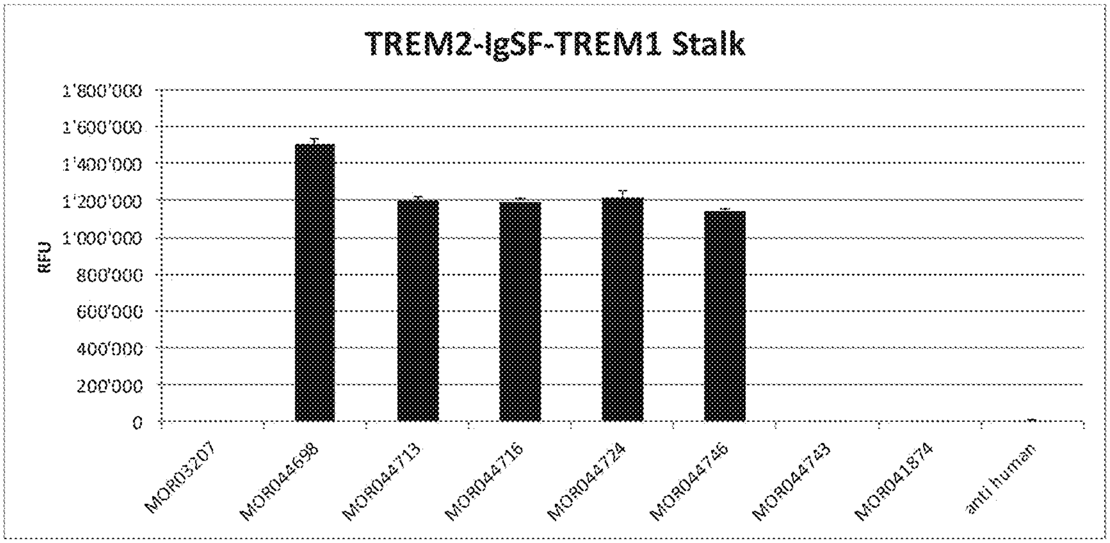
FIG. 4B shows binding of antibodies to TREM2-TREM1 chimeric protein (TREM2-IgSF-TREM1 Stalk) recombinantly expressed in CHO-hDAP12 cells.
Figure 4C:
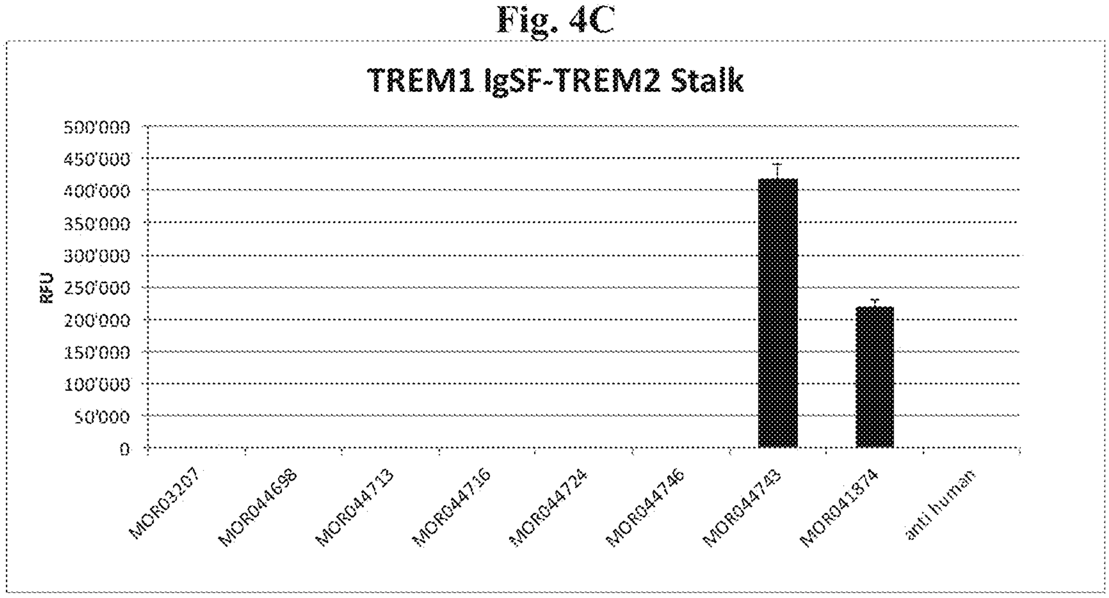
FIG. 4C shows binding of antibodies to TREM2-TREM1 chimeric protein (TREM1-IgSF-TREM2 Stalk) recombinantly expressed in CHO-hDAP12 cells.

CHO cells that recombinantly express chimeric TREM2-TREM1 constructs were used to identify the binding site of the antibodies within the TREM2 protein. Using FACS analysis, it is demonstrated that all antibodies bind to full length WT-human TREM2 (FIG. 4A). Antibodies MOR044698, MOR044713, MOR044716, MOR044724 and MOR044746 bind to the cell lines expressing the TREM2-IgSF-TREM1 stalk protein (FIG. 4B) but not to the TREM1-IgSF-TREM2 stalk protein (FIG. 4C). The antibodies MOR44743 and MOR041874 showed the reverse binding pattern, i.e. these antibodies bound to the TREM1-IgSF-TREM2 stalk protein but not to TREM2-IgSF-TREM1 stalk protein expressing cell lines. MOR3207 is an isotype control antibody and anti-human is secondary FACS-staining antibody only.

In the next set of experiments the potency of the antibodies using recombinant cellular expression system was evaluated. $EC_{50}$ of antibodies was determined using FACS analysis at CHO cells recombinantly expressing cynomolgus or human TREM2 (Table 23). In CHO cells expressing human TREM2 it was shown that antibodies display subnanomolar binding affinities. In the cell lines expressing cynomolgus TREM2, binding affinities are in the similar range compared to cells expressing human TREM2.

TABLE 23

Determination of cellular $EC_{50}$ at CHO-cynoTREM2 and CHO-human TREM2 expressing cell lines using FACS analysis.

Figure 5:
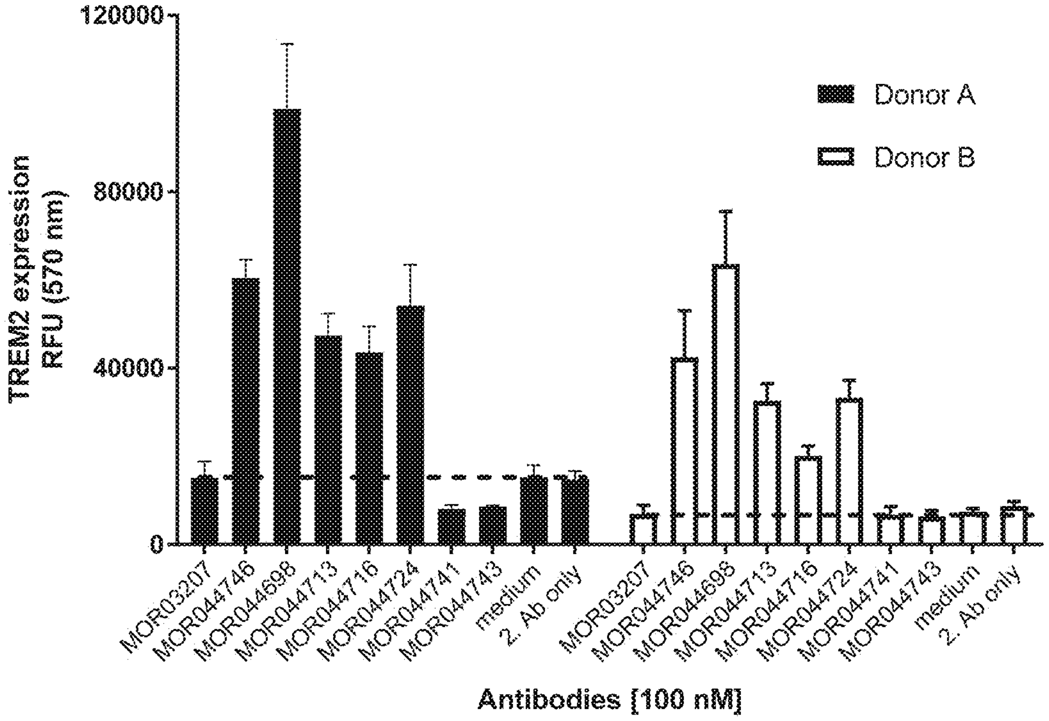
FIG. 5 shows stabilization of TREM2 at cell surface of hM2A by TREM2 antibodies.

| Antibodies | CHO-hTREM2 [nM] | CHO-cyTREM2 [nM] |
|---|---|---|
| MOR044746 | 0.16 | 0.65 |
| MOR044698 | 0.20 | 0.46 |
| MOR044713 | 0.26 | 0.71 |
| MOR044716 | 0.24 | 0.63 |
| MOR044724 | 0.13 | 0.31 |

hM2A from different donors were treated o/n with 100 nM of anti-TREM2 antibodies. Next, TREM2 expression at the cell surface was assessed using the non-crossblocking Fab fragment MOR041895. Incubation with the antibodies MOR044746, MOR044698, MOR044713, MOR044716 and MOR044724 entailed stabilization of TREM2 at the cell surface in contrast to antibodies MOR044741, MOR044743. All antibodies display subnanomolar affinities and similar Bmax to TREM2 (as determined before). However, MOR044746, MOR044698, MOR044713, MOR044716 and MOR044724 bind to the IgSF domain, while MOR044741 and MOR044743 bind to the stalk region of TREM2 (FIG. 5). Table 24 shows the fold increase of TREM2 cell surface expression in relation to the isotype control (MOR03207). n represents the number of different experiments, and in every experiment macrophages were derived from different donors.

These data indicate that antibodies that bind to the IgSF domain of TREM2 inhibit ectodomain release by sheddases like ADAM17 and increase cell surface expression of TREM2.

TABLE 24

Quantification of the stabilization of TREM2 at cell surface in hM2A by anti-TREM2 antibodies.

Figure 6A:
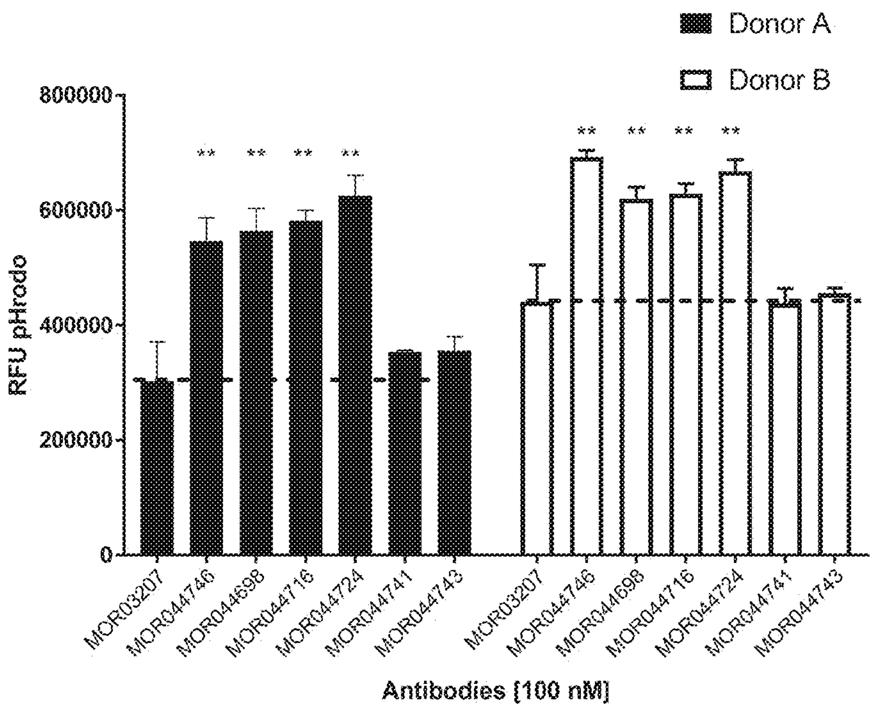
FIGS. 6A and 6B show that antibodies that stabilize TREM2 at the cell surface also increase phagocytic capacity of human M2A. Statistics were calculated using Student's T-test, *Pval<0.05, Pval<0.01, *Pval<0.001 compared to isotype control.
Figure 6B:
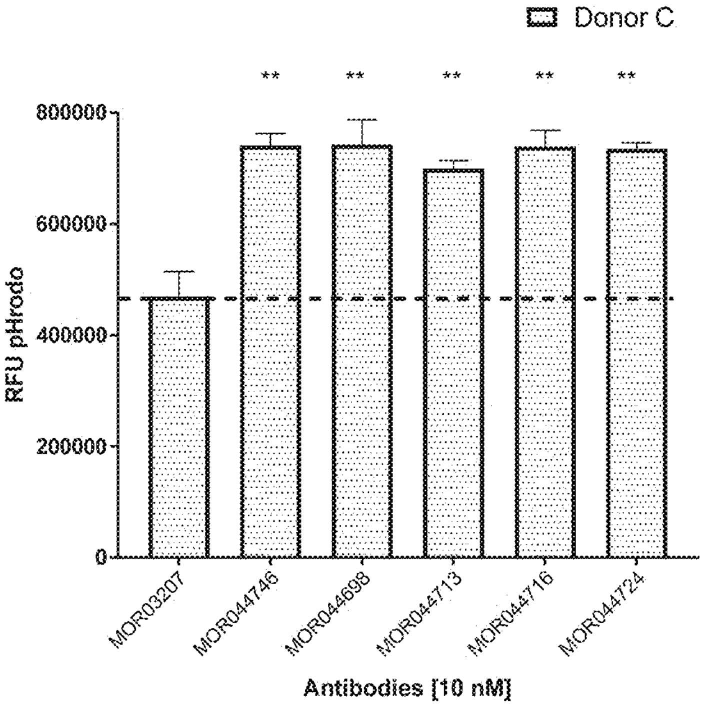

| Antibodies | Fold TREM2 cell surface increase compared to isotype | n |
|---|---|---|
| MOR044746 | 5.1 | 3 |
| MOR044698 | 7.9 | 3 |
| MOR044713 | 3.9 | 3 |
| MOR044716 | 2.9 | 3 |
| MOR044724 | 4.2 | 3 |
| MOR044741 | 0.7 | 2 |
| MOR044743 | 0.8 | 2 |

hM2A from different donors were treated with 100 nM (FIG. 6A) or 10 nM (FIG. 6B) of anti-TREM2 antibodies. 16-20 h later cells were subjected to phagocytosis assay using pHrodo labeled staph-aureus bioparticles as prey. Antibodies that stabilized TREM2 cell surface expression (MOR044746, MOR044698, MOR044713, MOR044716 and MOR044724) facilitate phagocytosis in hM2A. In contrast, MOR044741 and MOR044743 that did not increase cell surface expression also do not enhance uptake of pHrodo staph. *aureus* bioparticles. Antibodies MOR044746, MOR044698, MOR044713, MOR044716 and MOR044724 were efficacious in the phagocytosis assay also at 10 nM (FIG. 6B). These data indicate that antibodies that bind to the IgSF domain of TREM2 increase phagocytic capacity of hM2A.

Figure 7A:
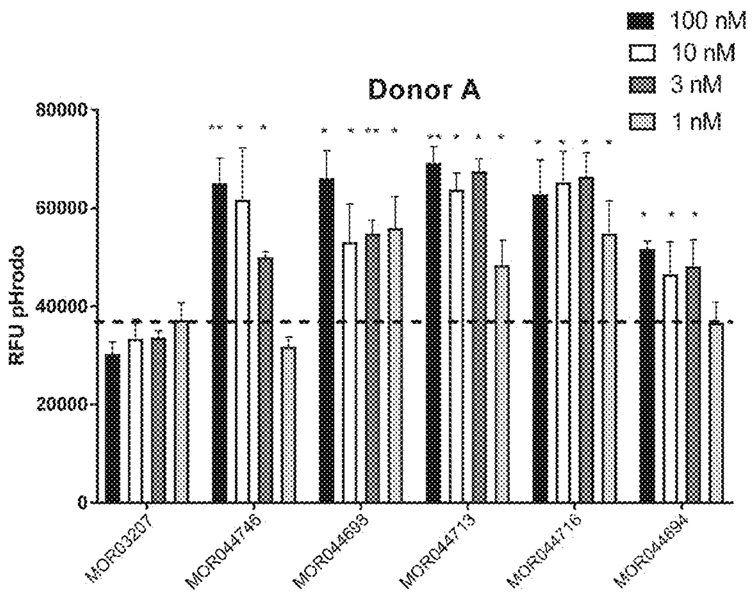
FIGS. 7A and 7B show determination of lowest efficacious dose in phagocytosis assay in hM2A. Statistics were calculated using Student's T-test, *Pval<0.05, Pval<0.01, *Pval<0.001 compared to isotype control.
Figure 7B:
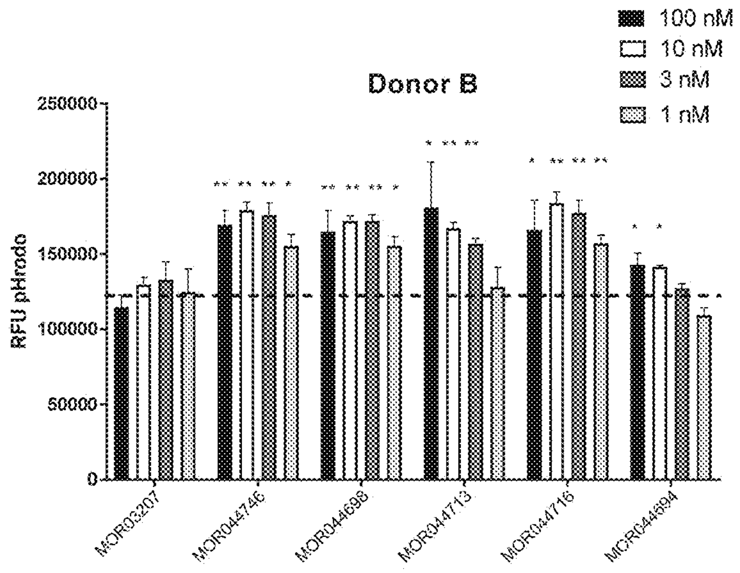

Next different concentration of TREM2 stabilizing antibodies were incubated with hM2A macrophages followed by a phagocytosis assay 16-20 h later. Antibodies 44698 and 44716 enhanced uptake of pHrodo staph. *aureus* bioparticles into hM2A even at the lowest concentration tested (1 nM) at both donors in comparison to the isotype control. The lowest active concentration for antibodies 44746 and 44713 was also 1 nM, however at only one donor. The lowest active concentration of 44694 was 3 nM, but also only at one donor (FIG. 7 A, B).

Figure 8:
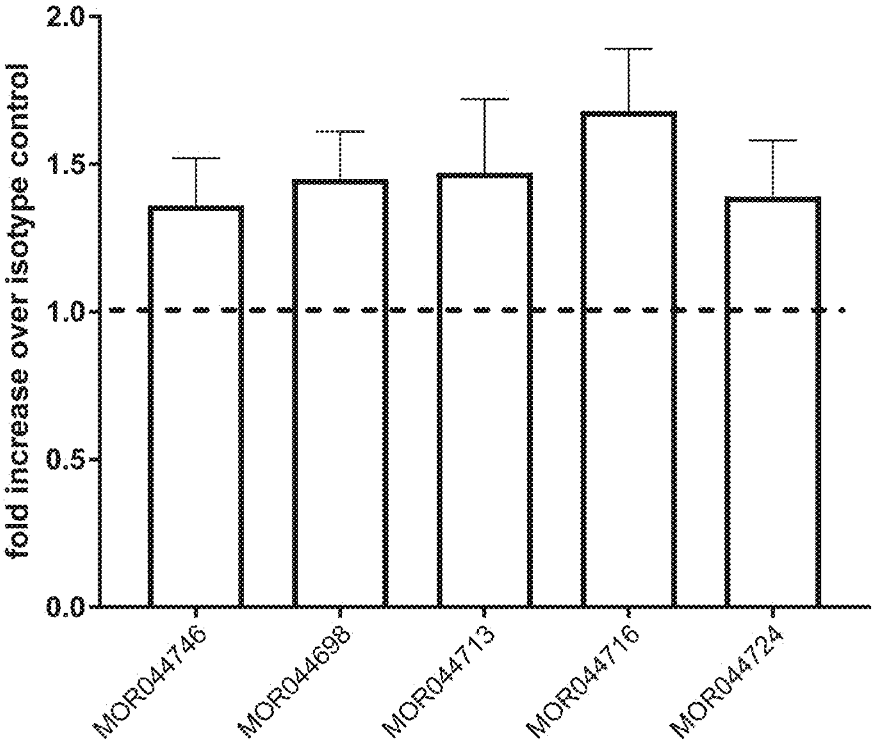
FIG. 8 shows that plate-bound TREM2 antibodies induce TREM2-dependent NFAT promotor dependent gene transcription.

FIG. 8 shows that activation of endogenously expressed TREM2 in THP1-B5 cells by antibodies induces NFAT promotor driven luciferase activity. Plates were coated with isotype control or different anti-TREM2 antibodies. Antibodies MOR044746, MOR044698, MOR044713, MOR044716 and MOR044724 activate TREM2 dependent gene transcription.

Figure 9A:
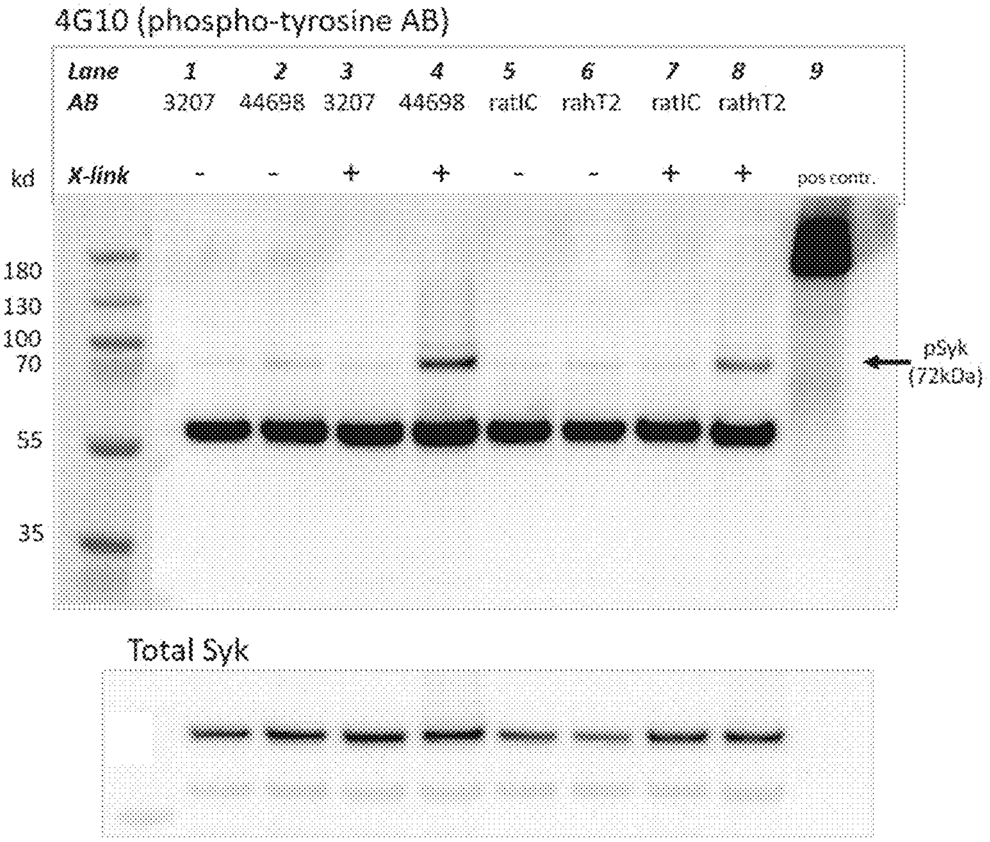
FIGS. 9A and 9B show that TREM2 antibodies increase Syk phosphorylation in human M2A macrophages.
Figure 9B:
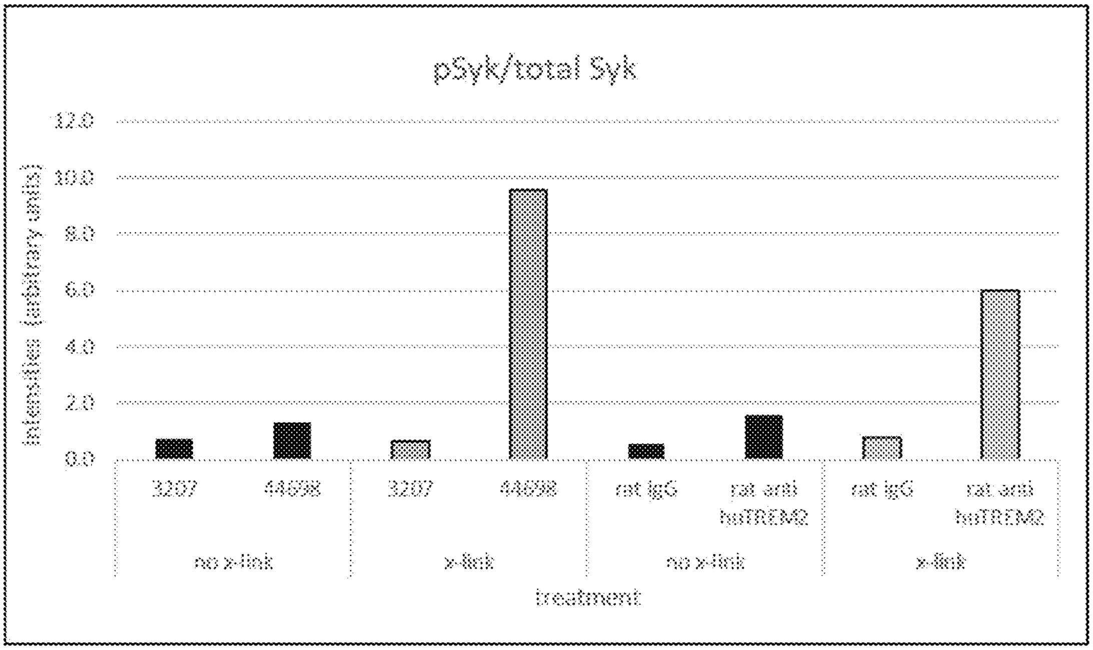

FIG. 9 (A, B) shows Syk phosphorylation as determined by Western blot from human M2A macrophages after treatment with isotype control antibody (MOR03207 or ratIC) or anti-TREM2 antibody (MOR044698 or rathT2). Where indicated (X-link: +) this was followed by treatment with anti-Fc crosslinking antibody (x-link).

As shown in FIG. 9A TREM2 antibody 44698 increases TREM2-elicited Syk phosphorylation in human M2A macrophages. MOR044698 as well as the commercially available R&D rat anti-human TREM2 antibody enhance syk phosphorylation even in the absence of the anti-Fc crosslinking antibody (compare lanes 1 with 2 and lanes 5 with 6 in FIG. 9A). This effect is strongly enhanced upon the addition of the crosslinking antibody (compare lanes 3 with 4 and lanes 7 with 8). After addition of the crosslinking antibody MOR044698 a stronger effect on syk phosphorylation is observed compared to the rat anti human TREM2 antibody (see lanes 4 and 8).

These experiments indicate that Ab MOR044698 displays—concomitantly to the TREM2 stabilizing activity—also TREM2 agonistic activity in a human cellular system with endogenous TREM2 expression.

In a next set of experiments the presence of high molecular weight species, low molecular weight species as well as the purity of the purified antibodies were evaluated (Table 25). Size Exclusion Chromatography (SEC) was used to separate monoclonal antibody variants of different size under native conditions. Short-term aggregation is represented by the formation of low molecular weight species (LMW) Short-term aggregation is represented by the formation of low molecular weight species (LMW). High molecular weight species (HMW) is measured by size exclusion chromatography (SEC) and Capillary gel Electrophoresis using Sodium Dodecyl Sulfate (CE-SDS) and indicates the propensity of the antibody to form aggregates, which are unwanted for immunogenicity reasons among other. High molecular weight species (HMWs) represent an unwanted property of the purified material. Capillary gel Electrophoresis using Sodium Dodecyl Sulfate (CE-SDS) was used to separate protein based on differences in molecular weight and can be performed under non-reducing or reducing conditions. The content of degradation products, Low Molecular Weight species (LMWs), including clipping, and by-products (HMWs) indicate the quality of the purified material. As represented below, all molecules show favorable quality attributes regarding developability.

TABLE 25

Final analytical characterization: purity and high/low molecular weight species of purified antibodies.

| Antibody | HMWs (%, SEC) | LMWs (%, SEC) | LMWs* (%, red. CE-SDS Beckman) | Purity (%, red. CE-SDS Beckman) | LMWs** (%, non-red. CE-SDS Beckman) | Purity (%, non-red. CE-SDS Beckman) |
|---|---|---|---|---|---|---|
| MOR044698D | 0.0 | 0.1 | 1.1 | 98.4 | 3.5 | 96.5 |
| MOR044746D | 0.1 | 0.0 | 2.9 | 95.9 | 3.6 | 96.4 |
| MOR044698E | 0.1 | 0.2 | 1.0 | 98.4 | 3.6 | 96.4 |
| MOR044746E | 0.8 | 0.0 | 2.8 | 96.2 | 3.0 | 97.0 |
| MOR044698 B | 0.0 | 0.1 | 1.1 | 98.0 | 3.5 | 96.5 |
| MOR044746B | 0.2 | 0.0 | 2.6 | 96.3 | 3.4 | 96.6 |
| MOR044698C | 0.0 | 0.1 | 1.2 | 98.0 | 3.7 | 96.3 |
| MOR044746C | 0.2 | 0.0 | 2.8 | 96.4 | 3.6 | 96.4 |
| MOR044698F | 0.0 | 0.1 | 1.2 | 98.0 | 3.9 | 96.1 |
| MOR044746F | 0.1 | 0.0 | 2.9 | 95.9 | 3.2 | 96.8 |

Comments:
* Reduced CE-SDS: Reported LMWs include potential non-glycosylated HC.
** Non-reduced CE-SDS: Reported LMWs include potential antibody fragments.

In further experiments the molecular mass, the glycation, the glycosylation, clipping products and sequence variants of the purified antibodies were investigated (Table 26). Protein glycation is a non-enzymatic glycosylation between a reducing sugar (e.g. glucose, galactose and fructose) and the protein amine groups. For therapeutic proteins, the potential effects of glycation includes blocking the biologically functional site or further degradation that induces aggregation. Glycosylation, as a common form of protein post-translational modifications, is the diverse, enzyme mediated process by which oligosaccharide side chains are covalently attached to either the side chain of asparagine (N-linked) or serine/threonine (O-linked). The carbohydrate component of a therapeutic glycoprotein is often key in determining its pharmacological properties including stability, solubility/bioavailability, in vivo activity, pharmacokinetics and immunogenicity. Clipping (fragmentation) is a common type of biochemical degradations of recombinant therapeutic proteins. It often links to protease activities in host cell line and has an impact on the quality, physical stability and potential immunogenicity of protein pharmaceuticals. As represented below, all molecules show a favorable MS profile regarding developability.

TABLE 26

Final analytical characterization: antibody mass, glycation, glycosylation clipping and sequence variants of purified antibodies.

| Antibody | Mass complies (HC, LC) | Glycation LC [%] | N-glycosylation | CDR clipping [%] | Other clipping [%] | Sequence variants |
|---|---|---|---|---|---|---|
| MOR044698D | Yes | ≤2 | Normal complex | <LOD | <LOD | <LOD |
| MOR044746D | Yes | 3 | Normal complex | <LOD | <LOD | <LOD |
| MOR044698E | Yes | 3 | Normal complex | <LOD | <LOD | <LOD |
| MOR044746E | Yes | 3 | Normal complex | <LOD | <LOD | <LOD |
| MOR044698 B | Yes | 3 | Normal complex | <LOD | <LOD | <LOD |
| MOR044746B | Yes | ≤2 | Normal complex | <LOD | <LOD | <LOD |
| MOR044698C | Yes | 3 | Normal complex | <LOD | <LOD | <LOD |
| MOR044746C | Yes | 3 | Normal complex | <LOD | <LOD | <LOD |
| MOR044698F | Yes | 3 | Normal complex | <LOD | <LOD | <LOD |
| MOR044746F | Yes | 3 | Normal complex | <LOD | <LOD | <LOD |

HC: Heavy Chain
LC: Light Chain
LOD: Limit of Detection

The next set of experiments assessed the biophysical properties (i.e. differential interaction parameter, viscosity, hydrophobicity, melting temperature and isoelectric point) of the purified antibodies (Table 27). The Differential Interaction Parameter (DIP) is a measure of the colloidal stability, which is the propensity of molecules to associate because of week, attractive forces associates with hydrophobic surface residues, etc. It can be correlated to the viscosity of a molecule. Viscosity is the flow resistance due to internal friction forces, which occurs when a fluid is in motion. It has a strong impact on the developability and administration of a molecule. A direct way to measure the surface hydrophobicity of a protein is to determine its retention time during elution with an ammonium sulfate. Hydrophobicity is a key risk factor for protein aggregation and unfavorable effects during concentration processes. Differential Scanning Fluorimetry (DSF) determines the transition unfolding temperature of proteins by applying an increasing temperature gradient. Thermal stability (melting temperature Tm measured by Differential Scanning Fluorimetry DSF at pH 5.5) is the propensity of a protein to aggregate and/or unfold with temperature, generally because of exposure of the hydrophobic core. Thermally induced unfolding is a typical two-state model with a sharp transition between the folded and the unfolded states, where the Tm value is defined as the midpoint of temperature of the protein-unfolding transition. The Tm of the Fab is reported and is an indicator for thermal stability of the molecule. The unfolding onset is an additional indicator for the thermal stability of a molecule, determining the temperature at which the protein starts to unfold. The Isoelectric point (pI) is the pH at which the antibody has no net electrical charge and its value depends on the charged amino acids the antibody contains. It has an impact on the purification process of the molecules. pI of mAbs is known to have a substantial effect on PK behavior independent of recycling mediated by the neonatal Fc receptor, FcRn. Therapeutic antibodies with pI values in the range of 8-9 are taken up adequately after administration since the physiological pH is 7.4. As represented below, all molecules show favorable biophysical properties regarding developability.

TABLE 27

Final analytical characterization: biophysical properties of purified antibodies.

| Antibody | DIP [mL/g] | Viscosity at 50 mg/mL (cP) | HIC [M] $(NH_4)_2SO_4$, pH 6.0 | Tm by DSF at pH 5.5 [° C.] | Unfolding Onset (° C., DSF) | pI (in-silico) |
|---|---|---|---|---|---|---|
| MOR044698D | 22 | 1.51 | 1.02 | 75 | 56 | 9.4 |
| MOR044746D | 5 | 1.48 | 0.86 | 76 | 58 | 8.6 |
| MOR044698E | 20 | 1.43 | 1.02 | 75 | 54 | 9.5 |
| MOR044746E | 8 | 1.45 | 0.86 | 75 | 57 | 8.9 |
| MOR044698 B | 28 | 1.43 | 1.04 | 76 | 58 | 9.4 |
| MOR044746B | 8 | 1.46 | 0.88 | 75 | 57 | 8.6 |
| MOR044698C | 20 | 1.49 | 1.05 | 76 | 55 | 9.5 |
| MOR044746C | 7 | 1.51 | 0.88 | 75 | 54 | 8.9 |
| MOR044698F | 13 | 1.44 | 1.02 | 76 | 51 | 9.3 |
| MOR044746F | 18 | 1.43 | 0.86 | 75 | 51 | 8.2 |

Anti-TREM2 antibodies were profiled on a human plasma membrane protein binding cell array to test their selectivity (Table 28). MOR044716 bound to cells expressing TYRO3, SEZ6L2 and TGM2. Background signal for MOR044716 to untransfected cells might be related to endogenous expression of one of these off-targets. Contrarily to SEZL2 and TGM2, TYRO3 is frequently identified in Retrogenix screens and considered as a "sticky" receptor on this platform. Nevertheless, signal intensity (weak/medium) is strong enough to consider it as a potential specific off-target. MOR044724 bound to cells expressing CD36 and CRHBP.

TREM2 was the only specific target of MOR044746, MOR044698 and MOR044713, suggesting a high level of selectivity of these antibodies. In addition to their primary target, MOR044716 and MOR044724 recognize 3 and 2 relevant off-targets, respectively.

TABLE 28

Binding profile assessment of TREM2 antibodies using a human plasma membrane protein cell array.

| | | Test molecule | | | | |
|---|---|---|---|---|---|---|
| Hit | Accession | MOR044746 | MOR044698 | MOR044713 | MOR044716 | MOR044724 |
| TREM2 (isoform 3) | BC032362 | Strong | strong | strong | medium | med/strong |
| TYRO3 | NM_006293.3 | | | | weak/med | |
| SEZ6L2 | BC000567.2 | | | | weak/med | |
| CD36 | BC008406 | | | | | weak/med |
| TGM2 | NM_004613.2 | | | | weak | |
| CRHBP | BC018038.1 | | | | | weak/med |

Figure 10:
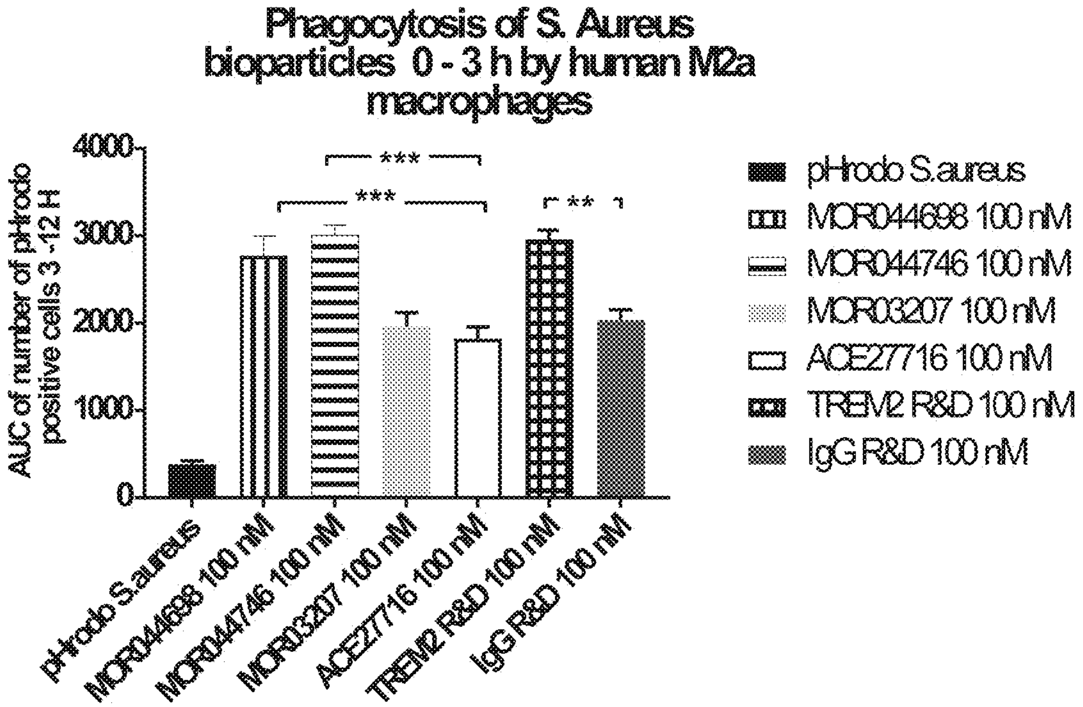
FIG. 10 shows phagocytosis of *S. aureus* bioparticles 0-3 h by human M2A macrophages.

Phagocytosis experiments were carried out in human M2A macrophages after pre-treatment with anti-TREM2 antibodies using a technology independent of FACS analysis (FIG. 10). In addition, two different isotype control antibodies (MOR3207 and ACE27716) as well as a commercially available TREM2 antiserum (TREM2 R&D) was used. In contrast to the FACS-based phagocytosis assay, phagocytosis was followed over a period of 3 hours and area under the curve for accumulation of intracellular pHrodo bioparticles was assessed. MOR044746 and MOR044698 showed statistical significant facilitation of phagocytosis in comparison to the hIgG isotype control antibodies.

Figure 11:
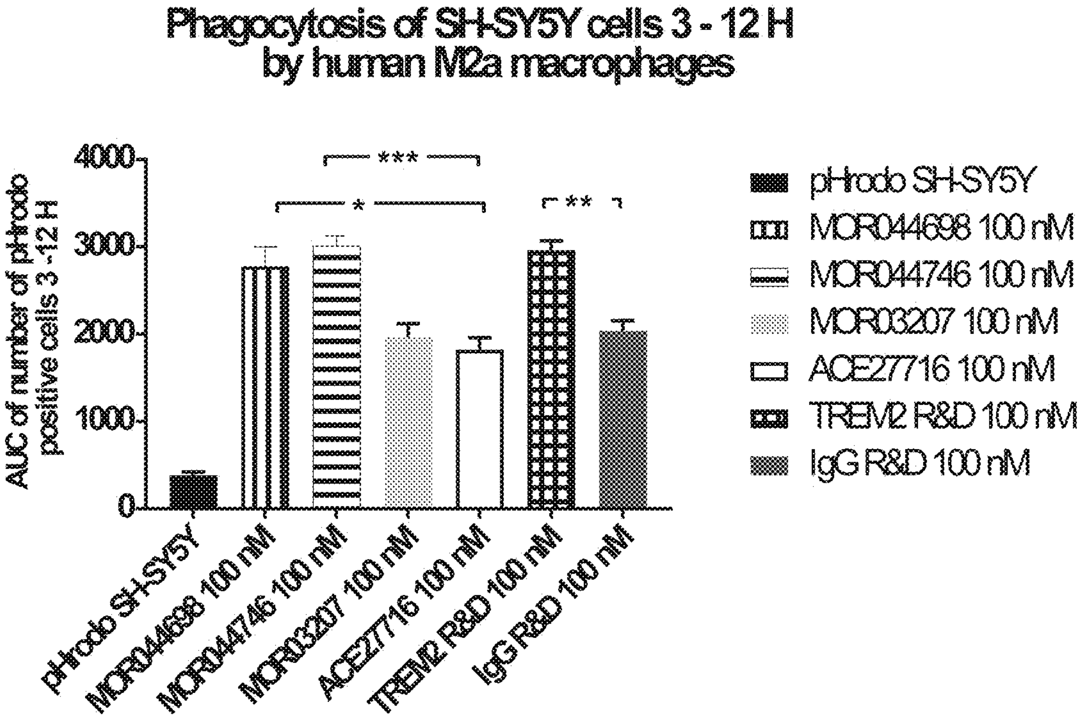
FIG. 11 shows phagocytosis of SH-SY5Y cells 3-12 h by human M2A macrophages.

Facilitation of phagocytosis in hM2A macrophages using commercially available pHrodo labelled Staph. *aureus* as prey has been demonstrated (see FIGS. 6, 7, and 10). Phosphatidylserine has been described as a ligand that binds to TREM2 (Kober, C and Bret, TJ J Mol Biol, 2017. 429(11):p. 1607-1629) and is exposed in apopotitic cells at the plasma membrane. In addition, in vivo TREM2 seems to be involved in removing cellular debris. Therefore, apoptotic SH-SY5Y cells were labelled with the pH sensitive dye pHrodo and used as phagocytic prey (FIG. 11). Similarly, to the results obtained with pHrodo labelled Staph. Aureus pre-incubation with anti-TREM2 antibodies MOR044698 and MOR044746 increased phagocytic capacity of M2A macrophages over a period of 3-12 hours in comparison to the two isotype control antibodies MOR03207 and ACE27716.

In summary FIGS. 6, 7, 10 and 11 demonstrate that anti-TREM2 antibodies MOR044698 and MOR044746 increase the phagocytic capacity of M2A macrophages when using two different preys and two different experimental readouts.

Figure 12:
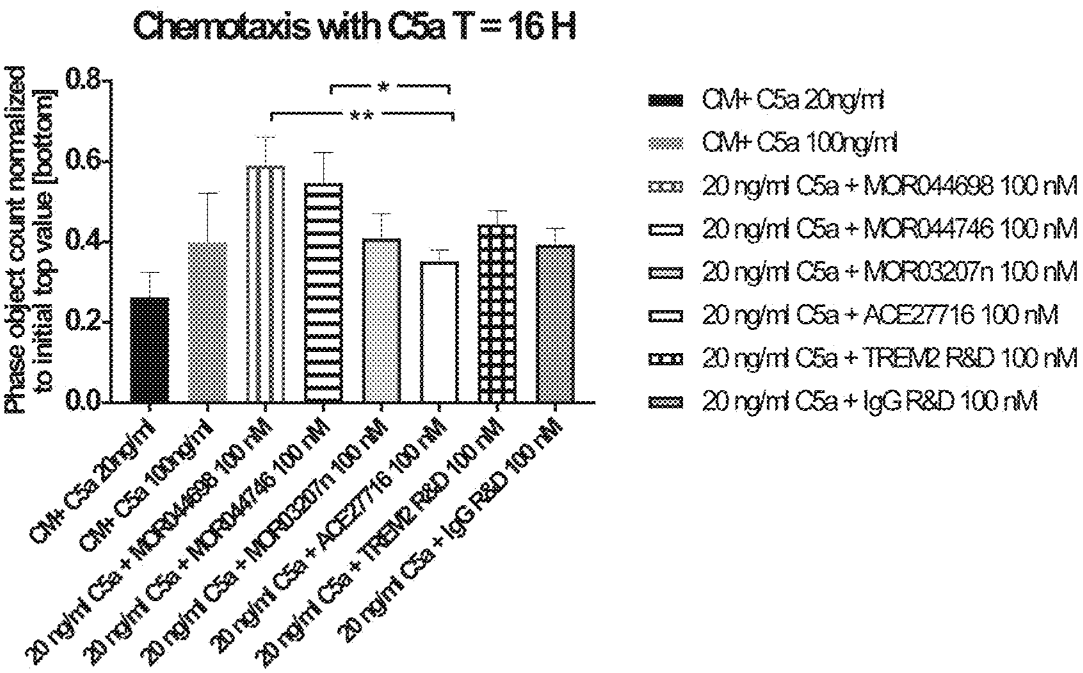
FIG. 12 shows that TREM2 antibodies facilitate chemotaxis of human M2A macrophages.

TREM2 has been shown to be involved in chemotactic responses of osteoclasts (Humphrey et al. J Bone Min Res, 2006. 21:237-245. 201(4):p. 647-657). Therefore, the effect of the anti-TREM2 antibodies on chemotactic response was evaluated in human M2a macrophages. Using 20 ng/ml of the chemoattractant C5a in combination with 100 nM MOR044698 or MOR044746 a statistical significant enhancement of chemotaxis in comparison to the two isotype control antibodies MOR03207 and ACE27716 was observed (see FIG. 12).

This experiment shows that MOR044698 and MOR044746 display efficacy in human M2A macrophages on a second TREM2 dependent physiological cellular readout (chemotaxis).

Figure 13:
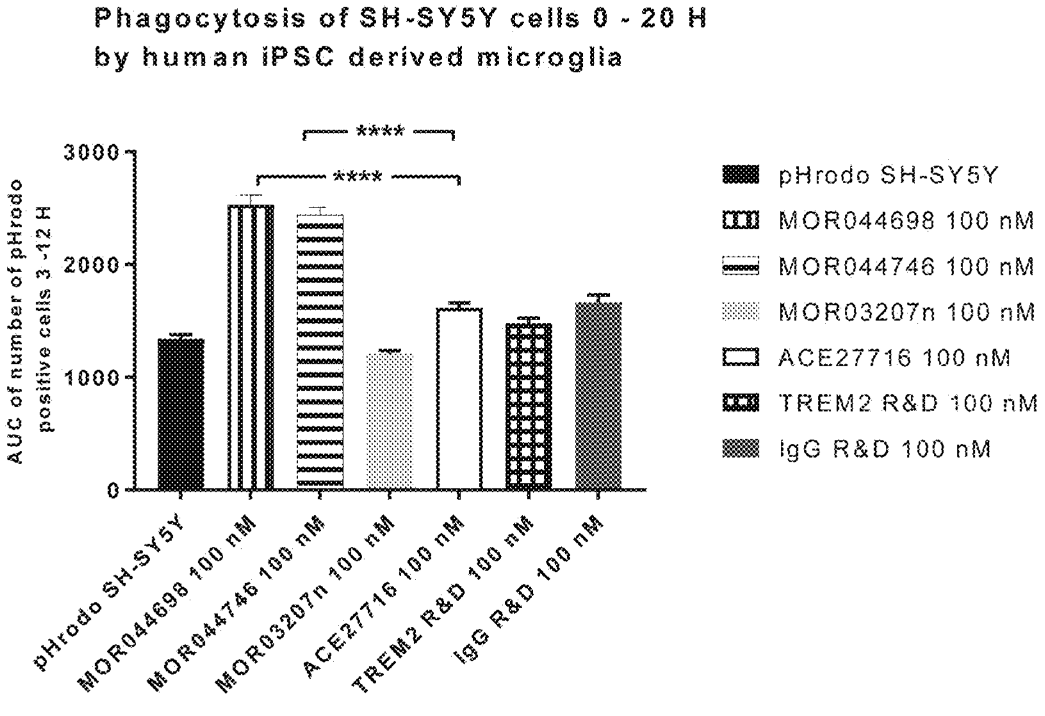
FIG. 13 shows that TREM2 antibodies facilitate phagocytosis in human iPS derived microglia using apoptotic pHrodo-labeled SH-SY5Y cells and cumulative phagocytosis as readout.

Similarly, to the results obtained with human M2A macrophages pre-incubation of human iPS derived microglia like cells with anti-TREM2 antibodies MOR044698 and MOR044746 increased phagocytic capacity of pHrodo-labeled apoptotic SH-SY5Y cell over a period of 20 hours in comparison to the two isotype control antibodies MOR03207 and ACE27716 (see FIG. 13).

Figure 14:
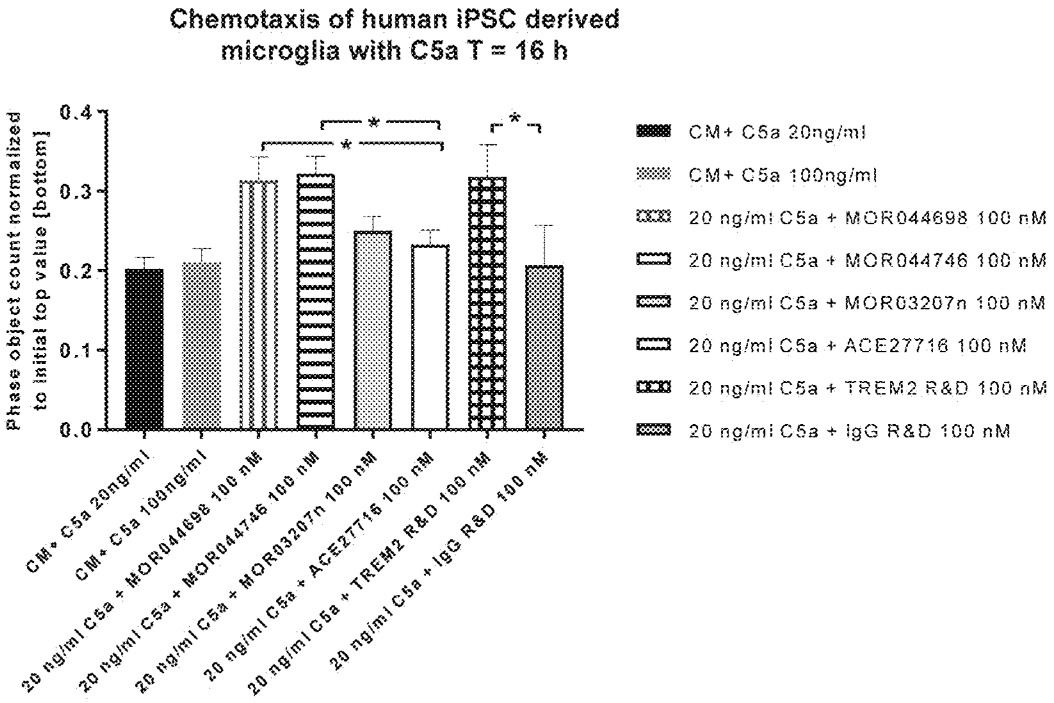
FIG. 14 shows that TREM2 antibodies facilitate chemotaxis of human iPS derived microglia

TREM2 has been shown to be involved in chemotactic responses of microglia cells (Takahashi, K et al. J Exp Med, 2005. 201(4):p. 647-657). Therefore, the effect of the anti-TREM2 antibodies on chemotactic response was evaluated in human iPS derived microglia like cells. Using 20 ng/ml of the chemoattractant C5a in combination with 100 nM MOR044698 or MOR044746 a statistical significant enhancement of chemotaxis in comparison to the two isotype control antibodies MOR03207 and ACE27716 was observed (see FIG. 14).

These experiments show that MOR044698 or MOR044746 increase the phagocytotic efficacy in another human derived cellular system (microglia) and on a second TREM2 dependent physiological cellular readout (chemotaxis).

Figure 15A:
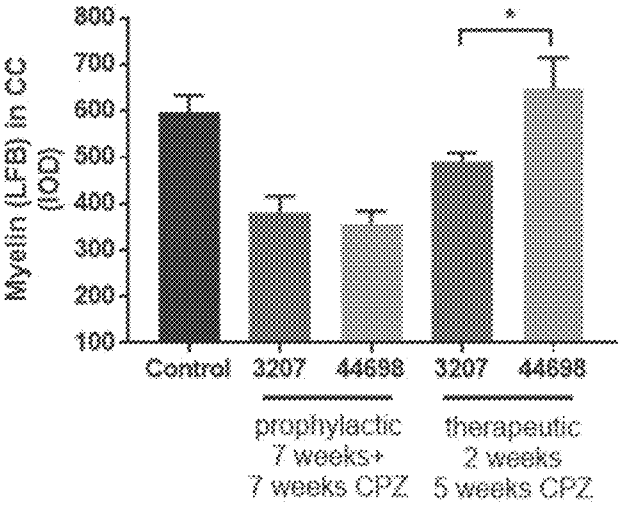
FIGS. 15A-15E shows the results of prophylactic/concomitant and therapeutic treatment with TREM2 antibody in the cuprizone model.
Figure 15B:
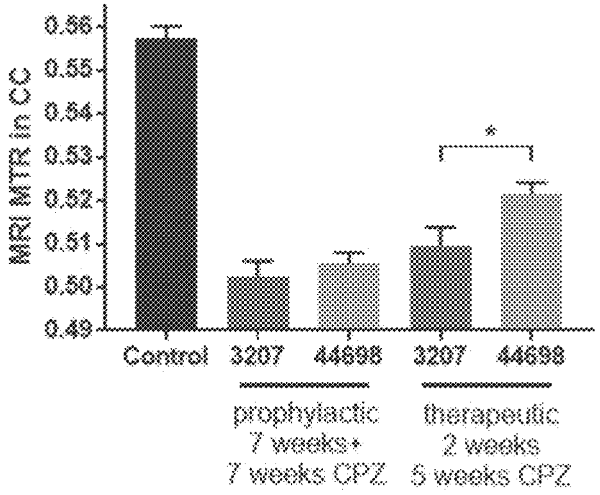
Figure 15C:
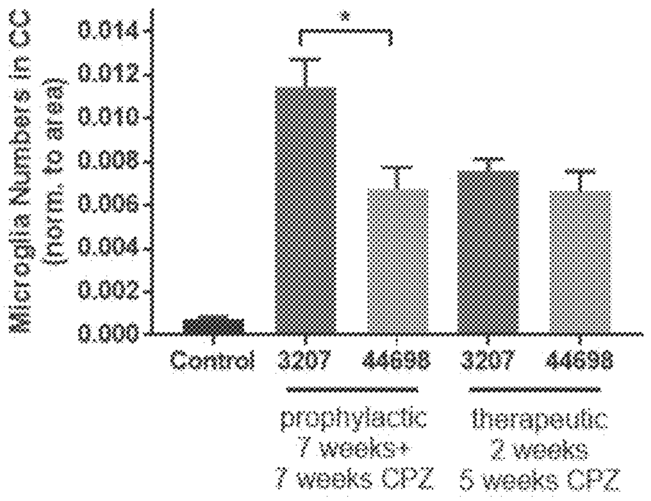
Figure 15D:
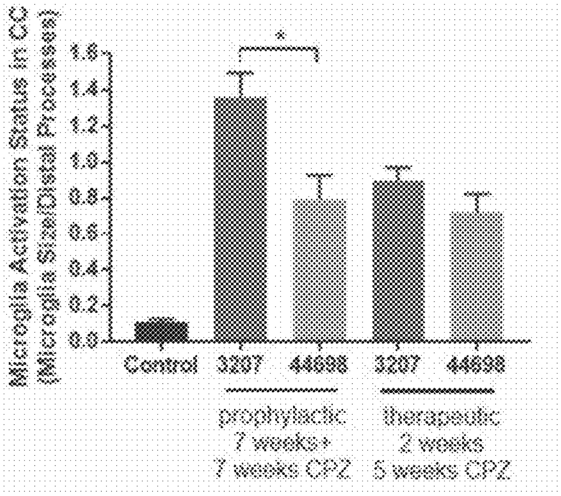
Figure 15E:
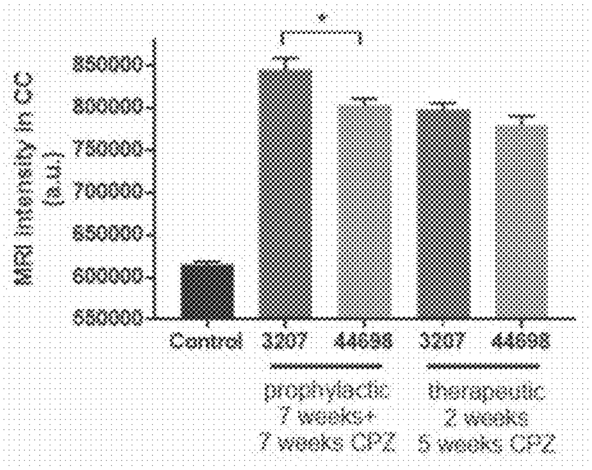

Cuprizone Model in Humanized TREM2 Crispr-Knock-In Mice Prophylactic/Concomitant Treatment of the Murinized MOR44698 TREM2 Antibody in the Cuprizone Model As shown in FIG. 15A Luxol fast blue detected no difference in myelin in the corpus callosum (CC). This is in accordance to the MRI (FIG. 15B), which also showed no obvious difference in MTR in the CC. Quantitative immunohistological analysis for the microglia marker Iba1 showed reduced numbers (FIG. 15C) and lower activation status (FIG. 15D) in the CC in 44698 treated mice than isotype. This was in accordance to the MRI that observed a reduced MRI intensity in the CC (FIG. 15E).

Therapeutic Treatment of the Murinized MOR44698 TREM2 Antibody in the Cuprizone Model As shown in FIG. 15A, Luxol fast blue detected a significant increase in myelin in the CC compared to 3207. This is in accordance to the MRI, which also showed an increase in MTR in the CC with 44698 treatment (FIG. 15B). Quantitative immunohistological analysis for the microglia marker Iba1 showed no difference in numbers (FIG. 15C) and activation status (FIG. 15D) in the CC in 44698 treated mice compared to isotype control. This was in accordance to the MRI that observed no change in MRI intensity in the CC between the treatment groups (FIG. 15E).

These data indicate that 44698 anti-TREM2 antibody has a beneficial effect on myelination processes if given therapeutically and alters microglia numbers and activation, which implies a potential therapeutic benefit of the TREM2 antibody in any disease where demyelination occurs or re-myelination would be desired both in the central or peripheral nervous system, including but not limited to: multiple sclerosis including clinical isolated syndrome, primary progressive MS, relapsing-remitting MS, Marburg multiple sclerosis and secondary progressive MS, Guillain-Barre syndrome and its chronic counterpart, chronic inflammatory demyelinating polyneuropathy, Anti-MAG peripheral neuropathy, Charcot-Marie-Tooth disease and its counterpart Hereditary neuropathy with liability to pressure palsy, Vitamin B12 deficiency-associated neuropathies, Balo concentric sclerosis, Schilder's diffuse sclerosis, and Devic's disease, centralpontine myelinolysis, myelopathies like tabes dorsalis (syphilitic myelopathy), leukoencephalopathies such as progressive multifocal leukoencephalopathy (caused by JC virus activation), leukodystrophies, optic neurilis, transverse myelitis, neuromyelitis optica, copper deficiency-associated conditions (peripheral neuropathy, myelopathy, and optic neuropathy), progressive inflammatory peripheral neuropathy, chronic inflammatory demyelinating polyneuropathy (CIDP) and other disorders with immune system involvement summarized under the term inflammatory demyelinating diseases.

MPTP Model in Humanized TREM2 Crispr-Knock-In Mice

Seven days after the MPTP treatment animals were killed and immunofluorescence on coronal brain free-floating sections was performed. Tyrosine hydroxylase (TH) was stained with an antibody, microscopic pictures taken and the area stained in the striatum was quantified with the Fiji software. TH is specifically expressed by dopaminergic neurons and upon their death TH reduction can be observed in the striatum to where the dopaminergic cells that reside in the substantia nigra project to with their long axons.

Figure 16A:
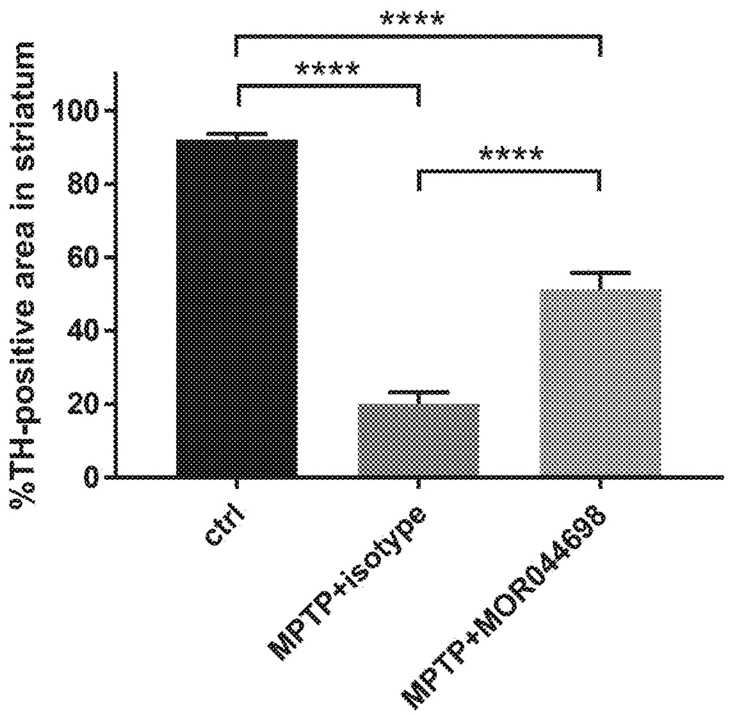
FIG. 16A shows the image analysis results of the MPTP Model in humanized TREM2 mice.
Figure 16B:
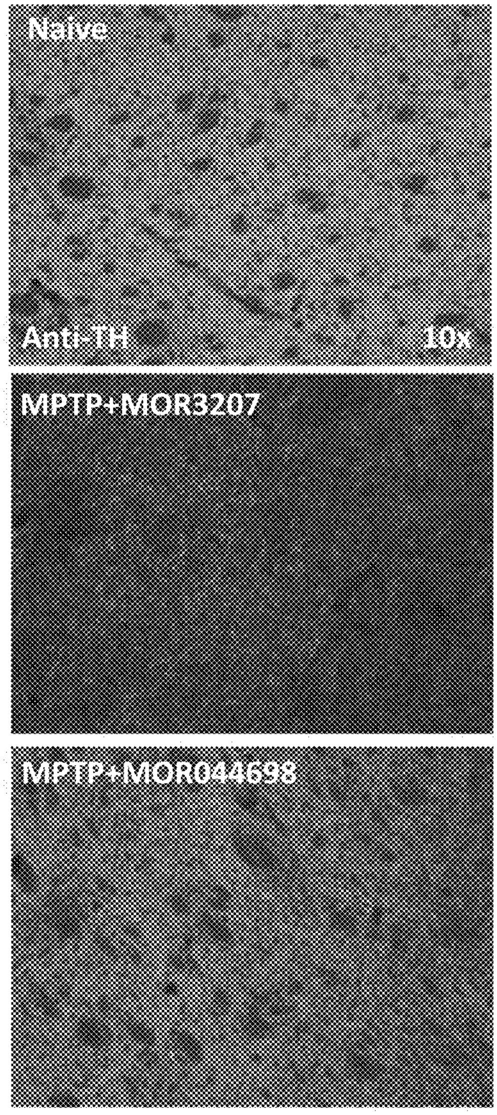
FIG. 16B shows a representative microscopy picture for each group.

As shown in FIG. 16A, animals treated with MPTP and the isotype control 3207 showed quite reduced TH-positive staining in the striatum (% area) compared to naïve animals (untreated control wildtypes), while 44698-treated mice displayed substantially more TH stain than animals with isotype control. In FIG. 16B are representative microscopic fluorescence pictures (magnification 10×) of the striatum from the different treatment groups.

This data indicates a potential neuroprotective effect of the TREM2 antibody that implies a general potential benefit for neurodegenerative diseases, including but not limited to: Parkinson's disease, multiple system atrophy, progressive supranuclear palsy, corticobasal degeneration, and dementia with Lewy bodies (DLB), synucleinopathies, tauopathies, Wilson's disease, neurodegeneration with brain iron accumulation, idiopathic basal ganglia calcification, frontotemporal dementia and parkinsonism linked to chromosome 17, fragile X-associated tremor/ataxia syndrome, ischemic stroke, hemorrhagic stroke, transient ischemic attack, amyotrophic lateral sclerosis (ALS), also known as motor neurone disease (MND) or Lou Gehrig's disease, primary lateral sclerosis (PLS), progressive muscular atrophy (PMA), progressive bulbar palsy, pseudobulbar palsy, and monomelic amyotrophy (MMA), frontotemporal dementias (FTD), behavioral variant of FTD, semantic variant primary progressive aphasia, nonfluent agrammatic variant primary progressive aphasia, corticobasal syndrome, progressive supranuclear palsy, and FTD associated with motor neuron disease, Pick's disease, frontotemporal lobar degenerations, alcoholic dementia, vascular dementia, corticobasal degeneration and Creutzfeldt-Jakob disease.

Example 3: Cross-Blocking Experiment

Material and Methods

CHO-hDAP12-hTREM2 cells were used to assess cross-blocking activity of Fab MOR041877 or Fab MOR041895 or Fab MOR042596 with full IgG MOR041877 (IgSF binder), MOR41895 (needs stalk and IgSF for binding), MOR042596 (IgSF binder and parent of MOR044698), MOR044698 and MOR03207 (isotype control). CHO-hDAP12-hTREM2 cells were cultured overnight in culture medium supplemented with 5 μM DPC333 to increase cell surface expression of TREM2. Next day, CHO-hDAP12-hTREM2 cells were detached with accutase, washed once with PBS and resuspended in FACS buffer (PBS, 2% FBS, 0.5 mM EDTA, pH 8.0) at a concentration of $4\times10^6$ cells/ml. Fab fragments MOR041877, MOR041895 and MOR042596 were labeled with Alexa Fluor 647 (AF647) according to manufacturer's protocol MAN0006869 from Invitrogen. 100 nM of full IgG antibodies were mixed in a total volume of 30 μl with 15 μl of the cell suspension and incubated for 30 min on ice. Cells were washed once with PBS and incubated with 100 nM of AF647-labeled Fab fragments for 30 min on ice, washed twice with PBS, fixed with cell fixation buffer (Biolegend) and resuspended in FACS buffer. Acquisitions were carried out on a BD FACS canto apparatus.

Results

Figure 17A:
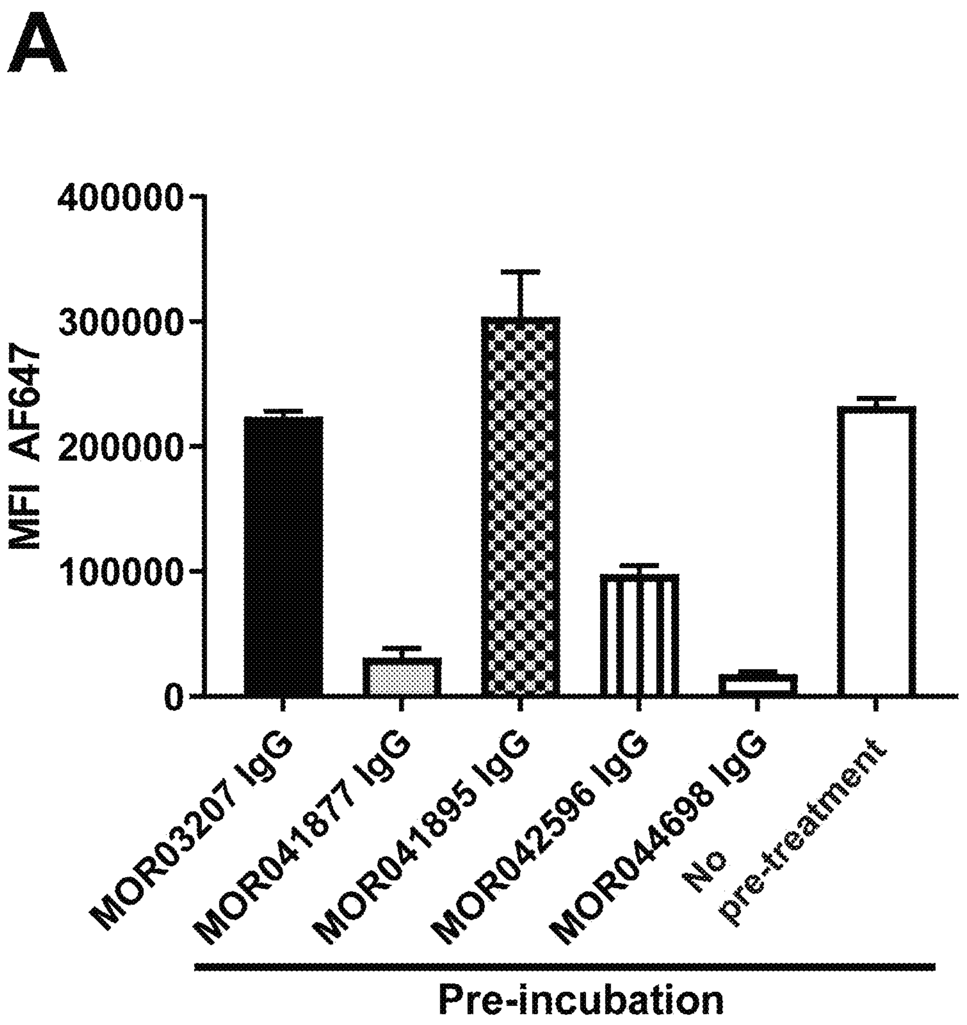
FIGS. 17A-17C show the results of cross-blocking experiments of Fab MOR041877, MOR041895 and MOR042596 with full IgG MOR041877, MOR41895, MOR042596, MOR044698 and MOR03207 in CHO-hDAP12-hTREM2 cells.
Figure 17B:
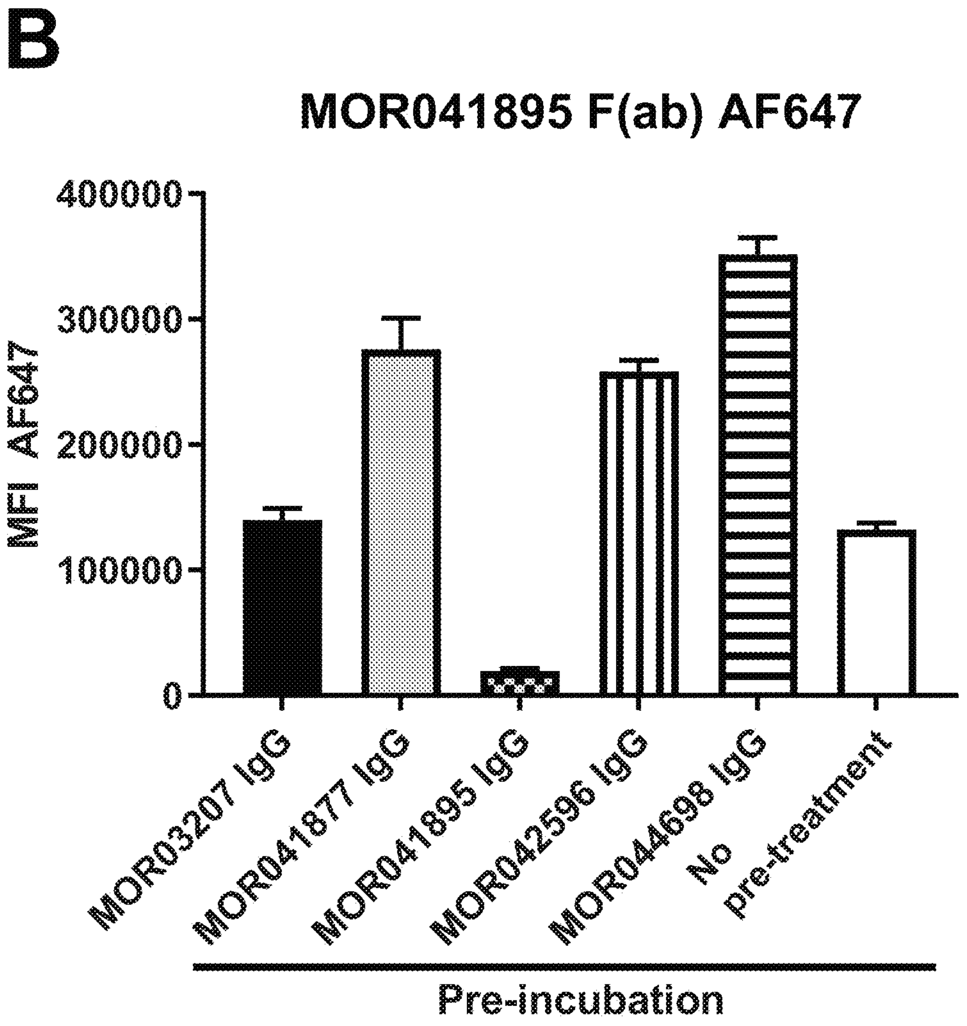
Figure 17C:
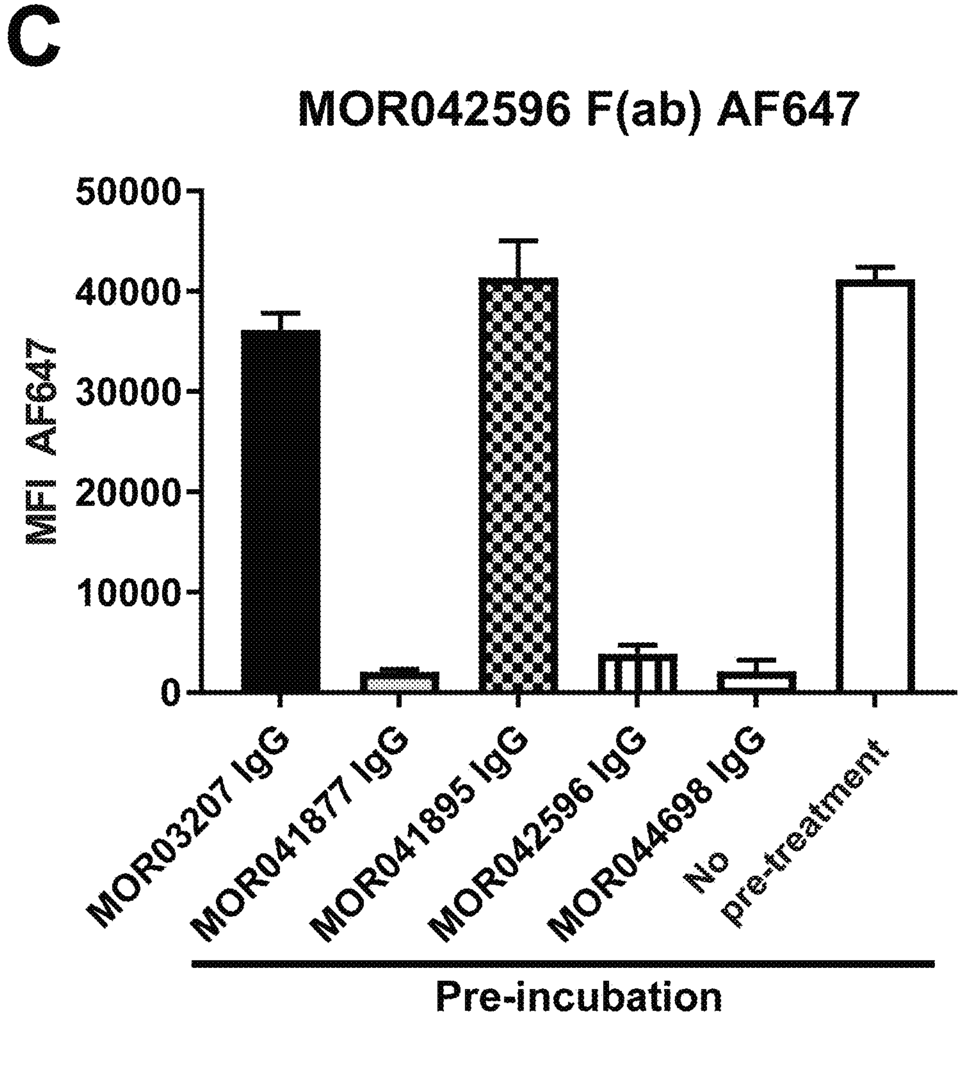

Binding of Fab fragment MOR041877 is not affected by pre-incubation with MOR041895 (FIG. 17A), since a similar signal is achieved as with pre-incubation with the isotype control MOR03207 or without any pre-treatment (last column). Pre-incubation with MOR042596 and MOR044698 strongly reduces binding of Fab MOR041877, showing overlapping epitopes for these three antibodies. Binding of Fab MOR41895 is reduced by pre-incubation with the full IgG from which this Fab is derived, but not by MOR041877, MOR044698 or MOR042596. Binding of full IgG MOR041877, MOR044698 and MOR042596 to TREM2 seems to facilitate access for the Fab41895 leading to an increase in signal intensity (FIG. 17B). Finally, pre-binding of full IgG MOR041877, MOR044698 or MOR042596 completely inhibits later binding of Fab MOR042596, demonstrating that MOR041877 and MOR044698 share the same epitope with MOR042596 (FIG. 17C). In summary, these experiments show that affinity maturated MOR044698 binds to the same epitope as the parental antibody MOR042596.

Example 4: Characterisation of MOR041877 and MOR042596

Antibodies MOR041877 and MOR042596 bind to human TREM2 recombinantly expressed in CHO-hDAP12-hTREM2 cells as well as to TREM2 expressed in human M2A macrophages and activate TREM2 dependent reporter-gene activity in THP-B5 cells (see table 29). These data show that both antibodies display high affinity to TREM2 and directly activate TREM2.

TABLE 29

Characterisation of MOR041877 and MOR042596 in different cellular systems.

| Assay | MOR041877 | MOR042596 |
|---|---|---|
| FACS in CHO-hDAP12-hTREM2 ($EC_{50}$, nM) | 0.5 | 3.4 |
| FACS in hM2A ($EC_{50}$, nM) | 0.7 | 37 |
| RGA in THP-B5 cells (fold increase over BG) | 2.1 | 1.8 |

Figure 18:
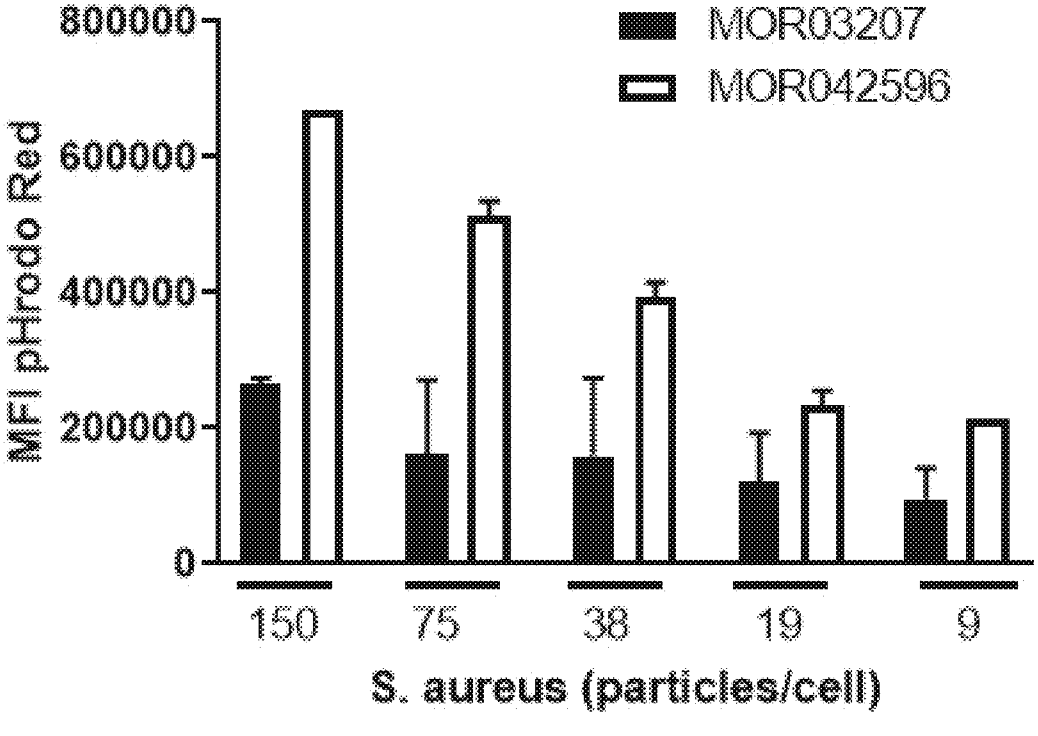
FIG. 18 shows the increase in phagocytic capacity of hM2A after treatment with MOR042596.

Furthermore, hM2A macrophages were treated with 100 nM of anti-TREM2 antibodies MOR042596 or isotype control (MOR03207). 16-20 h later, cells were subjected to a phagocytosis assay using different concentrations of pHrodo-labeled *Staphylococcus aureus* as phagocytic prey. MOR042596 strongly increased the phagocytic capacity of hM2A macrophages over the entire concentration range of *S. aureus* used (FIG. 18). This indicates that MOR042596 increases TREM2 signaling and TREM2 dependent effector functions in M2A macrophages.

Example 5: X-Ray Crystal Structure of the Human TREM2/MOR042596 Fab Complex

The crystal structure of a human TREM2 (residues 19-174 of SEQ ID NO: 1, followed by His-tag; SEQ ID NO: 139) bound to the Fab fragment of MOR042596 (residues 1-222 of SEQ ID NO: 15, and residues 1-214 of SEQ ID NO: 82) was determined. As detailed below, the individual components of the complex were produced using separate expression systems and were combined to generate the purified complex. X-ray crystallography was then employed to generate diffraction data for TREM2 bound to the MOR042596, elucidating the antigen-binding site.

```
                                           SEQ ID NO. 139
HNTTVFQGVA GQSLQVSCPY DSMKHWGRRK AWCRQLGEKG

PCQRVVSTHN LWLLSFLRRW NGSTAITDDT LGGTLTITLR

NLQPHDAGLY QCQSLHGSEA DTLRKVLVEV LADPLDHRDA

GDLWFPGESE SFEDAHVEHS ISRSLLEGEI PFPPTSHHHH HH
```

Protein Production

The human TREM-2 (residues 19-174 of SEQ ID NO: 1, followed by His-tag; SEQ ID NO: 139) was expressed in mammalian cells by large-scale transient transfection. Briefly, plasmid DNA was mixed 1:2 with polyethylene amine (PEI 25k, PolyScience) and allowed to form micellar complexes for 30 min. The starting seeding culture had 2 mg DNA and 4 mg PEI per 1 L culture. Transfection was achieved by adding these mixtures to HEK 293-6E cells (Invitrogen) at a ratio of 2 μg DNA: $3\times10^6$ cells. Cells were allowed to grow in V3 medium (Bioconcept Ltd. Amimed) with shaking in vented flasks at 37° C. and 5% C02. Culture supernatants were collected at 130 h post-transfection, modified by addition of 50 mM Tris pH 8.5, 300 mM NaCl, 5% glycerol and 10 mM imidazole, and then purified using NiNTA-affinity chromatography. Proteins were washed on column using the same buffer containing 20 mM imidazole and eluted in 250 mM imidazole. TREM2 was further purified by size exclusions chromatography (superdex 75) with buffer containing 50 mM Tris pH7.5, 150 mM NaCl, 10% glycerol. The resulting proteins were >90% pure as assessed by SDS-PAGE.

For production of MOR042596, eukaryotic HEK293-T cells were transfected with mammalian expression vector DNA encoding both heavy and light chains of disulfide-bridged FabCys. Cell culture supernatants were harvested on day 7 post transfection and subjected to CH1 affinity chromatography (Capture Select IgG-CH1, Thermo Scientific). Buffer exchange was performed to 20 mM Tris, 100 mM NaCl pH 7.5 and samples were sterile filtered (0.2 μm pore size). Protein concentrations were determined by UV-spectrophotometry and purities of FabCys were analyzed under denaturing, reducing and non-reducing conditions using SDS-PAGE. HP-SEC was performed to analyze FabCys preparations in native state.

In Vitro Reconstitution of the TREM2-MOR042596 Fab Complex

Purified TREM2 was then mixed with MOR042596 Fab at a molar ratio of 1:1 (concentration measured by OD A280). The complex was then concentrated before being loaded onto a Superdex 75 column (GE Healthcare Life Sciences) equilibrated with 50 mM Tris pH7.5, 150 mM NaCl, 5% glycerol. Peak fractions underwent analysis by SDS-PAGE and selected fractions were combined for crystallization trials.

Crystallization and Structure Determination

The TREM2-MOR042596 Fab complex was concentrated to 7.5 mg/ml, followed by centrifugation at 20,000×g for 10 min prior to dispensing crystallization screens. Crystals were grown at 20° C. using a sitting drop vapor diffusion setup. 0.2 μl of the TREM2-MOR42596 complex was mixed with 0.2 μl of a reservoir solution containing 20% PEG3350, 0.2M Potassium Sodium Tartrate and the drop was equilibrated against 80 μl of the reservoir solution. Crystals were harvested from their mother liquor with 20% glycerol as crypotectant and directly flash-frozen in liquid nitrogen.

Data sets were collected at 1.000 Å wavelength with a PILATUS 6M detector at the Swiss Light Source beamline X10SA (Villigen, Switzerland). Diffraction images recorded at 0.250 oscillation angle wedges were processed and scaled using XDS and XSCALE (Kabsch W, 1993. Automatic processing of rotation diffraction data from crystals of initially unknown symmetry and cell constants J. Appl. Cryst. 26: 795-800), respectively, in the APRV program suite (Kroemer M, Dreyer M K, Wendt K U 2004. APRV—a program for automated data processing, refinement and visualization. Acta Cryst. D60: 1679-82). An initial structure was obtained by molecular replacement using Phaser (McCoy A J, Grosse-Kunstleve R W, Adams P D et al. 2007. Phaser crystallographic software. J. Appl. Cryst. 40: 658-74.) and the homology models of Fab and TREM2 Ig domain as search models. Manual rebuilding of the model and subsequent structure refinement were carried out in Coot (Emsley P, Cowtan K (2004) Coot: model-building tools for molecular graphics. Acta Cryst. D60: 2126-32.) and autoBuster (Bricogne G, Blanc E, Brandl M et al. (2009) BUSTER, version 2.8.0. Cambridge, UK, Global Phasing Ltd.), respectively.

Elucidation of the MOR042596-Binding Epitope on hTREM2

Figure 19:
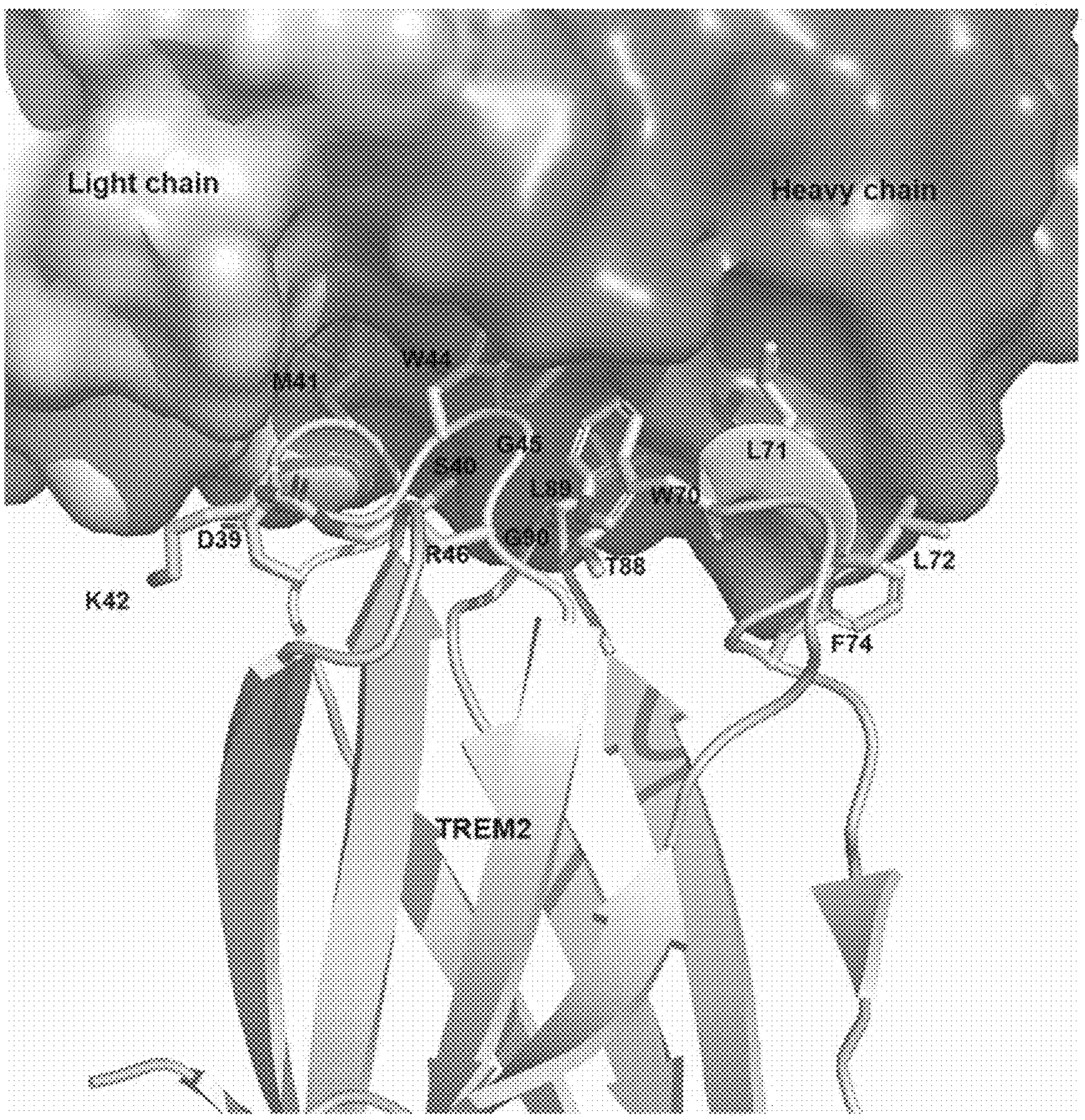
FIG. 19 shows the epitope of TREM2 binding to MOR042596 as determined by X-ray crystallography. The protein backbone of TREM2 is shown in the cartoon representation and the sidechains of TREM2 residues within 5 Å distance from the Fab are shown as sticks. The Fab heavy chain is shown as dark grey surface and the light chain as light grey surface.

We obtained the X-ray co-crystal structure of the Human TREM2/MOR042596 Fab Complex as described above. FIG. 19 shows an overview of the TREM2 residues interacting with MOR042596.

From the TREM2/MOR042596-Fab complex structure, we deduce the TREM2 epitope which encompasses three separate sequence regions on huTREM, given in Table 30. All hTREM2 isoforms (SEQ ID NOs. 1-3) have the first 161 residues in common, which comprises the signal peptide and the whole IgSF domain; therefore, the epitopes and residue numbering in this range (i.e. up to and including the residue R161) as in the below (e.g. Tables 30, 31 and 33) are the same for all the three hTREM2 isoforms.

TABLE 30

Epitope of TREM2 binding to MOR042596.

| Sequence stretch on hTREM2 | Residues |
|---|---|
| Region 1 | D39-S40-M41-K42; W44-G45-R46 |
| Region 2 | W70-L71-L72; F74 |
| Region 3 | T88-L89-G90 |

Similarity Between MOR044698 and MOR042596 and hTREM2 Epitope Binding to MOR044698

As shown in FIG. 19, hTREM2 interacts with both heavy and light chain of MOR042596. The closely related Fab MOR044698 shares the identical sequence in five out of the six TREM2-binding loops with MOR042596, namely HCDR1, HCDR2, HCDR2, LCDR1 and LCDR2 with only LCDR3 being different. The sequences of those loops as well as TREM2 residues within 5 Å distance in the TREM2/MOR042596 Fab Complex structure are given in Table 31 and a comparison of LCDR3 sequences of MOR042596 and MOR044698 is given in Table 32.

TABLE 31

HCDR and LCDR sequences for MOR042596 and interacting residues on TREM2 within 5 Å.

| CDR | Sequence | SEQ ID NO | ID Interacting Residues on hTREM2 within 5Å |
|---|---|---|---|
| HCDR1 | GYTFTGYHMS | 4 | W44; W70-L71; T88-L89 |
| HCDR2 | VINPVSGNTVYAQKFQG | 5 | W44; L71-L72; F74; L89-G90 |
| HCDR3 | IPSYTY AFDY | 6 | M41; W44-G45; W70-L71 |
| LCDR1 | RASQDISNYLA | 17 | M41-K42; R46 |
| LCDR2 | RASSLQS | 18 | R46 |
| LCDR3 | QQHGHSPTT | 78 | D39-S40-M41-K42 |

TABLE 32

LCDR3 sequences of MOR042596 and MOR044698.

| Candidate ID | LCDR3 | | | | | | | | | |
|---|---|---|---|---|---|---|---|---|---|---|
| MOR044698 | F | Q | Y | R | H | M | P | S | Q | T |
| MOR042596 | Q | Q | H | G | H | S | P | — | T | T |
| Sequence numbering (Kabat) | 89 | 90 | 91 | 92 | 93 | 94 | 95 | 95a | 96 | 97 |

Figure 20:
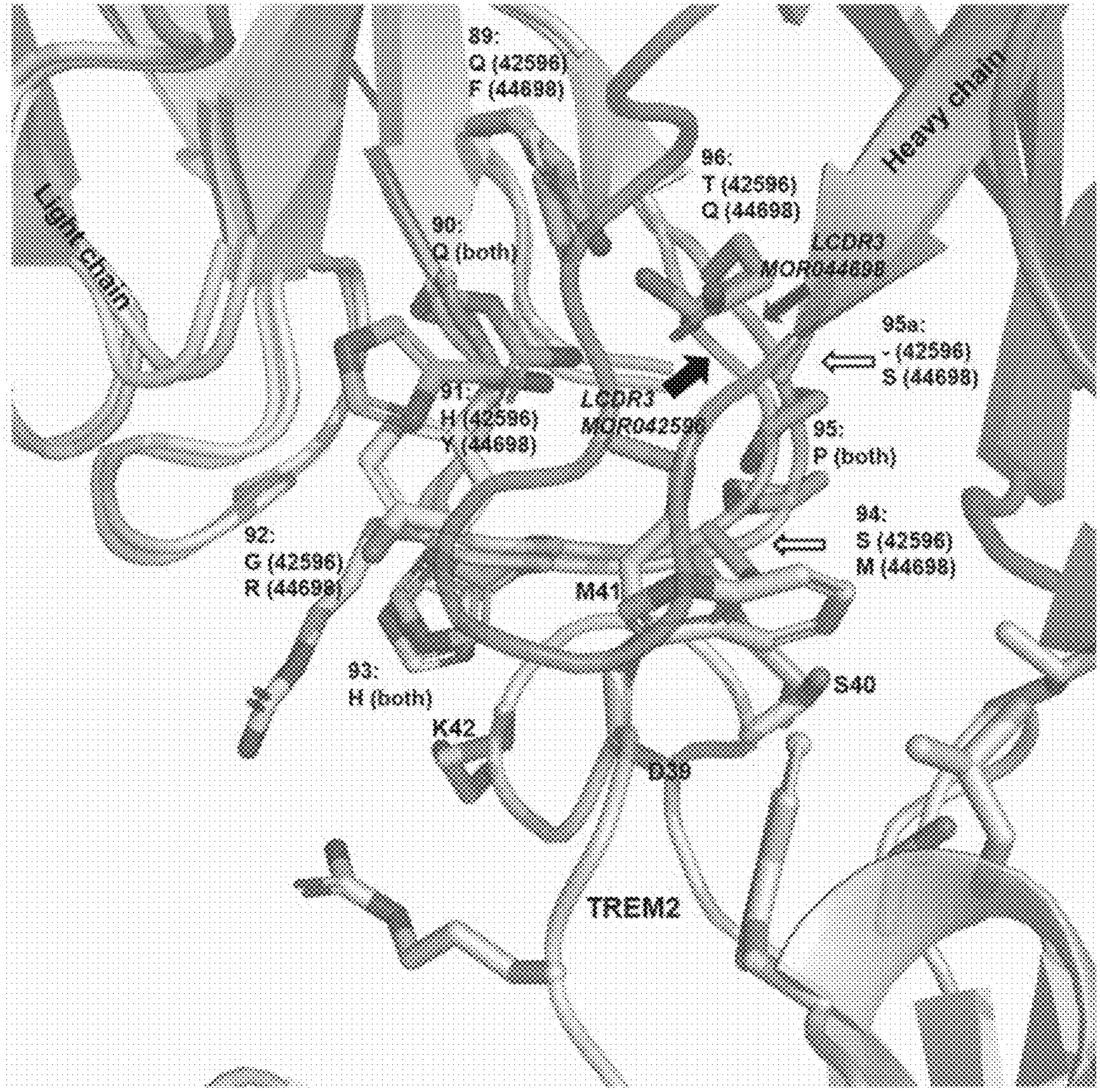
FIG. 20 shows close-up view of the TREM2-Fab interface (cf.

To gauge the structural implications of the differences in LCDR3 between both Fabs, we built a homology model for MOR044698. We used the crystal structure of MOR042596 as template and built the model with CCG MOE release 2018.01 as modelling software at standard settings [Molecular Operating Environment (MOE), 2018.01; Chemical Computing Group ULC: Montreal, QC, Canada, 2018]. FIG. 20 shows the interface of both Fabs to TREM2. With HCDR1-3 and LCDR1-2 being identical, the only differences to be discussed are in LCDR3. There are several conserved residues (e.g. Pro95 which decisively influences the LCDR3 loop conformation) as can be gleaned from Table 32. At the interface of TREM2 and the two Fabs, there are three positions where major changes/mutations occur comparing MOR042596 to MOR044698: changing Glycine 92 to Arginine, Serine 94 to Methionine and the insertion of a serine at position 95a for MOR044698. The serine 95a insertion does not cause a major conformational change but rather a slight adaptation of the protein backbone. The remaining two major amino acid changes in positions 92 and 94, while representing major changes in side chains, can be built into the pre-existing loop structure of LCDR3 as observed in the MOR042596 crystal structure without leading to any clashes or unfavorable contacts with TREM2. There are further differences in positions 89, 91 and 96. Positions 89 and 96 are not involved in any contacts with TREM2 and the Histidine-to-Tyrosine mutation in position 91 is tolerated with only a small adaptation of sidechain conformation. Overall, with the heavy chains being identical, the light chains being identical in LCDR1 and LCDR2 and LCDR3 appearing to have an unchanged loop conformation and conserved contacts to TREM2 in MOR044698, we therefore conclude that the TREM2 epitope is identical between the two Fabs MOR042596 and MOR044698.

X-Ray Crystal Structure of the Human TREM2/MOR041877 Fab Complex

The crystal structure of a human TREM2 (residues 19-174 of SEQ ID NO: 1, followed by His-tag; SEQ ID NO: 139) bound to the Fab fragment of MOR041877 (residues 1-224 of SEQ ID NO: 95, and residues 1-216 of SEQ ID NO: 106) was determined. As detailed below, the individual components of the complex were produced using separate expression systems and were combined to generate the purified complex. X-ray crystallography was then employed to generate diffraction data for TREM2 bound to the MOR041877, elucidating the antigen-binding site.

Protein Production

The human TREM-2 protein was expressed and purified as described above for MOR042596.

For production of MOR041877, eukaryotic HKB11 cells were transfected with mammalian expression vector DNA encoding both heavy and light chains of disulfide-bridged FabCys. Cell culture supernatants were harvested on day 3 or 7 post transfection and subjected to CH1 affinity chromatography (Capture Select IgG-CH1, Thermo Scientific). Buffer exchange was performed to 1× Dulbecco's PBS (pH 7.2, Invitrogen) and samples were sterile filtered (0.2 μm pore size). Protein concentrations were determined by UV-spectrophotometry and purities of FabCys were analyzed under denaturing, reducing and non-reducing conditions using CE-SDS (LabChip GXII, Perkin Elmer). HP-SEC was performed to analyze FabCys preparations in native state.

In Vitro Reconstitution of the TREM2-MOR041877 Fab Complex

Purified TREM2 was then mixed with MOR042596 Fab at a molar ratio of 1:1 (concentration measured by OD A280). The complex was then concentrated before being loaded onto a Superdex 75 column (GE Healthcare Life Sciences) equilibrated with 50 mM Tris pH7.5, 150 mM NaCl, 5% glycerol. Peak fractions underwent analysis by SDS-PAGE and selected fractions were combined for crystallization trials.

Crystallization and Structure Determination

The TREM2-MOR042596 complex was concentrated to 7.5 mg/ml, followed by centrifugation at 20,000×g for 10 min prior to dispensing crystallization screens. Crystals were grown at 20° C. using a sitting drop vapor diffusion setup. 0.2 μl of the TREM2-MOR41877 complex was mixed with 0.2 μl of a reservoir solution containing 20% PEG3350, 0.2M Potassium Sodium Tartrate and the drop was equilibrated against 80 μl of the reservoir solution. Crystals were harvested from their mother liquor with 20% glycerol as crypotectant and directly flash-frozen in liquid nitrogen.

Data sets were collected at 1.000 Å wavelength with a PILATUS 6M detector at the Swiss Light Source beamline X10SA (Villigen, Switzerland). Diffraction images recorded at 0.25° oscillation angle wedges were processed and scaled using XDS and XSCALE (Kabsch W J 1993), respectively, in the APRV program suite (Kroemer M et al. 2004). An initial structure was obtained by molecular replacement using Phaser (McCoy A J et al., 2007) and the homology models of Fab and TREM2 Ig domain as search models. Manual rebuilding of the model and subsequent structure refinement were carried out in Coot (Emsley P et al. 2004) and autoBuster (G et al. 2009), respectively.

Elucidation of the MOR041877-Binding Epitope on hTREM2

Figure 21:
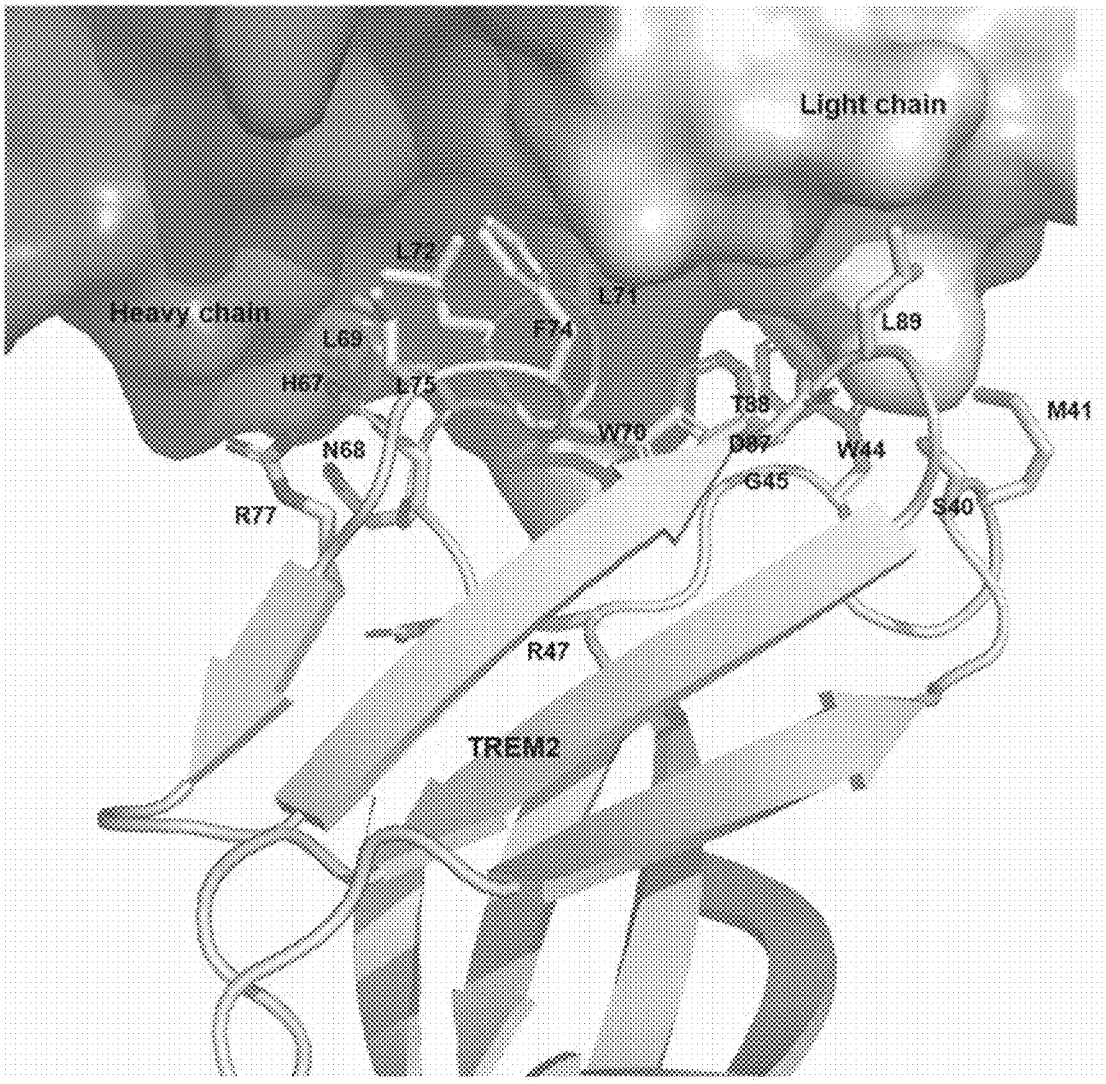
FIG. 21 shows the epitope of TREM2 binding to MOR041877 as determined by X-ray crystallography. The protein backbone of TREM2 is shown in the cartoon representation and the sidechains of TREM2 residues within 5 Å distance from the Fab are shown as sticks. The Fab heavy chain is shown as dark grey surface and the light chain as light grey surface.

We obtained the X-ray co-crystal structure of the Human TREM2/MOR041877 Fab Complex as described above. FIG. 21 shows an overview of the TREM2 residues interacting with MOR041877.

From the TREM2/MOR041877 Fab Complex structure, we deduce the TREM2 epitope binding to MOR041877, as shown in Table 33.

TABLE 33

Epitope of TREM2 binding to MOR041877.

| Sequence stretch on hTREM2 | Residues |
|---|---|
| Region 1 | S40-M41; W44-G45; R47 |
| Region 2 | H67-N68-L69-W70-L71-L72; F74-L75; R77 |
| Region 3 | D87-T88-L89 |

The sequences of the HCDR and LCDR loops as well as TREM2 residues within 5 Å distance in the TREM2/MOR041877 Fab Complex structure are given in Table 34.

TABLE 34

HCDR and LCDR sequences for MOR041877 and interacting residues on TREM2 within 5 Å.

| CDR | Sequence | SEQ ID NO | Interacting Residues on hTREM2 within 5Å |
|---|---|---|---|
| HCDR1 | GFSLSTSGVGVS | 84 | N68-L69 |
| HCDR2 | LIFSDHDKIYSTSLKT | 85 | H67; L69; L72; F74-L75; R77 |
| HCDR3 | TLIDRSVYFDY | 86 | W44-G45; R47; N68-L69-W70-L71-L72 |
| LCDR1 | SGSSSNIGHHYVS | 97 | S40-M41; W44; W70-L71; T88-L89 |
| LCDR2 | DNTNRPS | 98 | — |
| LCDR3 | ATWDGLMNSIV | 99 | L71-L72; F74; D87; L89 |

Example 6: Prophylactic/Concomitant Treatment of the Murinized TREM2 Antibody (MOR044698-Mu) in the 3-Week Cuprizone Model The cuprizone model is a toxin-induced demyelination model to study myelination processes in the CNS with only minor involvement of the peripheral immune system. Cuprizone, a copper chelator, induces mitochondrial damage and eventually oligondendrocyte dell death, whereas oligodendrocyte precursor cells are not affected and can still exert their proper function (proliferate, maturate and remyelinate). The cuprizone model is well suited to test regenerative treatment paradigms for demyelinating disease such as e.g. MS that enhance remyelination independently of invading peripheral immune cells.

Humanized TREM2 mice were generated by the introduction of human TREM2 cDNA including bovine growth hormone polyA signal sequence into the ATG of the mouse TREM2 gene by CRISPR/Cas technology. Founder lines were characterized by their expression of hTREM2 in bone-marrow derived macrophages and in microglia in the brain. The integration of the transgene was then confirmed by targeted locus amplification (TLA).

Humanized TREM2 Crispr-knock-in mice (hTREM-KI) were treated with cuprizone (0.2% in food) for 3 weeks with one day before and twice weekly thereafter with MOR044698-mu (comprising light chain sequence of SEQ ID NO: 140 and heavy chain sequence of SEQ ID NO: 141) and the isotype control MOR03207 (short: 3207) i.p., 30 mg/kg. After 3 weeks of prophylactic/concomitant treatment with antibody and cuprizone animals were killed and histology on coronal free-floating brain sections (20-30 μm thick) was performed. TREM2 and Iba1 antibodies were used to evaluate hTREM2 levels in microglia.

Figure 22A:
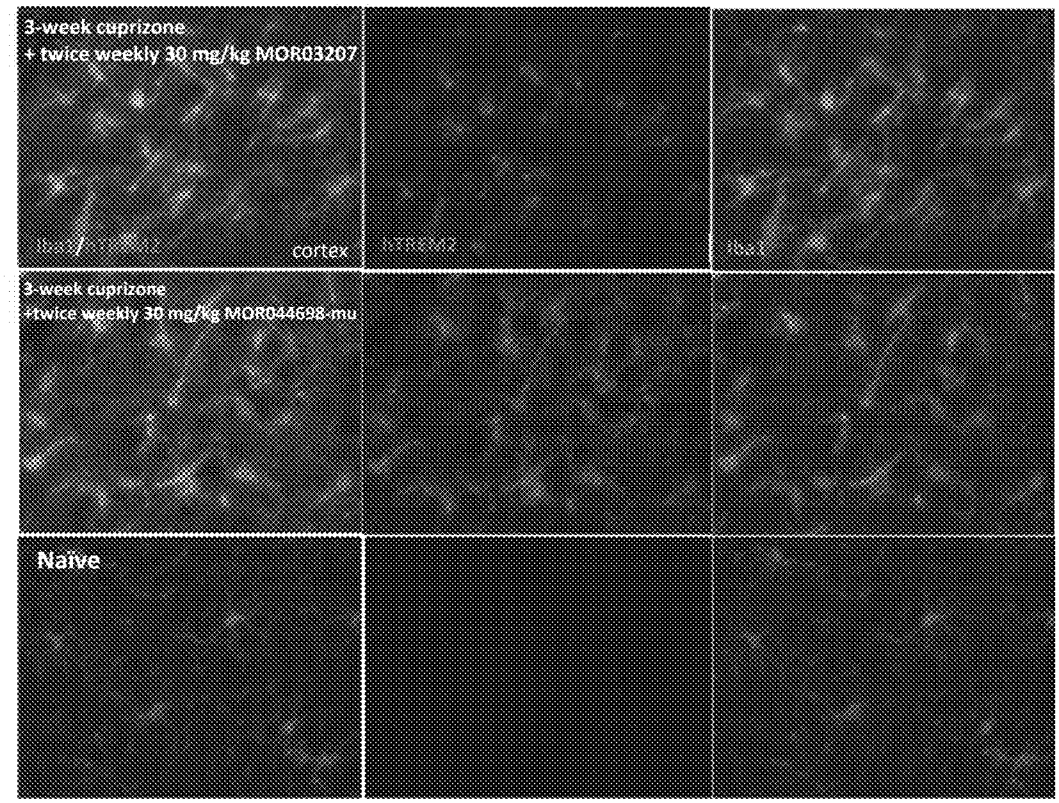
FIGS. 22A and 22B show brain cortex of hTREM2-KI mice treated with cuprizone and either MOR044698-mu or isotype control antibody, together with naive mice as control, stained for TREM2 and Iba1 (FIG. 22A). A quantitive analysis of the normalized area positive for hTREM2 is provided (FIG. 22B).
Figure 22B:
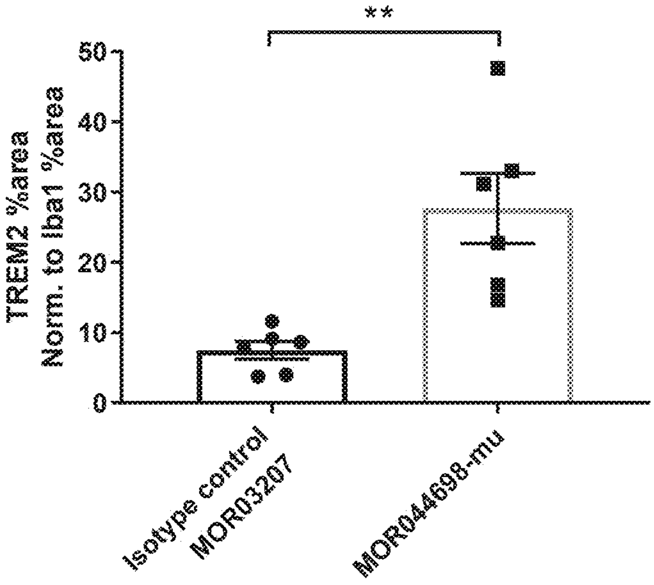

As shown in FIG. 22A,B hTREM2 levels in Iba1-positive microglia in the cortex were approx. 3 times higher in MOR044698-mu treated animals than isotype in the 3-week cuprizone model. Quantification of hTREM2 (stained with AF1828 antibody) was performed by quantifying fluorescence tiff images (stack maximized and exported as tiff snapshot without image adjustments, 20×) by Fiji (converted to 8-bit) with threshold (Iba1, green: 10, TREM2, red: 15). Readouts: % area; TREM2% area is normalized to Iba1% area (×100), average of two image stacks from cortex per animal, 2 brain sections per animal stained, 1 image stack per brain section.

Conclusion

These data indicate that systemic treatment with MOR044698 stabilizes TREM2 in the brain in microglia and thereby increases its levels and could lead to an enhancement of TREM2 signaling and function.

Summary

In summary, a strategy was employed to identify TREM2 antibodies that facilitate the function of TREM2 in a human cellular system (i.e. macrophages or microglia) by reducing constitutive or inflammation-induced shedding of TREM2 and thereby increasing the cellular activities of TREM2. Such antibodies are useful for the treatment of a variety of neurodegenerative diseases.

Anti-TREM2 antibodies (hTREM2 antibodies) have been identified, they bind with sub-nanomolar cellular affinities to human M2A macrophages and show very little donor to donor variability. The present antibodies bind to the IgSF domain of human TREM2 and also recognize cynomolgus TREM2. This has been demonstrated both in an in vitro ELISA as well as in cell lines. Surprisingly, binding of these antibodies to TREM2 inhibits shedding of TREM2 ectodomain from human M2A macrophages and as a consequence increases TREM2 expression at the cell surface. Functionally, the present TREM2 antibodies also increase phagocytic capacity and also enhance C5a mediated chemotaxis both in human macrophages as well as in human iPS derived microglia-like cells. Furthermore, the present antibodies also enhance chemotaxis of human macrophages as well as of human iPS derived microglia-like cells. The present antibodies also directly activate TREM2 as shown by NFAT dependent cellular reporter gene assay as well as by increased syk phosphorylation in human macrophages after TREM2 stimulation.

The present antibodies display high specificity for TREM2, do not to bind to any other target and are fully human antibodies. The present antibodies display binding to a new epitope on TREM2 within the IgSF region, and are shown to stabilize and activate TREM2.

The present antibodies have also been selected based on their suitability for development: e.g. the present antibodies lack posttranslational modifications in the CDR, they do not aggregate, they are produced in high quantities by cellular systems, they do not show clipping products and display a well-defined melting point and isoelectric point. Finally, their increased half-life leads to longer lasting effect in the brain, allowing dose optimization to achieve the desired clinical effect and reducing dosing frequencies thereby increasing patient compliance.

The invention claimed is:

1. A nucleic acid molecule or set of nucleic acid molecules encoding an anti-TREM2 antibody or antigen-binding fragment thereof, wherein the anti-TREM2 antibody or antigen-binding fragment thereof comprises three heavy chain complementarity determining regions (HCDR1, HCDR2, and HCDR3) and three light chain complementarity determining regions (LCDR1, LCDR2, and LCDR3), wherein:

(i) the HCDR1 comprises the amino acid sequence of SEQ ID NO: 7, the HCDR2 comprises the amino acid sequence of SEQ ID NO: 5, the HCDR3 comprises the amino acid sequence of SEQ ID NO: 6, the LCDR1 comprises the amino acid sequence of SEQ ID NO: 17, the LCDR2 comprises the amino acid sequence of SEQ ID NO: 18, and the LCDR3 comprises the amino acid sequence of SEQ ID NO: 19, as defined by the Kabat numbering system;

(ii) the HCDR1 comprises the amino acid sequence of SEQ ID NO: 8, the HCDR2 comprises the amino acid sequence of SEQ ID NO: 9, the HCDR3 comprises the amino acid sequence of SEQ ID NO: 6, the LCDR1 comprises the amino acid sequence of SEQ ID NO: 20, the LCDR2 comprises the amino acid sequence of SEQ ID NO: 21, and the LCDR3 comprises the amino acid sequence of SEQ ID NO: 22, as defined by the Chothia numbering system;

(iii) the HCDR1 comprises the amino acid sequence of SEQ ID NO: 10, the HCDR2 comprises the amino acid sequence of SEQ ID NO: 11, the HCDR3 comprises the amino acid sequence of SEQ ID NO: 12, the LCDR1 comprises the amino acid sequence of SEQ ID NO: 23, the LCDR2 comprises the amino acid sequence of SEQ ID NO: 21, and the LCDR3 comprises the amino acid sequence of SEQ ID NO: 19, as defined by the IMGT numbering system;

(iv) the HCDR1 comprises the amino acid sequence of SEQ ID NO: 4, the HCDR2 comprises the amino acid sequence of SEQ ID NO: 5, the HCDR3 comprises the amino acid sequence of SEQ ID NO: 6, the LCDR1 comprises the amino acid sequence of SEQ ID NO: 17, the LCDR2 comprises the amino acid sequence of SEQ ID NO: 18, and the LCDR3 comprises the amino acid sequence of SEQ ID NO: 19, as defined by the Combined numbering system.

2. The nucleic acid molecule or set of nucleic acid molecules of claim 1, wherein the anti-TREM2 antibody or antigen-binding fragment thereof comprises a heavy chain variable region comprising the amino acid sequence of SEQ ID NO: 13 and a light chain variable region comprising the amino acid sequence of SEQ ID NO: 24.

3. The nucleic acid molecule or set of nucleic acid molecules of claim 1, wherein the anti-TREM2 antibody or antigen-binding fragment thereof comprises a modified Fc domain that has reduced antibody-dependent cellular cytotoxicity (ADCC) or complement-dependent cytotoxicity (CDC) activity compared to the antibody or antigen-binding fragment thereof without the modified Fc domain.

4. The nucleic acid molecule or set of nucleic acid molecules of claim 1, wherein the anti-TREM2 antibody or antigen-binding fragment thereof comprises:

a heavy chain comprising the amino acid sequence of SEQ ID NO: 37 and a light chain comprising the amino acid sequence of SEQ ID NO: 26.

5. The nucleic acid molecule or set of nucleic acid molecules of claim 4, wherein:

the heavy chain variable region is encoded by the nucleic acid sequence of SEQ ID NO: 28 and the light chain variable region is encoded by the nucleic acid sequence of SEQ ID NO: 31.

6. A vector comprising the nucleic acid molecule or set of nucleic acid molecules of claim 1.

7. The vector of claim 6, wherein the vector is selected from a DNA vector, an RNA vector, a plasmid, a cosmid, or a viral vector.

8. A cell comprising the nucleic acid molecule or set of nucleic acid molecules of claim 1.

9. A method of producing an anti-TREM2 antibody or antigen-binding fragment thereof, the method comprising: (i) culturing the cell of claim 8 under conditions suitable to produce an anti-TREM2 antibody or antigen-binding fragment thereof and (ii) isolating the anti-TREM2 antibody or antigen-binding fragment thereof from the culture.

10. The nucleic acid molecule or set of nucleic acid molecules of claim 4, wherein the heavy chain is encoded by the nucleic acid sequence of SEQ ID NO: 38 and the light chain is encoded by the nucleic acid sequence of SEQ ID NO: 32.

* * * * *

SEQUENCE LISTING

```
Sequence total quantity: 141
SEQ ID NO: 1            moltype = AA  length = 230
FEATURE                 Location/Qualifiers
source                  1..230
                        mol_type = protein
                        organism = Homo sapiens
SEQUENCE: 1
MEPLRLLILL FVTELSGAHN TTVFQGVAGQ SLQVSCPYDS MKHWGRRKAW CRQLGEKGPC  60
QRVVSTHNLW LLSFLRRWNG STAITDDTLG GTLTITLRNL QPHDAGLYQC QSLHGSEADT  120
LRKVLVEVLA DPLDHRDAGD LWFPGESESF EDAHVEHSIS RSLLEGEIPF PPTSILLLLA  180
CIFLIKILAA SALWAAAWHG QKPGTHPPSE LDCGHDPGYQ LQTLPGLRDT             230

SEQ ID NO: 2            moltype = AA  length = 219
FEATURE                 Location/Qualifiers
source                  1..219
                        mol_type = protein
                        organism = Homo sapiens
SEQUENCE: 2
MEPLRLLILL FVTELSGAHN TTVFQGVAGQ SLQVSCPYDS MKHWGRRKAW CRQLGEKGPC  60
QRVVSTHNLW LLSFLRRWNG STAITDDTLG GTLTITLRNL QPHDAGLYQC QSLHGSEADT  120
LRKVLVEVLA DPLDHRDAGD LWFPGESESF EDAHVEHSIS RAERHVKEDD GRKSPGEVPP  180
GTSPACILAT WPPGLLVLLW QETTLPEHCF SWTLEAGTG                        219

SEQ ID NO: 3            moltype = AA  length = 222
FEATURE                 Location/Qualifiers
source                  1..222
                        mol_type = protein
                        organism = Homo sapiens
SEQUENCE: 3
MEPLRLLILL FVTELSGAHN TTVFQGVAGQ SLQVSCPYDS MKHWGRRKAW CRQLGEKGPC  60
QRVVSTHNLW LLSFLRRWNG STAITDDTLG GTLTITLRNL QPHDAGLYQC QSLHGSEADT  120
LRKVLVEVLA DPLDHRDAGD LWFPGESESF EDAHVEHSIS RPSQGSHLPS CLSKEPLGRR  180
NPLPTHFHPS PPGLHLSHQD SSSQRPLGCS LAWTEARDTS TQ                     222

SEQ ID NO: 4            moltype = AA  length = 10
FEATURE                 Location/Qualifiers
REGION                  1..10
                        note = Synthetic polypeptide
source                  1..10
                        mol_type = protein
                        organism = synthetic construct
SEQUENCE: 4
GYTFTGYHMS                                                         10

SEQ ID NO: 5            moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 5
VINPVSGNTV YAQKFQG                                                 17

SEQ ID NO: 6            moltype = AA  length = 10
FEATURE                 Location/Qualifiers
REGION                  1..10
                        note = Synthetic polypeptide
source                  1..10
                        mol_type = protein
                        organism = synthetic construct
SEQUENCE: 6
IPSYTYAFDY                                                         10

SEQ ID NO: 7            moltype = AA  length = 5
```

-continued

```
FEATURE                Location/Qualifiers
REGION                 1..5
                       note = Synthetic polypeptide
source                 1..5
                       mol_type = protein
                       organism = synthetic construct
SEQUENCE: 7
GYHMS                                                                        5

SEQ ID NO: 8           moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 8
GYTFTGY                                                                      7

SEQ ID NO: 9           moltype = AA  length = 6
FEATURE                Location/Qualifiers
REGION                 1..6
                       note = Synthetic polypeptide
source                 1..6
                       mol_type = protein
                       organism = synthetic construct
SEQUENCE: 9
NPVSGN                                                                       6

SEQ ID NO: 10          moltype = AA  length = 8
FEATURE                Location/Qualifiers
REGION                 1..8
                       note = Synthetic polypeptide
source                 1..8
                       mol_type = protein
                       organism = synthetic construct
SEQUENCE: 10
GYTFTGYH                                                                     8

SEQ ID NO: 11          moltype = AA  length = 8
FEATURE                Location/Qualifiers
REGION                 1..8
                       note = Synthetic polypeptide
source                 1..8
                       mol_type = protein
                       organism = synthetic construct
SEQUENCE: 11
INPVSGNT                                                                     8

SEQ ID NO: 12          moltype = AA  length = 12
FEATURE                Location/Qualifiers
REGION                 1..12
                       note = Synthetic polypeptide
source                 1..12
                       mol_type = protein
                       organism = synthetic construct
SEQUENCE: 12
ARIPSYTYAF DY                                                                12

SEQ ID NO: 13          moltype = AA  length = 119
FEATURE                Location/Qualifiers
REGION                 1..119
                       note = Synthetic polypeptide
source                 1..119
                       mol_type = protein
                       organism = synthetic construct
SEQUENCE: 13
QVQLVQSGAE VKKPGASVKV SCKASGYTFT GYHMSWVRQA PGQGLEWMGV INPVSGNTVY  60
AQKFQGRVTM TRDTSISTAY MELSRLRSED TAVYYCARIP SYTYAFDYWG QGTLVTVSS   119

SEQ ID NO: 14          moltype = DNA  length = 357
FEATURE                Location/Qualifiers
misc_feature           1..357
                       note = Synthetic polynucleotide
source                 1..357
                       mol_type = other DNA
                       organism = synthetic construct
SEQUENCE: 14
caggtgcaat tggtgcagag cggtgcggaa gtgaaaaaac cgggtgccag cgtgaaagtt  60
```

```
agctgcaaag cgtccggata taccttcact ggttaccata tgtcttgggt gcgccaggcc  120
ccgggccagg gcctcgagtg gatgggcgtt atcaacccgg tttctggcaa cacggtttac  180
gcgcagaaat ttcagggccg ggtgaccatg acccgtgata ccagcattag caccgcgtat  240
atggaactga gccgtctgcg tagcgaagat acggccgtgt attattgcgc gcgtatcccg  300
tcttacactt acgctttcga ttactggggc caaggcaccc tggtgactgt tagctca     357

SEQ ID NO: 15           moltype = AA  length = 449
FEATURE                 Location/Qualifiers
REGION                  1..449
                        note = Synthetic polypeptide
source                  1..449
                        mol_type = protein
                        organism = synthetic construct
SEQUENCE: 15
QVQLVQSGAE VKKPGASVKV SCKASGYTFT GYHMSWVRQA PGQGLEWMGV INPVSGNTVY  60
AQKFQGRVTM TRDTSISTAY MELSRLRSED TAVYYCARIP SYTYAFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPEAAGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                     449

SEQ ID NO: 16           moltype = DNA  length = 1347
FEATURE                 Location/Qualifiers
misc_feature            1..1347
                        note = Synthetic polynucleotide
source                  1..1347
                        mol_type = other DNA
                        organism = synthetic construct
SEQUENCE: 16
caggtgcaat tggtgcagag cggtgcggaa gtgaaaaaac cgggtgccag cgtgaaagtt  60
agctgcaaag cgtccggata taccttcact ggttaccata tgtcttgggt gcgccaggcc  120
ccgggccagg gcctcgagtg gatgggcgtt atcaacccgg tttctggcaa cacggtttac  180
gcgcagaaat ttcagggccg ggtgaccatg acccgtgata ccagcattag caccgcgtat  240
atggaactga gccgtctgcg tagcgaagat acggccgtgt attattgcgc gcgtatcccg  300
tcttacactt acgctttcga ttactggggc caaggcaccc tggtgactgt tagctcagcc  360
tccaccaagg gtccatcggt cttccccctg gcaccctcct ccaagagcac ctctgggggc  420
acagcggccc tgggctgcct ggtcaaggac tacttccccg aaccggtgac ggtgtcgtgg  480
aactcaggcg ccctgaccag cggcgtgcac accttcccgg ctgtcctaca gtcctcagga  540
ctctactccc tcagcagcgt ggtgaccgtg ccctccagca gcttgggcac ccagacctac  600
atctgcaacg tgaatcacaa gcccagcaac accaaggtgg acaagagagt tgagcccaaa  660
tcttgtgaca aaactcacac atgcccaccg tgcccagcac ctgaagcagc gggggggaccg  720
tcagtcttcc tcttcccccc aaaacccaag gacaccctca tgatctcccg gacccctgag  780
gtcacatgcg tggtggtgga cgtgagccac gaagaccctg aggtcaagtt caactggtac  840
gtggacggcg tggaggtgca taatgccaag acaaagccgc gggaggagca gtacaacagc  900
acgtaccggg tggtcagcgt cctcaccgtc ctgcaccagg actggctgaa tggcaaggag  960
tacaagtgca aggtctccaa caaagccctc ccagccccca tcgagaaaac catctccaaa  1020
gccaaagggc agccccgaga accacaggtg tacaccctgc ccccatcccg ggaggagatg  1080
accaagaacc aggtcagcct gacctgcctg gtcaaaggct tctatcccag cgacatcgcc  1140
gtggagtggg agagcaatgg gcagccggag aacaactaca agaccacgcc tcccgtgctg  1200
gactccgacg gctccttctt cctctacagc aagctcaccg tggacaagag caggtggcag  1260
caggggaacg tcttctcatg ctccgtgatg catgaggctc tgcacaacca ctacacgcag  1320
aagagcctct ccctgtctcc gggtaaa                                       1347

SEQ ID NO: 17           moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 17
RASQDISNYL A                                                        11

SEQ ID NO: 18           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 18
RASSLQS                                                             7

SEQ ID NO: 19           moltype = AA  length = 10
FEATURE                 Location/Qualifiers
REGION                  1..10
                        note = Synthetic polypeptide
```

-continued

```
source                  1..10
                        mol_type = protein
                        organism = synthetic construct
SEQUENCE: 19
FQYRHMPSQT                                                   10

SEQ ID NO: 20           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 20
SQDISNY                                                      7

SEQ ID NO: 21           moltype =   length =
SEQUENCE: 21
000

SEQ ID NO: 22           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 22
YRHMPSQ                                                      7

SEQ ID NO: 23           moltype = AA  length = 6
FEATURE                 Location/Qualifiers
REGION                  1..6
                        note = Synthetic polypeptide
source                  1..6
                        mol_type = protein
                        organism = synthetic construct
SEQUENCE: 23
QDISNY                                                       6

SEQ ID NO: 24           moltype = AA  length = 108
FEATURE                 Location/Qualifiers
REGION                  1..108
                        note = Synthetic polypeptide
source                  1..108
                        mol_type = protein
                        organism = synthetic construct
SEQUENCE: 24
DIQMTQSPSS LSASVGDRVT ITCRASQDIS NYLAWYQQKP GKAPKLLIYR ASSLQSGVPS  60
RFSGSGSGTD FTLTISSLQP EDFATYYCFQ YRHMPSQTFG QGTKVEIK             108

SEQ ID NO: 25           moltype = DNA  length = 324
FEATURE                 Location/Qualifiers
misc_feature            1..324
                        note = Synthetic polynucleotide
source                  1..324
                        mol_type = other DNA
                        organism = synthetic construct
SEQUENCE: 25
gatatccaga tgacccagag cccgagcagc ctgagcgcca gcgtgggcga tcgcgtgacc  60
attacctgca gagccagcca ggacatttct aactacctgg cttggtacca gcagaaaccg  120
ggcaaagcgc cgaaactatt aatctaccgt gcttcttctc tgcaaagcgg cgtgccgagc  180
cgctttagcg gcagcggatc cggcaccgat ttcaccctga ccattagctc tctgcaaccg  240
gaagactttg cgacctatta ttgcttccag taccgtcata tgccgtctca gacctttggc  300
cagggcacga aagttgaaat taaa                                   324

SEQ ID NO: 26           moltype = AA  length = 215
FEATURE                 Location/Qualifiers
REGION                  1..215
                        note = Synthetic polypeptide
source                  1..215
                        mol_type = protein
                        organism = synthetic construct
SEQUENCE: 26
DIQMTQSPSS LSASVGDRVT ITCRASQDIS NYLAWYQQKP GKAPKLLIYR ASSLQSGVPS  60
RFSGSGSGTD FTLTISSLQP EDFATYYCFQ YRHMPSQTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                        215
```

-continued

```
SEQ ID NO: 27           moltype = DNA  length = 645
FEATURE                 Location/Qualifiers
misc_feature            1..645
                        note = Synthetic polynucleotide
source                  1..645
                        mol_type = other DNA
                        organism = synthetic construct
SEQUENCE: 27
gatatccaga tgacccagag cccgagcagc ctgagcgcca gcgtgggcga tcgcgtgacc  60
attacctgca gagccagcca ggacatttct aactacctgg cttggtacca gcagaaaccg  120
ggcaaagcgc cgaaactatt aatctaccgt gcttcttctc tgcaaagcgg cgtgccgagc  180
cgctttagcg gcagcggatc cggcaccgat ttcaccctga ccattagctc tctgcaaccg  240
gaagactttg cgacctatta ttgcttccag taccgtcata tgccgtctca gacctttggc  300
cagggcacga aagttgaaat taaacgtacg gtggccgctc ccagcgtgtt catcttcccc  360
cccagcgacg agcagctgaa gagcggcacc gccagcgtgg tgtgcctgct gaacaacttc  420
taccccccggg aggccaaggt gcagtggaag gtggacaacg ccctgcagag cggcaacagc  480
caggaaagcg tcaccgagca ggacagcaag gactccacct acagcctgag cagcaccctg  540
accctgagca aggccgacta cgagaagcac aaggtgtacg cctgcgaggt gacccaccag  600
ggcctgtcca gccccgtgac caagagcttc aaccggggcg agtgt                  645

SEQ ID NO: 28           moltype = DNA  length = 357
FEATURE                 Location/Qualifiers
misc_feature            1..357
                        note = Synthetic polynucleotide
source                  1..357
                        mol_type = other DNA
                        organism = synthetic construct
SEQUENCE: 28
caagtgcaac tcgtgcagtc aggagccgaa gtcaagaagc ctggagcctc ggtcaaggtg  60
tcctgcaagg ccagcggata cactttcact ggataccaca tgtcgtgggt cagacaggct  120
cctggccaag ggctggagtg gatgggcgtc atcaacccgg tgtcgggtaa taccgtgtac  180
gcccagaagt tccagggtcg cgtgaccatg acccgggata cctccattag caccgcgtac  240
atggagctca gccggttgag atccgaggat accgccgtgt actactgtgc gcggatcccg  300
tcctacactt acgccttcga ctattggggc caggggactc ttgtcaccgt gtcctcg     357

SEQ ID NO: 29           moltype = AA  length = 449
FEATURE                 Location/Qualifiers
REGION                  1..449
                        note = Synthetic polypeptide
source                  1..449
                        mol_type = protein
                        organism = synthetic construct
SEQUENCE: 29
QVQLVQSGAE VKKPGASVKV SCKASGYTFT GYHMSWVRQA PGQGLEWMGV INPVSGNTVY  60
AQKFQGRVTM TRDTSISTAY MELSRLRSED TAVYYCARIP SYTYAFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                    449

SEQ ID NO: 30           moltype = DNA  length = 1347
FEATURE                 Location/Qualifiers
misc_feature            1..1347
                        note = Synthetic polynucleotide
source                  1..1347
                        mol_type = other DNA
                        organism = synthetic construct
SEQUENCE: 30
caagtgcaac tcgtgcagtc aggagccgaa gtcaagaagc ctggagcctc ggtcaaggtg  60
tcctgcaagg ccagcggata cactttcact ggataccaca tgtcgtgggt cagacaggct  120
cctggccaag ggctggagtg gatgggcgtc atcaacccgg tgtcgggtaa taccgtgtac  180
gcccagaagt tccagggtcg cgtgaccatg acccgggata cctccattag caccgcgtac  240
atggagctca gccggttgag atccgaggat accgccgtgt actactgtgc gcggatcccg  300
tcctacactt acgccttcga ctattggggc caggggactc ttgtcaccgt gtcctcggcc  360
tccactaagg gcccaagtgt gtttcccctg gcccccagca gcaagtctac ttccggcgga  420
actgctgccc tgggttgcct ggtgaaggac tacttccccg agcccgtgac agtgtcctgg  480
aactctgggg ctctgacttc cggcgtgcac accttccccg ccgtgctgca gagcagcggc  540
ctgtacagcc tgagcagcgt ggtgacagtg ccctccagct ctctgggaac ccagacctat  600
atctgcaacg tgaaccacaa gcccagcaac accaaggtgg acaagagagt ggagcccaag  660
agctgcgaca agacccacac ctgcccccc tgcccagctc cagaactgct gggagggcct  720
tccgtgttcc tgttcccccc caagcccaag gacaccctga tgatcagcag gacccccgag  780
gtgacctgcg tggtggtgga cgtgtcccac gaggacccag aggtgaagtt caactggtac  840
gtggacggcg tggaggtgca caacgccaag accaagccca gagaggagca gtacaacagc  900
acctacaggg tggtgtccgt gctgaccgtg ctgcaccagg actggctgaa cggcaaagaa  960
tacaagtgca aagtctccaa caaggccctg ccagccccaa tcgaaaagac aatcagcaag  1020
gccaagggcc agccacggga gccccaggtg tacaccctgc cccccagccg ggaggagatg  1080
accaagaacc aggtgtccct gacctgtctg gtgaagggct tctaccccag cgatatcgcc  1140
```

```
gtggagtggg agagcaacgg ccagcccgag aacaactaca agaccacccc cccagtgctg  1200
gacagcgacg gcagcttctt cctgtacagc aagctgaccg tggacaagtc caggtggcag  1260
cagggcaacg tgttcagctg cagcgtgatg cacgaggccc tgcacaacca ctacacccag  1320
aagtccctga gcctgagccc cggcaag                                     1347

SEQ ID NO: 31          moltype = DNA  length = 324
FEATURE                Location/Qualifiers
misc_feature           1..324
                       note = Synthetic polynucleotide
source                 1..324
                       mol_type = other DNA
                       organism = synthetic construct
SEQUENCE: 31
gacattcaga tgacccagtc cccgtcgtcc ctgtccgcat ccgtgggcga cagagtcacc  60
atcacttgcc gggcctcaca ggatatttcc aactacctgg cctggtatca gcagaagcct  120
ggaaaggccc cgaagctgct gatctaccgg gcgtcctcct tgcaatcggg agtgccaagc  180
cgcttttctg gttccgggag cgggactgac ttcaccctga ctattagcag cctgcagccc  240
gaagatttcg ctacctacta ctgcttccag taccggcaca tgccctcaca aaccttcgga  300
cagggcacca aagtcgagat caag                                        324

SEQ ID NO: 32          moltype = DNA  length = 645
FEATURE                Location/Qualifiers
misc_feature           1..645
                       note = Synthetic polynucleotide
source                 1..645
                       mol_type = other DNA
                       organism = synthetic construct
SEQUENCE: 32
gacattcaga tgacccagtc cccgtcgtcc ctgtccgcat ccgtgggcga cagagtcacc  60
atcacttgcc gggcctcaca ggatatttcc aactacctgg cctggtatca gcagaagcct  120
ggaaaggccc cgaagctgct gatctaccgg gcgtcctcct tgcaatcggg agtgccaagc  180
cgcttttctg gttccgggag cgggactgac ttcaccctga ctattagcag cctgcagccc  240
gaagatttcg ctacctacta ctgcttccag taccggcaca tgccctcaca aaccttcgga  300
cagggcacca aagtcgagat caagcgtacg gtggccgctc ccagcgtgtt catcttcccc  360
cccagcgacg agcagctgaa gagcggcacc gccagcgtgg tgtgcctgct gaacaacttc  420
tacccccggg aggccaaggt gcagtggaag gtggacaacg ccctgcagag cggcaacagc  480
caggagagcg tcaccgagca ggacagcaag gactccacct acagcctgag cagcaccctg  540
accctgagca aggccgacta cgagaagcat aaggtgtacg cctgcgaggt gacccaccag  600
ggcctgtcca gccccgtgac caagagcttc aacaggggcg agtgc                  645

SEQ ID NO: 33          moltype = AA  length = 449
FEATURE                Location/Qualifiers
REGION                 1..449
                       note = Synthetic polypeptide
source                 1..449
                       mol_type = protein
                       organism = synthetic construct
SEQUENCE: 33
QVQLVQSGAE VKKPGASVKV SCKASGYTFT GYHMSWVRQA PGQGLEWMGV INPVSGNTVY  60
AQKFQGRVTM TRDTSISTAY MELSRLRSED TAVYYCARIP SYTYAFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPELLGGP  240
SVFLFPPKPK DTLMISRTPE VTCVVVAVSH EDPEVKFNWY VDGVEVHNAK TKPREEQYNS  300
TYRVVSVLTV LHQDWLNGKE YKCKVSNKAL AAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                   449

SEQ ID NO: 34          moltype = DNA  length = 1347
FEATURE                Location/Qualifiers
misc_feature           1..1347
                       note = Synthetic polynucleotide
source                 1..1347
                       mol_type = other DNA
                       organism = synthetic construct
SEQUENCE: 34
caagtgcaac tcgtgcagtc aggagccgaa gtcaagaagc ctggagcctc ggtcaaggtg  60
tcctgcaagg ccagcggata cactttcact ggataccaca tgtcgtgggt cagacaggct  120
cctggccaag ggctggagtg gatgggcgtc atcaacccgg tgtcgggtaa taccgtgtac  180
gcccagaagt tccagggtcg cgtgaccatg acccgggata cctccattag caccgcgtac  240
atggagctca gccggttgag atccgaggat accgccgtgt actactgtgc gcggatcccg  300
tcctacactt acgccttcga ctattggggc caggggactc ttgtcaccgt gtcctcggcc  360
tccactaagg gcccgtcagt gttccccctt gcgccatcct cgaagtcaac ctccggagga  420
actgccgcac tgggttgcct cgtgaaagac tatttcccgg aacccgtcac tgtctcctgg  480
aactcaggag cgctcaccag cggagtgcat acctttcctg cggtgctgca gtccagcggc  540
ctgtactccc tgagctccgt cgtgaccgtc ccctcgtcgt ccctgggaac ccaaacctac  600
atttgcaacg tcaatcacaa gccaagcaac actaaggtgg acaagagagt ggagcccaag  660
tcctgcgata agacccacac ctgtcctccc tgtccggcac ctgaactgct tggtggacct  720
tccgtgttcc tgttcccgcc caagccaaaa gacaccctga tgatctcccg cactccggaa  780
gtcacttgcg tggtcgtggc cgtgtcccac gaggaccccg aggtcaagtt taattggtac  840
```

```
gtggacggag tggaagtgca caacgccaag accaagccgc gggaagaaca gtacaactcc  900
acctaccgcg tggtgtccgt cctgactgtg ctccaccagg actggctgaa cggaaaggag  960
tacaagtgca aagtgtccaa caaggcactg gctgccccta tcgaaaagac tatctccaag  1020
gccaagggcc aacctaggga gccccaggtg tacacgttgc ctccttcccg cgaagaaatg  1080
actaagaacc aggtgtcgct gacctgtctc gtgaaagggt tctacccctc tgacatcgcc  1140
gtggaatggg agtcaaacgg acagcctgag aacaactata agaccacacc acctgtcctg  1200
gactccgacg gctccttctt cctgtactca aagttgaccg tggacaagtc gcggtggcaa  1260
cagggcaacg tgttctcttg ctccgtgatg cacgaagccc tgcacaacca ctacacccaa  1320
aagtcgctca gcctctcccc cggaaag                                     1347

SEQ ID NO: 35           moltype = AA  length = 449
FEATURE                 Location/Qualifiers
REGION                  1..449
                        note = Synthetic polypeptide
source                  1..449
                        mol_type = protein
                        organism = synthetic construct
SEQUENCE: 35
QVQLVQSGAE VKKPGASVKV SCKASGYTFT GYHMSWVRQA PGQGLEWMGV INPVSGNTVY  60
AQKFQGRVTM TRDTSISTAY MELSRLRSED TAVYYCARIP SYTYAFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVL HEALHSHYTQ KSLSLSPGK                                   449

SEQ ID NO: 36           moltype = DNA  length = 1347
FEATURE                 Location/Qualifiers
misc_feature            1..1347
                        note = Synthetic polynucleotide
source                  1..1347
                        mol_type = other DNA
                        organism = synthetic construct
SEQUENCE: 36
caagtgcaac tcgtgcagtc aggagccgaa gtcaagaagc ctggagcctc ggtcaaggtg  60
tcctgcaagg ccagcggata cactttcact ggataccaca tgtcgtgggt cagacaggct  120
cctggccaag ggctggagtg gatgggcgtc atcaacccgg tgtcgggtaa taccgtgtac  180
gcccagaagt tccagggtcg cgtgaccatg acccgggata cctccattag caccgcgtac  240
atggagctca gccggttgag atccgaggat accgccgtgt actactgtgc gcggatcccg  300
tcctacactt acgccttcga ctattggggc caggggactc ttgtcaccgt gtcctcggcc  360
tccactaagg gcccgtcagt gttcccctt gcgccatcct cgaagtcaac ctccggagga  420
actgccgcac tgggttgcct cgtgaaagac tatttcccgg aacccgtcac tgtctcctgg  480
aactcaggag cgctcaccag cggagtgcat acctttcctg cggtgctgca gtccagcggc  540
ctgtactccc tgagctccgt cgtgaccgtc ccctcgtcgt ccctgggaac ccaaacctac  600
atttgcaacg tcaatcacaa gccaagcaac actaaggtgg acaagagagt ggagcccaag  660
tcctgcgata agacccacac ctgtcctccc tgtccggcac ctgaactgct tggtggacct  720
tccgtgttcc tgttcccgcc caagccaaaa gacaccctga tgatctcccg cactccggaa  780
gtcacttgcg tggtcgtgga cgtgtcccac gaggaccccg aggtcaagtt taattggtac  840
gtggacggag tggaagtgca caacgccaag accaagccgc gggaagaaca gtacaactcc  900
acctaccgcg tggtgtccgt cctgactgtg ctccaccagg actggctgaa cggaaaggag  960
tacaagtgca aagtgtccaa caaggcactg ccagcccccta tcgaaaagac tatctccaag  1020
gccaagggcc aacctaggga gccccaggtg tacacgttgc ctccttcccg cgaagaaatg  1080
actaagaacc aggtgtcgct gacctgtctc gtgaaagggt tctacccctc tgacatcgcc  1140
gtggaatggg agtcaaacgg acagcctgag aacaactata agaccacacc acctgtcctg  1200
gactccgacg gctccttctt cctgtactca aagttgaccg tggacaagtc gcggtggcaa  1260
cagggcaacg tgttctcttg ctccgtgctg cacgaagccc tgcacagcca ctacacccaa  1320
aagtcgctca gcctctcccc cggaaag                                     1347

SEQ ID NO: 37           moltype = AA  length = 449
FEATURE                 Location/Qualifiers
REGION                  1..449
                        note = Synthetic polypeptide
source                  1..449
                        mol_type = protein
                        organism = synthetic construct
SEQUENCE: 37
QVQLVQSGAE VKKPGASVKV SCKASGYTFT GYHMSWVRQA PGQGLEWMGV INPVSGNTVY  60
AQKFQGRVTM TRDTSISTAY MELSRLRSED TAVYYCARIP SYTYAFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPELLGGP  240
SVFLFPPKPK DTLMISRTPE VTCVVVAVSH EDPEVKFNWY VDGVEVHNAK TKPREEQYNS  300
TYRVVSVLTV LHQDWLNGKE YKCKVSNKAL AAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVL HEALHSHYTQ KSLSLSPGK                                   449

SEQ ID NO: 38           moltype = DNA  length = 1347
FEATURE                 Location/Qualifiers
misc_feature            1..1347
```

```
                          note = Synthetic polynucleotide
source                    1..1347
                          mol_type = other DNA
                          organism = synthetic construct
SEQUENCE: 38
caagtgcaac tcgtgcagtc aggagccgaa gtcaagaagc ctggagcctc ggtcaaggtg  60
tcctgcaagg ccagcggata cactttcact ggataccaca tgtcgtgggt cagacaggct  120
cctggccaag ggctggagtg gatgggcgtc atcaacccgg tgtcgggtaa taccgtgtac  180
gcccagaagt tccagggtcg cgtgaccatg acccgggata cctccattag caccgcgtac  240
atggagctca gccggttgag atccgaggat accgccgtgt actactgtgc gcggatcccg  300
tcctacactt acgccttcga ctattggggc caggggactc ttgtcaccgt gtcctcggcc  360
tccactaagg gcccgtcagt gttccccctt gcgccatcct cgaagtcaac ctccggagga  420
actgccgcac tgggttgcct cgtgaaagac tatttcccgg aacccgtcac tgtctcctgg  480
aactcaggag cgctcaccag cggagtgcat acctttcctg cggtgctgca gtccagcggc  540
ctgtactccc tgagctccgt cgtgaccgtc ccctcgtcgt ccctgggaac ccaaacctac  600
atttgcaacg tcaatcacaa gccaagcaac actaaggtgg acaagagagt ggagcccaag  660
tcctgcgata agacccacac ctgtcctccc tgtccggcac ctgaactgct tggtggacct  720
tccgtgttcc tgttcccgcc caagccaaaa gacaccctga tgatctcccg cactccggaa  780
gtcacttgcg tggtcgtggc cgtgtcccac gaggaccccg aggtcaagtt taattggtac  840
gtggacggag tggaagtgca caacgccaag accaagccgc gggaagaaca gtacaactcc  900
acctaccgcg tggtgtccgt cctgactgtg ctccaccagg actggctgaa cggaaaggag  960
tacaagtgca aagtgtccaa caaggcactg gctgccccta tcgaaaagac tatctccaag  1020
gccaagggcc aacctaggga gccccaggtg tacacgttgc ctccttcccg cgaagaaatg  1080
actaagaacc aggtgtcgct gacctgtctc gtgaaagggt tctacccctc tgacatcgcc  1140
gtggaatggg agtcaaacgg acagcctgag aacaactata agaccacacc acctgtcctg  1200
gactccgacg gctccttctt cctgtactca aagttgaccg tggacaagtc gcggtggcaa  1260
cagggcaacg tgttctcttg ctccgtgctg cacgaagccc tgcacagcca ctacacccaa  1320
aagtcgctca gcctctcccc cggaaag                                     1347

SEQ ID NO: 39             moltype = AA  length = 449
FEATURE                   Location/Qualifiers
REGION                    1..449
                          note = Synthetic polypeptide
source                    1..449
                          mol_type = protein
                          organism = synthetic construct
SEQUENCE: 39
QVQLVQSGAE VKKPGASVKV SCKASGYTFT GYHMSWVRQA PGQGLEWMGV INPVSGNTVY  60
AQKFQGRVTM TRDTSISTAY MELSRLRSED TAVYYCARIP SYTYAFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPELLGGP  240
SVFLFPPKPK DTLYITREPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                   449

SEQ ID NO: 40             moltype = DNA  length = 1347
FEATURE                   Location/Qualifiers
misc_feature              1..1347
                          note = Synthetic polynucleotide
source                    1..1347
                          mol_type = other DNA
                          organism = synthetic construct
SEQUENCE: 40
caagtgcaac tcgtgcagtc aggagccgaa gtcaagaagc ctggagcctc ggtcaaggtg  60
tcctgcaagg ccagcggata cactttcact ggataccaca tgtcgtgggt cagacaggct  120
cctggccaag ggctggagtg gatgggcgtc atcaacccgg tgtcgggtaa taccgtgtac  180
gcccagaagt tccagggtcg cgtgaccatg acccgggata cctccattag caccgcgtac  240
atggagctca gccggttgag atccgaggat accgccgtgt actactgtgc gcggatcccg  300
tcctacactt acgccttcga ctattggggc caggggactc ttgtcaccgt gtcctcggcc  360
tccactaagg gcccgtcagt gttccccctt gcgccatcct cgaagtcaac ctccggagga  420
actgccgcac tgggttgcct cgtgaaagac tatttcccgg aacccgtcac tgtctcctgg  480
aactcaggag cgctcaccag cggagtgcat acctttcctg cggtgctgca gtccagcggc  540
ctgtactccc tgagctccgt cgtgaccgtc ccctcgtcgt ccctgggaac ccaaacctac  600
atttgcaacg tcaatcacaa gccaagcaac actaaggtgg acaagagagt ggagcccaag  660
tcctgcgata agacccacac ctgtcctccc tgtccggcac ctgaactgct tggtggacct  720
tccgtgttcc tgttcccgcc caagccaaaa gacaccctgt atatcactcg cgaaccggaa  780
gtcacttgcg tggtcgtgga cgtgtcccac gaggaccccg aggtcaagtt taattggtac  840
gtggacggag tggaagtgca caacgccaag accaagccgc gggaagaaca gtacaactcc  900
acctaccgcg tggtgtccgt cctgactgtg ctccaccagg actggctgaa cggaaaggag  960
tacaagtgca aagtgtccaa caaggcactg ccagcccccta tcgaaaagac tatctccaag  1020
gccaagggcc aacctaggga gccccaggtg tacacgttgc ctccttcccg cgaagaaatg  1080
actaagaacc aggtgtcgct gacctgtctc gtgaaagggt tctacccctc tgacatcgcc  1140
gtggaatggg agtcaaacgg acagcctgag aacaactata agaccacacc acctgtcctg  1200
gactccgacg gctccttctt cctgtactca aagttgaccg tggacaagtc gcggtggcaa  1260
cagggcaacg tgttctcttg ctccgtgatg cacgaagccc tgcacaacca ctacacccaa  1320
aagtcgctca gcctctcccc cggaaag                                     1347

SEQ ID NO: 41             moltype = AA  length = 12
```

```
FEATURE                Location/Qualifiers
REGION                 1..12
                       note = Synthetic polypeptide
source                 1..12
                       mol_type = protein
                       organism = synthetic construct
SEQUENCE: 41
GDSVSSSSAA WN                                                12

SEQ ID NO: 42          moltype = AA  length = 18
FEATURE                Location/Qualifiers
REGION                 1..18
                       note = Synthetic polypeptide
source                 1..18
                       mol_type = protein
                       organism = synthetic construct
SEQUENCE: 42
HIGYRSKWYN EYAVSVKS                                          18

SEQ ID NO: 43          moltype = AA  length = 16
FEATURE                Location/Qualifiers
REGION                 1..16
                       note = Synthetic polypeptide
source                 1..16
                       mol_type = protein
                       organism = synthetic construct
SEQUENCE: 43
GMYGSVPYKE GYYFDI                                            16

SEQ ID NO: 44          moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 44
SSSAAWN                                                      7

SEQ ID NO: 45          moltype = AA  length = 9
FEATURE                Location/Qualifiers
REGION                 1..9
                       note = Synthetic polypeptide
source                 1..9
                       mol_type = protein
                       organism = synthetic construct
SEQUENCE: 45
GDSVSSSSA                                                    9

SEQ ID NO: 46          moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 46
GYRSKWY                                                      7

SEQ ID NO: 47          moltype = AA  length = 10
FEATURE                Location/Qualifiers
REGION                 1..10
                       note = Synthetic polypeptide
source                 1..10
                       mol_type = protein
                       organism = synthetic construct
SEQUENCE: 47
GDSVSSSSAA                                                   10

SEQ ID NO: 48          moltype = AA  length = 9
FEATURE                Location/Qualifiers
REGION                 1..9
                       note = Synthetic polypeptide
source                 1..9
                       mol_type = protein
                       organism = synthetic construct
SEQUENCE: 48
IGYRSKWYN                                                    9
```

```
SEQ ID NO: 49          moltype = AA  length = 18
FEATURE                Location/Qualifiers
REGION                 1..18
                       note = Synthetic polypeptide
source                 1..18
                       mol_type = protein
                       organism = synthetic construct
SEQUENCE: 49
ARGMYGSVPY KEGYYFDI                                                18

SEQ ID NO: 50          moltype = AA  length = 128
FEATURE                Location/Qualifiers
REGION                 1..128
                       note = Synthetic polypeptide
source                 1..128
                       mol_type = protein
                       organism = synthetic construct
SEQUENCE: 50
QVQLQQSGPG LVKPSQTLSL TCAISGDSVS SSSAAWNWIR QSPSRGLEWL GHIGYRSKWY  60
NEYAVSVKSR ITINPDTSKN QFSLQLNSVT PEDTAVYYCA RGMYGSVPYK EGYYFDIWGQ  120
GTLVTVSS                                                           128

SEQ ID NO: 51          moltype = DNA  length = 384
FEATURE                Location/Qualifiers
misc_feature           1..384
                       note = Synthetic polynucleotide
source                 1..384
                       mol_type = other DNA
                       organism = synthetic construct
SEQUENCE: 51
caggtgcaat tgcagcagag cggtccgggc ctggtgaaac cgagccagac cctgagcctg  60
acctgcgcga tttccggaga tagcgtgagc tcttcttctg ctgcttggaa ctggattcgt  120
cagagcccga gccgtggcct cgagtggctg ggccatatcg gttaccgtag caaatggtac  180
aacgaatatg ccgtgagcgt gaaaagccgc attaccatta acccggatac ttcgaaaaac  240
cagtttagcc tgcaactgaa cagcgtgacc ccggaagata cggccgtgta ttattgcgcg  300
cgtggtatgt acggttctgt tccctacaaa gaaggttact acttcgatat ttggggccaa  360
ggcaccctgg tgactgttag ctca                                         384

SEQ ID NO: 52          moltype = AA  length = 458
FEATURE                Location/Qualifiers
REGION                 1..458
                       note = Synthetic polypeptide
source                 1..458
                       mol_type = protein
                       organism = synthetic construct
SEQUENCE: 52
QVQLQQSGPG LVKPSQTLSL TCAISGDSVS SSSAAWNWIR QSPSRGLEWL GHIGYRSKWY  60
NEYAVSVKSR ITINPDTSKN QFSLQLNSVT PEDTAVYYCA RGMYGSVPYK EGYYFDIWGQ  120
GTLVTVSSAS TKGPSVFPLA PSSKSTSGGT AALGCLVKDY FPEPVTVSWN SGALTSGVHT  180
FPAVLQSSGL YSLSSVVTVP SSSLGTQTYI CNVNHKPSNT KVDKRVEPKS CDKTHTCPPC  240
PAPEAAGGPS VFLFPPKPKD TLMISRTPEV TCVVVDVSHE DPEVKFNWYV DGVEVHNAKT  300
KPREEQYNST YRVVSVLTVL HQDWLNGKEY KCKVSNKALP APIEKTISKA KGQPREPQVY  360
TLPPSREEMT KNQVSLTCLV KGFYPSDIAV EWESNGQPEN NYKTTPPVLD SDGSFFLYSK  420
LTVDKSRWQQ GNVFSCSVMH EALHNHYTQK SLSLSPGK                          458

SEQ ID NO: 53          moltype = DNA  length = 1374
FEATURE                Location/Qualifiers
misc_feature           1..1374
                       note = Synthetic polynucleotide
source                 1..1374
                       mol_type = other DNA
                       organism = synthetic construct
SEQUENCE: 53
caggtgcaat tgcagcagag cggtccgggc ctggtgaaac cgagccagac cctgagcctg  60
acctgcgcga tttccggaga tagcgtgagc tcttcttctg ctgcttggaa ctggattcgt  120
cagagcccga gccgtggcct cgagtggctg ggccatatcg gttaccgtag caaatggtac  180
aacgaatatg ccgtgagcgt gaaaagccgc attaccatta acccggatac ttcgaaaaac  240
cagtttagcc tgcaactgaa cagcgtgacc ccggaagata cggccgtgta ttattgcgcg  300
cgtggtatgt acggttctgt tccctacaaa gaaggttact acttcgatat ttggggccaa  360
ggcaccctgg tgactgttag ctcagcctcc accaagggtc catcggtctt cccccctggca  420
ccctcctcca agagcacctc tgggggcaca gcggccctgg gctgcctggt caaggactac  480
ttccccgaac cggtgacggt gtcgtggaac tcaggcgccc tgaccagcgg cgtgcacacc  540
ttcccggctg tcctacagtc ctcaggactc tactccctca gcagcgtggt gaccgtgccc  600
tccagcagct tgggcaccca gacctacatc tgcaacgtga atcacaagcc cagcaacacc  660
aaggtggaca agagagttga gcccaaatct tgtgacaaaa ctcacacatg cccaccgtgc  720
ccagcacctg aagcagcggg gggaccgtca gtcttcctct tcccccccaaa acccaaggac  780
accctcatga tctcccggac ccctgaggtc acatgcgtgg tggtggacgt gagccacgaa  840
gaccctgagg tcaagttcaa ctggtacgtg gacggcgtgg aggtgcataa tgccaagaca  900
aagccgcggg aggagcagta caacagcacg taccgggtgg tcagcgtcct caccgtcctg  960
```

-continued

```
caccaggact ggctgaatgg caaggagtac aagtgcaagg tctccaacaa agccctccca  1020
gcccccatcg agaaaaccat ctccaaagcc aaagggcagc cccgagaacc acaggtgtac  1080
accctgcccc catcccggga ggagatgacc aagaaccagg tcagcctgac ctgcctggtc  1140
aaaggcttct atcccagcga catcgccgtg gagtgggaga gcaatgggca gccggagaac  1200
aactacaaga ccacgcctcc cgtgctggac tccgacggct ccttcttcct ctacagcaag  1260
ctcaccgtgg acaagagcag gtggcagcag gggaacgtct tctcatgctc cgtgatgcat  1320
gaggctctgc acaaccacta cacgcagaag agcctctccc tgtctccggg taaa        1374

SEQ ID NO: 54           moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 54
RASQGISSDL N                                                       11

SEQ ID NO: 55           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 55
AASNLQS                                                            7

SEQ ID NO: 56           moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 56
QQYTDESMT                                                          9

SEQ ID NO: 57           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 57
SQGISSD                                                            7

SEQ ID NO: 58           moltype =   length =
SEQUENCE: 58
000

SEQ ID NO: 59           moltype = AA  length = 6
FEATURE                 Location/Qualifiers
REGION                  1..6
                        note = Synthetic polypeptide
source                  1..6
                        mol_type = protein
                        organism = synthetic construct
SEQUENCE: 59
YTDESM                                                             6

SEQ ID NO: 60           moltype = AA  length = 6
FEATURE                 Location/Qualifiers
REGION                  1..6
                        note = Synthetic polypeptide
source                  1..6
                        mol_type = protein
                        organism = synthetic construct
SEQUENCE: 60
QGISSD                                                             6

SEQ ID NO: 61           moltype = AA  length = 107
FEATURE                 Location/Qualifiers
REGION                  1..107
                        note = Synthetic polypeptide
source                  1..107
                        mol_type = protein
                        organism = synthetic construct
```

```
SEQUENCE: 61
DIQMTQSPSS LSASVGDRVT ITCRASQGIS SDLNWYQQKP GKAPKLLIYA ASNLQSGVPS  60
RFSGSGSGTD FTLTISSLQP EDFATYYCQQ YTDESMTFGQ GTKVEIK               107

SEQ ID NO: 62          moltype = DNA  length = 321
FEATURE                Location/Qualifiers
misc_feature           1..321
                       note = Synthetic polynucleotide
source                 1..321
                       mol_type = other DNA
                       organism = synthetic construct
SEQUENCE: 62
gatatccaga tgacccagag cccgagcagc ctgagcgcca gcgtgggcga tcgcgtgacc  60
attacctgca gagccagcca gggtatttct tctgacctga actggtacca gcagaaaccg  120
ggcaaagcgc cgaaactatt aatctacgct gcttctaacc tgcaaagcgg cgtgccgagc  180
cgctttagcg gcagcggatc cggcaccgat ttcaccctga ccattagctc tctgcaaccg  240
gaagactttg cgacctatta ttgccagcag tacactgacg aatctatgac ctttggccag  300
ggcacgaaag ttgaaattaa a                                            321

SEQ ID NO: 63          moltype = AA  length = 214
FEATURE                Location/Qualifiers
REGION                 1..214
                       note = Synthetic polypeptide
source                 1..214
                       mol_type = protein
                       organism = synthetic construct
SEQUENCE: 63
DIQMTQSPSS LSASVGDRVT ITCRASQGIS SDLNWYQQKP GKAPKLLIYA ASNLQSGVPS  60
RFSGSGSGTD FTLTISSLQP EDFATYYCQQ YTDESMTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 64          moltype = DNA  length = 642
FEATURE                Location/Qualifiers
misc_feature           1..642
                       note = Synthetic polynucleotide
source                 1..642
                       mol_type = other DNA
                       organism = synthetic construct
SEQUENCE: 64
gatatccaga tgacccagag cccgagcagc ctgagcgcca gcgtgggcga tcgcgtgacc  60
attacctgca gagccagcca gggtatttct tctgacctga actggtacca gcagaaaccg  120
ggcaaagcgc cgaaactatt aatctacgct gcttctaacc tgcaaagcgg cgtgccgagc  180
cgctttagcg gcagcggatc cggcaccgat ttcaccctga ccattagctc tctgcaaccg  240
gaagactttg cgacctatta ttgccagcag tacactgacg aatctatgac ctttggccag  300
ggcacgaaag ttgaaattaa acgtacggtg gccgctccca gcgtgttcat cttccccccc  360
agcgacgagc agctgaagag cggcaccgcc agcgtggtgt gcctgctgaa caacttctac  420
ccccgggagg ccaaggtgca gtggaaggtg gacaacgccc tgcagagcgg caacagccag  480
gaaagcgtca ccgagcagga cagcaaggac tccacctaca gcctgagcag caccctgacc  540
ctgagcaagg ccgactacga gaagcacaag gtgtacgcct gcgaggtgac ccaccagggc  600
ctgtccagcc ccgtgaccaa gagcttcaac cggggcgagt gt                     642

SEQ ID NO: 65          moltype = DNA  length = 384
FEATURE                Location/Qualifiers
misc_feature           1..384
                       note = Synthetic polynucleotide
source                 1..384
                       mol_type = other DNA
                       organism = synthetic construct
SEQUENCE: 65
caagtgcaac tccagcagtc aggaccgggg ttggtcaagc cttcgcagac cctgtccctc  60
acttgcgcca ttagcggaga ttcggtgtcg tcgtcgtcag ccgcctggaa ctggattaga  120
cagtcccctt cccgagggct ggagtggctg ggccacatcg gataccgcag caagtggtac  180
aacgaatacg ccgtcagcgt gaagtcacgc atcaccatca acccggatac tagcaagaac  240
cagttcagcc tccagttgaa ctccgtgacc ccggaggata ccgccgtgta ctactgtgcg  300
cggggcatgt acggatccgt gccgtacaag gagggatact acttcgacat ttggggccag  360
gggactcttg tcaccgtgtc ctcg                                         384

SEQ ID NO: 66          moltype = AA  length = 458
FEATURE                Location/Qualifiers
REGION                 1..458
                       note = Synthetic polypeptide
source                 1..458
                       mol_type = protein
                       organism = synthetic construct
SEQUENCE: 66
QVQLQQSGPG LVKPSQTLSL TCAISGDSVS SSSAAWNWIR QSPSRGLEWL GHIGYRSKWY  60
NEYAVSVKSR ITINPDTSKN QFSLQLNSVT PEDTAVYYCA RGMYGSVPYK EGYYFDIWGQ  120
GTLVTVSSAS TKGPSVFPLA PSSKSTSGGT AALGCLVKDY FPEPVTVSWN SGALTSGVHT  180
```

-continued

```
FPAVLQSSGL YSLSSVVTVP SSSLGTQTYI CNVNHKPSNT KVDKRVEPKS CDKTHTCPPC  240
PAPELLGGPS VFLFPPKPKD TLMISRTPEV TCVVVDVSHE DPEVKFNWYV DGVEVHNAKT  300
KPREEQYNST YRVVSVLTVL HQDWLNGKEY KCKVSNKALP APIEKTISKA KGQPREPQVY  360
TLPPSREEMT KNQVSLTCLV KGFYPSDIAV EWESNGQPEN NYKTTPPVLD SDGSFFLYSK  420
LTVDKSRWQQ GNVFSCSVMH EALHNHYTQK SLSLSPGK                          458

SEQ ID NO: 67          moltype = DNA  length = 1374
FEATURE                Location/Qualifiers
misc_feature           1..1374
                       note = Synthetic polynucleotide
source                 1..1374
                       mol_type = other DNA
                       organism = synthetic construct
SEQUENCE: 67
caagtgcaac tccagcagtc aggaccgggg ttggtcaagc cttcgcagac cctgtccctc  60
acttgcgcca ttagcggaga ttcggtgtcg tcgtcgtcag ccgcctggaa ctggattaga  120
cagtcccctt cccgagggct ggagtggctg ggccacatcg gataccgcag caagtggtac  180
aacgaatacg ccgtcagcgt gaagtcacgc atcaccatca acccggatac tagcaagaac  240
cagttcagcc tccagttgaa ctccgtgacc ccggaggata ccgccgtgta ctactgtgcg  300
cggggcatgt acggatccgt gccgtacaag gagggatact acttcgacat ttggggccag  360
gggactcttg tcaccgtgtc ctcggcctcc actaagggcc caagtgtgtt tcccctggcc  420
cccagcagca agtctacttc cggcggaact gctgccctgg gttgcctggt gaaggactac  480
ttccccgagc ccgtgacagt gtcctggaac tctggggctc tgacttccgg cgtgcacacc  540
ttccccgccg tgctgcagag cagcggcctg tacagcctga gcagcgtggt gacagtgccc  600
tccagctctc tgggaaccca gacctatatc tgcaacgtga accacaagcc cagcaacacc  660
aaggtggaca agagagtgga gcccaagagc tgcgacaaga cccacacctg cccccccctgc  720
ccagctccag aactgctggg agggccttcc gtgttcctgt tcccccccaa gcccaaggac  780
accctgatga tcagcaggac ccccgaggtg acctgcgtgg tggtggacgt gtcccacgag  840
gacccagagg tgaagttcaa ctggtacgtg gacggcgtgg aggtgcacaa cgccaagacc  900
aagcccagag aggagcagta caacagcacc tacagggtgg tgtccgtgct gaccgtgctg  960
caccaggact ggctgaacgg caaagaatac aagtgcaaag tctccaacaa ggccctgcca  1020
gccccaatcg aaaagacaat cagcaaggcc aagggccagc cacgggagcc ccaggtgtac  1080
accctgcccc ccagccggga ggagatgacc aagaaccagg tgtccctgac ctgtctggtg  1140
aagggcttct accccagcga tatcgccgtg gagtgggaga gcaacggcca gcccgagaac  1200
aactacaaga ccacccccc agtgctggac agcgacggca gcttcttcct gtacagcaag  1260
ctgaccgtgg acaagtccag gtggcagcag ggcaacgtgt tcagctgcag cgtgatgcac  1320
gaggccctgc acaaccacta cacccagaag tccctgagcc tgagccccgg caag        1374

SEQ ID NO: 68          moltype = DNA  length = 321
FEATURE                Location/Qualifiers
misc_feature           1..321
                       note = Synthetic polynucleotide
source                 1..321
                       mol_type = other DNA
                       organism = synthetic construct
SEQUENCE: 68
gacattcaga tgacccagtc cccgtcgtcc ctgtccgcat ccgtgggcga cagagtcacc  60
atcacttgcc gggcctcaca gggaatttcc tccgacctga actggtatca gcagaagcct  120
ggaaaggccc cgaagctgct gatctacgcc gcgtccaact tgcaatcggg agtgccaagc  180
cgcttttctg gttccgggag cgggactgac ttcaccctga ctattagcag cctgcagccc  240
gaagatttcg ctacctacta ctgccaacag tacacagatg aatccatgac cttcggacag  300
ggcaccaaag tcgagatcaa g                                            321

SEQ ID NO: 69          moltype = DNA  length = 642
FEATURE                Location/Qualifiers
misc_feature           1..642
                       note = Synthetic polynucleotide
source                 1..642
                       mol_type = other DNA
                       organism = synthetic construct
SEQUENCE: 69
gacattcaga tgacccagtc cccgtcgtcc ctgtccgcat ccgtgggcga cagagtcacc  60
atcacttgcc gggcctcaca gggaatttcc tccgacctga actggtatca gcagaagcct  120
ggaaaggccc cgaagctgct gatctacgcc gcgtccaact tgcaatcggg agtgccaagc  180
cgcttttctg gttccgggag cgggactgac ttcaccctga ctattagcag cctgcagccc  240
gaagatttcg ctacctacta ctgccaacag tacacagatg aatccatgac cttcggacag  300
ggcaccaaag tcgagatcaa gcgtacggtg gccgctccca gcgtgttcat cttccccccc  360
agcgacgagc agctgaagag cggcaccgcc agcgtggtgt gcctgctgaa caacttctac  420
ccccgggagg ccaaggtgca gtggaaggtg gacaacgccc tgcagagcgg caacagccag  480
gagagcgtca ccgagcagga cagcaaggac tccacctaca gcctgagcag caccctgacc  540
ctgagcaagg ccgactacga gaagcataag gtgtacgcct gcgaggtgac ccaccagggc  600
ctgtccagcc ccgtgaccaa gagcttcaac aggggcgagt gc                     642

SEQ ID NO: 70          moltype = AA  length = 458
FEATURE                Location/Qualifiers
REGION                 1..458
                       note = Synthetic polypeptide
source                 1..458
                       mol_type = protein
```

-continued

```
                        organism = synthetic construct
SEQUENCE: 70
QVQLQQSGPG LVKPSQTLSL TCAISGDSVS SSSAAWNWIR QSPSRGLEWL GHIGYRSKWY  60
NEYAVSVKSR ITINPDTSKN QFSLQLNSVT PEDTAVYYCA RGMYGSVPYK EGYYFDIWGQ  120
GTLVTVSSAS TKGPSVFPLA PSSKSTSGGT AALGCLVKDY FPEPVTVSWN SGALTSGVHT  180
FPAVLQSSGL YSLSSVVTVP SSSLGTQTYI CNVNHKPSNT KVDKRVEPKS CDKTHTCPPC  240
PAPELLGGPS VFLFPPKPKD TLMISRTPEV TCVVVAVSHE DPEVKFNWYV DGVEVHNAKT  300
KPREEQYNST YRVVSVLTVL HQDWLNGKEY KCKVSNKALA APIEKTISKA KGQPREPQVY  360
TLPPSREEMT KNQVSLTCLV KGFYPSDIAV EWESNGQPEN NYKTTPPVLD SDGSFFLYSK  420
LTVDKSRWQQ GNVFSCSVMH EALHNHYTQK SLSLSPGK                          458

SEQ ID NO: 71           moltype = DNA  length = 1374
FEATURE                 Location/Qualifiers
misc_feature            1..1374
                        note = Synthetic polynucleotide
source                  1..1374
                        mol_type = other DNA
                        organism = synthetic construct
SEQUENCE: 71
caagtgcaac tccagcagtc aggaccgggg ttggtcaagc cttcgcagac cctgtccctc  60
acttgcgcca ttagcggaga ttcggtgtcg tcgtcgtcag ccgcctggaa ctggattaga  120
cagtcccctt cccgagggct ggagtggctg ggccacatcg gataccgcag caagtggtac  180
aacgaatacg ccgtcagcgt gaagtcacgc atcaccatca acccggatac tagcaagaac  240
cagttcagcc tccagttgaa ctccgtgacc ccggaggata ccgccgtgta ctactgtgcg  300
cggggcatgt acggatccgt gccgtacaag gagggatact acttcgacat ttggggccag  360
gggactcttg tcaccgtgtc ctcggcctcc actaagggcc cgtcagtgtt ccccccttgcg  420
ccatcctcga agtcaacctc cggaggaact gccgcactgg gttgcctcgt gaaagactat  480
ttcccggaac ccgtcactgt ctcctggaac tcaggagcgc tcaccagcgg agtgcatacc  540
tttcctgcgg tgctgcagtc cagcggcctg tactccctga gctccgtcgt gaccgtcccc  600
tcgtcgtccc tgggaaccca aacctacatt tgcaacgtca atcacaagcc aagcaacact  660
aaggtggaca agagagtgga gcccaagtcc tgcgataaga cccacacctg tcctccctgt  720
ccggcacctg aactgcttgg tggaccttcc gtgttcctgt tcccgcccaa gccaaaagac  780
accctgatga tctcccgcac tccggaagtc acttgcgtgg tcgtggccgt gtcccacgag  840
gaccccgagg tcaagtttaa ttggtacgtg gacggagtgg aagtgcacaa cgccaagacc  900
aagccgcggg aagaacagta caactccacc taccgcgtgg tgtccgtcct gactgtgctc  960
caccaggact ggctgaacgg aaaggagtac aagtgcaaag tgtccaacaa ggcactggct  1020
gcccctatcg aaaagactat ctccaaggcc aagggccaac ctagggagcc ccaggtgtac  1080
acgttgcctc cttcccgcga agaaatgact aagaaccagg tgtcgctgac ctgtctcgtg  1140
aaagggttct accccctctga catcgccgtg gaatgggagt caaacggaca gcctgagaac  1200
aactataaga ccacaccacc tgtcctggac tccgacggct ccttcttcct gtactcaaag  1260
ttgaccgtgg acaagtcgcg gtggcaacag ggcaacgtgt tctcttgctc cgtgatgcac  1320
gaagccctgc acaaccacta cacccaaaag tcgctcagcc tctcccccgg aaag        1374

SEQ ID NO: 72           moltype = AA  length = 458
FEATURE                 Location/Qualifiers
REGION                  1..458
                        note = Synthetic polypeptide
source                  1..458
                        mol_type = protein
                        organism = synthetic construct
SEQUENCE: 72
QVQLQQSGPG LVKPSQTLSL TCAISGDSVS SSSAAWNWIR QSPSRGLEWL GHIGYRSKWY  60
NEYAVSVKSR ITINPDTSKN QFSLQLNSVT PEDTAVYYCA RGMYGSVPYK EGYYFDIWGQ  120
GTLVTVSSAS TKGPSVFPLA PSSKSTSGGT AALGCLVKDY FPEPVTVSWN SGALTSGVHT  180
FPAVLQSSGL YSLSSVVTVP SSSLGTQTYI CNVNHKPSNT KVDKRVEPKS CDKTHTCPPC  240
PAPELLGGPS VFLFPPKPKD TLMISRTPEV TCVVVDVSHE DPEVKFNWYV DGVEVHNAKT  300
KPREEQYNST YRVVSVLTVL HQDWLNGKEY KCKVSNKALP APIEKTISKA KGQPREPQVY  360
TLPPSREEMT KNQVSLTCLV KGFYPSDIAV EWESNGQPEN NYKTTPPVLD SDGSFFLYSK  420
LTVDKSRWQQ GNVFSCSVLH EALHSHYTQK SLSLSPGK                          458

SEQ ID NO: 73           moltype = DNA  length = 1374
FEATURE                 Location/Qualifiers
misc_feature            1..1374
                        note = Synthetic polynucleotide
source                  1..1374
                        mol_type = other DNA
                        organism = synthetic construct
SEQUENCE: 73
caagtgcaac tccagcagtc aggaccgggg ttggtcaagc cttcgcagac cctgtccctc  60
acttgcgcca ttagcggaga ttcggtgtcg tcgtcgtcag ccgcctggaa ctggattaga  120
cagtcccctt cccgagggct ggagtggctg ggccacatcg gataccgcag caagtggtac  180
aacgaatacg ccgtcagcgt gaagtcacgc atcaccatca acccggatac tagcaagaac  240
cagttcagcc tccagttgaa ctccgtgacc ccggaggata ccgccgtgta ctactgtgcg  300
cggggcatgt acggatccgt gccgtacaag gagggatact acttcgacat ttggggccag  360
gggactcttg tcaccgtgtc ctcggcctcc actaagggcc cgtcagtgtt ccccccttgcg  420
ccatcctcga agtcaacctc cggaggaact gccgcactgg gttgcctcgt gaaagactat  480
ttcccggaac ccgtcactgt ctcctggaac tcaggagcgc tcaccagcgg agtgcatacc  540
tttcctgcgg tgctgcagtc cagcggcctg tactccctga gctccgtcgt gaccgtcccc  600
tcgtcgtccc tgggaaccca aacctacatt tgcaacgtca atcacaagcc aagcaacact  660
```

-continued

```
aaggtggaca agagagtgga gcccaagtcc tgcgataaga cccacacctg tcctccctgt  720
ccggcacctg aactgcttgg tggaccttcc gtgttcctgt tcccgcccaa gccaaaagac  780
accctgatga tctcccgcac tccggaagtc acttgcgtgg tcgtggacgt gtcccacgag  840
gaccccgagg tcaagtttaa ttggtacgtg gacggagtgg aagtgcacaa cgccaagacc  900
aagccgcggg aagaacagta caactccacc taccgcgtgg tgtccgtcct gactgtgctc  960
caccaggact ggctgaacgg aaaggagtac aagtgcaaag tgtccaacaa ggcactgcca  1020
gcccctatcg aaaagactat ctccaaggcc aagggccaac ctagggagcc ccaggtgtac  1080
acgttgcctc cttcccgcga agaaatgact aagaaccagg tgtcgctgac ctgtctcgtg  1140
aaagggttct acccctctga catcgccgtg gaatgggagt caaacggaca gcctgagaac  1200
aactataaga ccacaccacc tgtcctggac tccgacggct ccttcttcct gtactcaaag  1260
ttgaccgtgg acaagtcgcg gtggcaacag ggcaacgtgt tctcttgctc cgtgctgcac  1320
gaagccctgc acagccacta cacccaaaag tcgctcagcc tctcccccgg aaag        1374
```

```
SEQ ID NO: 74          moltype = AA  length = 458
FEATURE                Location/Qualifiers
REGION                 1..458
                       note = Synthetic polypeptide
source                 1..458
                       mol_type = protein
                       organism = synthetic construct
SEQUENCE: 74
QVQLQQSGPG LVKPSQTLSL TCAISGDSVS SSSAAWNWIR QSPSRGLEWL GHIGYRSKWY  60
NEYAVSVKSR ITINPDTSKN QFSLQLNSVT PEDTAVYYCA RGMYGSVPYK EGYYFDIWGQ  120
GTLVTVSSAS TKGPSVFPLA PSSKSTSGGT AALGCLVKDY FPEPVTVSWN SGALTSGVHT  180
FPAVLQSSGL YSLSSVVTVP SSSLGTQTYI CNVNHKPSNT KVDKRVEPKS CDKTHTCPPC  240
PAPELLGGPS VFLFPPKPKD TLMISRTPEV TCVVVAVSHE DPEVKFNWYV DGVEVHNAKT  300
KPREEQYNST YRVVSVLTVL HQDWLNGKEY KCKVSNKALA APIEKTISKA KGQPREPQVY  360
TLPPSREEMT KNQVSLTCLV KGFYPSDIAV EWESNGQPEN NYKTTPPVLD SDGSFFLYSK  420
LTVDKSRWQQ GNVFSCSVLH EALHSHYTQK SLSLSPGK                          458
```

```
SEQ ID NO: 75          moltype = DNA  length = 1374
FEATURE                Location/Qualifiers
misc_feature           1..1374
                       note = Synthetic polynucleotide
source                 1..1374
                       mol_type = other DNA
                       organism = synthetic construct
SEQUENCE: 75
caagtgcaac tccagcagtc aggaccgggg ttggtcaagc cttcgcagac cctgtccctc  60
acttgcgcca ttagcggaga ttcggtgtcg tcgtcgtcag ccgcctggaa ctggattaga  120
cagtcccctt cccgagggct ggagtggctg ggccacatcg gataccgcag caagtggtac  180
aacgaatacg ccgtcagcgt gaagtcacgc atcaccatca acccggatac tagcaagaac  240
cagttcagcc tccagttgaa ctccgtgacc ccggaggata ccgccgtgta ctactgtgcg  300
cggggcatgt acggatccgt gccgtacaag gagggatact acttcgacat ttggggccag  360
gggactcttg tcaccgtgtc ctcggcctcc actaagggcc cgtcagtgtt ccccccttgcg  420
ccatcctcga agtcaacctc cggaggaact gccgcactgg gttgcctcgt gaaagactat  480
ttcccggaac ccgtcactgt ctcctggaac tcaggagcgc tcaccagcgg agtgcatacc  540
tttcctgcgg tgctgcagtc cagcggcctg tactccctga gctccgtcgt gaccgtcccc  600
tcgtcgtccc tgggaaccca aacctacatt tgcaacgtca atcacaagcc aagcaacact  660
aaggtggaca agagagtgga gcccaagtcc tgcgataaga cccacacctg tcctccctgt  720
ccggcacctg aactgcttgg tggaccttcc gtgttcctgt tcccgcccaa gccaaaagac  780
accctgatga tctcccgcac tccggaagtc acttgcgtgg tcgtggccgt gtcccacgag  840
gaccccgagg tcaagtttaa ttggtacgtg gacggagtgg aagtgcacaa cgccaagacc  900
aagccgcggg aagaacagta caactccacc taccgcgtgg tgtccgtcct gactgtgctc  960
caccaggact ggctgaacgg aaaggagtac aagtgcaaag tgtccaacaa ggcactggct  1020
gcccctatcg aaaagactat ctccaaggcc aagggccaac ctagggagcc ccaggtgtac  1080
acgttgcctc cttcccgcga agaaatgact aagaaccagg tgtcgctgac ctgtctcgtg  1140
aaagggttct acccctctga catcgccgtg gaatgggagt caaacggaca gcctgagaac  1200
aactataaga ccacaccacc tgtcctggac tccgacggct ccttcttcct gtactcaaag  1260
ttgaccgtgg acaagtcgcg gtggcaacag ggcaacgtgt tctcttgctc cgtgctgcac  1320
gaagccctgc acagccacta cacccaaaag tcgctcagcc tctcccccgg aaag        1374
```

```
SEQ ID NO: 76          moltype = AA  length = 458
FEATURE                Location/Qualifiers
REGION                 1..458
                       note = Synthetic polypeptide
source                 1..458
                       mol_type = protein
                       organism = synthetic construct
SEQUENCE: 76
QVQLQQSGPG LVKPSQTLSL TCAISGDSVS SSSAAWNWIR QSPSRGLEWL GHIGYRSKWY  60
NEYAVSVKSR ITINPDTSKN QFSLQLNSVT PEDTAVYYCA RGMYGSVPYK EGYYFDIWGQ  120
GTLVTVSSAS TKGPSVFPLA PSSKSTSGGT AALGCLVKDY FPEPVTVSWN SGALTSGVHT  180
FPAVLQSSGL YSLSSVVTVP SSSLGTQTYI CNVNHKPSNT KVDKRVEPKS CDKTHTCPPC  240
PAPELLGGPS VFLFPPKPKD TLYITREPEV TCVVVDVSHE DPEVKFNWYV DGVEVHNAKT  300
KPREEQYNST YRVVSVLTVL HQDWLNGKEY KCKVSNKALP APIEKTISKA KGQPREPQVY  360
TLPPSREEMT KNQVSLTCLV KGFYPSDIAV EWESNGQPEN NYKTTPPVLD SDGSFFLYSK  420
LTVDKSRWQQ GNVFSCSVMH EALHNHYTQK SLSLSPGK                          458
```

-continued

```
SEQ ID NO: 77          moltype = DNA  length = 1374
FEATURE                Location/Qualifiers
misc_feature           1..1374
                       note = Synthetic polynucleotide
source                 1..1374
                       mol_type = other DNA
                       organism = synthetic construct
SEQUENCE: 77
caagtgcaac tccagcagtc aggaccgggg ttggtcaagc cttcgcagac cctgtccctc  60
acttgcgcca ttagcggaga ttcggtgtcg tcgtcgtcag ccgcctggaa ctggattaga  120
cagtcccctt cccgagggct ggagtggctg ggccacatcg gataccgcag caagtggtac  180
aacgaatacg ccgtcagcgt gaagtcacgc atcaccatca acccggatac tagcaagaac  240
cagttcagcc tccagttgaa ctccgtgacc ccggaggata ccgccgtgta ctactgtgcg  300
cggggcatgt acggatccgt gccgtacaag gagggatact acttcgacat ttggggccag  360
gggactcttg tcaccgtgtc ctcggcctcc actaagggcc cgtcagtgtt ccccccttgcg  420
ccatcctcga agtcaacctc cggaggaact gccgcactgg gttgcctcgt gaaagactat  480
ttccccggaac ccgtcactgt ctcctggaac tcaggagcgc tcaccagcgg agtgcatacc  540
tttcctgcgg tgctgcagtc cagcggcctg tactccctga gctccgtcgt gaccgtcccc  600
tcgtcgtccc tgggaaccca aacctacatt tgcaacgtca atcacaagcc aagcaacact  660
aaggtggaca agagagtgga gcccaagtcc tgcgataaga cccacacctg tcctccctgt  720
ccggcacctg aactgcttgg tggaccttcc gtgttcctgt tcccgcccaa gccaaaagac  780
accctgtata tcactcgcga accggaagtc acttgcgtgg tcgtggacgt gtcccacgag  840
gaccccgagg tcaagtttaa ttggtacgtg gacggagtgg aagtgcacaa cgccaagacc  900
aagccgcggg aagaacagta caactccacc taccgcgtgg tgtccgtcct gactgtgctc  960
caccaggact ggctgaacgg aaaggagtac aagtgcaaag tgtccaacaa ggcactgcca  1020
gcccctatcg aaaagactat ctccaaggcc aagggccaac ctagggagcc ccaggtgtac  1080
acgttgcctc cttcccgcga agaaatgact aagaaccagg tgtcgctgac ctgtctcgtg  1140
aaagggttct accccctctga catcgccgtg gaatgggagt caaacggaca gcctgagaac  1200
aactataaga ccacaccacc tgtcctggac tccgacggct ccttcttcct gtactcaaag  1260
ttgaccgtgg acaagtcgcg gtggcaacag ggcaacgtgt tctcttgctc cgtgatgcac  1320
gaagccctgc acaaccacta cacccaaaag tcgctcagcc tctcccccgg aaag        1374

SEQ ID NO: 78          moltype = AA  length = 9
FEATURE                Location/Qualifiers
REGION                 1..9
                       note = Synthetic polypeptide
source                 1..9
                       mol_type = protein
                       organism = synthetic construct
SEQUENCE: 78
QQHGHSPTT                                                         9

SEQ ID NO: 79          moltype = AA  length = 6
FEATURE                Location/Qualifiers
REGION                 1..6
                       note = Synthetic polypeptide
source                 1..6
                       mol_type = protein
                       organism = synthetic construct
SEQUENCE: 79
HGHSPT                                                            6

SEQ ID NO: 80          moltype = AA  length = 107
FEATURE                Location/Qualifiers
REGION                 1..107
                       note = Synthetic polypeptide
source                 1..107
                       mol_type = protein
                       organism = synthetic construct
SEQUENCE: 80
DIQMTQSPSS LSASVGDRVT ITCRASQDIS NYLAWYQQKP GKAPKLLIYR ASSLQSGVPS  60
RFSGSGSGTD FTLTISSLQP EDFATYYCQQ HGHSPTTFGQ GTKVEIK              107

SEQ ID NO: 81          moltype = DNA  length = 321
FEATURE                Location/Qualifiers
misc_feature           1..321
                       note = Synthetic polynucleotide
source                 1..321
                       mol_type = other DNA
                       organism = synthetic construct
SEQUENCE: 81
gatatccaga tgacccagag cccgagcagc ctgagcgcca gcgtgggcga tcgcgtgacc  60
attacctgca gagccagcca ggacatttct aactacctgg cttggtacca gcagaaaccg  120
ggcaaagcgc cgaaactatt aatctaccgt gcttcttctc tgcaaagcgg cgtgccgagc  180
cgctttagcg gcagcggatc cggcaccgat ttcaccctga ccattagctc tctgcaaccg  240
gaagactttg cgacctatta ttgccagcag catggtcatt ctccgactac ctttggccag  300
ggcacgaaag ttgaaattaa a                                           321

SEQ ID NO: 82          moltype = AA  length = 214
```

```
FEATURE                Location/Qualifiers
REGION                 1..214
                       note = Synthetic polypeptide
source                 1..214
                       mol_type = protein
                       organism = synthetic construct
SEQUENCE: 82
DIQMTQSPSS LSASVGDRVT ITCRASQDIS NYLAWYQQKP GKAPKLLIYR ASSLQSGVPS  60
RFSGSGSGTD FTLTISSLQP EDFATYYCQQ HGHSPTTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 83          moltype = DNA  length = 642
FEATURE                Location/Qualifiers
misc_feature           1..642
                       note = Synthetic polynucleotide
source                 1..642
                       mol_type = other DNA
                       organism = synthetic construct
SEQUENCE: 83
gatatccaga tgacccagag cccgagcagc ctgagcgcca gcgtgggcga tcgcgtgacc  60
attacctgca gagccagcca ggacatttct aactacctgg cttggtacca gcagaaaccg  120
ggcaaagcgc cgaaactatt aatctaccgt gcttcttctc tgcaaagcgg cgtgccgagc  180
cgctttagcg gcagcggatc cggcaccgat ttcaccctga ccattagctc tctgcaaccg  240
gaagactttg cgacctatta ttgccagcag catggtcatt ctccgactac ctttggccag  300
ggcacgaaag ttgaaattaa acgtacggtg gccgctccca gcgtgttcat cttccccccc  360
agcgacgagc agctgaagag cggcaccgcc agcgtggtgt gcctgctgaa caacttctac  420
ccccgggagg ccaaggtgca gtggaaggtg gacaacgccc tgcagagcgg caacagccag  480
gaaagcgtca ccgagcagga cagcaaggac tccacctaca gcctgagcag caccctgacc  540
ctgagcaagg ccgactacga gaagcacaag gtgtacgcct gcgaggtgac ccaccagggc  600
ctgtccagcc ccgtgaccaa gagcttcaac cggggcgagt gt                     642

SEQ ID NO: 84          moltype = AA  length = 12
FEATURE                Location/Qualifiers
REGION                 1..12
                       note = Synthetic polypeptide
source                 1..12
                       mol_type = protein
                       organism = synthetic construct
SEQUENCE: 84
GFSLSTSGVG VS                                                      12

SEQ ID NO: 85          moltype = AA  length = 16
FEATURE                Location/Qualifiers
REGION                 1..16
                       note = Synthetic polypeptide
source                 1..16
                       mol_type = protein
                       organism = synthetic construct
SEQUENCE: 85
LIFSDHDKIY STSLKT                                                  16

SEQ ID NO: 86          moltype = AA  length = 11
FEATURE                Location/Qualifiers
REGION                 1..11
                       note = Synthetic polypeptide
source                 1..11
                       mol_type = protein
                       organism = synthetic construct
SEQUENCE: 86
TLIDRSVYFD Y                                                       11

SEQ ID NO: 87          moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 87
TSGVGVS                                                            7

SEQ ID NO: 88          moltype = AA  length = 9
FEATURE                Location/Qualifiers
REGION                 1..9
                       note = Synthetic polypeptide
source                 1..9
                       mol_type = protein
                       organism = synthetic construct
```

```
SEQUENCE: 88
GFSLSTSGV                                                     9

SEQ ID NO: 89          moltype = AA  length = 5
FEATURE                Location/Qualifiers
REGION                 1..5
                       note = Synthetic polypeptide
source                 1..5
                       mol_type = protein
                       organism = synthetic construct
SEQUENCE: 89
FSDHD                                                         5

SEQ ID NO: 90          moltype = AA  length = 10
FEATURE                Location/Qualifiers
REGION                 1..10
                       note = Synthetic polypeptide
source                 1..10
                       mol_type = protein
                       organism = synthetic construct
SEQUENCE: 90
GFSLSTSGVG                                                    10

SEQ ID NO: 91          moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 91
IFSDHDK                                                       7

SEQ ID NO: 92          moltype = AA  length = 13
FEATURE                Location/Qualifiers
REGION                 1..13
                       note = Synthetic polypeptide
source                 1..13
                       mol_type = protein
                       organism = synthetic construct
SEQUENCE: 92
ARTLIDRSVY FDY                                                13

SEQ ID NO: 93          moltype = AA  length = 121
FEATURE                Location/Qualifiers
REGION                 1..121
                       note = Synthetic polypeptide
source                 1..121
                       mol_type = protein
                       organism = synthetic construct
SEQUENCE: 93
QVQLKESGPA LVKPTQTLTL TCTFSGFSLS TSGVGVSWIR QPPGKALEWL ALIFSDHDKI  60
YSTSLKTRLT ISKDTSKNQV VLTMTNMDPV DTATYYCART LIDRSVYFDY WGQGTLVTVS  120
S                                                             121

SEQ ID NO: 94          moltype = DNA  length = 363
FEATURE                Location/Qualifiers
misc_feature           1..363
                       note = Synthetic polynucleotide
source                 1..363
                       mol_type = other DNA
                       organism = synthetic construct
SEQUENCE: 94
caggtgcaat tgaaagaaag cggtccggcg ctggtgaaac cgacccagac cctgaccctg  60
acgtgcacct tttccggatt cagcctgtct acttccggtg ttggtgtgag ctggattcgc  120
cagccgccgg gcaaagcgct cgagtggctg gcgctgatct tctctgacca tgacaagatc  180
tatagcacca gcctgaaaac ccgtctgacc attagcaaag atacttcgaa aaaccaggtg  240
gtgctgacca tgaccaacat ggacccggtg gataccgcga cctattattg cgcgcgtact  300
ctgatcgacc gttctgttta cttcgattac tggggccaag gcaccctggt gactgttagc  360
tca                                                           363

SEQ ID NO: 95          moltype = AA  length = 451
FEATURE                Location/Qualifiers
REGION                 1..451
                       note = Synthetic polypeptide
source                 1..451
                       mol_type = protein
                       organism = synthetic construct
SEQUENCE: 95
```

-continued

```
QVQLKESGPA LVKPTQTLTL TCTFSGFSLS TSGVGVSWIR QPPGKALEWL ALIFSDHDKI  60
YSTSLKTRLT ISKDTSKNQV VLTMTNMDPV DTATYYCART LIDRSVYFDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPEAAG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 96          moltype = DNA  length = 1353
FEATURE                Location/Qualifiers
misc_feature           1..1353
                       note = Synthetic polynucleotide
source                 1..1353
                       mol_type = other DNA
                       organism = synthetic construct
SEQUENCE: 96
caggtgcaat tgaaagaaag cggtccggcg ctggtgaaac cgacccagac cctgaccctg  60
acgtgcacct tttccggatt cagcctgtct acttccggtg ttggtgtgag ctggattcgc  120
cagccgccgg gcaaagcgct cgagtggctg gcgctgatct tctctgacca tgacaagatc  180
tatagcacca gcctgaaaac ccgtctgacc attagcaaag atacttcgaa aaaccaggtg  240
gtgctgacca tgaccaacat ggacccggtg gataccgcga cctattattg cgcgcgtact  300
ctgatcgacc gttctgttta cttcgattac tggggccaag gcaccctggt gactgttagc  360
tcagcctcca ccaagggtcc atcggtcttc cccctggcac cctcctccaa gagcacctct  420
gggggcacag cggccctggg ctgcctggtc aaggactact tccccgaacc ggtgacggtg  480
tcgtggaact caggcgccct gaccagcggc gtgcacacct tcccggctgt cctacagtcc  540
tcaggactct actccctcag cagcgtggtg accgtgccct ccagcagctt gggcacccag  600
acctacatct gcaacgtgaa tcacaagccc agcaacacca aggtggacaa gagagttgag  660
cccaaatctt gtgacaaaac tcacacatgc ccaccgtgcc cagcacctga agcagcgggg  720
ggaccgtcag tcttcctctt ccccccaaaa cccaaggaca ccctcatgat ctcccggacc  780
cctgaggtca catgcgtggt ggtggacgtg agccacgaag accctgaggt caagttcaac  840
tggtacgtgg acggcgtgga ggtgcataat gccaagacaa agccgcggga ggagcagtac  900
aacagcacgt accgggtggt cagcgtcctc accgtcctgc accaggactg gctgaatggc  960
aaggagtaca agtgcaaggt ctccaacaaa gccctcccag cccccatcga gaaaaccatc  1020
tccaaagcca aagggcagcc ccgagaacca caggtgtaca ccctgccccc atcccgggag  1080
gagatgacca agaaccaggt cagcctgacc tgcctggtca aaggcttcta tcccagcgac  1140
atcgccgtgg agtgggagag caatgggcag ccggagaaca actacaagac cacgcctccc  1200
gtgctggact ccgacggctc cttcttcctc tacagcaagc tcaccgtgga caagagcagg  1260
tggcagcagg ggaacgtctt ctcatgctcc gtgatgcatg aggctctgca caaccactac  1320
acgcagaaga gcctctccct gtctccgggt aaa                                1353

SEQ ID NO: 97          moltype = AA  length = 13
FEATURE                Location/Qualifiers
REGION                 1..13
                       note = Synthetic polypeptide
source                 1..13
                       mol_type = protein
                       organism = synthetic construct
SEQUENCE: 97
SGSSSNIGHH YVS                                                     13

SEQ ID NO: 98          moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 98
DNTNRPS                                                            7

SEQ ID NO: 99          moltype = AA  length = 11
FEATURE                Location/Qualifiers
REGION                 1..11
                       note = Synthetic polypeptide
source                 1..11
                       mol_type = protein
                       organism = synthetic construct
SEQUENCE: 99
ATWDGLMNSI V                                                       11

SEQ ID NO: 100         moltype = AA  length = 9
FEATURE                Location/Qualifiers
REGION                 1..9
                       note = Synthetic polypeptide
source                 1..9
                       mol_type = protein
                       organism = synthetic construct
SEQUENCE: 100
```

```
SSSNIGHHY                                                            9

SEQ ID NO: 101          moltype =   length =
SEQUENCE: 101
000

SEQ ID NO: 102          moltype = AA  length = 8
FEATURE                 Location/Qualifiers
REGION                  1..8
                        note = Synthetic polypeptide
source                  1..8
                        mol_type = protein
                        organism = synthetic construct
SEQUENCE: 102
WDGLMNSI                                                             8

SEQ ID NO: 103          moltype = AA  length = 8
FEATURE                 Location/Qualifiers
REGION                  1..8
                        note = Synthetic polypeptide
source                  1..8
                        mol_type = protein
                        organism = synthetic construct
SEQUENCE: 103
SSNIGHHY                                                             8

SEQ ID NO: 104          moltype = AA  length = 110
FEATURE                 Location/Qualifiers
REGION                  1..110
                        note = Synthetic polypeptide
source                  1..110
                        mol_type = protein
                        organism = synthetic construct
SEQUENCE: 104
DIVLTQPPSV SGAPGQRVTI SCSGSSSNIG HHYVSWYQQL PGTAPKLLIY DNTNRPSGVP  60
DRFSGSKSGT SASLAITGLQ AEDEADYYCA TWDGLMNSIV FGGGTKLTVL             110

SEQ ID NO: 105          moltype = DNA  length = 330
FEATURE                 Location/Qualifiers
misc_feature            1..330
                        note = Synthetic polynucleotide
source                  1..330
                        mol_type = other DNA
                        organism = synthetic construct
SEQUENCE: 105
gatatcgtgc tgacccagcc gccgagcgtg agcggtgcac cgggccagcg cgtgaccatt  60
agctgtagcg gcagcagcag caacattggt catcattacg tgtcttggta ccagcagctg  120
ccgggcacgg cgccgaaact gctgatctac gacaacacta accgcccgag cggcgtgccg  180
gatcgcttta gcggatccaa aagcggcacc agcgccagcc tggcgattac cggcctgcaa  240
gcagaagacg aagcggatta ttactgcgct acttgggacg gtctgatgaa ctctatcgtg  300
tttggcggcg gcacgaagtt aaccgtccta                                   330

SEQ ID NO: 106          moltype = AA  length = 216
FEATURE                 Location/Qualifiers
REGION                  1..216
                        note = Synthetic polypeptide
source                  1..216
                        mol_type = protein
                        organism = synthetic construct
SEQUENCE: 106
DIVLTQPPSV SGAPGQRVTI SCSGSSSNIG HHYVSWYQQL PGTAPKLLIY DNTNRPSGVP  60
DRFSGSKSGT SASLAITGLQ AEDEADYYCA TWDGLMNSIV FGGGTKLTVL GQPKAAPSVT  120
LFPPSSEELQ ANKATLVCLI SDFYPGAVTV AWKADSSPVK AGVETTTPSK QSNNKYAASS  180
YLSLTPEQWK SHRSYSCQVT HEGSTVEKTV APTECS                             216

SEQ ID NO: 107          moltype = DNA  length = 648
FEATURE                 Location/Qualifiers
misc_feature            1..648
                        note = Synthetic polynucleotide
source                  1..648
                        mol_type = other DNA
                        organism = synthetic construct
SEQUENCE: 107
gatatcgtgc tgacccagcc gccgagcgtg agcggtgcac cgggccagcg cgtgaccatt  60
agctgtagcg gcagcagcag caacattggt catcattacg tgtcttggta ccagcagctg  120
ccgggcacgg cgccgaaact gctgatctac gacaacacta accgcccgag cggcgtgccg  180
gatcgcttta gcggatccaa aagcggcacc agcgccagcc tggcgattac cggcctgcaa  240
gcagaagacg aagcggatta ttactgcgct acttgggacg gtctgatgaa ctctatcgtg  300
tttggcggcg gcacgaagtt aaccgtccta ggtcagccca aggctgcccc ctcggtcact  360
```

-continued

```
ctgttcccgc cctcctctga ggagcttcaa gccaacaagg ccacactggt gtgtctcata  420
agtgacttct acccgggagc cgtgacagtg gcctggaagg cagatagcag ccccgtcaag  480
gcgggagtgg agaccaccac accctccaaa caaagcaaca acaagtacgc ggccagcagc  540
tatctgagcc tgacgcctga gcagtggaag tcccacagaa gctacagctg ccaggtcacg  600
catgaaggga gcaccgtgga gaagacagtg gcccctacag aatgttca               648

SEQ ID NO: 108         moltype = AA  length = 10
FEATURE                Location/Qualifiers
REGION                 1..10
                       note = Synthetic polypeptide
source                 1..10
                       mol_type = protein
                       organism = synthetic construct
SEQUENCE: 108
GFTFSSYAMD                                                         10

SEQ ID NO: 109         moltype = AA  length = 19
FEATURE                Location/Qualifiers
REGION                 1..19
                       note = Synthetic polypeptide
source                 1..19
                       mol_type = protein
                       organism = synthetic construct
SEQUENCE: 109
RIKSKADSYT ADYAAPVKG                                               19

SEQ ID NO: 110         moltype = AA  length = 8
FEATURE                Location/Qualifiers
REGION                 1..8
                       note = Synthetic polypeptide
source                 1..8
                       mol_type = protein
                       organism = synthetic construct
SEQUENCE: 110
SHYSAFAY                                                           8

SEQ ID NO: 111         moltype = AA  length = 5
FEATURE                Location/Qualifiers
REGION                 1..5
                       note = Synthetic polypeptide
source                 1..5
                       mol_type = protein
                       organism = synthetic construct
SEQUENCE: 111
SYAMD                                                              5

SEQ ID NO: 112         moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 112
GFTFSSY                                                            7

SEQ ID NO: 113         moltype = AA  length = 8
FEATURE                Location/Qualifiers
REGION                 1..8
                       note = Synthetic polypeptide
source                 1..8
                       mol_type = protein
                       organism = synthetic construct
SEQUENCE: 113
KSKADSYT                                                           8

SEQ ID NO: 114         moltype = AA  length = 8
FEATURE                Location/Qualifiers
REGION                 1..8
                       note = Synthetic polypeptide
source                 1..8
                       mol_type = protein
                       organism = synthetic construct
SEQUENCE: 114
GFTFSSYA                                                           8

SEQ ID NO: 115         moltype = AA  length = 10
FEATURE                Location/Qualifiers
REGION                 1..10
```

-continued

```
                         note = Synthetic polypeptide
source                   1..10
                         mol_type = protein
                         organism = synthetic construct
SEQUENCE: 115
IKSKADSYTA                                                      10

SEQ ID NO: 116           moltype = AA  length = 10
FEATURE                  Location/Qualifiers
REGION                   1..10
                         note = Synthetic polypeptide
source                   1..10
                         mol_type = protein
                         organism = synthetic construct
SEQUENCE: 116
ARSHYSAFAY                                                      10

SEQ ID NO: 117           moltype = AA  length = 119
FEATURE                  Location/Qualifiers
REGION                   1..119
                         note = Synthetic polypeptide
source                   1..119
                         mol_type = protein
                         organism = synthetic construct
SEQUENCE: 117
EVQLVESGGG LVKPGGSLRL SCAASGFTFS SYAMDWVRQA PGKGLEWVGR IKSKADSYTA  60
DYAAPVKGRF TISRDDSKNT LYLQMNSLKT EDTAVYYCAR SHYSAFAYWG QGTLVTVSS   119

SEQ ID NO: 118           moltype = DNA  length = 357
FEATURE                  Location/Qualifiers
misc_feature             1..357
                         note = Synthetic polynucleotide
source                   1..357
                         mol_type = other DNA
                         organism = synthetic construct
SEQUENCE: 118
gaggtgcaat tggtggaaag cggcggtggc ctggtgaaac caggcggcag cctgcgcctg  60
agctgcgccg cctccggatt caccttttct tcttacgcta tggactgggt gcgccaggcc  120
ccgggcaaag gtctcgagtg ggtgggccgt atcaaatcta aagctgactc ttacactgct  180
gactatgccg ccccagtgaa aggccgcttt accattagcc gcgatgattc gaaaaacacc  240
ctgtatctgc aaatgaacag cctgaaaacc gaagatacgg ccgtgtatta ttgcgcgcgt  300
tctcattact ctgctttcgc ttactggggc caaggcaccc tggtgactgt tagctca     357

SEQ ID NO: 119           moltype = AA  length = 449
FEATURE                  Location/Qualifiers
REGION                   1..449
                         note = Synthetic polypeptide
source                   1..449
                         mol_type = protein
                         organism = synthetic construct
SEQUENCE: 119
EVQLVESGGG LVKPGGSLRL SCAASGFTFS SYAMDWVRQA PGKGLEWVGR IKSKADSYTA  60
DYAAPVKGRF TISRDDSKNT LYLQMNSLKT EDTAVYYCAR SHYSAFAYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPEAAGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                 449

SEQ ID NO: 120           moltype = DNA  length = 1347
FEATURE                  Location/Qualifiers
misc_feature             1..1347
                         note = Synthetic polynucleotide
source                   1..1347
                         mol_type = other DNA
                         organism = synthetic construct
SEQUENCE: 120
gaggtgcaat tggtggaaag cggcggtggc ctggtgaaac caggcggcag cctgcgcctg  60
agctgcgccg cctccggatt caccttttct tcttacgcta tggactgggt gcgccaggcc  120
ccgggcaaag gtctcgagtg ggtgggccgt atcaaatcta aagctgactc ttacactgct  180
gactatgccg ccccagtgaa aggccgcttt accattagcc gcgatgattc gaaaaacacc  240
ctgtatctgc aaatgaacag cctgaaaacc gaagatacgg ccgtgtatta ttgcgcgcgt  300
tctcattact ctgctttcgc ttactggggc caaggcaccc tggtgactgt tagctcagcc  360
tccaccaagg gtccatcggt cttccccctg gcaccctcct ccaagagcac ctctgggggc  420
acagcggccc tgggctgcct ggtcaaggac tacttccccg aaccggtgac ggtgtcgtgg  480
aactcaggcg ccctgaccag cggcgtgcac accttcccgg ctgtcctaca gtcctcagga  540
ctctactccc tcagcagcgt ggtgaccgtg ccctccagca gcttgggcac ccagacctac  600
atctgcaacg tgaatcacaa gcccagcaac accaaggtgg acaagagagt tgagcccaaa  660
```

-continued

```
tcttgtgaca aaactcacac atgcccaccg tgcccagcac ctgaagcagc ggggggaccg  720
tcagtcttcc tcttcccccc aaaacccaag gacaccctca tgatctcccg gacccctgag  780
gtcacatgcg tggtggtgga cgtgagccac gaagaccctg aggtcaagtt caactggtac  840
gtggacggcg tggaggtgca taatgccaag acaaagccgc gggaggagca gtacaacagc  900
acgtaccggg tggtcagcgt cctcaccgtc ctgcaccagg actggctgaa tggcaaggag  960
tacaagtgca aggtctccaa caaagccctc ccagccccca tcgagaaaac catctccaaa  1020
gccaaagggc agccccgaga accacaggtg tacaccctgc ccccatcccg ggaggagatg  1080
accaagaacc aggtcagcct gacctgcctg gtcaaaggct tctatcccag cgacatcgcc  1140
gtggagtggg agagcaatgg gcagccggag aacaactaca agaccacgcc tcccgtgctg  1200
gactccgacg gctccttctt cctctacagc aagctcaccg tggacaagag caggtggcag  1260
caggggaacg tcttctcatg ctccgtgatg catgaggctc tgcacaacca ctacacgcag  1320
aagagcctct ccctgtctcc gggtaaa                                      1347

SEQ ID NO: 121          moltype = AA  length = 13
FEATURE                 Location/Qualifiers
REGION                  1..13
                        note = Synthetic polypeptide
source                  1..13
                        mol_type = protein
                        organism = synthetic construct
SEQUENCE: 121
SGSSSNIGSN SVN                                                     13

SEQ ID NO: 122          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 122
RNSNRPS                                                            7

SEQ ID NO: 123          moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 123
SAFDESTKGV V                                                       11

SEQ ID NO: 124          moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 124
SSSNIGSNS                                                          9

SEQ ID NO: 125          moltype =   length =
SEQUENCE: 125
000

SEQ ID NO: 126          moltype = AA  length = 8
FEATURE                 Location/Qualifiers
REGION                  1..8
                        note = Synthetic polypeptide
source                  1..8
                        mol_type = protein
                        organism = synthetic construct
SEQUENCE: 126
FDESTKGV                                                           8

SEQ ID NO: 127          moltype = AA  length = 8
FEATURE                 Location/Qualifiers
REGION                  1..8
                        note = Synthetic polypeptide
source                  1..8
                        mol_type = protein
                        organism = synthetic construct
SEQUENCE: 127
SSNIGSNS                                                           8

SEQ ID NO: 128          moltype = AA  length = 110
FEATURE                 Location/Qualifiers
```

```
REGION                 1..110
                       note = Synthetic polypeptide
source                 1..110
                       mol_type = protein
                       organism = synthetic construct
SEQUENCE: 128
DIVLTQPPSV SGAPGQRVTI SCSGSSSNIG SNSVNWYQQL PGTAPKLLIY RNSNRPSGVP  60
DRFSGSKSGT SASLAITGLQ AEDEADYYCS AFDESTKGVV FGGGTKLTVL            110

SEQ ID NO: 129         moltype = DNA  length = 330
FEATURE                Location/Qualifiers
misc_feature           1..330
                       note = Synthetic polynucleotide
source                 1..330
                       mol_type = other DNA
                       organism = synthetic construct
SEQUENCE: 129
gatatcgtgc tgacccagcc gccgagcgtg agcggtgcac cgggccagcg cgtgaccatt  60
agctgtagcg gcagcagcag caacattggt tctaactctg tgaactggta ccagcagctg  120
ccgggcacgg cgccgaaact gctgatctac cgtaactcta accgcccgag cggcgtgccg  180
gatcgcttta gcggatccaa aagcggcacc agcgccagcc tggcgattac cggcctgcaa  240
gcagaagacg aagcggatta ttactgctct gctttcgacg aatctactaa aggtgttgtg  300
tttggcggcg gcacgaagtt aaccgtccta                                   330

SEQ ID NO: 130         moltype = AA  length = 216
FEATURE                Location/Qualifiers
REGION                 1..216
                       note = Synthetic polypeptide
source                 1..216
                       mol_type = protein
                       organism = synthetic construct
SEQUENCE: 130
DIVLTQPPSV SGAPGQRVTI SCSGSSSNIG SNSVNWYQQL PGTAPKLLIY RNSNRPSGVP  60
DRFSGSKSGT SASLAITGLQ AEDEADYYCS AFDESTKGVV FGGGTKLTVL GQPKAAPSVT  120
LFPPSSEELQ ANKATLVCLI SDFYPGAVTV AWKADSSPVK AGVETTTPSK QSNNKYAASS  180
YLSLTPEQWK SHRSYSCQVT HEGSTVEKTV APTECS                            216

SEQ ID NO: 131         moltype = DNA  length = 648
FEATURE                Location/Qualifiers
misc_feature           1..648
                       note = Synthetic polynucleotide
source                 1..648
                       mol_type = other DNA
                       organism = synthetic construct
SEQUENCE: 131
gatatcgtgc tgacccagcc gccgagcgtg agcggtgcac cgggccagcg cgtgaccatt  60
agctgtagcg gcagcagcag caacattggt tctaactctg tgaactggta ccagcagctg  120
ccgggcacgg cgccgaaact gctgatctac cgtaactcta accgcccgag cggcgtgccg  180
gatcgcttta gcggatccaa aagcggcacc agcgccagcc tggcgattac cggcctgcaa  240
gcagaagacg aagcggatta ttactgctct gctttcgacg aatctactaa aggtgttgtg  300
tttggcggcg gcacgaagtt aaccgtccta ggtcagccca aggctgcccc ctcggtcact  360
ctgttcccgc cctcctctga ggagcttcaa gccaacaagg ccacactggt gtgtctcata  420
agtgacttct acccgggagc cgtgacagtg gcctggaagg cagatagcag ccccgtcaag  480
gcgggagtgg agaccaccac accctccaaa caaagcaaca acaagtacgc ggccagcagc  540
tatctgagcc tgacgcctga gcagtggaag tcccacagaa gctacagctg ccaggtcacg  600
catgaaggga gcaccgtgga gaagacagtg gcccctacag aatgttca                648

SEQ ID NO: 132         moltype = AA  length = 10
FEATURE                Location/Qualifiers
REGION                 1..10
                       note = Synthetic polypeptide
source                 1..10
                       mol_type = protein
                       organism = synthetic construct
SEQUENCE: 132
AHVEHSISRS                                                         10

SEQ ID NO: 133         moltype = DNA  length = 1076
FEATURE                Location/Qualifiers
source                 1..1076
                       mol_type = other DNA
                       organism = Homo sapiens
SEQUENCE: 133
gggcagcgcc tgacatgcct gatcctctct tttctgcagt tcaagggaaa gacgagatct  60
tgcacaaggc actctgcttc tgcccttggc tggggaaggg tggcatggag cctctccggc  120
tgctcatctt actctttgtc acagagctgt ccggagccca caacaccaca gtgttccagg  180
gcgtggcggg ccagtccctg caggtgtctt gcccctatga ctccatgaag cactggggga  240
ggcgcaaggc ctggtgccgc cagctgggag agaagggccc atgccagcgt gtggtcagca  300
cgcacaactt gtggctgctg tccttcctga ggaggtggaa tgggagcaca gccatcacag  360
```

-continued

```
acgataccct gggtggcact ctcaccatta cgctgcggaa tctacaaccc catgatgcgg  420
gtctctacca gtgccagagc ctccatggca gtgaggctga caccctcagg aaggtcctgg  480
tggaggtgct ggcagacccc ctggatcacc gggatgctgg agatctctgg ttccccgggg  540
agtctgagag cttcgaggat gcccatgtgg agcacagcat ctccaggagc ctcttggaag  600
gagaaatccc cttcccaccc acttccatcc ttctcctcct ggcctgcatc tttctcatca  660
agattctagc agccagcgcc ctctgggctg cagcctggca tggacagaag ccagggacac  720
atccacccag tgaactggac tgtggccatg acccagggta tcagctccaa actctgccag  780
ggctgagaga cacgtgaagg aagatgatgg gaggaaaagc ccaggagaag tcccaccagg  840
gaccagccca gcctgcatac ttgccacttg gccaccagga ctccttgttc tgctctggca  900
agagactact ctgcctgaac actgcttctc ctggaccctg gaagcaggga ctggttgagg  960
gagtggggag gtggtaagaa cacctgacaa cttctgaata ttggacattt taaacactta  1020
caaataaatc caagactgtc atatttagct ggataaaaaa aaaaaaaaaa aaaaaa      1076

SEQ ID NO: 134         moltype = DNA  length = 280
FEATURE                Location/Qualifiers
misc_feature           1..280
                       note = Synthetic polynucleotide
source                 1..280
                       mol_type = other DNA
                       organism = synthetic construct
SEQUENCE: 134
cgttacataa cttacggtaa atggcccgcc tggctgaccg cccaacgacc cccgcccatt  60
gacgtcaata atgacgtatg ttcccatagt aacgccaata gggactttcc attgacgtca  120
atgggtggag tatttacggt aaactgccca cttggcagta catcaagtgt atcatatgcc  180
aagtacgccc cctattgacg tcaatgacgg taaatggccc gcctggcatt atgcccagta  240
catgacctta tgggactttc ctacttggca gtacatctac                        280

SEQ ID NO: 135         moltype = DNA  length = 266
FEATURE                Location/Qualifiers
misc_feature           1..266
                       note = Synthetic polynucleotide
source                 1..266
                       mol_type = other DNA
                       organism = synthetic construct
SEQUENCE: 135
ccacgttctg cttcactctc cccatctccc ccccctcccc acccccaatt ttgtatttat  60
ttatttttta attattttgt gcagcgatgg gggcgggggg gggggggggg cgcgcgccag  120
gcggggcggg gcggggcgag gggcggggcg gggcgaggcg gagaggtgcg gcggcagcca  180
atcagagcgg cgcgctccga aagtttcctt ttatggcgag gcggcggcgg cggcggccct  240
ataaaaagcg aagcgcgcgg cgggcg                                       266

SEQ ID NO: 136         moltype = DNA  length = 552
FEATURE                Location/Qualifiers
misc_feature           1..552
                       note = Synthetic polynucleotide
source                 1..552
                       mol_type = other DNA
                       organism = synthetic construct
SEQUENCE: 136
cgttacataa cttacggtaa atggcccgcc tggctgaccg cccaacgacc cccgcccatt  60
gacgtcaata atgacgtatg ttcccatagt aacgccaata gggactttcc attgacgtca  120
atgggtggag tatttacggt aaactgccca cttggcagta catcaagtgt atcatatgcc  180
aagtacgccc cctattgacg tcaatgacgg taaatggccc gcctggcatt atgcccagta  240
catgacctta tgggactttc ctacttggca gtacatctac tcgaggccac gttctgcttc  300
actctcccca tctccccccc ctccccaccc ccaattttgt atttatttat tttttaatta  360
ttttgtgcag cgatgggggc gggggggggg ggggggcgcg cgccaggcgg ggcggggcgg  420
ggcgaggggc ggggcggggc gaggcggaga ggtgcggcgg cagccaatca gagcggcgcg  480
ctccgaaagt ttccttttat ggcgaggcgg cggcggcggc ggccctataa aaagcgaagc  540
gcgcggcggg cg                                                      552

SEQ ID NO: 137         moltype = DNA  length = 97
FEATURE                Location/Qualifiers
misc_feature           1..97
                       note = Synthetic polynucleotide
source                 1..97
                       mol_type = other DNA
                       organism = synthetic construct
SEQUENCE: 137
gtaagtttag tctttttgtc ttttatttca ggtcccggat ccggtggtgg tgcaaatcaa  60
agaactgctc ctcagtggat gttgccttta cttctag                           97

SEQ ID NO: 138         moltype = DNA  length = 232
FEATURE                Location/Qualifiers
misc_feature           1..232
                       note = Synthetic polynucleotide
source                 1..232
                       mol_type = other DNA
                       organism = synthetic construct
SEQUENCE: 138
```

-continued

```
ctagagctcg ctgatcagcc tcgactgtgc cttctagttg ccagccatct gttgtttgcc  60
cctcccccgt gccttccttg accctggaag gtgccactcc cactgtcctt tcctaataaa  120
atgaggaaat tgcatcgcat tgtctgagta ggtgtcattc tattctgggg ggtggggtgg  180
ggcaggacag caagggggag gattgggaag acaatagcag gcatgctggg ga          232

SEQ ID NO: 139          moltype = AA  length = 162
FEATURE                 Location/Qualifiers
REGION                  1..162
                        note = hTREM2 residues 19-174 plus His-tag
source                  1..162
                        mol_type = protein
                        organism = synthetic construct
SEQUENCE: 139
HNTTVFQGVA GQSLQVSCPY DSMKHWGRRK AWCRQLGEKG PCQRVVSTHN LWLLSFLRRW  60
NGSTAITDDT LGGTLTITLR NLQPHDAGLY QCQSLHGSEA DTLRKVLVEV LADPLDHRDA  120
GDLWFPGESE SFEDAHVEHS ISRSLLEGEI PFPPTSHHHH HH                     162

SEQ ID NO: 140          moltype = AA  length = 215
FEATURE                 Location/Qualifiers
REGION                  1..215
                        note = Synthetic polypeptide
source                  1..215
                        mol_type = protein
                        organism = synthetic construct
SEQUENCE: 140
DIQMTQSPSS LSASVGDRVT ITCRASQDIS NYLAWYQQKP GKAPKLLIYR ASSLQSGVPS  60
RFSGSGSGTD FTLTISSLQP EDFATYYCFQ YRHMPSQTFG QGTKVEIKRT DAAPTVSIFP  120
PSSEQLTSGG ASVVCFLNNF YPKDINVKWK IDGSERQNGV LNSWTDQDSK DSTYSMSSTL  180
TLTKDEYERH NSYTCEATHK TSTSPIVKSF NRNEC                             215

SEQ ID NO: 141          moltype = AA  length = 449
FEATURE                 Location/Qualifiers
REGION                  1..449
                        note = Synthetic polypeptide
source                  1..449
                        mol_type = protein
                        organism = synthetic construct
SEQUENCE: 141
QVQLVQSGAE VKKPGASVKV SCKASGYTFT GYHMSWVRQA PGQGLEWMGV INPVSGNTVY  60
AQKFQGRVTM TRDTSISTAY MELSRLRSED TAVYYCARIP SYTYAFDYWG QGTLVTVSSA  120
KTTAPSVYPL APVCGDTTGS SVTLGCLVKG YFPEPVTLTW NSGSLSSGVH TFPAVLQSDL  180
YTLSSSVTVT SSTWPSQSIT CNVAHPASST KVDKKIEPRG PTIKPCPPCK CPAPNLLGGP  240
SVFIFPPKIK DVLMISLSPI VTCVVVAVSE DDPDVQISWF VNNVEVHTAQ TQTHREDYNS  300
TLRVVSALPI QHQDWMSGKE FKCKVNNKDL AAPIERTISK PKGSVRAPQV YVLPPPEEEM  360
TKKQVTLTCM VTDFMPEDIY VEWTNNGKTE LNYKNTEPVL DSDGSYFMYS KLRVEKKNWV  420
ERNSYSCSVV HEGLHNHHTT KSFSRTPGK                                    449
```